(12) United States Patent
Eccles et al.

(10) Patent No.: US 9,732,093 B2
(45) Date of Patent: *Aug. 15, 2017

(54) FLAP MODULATORS

(71) Applicant: JANSSEN PHARMACEUTICA NV, Beerse (BE)

(72) Inventors: Wendy Eccles, San Diego, CA (US); Anne E. Fitzgerald, San Diego, CA (US); Michael D. Hack, San Diego, CA (US); Natalie A. Hawryluk, San Diego, CA (US); William M. Jones, San Diego, CA (US); John M. Keith, San Diego, CA (US); Paul Krawczuk, San Diego, CA (US); Alec D. Lebsack, Ladera Ranch, CA (US); Jing Liu, San Diego, CA (US); Neelakandha S. Mani, San Diego, CA (US); Kelly J. McClure, San Diego, CA (US); Steven P. Meduna, San Diego, CA (US); Mark D. Rosen, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/765,552

(22) PCT Filed: Jan. 31, 2014

(86) PCT No.: PCT/US2014/014088
§ 371 (c)(1),
(2) Date: Aug. 3, 2015

(87) PCT Pub. No.: WO2014/121040
PCT Pub. Date: Aug. 7, 2014

(65) Prior Publication Data
US 2015/0368270 A1    Dec. 24, 2015

Related U.S. Application Data

(60) Provisional application No. 61/760,615, filed on Feb. 4, 2013, provisional application No. 61/798,951, filed on Mar. 15, 2013.

(51) Int. Cl.
| | | |
|---|---|---|
| *A61K 31/497* | (2006.01) | |
| *A61K 31/505* | (2006.01) | |
| *A61K 31/506* | (2006.01) | |
| *A61K 31/4965* | (2006.01) | |
| *C07D 239/42* | (2006.01) | |
| *C07D 241/20* | (2006.01) | |

(Continued)

(52) U.S. Cl.
CPC ......... *C07D 513/04* (2013.01); *C07D 213/73* (2013.01); *C07D 237/20* (2013.01); *C07D 239/42* (2013.01); *C07D 239/47* (2013.01); *C07D 241/20* (2013.01); *C07D 241/26* (2013.01); *C07D 401/12* (2013.01); *C07D 403/12* (2013.01); *C07D 403/14* (2013.01); *C07D 405/12* (2013.01); *C07D 409/14* (2013.01); *C07D 413/12* (2013.01); *C07D 417/12* (2013.01); *C07D 471/04* (2013.01); *C07D 487/04* (2013.01); *C07D 491/10* (2013.01); *C07D 491/113* (2013.01); *C07D 495/04* (2013.01); *C07D 498/04* (2013.01); *C07F 7/1804* (2013.01); *C07F 7/188* (2013.01); *C07F 7/1892* (2013.01)

(58) Field of Classification Search
CPC ... C07D 239/42; C07D 241/20; C07D 403/12
See application file for complete search history.

(56) References Cited

U.S. PATENT DOCUMENTS

| | | |
|---|---|---|
| 5,780,473 A | 7/1998 | Murugesan et al. |
| 6,040,327 A | 3/2000 | De Nanteuil et al. |

(Continued)

FOREIGN PATENT DOCUMENTS

| | | |
|---|---|---|
| CA | 2137443 A1 | 6/1995 |
| CN | 105-2306 A | 6/1991 |

(Continued)

OTHER PUBLICATIONS

Abramovitz et al, "5-lipoxygenase-activating protein stimulates the utilization of arachidonic acid by 5-lipoxygenase," *Eur. J. Biochem.*, 1993, 215:105-111.

(Continued)

*Primary Examiner* — Brian McDowell

(57) ABSTRACT

The present invention relates to compounds of Formula (I), or a form thereof, wherein ring A, $R_1$, L and $R_2$ are as defined herein, useful as FLAP modulators. The invention also relates to pharmaceutical compositions comprising compounds of Formula (I). Methods of making and using the compounds of Formula (I) are also within the scope of the invention.

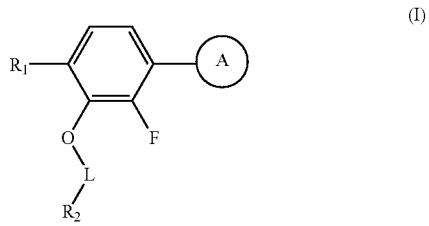

(I)

18 Claims, No Drawings

(51) Int. Cl.

| | | |
|---|---|---|
| C07D 403/12 | (2006.01) | |
| C07D 513/04 | (2006.01) | |
| C07D 213/73 | (2006.01) | |
| C07D 241/26 | (2006.01) | |
| C07D 401/12 | (2006.01) | |
| C07D 403/14 | (2006.01) | |
| C07D 405/12 | (2006.01) | |
| C07D 409/14 | (2006.01) | |
| C07D 413/12 | (2006.01) | |
| C07D 487/04 | (2006.01) | |
| C07D 491/113 | (2006.01) | |
| C07D 498/04 | (2006.01) | |
| C07F 7/18 | (2006.01) | |
| C07D 237/20 | (2006.01) | |
| C07D 417/12 | (2006.01) | |
| C07D 471/04 | (2006.01) | |
| C07D 491/10 | (2006.01) | |
| C07D 239/47 | (2006.01) | |
| C07D 495/04 | (2006.01) | |

(56) References Cited

U.S. PATENT DOCUMENTS

| | | |
|---|---|---|
| 7,314,849 B2 | 1/2008 | Balko et al. |
| 8,188,092 B2 | 5/2012 | Birch et al. |
| 8,586,754 B2 | 11/2013 | Bruncko et al. |
| 9,073,876 B2 | 7/2015 | Eccles et al. |
| 9,079,866 B2 | 7/2015 | Bacani et al. |
| 2005/0009894 A1 | 1/2005 | Babin et al. |
| 2007/0232620 A1 | 10/2007 | Dorsch et al. |
| 2007/0299074 A1 | 12/2007 | Netz et al. |
| 2009/0253735 A1 | 10/2009 | Almario-Garcia et al. |
| 2013/0267493 A1 | 10/2013 | Bhattacharya et al. |

FOREIGN PATENT DOCUMENTS

| | | |
|---|---|---|
| CN | 1013-56169 A | 1/2009 |
| EP | 0372934 A | 6/1990 |
| EP | 0562599 A1 | 9/1993 |
| EP | 0657459 A1 | 6/1995 |
| EP | 0894795 A1 | 2/1999 |
| EP | 1308441 A1 | 5/2003 |
| EP | 1354877 A1 | 10/2003 |
| EP | 1359139 A1 | 11/2003 |
| EP | 1389616 A1 | 2/2004 |
| EP | 247-1776 A1 | 7/2012 |
| EP | 2471776 A | 7/2012 |
| JP | 2009023986 * | 5/2009 |
| WO | WO00/47578 A1 | 8/2000 |
| WO | WO01/74793 A2 | 10/2001 |
| WO | WO02/11724 A2 | 2/2002 |
| WO | WO02/22602 A2 | 3/2002 |
| WO | WO03/007955 A2 | 1/2003 |
| WO | WO03/035644 A1 | 5/2003 |
| WO | WO03/093248 A1 | 11/2003 |
| WO | WO2004/009017 A2 | 1/2004 |
| WO | WO2005/067923 A1 | 7/2005 |
| WO | WO2005/082871 A2 | 9/2005 |
| WO | WO2005/103022 A1 | 11/2005 |
| WO | WO2005/105744 A1 | 11/2005 |
| WO | WO2005/123688 A2 | 12/2005 |
| WO | WO2006/020767 A2 | 2/2006 |
| WO | WO2006/038100 A1 | 4/2006 |
| WO | WO2006/063167 A1 | 6/2006 |
| WO | WO2006/074262 A1 | 7/2006 |
| WO | WO2006/132811 A2 | 12/2006 |
| WO | WO2007/034282 A2 | 3/2007 |
| WO | WO2007/082076 A | 7/2007 |
| WO | WO2007/082098 A | 7/2007 |
| WO | WO2007/126957 A2 | 11/2007 |
| WO | WO2008/018655 A1 | 2/2008 |
| WO | WO2008/034974 A1 | 3/2008 |
| WO | WO2008/104278 A1 | 9/2008 |
| WO | WO2008/150899 A1 | 12/2008 |
| WO | WO2008/152014 A2 | 12/2008 |
| WO | WO2009/100438 A2 | 8/2009 |
| WO | WO2009/121535 A2 | 10/2009 |
| WO | WO2009/129625 A1 | 10/2009 |
| WO | WO2010/012747 A1 | 2/2010 |
| WO | WO2010/019828 A1 | 2/2010 |
| WO | WO2010/115736 A2 | 10/2010 |
| WO | WO2011/047129 A1 | 4/2011 |
| WO | WO2011/053705 A1 | 5/2011 |
| WO | WO2011/072275 A2 | 6/2011 |
| WO | WO2011/106273 A1 | 9/2011 |
| WO | WO2012/006068 A2 | 1/2012 |
| WO | WO2012/064715 A1 | 5/2012 |
| WO | WO2012/166145 A1 | 8/2012 |
| WO | WO2012/119978 A1 | 9/2012 |
| WO | WO 2012/121939 A2 | 9/2012 |

OTHER PUBLICATIONS

Avis et al, Editors, *Pharmaceutical Dosage Forms: Parenteral Medications*, 2nd Edition, vol. 1, published by Marcel Dekker, Inc., 1992, Table of Contents and Index.

Avis et al, Editors, *Pharmaceutical Dosage Forms: Parenteral Medications*, vol. 2, published by Marcel Dekker, Inc., 1993, Table of Contents and Index.

Baldwin et al, "Kinase array design, back to front: Biaryl amides", *Bioorganic & Medicinal Chemistry Letters* (2008) 18(19):5285-5289.

Berge et al, "Pharmaceutical Salts," *Journal of Pharmaceutical Sciences*, 1997, 66(1):1-19.

Bundgaard, Editor, *Design of Prodrugs*, published by Elsevier, 1985, Table of Contents.

Chi et al, "Interaction between ALOX5AP and CYP3A5 gene variants significantly increases the risk for cerebral infarctions in Chinese," *NeuroReport*, 2014, 25(7):452-457.

Chu et al, "Involvement of 5-lipoxygenase activating protein in the amyloidotic phenotype of an Alzheimer's disease mouse model," *Journal of Neuroinflammation*, 2012, 9:127.

Chwieśko-Minarowska et al, "The role of leukotrienes in the pathogenesis of systemic sclerosis," *Folia Histochemica et Cytobiologica*, 2012, 50(2), 180-85.

Gould, "Salt selection for basic drugs," *International Journal of Pharmaceutics*, 1986, 33:201-217.

Greene et al, Editors, *Protective Groups in Organic Synthesis*, 3rd Edition, published by John Wiley & Sons, 1999, Index.

Griffiths et al, "Collagen-induced Arthritis is Reduced in 5-Lipoxygenase-activating Protein-deficient Mice," *J. Exp. Med.*, 1997, 185(6):1123-29.

Haeggström et al, "Lipoxygenase and Leukotriene Pathways: Biochemistry, Biology, and Roles in Disease," *Chemical Reviews*, 2011, 111(10):5866-98.

Helgadottir et al, "The gene encoding 5-lipoxygenase activating protein confers risk of myocardial infarction, atherosclerosis and stroke," *Nature Genetics*, Mar. 2004, 36(3):233-39.

Holloway et al, "The role of LTA4H and ALOX5AP polymorphism in asthma and allergy susceptibility," *Allergy*, 2008, 63(8):1046-53.

Ji et al, "Genetic Variants in the Promoter Region of the ALOX5AP Gene and Susceptibility of Ischemic Stroke," *Cerebrovascular Diseases*, 2011, 32(3), 261-68.

Krawiec et al, "Leukotriene inhibitors and non-steroidal therapies in the treatment of asthma," *Expert Opinion on Pharmacotherapy*, 2001, 2(1), 47-65.

Lieberman et al, Editors, *Pharmaceutical Dosage Forms: Tablets*, Second Edition, vol. 1, published by Marcel Dekker, Inc., 1989, Table of Contents and Index.

Lieberman et al, Editors, *Pharmaceutical Dosage Forms: Tablets*, Second Edition, vol. 2, published by Marcel Dekker, Inc., 1990, Table of Contents and Index.

Lieberman et al, Editors, *Pharmaceutical Dosage Forms: Tablets*, Second Edition, vol. 3, published by Marcel Dekker, Inc., 1990, Table of Contents and Index.

(56) References Cited

OTHER PUBLICATIONS

Lieberman et al, Editors, *Pharmaceutical Dosage Forms: Disperse Systems*, vol. 1, published by Marcel Dekker, Inc., 1996, Table of Contents and Index.
Lieberman et al, Editors, *Pharmaceutical Dosage Forms: Disperse Systems*, vol. 2, published by Marcel Dekker, Inc., 1996, Table of Contents and Index.
Loell et al, "Activated LTB4 pathway in muscle tissue of patients with polymyositis or dermatomyositis," *Ann. Rheum. Dis.*, 2013, 72(2):293-99.
McComie, Editor, *Protective Groups in Organic Chemistry*, published Plenum Press, 1973, Index and Table of Contents.
McMillan et al, "Designing therapeutically Effective 5-lipoxygenase Inhibitors", *Trends in Pharmacological Sciences*, 1992, 13:323-330.
Nair et al, "Expression Analysis of Leukotriene-Inflammatory Gene Interaction Network in Patients with Coronary Artery Disease," *Journal of Atherosclerosis and Thrombosis*, 2013, 20:000-000.
Queener, "Inhibition of Pneumocystis Dihydrofolate Reductase by Analogs of Pyrimethamine, Methotrexate and Trimetrexate", *Journal of Protozoology*, 1991, 38(6):1545-1575.
Reicin et al, "Montelukast, a Leukotriene Receptor Antagonist, in Combination with Loratadine, a Histamine Receptor Antagonist, in the Treatment of Chronic Asthma," *Arch. Intern. Med.*, 2000, 160(16):2418-88.
Rosnowska et al, "Leukotrienes C4 and B4 in cerebrospinal fluid of patients with multiple sclerosis," *Polski Merkuriusz Lekarski*, 1997, 2:254-55. (English Abstract).
Rowe et al, Editors, *The Handbook of Pharmaceutical Excipients*, 5th Edition, published by the American Pharmaceutical Association and the Pharmaceutical Society of Great Britain, 2006, Table of Contents and Index.
Samuelsson, "Leukotrienes: Mediators of Immediate Hypersensitivity Reactions and Inflammation," *Science*, 1983, 220:568-75).
Sanada et al, "The effectiveness of montelukast for the treatment of anti-histamine-resistant chronic urticaria," *Arch. Dermatol. Res.*, 2005, 297(3):134-138.
Strid et al, "Distinct parts of leukotriene C(4) synthase interact with 5-lipoxygenase and 5-lipoxygenase activating protein," *Biochemical and Biophysical Research Communications*, 2009, 381(4):518-22.
Tulah et al, "The role of ALOX5AP, LTA4H and LTB4R polymorphisms in determining baseline lung function and COPD susceptibility in UK smokers," *BMC Medical Genetics*, 2011, 29(12), 173.
Wang et al, "Eicosanoids and cancer," *Nature Reviews—Cancer*, 2010, 10(3), 181-93.
Yu et al, "Disruption of the 5-lipoxygenase pathway attenuates atherogenesis consequent to COX-2 deletion in mice," *Proc. Natl. Acad. Sci. (PNAS)*, 2012, 109(17):6727-32.
International Search Report Dated May 23, 2014, for Corresponding International Application PCT/US2014/014088.
Yu et al, "Myeloid Cell 5-Lipoxygenase Activating Protein Modulates the Response to Vascular Injury," *Circulation Research*, 2013, 112:432-440.
International search report dated Jul. 8, 2014, for corresponding international application PCT/US2014/014111.
International search report dated Aug. 19, 2014, for corresponding international application PCT/US2014/014111.
Abet at al "A New Class of Pyrazolopyridine Nucleus With Fluorescent Properties Obtained Through Either a Radical or a PD Arylation Pathway From N-Azinylpiridinium N-Aminides" The Journal of Organic Chemistry 2008 vol. 73(22) pp. 8800-8807.
Registry Database Chemical Abstracts Service, Columbus Ohio, Registry Nos. 1309199-07-2 (Entered STN: Jun. 13, 2011 ),1269234-42-5 (Entered STN: Mar. 21, 2011 ), RN 1269159-98-9 (Entered STN: Mar. 21, 2011 ), 1125448-01-2 (Entered STN:Mar. 23, 2009), and RN 1125444-06-5.
RN 1269234-42-5, [Database Registry Chemical Abstracts Service, Columbus, Ohio, Accession No. RN 1269234-42-5, Entered STN:Mar. 21, 2011];p. 1 .
Extended European Search Report for European Application No. EP16164934 8 dated Aug. 8, 2016.
Search Report for Chinese Application No. CN201480019599.1 dated Jul. 15, 2016.
United States Non-Final Office Action for U.S. Appl. No. 14/765,556 Dated Jul. 18, 2016.

* cited by examiner

FLAP MODULATORS

CROSS REFERENCE TO RELATED APPLICATIONS

This application is a national phase of International Application No. PCT/US2014/014088 filed on Jan. 31, 2014, which claims the benefit of U.S. Provisional Application No. 61/760,615 filed on Feb. 4, 2013 and U.S. Provisional Application No. 61/798,951 filed on Mar. 15, 2013, each of which are incorporated herein by reference in its entirety.

FIELD OF THE INVENTION

The present invention relates to substituted compounds useful as 5-lipoxygenase-activating protein (FLAP) modulators, pharmaceutical compositions of such compounds, methods of preparation and use thereof. More particularly, FLAP modulators are useful for preventing, treating or ameliorating FLAP-mediated diseases and/or disorders, including those inflammation diseases and/or disorders associated with dermatological and respiratory disorders, allergic disorders, autoimmunity, cancer, cardiovascular and metabolic disorders.

BACKGROUND OF THE INVENTION

FLAP is a key initiator of the leukotriene synthesis pathway that binds and then transfers arachidonic acid to 5-lipoxygenase (M. Abramovitz et al., "5-lipoxygenase-activating protein stimulates the utilization of arachidonic acid by 5-lipoxygenase," *Eur. J. Biochem.*, 1993, 215, 105-11). FLAP has been demonstrated to interact with $LTC_4$ synthase, and could putatively modulate the production of $LTC_4$ (T. Strid et al., "Distinct parts of leukotriene C(4) synthase interact with 5-lipoxygenase and 5-lipoxygenase activating protein," *Biochem. Biophys. Res. Comm.*, 2009, 381(4), 518-22). Modulation (including without limitation inhibition) or genetic deletion of FLAP blocks leukotriene production, specifically $LTB_4$, the cysteinyl leukotrienes ($LTC_4$, $LTD_4$ and $LTE_4$) as well as 5-oxo-ETE (J. Z. Haeggström et al., "Lipoxygenase and leukotriene pathways: biochemistry, biology, and roles in disease," *Chem Rev.*, 2011, 111(10), 5866-98).

Leukotrienes are immune-modulating lipids formed from arachidonic acid (reviewed in B. Samuelsson, "Leukotrienes: mediators of immediate hypersensitivity reactions and inflammation," *Science*, 1983, 220, 568-75). They are synthesized primarily by eosinophils, neutrophils, mast cells, basophils, dendritic cells, macrophages and monocytes. Leukotrienes mediate multiple biological effects including, by way of example only, smooth muscle contraction, leukocyte recruitment and activation, cytokine secretion, fibrosis, mucous secretion, and vascular function (J. Z. Haeggström, at 5866-98).

FLAP-deficient mice are healthy and reproduce normally. They do not produce leukotrienes and have decreased susceptibility in mouse models of arthritis (R. J. Griffiths et al., "Collagen-induced arthritis is reduced in 5-lipoxygenase-activating protein-deficient mice," *J. Exp. Med.*, 1997, 185, 1123-29). In humans, FLAP itself has been linked by genetic studies to respiratory disorders and cardiovascular disease, including myocardial infarction, atherosclerosis, cerebral infarctions, coronary artery disease and stroke (A. Helgadottir et al., "The gene encoding 5-lipoxygenase activating protein confers risk of myocardial infarction, atherosclerosis and stroke," *Nat. Genet.*, 2004, 36, 233-39; A. S. Tulah et al., "The role of ALOX5AP, LTA4H and LTB4R polymorphisms in determining baseline lung function and COPD susceptibility in UK smokers," *BMC Med. Genet.*, 2011, 29(12), 173; R. Ji et al., "Genetic variants in the promoter region of the ALOX5AP gene and susceptibility of ischemic stroke," *Cerebrovasc. Dis.*, 2011, 32(3), 261-68; J. W. Holloway et al., "The role of LTA4H and ALOX5AP polymorphism in asthma and allergy susceptibility," *Allergy*, 2008, 63(8), 1046-53; J. Nair et al., "Expression analysis of leukotriene-inflammatory gene interaction network in patients with coronary artery disease," *J Atheroscler. Thromb.*, 2013; L. F. Chi et al., "Interaction between ALOX5AP and CYP3A5 gene variants significantly increases the risk for cerebral infarctions in Chinese," *Neuroreport.*, 2013). In addition, studies using animal models support a causative role for leukotrienes in aortic aneurisms, atherosclerosis, pulmonary arterial hypertension, myocardial infarction, atherosclerosis, and stroke (reviewed in J. Z. Haeggström, at 5866-98).

Leukotrienes also play a role in autoimmune disorders such as rheumatoid arthritis, inflammatory bowel disease, nephritis, spondyloarthritis, polymyositis, dermatomyositis, gouty effusions, systemic lupus erythematosus, systemic sclerosis, Alzheimer's disease and multiple sclerosis (S. Chwieśko-Minarowska et al., "The role of leukotrienes in the pathogenesis of systemic sclerosis," *Folia Histochem. Cytobiol.*, 2012, 50(2), 180-85; M. Rosnowska et al., "Leukotrienes C4 and B4 in cerebrospinal fluid of patients with multiple sclerosis," *Pol. Merkuriusz Lek.*, 1997, 2, 254-55; and reviewed in J. Z. Haeggström, at 5866-98; I. Loell et al., "Activated LTB4 pathway in muscle tissue of patients with polymyositis or dermatomyositis," *Ann. Rheum. Dis.*, 2013, 72(2), 293-99; J. Chu et al., "Involvement of 5-lipoxygenase activating protein in the amyloidotic phenotype of an Alzheimer's disease mouse model," *J. Neuroinflammation*, 2012, 9, 127). Leukotrienes have also been implicated in several aspects of carcinogenesis including tumor cell proliferation, differentiation, and apoptosis, tumor-associated angiogenesis, as well as the migration and invasion of carcinoma cells (D. Wang and R. N. Dubois, "Eicosanoids and cancer," *Nat. Rev. Cancer*, 2010, 10(3), 181-93).

Leukotrienes play a key role in allergic disorders such as allergic rhinitis, allergic dermatitis and asthma, as well as respiratory disorders such as exacerbations, non-allergic asthma, aspirin exacerbated respiratory disease, fibrotic lung diseases, acute respiratory distress syndrome and chronic obstructive pulmonary disease (reviewed in J. Z. Haeggström at 5866-98). Approved antagonists of the $LTC_4$ receptor and leukotriene synthesis modulators such as zileuton have shown clinical efficacy in a variety of respiratory disorders (reviewed in M. E. Krawiec and S. E. Wenzel, "Leukotriene modulators and non-steroidal therapies in the treatment of asthma," *Expert. Opin. Pharmacotherapy*, 2001, 2(1), 47-65).

All the above evidence supports a key role of leukotrienes in a variety of human diseases and/or disorders, and FLAP modulation would be effective for the prevention, treatment, or amelioration of these immune-mediated inflammatory diseases and/or disorders. Furthermore, there still remains a need for FLAP modulator compounds that have pharmacokinetic and pharmacodynamic properties suitable for use as human pharmaceuticals.

SUMMARY OF THE INVENTION

In its many embodiments, the present invention provides novel compounds useful as, for example, FLAP modulators (including without limitation novel compounds that inhibit FLAP), methods of preparing such compounds, pharmaceutical compositions comprising one or more such compounds, methods of preparing pharmaceutical compositions comprising one or more such compounds, and methods of prophylaxis, treatment, amelioration, including without limitation inhibition, of one or more diseases and/or disorders associated with FLAP using such compounds or pharmaceutical compositions.

One aspect of the present invention is directed to compounds, methods, and compositions for the treatment or prophylaxis or amelioration of a variety of diseases and/or disorders that are mediated or sustained through the activity of leukotrienes, including pulmonary, allergic, fibrotic, neurological, inflammatory, autoimmune and cardiovascular diseases and cancer or associated symptoms or complications thereof. More specifically, this invention is directed to a method of treating exacerbations, non-allergic asthma, fibrotic lung diseases, acute respiratory distress syndrome and chronic obstructive pulmonary disease, or associated symptoms or complications thereof, in a subject afflicted with such a disease and/or disorder, wherein the method comprises administering a FLAP modulator.

Another aspect of the present invention is directed to compounds, methods, and compositions for the treatment or prophylaxis or amelioration of cardiac and cardiovascular diseases and/or disorders, or associated symptoms or complications thereof, that include but are not limited to myocardial infarction, atherosclerosis, stroke and atherosclerosis aortic aneurisms, or associated symptoms or complications thereof, in a subject afflicted with such a disease and/or disorder, wherein the method comprises administering a FLAP modulator.

Yet another aspect of the present invention is directed to compounds, methods, and compositions for the prophylaxis, treatment, or amelioration of autoimmune diseases and/or disorders, or associated symptoms or complications thereof, that include but are not limited to rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis or allergic disorders that include but are not limited to allergic rhinitis, allergic dermatitis and asthma, or associated symptoms or complications thereof, in a subject afflicted with such a disease and/or disorder, wherein the method comprises administering a FLAP modulator.

Finally, one aspect of the present invention is directed to compounds, methods, and compositions for the prophylaxis, treatment, or amelioration of carcinogenesis including but not limited to tumor cell proliferation, differentiation, apoptosis, tumor-associated angiogenesis, as well as the migration and invasion of carcinoma cells, or associated symptoms or complications thereof, in a subject afflicted with such a disease and/or disorder, wherein the method comprises administering a FLAP modulator.

Another aspect of the present invention features a compound of Formula (I)

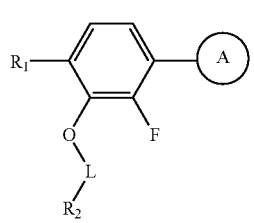

(I)

wherein

L is a bond, —CH—, —CH$_2$CH$_2$—, —CH$_2$CH$_2$CH$_2$—, —CH$_2$CH$_2$NH—, —CH$_2$C(=O)NH—, —CH$_2$C(OH)(H)CH$_2$—, or —CH$_2$C(OH)(H)CH$_2$NH—;

R$_1$ is halo, C$_{1-5}$alkyl, C$_{3-6}$cycloalkyl, or cyclohexylmethyl;

R$_2$ is H, C$_{1-4}$alkyl, hydroxyl, amino, cyano, —CH$_2$C(=O)O-(tert-butyl), —CH$_2$C(=O)O-(ethyl), —CH$_2$C(=O)OH, —NHS(=O)$_2$CH$_3$, tert-butyl(dimethyl)silyl-oxy, —NHCH$_3$, —N(CH$_3$)$_2$, —NH-(Isopropyl), optionally substituted phenyl, optionally substituted 5-membered or 6-membered heteroaryl, C$_{3-6}$cycloalkyl, or optionally substituted heterocyclyl;

wherein the 5-membered or 6-membered heteroaryl, the heterocyclyl, or the phenyl is optionally and independently substituted with 1-4 substituents selected from the group consisting of:

C$_{1-4}$alkyl, —CH$_2$-methoxy, —C(=O)OH, —CH$_2$C(=O)OH, —C(=O)—O—CH$_2$CH$_3$, —C(=O)—O—CH$_3$, —C(=O)—O-(tert-butyl), —NH$_2$, —NHCH$_3$, —N(CH$_3$)$_2$, —NH-(isobutyl), —NH(CH$_2$)$_2$NHC(=O)—O-tert-butyl, —NH(CH$_2$)$_2$NH$_2$, —NH(CH$_2$)$_2$N(CH$_3$)$_2$, —C(=O)NH$_2$, —C(=O)CH$_3$, oxo, halo, hydroxyl, methoxy, trifluoromethyl, trifluoromethoxy, methoxymethyl, —S(=O)$_2$CH$_3$, —S(=O)$_2$NH$_2$, —S(=O)$_2$NH(CH$_3$), —S(=O)$_2$N(CH$_3$)$_2$, —S—CH$_3$, cyano, 1H-tetrazol-5-yl, thiophen-2-yl, cyclopropyl, azetidin-1-yl, phenyl, 4'-(trifluoromethyl)phenyl, benzyl, 1,5-dioxa-9-azaspiro[5.5]undecan-9-yl, 5-pyrimidine-2-amine, and pentafluoro-lambda~6~-sulfanyl;

ring A is selected from the group consisting of:

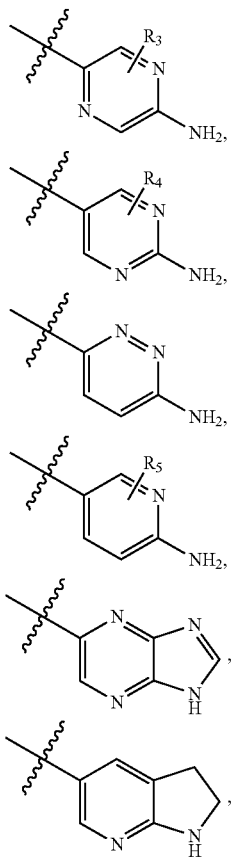

-continued

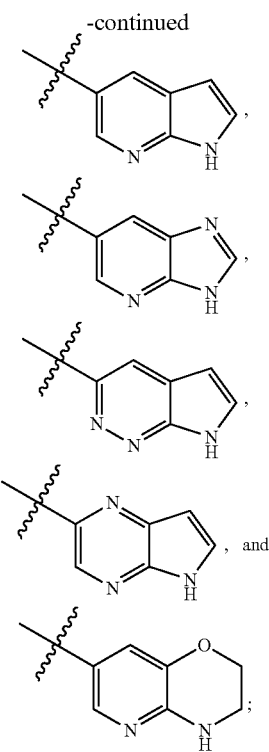

R$_3$ is H, cyano, methyl, methoxy, halo, or —NH$_2$;
R$_4$ is H, or methyl; and
R$_5$ is H, cyano, halo, CF$_3$, or —NH$_2$;
or an optical isomer, hydrate, metabolite, enantiomer, diastereomer, cis-trans isomer, racemate, prodrug or pharmaceutically acceptable salt thereof.

Another aspect of the present invention features a pharmaceutical composition comprising at least one compound of Formula (I) and at least one pharmaceutically acceptable carrier. The invention is also directed towards providing a process for formulating a pharmaceutical composition, comprising formulating a pharmaceutical composition of at least one compound of Formula (I) and at least one pharmaceutically acceptable carrier. The present invention further relates to a process for making a pharmaceutical composition comprising mixing any of the compounds according to Formula (I) and a pharmaceutically acceptable carrier.

The present invention also features a method of treating a subject suffering from or diagnosed with a disease and/or disorder mediated by FLAP activity, comprising administering to the subject a therapeutically effective amount of at least one compound of Formula (I). Such a disease and/or disorder can include, but is not limited to respiratory disorders, cardiac and cardiovascular diseases, autoimmune disorders, carcinogenesis or associated symptoms or complications. More specifically, this invention is directed to a method of treating exacerbations, non-allergic asthma, fibrotic lung diseases, acute respiratory distress syndrome, chronic obstructive pulmonary disease myocardial infarction, atherosclerosis and stroke aortic aneurisms, atherosclerosis, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, tumor cell proliferation, differentiation, and apoptosis, tumor-associated angiogenesis, as well as the migration and invasion of carcinoma cells, or associated symptoms or complications thereof, in a subject afflicted with such a disease and/or disorder, or associated symptoms or complications thereof, wherein the method comprises administering a FLAP modulator to a subject in need thereof, a therapeutically effective amount of at least one compound of Formula (I), preferably in a pharmaceutical composition comprising at least one compound of Formula (I).

Additional embodiments and advantages of the invention will become apparent from the detailed discussion, schemes, examples, and claims below.

DETAILED DESCRIPTION OF THE INVENTION

This invention relates to novel FLAP modulators and compositions thereof for the prophylaxis, treatment, or amelioration of numerous diseases and/or disorders, including but not limited to respiratory diseases and/or disorders, cardiac and cardiovascular diseases and/or disorders, autoimmune diseases and/or disorders, carcinogenesis, and associated symptoms or complications thereof.

One aspect of the present invention features a compound of Formula (I)

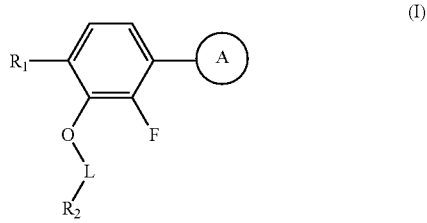

wherein
L is a bond, —CH$_2$—, —CH$_2$CH$_2$—, —CH$_2$C(OH)(H)CH$_2$, —CH$_2$CH$_2$CH$_2$—, —CH$_2$CH$_2$NH—, —CH$_2$C(=O)NH—, or —CH$_2$C(OH)(H)CH$_2$NH—;
R$_1$ is halo, C$_{1-5}$alkyl, C$_{3-6}$cycloalkyl, or cyclohexylmethyl;
R$_2$ is H, C$_{1-4}$alkyl, hydroxyl, amino, cyano, —CH$_2$C(=O)O-(tert-butyl), —CH$_2$C(=O)O-(ethyl), —CH$_2$C(=O)OH, —NHS(=O)$_2$CH$_3$, tert-butyl(dimethyl)silyl-oxy, —NHCH$_3$, —N(CH$_3$)$_2$, —NH-(Isopropyl), optionally substituted phenyl, optionally substituted 5-membered or 6-membered heteroaryl, C$_{3-6}$cycloalkyl, or optionally substituted heterocyclyl;
wherein the 5-membered or 6-membered heteroaryl, the heterocyclyl, or the phenyl is optionally and independently substituted with 1-4 substituents selected from the group consisting of:
C$_{1-4}$alkyl, —CH$_2$-methoxy, —C(=O)OH, —CH$_2$C(=O)OH, —C(=O)—O—CH$_2$CH$_3$, —C(=O)—O—CH$_3$, —C(=O)—O-(tert-butyl), —NH$_2$, —NHCH$_3$, —N(CH$_3$)$_2$, —NH-(isobutyl), —NH(CH$_2$)$_2$NHC(=O)—O-tert-butyl, —NH(CH$_2$)$_2$NH$_2$, —NH(CH$_2$)$_2$N(CH$_3$)$_2$, —C(=O)NH$_2$, —C(=O)CH$_3$, oxo, halo, hydroxyl, methoxy, trifluoromethyl, trifluoromethoxy, methoxymethyl, —S(=O)$_2$CH$_3$, —S(=O)$_2$NH$_2$, —S(=O)$_2$NH(CH$_3$), —S(=O)$_2$N(CH$_3$)$_2$, —S—CH$_3$, cyano, 1H-tetrazol-5-yl, thiophen-2-yl, cyclopropyl, azetidin-1-yl, phenyl, 4'-(trifluoromethyl)phenyl, benzyl, 1,5-dioxa-9-azaspiro[5.5]undecan-9-yl, 5-pyrimidine-2-amine, and pentafluoro-lambda~6~-sulfanyl;

ring A is selected from the group consisting of:

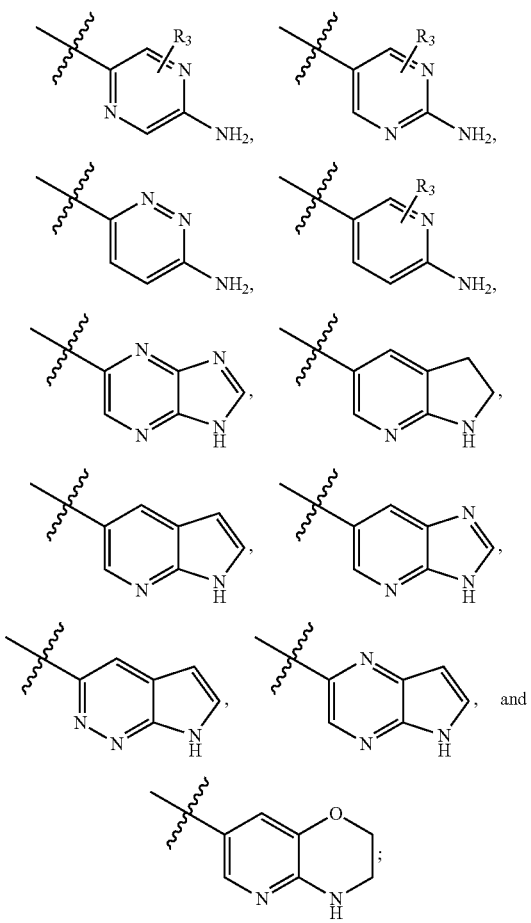

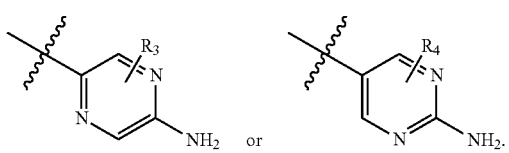

R₃ is H, cyano, methyl, methoxy, halo, or —NH₂;
R₄ is H, or methyl; and
R₅ is H, cyano, halo, CF₃, or —NH₂.

Some embodiments of the present invention are given by compounds of Formula (I), wherein R₁ is tert-butyl, cyclopropyl, cyclobutyl, or cyclopentyl, R₃ is H or cyano, R₄ is H, and R₅ is H.

Other embodiments are given by compounds of Formula (I), wherein R₁ is tert-butyl, cyclobutyl, or cyclopentyl.

Yet, other embodiments are given by compounds of Formula (I), wherein R₁ is tert-butyl or cyclobutyl, R₃ is H or cyano, R₄ is H, and R₅ is H.

Some embodiments are given by compounds of Formula (I), wherein ring A is

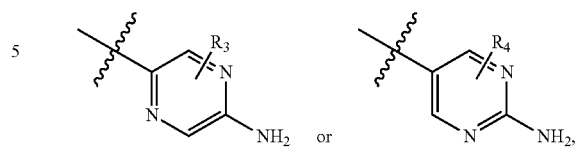

In some of these embodiments, wherein ring A is NH₂ or


R₃ is cyano, and R₄ is cyano.
In some of these embodiments, wherein ring A is

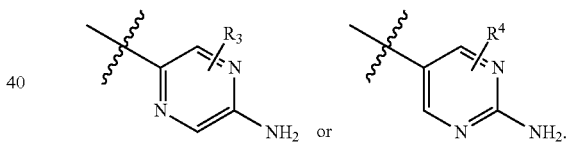

R₃ is H, and R₄ is H.
Some embodiments are given by compounds of Formula (I), wherein R₁ is tert-butyl.
Some embodiments are given by compounds of Formula (I), wherein R₁ is cyclobutyl.
In some of these embodiments, wherein R₁ is cyclobutyl, R₂ is —CH₂C(=O)O-(tert-butyl), —CH₂C(=O)O-(ethyl), —CH₂C(=O)OH, or —NHS(=O)₂CH₃.
In some of these embodiments, wherein R₁ is cyclobutyl, R₂ is optionally substituted phenyl, or optionally substituted 5-membered or 6-membered heteroaryl.
In some of these embodiments, wherein R₁ is cyclobutyl, L is a bond or —CH₂—.
In some of these embodiments, wherein R₁ is cyclobutyl, ring A is

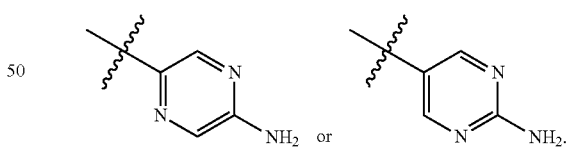

In some of these embodiments, wherein R₁ is cyclobutyl, ring A is

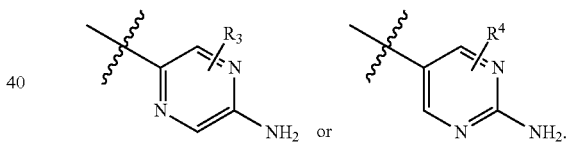

In some of these embodiments, wherein R₁ is cyclobutyl, ring A is

Some embodiments are given by compounds of Formula (I), wherein L is a bond or —CH₂—.
In some of these embodiments, wherein L is a bond or —CH₂—, R₁ is cyclobutyl, and ring A is

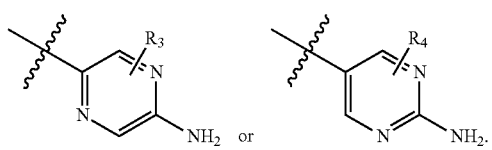

In another embodiment, the present invention includes a compound of Formula (I) wherein:

L is a bond or —CH$_2$—;

R$_1$ is tert-butyl or cyclobutyl;

R$_2$ is optionally substituted phenyl or an optionally substituted 6-membered heteroaryl;

wherein the substitution of the phenyl or the 6-membered heteroaryl is selected from a group consisting of:

hydroxyl, fluoro, methoxy, cyano, amino, —C(=O)—NH$_2$, and pentafluoro-lambda~6~-sulfanyl;

ring A is

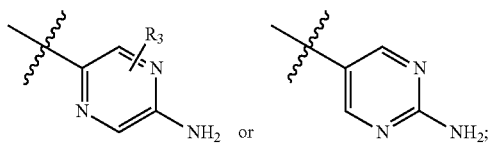

R$_3$ is H or cyano.

In yet another embodiment, the present invention includes a compound of Formula (I) wherein:

L is a bond or —CH$_2$—;

R$_1$ is tert-butyl or cyclobutyl;

R$_2$ is optionally substituted phenyl, optionally substituted pyridine or optionally substituted pyrimidine;

wherein the substitution of the phenyl, the pyridine or the pyrimidine is selected from a group consisting of:

hydroxyl, fluoro, methoxy, cyano, amino, —C(=O)—NH$_2$, and pentafluoro-lambda~6~-sulfanyl; and ring A is

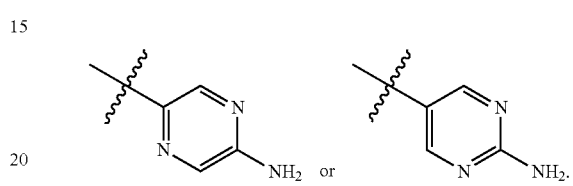

The embodiments of the present invention also include the optical isomers, hydrates, metabolites, enantiomers, diastereomers, cis-trans isomers, racemates, prodrugs or pharmaceutically acceptable salts thereof.

It is an embodiment of the present invention to provide a compound selected from the compounds listed in Table 1.

TABLE 1

5-(4-Cyclobutyl-2-fluoro-3-methoxyphenyl)pyrazin-2-amine,
3-(5-Aminopyrazin-2-yl)-6-cyclobutyl-2-fluorophenol,
3-(5-Aminopyrazin-2-yl)-6-cyclobutyl-2-fluorophenol,
5-(4-Cyclobutyl-2-fluoro-3-{[4-(trifluoromethyl)benzyl]oxy}phenyl)pyrazin-2-amine,
5-(4-Cyclobutyl-2-fluoro-3-{[3-(trifluoromethyl)benzyl]oxy}phenyl)pyrazin-2-amine,
5-(4-Cyclobutyl-2-fluoro-3-{[2-(trifluoromethyl)benzyl]oxy}phenyl)pyrazin-2-amine,
3-{[3-(5-Aminopyrazin-2-yl)-6-cyclobutyl-2-fluorophenoxy]methyl}benzoic acid,
4-{[3-(5-Aminopyrazin-2-yl)-6-cyclobutyl-2-fluorophenoxy]methyl}benzoic acid,
5-(4-Cyclobutyl-2-fluoro-3-{[3-(methylsulfonyl)benzyl]oxy}phenyl)pyrazin-2-amine,
5-(4-Cyclobutyl-2-fluoro-3-{[4-(methylsulfonyl)benzyl]oxy}phenyl)pyrazin-2-amine,
5-(4-Cyclobutyl-2-fluoro-3-{[2-(trifluoromethoxy)benzyl]oxy}phenyl)pyrazin-2-amine,
5-(4-Cyclobutyl-2-fluoro-3-{[3-(trifluoromethoxy)benzyl]oxy}phenyl)pyrazin-2-amine,
5-(4-Cyclobutyl-2-fluoro-3-{[4-(trifluoromethoxy)benzyl]oxy}phenyl)pyrazin-2-amine,
5-(3-{[4-Chloro-2-(methylsulfonyl)benzyl]oxy}-4-cyclobutyl-2-fluorophenyl)pyrazin-2-amine
1-(4-{[3-(5-Aminopyrazin-2-yl)-6-cyclobutyl-2-fluorophenoxy]methyl}phenyl)-ethanone,
5-[4-Cyclobutyl-2-fluoro-3-(pyridin-3-ylmethoxy)phenyl]pyrazin-2-amine,
5-[4-Cyclobutyl-2-fluoro-3-(pyridin-4-ylmethoxy)phenyl]pyrazin-2-amine,
4-{[3-(5-Aminopyrazin-2-yl)-6-cyclobutyl-2-fluorophenoxy]methyl}benzonitrile,
3-{[3-(5-Aminopyrazin-2-yl)-6-cyclobutyl-2-fluorophenoxy]methyl}benzonitrile,
3-{[3-(5-Aminopyrazin-2-yl)-6-cyclobutyl-2-fluorophenoxy]methyl}benzamide,
2-{[3-(5-Aminopyrazin-2-yl)-6-cyclobutyl-2-fluorophenoxy]methyl}benzonitrile,
2-{[3-(5-Aminopyrazin-2-yl)-6-cyclobutyl-2-fluorophenoxy]methyl}benzamide,
5-(4-Cyclobutyl-2-fluoro-3-{[4-(1H-tetrazol-5-yl)benzyl]oxy}phenyl)pyrazin-2-amine,
5-(4-Cyclobutyl-2-fluoro-3-{[3-(1H-tetrazol-5-yl)benzyl]oxy}phenyl)pyrazin-2-amine, TABLE 1-continued 5-(4-Cyclobutyl-2-fluoro-3-{[2-(1H-tetrazol-5-yl)benzyl]oxy}phenyl)pyrazin-2-amine,
(4-{[3-(5-Aminopyrazin-2-yl)-6-cyclobutyl-2-fluorophenoxy]methyl}phenyl)acetic acid,
5-[4-Cyclobutyl-2-fluoro-3-(pyridin-2-ylmethoxy)phenyl]pyrazin-2-amine,
4-{[3-(5-Aminopyrazin-2-yl)-6-cyclobutyl-2-fluorophenoxy]methyl}-N,N-dimethyl-benzenesulfonamide,
4-{[3-(5-Aminopyrazin-2-yl)-6-cyclobutyl-2-fluorophenoxy-methyl}-benzenesulfonamide,
4-{[3-(5-Aminopyrazin-2-yl)-6-cyclobutyl-2-fluorophenoxy]methyl}-N-methylbenzenesulfonamide,
5-{4-Cyclobutyl-2-fluoro-3-[(4-fluorobenzyl)oxy]phenyl}pyrazin-2-amine,
5-{4-Cyclobutyl-2-fluoro-3-[(3-fluorobenzyl)oxy]phenyl}pyrazin-2-amine,
5-{4-Cyclobutyl-2-fluoro-3-[(2-fluorobenzyl)oxy]phenyl}pyrazin-2-amine,
5-{4-Cyclobutyl-3-[(2,6-difluorobenzyl)oxy]-2-fluorophenyl}pyrazin-2-amine,
5-{4-Cyclobutyl-3-[(2,3-difluorobenzyl)oxy]-2-fluorophenyl}pyrazin-2-amine,
5-{4-Cyclobutyl-3-[(3,4-difluorobenzyl)oxy]-2-fluorophenyl}pyrazin-2-amine,
5-{3-[(2-Chlorobenzyl)oxy]-4-cyclobutyl-2-fluorophenyl}pyrazin-2-amine,
5-{3-[(3-Chlorobenzyl)oxy]-4-cyclobutyl-2-fluorophenyl}pyrazin-2-amine,
5-{3-[(4-Chlorobenzyl)oxy]-4-cyclobutyl-2-fluorophenyl}pyrazin-2-amine,
5-{4-Cyclobutyl-3-[(2,6-dichlorobenzyl)oxy]-2-fluorophenyl}pyrazin-2-amine,
5-{4-Cyclobutyl-3-[(2,5-dichlorobenzyl)oxy]-2-fluorophenyl}pyrazin-2-amine,
5-{4-Cyclobutyl-3-[(2,3-dichlorobenzyl)oxy]-2-fluorophenyl}pyrazin-2-amine,
5-{4-Cyclobutyl-3-[(2,4-dichlorobenzyl)oxy]-2-fluorophenyl}pyrazin-2-amine,
5-{4-Cyclobutyl-3-[(3,4-dimethylbenzyl)oxy]-2-fluorophenyl}pyrazin-2-amine,
5-(3-{[2-Chloro-3-(trifluoromethyl)benzyl]oxy}-4-cyclobutyl-2-fluorophenyl)pyrazin-2-amine,
5-(3-{[5-Chloro-2-(trifluoromethyl)benzyl]oxy}-4-cyclobutyl-2-fluorophenyl)pyrazin-2-amine,
5-(4-Cyclobutyl-2-fluoro-3-{[4-fluoro-2-(trifluoromethyl)benzyl]oxy}phenyl)pyrazin-2-amine,
5-{3-[(2-Chloro-5-fluorobenzyl)oxy]-4-cyclobutyl-2-fluorophenyl}pyrazin-2-amine,
2-{[3-(5-Aminopyrazin-2-yl)-6-cyclobutyl-2-fluorophenoxy]methyl}benzoic acid,
5-{4-Cyclobutyl-2-fluoro-3-[(1-methyl-1H-pyrazol-3-yl)methoxy]phenyl}pyrazin-2-amine,
5-{4-Cyclobutyl-3-[(3-cyclopropyl-1,2,4-oxadiazol-5-yl)methoxy]-2-fluorophenyl}pyrazin-2-amine,
tert-Butyl [3-(5-aminopyrazin-2-yl)-6-cyclobutyl-2-fluorophenoxy]acetate,
[3-(5-Aminopyrazin-2-yl)-6-cyclobutyl-2-fluorophenoxy]acetic acid,
racemic 1-(3-(3-(5-Aminopyrazin-2-yl)-6-cyclobutyl-2-fluorophenoxy)-2-hydroxypropyl)pyridin-2(1H)-one,
racemic 3-(3-(3-(5-Aminopyrazin-2-yl)-6-cyclobutyl-2-fluorophenoxy)-2-hydroxypropyl)pyrimidin-4(3H)-one,
racemic 2-(3-(3-(5-Aminopyrazin-2-yl)-6-cyclobutyl-2-fluorophenoxy)-2-hydroxypropyl)pyridazin-3(2H)-one,
racemic 1-(3-(3-(5-Aminopyrazin-2-yl)-6-cyclobutyl-2-fluorophenoxy)-2-hydroxypropyl)pyrazin-2(1H)-one,
racemic 1-(3-(5-Aminopyrazin-2-yl)-6-cyclobutyl-2-fluorophenoxy)-3-(pyrimidin-5-ylamino)propan-2-ol,
racemic 1-(3-(5-Aminopyrazin-2-yl)-6-cyclobutyl-2-fluorophenoxy)-3-(pyrimidin-2-ylamino)propan-2-ol,
racemic 1-(3-(5-Aminopyrazin-2-yl)-6-cyclobutyl-2-fluorophenoxy)-3-(pyrazin-2-yamino)propan-2-ol,
racemic 1-(3-(5-Aminopyrazin-2-yl)-6-cyclobutyl-2-fluorophenoxy)-3-((5-aminopyrimidin-2-yl)amino)propan-2-ol,
racemic 1-(3-(5-Aminopyrazin-2-yl)-6-cyclobutyl-2-fluorophenoxy)-3-((6-aminopyrimidin-4-yl)amino)propan-2-ol,
racemic 1-(3-(5-Aminopyrazin-2-yl)-6-cyclobutyl-2-fluorophenoxy)-3-(1H-pyrazol-1-yl)propan-2-ol,
racemic 1-(3-(5-Aminopyrazin-2-yl)-6-cyclobutyl-2-fluorophenoxy)-3-(1H-imidazol-1-yl)propan-2-ol,
racemic 1-(3-(5-Aminopyrazin-2-yl)-6-cyclobutyl-2-fluorophenoxy)-3-(1H-1,2,4-triazol-1-yl)propan-2-ol,
racemic 1-(3-(5-Aminopyrazin-2-yl)-6-cyclobutyl-2-fluorophenoxy)-3-(1H-1,2,3-triazol-1-yl)propan-2-ol,
racemic 1-(3-(5-Aminopyrazin-2-yl)-6-cyclobutyl-2-fluorophenoxy)-3-(2H-1,2,3-triazol-2-yl)propan-2-ol,
racemic 5-Amino-1-(3-(3-(5-aminopyrazin-2-yl)-6-cyclobutyl-2-fluorophenoxy)-2-hydroxypropyl)-1H-pyrazole-4-carbonitrile, TABLE 1-continued racemic 1-(5-Amino-1H-1,2,3-triazol-1-yl)-3-(3-(5-aminopyrazin-2-yl)-6-cyclobutyl-2-fluorophenoxy)propan-2-ol,
racemic 1-((1H-Pyrazol-5-yl)amino)-3-(3-(5-aminopyrazin-2-yl)-6-cyclobutyl-2-fluorophenoxy)propan-2-ol,
5-(4-Cyclobutyl-2-fluoro-3-{[1-(methylsulfonyl)piperidin-4-yl]methoxy}-phenyl)-pyrazin-2-amine,
5-{4-Cyclobutyl-2-fluoro-3-[(4-methylpyrimidin-2-yl)-oxy]-phenyl}pyrazin-2-amine,
5-{4-Cyclobutyl-2-fluoro-3-[(5-methyl-1,2,4-oxadiazol-3-yl)methoxy]phenyl}pyrazin-2-amine,
5-[4-Cyclobutyl-3-(cyclohexylmethoxy)-2-fluorophenyl]pyrazin-2-amine,
5-[4-Cyclobutyl-3-(cyclopropylmethoxy)-2-fluorophenyl]pyrazin-2-amine,
Ethyl 5-{[3-(5-aminopyrazin-2-yl)-6-cyclobutyl-2-fluorophenoxy]methyl}furan-2-carboxylate,
tert-Butyl 4-{[3-(5-aminopyrazin-2-yl)-6-cyclobutyl-2-fluorophenoxy]-methylpiperidine-1-carboxylate,
5-{4-Cyclobutyl-2-fluoro-3-[(3-methyl-1,2,4-oxadlazol-5-yl)-methoxy]-phenyl}-pyrazin-2-amine,
5-(4-Cyclobutyl-2-fluoro-3-{[2-methoxy-5-(pentafluoro-lambda~6~sulfanyl)-benzyl]-oxy}-phenyl)pyrazin-2-amine,
5-(4-Cyclobutyl-2-fluoro-3-{[2-fluoro-5-(pentafluoro-lambda~6~sulfanyl)benzyl]-oxy}-phenyl)pyrazin-2-amine,
5-(4-Cyclobutyl-2-fluoro-3-{[2-fluoro-4-(pentafluoro-lambda~6~sulfanyl)benzyl]-oxy}-phenyl)pyrazin-2-amine,
5-(4-Cyclobutyl-2-fluoro-3-{[4-(pentafluoro-lambda~6~sulfanyl)benzyl]-oxyl-phenyl)pyrazin-2-amine,
5-(4-Cyclobutyl-2-fluoro-3-{[3-(pentafluoro-lambda~6~sulfanyl)benzyl]-oxy}-phenyl)pyrazin-2-amine,
5-(4-Cyclobutyl-2-fluoro-3-{[2-(pentafluoro-lambda~6~sulfanyl)benzyl]-oxyyphenyl)-pyrazin-2-amine,
5-[4-Cyclobutyl-3-(cyclobutylmethoxy)-2-fluorophenyl]pyrazin-2-amine,
5-[3-(Benzyloxy)-4-cyclobutyl-2-fluorophenyl]pyrazin-2-amine,
4-{2-[3-(5-Aminopyrazin-2-yl)-6-cyclobutyl-2-fluorophenoxy]ethyl}benzoic acid,
5-{[3-(5-Aminopyrazin-2-yl)-6-cyclobutyl-2-fluorophenoxy]methyl}furan-2-carboxylic acid,
2-[3-(5-Aminopyrazin-2-yl)-6-cyclobutyl-2-fluorophenoxy]-6-methylpyrimidin-4-amine,
5-{4-Cyclobutyl-2-fluoro-3-[(4-phenylpyrimidin-2-yl)oxy]phenyl}pyrazin-2-amine,
5-(4-Cyclobutyl-2-fluoro-3-{[4-(methylsulfanyl)pyrimidin-2-yl]oxy}phenyl)pyrazin-2-amine,
5-{4-Cyclobutyl-3-[(4,6-dimethylpyrimidin-2-yl)oxy]-2-fluorophenyl}pyrazin-2-amine,
5-(4-Cyclobutyl-2-fluoro-3-{[4-(1-methylethyl)pyrimidin-2-yl]oxy}phenyl)pyrazin-2-amine,
5-{4-Cyclobutyl-2-fluoro-3-[(4-thiophen-2-ylpyrimidin-2-yl)oxy]phenyl}pyrazin-2-amine,
2-[3-(5-Aminopyrazin-2-yl)-6-cyclobutyl-2-fluorophenoxy]pyrimidine-4-carbonitrile,
5-{4-Cyclobutyl-2-fluoro-3-[(4-methoxypyrimidin-2-yl)oxy]phenyl}pyrazin-2-amine,
5-{4-Cyclobutyl-2-fluoro-3-[(5-methoxypyrimidin-2-yl)oxy]phenyl}pyrazin-2-amine,
5-(4-Cyclobutyl-2-fluoro-3-{[4-(methylsulfonyl)pyrimidin-2-yl]oxy}phenyl)pyrazin-2-amine,
4-[3-(5-Aminopyrazin-2-yl)-6-cyclobutyl-2-fluorophenoxy]-6-methylpyrimidin-2-amine,
5-{4-Cyclobutyl-2-fluoro-3-[(6-methoxypyrimidin-4-yl)oxy]phenyl}pyrazin-2-amine,
6-[3-(5-Aminopyrazin-2-yl)-6-cyclobutyl-2-fluorophenoxy]pyrimidin-4-ol,
4-[3-(5-Aminopyrazin-2-yl)-6-cyclobutyl-2-fluorophenoxy]-6-methoxypyrimidin-2-amine,
6-[3-(5-Aminopyrazin-2-yl)-6-cyclobutyl-2-fluorophenoxy]-2-methoxypyrimidin-4-amine,
4-[3-(5-Aminopyrazin-2-yl)-6-cyclobutyl-2-fluorophenoxy]benzonitrile,
5-(4-Cyclobutyl-2-fluoro-3-{[6-(trifluoromethyl)pyridin-2-yl]oxy}phenyl)pyrazin-2-amine,
Methyl 4-[3-(5-aminopyrazin-2-yl)-6-cyclobutyl-2-fluorophenoxy]benzoate,
5-(4-Cyclobutyl-2-fluoro-3-{[5-(trifluoromethyl)pyrimidin-2-yl]oxy}phenyl)pyrazin-2-amine,
5-(4-Cyclobutyl-2-fluoro-3-{[5-(trifluoromethyl)pyrazin-2-yl]oxy}phenyl)pyrazin-2-amine,
5-(4-Cyclobutyl-2-fluoro-3-{[6-(trifluoromethyl)pyridazin-3-yl]oxy}phenyl)pyrazin-2-amine,
Methyl 6-[3-(5-aminopyrazin-2-yl)-6-cyclobutyl-2-fluorophenoxy]pyridine-3-carboxylate,
5-[3-(5-Aminopyrazin-2-yl)-6-cyclobutyl-2-fluorophenoxy]pyridine-2-carbonitrile,

TABLE 1-continued

4-[3-(5-Aminopyrazin-2-yl)-6-cyclobutyl-2-fluorophenoxy]pyridine-2-carbonitrile,
2-[3-(5-Aminopyrazin-2-yl)-6-cyclobutyl-2-fluorophenoxy]pyridine-3-carbonitrile,
6-[3-(5-Aminopyrazin-2-yl)-6-cyclobutyl-2-fluorophenoxy]pyridine-2-carbonitrile,
3-[3-(5-Aminopyrazin-2-yl)-6-cyclobutyl-2-fluorophenoxy]pyridine-2-carbonitrile,
5-(4-Cyclobutyl-2-fluoro-3-{[5-(trifluoromethyl)pyridin-2-yl]oxy}phenyl)pyrazin-2-amine,
6-[3-(5-Aminopyrazin-2-yl)-6-cyclobutyl-2-fluorophenoxy]pyridine-3-carbonitrile,
5-{4-Cyclobutyl-2-fluoro-3-[4-(pentafluoro-lambda~6~sulfanyl)phenoxy]-phenyl}-pyrazin-2-amine,
5-{4-Cyclobutyl-2-fluoro-3-[4-(methylsulfonyl)phenoxy]phenyl}pyrazin-2-amine,
5-{4-Cyclobutyl-2-fluoro-3-[2-(methylsulfonyl)phenoxy]phenyl}pyrazin-2-amine,
5-[4-Cyclobutyl-2-fluoro-3-(pyrimidin-2-yloxy)phenyl]pyrazin-2-amine,
2-[3-(5-Aminopyrazin-2-yl)-6-cyclobutyl-2-fluorophenoxy]pyrimidin-4-amine,
5-{3-[3,4-Bis(trifluoromethyl)phenoxy]-4-cyclobutyl-2-fluorophenyl}pyrazin-2-amine,
5-(4-Cyclobutyl-2-fluoro-3-{[3-(trifluoromethyl)pyridin-2-yl]oxy}phenyl)pyrazin-2-amine,
5-{3-[(3-Chloropyridin-2-yl)oxy]-4-cyclobutyl-2-fluorophenyl}pyrazin-2-amine,
5-{3-[2-Chloro-4-(methylsulfonyl)phenoxy]-4-cyclobutyl-2-fluorophenyl}pyrazin-2-amine,
5-(4-Cyclobutyl-2-fluoro-3-{[2-(trifluoromethyl)pyrimidin-4-yl]oxy}phenyl)pyrazin-2-amine,
5-(4-Cyclobutyl-2-fluoro-3-{16-(trifluoromethyl)pyrimidin-4-yl]oxy}phenyl)pyrazin-2-amine,
5-{4-Cyclobutyl-2-fluoro-3-[3-methyl-4-(methylsulfonyl)phenoxy]phenyl}pyrazin-2-amine,
5-(4-cyclobutyl-2-fluoro-3-(4-(methylsulfonyl)-2-(trifluoromethyl)phenoxy)-phenyl)-pyrazin-2-amine,
5-(4-Cyclobutyl-2-fluoro-3-{[6-(trifluoromethyl)pyridin-3-yl]oxy}phenyl)pyrazin-2-amine,
5-{4-Cyclobutyl-2-fluoro-3-[(3-methoxypyridin-2-yl)oxy]phenyl}pyrazin-2-amine,
4-[3-(5-Aminopyrazin-2-yl)-6-cyclobutyl-2-fluorophenoxy]pyrimidin-2-amine,
5-(4-Cyclobutyl-2-fluoro-3-{[4-(trifluoromethyl)pyrimidin-2-yl]oxy}phenyl)pyrazin-2-amine,
2-[3-(5-Aminopyrazin-2-yl)-6-cyclobutyl-2-fluorophenoxy]-5-(methylsulfonyl)-benzonitrile,
5-{4-Cyclobutyl-2-fluoro-3-[4-(methylsulfonyl)-3-(trifluoromethyl)-phenoxy]-phenyl}-pyrazin-2-amine,
5-{4-Cyclobutyl-2-fluoro-3-[(2-methylpyrimidin-4-yl)oxy]phenyl}pyrazin-2-amine,
5-(4-Cyclobutyl-2-fluoro-3-{[2-(1-methylethyl)pyrimidin-4-yl]oxy}phenyl)pyrazin-2-amine,
6-[3-(5-Aminopyrazin-2-yl)-6-cyclobutyl-2-fluorophenoxy]pyrimidin-4-amine,
5-{3-[(2-Chloropyrimidin-4-yl)oxy]-4-cyclobutyl-2-fluorophenyl}pyrazin-2-amine,
5-{3-[(6-Azetidin-1-ylpyrimidin-4-yl)oxy]-4-cyclobutyl-2-fluorophenyl}pyrazin-2-amine trifluoroacetate salt,
6-[3-(5-Aminopyrazin-2-yl)-6-cyclobutyl-2-fluorophenoxy]-N,N-dimethyl-2-(trifluoromethyl)pyrimidin-4-amine,
6-[3-(5-Aminopyrazin-2-yl)-6-cyclobutyl-2-fluorophenoxy]-2-methylpyrimidin-4-amine trifluoroacetate salt,
5-{4-Cyclobutyl-3-[(6-cyclopropylpyrimidin-4-yl)oxy]-2-fluorophenyl}pyrazin-2-amine,
4-[3-(5-Aminopyrazin-2-yl)-6-cyclobutyl-2-fluorophenoxy]-6-(methoxymethyl)pyrimidin-2-amine,
4-[3-(5-Aminopyrazin-2-yl)-6-cyclobutyl-2-fluorophenoxy]-6-chloropyrimidin-2-amine,
5-{4-Cyclobutyl-2-fluoro-3-[(2-phenylpyrimidin-4-yl)oxy]phenyl}pyrazin-2-amine,
5-{4-Cyclobutyl-2-fluoro-3-[(6-phenylpyrimidin-4-yl)oxy]phenyl}pyrazin-2-amine,
6-[3-(5-Aminopyrazin-2-yl)-6-cyclobutyl-2-fluorophenoxy]-2-benzylpyrimidin-4-amine,
5-(4-Cyclobutyl-2-fluoro-3-{[6-(1-methylethyl)pyrimidin-4-yl]oxy}phenyl)pyrazin-2-amine,
3-[3-(5-Aminopyrazin-2-yl)-6-cyclobutyl-2-fluorophenoxy]-1-methyl-5-(trifluoromethyl)-1H-pyrazole-4-carbonitrile, TABLE 1-continued tert-Butyl [2-({2-[3-(5-aminopyrazin-2-yl)-6-cyclobutyl-2-fluorophenoxy]pyrimidin-4-yl}amino)ethyl]carbamate,
N-{4-[3-(5-Aminopyrazin-2-yl)-6-cyclobutyl-2-fluorophenoxy]pyrimidin-2-yl}ethane-1,2-diamine,
Methyl 2-[3-(5-aminopyrazin-2-yl)-6-cyclobutyl-2-fluorophenoxy]pyrimidine-4-carboxylate trifluoroacetate salt,
2-[3-(5-Aminopyrazin-2-yl)-6-cyclobutyl-2-fluorophenoxy]pyrimidine-4-carboxylic acid,
4-[3-(5-Aminopyrazin-2-yl)-6-cyclobutyl-2-fluorophenoxy]benzoic acid,
6-[3-(5-Aminopyrazin-2-yl)-6-cyclobutyl-2-fluorophenoxy]pyridine-3-carboxylic acid,
4-[3-(5-Aminopyrazin-2-yl)-6-cyclobutyl-2-fluorophenoxy]benzamide,
N'-{4-[3-(5-Aminopyrazin-2-yl)-6-cyclobutyl-2-fluorophenoxy]pyrimidin-2-yl}-N,N-dimethylethane-1,2-diamine hydrochloride,
2-[3-(5-Aminopyrazin-2-yl)-6-cyclobutyl-2-fluorophenoxy]pyrimidine-4-carboxamide,
2-[3-(5-Aminopyrazin-2-yl)-6-cyclobutyl-2-fluorophenoxy]pyrimidin-5-amine,
5-(4-Cyclobutyl-2-fluoro-3-methoxyphenyl)pyrimidin-2-amine,
3-(2-Aminopyrimidin-5-yl)-6-cyclobutyl-2-fluorophenol,
5-[4-Cyclobutyl-2-fluoro-3-(pyrimidin-2-yloxy)phenyl]pyrimidin-2-amine,
5-{3-[(4-Aminopyrimidin-2-yl)oxy]-4-cyclobutyl-2-fluorophenyl}pyrimidin-2-amine,
4-[3-(2-Aminopyrimidin-5-yl)-6-cyclobutyl-2-fluorophenoxy]-6-(methoxymethyl)pyrimidin-2-amine,
5-{4-Cyclobutyl-2-fluoro-3-[(4-methylpyrimidin-2-yl)oxy]phenyl}pyrimidin-2-amine,
5-{3-[(6-Aminopyrimidin-4-yl)oxy]-4-cyclobutyl-2-fluorophenyl}pyrimidin-2-amine,
5-(4-Cyclobutyl-2-fluoro-3-{[4-(1-methylethyl)pyrimidin-2-yl]oxy}phenyl)pyrimidin-2-amine,
4-[3-(2-Aminopyrimidin-5-yl)-6-cyclobutyl-2-fluorophenoxy]pyrimidin-2-amine,
5-{4-Cyclobutyl-3-[(4,6-dimethylpyrimidin-2-yl)oxy]-2-fluorophenyl}pyrimidin-2-amine,
4-(3-(2-aminopyrimidin-5-yl)-6-cyclobutyl-2-fluorophenoxy)-6-isopropylpyrimidin-2-amine,
2-[3-(2-Aminopyrimidin-5-yl)-6-cyclobutyl-2-fluorophenoxy]pyrimidine-4-carboxamide,
5-(4-cyclobutyl-2-fluoro-3-((6-methoxypyrimidin-4-yl)oxy)phenyl)pyrimidin-2-amine trifluoroacetate salt,
6-[3-(2-Aminopyrimidin-5-yl)-6-cyclobutyl-2-fluorophenoxy]pyrimidin-4-ol trifluoroacetate salt,
6-Amino-3-(4-cyclobutyl-2-fluoro-3-methoxyphehyl)pyrazine-2-carbonitrile,
6-Amino-3-(4-cyclobutyl-2-fluoro-3-hydroxyphenyl)pyrazine-2-carbonitrile,
3-{[3-(5-Amino-3-cyanopyrazin-2-yl)-6-cyclobutyl-2-fluorophenoxy]methyl}benzoic acid,
2-(4-Cyclobutyl-2-fluoro-3-methoxyphenyl)-5H-pyrrolo[2,3-b]pyrazine,
6-Cyclobutyl-2-fluoro-3-(5H-pyrrolo[2,3-b]pyrazin-2-yl)phenol,
2-(4-Cyclobutyl-2-fluoro-3-{[4-(trifluoromethyl)benzyl]oxy}phenyl)-5H-pyrrolo[2,3-b]pyrazine trifluoroacetate salt,
2-[3-(Benzyloxy)-4-cyclobutyl-2-fluorophenyl]-5H-pyrrolo[2,3-b]pyrazine,
5-(4-Cyclobutyl-2-fluoro-3-methoxyphenyl)pyridin-2-amine hydrochloride salt,
5-(4-Cyclobutyl-2-fluoro-3-hydroxyphenyl)pyridin-2-amine,
5-Methyl-4-((3-(6-aminopyridin-3-yl)-6-cyclobutyl-2-fluorophenoxy)methyl)benzoate,
4-((3-(6-Aminopyridin-3-yl)-6-cyclobutyl-2-fluorophenoxy)methyl)benzoic acid,
5-(4-cyclobutyl-2-fluoro-3-methoxyphenyl)-1H-imidazo[4,5-b]pyrazine,
6-(4-Cyclobutyl-2-fluoro-3-methoxyphenyl)-3H-imidazo[4,5-b]pyridine,
7-(4-Cyclobutyl-2-fluoro-3-methoxyphenyl)-3,4-dihydro-2H-pyrido[3,2-b][1,4]oxazine,
6-Cyclobutyl-3-(3,4-dihydro-2H-pyrdo[3,2-b][1,4]oxazin-7-yl)-2-fluorophenol,
7-[3-(Benzyloxy)-4-cyclobutyl-2-fluorophenyl]-3,4-dihydro-2H-pyrido[3,2-b][1,4]oxazine,
3-{[6-Cyclobutyl-3-(3,4-dihydro-2H-pyrido[3,2-b][1,4]oxazin-7-yl)-2-fluorophenoxy]methyl}benzonitrile,
7-(4-Cyclobutyl-2-fluoro-3-{[3-(methylsulfonyl)benzyl]oxy}phenyl)-3,4-dihydro-2H-pyrido[3,2-b][1,4]oxazine,
7-(4-Cyclobutyl-2-fluoro-3-{[4-(methylsulfonyl)benzyl]oxy}phenyl)-3,4-dihydro-2H-pyrido[3,2-b][1,4]oxazine,
4-{[6-Cyclobutyl-3-(3,4-dihydro-2H-pyrido[3,2-b][1,4]oxazin-7-yl)-2-fluorophenoxy]methyl}benzonitrile,
7-(4-Cyclobutyl-2-fluoro-3-{[4-(trifluoromethyl)benzyl]oxy}phenyl)-3,4-dihydro-2H-pyrido[3,2-b][1,4]oxazine,
3-{[6-Cyclobutyl-3-(3,4-dihydro-2H-pyrido[3,2-b][1,4]oxazin-7-yl)-2-fluorophenoxy]methyl}benzamide, TABLE 1-continued 4-{[6-Cyclobutyl-3-(3,4-dihydro-2H-pyrido[3,2-b][1,4]oxazin-7-yl)-2-fluorophenoxy]methyl}benzamide,
7-(4-Cyclobutyl-2-fluoro-3-{[6-(trifluoromethyl)pyridin-2-yl]oxy}phenyl)-3,4-dihydro-2H-pyrido[3,2-b][1,4]oxazine,
(4-{[6-Cyclobutyl-3-(3,4-dihydro-2H-pyrido[3,2-b][1,4]oxazin-7-yl)-2-fluorophenoxy]methyl}phenyl)acetic acid,
4-{[6-Cyclobutyl-3-(3,4-dihydro-2H-pyrido[3,2-b][1,4]oxazin-7-yl)-2-fluorophenoxy]methyl}benzoic acid,
3-(4-Cyclobutyl-2-fluoro-3-methoxyphenyl)-7H-pyrrolo[2,3-c]pyridazine,
5-(4-Cyclobutyl-2-fluoro-3-methoxyphenyl)-2,3-dihydro-1H-pyrrolo[2,3-b]pyridine,
6-Cyclobutyl-3-(2,3-dihydro-1H-pyrrolo[2,3-b]pyridin-5-yl)-2-fluorophenol,
3-(5-Aminopyrazin-2-yl)-6-tert-butyl-2-fluorophenol,
5-(4-tert-Butyl-3-{[tert-butyl(dimethyl)silyl]oxy}-2-fluorophenyl)pyrazin-2-amine,
5-[4-tert-Butyl-2-fluoro-3-(pyrimidin-2-yloxy)phenyl]pyrazin-2-amine,
6-[3-(5-Aminopyrazin-2-yl)-6-tert-butyl-2-fluorophenoxy]pyrimidin-4-amine,
2-[3-(5-Aminopyrazin-2-yl)-6-tert-butyl-2-fluorophenoxy]pyrimidin-4-amine,
5-{4-tert-Butyl-2-fluoro-3-[(6-methoxypyrimidin-4-yl)oxy]phenyl}pyrazin-2-amine,
5-(4-tert-Butyl-2-fluoro-3-methoxyphenyl)pyrazin-2-amine,
3-(2-Aminopyrimidin-5-yl)-6-tert-butyl-2-fluorophenol,
5-(4-tert-Butyl-3-{[tert-butyl(dimethyl)silyl]oxy}-2-fluorophenyl)pyrimidin-2-amine,
5-[4-tert-Butyl-2-fluoro-3-(pyrimidin-2-yloxy)phenyl]pyrimidin-2-amine,
5-{3-[(6-Aminopyrimidin-4-yl)oxy]-4-tert-butyl-2-fluorophenyl}pyrimidin-2-amine,
5-{3-[(4-Aminopyrimidin-2-yl)oxy]-4-tert-butyl-2-fluorophenyl}pyrimidin-2-amine,
5-(4-Cyclopentyl-2-fluoro-3-methoxyphenyl)pyrazin-2-amine,
5-[3-(Benzyloxy)-4-cyclopentyl-2-fluorophenyl]pyrazin-2-amine,
5-[4-Cyclopentyl-2-fluoro-3-(1-methylethoxy)phenyl]pyrazin-2-amine,
2-[3-(Benzyloxy)-4-cyclopentyl-2-fluorophenyl]-5H-pyrrolo[2,3-b]pyrazine,
5-[3-(Benzyloxy)-4-tert-butylphenyl]pyrazin-2-amine,
5-[3-(Benzyloxy)-4-cyclobutylphenyl]pyrazin-2-amine,
3-amino-6-(4-cyclobutyl-2-fluoro-3-methoxyphenyl)pyrazine-2-carbonitrile,
6-(4-cyclobutyl-2-fluoro-3-methoxyphenyl)pyridazin-3-amine,
6-cyclobutyl-2-fluoro-3-(1H-pyrrolo[2,3-b]pyridin-5-yl)phenol,
6-cyclobutyl-2-fluoro-3-(7H-pyrrolo[2,3-c]pyridazin-3-yl)phenol,
3-amino-6-(4-cyclobutyl-2-fluoro-3-hydroxyphenyl)pyrazine-2-carbonitnle,
3-(6-aminopyridazin-3-yl)-6-cyclobutyl-2-fluorophenol,
7-(4-cyclobutyl-2-fluoro-3-(pyrimidin-2-yloxy)phenyl)-3,4-dihydro-2H-pyrido[3,2-b][1,4]oxazine,
2-(6-cyclobutyl-3-(3,4-dihydro-2H-pyrido[3,2-b][1,4]oxazin-7-yl)-2-fluorophenoxy)pyrimidin-4-amine,
7-(4-cyclobutyl-2-fluoro-3-((6-methoxypyrimidin-4-yl)oxy)phenyl)-3,4-dihydro-2H-pyrido[3,2-b][1,4]oxazine,
5-(4-cyclobutyl-2-fluoro-34(6-methoxypyrimidin-4-yl)oxy)phenyl)-1H-pyrrolo[2,3-b]pyridine,
2-(4-cyclobutyl-2-fluoro-3-((6-methoxypyrimidin-4-yl)oxy)phenyl)-5H-pyrrolo[2,3-b]pyrazine,
2-(4-cyclobutyl-2-fluoro-3-(pyrimidin-2-yloxy)phenyl)-5H-pyrrolo[2,3-b]pyrazine,
6-(4-cyclobutyl-2-fluoro-3-(pyrimidin-2-yloxy)phenyl)pyridazin-3-amine,
6-(4-cyclobutyl-2-fluoro-3-((6-methoxypyrimidin-4-yl)oxy)phenyl)pyridazin-3-amine,
6-(3-(6-aminopyridazin-3-yl)-6-cyclobutyl-2-fluorophenoxy)pyrimidin-4-ol,
4-(3-(5-Aminopyrazin-2-yl)-6-cyclobutyl-2-fluorophenoxy)pyrimidine-2-carbonitrile,
6-(3-(5-Aminopyrazin-2-yl)-6-cyclobutyl-2-fluorophenoxy)-N,N,2-trimethylpyrimidin-4-amine,
4-(3-(5-Aminopyrazin-2-yl)-6-cyclobutyl-2-fluorophenoxy)-N,N,6-trimethylpyrimidin-2-amine,
6-(3-(5-Aminopyrazin-2-yl)-6-cyclobutyl-2-fluorophenoxy)-N,N-dimethylpyrimidin-4-amine,
Ethyl 5-(3-(5-aminopyrazin-2-yl)-6-cyclobutyl-2-fluorophenoxy)-1-methyl-3-(trifluoromethyl)-1H-pyrazole-4-carboxylate,
5-(4-cyclobutyl-2-fluoro-3-((5-(methylsulfonyl)pyridin-2-yl)oxy)phenyl)pyrazin-2-amine,
4-(3-(5-aminopyrazin-2-yl)-6-cyclobutyl-2-fluorophenoxy)-6-(tert-butyl)pyrimidin-2-amine,
5-(3-((4-(1,5-dioxa-9-azaspiro[5.5]undecan-9-yl)pyrimidin-2-yl)oxy)-4-cyclobutyl-2-fluorophenyl)pyrazin-2-amine,
4-(3-(5-aminopyrazin-2-yl)-6-cyclobutyl-2-fluorophenoxy)-6-isobutylpyrimidin-2-amine, TABLE 1-continued 5-(4-Cyclobutyl-2-fluoro-3-methoxyphenyl)-1H-pyrrolo[2,3-b]pyridine,
N-(2-(3-(5-Aminopyrazin-2-yl)-6-cyclobutyl-2-fluorophenoxy)-ethyl)-methane-sulfonamide,
5-(4-Cyclobutyl-2-fluoro-3-(2-morpholinoethoxy)phenyl)pyrazin-2-amine,
Ethyl 4-(3-(5-aminopyrazin-2-yl)-6-cyclobutyl-2-fluorophenoxy)butanoate,
tert-Butyl 3-((3-(5-aminopyrazin-2-yl-6-cyclobutyl-2-fluorophenoxy)methyl)-azetidine-1-carboxylate,
tert-Butyl 3-((3-(5-aminopyrazin-2-yl)-6-cyclobutyl-2-fluorophenoxy)methyl)-pyrrolidine-1-carboxylate,
tert-Butyl 2-((3-(5-aminopyrazin-2-yl)-6-cyclobutyl-2-fluorophenoxy)methyl)-pyrrolidine-1-carboxylate,
tert-Butyl 3-((3-(5-aminopyrazin-2-yl)-6-cyclobutyl-2-fluorophenoxy)-methyl)-piperidine-1-carboxylate,
2-(3-(5-Aminopyrazin-2-yl)-6-cyclobutyl-2-fluorophenoxy)ethanol,
4-(3-(5-Aminopyrazin-2-yl)-6-cyclobutyl-2-fluorophenoxy)butanoic acid,
5-(4-Cyclobutyl-2-fluoro-3-((tetrahydrofuran-2-yl)methoxy)phenyl)pyrazin-2-amine,
racemic 1-(3-(5-Aminopyrazin-2-yl-6-cyclobutyl-2-fluorophenoxy)-3-(isobutylamino)-propan-2-ol,
racemic 3-(3-(5-Aminopyrazin-2-yl)-6-cyclobutyl-2-fluorophenoxy)propane-1,2-diol,
racemic 1-(3-(5-aminopyrazin-2-yl)-6-cyclobutyl-2-fluorophenoxy)-3-morpholinopropan-2-ol,
racemic 4-(3-(3-(5-Aminopyrazin-2-yl-6-cyclobutyl-2-fluorophenoxy)-2-hydroxypropyl)-thiomorpholine 1,1-dioxide,
5-(4-Cyclobutyl-2-fluoro-3-(pyridazin-4-yloxy)phenyl)pyrazin-2-amine,
3-(3-(5-Aminopyrazin-2-yl)-6-cyclobutyl-2-fluorophenoxy)pyrazin-2-amine,
5-(4-Cyclobutyl-2-fluoro-3-(pyrazin-2-yloxy)phenyl)pyrazin-2-amine,
5-(4-Cyclobutyl-2-fluoro-3-(pyrimidin-4-yloxy)phenyl)pyrazin-2-amine, and
4-(3-(5-Aminopyrazin-2-yl)-6-cyclobutyl-2-fluorophenoxy)-N-isobutylpyrimidin-2-amine trifluoroacetic acid salt.

Particularly, an embodiment of the present invention comprises a compound selected from the compounds listed in Table 2.

TABLE 2

5-(4-Cyclobutyl-2-fluoro-3-{[2-(pentafluoro-lambda~6~sulfanyl)benzyl]-oxy}phenyl)pyrazin-2-amine,
5-(4-Cyclobutyl-2-fluoro-3-{[3-(pentailuoro-lambda~6~sulianyl)benzyl]-oxy}phenyl)pyrazin-2-amine,
5-(4-Cyclobutyl-2-fluoro-3-{[4-(pentafluoro-lambda~6~sulfanyl)benzyl]oxy}-phenyl)pyrazin-2-amine,
5-(4-Cyclobutyl-2-fluoro-3-{[2-fluoro-4-(pentafluoro-lambda~6~sulfanyl)-benzyl]oxy}phenyl)pyrazin-2-amine,
5-(4-Cyclobutyl-2-fluoro-3-{[2-fluoro-5-(pentafluoro-lambda~6~sulfanyl)benzyl]oxy}phenyl)pyrazin-2-amine,
5-(4-Cyclobutyl-2-fluoro-3-{[2-methoxy-5-(pentafluoro-lambda~6~sulfanyl)benzyl]oxy}phenyl)pyrazin-2-amine,
2-[3-(5-Aminopyrazin-2-yl)-6-cyclobutyl-2-fluorophenoxy]pyridine-3-carbonitrile,
5-{4-Cyclobutyl-2-fluoro-3-[4-(pentafluoro-lambda~6~sulfanyl)phenoxy]phenyl}pyrazin-2-amine,
5-[4-Cyclobutyl-2-fluoro-3-(pyrimidin-2-yloxy)phenyl]pyrazin-2-amine,
2-[3-(5-Aminopyrazin-2-yl)-6-cyclobutyl-2-fluorophenoxy]pyrimidin-4-amine,
4-[3-(5-Aminopyrazin-2-yl)-6-cyclobutyl-2-fluorophenoxy]pyrimidin-2-amine,
6-[3-(5-Aminopyrazin-2-yl)-6-cyclobutyl-2-fluorophenoxy]pyrimidin-4-amine,
5-[4-Cyclobutyl-2-fluoro-3-(pyrimidin-2-yloxy)phenyl]pyrimidin-2-amine,
5-{3-[(4-Aminopyrimidin-2-yl)oxy]-4-cyclobutyl-2-fluorophenyl}pyrimidin-2-amine,
5-{3-[(6-Aminopyrimidin-4-yl)oxy]-4-cyclobutyl-2-fluorophenyl}pyrimidin-2-amine,
6-[3-(5-Aminopyrazin-2-yl)-6-cyclobutyl-2-fluorophenoxy]pyrimidin-4-ol,
4-[3-(5-Aminopyrazin-2-yl)-6-cyclobutyl-2-fluorophenoxy]-6-methoxypyrimidin-2-amine,
6-[3-(5-Aminopyrazin-2-yl)-6-cyclobutyl-2-fluorophenoxy]-2-methoxypyrimidin-4-amine,
4-[3-(2-Aminopyrimidin-5-yl)-6-cyclobutyl-2-fluorophenoxy]pyrimidin-2-amine,
6-[3-(2-Aminopyrimidin-5-yl)-6-cyclobutyl-2-fluorophenoxy]pyrimidin-4-ol trifluoroacetate, TABLE 2-continued 2-[3-(5-Aminopyrazin-2-yl)-6-tert-butyl-2-fluorophenoxy]pyrimidin-4-amine,
5-{4-Cyclobutyl-2-fluoro-3-[(6-methoxypyrimidin-4-yl)oxy]phenyl}pyrezin-2-amine,
5-{4-tert-Butyl-2-fluoro-3-[(6-methoxypyrimidin-4-yl)oxy]phenyl}pyrazin-2-amine,
2-[3-(5-Aminopyrazin-2-yl)-6-cyclobutyl-2-fluorophenoxy]pyrimidin-5-amine,
2-[3-(2-Aminopyrimidin-5-yl)-6-cyclobutyl-2-fluorophenoxy]pyrimidine-4-carboxamide,
5-{3-[(6-Aminopyrimidin-4-yl)oxy]-4-tert-butyl-2-fluorophenyl}pyrimidin-2-amine,
5-{3-[(4-Aminopyrimidin-2-yl)oxy]-4-tert-butyl-2-fluorophenyl}pyrimidin-2-amine,
5-[4-tert-Butyl-2-fluoro-3-(pyrimidin-2-yloxy)phenyl]pyrazin-2-amine,
5-[4-tert-Butyl-2-fluoro-3-(pyrimidin-2-yloxy)phenyl]pyrimidin-2-amine,
and
6-[3-(5-Aminopyrazin-2-yl)-6-tert-butyl-2-fluorophenoxy]pyrimidin-4-amine.

It is an embodiment of the present invention to provide a compound selected from the compounds listed in Table 1A.

TABLE 1A 3-(5-Aminopyrazin-2-yl)-6-ethyl-2-fluorophenol,
5-[4-tert-Butyl-2-fluoro-3-(pyrimidin-2-yloxy)phenyl]-1H-pyrrolo[2,3-b]pyridine,
5-{3-[(2-Aminopyridin-4-yl)oxy]-4-cyclobutyl-2-fluorophenyl}pyrazin-2-amine,
5-{3-[(6-Aminopyrazin-2-yl)oxy]-4-cyclobutyl-2-fluorophenyl}pyrazin-2-amine,
5-[4-Cyclobutyl-2-fluoro-3-(pyrimidin-5-yloxy)phenyl]pyrazin-2-amine,
6-[3-(5-Aminopyrazin-2-yl)-6-cyclobutyl-2-fluorophenoxy]pyridazin-4-amine,
3-(5-Aminopyrazin-2-yl)-6-cyclohexyl-2-fluorophenol,
3-(5-Aminopyrazin-2-yl)-6-(cyclohexylmethyl)-2-fluorophenol,
5-[4-Cyclopentyl-2-fluoro-3-(pyrimidin-2-yloxy)phenyl]pyrimidin-2-amine,
5-[4-Cyclopentyl-2-fluoro-3-(pyrimidin-2-yloxy)phenyl]pyrazin-2-amine,
2-[3-(5-Aminopyrazin-2-yl)-6-cyclopentyl-2-fluorophenoxy]pyrimidin-4-amine,
5-{3-[(4-Aminopyrimidin-2-yl)oxyl-4-cyclopentyl-2-fluorophenyl}pyrimidin-2-amine,
6-[3-(5-Aminopyrazin-2-yl)-6-cyclobutyl-2-fluorophenoxy]pyridazin-3-amine,
5-[4-Cyclobutyl-2-fluoro-3-(pyrimidin-2-ylmethoxy)phenyl]pyrazin-2-amine,
5-{3-[(4-Bromobenzyl)oxy]-4-cyclobutyl-2-fluorophenyl}pyrazin-2-amine,
5-(4-{[3-(5-Aminopyrazin-2-yl)-6-cyclobutyl-2-fluorophenoxy]methyl}phenyl)pyrimidin-2-amine,
5-(4-Cyclobutyl-2-fluoro-3-{[4'-(trifluoromethyl)biphenyl-4-yl]methoxy}phenyl)pyrazin-2-amine,
5-[4-Cyclohexyl-2-fluoro-3-(pyrimidin-2-yloxy)phenyl]pyrimidin-2-amine,
5-{3-[(4-Aminopyrimidin-2-yl)oxy]-4-cyclohexyl-2-fluorophenyl}pyrimidin-2-amine.

It is another embodiment of the present invention to provide a compound selected from the compounds listed in Table 1, Table 2 and Table 1A.

The invention is also directed to a pharmaceutical composition which include, without limitation, one or more of the disclosed compounds herein, and pharmaceutically acceptable carriers or excipients.

Another embodiment of the present invention is a pharmaceutical composition of the present invention that comprises at least a compound selected from the compounds listed in Table 1. Another embodiment of the present invention is a pharmaceutical composition of the present invention that comprises at least a compound selected from the compounds listed in Table 3.

Particularly, an embodiment of the present invention is a pharmaceutical composition of the present invention that comprises at least a compound selected from the compounds listed in Table 2.

The present invention also features a method of treating a subject suffering from or diagnosed with a disease and/or disorder mediated by FLAP activity, comprising administering to the subject a therapeutically effective amount of at least one compound of Formula (I).

The present invention also features a method for preventing, treating, ameliorating, including without limitation inhibiting, the progression of an FLAP-mediated disease and/or disorder in a subject in need thereof, comprising administering to said subject a therapeutically effective amount of at least one compound of Formula (I). Such a disease and/or disorder includes, but is not limited to diabetes, respiratory disorders, and associated symptoms or complications thereof. More specifically, this invention is directed to a method of treating, but not limited to, exacerbations, non-allergic asthma, fibrotic lung diseases, acute respiratory distress syndrome and chronic obstructive pulmonary disease, and their associated symptoms or complications, in a subject afflicted with such a disease and/or disorder.

In another embodiment, the compounds of the present invention are useful for the amelioration of symptoms associated with and/or the treatment of the following cardiac and cardiovascular diseases and/or disorders: myocardial infarction, atherosclerosis, atherosclerosis and stroke aortic aneurisms, or associated symptoms or complications thereof, in a subject afflicted with such a disease and/or disorder.

In another embodiment, the compounds of the present invention are useful for the amelioration of symptoms associated with and/or the treatment of autoimmune or allergic diseases and/or disorders, wherein said autoimmune or allergic diseases and/or disorders include, but are not limited to, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, or associated symptoms or complications thereof, in a subject afflicted with such a disease and/or disorder.

In a further embodiment, the compounds of the present invention are useful for the amelioration of symptoms associated with and/or the prophylaxis or treatment of carcinogenesis, wherein said carcinogenesis include, but is not limited to, tumor cell proliferation, differentiation, apoptosis, tumor-associated angiogenesis, as well as the migration and invasion of carcinoma cells.

It is a further embodiment of the invention to provide a process for making a pharmaceutical composition comprising admixing any of the compounds according to Formula (I) and a pharmaceutically acceptable carrier.

In a further embodiment of the invention, a method for treating or ameliorating an FLAP-mediated disease and/or disorder in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose. More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

It should also be noted that any atom with unsatisfied valences in the text, schemes, examples, structural formulae and any tables herein is assumed to have the hydrogen atom or atoms to satisfy the valences.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-n}$alkyl" means a saturated branched or straight-chain hydrocarbon radical having from 1 up to n carbon atoms, wherein n is 4 or 5, in a linear or branched arrangement. Examples include methyl, ethyl, 1-propyl, 2-propyl, isobutyl, tert-butyl, isopentyl, neopentyl, pentan-3-yl, and the like, and all that are exemplified in the below examples. An alkyl radical may be attached to a core molecule by any atom where allowed by available valences.

The term "$C_{3-6}$cycloalkyl" means a saturated or partially unsaturated, monocyclic, hydrocarbon ring system radical. Examples include cyclopropyl, cyclobutyl, cyclopentyl cyclohexyl and the like, and all that are exemplified in the below examples. A $C_{3-5}$cycloalkyl radical may be attached to a core molecule by any ring atom where allowed by available valences.

The term "aryl" means an unsaturated, aromatic monocyclic or polycyclic hydrocarbon ring system radical. Examples include phenyl and the like, and all that are exemplified in the below examples. An aryl radical may be attached to a core molecule by any ring atom where allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heteroaryl" means an unsaturated monocyclic, polycyclic aromatic "hetero" ring system radical, selected from the group consisting of pyrazolyl, oxadiazolyl, furanyl, imidazolyl, imidazolidinyl, triazolyl, pyridinyl, pyrimidinyl, pyridazinyl, pyrazinyl, benzimidazolyl, benzoxazolyl, quinoxalinyl, quinazolinyl, benzothiazolyl, isoxazolyl, thiazolyl, oxazolyl, thiazolopyridyl, thienopyrimidinyl and isoindolyl. Examples include 1H-pyrazol-1-yl, 1H-pyrazol-3-yl, 1H-pyrazol-5-yl, 1,2,4-oxadiazol-5-yl, 1,2,4-oxadiazol-3-yl, furan-2-yl, 1H-imidazol-1-yl, 1H-imidazol-2-yl, 1H-imidazol-4-yl, 1H-imidazol-5-yl, imidazolidin-1-yl, 1H-1,2,4-triazol-1-yl, 1H-1,2,4-triazol-2-yl, 1H-1,2,4-triazol-3-yl, 1H-1,2,4-triazol-4-yl, 1H-1,2,3-triazol-1-yl, 2H-1,2,3-triazol-2-yl, pyridin-3-yl, pyrimidin-1-yl, pyrimidin-2-yl, pyrimidin-4-yl, pyrimidin-5-yl, pyridazin-2-yl, pyridazin-3-yl, pyridazin-4-yl, pyrazin-1-yl, pyrazin-2-yl, pyrazin-3-yl, benzimidazol-1-yl, benzoxazol-2-yl, quinoxalin-2-yl, quinazolin-2-yl, benzothiazol-2-yl, isoxazol-3-yl, 1,3-thiazol-4-yl, 1,3-oxazol-2-yl, isoindol-1-yl, thiazolo[4,5-b]pyridyl, thieno[2,3-d]pyrimidinyl and the like, and all that are exemplified in the below examples. A heteroaryl radical may be attached to a core molecule by any ring atom where allowed by available valences.

The term "heterocyclyl" means a saturated monocyclic "hetero" ring system radical, selected from the group consisting of azetidinyl, pyrrolidinyl, piperidinyl, piperazinyl, tetrahydrofuranyl, morpholinyl, thiomorpholinyl, and tetrahydro-2H-pyranyl. Examples include azetidin-3-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, tetrahydrofuran-2-yl, morpholin-4-yl, thiomorpholin-4-yl, tetrahydro-2H-pyran-4-yl, and the like, and all that are exemplified in the below examples. A heterocyclyl radical may be attached to a core molecule by any ring atom where allowed by available valences.

The term "carboxy" means a radical of the formula: —C(O)OH.

The term "halogen" or "halo" means a radical selected from the group consisting of chloro, bromo, fluoro or iodo.

The term "oxo" means a radical of the formula: =O.

The term "substituted" refers to a radical in which one or more hydrogen atoms are each independently replaced with the same or different substituent(s). In a preferred embodiment, up to three hydrogen atoms are each independently replaced.

With reference to substituents, the term "independently" means that when more than one of such substituent is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

In general, unless specified otherwise, IUPAC nomenclature rules are used herein.

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The term "composition" is intended to encompass a product comprising the specified ingredients in the specified amounts, as well as any product which results, directly or indirectly, from combinations of the specified ingredients in the specified amounts.

The term "subject" as used herein, refers to a patient, such as an animal, a mammal or a human, who has been the object of treatment, observation or experiment and is at risk of (or susceptible to) developing an FLAP-mediated disorder.

The term "administering" further means that the individual ingredients to be combined may be administered at the same time or at different times during the treatment period, either as one preparation or as different preparations. Accordingly, the invention should be so interpreted that it encompasses any and every administration mode at the same time or at different times. The range of the combination of the compound of the invention and the other therapeutic agent useful for the above-mentioned disorders encompasses, in principle, all combinations of the compound of the invention and any and every pharmaceutical agent useful for the above-mentioned disorders.

The term "treating" refers, without limitation, to facilitating the eradication of, preventing, ameliorating or otherwise inhibiting the progression of or promoting stasis of an FLAP-mediated disease and/or disorder, or associated symptoms or complications thereof.

The term "prodrug" means a compound of Formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions. Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "Design of Prodrugs", ed. H. Bundgaard, Elsevier, 1985.

The term "metabolite" means a prodrug form of a compound of Formula (I) or a form thereof converted by in vivo metabolism or a metabolic process to a relatively less active functional derivative of said compound.

The term "medicament" or "medicine" refers to a product containing a compound of Formula (I) or a form thereof. The present invention includes use of such a medicament for treating an FLAP-mediated disorder.

The term "combination form" refers to the use of a combination product comprising a compound of Formula (I) or a form, pharmaceutical composition, medicine or medicament thereof and at least one therapeutic agent for treating an FLAP-mediated disorder.

Methods are known in the art for determining effective doses for therapeutic and prophylactic purposes for the disclosed pharmaceutical compositions or the disclosed drug combinations, whether or not formulated in the same composition.

For therapeutic purposes, the term "therapeutically effective amount" or "effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease and/or disorder being treated. For prophylactic purposes (i.e., inhibiting the progression of a disorder), the term "therapeutically effective amount" refers to that amount of each active compound or pharmaceutical agent, alone or in combination, that treats or inhibits in a subject the progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together. The effective amount of said compound is from about 0.001 mg/kg/day to about 300 mg/kg/day.

Advantageously, the effective amount of a combination product for treating an FLAP-mediated disease and/or disorder, or associated symptoms or complications thereof, may be a reduced amount of either or both, the compound or therapeutic agent, compared to the effective amount of the compound or therapeutic agent otherwise recommended for treating the disease and/or disorder, or associated symptoms or complications thereof. Therefore, it is contemplated that the compound is administered to the subject before, during or after the time the agent is administered.

The term "pharmaceutically acceptable salt" refers to non-toxic pharmaceutically acceptable salts (*Ref. Int'l J. Pharm.*, 1986, 33: 201-217; *J. Pharm. Sci.*, 1997 (January), 66(1): 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic" means an equimolar mixture of two enantiomeric species, wherein each of the isolated species rotates the plane of polarized light in the opposite direction such that the mixture is devoid of optical activity.

The term "enantiomer" means an isomer having a non-superimposable mirror image. The term "diastereomer" means stereoisomers that are not enantiomers.

The term "chiral" means a molecule that, in a given configuration, cannot be superimposed on its mirror image. This is in contrast to achiral molecules that can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to the Cahn-Ingold-Prelog priority rules. In the "E" configuration, the substituents having the highest priorities are on opposite sides in relationship to the carbon-carbon double bond. In the "Z" configuration, the substituents having the highest priorities are oriented on the same side in relationship to the carbon-carbon double bond.

Substituent atoms (other than hydrogen) attached to a ring system may be in a "cis" or "trans" configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

B) Compounds

Representative compounds of the present invention are listed in Table 3 below.

TABLE 3

| STRUCTURE | COMPOUND # | NAME |
| --- | --- | --- |
| 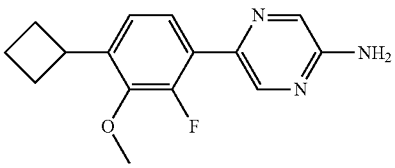 | A | 5-(4-Cyclobutyl-2-fluoro-3-methoxyphenyl)pyrazin-2-amine |
| 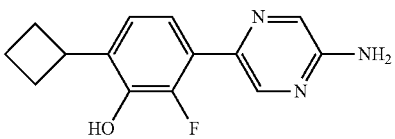 [SMILES: Nc1cnc(-c2ccc(C3CCC3)c(O)c2F)cn1] | B | 3-(5-Aminopyrazin-2-yl)-6-cyclobutyl-2-fluorophenol |
| 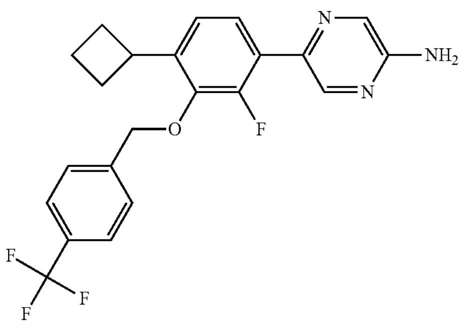 [SMILES: Nc1cnc(-c2ccc(C3CCC3)c(OCc3ccc(C(F)(F)F)cc3)c2F)cn1] | 1 | 5-(4-Cyclobutyl-2-fluoro-3-{[4-(trifluoromethyl)benzyl]oxy}phenyl)-pyrazin-2-amine |
| 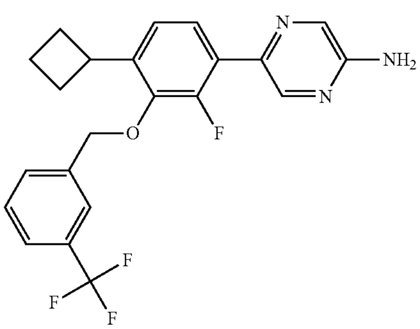 [SMILES: Nc1cnc(-c2ccc(C3CCC3)c(OCc3cccc(C(F)(F)F)c3)c2F)cn1] | 2 | 5-(4-Cyclobutyl-2-fluoro-3-{[3-(trifluoromethyl)benzyl]oxy}phenyl)-pyrazin-2-amine |
| 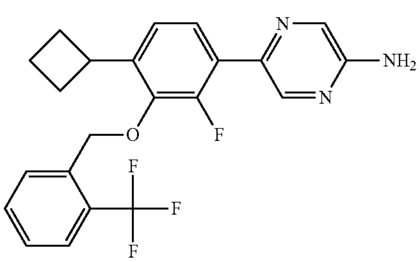 [SMILES: Nc1cnc(-c2ccc(C3CCC3)c(OCc3ccccc3C(F)(F)F)c2F)cn1] | 3 | 5-(4-Cyclobutyl-2-fluoro-3-{[2-(trifluoromethyl)benzyl]oxy}phenyl)-pyrazin-2-amine |

TABLE 3-continued

| STRUCTURE | COMPOUND # | NAME |
|---|---|---|
| 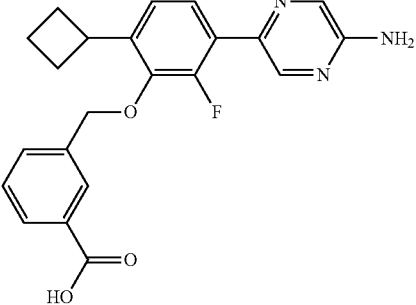 | 4 | 3-{[3-(5-Aminopyrazin-2-yl)-6-cyclobutyl-2-fluorophenoxy]methyl}benzoic acid |
| 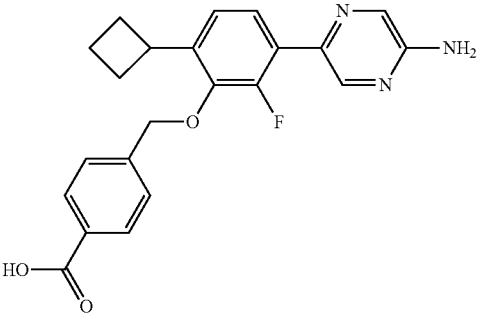 [SMILES: Nc1cnc(-c2ccc(C3CCC3)c(OCc3ccc(C(=O)O)cc3)c2F)cn1] | 5 | 4-{[3-(5-Aminopyrazin-2-yl)-6-cyclobutyl-2-fluorophenoxy]methyl}benzoic acid |
| 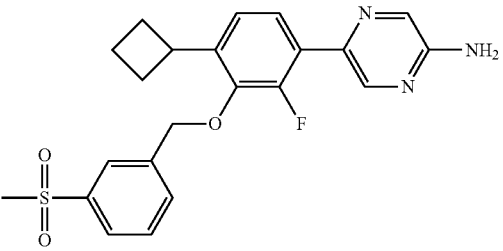 [SMILES: CS(=O)(=O)c1cccc(COc2c(C3CCC3)ccc(-c3cnc(N)cn3)c2F)c1] | 6 | 5-(4-Cyclobutyl-2-fluoro-3-{[3-(methylsulfonyl)benzyl]oxy}phenyl)-pyrazin-2-amine |
| 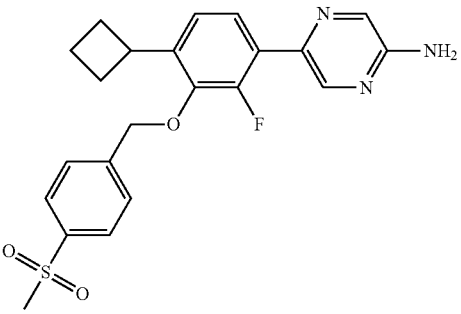 [SMILES: CS(=O)(=O)c1ccc(COc2c(C3CCC3)ccc(-c3cnc(N)cn3)c2F)cc1] | 7 | 5-(4-Cyclobutyl-2-fluoro-3-{[4-(methylsulfonyl)benzyl]oxy}phenyl)-pyrazin-2-amine |
| 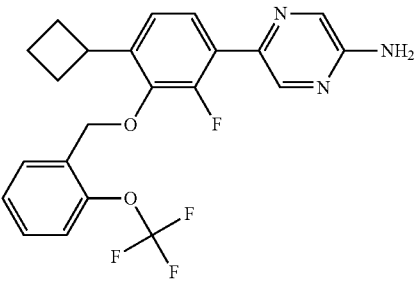 [SMILES: Nc1cnc(-c2ccc(C3CCC3)c(OCc3ccccc3OC(F)(F)F)c2F)cn1] | 8 | 5-(4-Cyclobutyl-2-fluoro-3-{[2-(trifluoromethoxy)benzyl]oxy}phenyl)-pyrazin-2-amine |

TABLE 3-continued

| STRUCTURE | COMPOUND # | NAME |
|---|---|---|
| 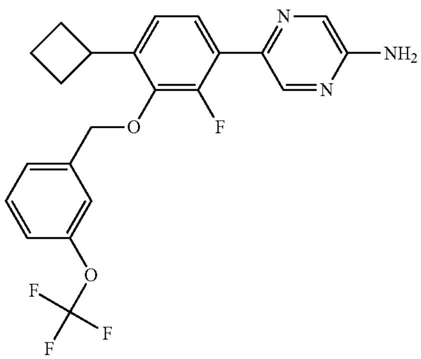 [SMILES: Nc1cnc(-c2ccc(C3CCC3)c(OCc3cccc(OC(F)(F)F)c3)c2F)cn1] | 9 | 5-(4-Cyclobutyl-2-fluoro-3-{[3-(trifluoromethoxy)benzyl]oxy}phenyl)-pyrazin-2-amine |
| 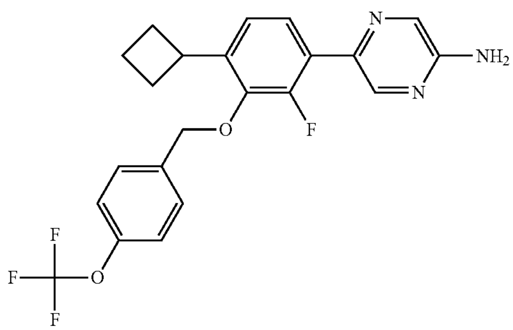 [SMILES: Nc1cnc(-c2ccc(C3CCC3)c(OCc3ccc(OC(F)(F)F)cc3)c2F)cn1] | 10 | 5-(4-Cyclobutyl-2-fluoro-3-{[4-(trifluoromethoxy)benzyl]oxy}phenyl)-pyrazin-2-amine |
| 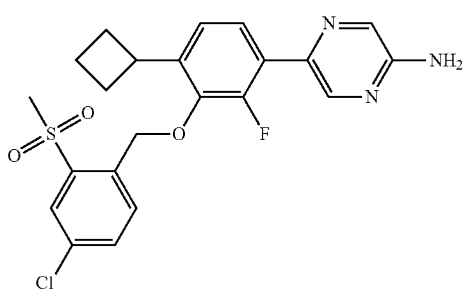 [SMILES: CS(=O)(=O)c1cc(Cl)ccc1COc1c(C2CCC2)ccc(-c2cnc(N)cn2)c1F] | 11 | 5-(3-{[4-Chloro-2-(methylsulfonyl)benzyl]oxy}-4-cyclobutyl-2-fluorophenyl)pyrazin-2-amine |
| 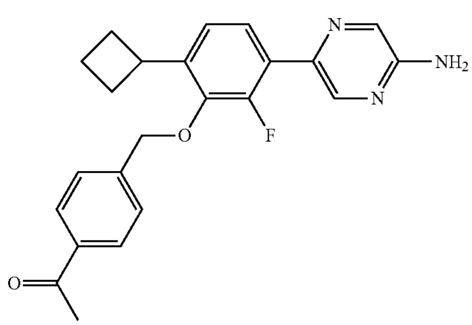 [SMILES: CC(=O)c1ccc(COc2c(C3CCC3)ccc(-c3cnc(N)cn3)c2F)cc1] | 12 | 1-(4-{[3-(5-Aminopyrazin-2-yl)-6-cyclobutyl-2-fluorophenoxy]methyl}phenyl)ethanone |
| 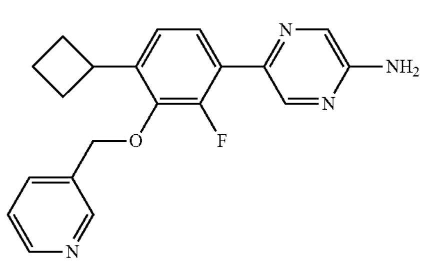 [SMILES: Nc1cnc(-c2ccc(C3CCC3)c(OCc3cccnc3)c2F)cn1] | 13 | 5-[4-Cyclobutyl-2-fluoro-3-(pyridin-3-ylmethoxy)phenyl]pyrazin-2-amine |

TABLE 3-continued

| STRUCTURE | COMPOUND # | NAME |
|---|---|---|
| 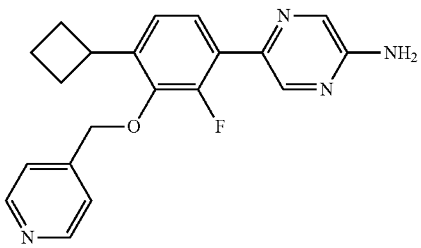 [SMILES: Nc1cnc(-c2ccc(C3CCC3)c(OCc3ccncc3)c2F)cn1] | 14 | 5-[4-Cyclobutyl-2-fluoro-3-(pyridin-4-ylmethoxy)phenyl]pyrazin-2-amine |
| 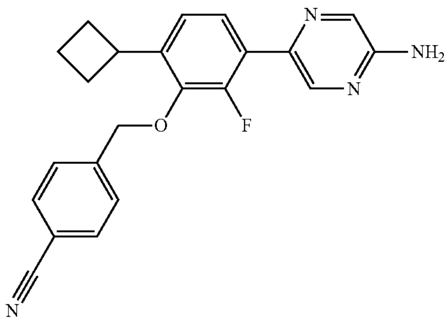 [SMILES: N#Cc1ccc(COc2c(C3CCC3)ccc(-c3cnc(N)cn3)c2F)cc1] | 15 | 4-{[3-(5-Aminopyrazin-2-yl)-6-cyclobutyl-2-fluorophenoxy]methyl}benzonitrile |
| 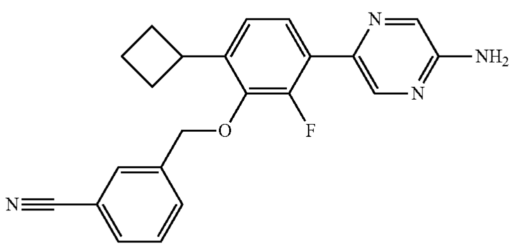 [SMILES: N#Cc1cccc(COc2c(C3CCC3)ccc(-c3cnc(N)cn3)c2F)c1] | 16 | 3-{[3-(5-Aminopyrazin-2-yl)-6-cyclobutyl-2-fluorophenoxy]methyl}benzonitrile |
| 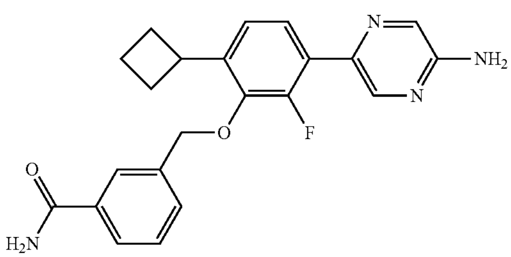 [SMILES: NC(=O)c1cccc(COc2c(C3CCC3)ccc(-c3cnc(N)cn3)c2F)c1] | 17 | 3-{[3-(5-Aminopyrazin-2-yl)-6-cyclobutyl-2-fluorophenoxy]methyl}benzamide |
| 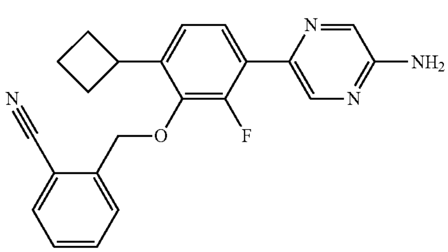 [SMILES: N#Cc1ccccc1COc1c(C2CCC2)ccc(-c2cnc(N)cn2)c1F] | 18 | 2-{[3-(5-Aminopyrazin-2-yl)-6-cyclobutyl-2-fluorophenoxy]methyl}benzonitrile |
| 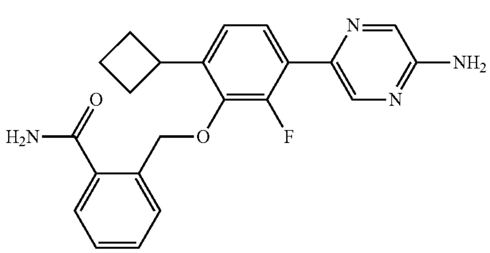 [SMILES: NC(=O)c1ccccc1COc1c(C2CCC2)ccc(-c2cnc(N)cn2)c1F] | 19 | 2-{[3-(5-Aminopyrazin-2-yl-6-cyclobutyl-2-fluorophenoxy]methyl}benzamide |

TABLE 3-continued

| STRUCTURE | COMPOUND # | NAME |
|---|---|---|
| 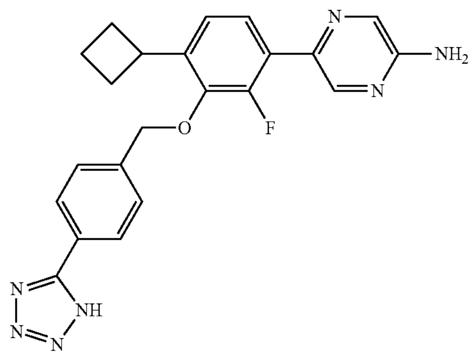 [SMILES: Nc1cnc(-c2ccc(C3CCC3)c(OCc3ccc(-c4nnn[nH]4)cc3)c2F)cn1] | 20 | 5-(4-Cyclobutyl-2-fluoro-3-{[4-(1H-tetrazol-5-yl)benzyl]oxy}phenyl)pyrazin-2-amine |
| 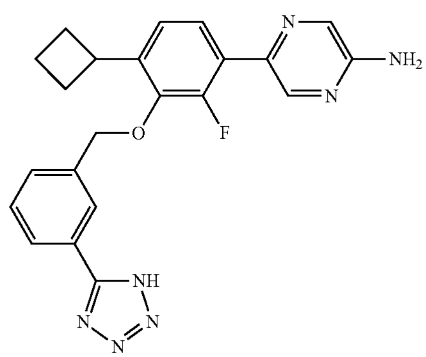 [SMILES: Nc1cnc(-c2ccc(C3CCC3)c(OCc3cccc(-c4nnn[nH]4)c3)c2F)cn1] | 21 | 5-(4-Cyclobutyl-2-fluoro-3-{[3-(1H-tetrazol-5-yl)benzyl]oxy}phenyl)pyrazin-2-amine |
| 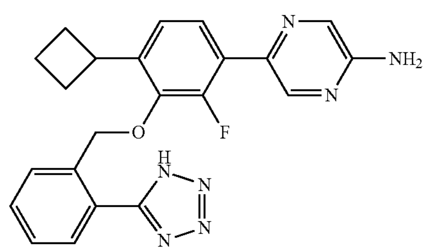 [SMILES: Nc1cnc(-c2ccc(C3CCC3)c(OCc3ccccc3-c3nnn[nH]3)c2F)cn1] | 22 | 5-(4-Cyclobutyl-2-fluoro-3-{[2-(1H-tetrazol-5-yl)benzyl]oxy}phenyl)pyrazin-2-amine |
| 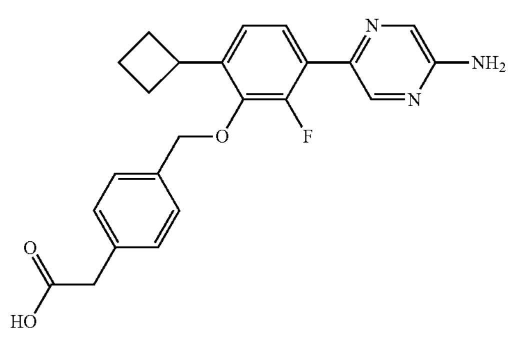 [SMILES: Nc1cnc(-c2ccc(C3CCC3)c(OCc3ccc(CC(=O)O)cc3)c2F)cn1] | 23 | (4-{[3-(5-Aminopyrazin-2-yl)-6-cyclobutyl-2-fluorophenoxy]methyl}phenyl)acetic acid |
| 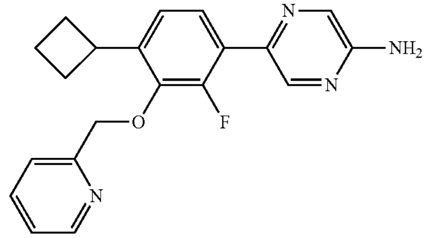 | 24 | 5-[4-Cyclobutyl-2-fluoro-3-(pyridin-2-ylmethoxy)phenyl]pyrazin-2-amine |

TABLE 3-continued
| STRUCTURE | COMPOUND # | NAME |
|---|---|---|
| 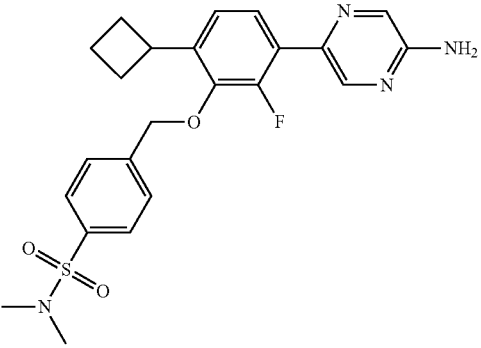 [SMILES: CN(C)S(=O)(=O)c1ccc(COc2c(C3CCC3)ccc(-c3cnc(N)cn3)c2F)cc1] | 25 | 4-{[3-(5-Aminopyrazin-2-yl)-6-cyclobutyl-2-fluorophenoxy]methyl}-N,N-dimethylbenzenesulfonamide |
| 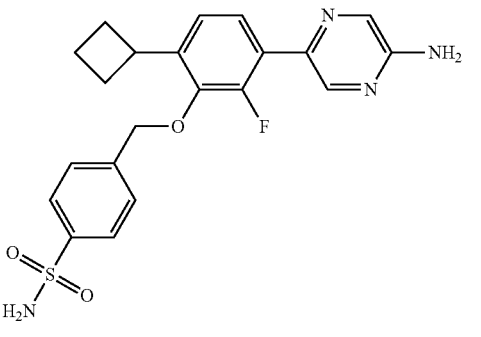 [SMILES: Nc1cnc(-c2ccc(C3CCC3)c(OCc3ccc(S(N)(=O)=O)cc3)c2F)cn1] | 26 | 4-{[3-(5-Aminopyrazin-2-yl)-6-cyclobutyl-2-fluorophenoxy]methyl}benzenesulfonamide |
| 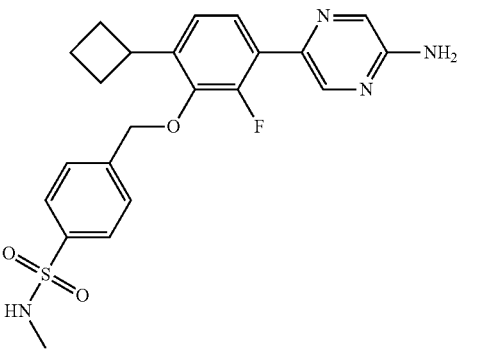 [SMILES: CNS(=O)(=O)c1ccc(COc2c(C3CCC3)ccc(-c3cnc(N)cn3)c2F)cc1] | 27 | 4-{[3-(5-Aminopyrazin-2-yl)-6-cyclobutyl-2-fluorophenoxy]methyl}-N-methylbenzenesulfonamide |
| 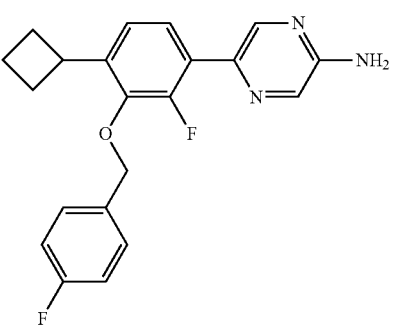 [SMILES: Nc1cnc(-c2ccc(C3CCC3)c(OCc3ccc(F)cc3)c2F)cn1] | 28 | 5-{4-Cyclobutyl-2-fluoro-3-[(4-fluorobenzyl)oxy]phenyl}pyrazin-2-amine |

TABLE 3-continued

| STRUCTURE | COMPOUND # | NAME |
|---|---|---|
| 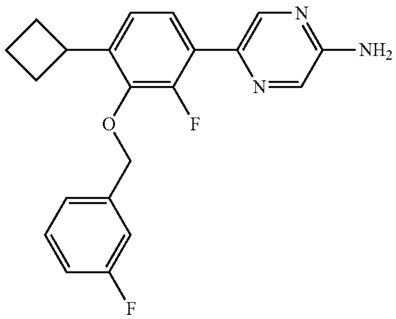 [SMILES: Nc1cnc(-c2ccc(C3CCC3)c(OCc3cccc(F)c3)c2F)cn1] | 29 | 5-{4-Cyclobutyl-2-fluoro-3-[(3-fluorobenzyl)oxy]phenyl}pyrazin-2-amine |
| 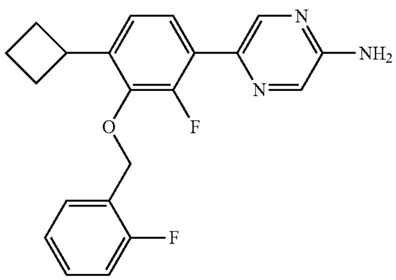 | 30 | 5-{4-Cyclobutyl-2-fluoro-3-[(2-fluorobenzyl)oxy]phenyl}pyrazin-2-amine |
| 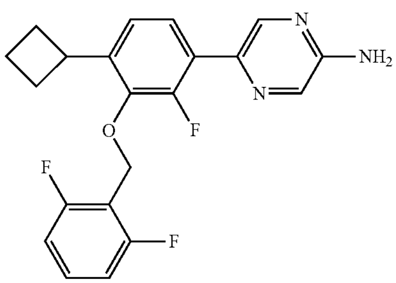 | 31 | 5-{4-Cyclobutyl-3-[(2,6-difluorobenzyl)oxy]-2-fluorophenyl}pyrazin-2-amine |
| 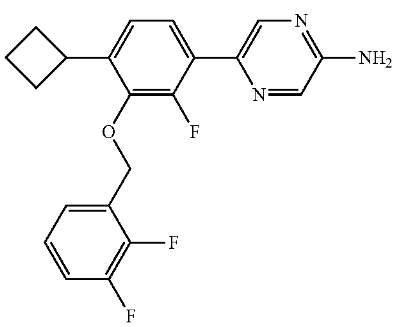 | 32 | 5-{4-Cyclobutyl-3-[(2,3-difluorobenzyl)oxy]-2-fluorophenyl}pyrazin-2-amine |
| 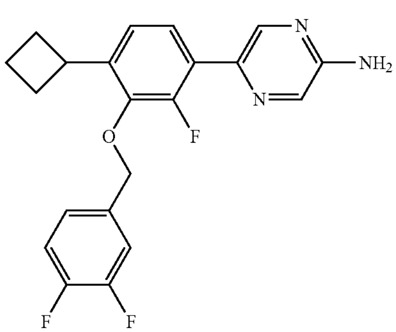 [SMILES: Nc1cnc(-c2ccc(C3CCC3)c(OCc3ccc(F)c(F)c3)c2F)cn1] | 33 | 5-{4-Cyclobutyl-3-[(3,4-difluorobenzyl)oxy]-2-fluorophenyl}pyrazin-2-amine |

TABLE 3-continued

| STRUCTURE | COMPOUND # | NAME |
|---|---|---|
| 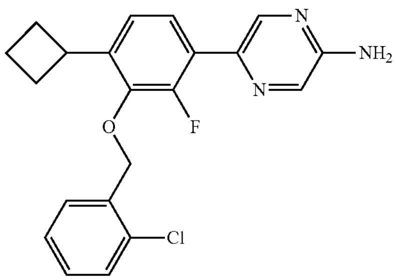 | 34 | 5-{3-[(2-Chlorobenzyl)oxy]-4-cyclobutyl-2-fluorophenyl}pyrazin-2-amine |
| 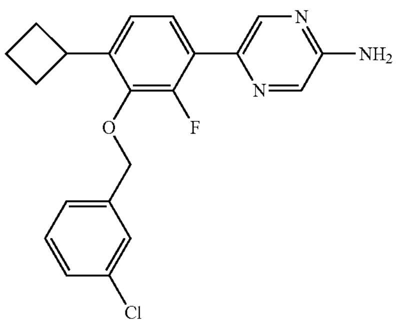 | 35 | 5-{3-[(3-Chlorobenzyl)oxy]-4-cyclobutyl-2-fluorophenyl}pyrazin-2-amine |
| 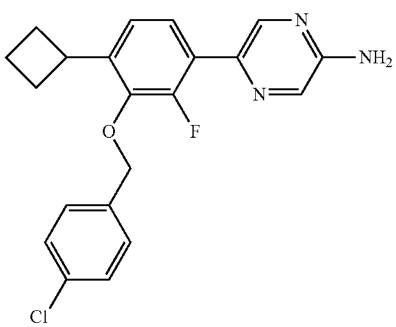 | 36 | 5-{3-[(4-Chlorobenzyl)oxy]-4-cyclobutyl-2-fluorophenyl}pyrazin-2-amine |
| 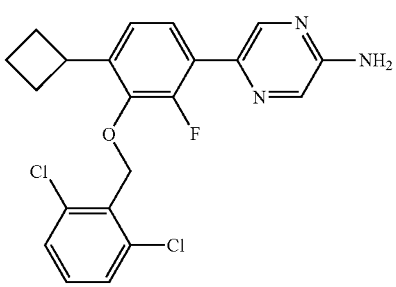 [SMILES: Nc1cnc(-c2ccc(C3CCC3)c(OCc3c(Cl)cccc3Cl)c2F)cn1] | 37 | 5-{4-Cyclobutyl-3-[(2,6-dichlorobenzyl)oxy]-2-fluorophenyl}pyrazin-2-amine |
| 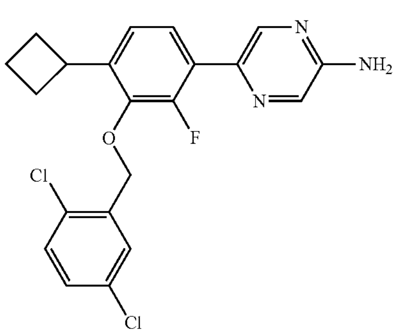 | 38 | 5-{4-Cyclobutyl-3-[(2,5-dichlorobenzyl)oxy]-2-fluorophenyl}pyrazin-2-amine |

TABLE 3-continued

| STRUCTURE | COMPOUND # | NAME |
|---|---|---|
| 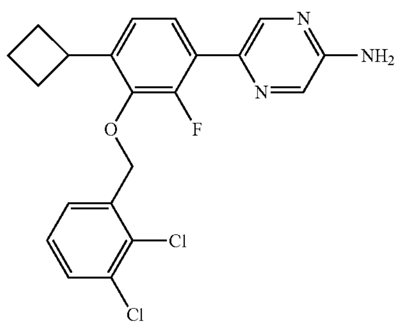 [SMILES: Nc1cnc(-c2ccc(C3CCC3)c(OCc3cccc(Cl)c3Cl)c2F)cn1] | 39 | 5-{4-Cyclobutyl-3-[(2,3-dichlorobenzy)oxy]-2-fluorophenyl}pyrazin-2-amine |
| 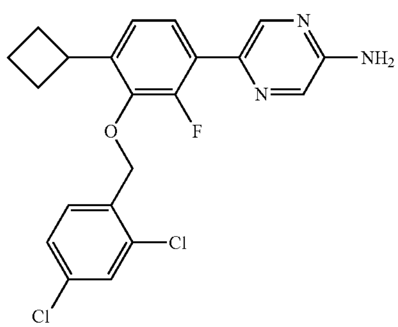 [SMILES: Nc1cnc(-c2ccc(C3CCC3)c(OCc3ccc(Cl)cc3Cl)c2F)cn1] | 40 | 5-{4-Cyclobutyl-3-[(2,4-dichlorobenzyl)oxy]-2-fluorophenyl}pyrazin-2-amine |
| 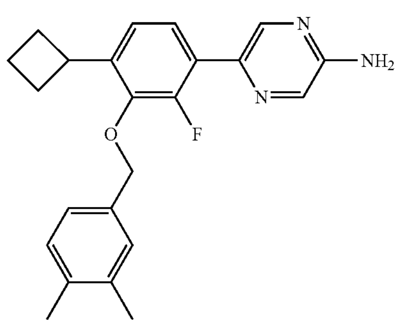 [SMILES: Cc1ccc(COc2c(C3CCC3)ccc(-c3cnc(N)cn3)c2F)cc1C] | 41 | 5-{4-Cyclobutyl-3-[(3,4-dimethybenzyl)oxy]-2-fluorophenyl}pyrazin-2-amine |
| 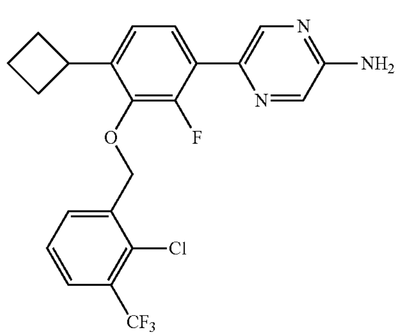 [SMILES: Nc1cnc(-c2ccc(C3CCC3)c(OCc3cccc(C(F)(F)F)c3Cl)c2F)cn1] | 42 | 5-(3-{[2-Chloro-3-(trifluoromethyl)benzyl]oxy}-4-cyclobutyl-2-fluorophenyl)pyrazin-2-amine |

TABLE 3-continued

| STRUCTURE | COMPOUND # | NAME |
|---|---|---|
| 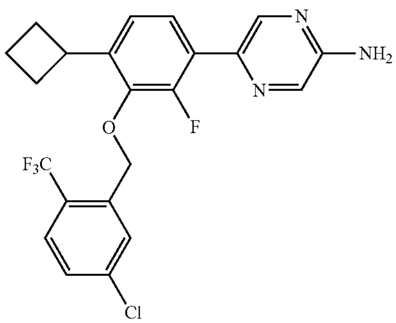 [SMILES: Nc1cnc(-c2ccc(C3CCC3)c(OCc3cc(Cl)ccc3C(F)(F)F)c2F)cn1] | 43 | 5-(3-{[5-Chloro-2-(trifluoromethyl)benzyl]oxy}-4-cyclobutyl-2-fluorophenyl)pyrazin-2-amine |
| 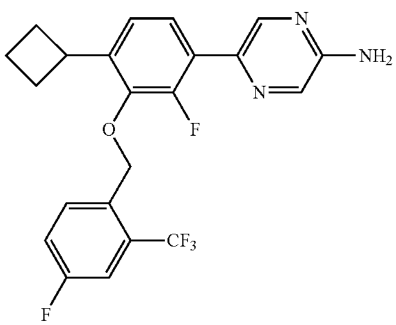 [SMILES: Nc1cnc(-c2ccc(C3CCC3)c(OCc3ccc(F)cc3C(F)(F)F)c2F)cn1] | 44 | 5-(4-Cyclobutyl-2-fluoro-3-{[4-fluoro-2-(trifluoromethyl)benzyl]oxy}phenyl)pyrazin-2-amine |
| 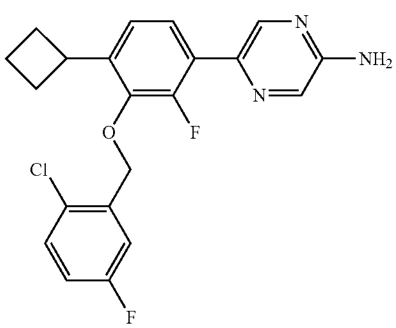 [SMILES: Nc1cnc(-c2ccc(C3CCC3)c(OCc3cc(F)ccc3Cl)c2F)cn1] | 45 | 5-{3-[(2-Chloro-5-fluorobenzyl)oxy]-4-cyclobutyl-2-fluorophenyl}pyrazin-2-amine |
| 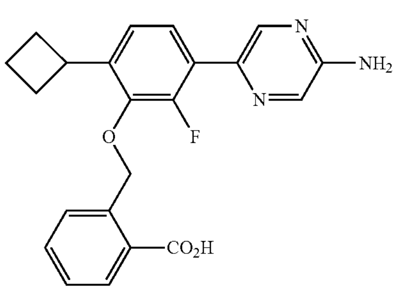 [SMILES: Nc1cnc(-c2ccc(C3CCC3)c(OCc3ccccc3C(=O)O)c2F)cn1] | 46 | 2-{[3-(5-Aminopyrazin-2-yl)-6-cyclobutyl-2-fluorophenoxy]methyl}benzoic acid |
| 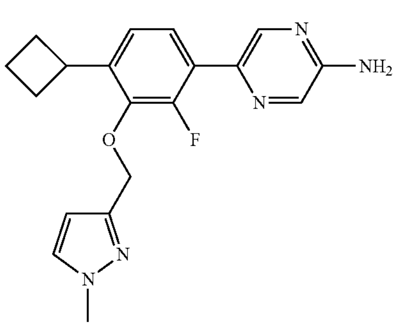 [SMILES: Cn1ccc(COc2c(C3CCC3)ccc(-c3cnc(N)cn3)c2F)n1] | 47 | 5-{4-Cyclobutyl-2-fluoro-3-[(1-methyl-1H-pyrazol-3-yl)methoxy]phenyl}pyrazin-2-amine |

TABLE 3-continued

| STRUCTURE | COMPOUND # | NAME |
|---|---|---|
| 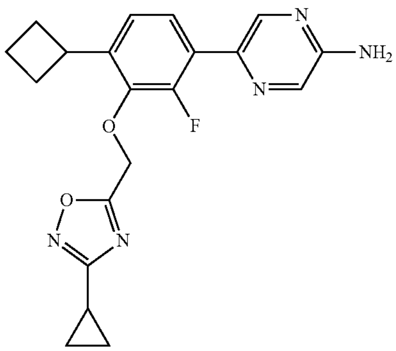 [SMILES: Nc1cnc(-c2ccc(C3CCC3)c(OCc3nc(C4CC4)no3)c2F)cn1] | 48 | 5-{4-Cyclobutyl-3-[(3-cyclopropyl-1,2,4-oxadiazol-5-yl)methoxy]-2-fluorophenyl}pyrazin-2-amine |
| 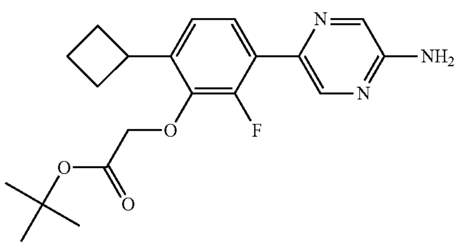 [SMILES: CC(C)(C)OC(=O)COc1c(C2CCC2)ccc(-c2cnc(N)cn2)c1F] | 49 | tert-Butyl [3-(5-aminopyrazin-2-yl)-6-cyclobutyl-2-fluorophenoxy]acetate |
| 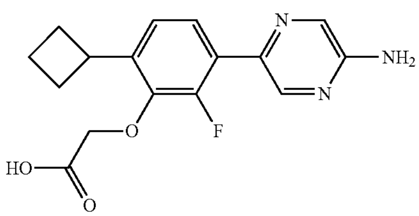 [SMILES: Nc1cnc(-c2ccc(C3CCC3)c(OCC(=O)O)c2F)cn1] | 50 | [3-(5-Aminopyrazin-2-yl)-6-cyclobutyl-2-fluorophenoxy]acetic acid |
| 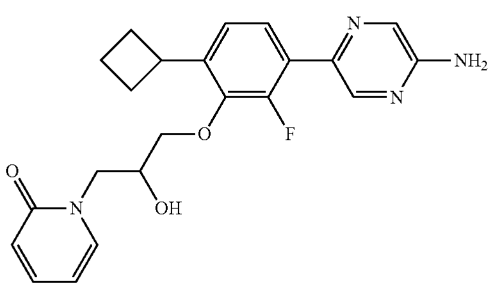 [SMILES: Nc1cnc(-c2ccc(C3CCC3)c(OCC(O)Cn3ccccc3=O)c2F)cn1] | 51 | racemic 1-(3-(3-(5-Aminopyrazin-2-yl)-6-cyclobutyl-2-fluorophenoxy)-2-hydroxypropyl)pyridin-2(1H)-one |
| 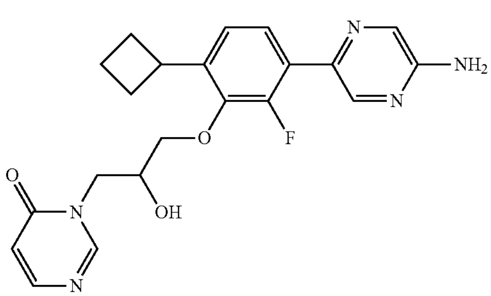 [SMILES: Nc1cnc(-c2ccc(C3CCC3)c(OCC(O)Cn3cnccc3=O)c2F)cn1] | 52 | racemic 3-(3-(3-(5-Aminopyrazin-2-yl)-6-cyclobutyl-2-fluorophenoxy)-2-hydroxypropyl)pyrimidin-4(3H)-one |

TABLE 3-continued

| STRUCTURE | COMPOUND # | NAME |
|---|---|---|
| 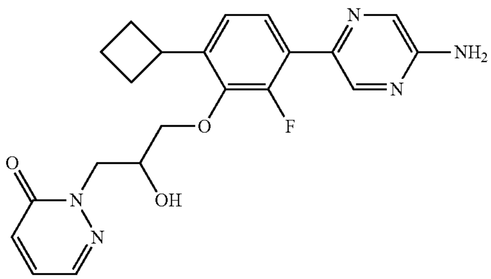 | 53 | racemic 2-(3-(3-(5-Aminopyrazin-2-yl)-6-cyclobutyl-2-fluorophenoxy)-2-hydroxypropyl)pyridazin-3(2H)-one |
| 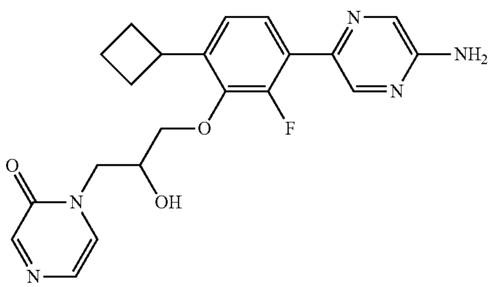 [SMILES: Nc1cnc(-c2ccc(C3CCC3)c(OCC(O)Cn3ccncc3=O)c2F)cn1] | 54 | racemic 1-(3-(3-(5-Aminopyrazin-2-yl)-6-cyclobutyl-2-fluorophenoxy)-2-hydroxypropyl)pyrazin-2(1H)-one |
| 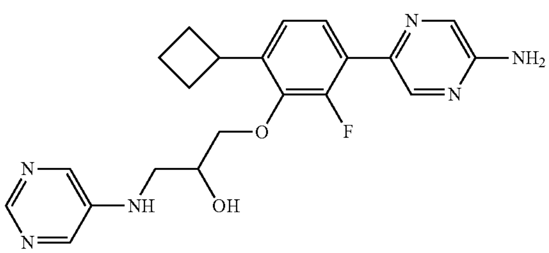 [SMILES: Nc1cnc(-c2ccc(C3CCC3)c(OCC(O)CNc3cncnc3)c2F)cn1] | 55 | racemic 1-(3-(5-Aminopyrazin-2-yl)-6-cyclobutyl-2-fluorophenoxy)-3-(pyrimidin-5-ylamino)propan-2-ol |
| 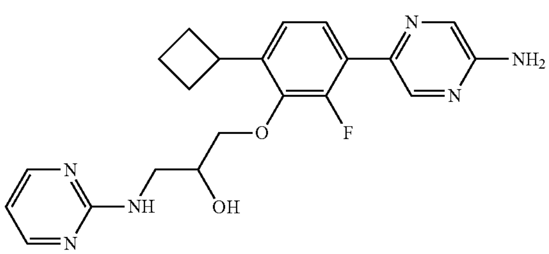 [SMILES: Nc1cnc(-c2ccc(C3CCC3)c(OCC(O)CNc3ncccn3)c2F)cn1] | 56 | racemic 1-(3-(5-Aminopyrazin-2-yl)-6-cyclobutyl-2-fluorophenoxy)-3-(pyrimidin-2-ylamino)propan-2-ol |
| 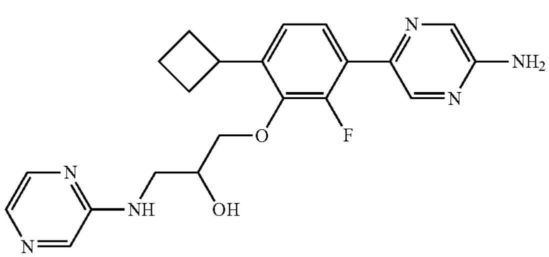 [SMILES: Nc1cnc(-c2ccc(C3CCC3)c(OCC(O)CNc3cnccn3)c2F)cn1] | 57 | racemic 1-(3-(5-Aminopyrazin-2-yl)-6-cyclobutyl-2-fluorophenoxy)-3-(pyrazin-2-ylamino)propan-2-ol |
| 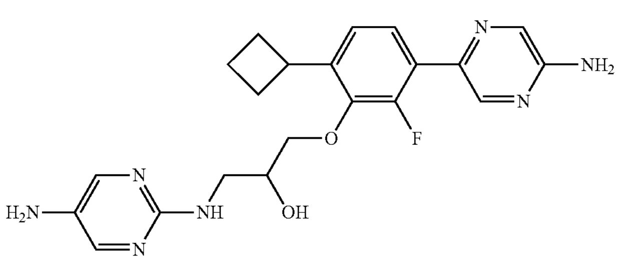 [SMILES: Nc1cnc(NCC(O)COc2c(C3CCC3)ccc(-c3cnc(N)cn3)c2F)nc1] | 58 | racemic 1-(3-(5-Aminopyrazin-2-yl)-6-cyclobutyl-2-fluorophenoxy)-3-((5-aminopyrimidin-2-yl)amino)propan-2-ol |

TABLE 3-continued

| STRUCTURE | COMPOUND # | NAME |
|---|---|---|
| 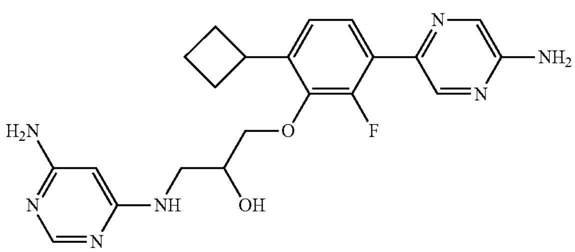 [SMILES: Nc1cnc(-c2ccc(C3CCC3)c(OCC(O)CNc3cc(N)ncn3)c2F)cn1] | 59 | racemic 1-(3-(5-Aminopyrazin-2-yl)-6-cyclobutyl-2-fluorophenoxy)-3-((6-aminopyrimidin-4-yl)amino)propan-2-ol |
| 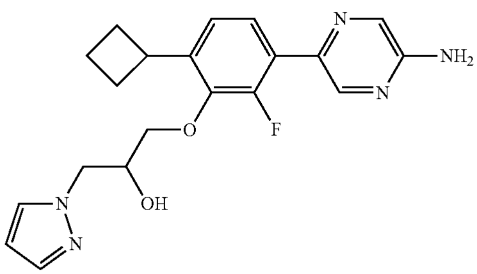 [SMILES: Nc1cnc(-c2ccc(C3CCC3)c(OCC(O)Cn3cccn3)c2F)cn1] | 60 | racemic 1-(3-(5-Aminopyrazin-2-yl)-6-cyclobutyl-2-fluorophenoxy)-3-(1H-pyrazol-1-yl)propan-2-ol |
| 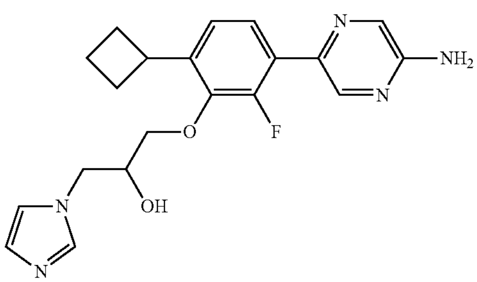 [SMILES: Nc1cnc(-c2ccc(C3CCC3)c(OCC(O)Cn3ccnc3)c2F)cn1] | 61 | racemic 1-(3-(5-Aminopyrazin-2-yl)-6-cyclobutyl-2-fluorophenoxy)-3-(1H-imidazol-1-yl)propan-2-ol |
| 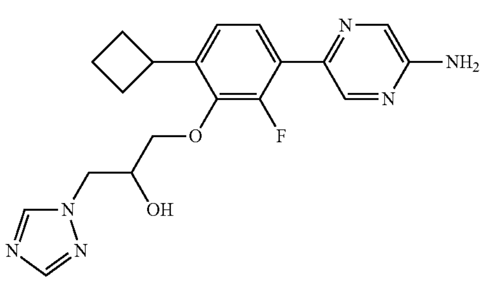 [SMILES: Nc1cnc(-c2ccc(C3CCC3)c(OCC(O)Cn3cncn3)c2F)cn1] | 62 | racemic 1-(3-(5-Aminopyrazin-2-yl)-6-cyclobutyl-2-fluorophenoxy)-3-(1H-1,2,4-triazol-1-yl)propan-2-ol |
| 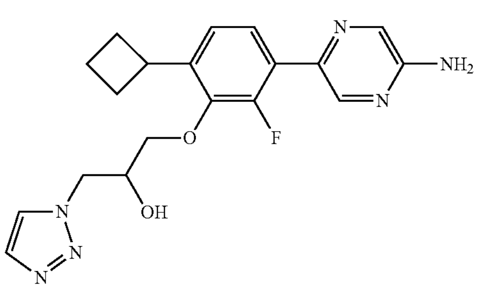 | 63 | racemic 1-(3-(5-Aminopyrazin-2-yl)-6-cyclobutyl-2-fluorophenoxy)-3-(1H-1,2,3-triazol-1-yl)propan-2-ol |

TABLE 3-continued

| STRUCTURE | COMPOUND # | NAME |
|---|---|---|
| 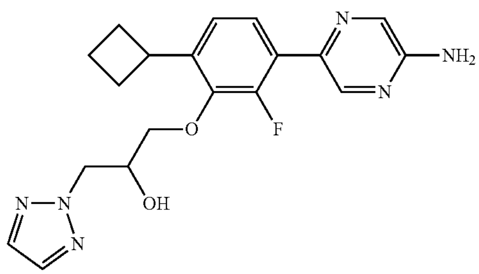 [SMILES: Nc1cnc(-c2ccc(C3CCC3)c(OCC(O)Cn3nccn3)c2F)cn1] | 64 | racemic 1-(3-(5-Aminopyrazin-2-yl)-6-cyclobutyl-2-fluorophenoxy)-3-(2H-1,2,3-triazol-2-yl)propan-2-ol |
| 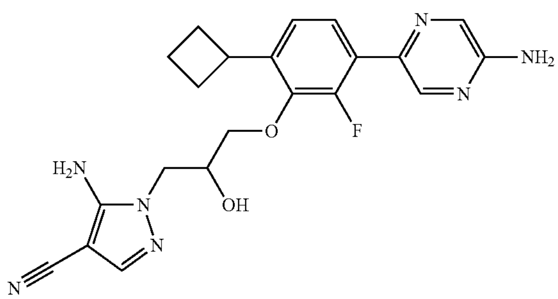 [SMILES: N#Cc1cnn(CC(O)COc2c(C3CCC3)ccc(-c3cnc(N)cn3)c2F)c1N] | 65 | racemic 5-Amino-1-(3-(3-(5-aminopyrazin-2-yl)-6-cyclobutyl-2-fluorophenoxy)-2-hydroxypropyl)-1H-pyrazole-4-carbonitrile |
| 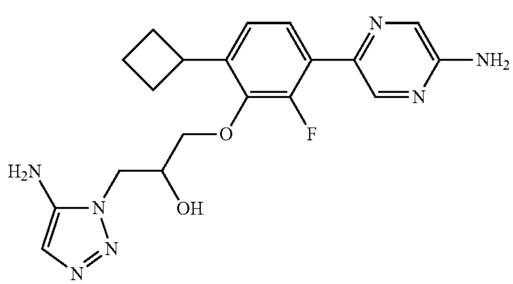 [SMILES: Nc1cnc(-c2ccc(C3CCC3)c(OCC(O)Cn3nncc3N)c2F)cn1] | 66 | racemic 1-(5-Amino-1H-1,2,3-triazol-1-yl)-3-(3-(5-aminopyrazin-2-yl)-6-cyclobutyl-2-fluorophenoxy)propan-2-ol |
| 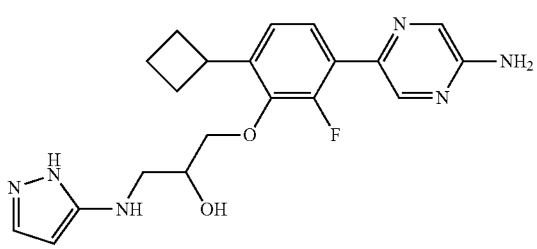 [SMILES: Nc1cnc(-c2ccc(C3CCC3)c(OCC(O)CNc3ccn[nH]3)c2F)cn1] | 67 | racemic 1-((1H-Pyrazol-5-yl)amino)-3-(3-(5-aminopyrazin-2-yl)-6-cyclobutyl-2-fluorophenoxy)propan-2-ol |
| 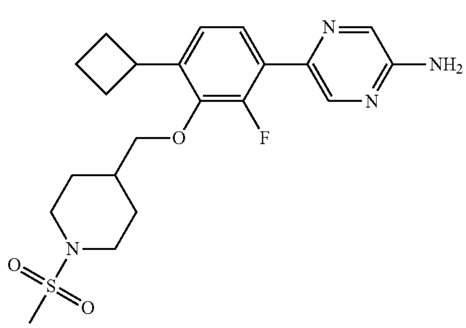 [SMILES: CS(=O)(=O)N1CCC(COc2c(C3CCC3)ccc(-c3cnc(N)cn3)c2F)CC1] | 68 | 5-(4-Cyclobutyl-2-fluoro-3-{[1-(methylsulfonyl)piperidin-4-yl]methoxy}phenyl)pyrazin-2-amine |

TABLE 3-continued

| STRUCTURE | COMPOUND # | NAME |
|---|---|---|
| 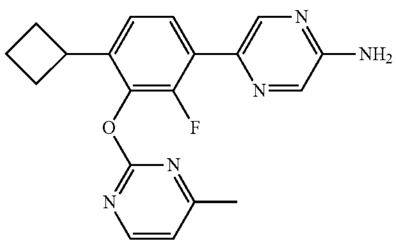 [SMILES: Cc1ccnc(Oc2c(C3CCC3)ccc(-c3cnc(N)cn3)c2F)n1] | 69 | 5-{4-Cyclobutyl-2-fluoro-3-[(4-methylpyrimidin-2-yl)oxy]phenyl}pyrazin-2-amine |
| 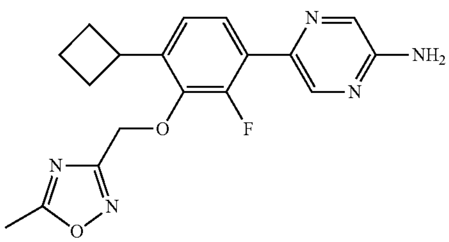 [SMILES: Cc1nc(COc2c(C3CCC3)ccc(-c3cnc(N)cn3)c2F)no1] | 70 | racemic 5-{4-Cyclobutyl-2-fluoro-3-[(5-methyl-1,2,4-oxadiazol-3-yl)methoxy]phenyl}pyrazin-2-amine |
| 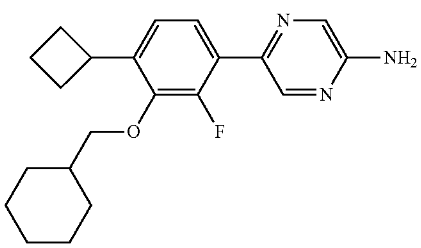 [SMILES: Nc1cnc(-c2ccc(C3CCC3)c(OCC3CCCCC3)c2F)cn1] | 71 | 5-[4-Cyclobutyl-3-(cyclohexylmethoxy)-2-fluorophenyl]pyrazin-2-amine |
| 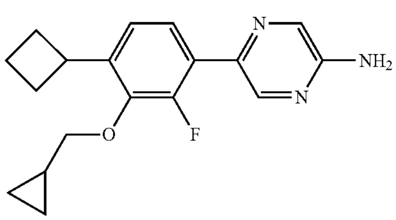 [SMILES: Nc1cnc(-c2ccc(C3CCC3)c(OCC3CC3)c2F)cn1] | 72 | 5-[4-Cyclobutyl-3-(cyclopropylmethoxy)-2-fluorophenyl]pyrazin-2-amine |
| 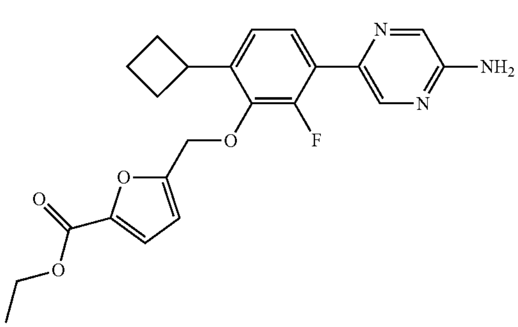 [SMILES: CCOC(=O)c1ccc(COc2c(C3CCC3)ccc(-c3cnc(N)cn3)c2F)o1] | 73 | Ethyl 5-{[3-(5-aminopyrazin-2-yl)-6-cyclobutyl-2-fluorophenoxy]methyl}furan-2-carboxylate |

TABLE 3-continued

| STRUCTURE | COMPOUND # | NAME |
|---|---|---|
| 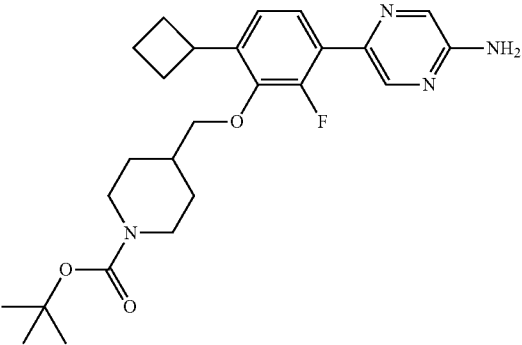 [SMILES: CC(C)(C)OC(=O)N1CCC(COc2c(C3CCC3)ccc(-c3cnc(N)cn3)c2F)CC1] | 74 | tert-Butyl 4-{[3-(5-aminopyrazin-2-yl)-6-cyclobutyl-2-fluorophenoxy]methyl}piperidine-1-carboxylate |
| 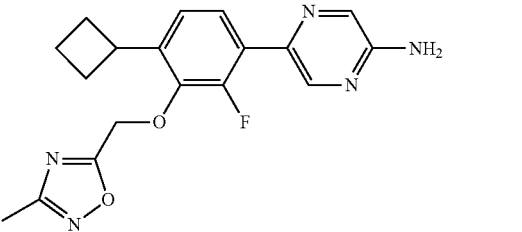 [SMILES: Cc1noc(COc2c(C3CCC3)ccc(-c3cnc(N)cn3)c2F)n1] | 75 | 5-{4-Cyclobutyl-2-fluoro-3-[(3-methyl-1,2,4-oxadiazol-5-yl)methoxy]phenyl}pyrazin-2-amine |
| 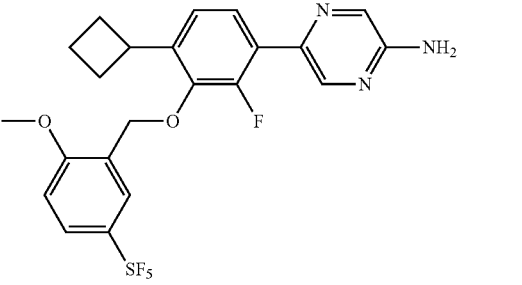 | 76 | 5-(4-Cyclobutyl-2-fluoro-3-{[2-methoxy-5-(pentafluoro-lambda~6~-sulfanyl)benzyl]oxy}phenyl)pyrazin-2-amine |
| 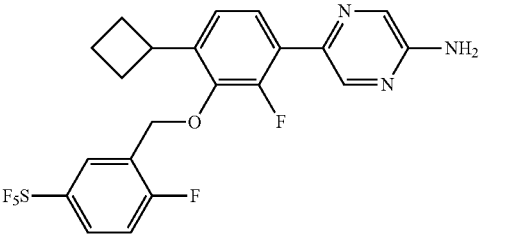 | 77 | 5-(4-Cyclobutyl-2-fluoro-3-{[2-fluoro-5-(pentafluoro-lambda~6~-sulfanyl)benzyl]oxy}phenyl)pyrazin-2-amine |
| 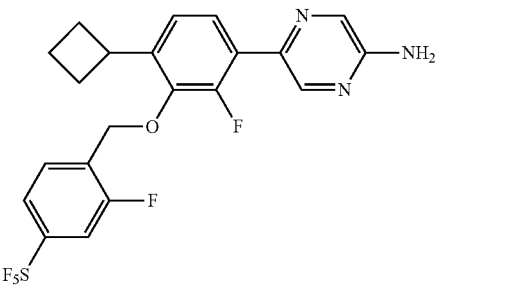 | 78 | 5-(4-Cyclobutyl-2-fluoro-3-{[2-fluoro-4-(pentafluoro-lambda~6~-sulfanyl)benzyl]oxy}phenyl)pyrazin-2-amine |

TABLE 3-continued

| STRUCTURE | COMPOUND # | NAME |
|---|---|---|
| 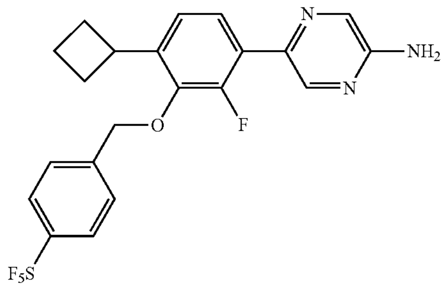 | 79 | 5-(4-Cyclobutyl-2-fluoro-3-{[4-(pentafluoro-lambda~6~-sulfanyl)benzyl]oxy}phenyl)pyrazin-2-amine |
| 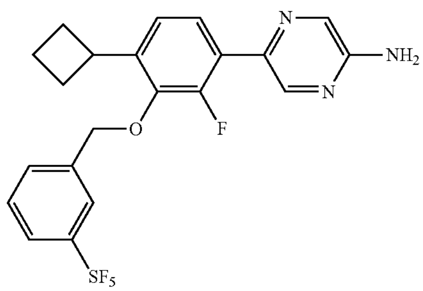 | 80 | 5-(4-Cyclobutyl-2-fluoro-3-{[3-(pentafluoro-lambda~6~-sulfanyl)benzyl]oxy}phenyl)pyrazin-2-amine |
| 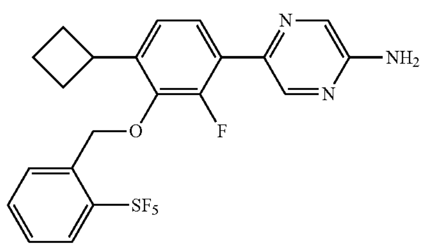 | 81 | 5-(4-Cyclobutyl-2-fluoro-3-{[2-(pentafluoro-lambda~6~-sulfanyl)benzyl]oxy}phenyl)pyrazin-2-amine |
| 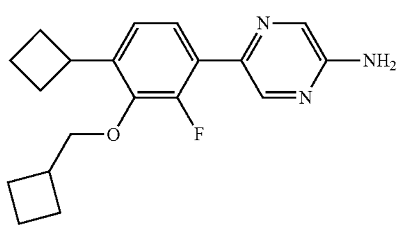 [SMILES: Nc1cnc(-c2ccc(C3CCC3)c(OCC3CCC3)c2F)cn1] | 82 | 5-[4-Cyclobutyl-3-(cyclobutylmethoxy)-2-fluorophenyl]pyrazin-2-amine |
| 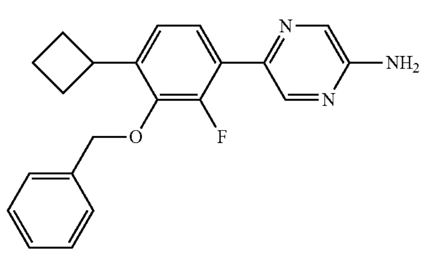 | 83 | 5-[3-(Benzyloxy)-4-cyclobutyl-2-fluorophenyl]-pyrazin-2-amine |
| 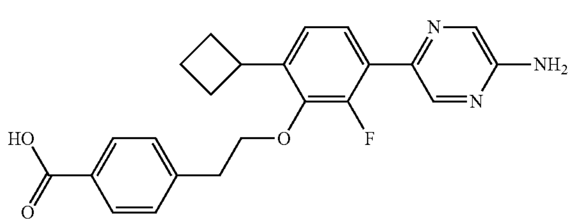 [SMILES: Nc1cnc(-c2ccc(C3CCC3)c(OCCc3ccc(C(=O)O)cc3)c2F)cn1] | 84 | 4-{2-[3-(5-Aminopyrazin-2-yl)-6-cyclobutyl-2-fluorophenoxy]ethyl}benzoic acid |

TABLE 3-continued

| STRUCTURE | COMPOUND # | NAME |
|---|---|---|
| 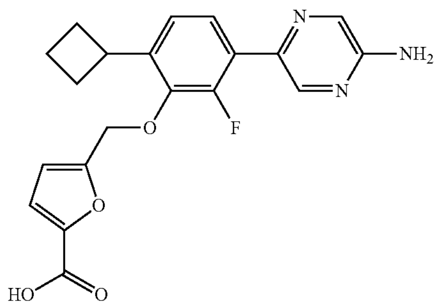 [SMILES: Nc1cnc(-c2ccc(C3CCC3)c(OCc3ccc(C(=O)O)o3)c2F)cn1] | 85 | 5-{[3-(5-Aminopyrazin-2-yl)-6-cyclobutyl-2-fluorophenoxy]methyl}furan-2-carboxylic acid |
| 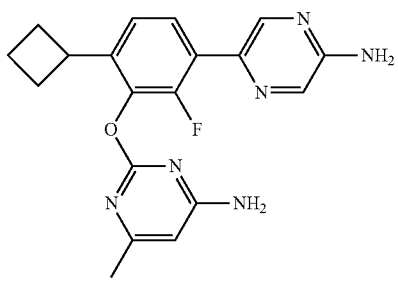 [SMILES: Cc1cc(N)nc(Oc2c(C3CCC3)ccc(-c3cnc(N)cn3)c2F)n1] | 86 | 2-[3-(5-Aminopyrazin-2-yl)-6-cyclobutyl-2-fluorophenoxy]-6-methylpyrimidin-4-amine |
| 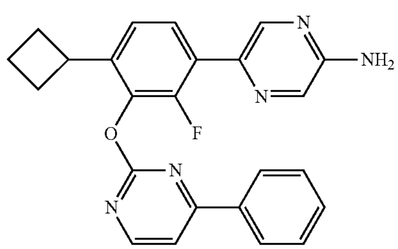 [SMILES: Nc1cnc(-c2ccc(C3CCC3)c(Oc3nccc(-c4ccccc4)n3)c2F)cn1] | 87 | 5-{4-Cyclobutyl-2-fluoro-3-[(4-phenylpyrimidin-2-yl)oxy]phenyl}pyrazin-2-amine |
| 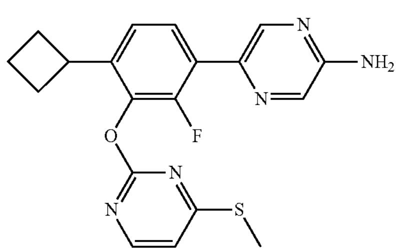 [SMILES: CSc1ccnc(Oc2c(C3CCC3)ccc(-c3cnc(N)cn3)c2F)n1] | 88 | 5-(4-Cyclobutyl-2-fluoro-3-{[4-(methylsulfanyl)pyrimidin-2-yl]oxy}phenyl)pyrazin-2-amine |
| 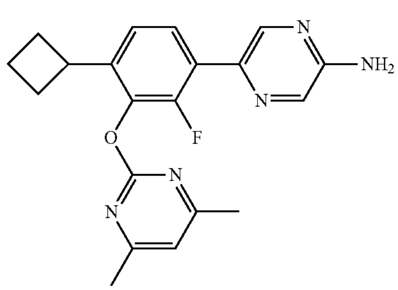 [SMILES: Cc1cc(C)nc(Oc2c(C3CCC3)ccc(-c3cnc(N)cn3)c2F)n1] | 89 | 5-{4-Cyclobutyl-3-[(4,6-dimethylpyrimidin-2-yl)oxy]-2-fluorophenyl}pyrazin-2-amine |

TABLE 3-continued

| STRUCTURE | COMPOUND # | NAME |
|---|---|---|
| 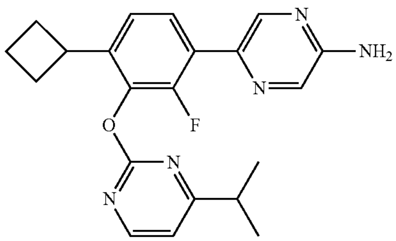 [SMILES: CC(C)c1ccnc(Oc2c(C3CCC3)ccc(-c3cnc(N)cn3)c2F)n1] | 90 | 5-(4-Cyclobutyl-2-fluoro-3-{[4-(1-methylethyl)pyrimidin-2-yl]oxy}phenyl)pyrazin-2-amine |
| 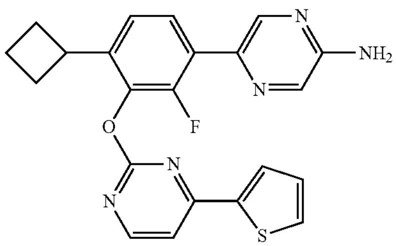 [SMILES: Nc1cnc(-c2ccc(C3CCC3)c(Oc3nccc(-c4cccs4)n3)c2F)cn1] | 91 | 5-{4-Cyclobutyl-2-fluoro-3-[(4-thiophen-2-ylpyrimidin-2-yl)oxy]phenyl}pyrazin-2-amine |
| 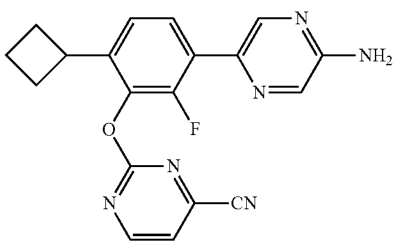 | 92 | 2-[3-(5-Aminopyrazin-2-yl)-6-cyclobutyl-2-fluorophenoxy]pyrimidine-4-carbonitrile |
| 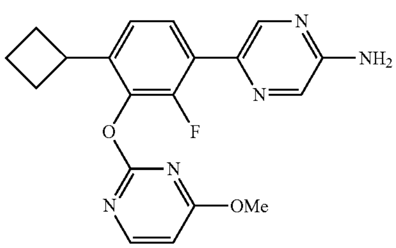 [SMILES: N#Cc1ccnc(Oc2c(C3CCC3)ccc(-c3cnc(N)cn3)c2F)n1] | 93 | 5-{4-Cyclobutyl-2-fluoro-3-[(4-methoxypyrimidin-2-yl)oxy]phenyl}pyrazin-2-amine |
| 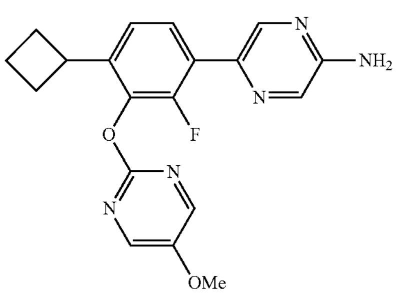 [SMILES: COc1cnc(Oc2c(C3CCC3)ccc(-c3cnc(N)cn3)c2F)nc1] | 94 | 5-{4-Cyclobutyl-2-fluoro-3-[(5-methoxypyrimidin-2-yl)oxy]phenyl}pyrazin-2-amine |
| 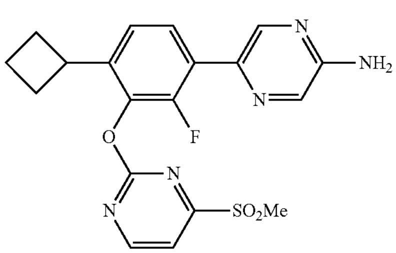 [SMILES: CS(=O)(=O)c1ccnc(Oc2c(C3CCC3)ccc(-c3cnc(N)cn3)c2F)n1] | 95 | 5-(4-Cyclobutyl-2-fluoro-3-{[4-(methylsulfonyl)pyrimidin-2-yl]oxy}phenyl)pyrazin-2-amine |

TABLE 3-continued

| STRUCTURE | COMPOUND # | NAME |
|---|---|---|
| 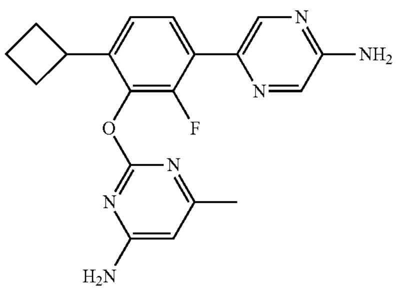 | 96 | 4-[3-(5-Aminopyrazin-2-yl)-6-cyclobutyl-2-fluorophenoxy]-6-methylpyrimidin-2-amine |
| 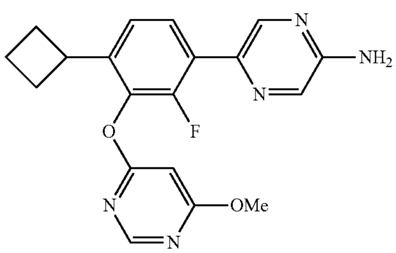 | 97 | 5-{4-Cyclobutyl-2-fluoro-3-[(6-methoxypyrimidin-4-yl)oxy]phenyl}pyrazin-2-amine |
| 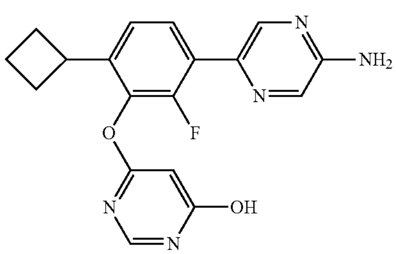 | 98 | 6-[3-(5-Aminopyrazin-2-yl)-6-cyclobutyl-2-fluorophenoxy]pyrimidin-4-ol |
| 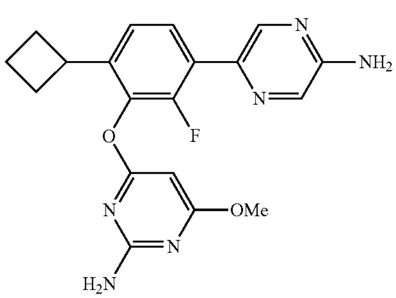 [SMILES: COc1cc(Oc2c(C3CCC3)ccc(-c3cnc(N)cn3)c2F)nc(N)n1] | 99 | 4-[3-(5-Aminopyrazin-2-yl)-6-cyclobutyl-2-fluorophenoxy]-6-methoxypyrimidin-2-amine |
| 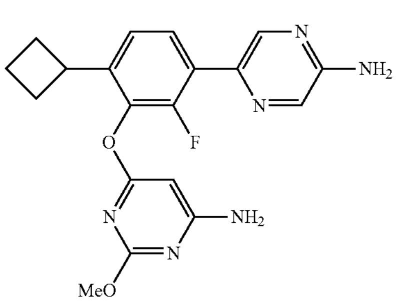 [SMILES: COc1nc(N)cc(Oc2c(C3CCC3)ccc(-c3cnc(N)cn3)c2F)n1] | 100 | 6-[3-(5-Aminopyrazin-2-yl)-6-cyclobutyl-2-fluorophenoxy]-2-methoxypyrimidin-4-amine |

TABLE 3-continued

| STRUCTURE | COMPOUND # | NAME |
|---|---|---|
| 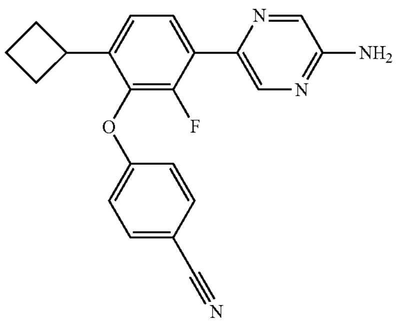 | 101 | 4-[3-(5-Aminopyrazin-2-yl)-6-cyclobutyl-2-fluorophenoxy]benzonitrile |
| 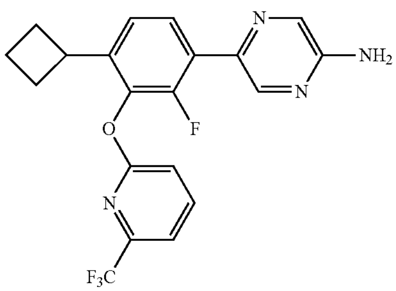 | 102 | 5-(4-Cyclobutyl-2-fluoro-3-{[6-(trifluoromethyl)pyridin-2-yl]oxy}phenyl)pyrazin-2-amine |
| 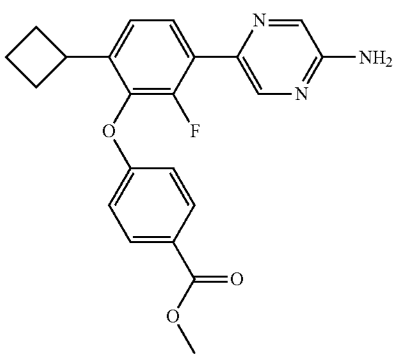 [SMILES: COC(=O)c1ccc(Oc2c(C3CCC3)ccc(-c3cnc(N)cn3)c2F)cc1] | 103 | Methyl 4-[3-(5-aminopyrazin-2-yl)-6-cyclobutyl-2-fluorophenoxy]benzoate |
| 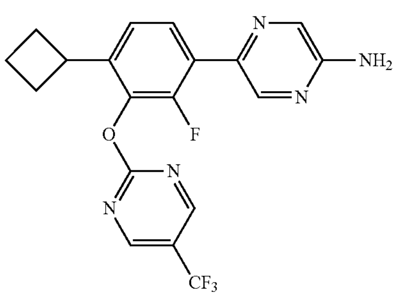 | 104 | 5-(4-Cyclobutyl-2-fluoro-3-{[5-(trifluoromethyl)pyrimidin-2-yl]oxy}phenyl)pyrazin-2-amine |
| 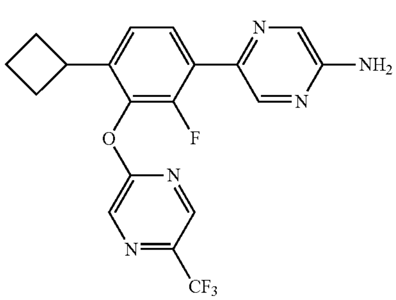 | 105 | 5-(4-Cyclobutyl-2-fluoro-3-{[5-(trifluoromethyl)pyrazin-2-yl]oxy}phenyl)pyrazin-2-amine |

TABLE 3-continued

| STRUCTURE | COMPOUND # | NAME |
|---|---|---|
| 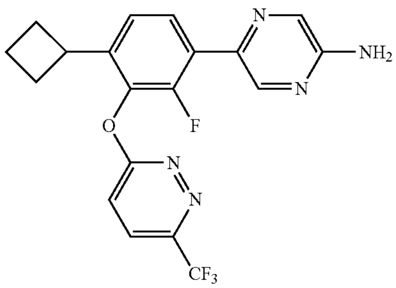 | 106 | 5-(4-Cyclobutyl-2-fluoro-3-{[6-(trifluoromethyl)pyridazin-3-yl]oxy}phenyl)pyrazin-2-amine |
| 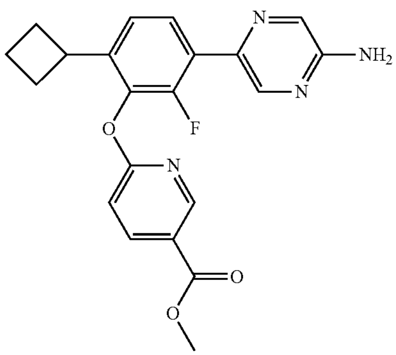 | 107 | Methyl 6-[3-(5-aminopyrazin-2-yl)-6-cyclobutyl-2-fluorophenoxy]pyridine-3-carboxylate |
| 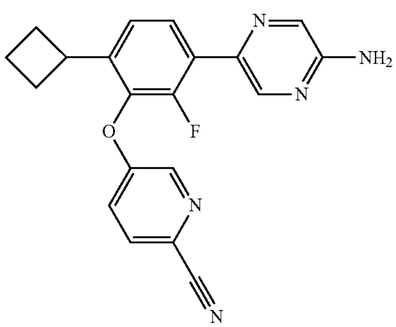 [SMILES: N#Cc1ccc(Oc2c(C3CCC3)ccc(-c3cnc(N)cn3)c2F)cn1] | 108 | 5-[3-(5-Aminopyrazin-2-yl)-6-cyclobutyl-2-fluorophenoxy]pyridine-2-carbonitrile |
| 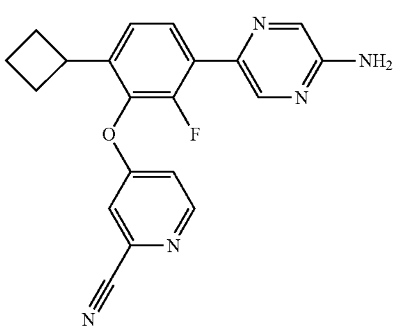 [SMILES: N#Cc1cc(Oc2c(C3CCC3)ccc(-c3cnc(N)cn3)c2F)ccn1] | 109 | 4-[3-(5-Aminopyrazin-2-yl)-6-cyclobutyl-2-fluorophenoxy]pyridine-2-carbonitrile |
| 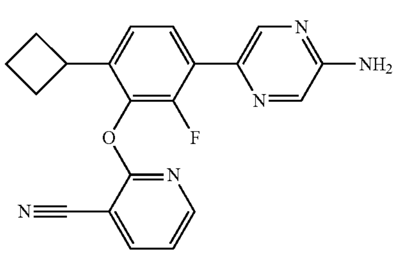 [SMILES: N#Cc1cccnc1Oc1c(C2CCC2)ccc(-c2cnc(N)cn2)c1F] | 110 | 2-[3-(5-Aminopyrazin-2-yl)-6-cyclobutyl-2-fluorophenoxy]pyridine-3-carbonitrile |

TABLE 3-continued

| STRUCTURE | COMPOUND # | NAME |
|---|---|---|
| 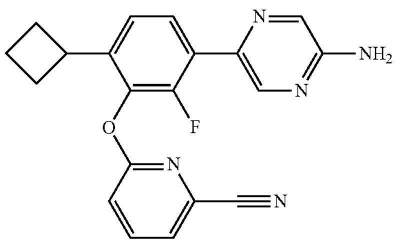 [SMILES: N#Cc1cccc(Oc2c(C3CCC3)ccc(-c3cnc(N)cn3)c2F)n1] | 111 | 6-[3-(5-Aminopyrazin-2-yl)-6-cyclobutyl-2-fluorophenoxy]pyridine-2-carbonitrile |
| 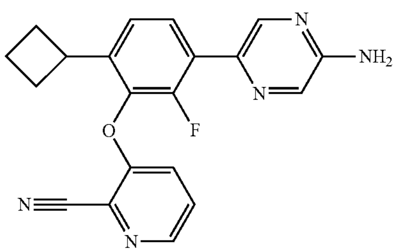 [SMILES: N#Cc1ncccc1Oc1c(C2CCC2)ccc(-c2cnc(N)cn2)c1F] | 112 | 3-[3-(5-Aminopyrazin-2-yl)-6-cyclobutyl-2-fluorophenoxy]pyridine-2-carbonitrile |
| 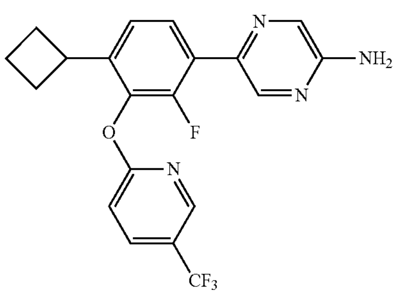 [SMILES: Nc1cnc(-c2ccc(C3CCC3)c(Oc3ccc(C(F)(F)F)cn3)c2F)cn1] | 113 | 5-(4-Cyclobutyl-2-fluoro-3-{[5-(trifluoromethyl)pyridin-2-yl]oxy}phenyl)pyrazin-2-amine |
| 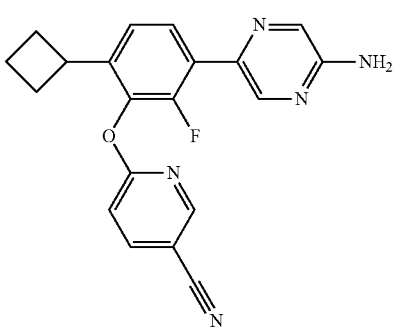 | 114 | 6-[3-(5-Aminopyrazin-2-yl)-6-cyclobutyl-2-fluorophenoxy]pyridine-3-carbonitrile |
| 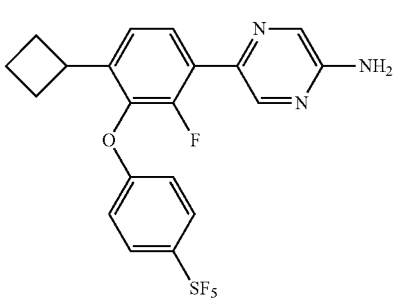 | 115 | 5-{4-Cyclobutyl-2-fluoro-3-[4-(pentafluoro-lambda~6~-sulfanyl)phenoxy]phenyl}pyrazin-2-amine |

TABLE 3-continued

| STRUCTURE | COMPOUND # | NAME |
|---|---|---|
| 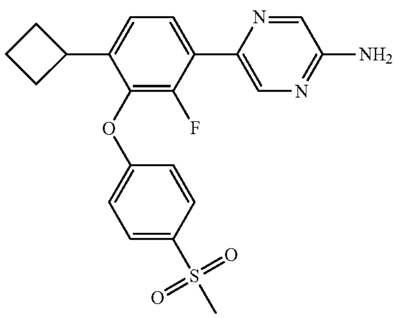 [SMILES: CS(=O)(=O)c1ccc(Oc2c(C3CCC3)ccc(-c3cnc(N)cn3)c2F)cc1] | 116 | 5-{4-Cyclobutyl-2-fluoro-3-[4-(methylsulfonyl)phenoxy]phenyl}pyrazin-2-amine |
| 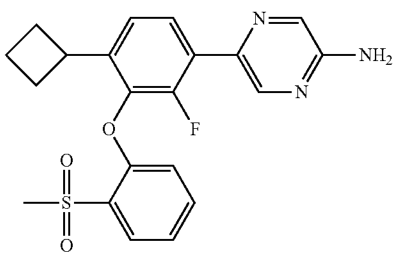 [SMILES: CS(=O)(=O)c1ccccc1Oc1c(C2CCC2)ccc(-c2cnc(N)cn2)c1F] | 117 | 5-{4-Cyclobutyl-2-fluoro-3-[2-(methylsulfonyl)phenoxy]phenyl}pyrazin-2-amine |
| 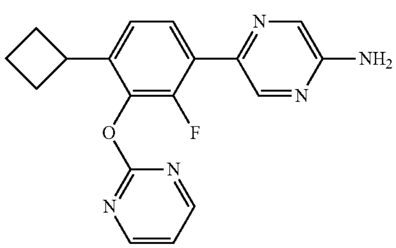 [SMILES: Nc1cnc(-c2ccc(C3CCC3)c(Oc3ncccn3)c2F)cn1] | 118 | 5-[4-Cyclobutyl-2-fluoro-3-(pyrimidin-2-yloxy)phenyl]pyrazin-2-amine |
| 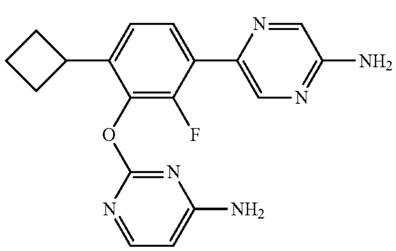 [SMILES: Nc1cnc(-c2ccc(C3CCC3)c(Oc3nccc(N)n3)c2F)cn1] | 119 | 2-[3-(5-Aminopyrazin-2-yl)-6-cyclobutyl-2-fluorophenoxy]pyrimidin-4-amine |
| 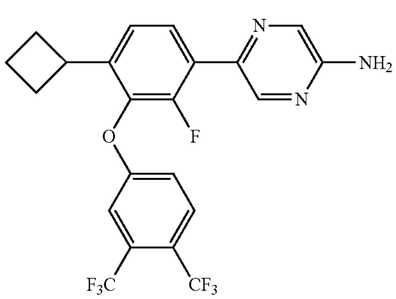 [SMILES: Nc1cnc(-c2ccc(C3CCC3)c(Oc3ccc(C(F)(F)F)c(C(F)(F)F)c3)c2F)cn1] | 120 | 5-{3-[3,4-Bis(trifluoromethyl)phenoxy]-4-cyclobutyl-2-fluorophenyl}pyrazin-2-amine |

TABLE 3-continued

| STRUCTURE | COMPOUND # | NAME |
|---|---|---|
| 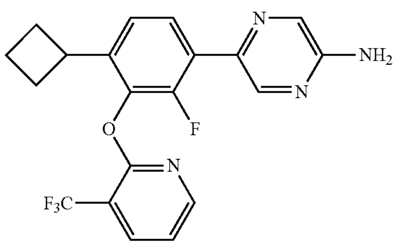 | 121 | 5-(4-Cyclobutyl-2-fluoro-3-{[3-(trifluoromethyl)pyridin-2-yl]oxy}phenyl)pyrazin-2-amine |
| 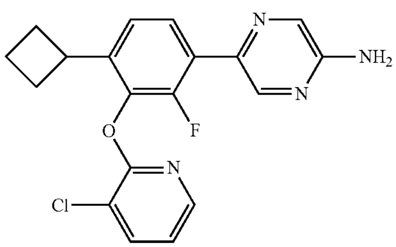 [SMILES: Nc1cnc(-c2ccc(C3CCC3)c(Oc3ncccc3C(F)(F)F)c2F)cn1] | 122 | 5-{3-[(3-Chloropyridin-2-yl)oxy]-4-cyclobutyl-2-fluorophenyl}pyrazin-2-amine |
| 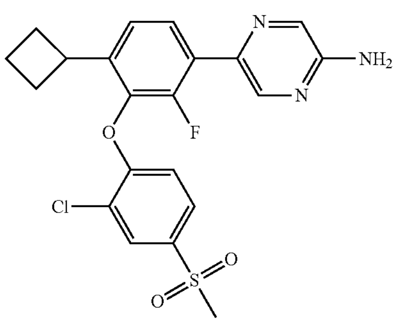 [SMILES: CS(=O)(=O)c1ccc(Oc2c(C3CCC3)ccc(-c3cnc(N)cn3)c2F)c(Cl)c1] | 123 | 5-{3-[2-Chloro-4-(methylsulfonyl)phenoxy]-4-cyclobutyl-2-fluorophenyl}pyrazin-2-amine |
| 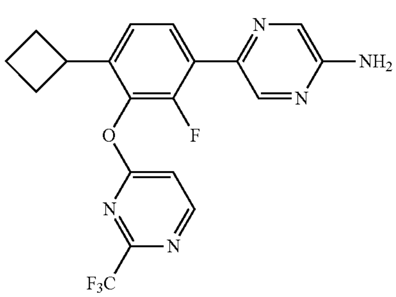 | 124 | 5-(4-Cyclobutyl-2-fluoro-3-{[2-(trifluoromethyl)pyrimidin-4-yl]oxy}phenyl)pyrazin-2-amine |
| 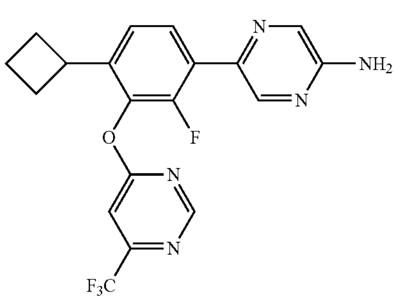 [SMILES: Nc1cnc(-c2ccc(C3CCC3)c(Oc3cc(C(F)(F)F)ncn3)c2F)cn1] | 125 | 5-(4-Cyclobutyl-2-fluoro-3-{[6-(trifluoromethyl)pyrimidin-4-yl]oxy}phenyl)pyrazin-2-amine |

TABLE 3-continued

| STRUCTURE | COMPOUND # | NAME |
|---|---|---|
| 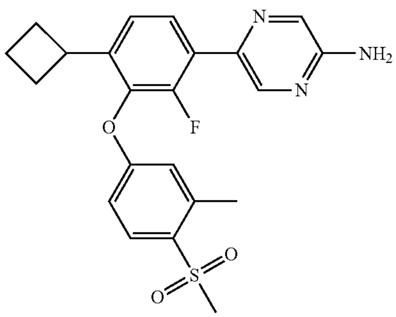 [SMILES: Cc1cc(Oc2c(C3CCC3)ccc(-c3cnc(N)cn3)c2F)ccc1S(C)(=O)=O] | 126 | 5-{4-Cyclobutyl-2-fluoro-3-[3-methyl-4-(methylsulfonyl)phenoxy]phenyl}pyrazin-2-amine |
| 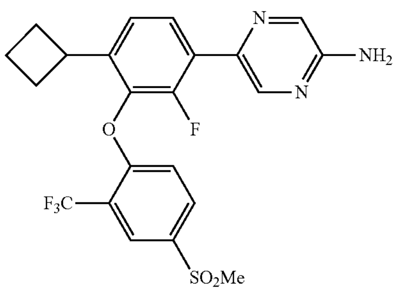 | 127 | 5-(4-cyclobutyl-2-fluoro-3-(4-(methylsulfonyl)-2-(trifluoromethyl)phenoxy)phenyl)pyrazin-2-amine |
| 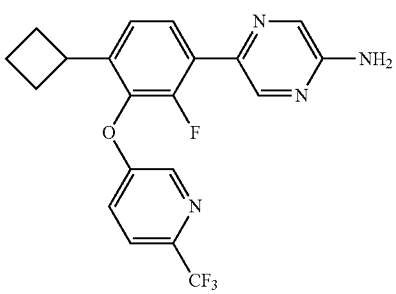 | 128 | 5-(4-Cyclobutyl-2-fluoro-3-{[6-(trifluoromethyl)pyridin-3-yl]oxy}phenyl)pyrazin-2-amine |
| 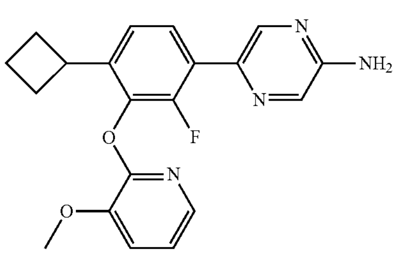 [SMILES: COc1cccnc1Oc1c(C2CCC2)ccc(-c2cnc(N)cn2)c1F] | 129 | 5-{4-Cyclobutyl-2-fluoro-3-[(3-methoxypyridin-2-yl)oxy]phenyl}pyrazin-2-amine |
| 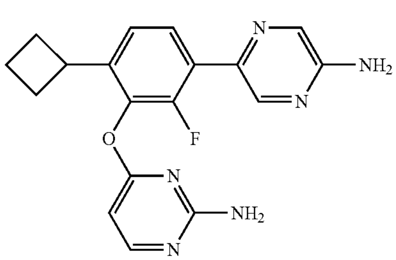 [SMILES: Nc1cnc(-c2ccc(C3CCC3)c(Oc3ccnc(N)n3)c2F)cn1] | 130 | 4-[3-(5-Aminopyrazin-2-yl)-6-cyclobutyl-2-fluorophenoxy]pyrimidin-2-amine |

TABLE 3-continued

| STRUCTURE | COMPOUND # | NAME |
|---|---|---|
| 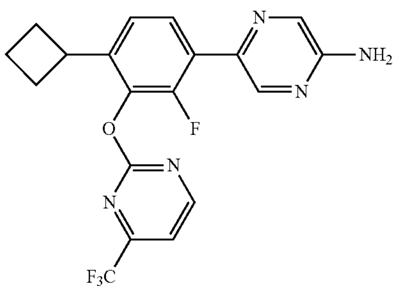 | 131 | 5-(4-Cyclobutyl-2-fluoro-3-{[4-(trifluoromethyl)pyrimidin-2-yl]oxy}phenyl)pyrazin-2-amine |
| 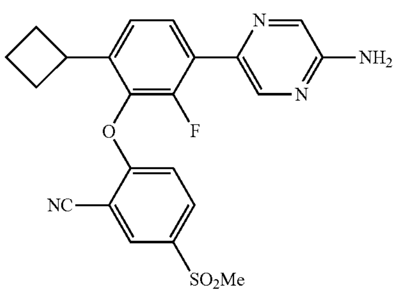 | 132 | 2-[3-(5-Aminopyrazin-2-yl)-6-cyclobutyl-2-fluorophenoxy]-5-(methylsulfonyl)benzonitrile |
| 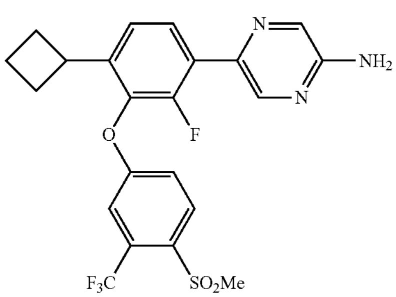 [SMILES: CS(=O)(=O)c1ccc(Oc2c(C3CCC3)ccc(-c3cnc(N)cn3)c2F)cc1C(F)(F)F] | 133 | 5-{4-Cyclobutyl-2-fluoro-3-[4-(methylsulfonyl)-3-(trifluoromethyl)phenoxy]phenyl}pyrazin-2-amine |
| 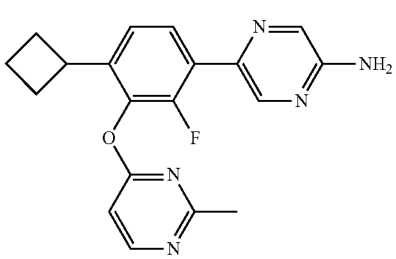 [SMILES: Cc1nccc(Oc2c(C3CCC3)ccc(-c3cnc(N)cn3)c2F)n1] | 134 | 5-{4-Cyclobutyl-2-fluoro-3-[(2-methylpyrimidin-4-yl)oxy]phenyl}pyrazin-2-amine |
| 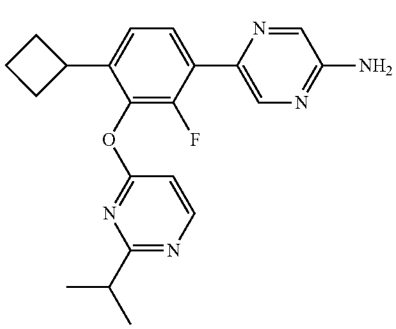 [SMILES: CC(C)c1nccc(Oc2c(C3CCC3)ccc(-c3cnc(N)cn3)c2F)n1] | 135 | 5-(4-Cyclobutyl-2-fluoro-3-{[2-(1-methylethyl)pyrimidin-4-yl]oxy}phenyl)pyrazin-2-amine |

| COMPOUND # | NAME |
|---|---|
| 136 | 6-[3-(5-Aminopyrazin-2-yl)-6-cyclobutyl-2-fluorophenoxy]pyrimidin-4-amine |
| 137 | 5-{3-[(2-Chloropyrimidin-4-yl)oxy]-4-cyclobutyl-2-fluorophenyl}pyrazin-2-amine |
| 138 | 5-{3-[(6-Azetidin-1-ylpyrimidin-4-yl)oxy]-4-cyclobutyl-2-fluorophenyl}pyrazin-2-amine trifluoroacetate salt |
| 139 | 6-[3-(5-Aminopyrazin-2-yl)-6-cyclobutyl-2-fluorophenoxy]-N,N-dimethyl-2-(trifluoromethyl)pyrimidin-4-amine |
| 140 | 6-[3-(5-Aminopyrazin-2-yl)-6-cyclobutyl-2-fluorophenoxy]-2-methylpyrimidin-4-amine trifluoroacetate salt |

TABLE 3-continued

| STRUCTURE | COMPOUND # | NAME |
|---|---|---|
| 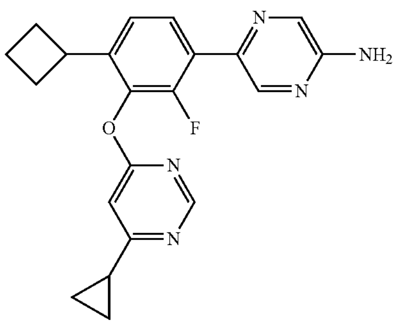 [SMILES: Nc1cnc(-c2ccc(C3CCC3)c(Oc3cc(C4CC4)ncn3)c2F)cn1] | 141 | 5-{4-Cyclobutyl-3-[(6-cyclopropylpyrimidin-4-yl)oxy]-2-fluorophenyl}pyrazin-2-amine |
| 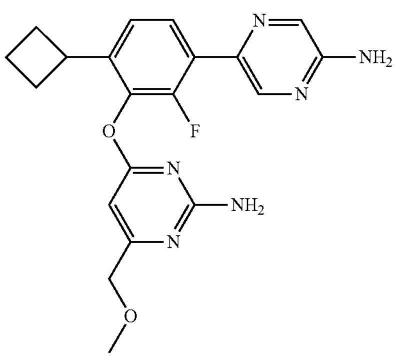 [SMILES: COCc1cc(Oc2c(C3CCC3)ccc(-c3cnc(N)cn3)c2F)nc(N)n1] | 142 | 4-[3-(5-Aminopyrazin-2-yl)-6-cyclobutyl-2-fluorophenoxy]-6-(methoxymethyl)pyrimidin-2-amine |
| 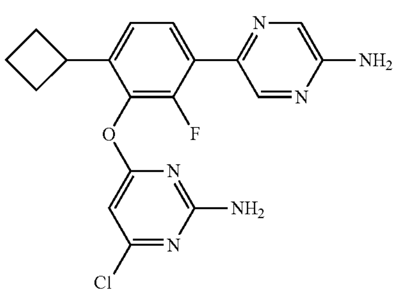 [SMILES: Nc1cnc(-c2ccc(C3CCC3)c(Oc3cc(Cl)nc(N)n3)c2F)cn1] | 143 | 4-[3-(5-Aminopyrazin-2-yl)-6-cyclobutyl-2-fluorophenoxy]-6-chloropyrimidin-2-amine |
| 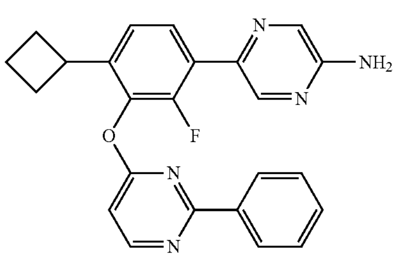 [SMILES: Nc1cnc(-c2ccc(C3CCC3)c(Oc3ccnc(-c4ccccc4)n3)c2F)cn1] | 144 | 5-{4-Cyclobutyl-2-fluoro-3-[(2-phenylpyrimidin-4-yl)oxy]phenyl}pyrazin-2-amine |
| 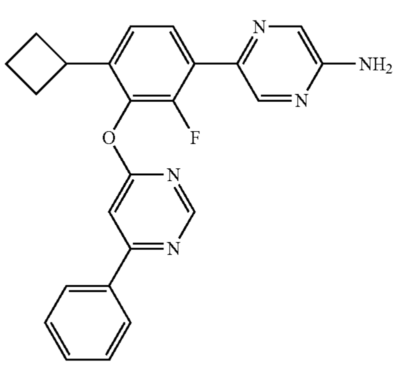 [SMILES: Nc1cnc(-c2ccc(C3CCC3)c(Oc3cc(-c4ccccc4)ncn3)c2F)cn1] | 145 | 5-{4-Cyclobutyl-2-fluoro-3-[(6-phenylpyrimidin-4-yl)oxy]phenyl}pyrazin-2-amine |

TABLE 3-continued

| STRUCTURE | COMPOUND # | NAME |
|---|---|---|
| 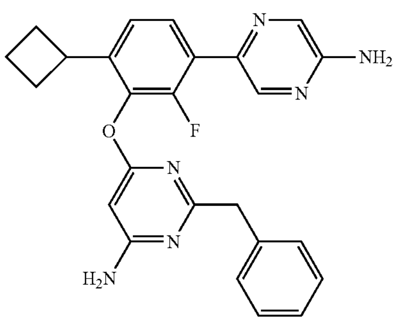 [SMILES: Nc1cnc(-c2ccc(C3CCC3)c(Oc3cc(N)nc(Cc4ccccc4)n3)c2F)cn1] | 146 | 6-[3-(5-Aminopyrazin-2-yl)-6-cyclobutyl-2-fluorophenoxy]-2-benzylpyrimidin-4-amine |
| 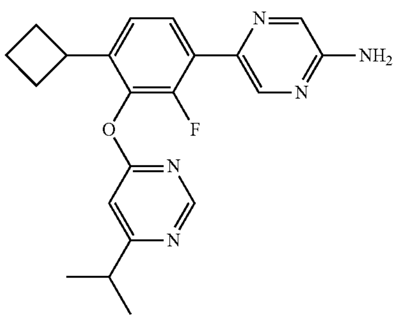 [SMILES: CC(C)c1cc(Oc2c(C3CCC3)ccc(-c3cnc(N)cn3)c2F)ncn1] | 147 | 5-(4-Cyclobutyl-2-fluoro-3-{[6-(1-methylethyl)pyrimidin-4-yl]oxy}phenyl)pyrazin-2-amine |
| 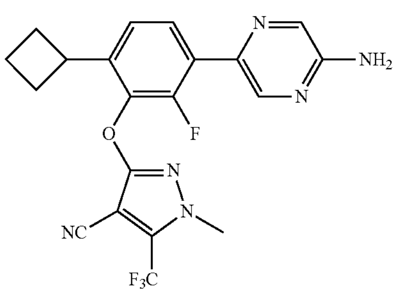 [SMILES: Cn1nc(Oc2c(C3CCC3)ccc(-c3cnc(N)cn3)c2F)c(C#N)c1C(F)(F)F] | 148 | 3-[3-(5-Aminopyrazin-2-yl)-6-cyclobutyl-2-fluorophenoxy]-1-methyl-5-(trifluoromethyl)-1H-pyrazole-4-carbonitrile |
| 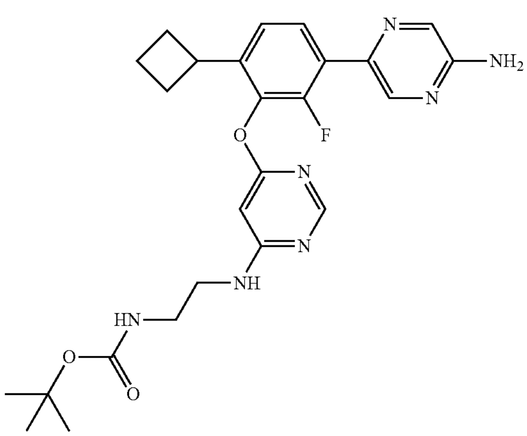 [SMILES: CC(C)(C)OC(=O)NCCNc1cc(Oc2c(C3CCC3)ccc(-c3cnc(N)cn3)c2F)ncn1] | 149 | tert-Butyl [2-({2-[3-(5-aminopyrazin-2-yl)-6-cyclobutyl-2-fluorophenoxy]pyrimidin-4-yl}amino)ethyl]carbamate |

TABLE 3-continued

| STRUCTURE | COMPOUND # | NAME |
|---|---|---|
| 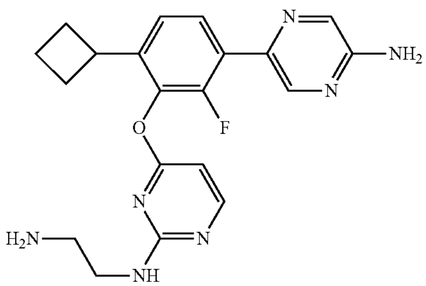 [SMILES: NCCNc1nccc(Oc2c(C3CCC3)ccc(-c3cnc(N)cn3)c2F)n1] | 150 | N-{4-[3-(5-Aminopyrazin-2-yl)-6-cyclobutyl-2-fluorophenoxy]pyrimidin-2-yl}ethane-1,2-diamine |
| 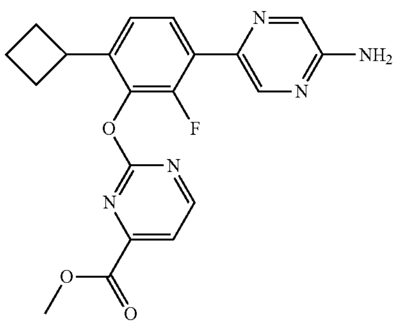 [SMILES: COC(=O)c1ccnc(Oc2c(C3CCC3)ccc(-c3cnc(N)cn3)c2F)n1] | 151 | Methyl 2-[3-(5-aminopyrazin-2-yl)-6-cyclobutyl-2-fluorophenoxy]pyrimidine-4-carboxylate trifluoroacetate salt |
| 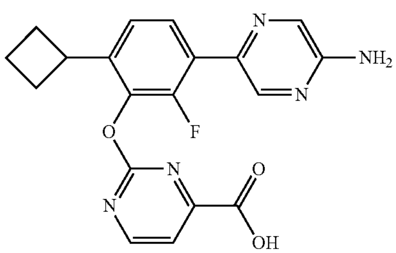 [SMILES: Nc1cnc(-c2ccc(C3CCC3)c(Oc3nccc(C(=O)O)n3)c2F)cn1] | 152 | 2-[3-(5-Aminopyrazin-2-yl)-6-cyclobutyl-2-fluorophenoxy]pyrimidine-4-carboxylic acid |
| 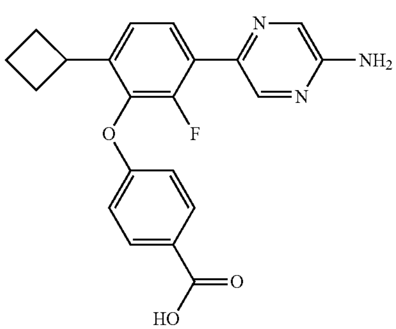 | 153 | 4-[3-(5-Aminopyrazin-2-yl)-6-cyclobutyl-2-fluorophenoxy]benzoic acid |
| 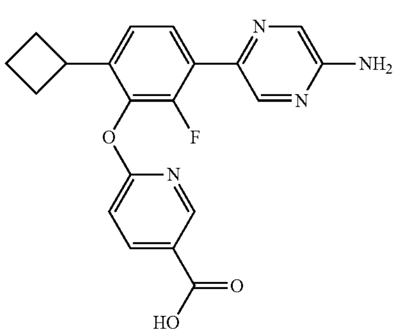 [SMILES: Nc1cnc(-c2ccc(C3CCC3)c(Oc3ccc(C(=O)O)cn3)c2F)cn1] | 154 | 6-[3-(5-Aminopyrazin-2-yl)-6-cyclobutyl-2-fluorophenoxy]pyridine-3-carboxylic acid |

TABLE 3-continued

| STRUCTURE | COMPOUND # | NAME |
|---|---|---|
| 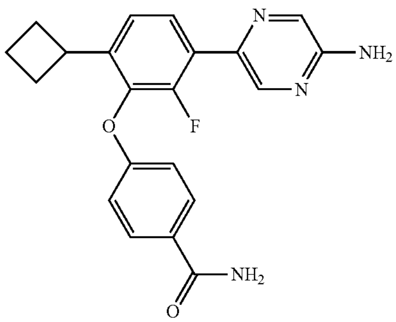 [SMILES: NC(=O)c1ccc(Oc2c(C3CCC3)ccc(-c3cnc(N)cn3)c2F)cc1] | 155 | 4-[3-(5-Aminopyrazin-2-yl)-6-cyclobutyl-2-fluorophenoxy]benzamide |
| 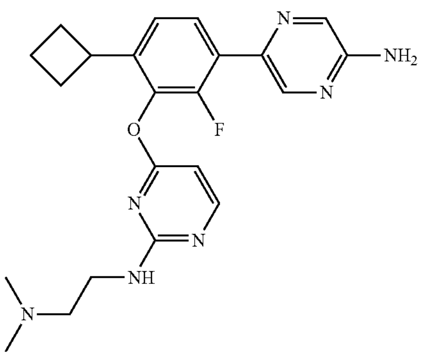 [SMILES: CN(C)CCNc1nccc(Oc2c(C3CCC3)ccc(-c3cnc(N)cn3)c2F)n1] | 156 | N'-{4-[3-(5-Aminopyrazin-2-yl)-6-cyclobutyl-2-fluorophenoxy]pyrimidin-2-yl}-N,N-dimethylethane-1,2-diamine hydrochloride |
| 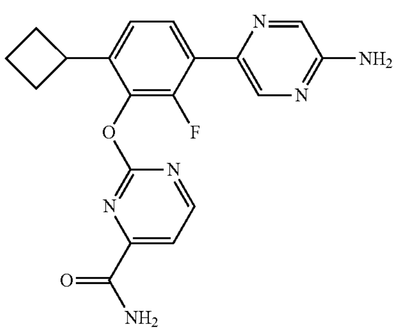 [SMILES: NC(=O)c1ccnc(Oc2c(C3CCC3)ccc(-c3cnc(N)cn3)c2F)n1] | 157 | 2-[3-(5-Aminopyrazin-2-yl)-6-cyclobutyl-2-fluorophenoxy]pyrimidine-4-carboxamide |
| 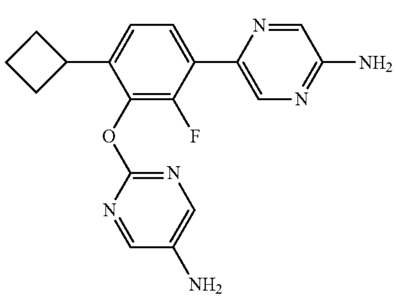 [SMILES: Nc1cnc(Oc2c(C3CCC3)ccc(-c3cnc(N)cn3)c2F)nc1] | 158 | 2-[3-(5-Aminopyrazin-2-yl)-6-cyclobutyl-2-fluorophenoxy]pyrimidin-5-amine |
| 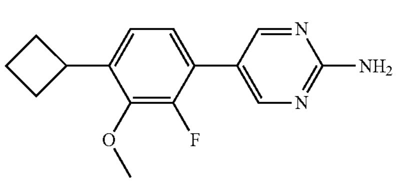 [SMILES: COc1c(C2CCC2)ccc(-c2cnc(N)nc2)c1F] | 159 | 5-(4-Cyclobutyl-2-fluoro-3-methoxyphenyl)pyrimidin-2-amine |

TABLE 3-continued

| STRUCTURE | COMPOUND # | NAME |
|---|---|---|
| 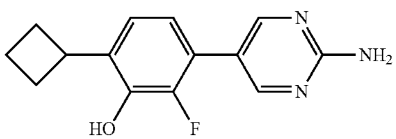 | E | 3-(2-Aminopyrimidin-5-yl)-6-cyclobutyl-2-fluorophenol |
| 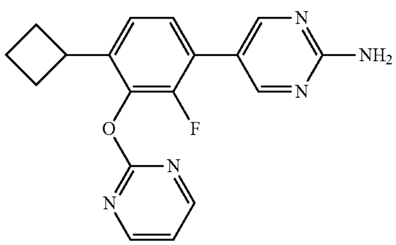 [SMILES: Nc1ncc(-c2ccc(C3CCC3)c(Oc3ncccn3)c2F)cn1] | 160 | 5-[4-Cyclobutyl-2-fluoro-3-(pyrimidin-2-yloxy)phenyl]pyrimidin-2-amine |
| 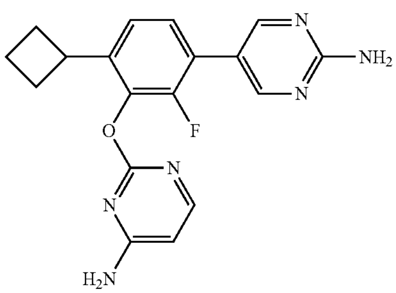 [SMILES: Nc1ccnc(Oc2c(C3CCC3)ccc(-c3cnc(N)nc3)c2F)n1] | 161 | 5-{3-[(4-Aminopyrimidin-2-yl)oxy]-4-cyclobutyl-2-fluorophenyl}pyrimidin-2-amine |
| 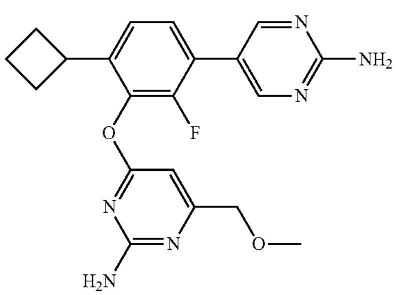 [SMILES: COCc1cc(Oc2c(C3CCC3)ccc(-c3cnc(N)nc3)c2F)nc(N)n1] | 162 | 4-[3-(2-Aminopyrimidin-5-yl)-6-cyclobutyl-2-fluorophenoxy]-6-(methoxymethyl)pyrimidin-2-amine |
| 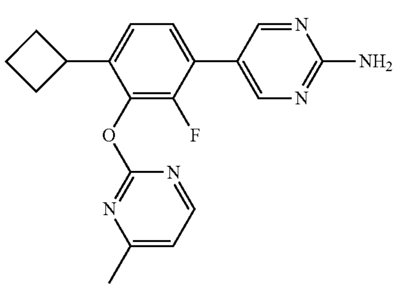 [SMILES: Cc1ccnc(Oc2c(C3CCC3)ccc(-c3cnc(N)nc3)c2F)n1] | 163 | 5-{4-Cyclobutyl-2-fluoro-3-[(4-methylpyrimidin-2-yl)oxy]phenyl}pyrimidin-2-amine |
| 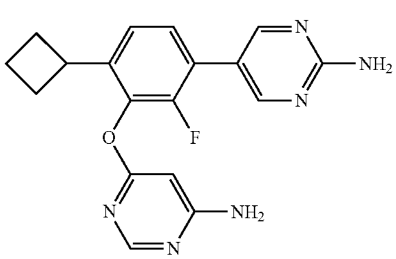 [SMILES: Nc1cc(Oc2c(C3CCC3)ccc(-c3cnc(N)nc3)c2F)ncn1] | 164 | 5-{3-[(6-Aminopyrimidin-4-yl)oxy]-4-cyclobutyl-2-fluorophenyl}pyrimidin-2-amine |

TABLE 3-continued

| STRUCTURE | COMPOUND # | NAME |
|---|---|---|
| 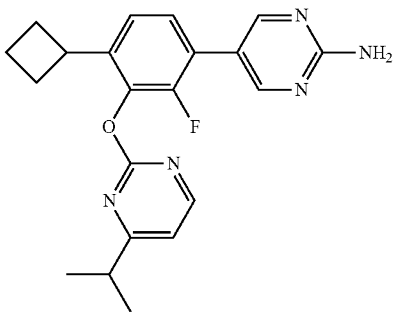 | 165 | 5-(4-Cyclobutyl-2-fluoro-3-{[4-(1-methylethyl)pyrimidin-2-yl]oxy}phenyl)pyrimidin-2-amine |
| 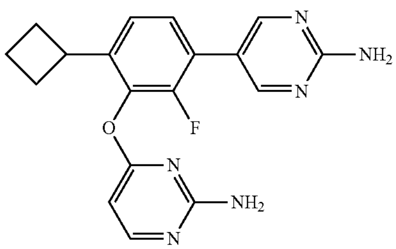 [SMILES: Nc1ncc(-c2ccc(C3CCC3)c(Oc3ccnc(N)n3)c2F)cn1] | 166 | 4-[3-(2-Aminopyrimidin-5-yl)-6-cyclobutyl-2-fluorophenoxy]pyrimidin-2-amine |
| 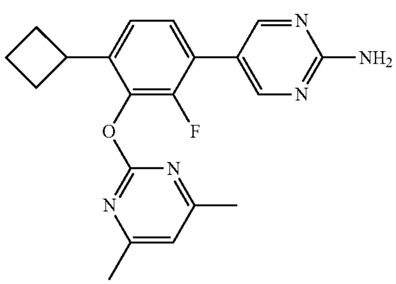 [SMILES: Cc1cc(C)nc(Oc2c(C3CCC3)ccc(-c3cnc(N)nc3)c2F)n1] | 167 | 5-{4-Cyclobutyl-3-[(4,6-dimethylpyrimidin-2-yl)oxy]-2-fluorophenyl}pyrimidin-2-amine |
| 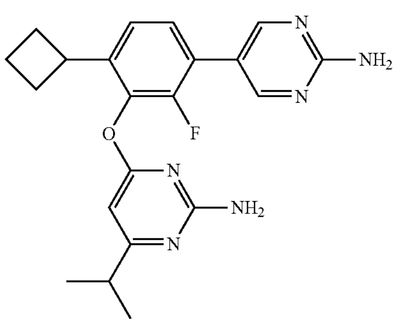 [SMILES: CC(C)c1cc(Oc2c(C3CCC3)ccc(-c3cnc(N)nc3)c2F)nc(N)n1] | 168 | 4-(3-(2-aminopyrimidin-5-yl)-6-cyclobutyl-2-fluorophenoxy)-6-isopropylpyrimidin-2-amine |
| 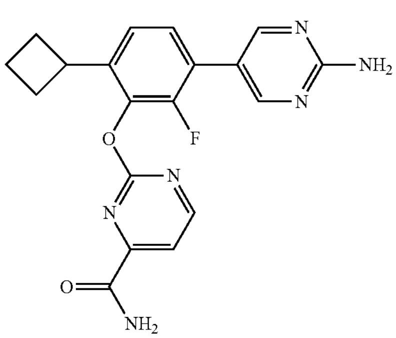 | 169 | 2-[3-(2-Aminopyrimidin-5-yl)-6-cyclobutyl-2-fluorophenoxy]pyrimidine-4-carboxamide |

TABLE 3-continued

| STRUCTURE | COMPOUND # | NAME |
|---|---|---|
| 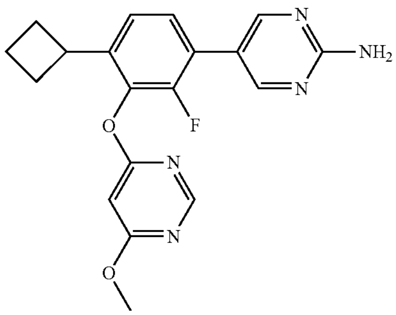 [SMILES: COc1cc(Oc2c(C3CCC3)ccc(-c3cnc(N)nc3)c2F)ncn1] | 170 | 5-(4-cyclobutyl-2-fluoro-3-((6-methoxypyrimidin-4-yl)oxy)phenyl)pyrimidin-2-amine trifluoroacetate salt |
| 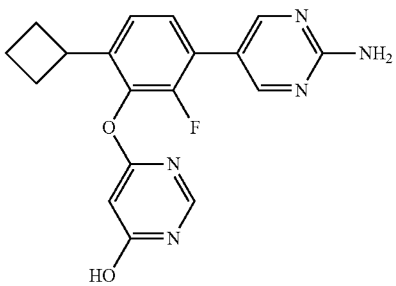 [SMILES: Nc1ncc(-c2ccc(C3CCC3)c(Oc3cc(O)ncn3)c2F)cn1] | 171 | 6-[3-(2-Aminopyrimidin-5-yl)-6-cyclobutyl-2-fluorophenoxy]pyrimidin-4-ol trifluoroacetate |
| 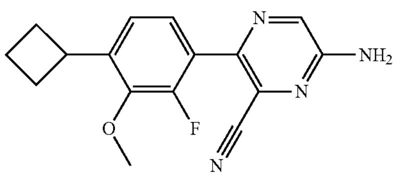 [SMILES: COc1c(C2CCC2)ccc(-c2ncc(N)nc2C#N)c1F] | 172 | 6-Amino-3-(4-cyclobutyl-2-fluoro-3-methoxyphenyl)pyrazine-2-carbonitrile |
| 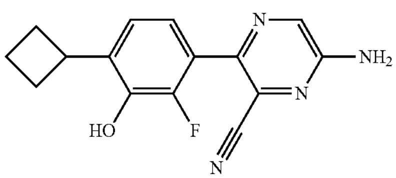 [SMILES: N#Cc1nc(N)cnc1-c1ccc(C2CCC2)c(O)c1F] | 173 | 6-Amino-3-(4-cyclobutyl-2-fluoro-3-hydroxyphenyl)pyrazine-2-carbonitrile |
| 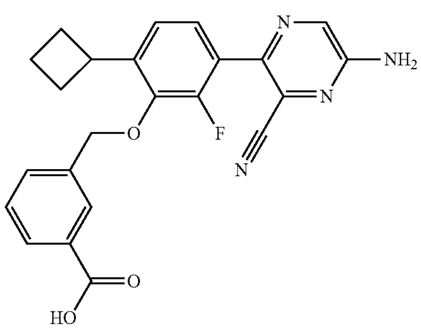 [SMILES: N#Cc1nc(N)cnc1-c1ccc(C2CCC2)c(OCc2cccc(C(=O)O)c2)c1F] | 174 | 3-{[3-(5-Amino-3-cyanopyrazin-2-yl)-6-cyclobutyl-2-fluorophenoxy]methyl}benzoic acid |
| 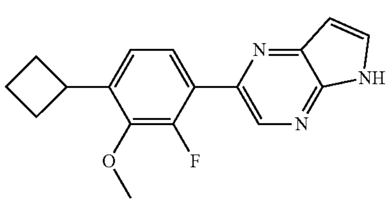 [SMILES: COc1c(C2CCC2)ccc(-c2cnc3[nH]ccc3n2)c1F] | 175 | 2-(4-Cyclobutyl-2-fluoro-3-methoxyphenyl)-5H-pyrrolo[2,3-b]pyrazine |

TABLE 3-continued

| STRUCTURE | COMPOUND # | NAME |
|---|---|---|
| 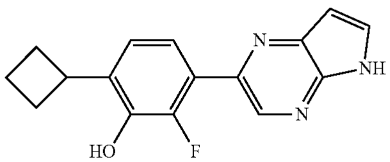 [SMILES: Oc1c(C2CCC2)ccc(-c2cnc3[nH]ccc3n2)c1F] | F | 6-Cyclobutyl-2-fluoro-3-(5H-pyrrolo[2,3-b]pyrazin-2-yl)phenol |
| 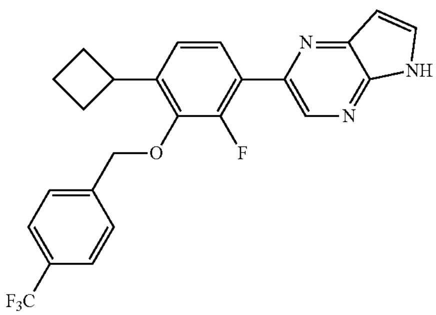 [SMILES: Fc1c(-c2cnc3[nH]ccc3n2)ccc(C2CCC2)c1OCc1ccc(C(F)(F)F)cc1] | 176 | 2-(4-Cyclobutyl-2-fluoro-3-{[4-(trifluoromethyl)benzyl]oxy}phenyl)-5H-pyrrolo[2,3-b]pyrazine trifluoroacetate salt |
| 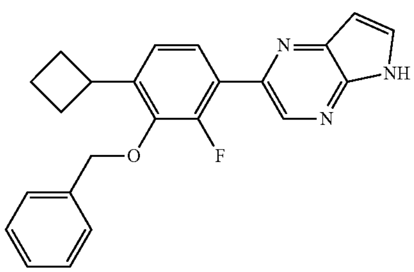 [SMILES: Fc1c(-c2cnc3[nH]ccc3n2)ccc(C2CCC2)c1OCc1ccccc1] | 177 | 2-[3-(Benzyloxy)-4-cyclobutyl-2-fluorophenyl]-5H-pyrrolo[2,3-b]pyrazine |
| 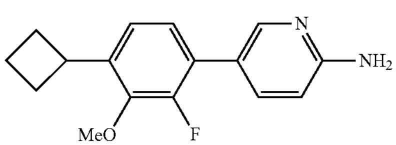 [SMILES: COc1c(C2CCC2)ccc(-c2ccc(N)nc2)c1F] | 178 | 5-(4-Cyclobutyl-2-fluoro-3-methoxyphenyl)pyridin-2-amine hydrochloride salt |
| 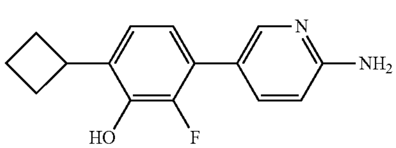 | 179 | 5-(4-Cyclobutyl-2-fluoro-3-hydroxyphenyl)pyridin-2-amine |
| 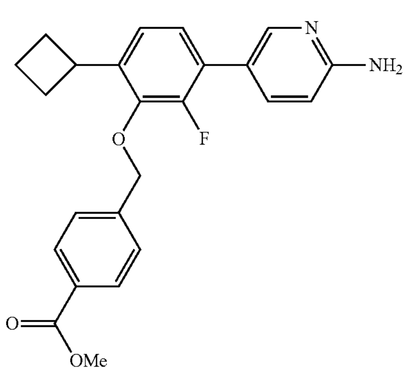 [SMILES: Nc1ccc(-c2ccc(C3CCC3)c(OCc3ccc(C(=O)O)cc3)c2F)cn1] | 180 | 5-Methyl-4-((3-(6-aminopyridin-3-yl)-6-cyclobutyl-2-fluorophenoxy)methyl)benzoate |

TABLE 3-continued

| STRUCTURE | COMPOUND # | NAME |
|---|---|---|
| 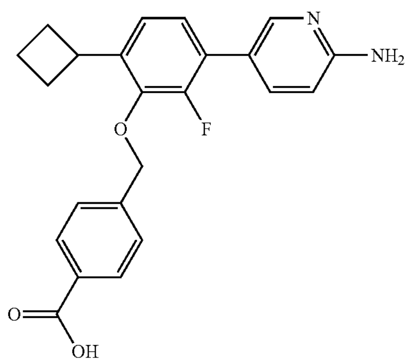 | 181 | 4-((3-(6-Aminopyridin-3-yl)-6-cyclobutyl-2-fluorophenoxy)methyl)benzoic acid |
| 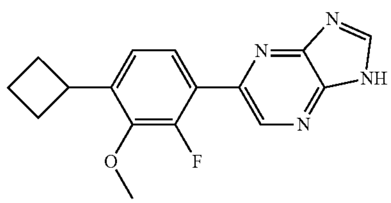 [SMILES: COc1c(C2CCC2)ccc(-c2cnc3[nH]cnc3n2)c1F] | 182 | 5-(4-cyclobutyl-2-fluoro-3-methoxyphenyl)-1H-imidazo[4,5-b]pyrazine |
| 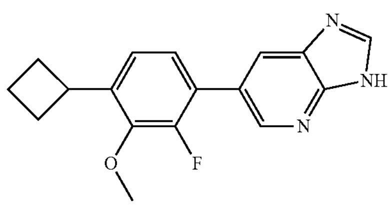 | 183 | 6-(4-Cyclobutyl-2-fluoro-3-methoxyphenyl)-3H-imidazo[4,5-b]pyridine |
| 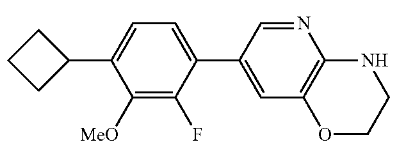 [SMILES: COc1c(C2CCC2)ccc(-c2cnc3c(c2)OCCN3)c1F] | 184 | 7-(4-Cyclobutyl-2-fluoro-3-methoxyphenyl)-3,4-dihydro-2H-pyrido[3,2-b][1,4]oxazine |
| 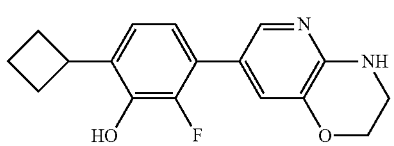 [SMILES: Oc1c(C2CCC2)ccc(-c2cnc3c(c2)OCCN3)c1F] | 185 | 6-Cyclobutyl-3-(3,4-dihydro-2H-pyrido[3,2-b][1,4]oxazin-7-yl)-2-fluorophenol |
| 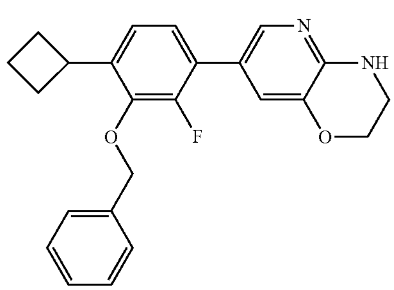 [SMILES: Fc1c(-c2cnc3c(c2)OCCN3)ccc(C2CCC2)c1OCc1ccccc1] | 186 | 7-[3-(Benzyloxy-4-cyclobutyl-2-fluorophenyl]-3,4-dihydro-2H-pyrido[3,2-b][1,4]oxazine |

TABLE 3-continued

| STRUCTURE | COMPOUND # | NAME |
|---|---|---|
| 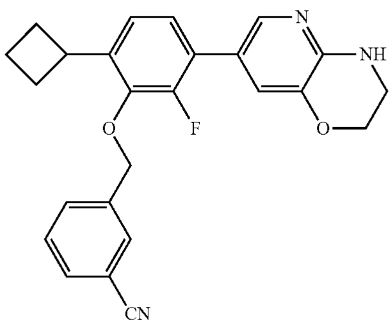 [SMILES: N#Cc1cccc(COc2c(C3CCC3)ccc(-c3cnc4c(c3)OCCN4)c2F)c1] | 187 | 3-{[6-Cyclobutyl-3-(3,4-dihydro-2H-pyrido[3,2-b][1,4]oxazin-7-yl)-2-fluorophenoxy]-methyl}-benzonitrile |
| 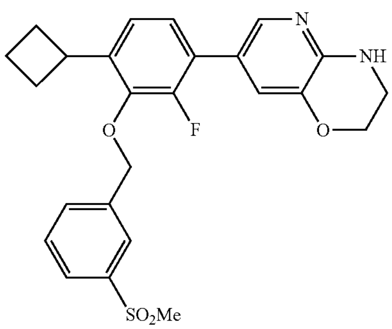 | 188 | 7-(4-Cyclobutyl-2-fluoro-3-{[3-(methylsulfonyl)-benzyl]oxy}phenyl)-3,4-dihydro-2H-pyrido[3,2-b][1,4]oxazine |
| 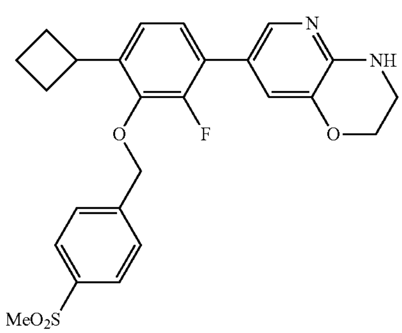 [SMILES: CS(=O)(=O)c1ccc(COc2c(C3CCC3)ccc(-c3cnc4c(c3)OCCN4)c2F)cc1] | 189 | 7-(4-Cyclobutyl-2-fluoro-3-{[4-(methylsulfonyl)-benzyl]-oxy}-phenyl)-3,4-dihydro-2H-pyrido[3,2-b][1,4]oxazine |
| 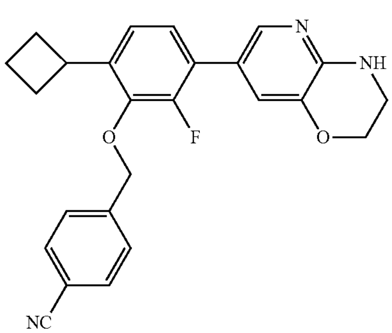 [SMILES: N#Cc1ccc(COc2c(C3CCC3)ccc(-c3cnc4c(c3)OCCN4)c2F)cc1] | 190 | 4-{[6-Cyclobutyl-3-(3,4-dihydro-2H-pyrido[3,2-b][1,4]oxazin-7-yl)-2-fluorophenoxy]-methyl}-benzonitrile |

TABLE 3-continued

| STRUCTURE | COMPOUND # | NAME |
|---|---|---|
| 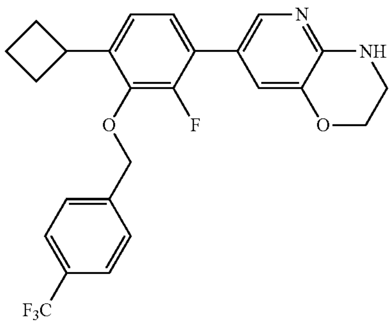 [SMILES: Fc1c(-c2cnc3c(c2)OCCN3)ccc(C2CCC2)c1OCc1ccc(C(F)(F)F)cc1] | 191 | 7-(4-Cyclobutyl-2-fluoro-3-{[4-(trifluoromethyl)benzyl]oxy}phenyl)-3,4-dihydro-2H-pyrido[3,2-b][1,4]oxazine |
| 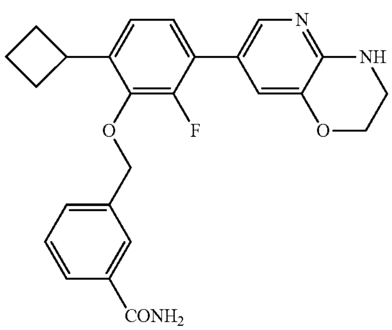 [SMILES: NC(=O)c1cccc(COc2c(C3CCC3)ccc(-c3cnc4c(c3)OCCN4)c2F)c1] | 192 | 3-{[6-Cyclobutyl-3-(3,4-dihydro-2H-pyrido[3,2-b][1,4]oxazin-7-yl)-2-fluorophenoxy]-methyl}-benzamide |
| 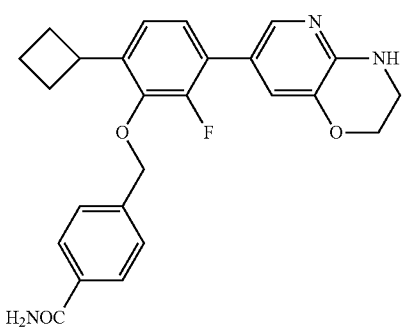 [SMILES: NC(=O)c1ccc(COc2c(C3CCC3)ccc(-c3cnc4c(c3)OCCN4)c2F)cc1] | 193 | 4-{[6-Cyclobutyl-3-(3,4-dihydro-2H-pyrido[3,2-b][1,4]oxazin-7-yl)-2-fluorophenoxy]-methyl}-benzamide |
| 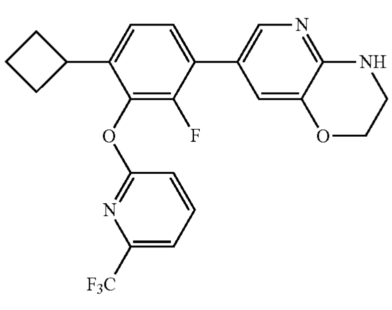 [SMILES: Fc1c(-c2cnc3c(c2)OCCN3)ccc(C2CCC2)c1Oc1cccc(C(F)(F)F)n1] | 194 | 7-(4-Cyclobutyl-2-fluoro-3-{[6-(trifluoromethyl)pyridin-2-yl]oxy}phenyl)-3,4-dihydro-2H-pyrido[3,2-b][1,4]oxazine |

TABLE 3-continued

| STRUCTURE | COMPOUND # | NAME |
|---|---|---|
| 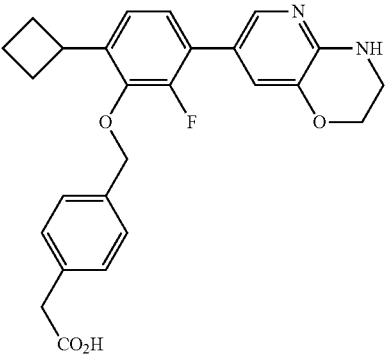 [SMILES: O=C(O)Cc1ccc(COc2c(C3CCC3)ccc(-c3cnc4c(c3)OCCN4)c2F)cc1] | 195 | (4-{[6-Cyclobutyl-3-(3,4-dihydro-2H-pyrido[3,2-b][1,4]oxazin-7-yl)-2-fluorophenoxy]methyl}phenyl)acetic acid |
| 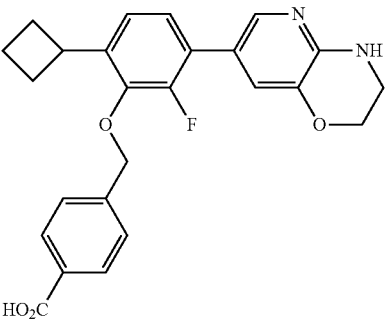 [SMILES: O=C(O)c1ccc(COc2c(C3CCC3)ccc(-c3cnc4c(c3)OCCN4)c2F)cc1] | 196 | 4-{[6-Cyclobutyl-3-(3,4-dihydro-2H-pyrido[3,2-b][1,4]oxazin-7-yl)-2-fluorophenoxy]methyl}benzoic acid |
| 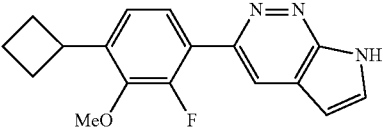 [SMILES: COc1c(C2CCC2)ccc(-c2cc3cc[nH]c3nn2)c1F] | 197 | 3-(4-Cyclobutyl-2-fluoro-3-methoxyphenyl)-7H-pyrrolo[2,3-c]pyridazine |
| 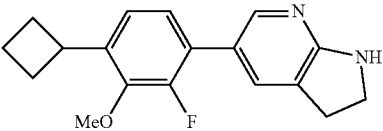 | 198 | 5-(4-Cyclobutyl-2-fluoro-3-methoxyphenyl)-2,3-dihydro-1H-pyrrolo[2,3-b]pyridine |
| 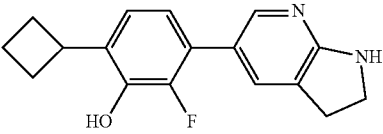 | 199 | 6-Cyclobutyl-3-(2,3-dihydro-1H-pyrrolo[2,3-b]pyridin-5-yl)-2-fluorophenol |
| 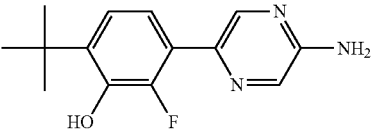 | G | 3-(5-Aminopyrazin-2-yl)-6-tert-butyl-2-fluorophenol |
| 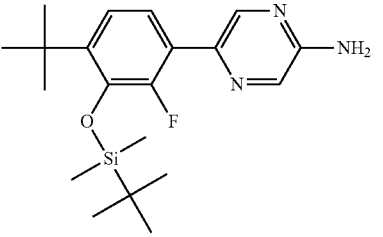 [SMILES: CC(C)(C)c1ccc(-c2cnc(N)cn2)c(F)c1O[Si](C)(C)C(C)(C)C] | 200 | 5-(4-tert-Butyl-3-{[tert-butyl(dimethyl)silyl]oxy}-2-fluorophenyl)pyrazin-2-amine |

TABLE 3-continued

| STRUCTURE | COMPOUND # | NAME |
|---|---|---|
| 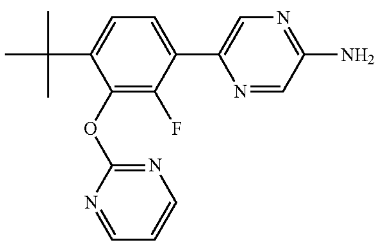 [SMILES: CC(C)(C)c1ccc(-c2cnc(N)cn2)c(F)c1Oc1ncccn1] | 201 | 5-[4-tert-Butyl-2-fluoro-3-(pyrimidin-2-yloxy)phenyl]pyrazin-2-amine |
| 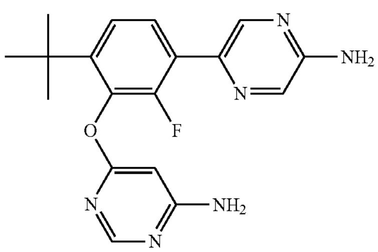 [SMILES: CC(C)(C)c1ccc(-c2cnc(N)cn2)c(F)c1Oc1cc(N)ncn1] | 202 | 6-[3-(5-Aminopyrazin-2-yl)-6-tert-butyl-2-fluorophenoxy]pyrimidin-4-amine |
| 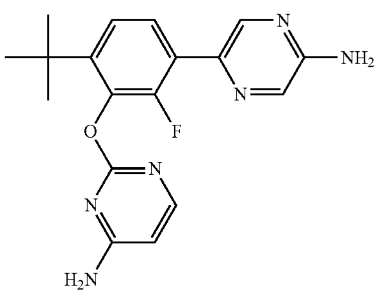 [SMILES: CC(C)(C)c1ccc(-c2cnc(N)cn2)c(F)c1Oc1nccc(N)n1] | 203 | 2-[3-(5-Aminopyrazin-2-yl)-6-tert-butyl-2-fluorophenoxy]pyrimidin-4-amine |
| 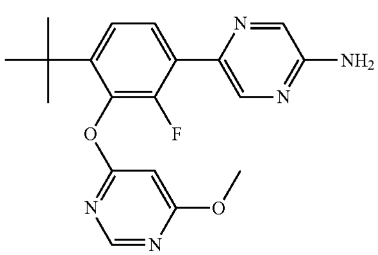 [SMILES: COc1cc(Oc2c(C(C)(C)C)ccc(-c3cnc(N)cn3)c2F)ncn1] | 204 | 5-{4-tert-Butyl-2-fluoro-3-[(6-methoxypyrimidin-4-yl)oxy]phenyl}pyrazin-2-amine |
| 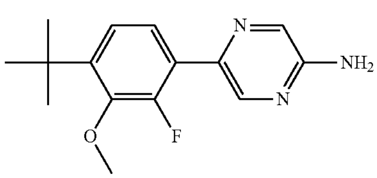 | 205 | 5-(4-tert-Butyl-2-fluoro-3-methoxyphenyl)pyrazin-2-amine |
| 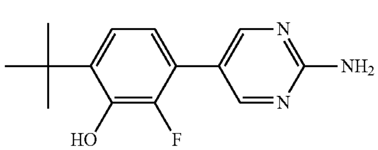 | H | 3-(2-Aminopyrimidin-5-yl)-6-tert-butyl-2-fluorophenol |

TABLE 3-continued

| STRUCTURE | COMPOUND # | NAME |
|---|---|---|
| 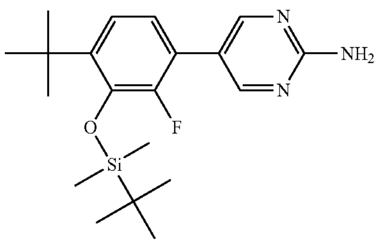 [SMILES: CC(C)(C)c1ccc(-c2cnc(N)nc2)c(F)c1O[Si](C)(C)C(C)(C)C] | 206 | 5-(4-tert-Butyl-3-{[tert-butyl(dimethyl)silyl]oxy}-2-fluorophenyl)pyrimidin-2-amine |
| 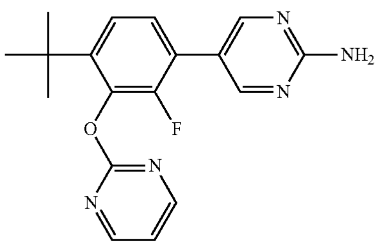 [SMILES: CC(C)(C)c1ccc(-c2cnc(N)nc2)c(F)c1Oc1ncccn1] | 207 | 5-[4-tert-Butyl-2-fluoro-3-(pyrimidin-2-yloxy)phenyl]pyrimidin-2-amine |
| 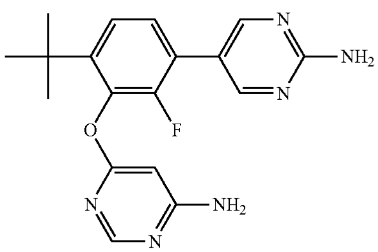 | 208 | 5-{3-[(6-Aminopyrimidin-4-yl)oxy]-4-tert-butyl-2-fluorophenyl}pyrimidin-2-amine |
| 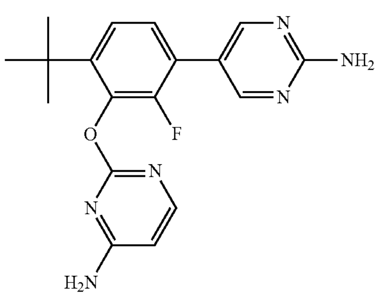 [SMILES: CC(C)(C)c1ccc(-c2cnc(N)nc2)c(F)c1Oc1nccc(N)n1] | 209 | 5-{3-[(4-Aminopyrimidin-2-yl)oxy]-4-tert-butyl-2-fluorophenyl}pyrimidin-2-amine |
| 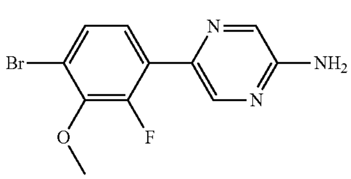 [SMILES: COc1c(Br)ccc(-c2cnc(N)cn2)c1F] | 210 | 5-(4-Bromo-2-fluoro-3-methoxyphenyl)pyrazin-2-amine |
| 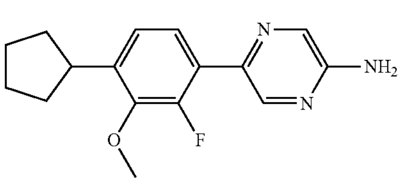 [SMILES: COc1c(C2CCCC2)ccc(-c2cnc(N)cn2)c1F] | 211 | 5-(4-Cyclopentyl-2-fluoro-3-methoxyphenyl)pyrazin-2-amine |

TABLE 3-continued

| STRUCTURE | COMPOUND # | NAME |
|---|---|---|
| 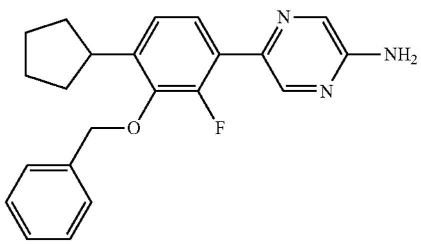 [SMILES: Nc1cnc(-c2ccc(C3CCCC3)c(OCc3ccccc3)c2F)cn1] | 212 | 5-[3-(Benzyloxy)-4-cyclopentyl-2-fluorophenyl]pyrazin-2-amine |
| 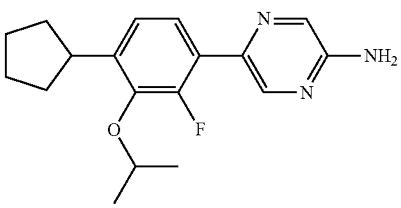 [SMILES: CC(C)Oc1c(C2CCCC2)ccc(-c2cnc(N)cn2)c1F] | 213 | 5-[4-Cyclopentyl-2-fluoro-3-(1-methylethoxy)phenyl]pyrazin-2-amine |
| 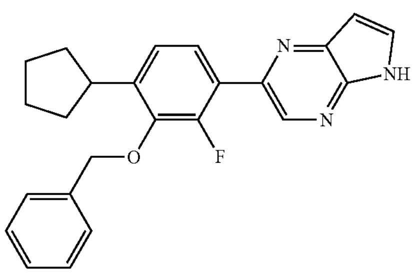 [SMILES: Fc1c(-c2cnc3[nH]ccc3n2)ccc(C2CCCC2)c1OCc1ccccc1] | 214 | 2-[3-(Benzyloxy)-4-cyclopentyl-2-fluorophenyl]-5H-pyrrolo[2,3-b]pyrazine |
| 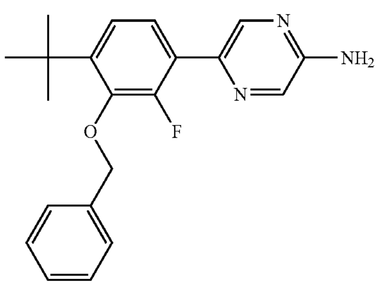 | 215 | 5-[3-(Benzyloxy)-4-tert-butylphenyl]pyrazin-2-amine |
| 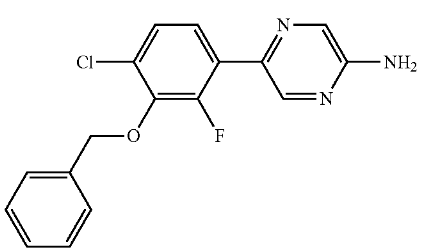 [SMILES: Nc1cnc(-c2ccc(Cl)c(OCc3ccccc3)c2F)cn1] | 216 | 5-[3-(Benzyloxy)-4-chloro-2-fluorophenyl]pyrazin-2-amine |
| 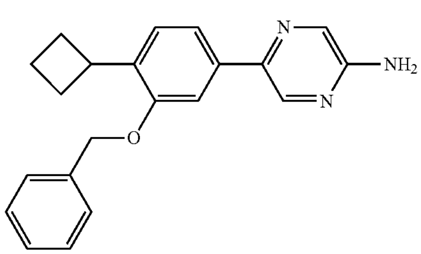 [SMILES: Nc1cnc(-c2ccc(C3CCC3)c(OCc3ccccc3)c2)cn1] | 217 | 5-[3-(Benzyloxy)-4-cyclobutylphenyl]pyrazin-2-amine |

TABLE 3-continued

| STRUCTURE | COMPOUND # | NAME |
|---|---|---|
| 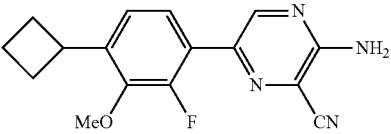 [SMILES: COc1c(C2CCC2)ccc(-c2cnc(N)c(C#N)n2)c1F] | 218 | 3-amino-6-(4-cyclobutyl-2-fluoro-3-methoxyphenyl)pyrazine-2-carbonitrile |
| 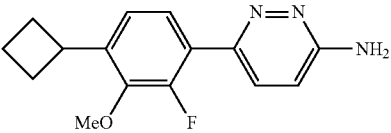 | 219 | 6-(4-cyclobutyl-2-fluoro-3-methoxyphenyl)pyridazin-3-amine |
| 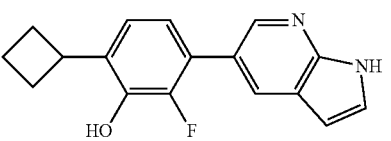 | 220 | 6-cyclobutyl-2-fluoro-3-(1H-pyrrolo[2,3-b]pyridin-5-yl)phenol |
| 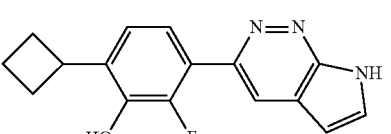 | 221 | 6-cyclobutyl-2-fluoro-3-(7H-pyrrolo[2,3-c]pyridazin-3-yl)phenol |
| 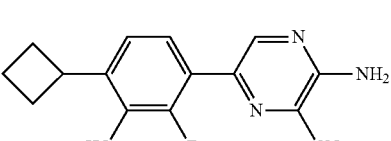 | 222 | 3-amino-6-(4-cyclobutyl-2-fluoro-3-hydroxyphenyl)pyrazine-2-carbonitrile |
| 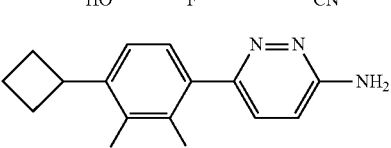 | 223 | 3-(6-aminopyridazin-3-yl)-6-cyclobutyl-2-fluorophenol |
| 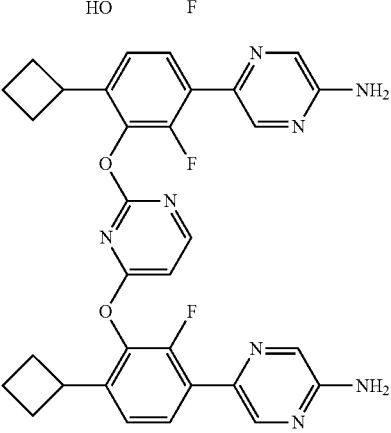 | 224 | 5,5'-((pyrimidine-2,4-diylbis(oxy))bis(4-cyclobutyl-2-fluoro-3,1-phenylene))bis(pyrazin-2-amine |
| 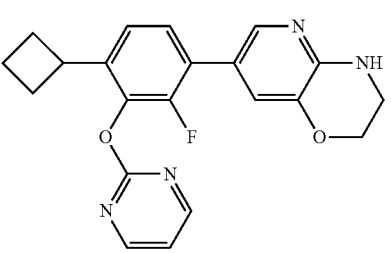 [SMILES: Fc1c(-c2cnc3c(c2)OCCN3)ccc(C2CCC2)c1Oc1ncccn1] | 225 | 7-(4-cyclobutyl-2-fluoro-3-(pyrimidin-2-yloxy)phenyl)-3,4-dihydro-2H-pyrido[3,2-b][1,4]oxazine |

TABLE 3-continued

| STRUCTURE | COMPOUND # | NAME |
|---|---|---|
| 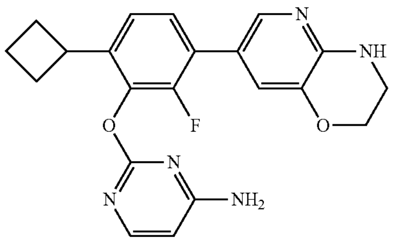 [SMILES: Nc1ccnc(Oc2c(C3CCC3)ccc(-c3cnc4c(c3)OCCN4)c2F)n1] | 226 | 2-(6-cyclobutyl-3-(3,4-dihydro-2H-pyrido[3,2-b][1,4]oxazin-7-yl)-2-fluorophenoxy)pyrimidin-4-amine |
| 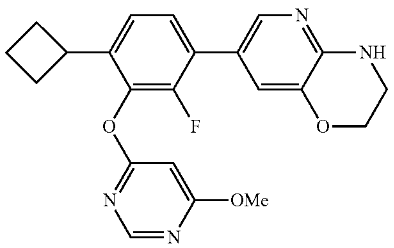 [SMILES: COc1cc(Oc2c(C3CCC3)ccc(-c3cnc4c(c3)OCCN4)c2F)ncn1] | 227 | 7-(4-cyclobutyl-2-fluoro-3-((6-methoxypyrimidin-4-yl)oxy)phenyl)-3,4-dihydro-2H-pyrido[3,2-b][1,4]oxazine |
| 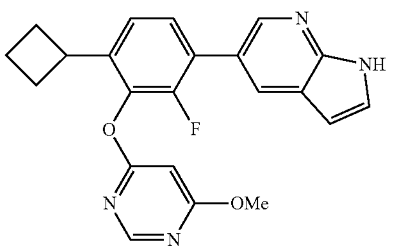 | 228 | 5-(4-cyclobutyl-2-fluoro-3-((6-methoxypyrimidin-4-yl)oxy)phenyl)-1H-pyrrolo[2,3-b]pyridine |
| 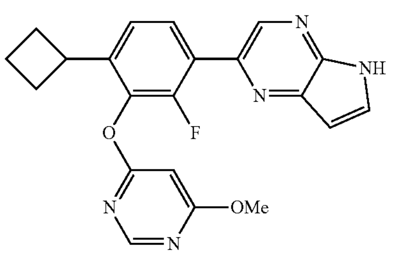 | 229 | 2-(4-cyclobutyl-2-fluoro-3-((6-methoxypyrimidin-4-yl)oxy)phenyl)-5H-pyrrolo[2,3-b]pyrazine |
| 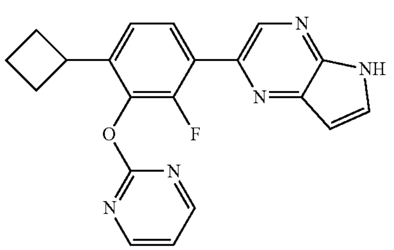 [SMILES: Fc1c(-c2cnc3[nH]ccc3n2)ccc(C2CCC2)c1Oc1ncccn1] | 230 | 2-(4-cyclobutyl-2-fluoro-3-(pyrimidin-2-yloxy)phenyl)-5H-pyrrolo[2,3-b]pyrazine |
| 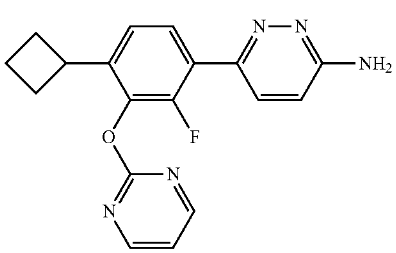 [SMILES: Nc1ccc(-c2ccc(C3CCC3)c(Oc3ncccn3)c2F)nn1] | 231 | 6-(4-cyclobutyl-2-fluoro-3-(pyrimidin-2-yloxy)phenyl)pyridazin-3-amine |

TABLE 3-continued

| STRUCTURE | COMPOUND # | NAME |
|---|---|---|
| 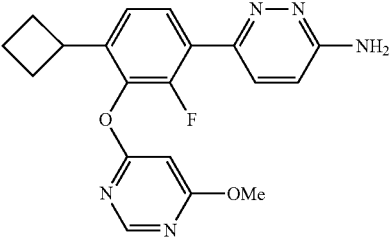 [SMILES: COc1cc(Oc2c(C3CCC3)ccc(-c3ccc(N)nn3)c2F)ncn1] | 232 | 6-(4-cyclobutyl-2-fluoro-3-((6-methoxypyrimidin-4-yl)oxy)phenyl)pyridazin-3-amine |
| 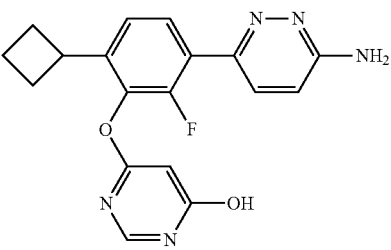 [SMILES: Nc1ccc(-c2ccc(C3CCC3)c(Oc3cc(O)ncn3)c2F)nn1] | 233 | 6-(3-(6-aminopyridazin-3-yl)-6-cyclobutyl-2-fluorophenoxy)pyrimidin-4-ol |
| 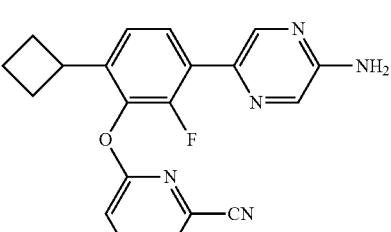 | 234 | 4-(3-(5-Aminopyrazin-2-yl)-6-cyclobutyl-2-fluorophenoxy)pyrimidine-2-carbonitrile |
| 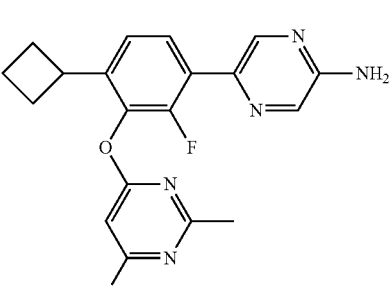 | 235 | 6-(3-(5-Aminopyrazin-2-yl)-6-cyclobutyl-2-fluorophenoxy)-N,N,2-trimethylpyrimidin-4-amine |
| 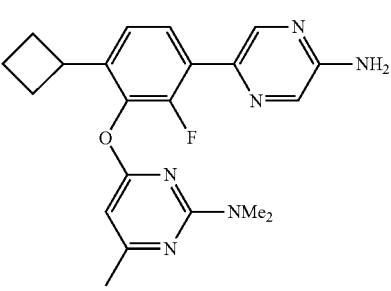 [SMILES: Cc1cc(Oc2c(C3CCC3)ccc(-c3cnc(N)cn3)c2F)nc(N(C)C)n1] | 236 | 4-(3-(5-Aminopyrazin-2-yl)-6-cyclobutyl-2-fluorophenoxy)-N,N,6-trimethylpyrimidin-2-amine |

| COMPOUND # | NAME |
|---|---|
| 237 | 6-(3-(5-Aminopyrazin-2-yl)-6-cyclobutyl-2-fluorophenoxy)-N,N-dimethylpyrimidin-4-amine |
| 238 | Ethyl 5-(3-(5-aminopyrazin-2-yl)-6-cyclobutyl-2-fluorophenoxy)-1-methyl-3-(trifluoromethyl)-1H-pyrazole-4-carboxylate |
| 239 | 5-(4-cyclobutyl-2-fluoro-3-((5-(methylsulfonyl)pyridin-2-yl)oxy)phenyl)pyrazin-2-amine |
| 240 | 4-(3-(5-aminopyrazin-2-yl)-6-cyclobutyl-2-fluorophenoxy)-6-(tert-butyl)pyrimidin-2-amine |
| 241 | 5-(3-((4-(1,5-dioxa-9-azaspiro[5.5]undecan-9-yl)pyrimidin-2-yl)oxy)-4-cyclobutyl-2-fluorophenyl)pyrazin-2-amine |

TABLE 3-continued

| STRUCTURE | COMPOUND # | NAME |
|---|---|---|
| 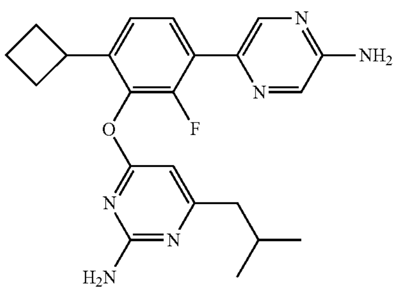 [SMILES: CC(C)Cc1cc(Oc2c(C3CCC3)ccc(-c3cnc(N)cn3)c2F)nc(N)n1] | 242 | 4-(3-(5-aminopyrazin-2-yl)-6-cyclobutyl-2-fluorophenoxy)-6-isobutylpyrimidin-2-amine |
| 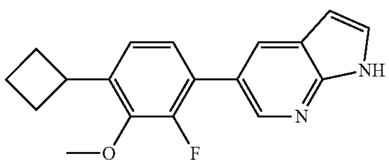 | I | 5-(4-Cyclobutyl-2-fluoro-3-methoxyphenyl)-1H-pyrrolo[2,3-b]pyridine |
| 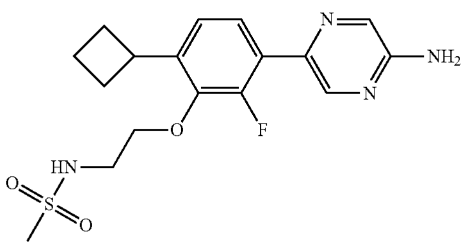 [SMILES: CS(=O)(=O)NCCOc1c(C2CCC2)ccc(-c2cnc(N)cn2)c1F] | 243 | N-(2-(3-(5-Aminopyrazin-2-yl)-6-cyclobutyl-2-fluorophenoxy)-ethyl)-methane-sulfonamide |
| 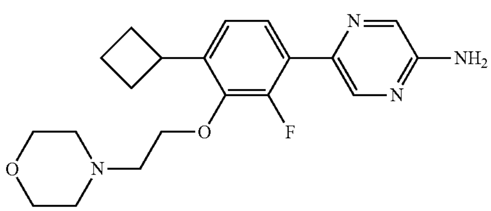 [SMILES: Nc1cnc(-c2ccc(C3CCC3)c(OCCN3CCOCC3)c2F)cn1] | 244 | 5-(4-Cyclobutyl-2-fluoro-3-(2-morpholinoethoxy)phenyl)pyrazin-2-amine |
| 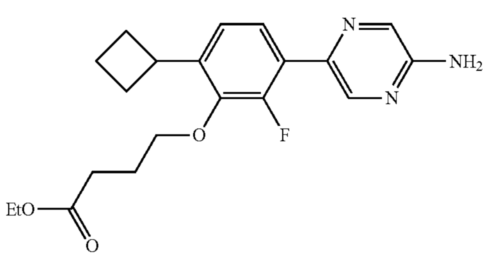 | 245 | Ethyl 4-(3-(5-aminopyrazin-2-yl)-6-cyclobutyl-2-fluorophenoxy)butanoate |
| 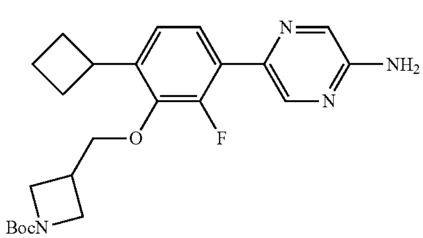 [SMILES: CC(C)(C)OC(=O)N1CC(COc2c(C3CCC3)ccc(-c3cnc(N)cn3)c2F)C1] | 246 | tert-Butyl 3-((3-(5-aminopyrazin-2-yl)-6-cyclobutyl-2-fluorophenoxy)methyl)azetidine-1-carboxylate |

TABLE 3-continued

| STRUCTURE | COMPOUND # | NAME |
|---|---|---|
| 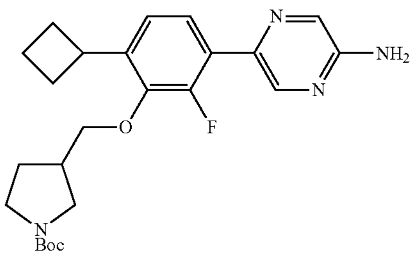 [SMILES: CC(C)(C)OC(=O)N1CCC(COc2c(C3CCC3)ccc(-c3cnc(N)cn3)c2F)C1] | 247 | tert-Butyl 3-((3-(5-aminopyrazin-2-yl)-6-cyclobutyl-2-fluorophenoxy)methyl)pyrrolidine-1-carboxylate |
| 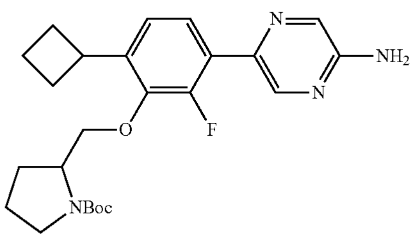 [SMILES: CC(C)(C)OC(=O)N1CCCC1COc1c(C2CCC2)ccc(-c2cnc(N)cn2)c1F] | 248 | tert-Butyl 2-((3-(5-aminopyrazin-2-yl)-6-cyclobutyl-2-fluorophenoxy)methyl)pyrrolidine-1-carboxylate |
| 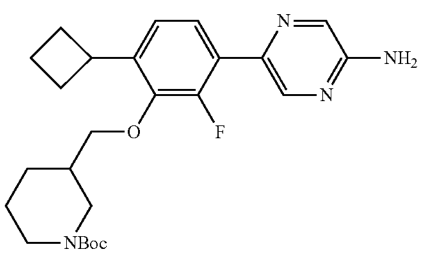 [SMILES: CC(C)(C)OC(=O)N1CCCC(COc2c(C3CCC3)ccc(-c3cnc(N)cn3)c2F)C1] | 249 | tert-Butyl 3-((3-(5-aminopyrazin-2-yl)-6-cyclobutyl-2-fluorophenoxy)methyl)piperidine-1-carboxylate |
| 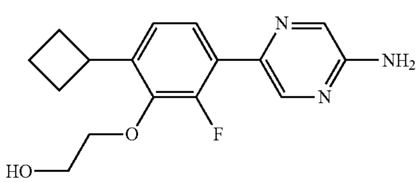 [SMILES: Nc1cnc(-c2ccc(C3CCC3)c(OCCO)c2F)cn1] | 250 | 2-(3-(5-Aminopyrazin-2-yl)-6-cyclobutyl-2-fluorophenoxy)ethanol |
| 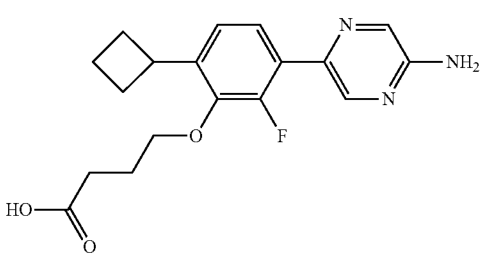 [SMILES: Nc1cnc(-c2ccc(C3CCC3)c(OCCCC(=O)O)c2F)cn1] | 251 | 4-(3-(5-Aminopyrazin-2-yl)-6-cyclobutyl-2-fluorophenoxy)butanoic acid |
| 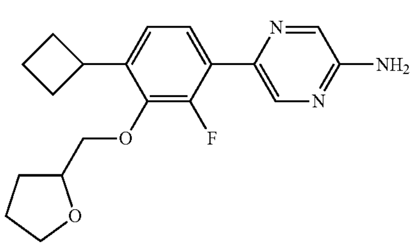 [SMILES: Nc1cnc(-c2ccc(C3CCC3)c(OCC3CCCO3)c2F)cn1] | 252 | 5-(4-Cyclobutyl-2-fluoro-3-((tetrahydrofuran-2-yl)methoxy)phenyl)pyrazin-2-amine |

TABLE 3-continued

| STRUCTURE | COMPOUND # | NAME |
|---|---|---|
| 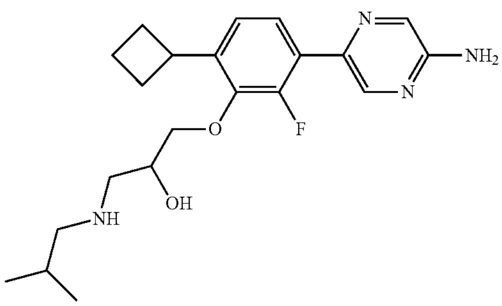 [SMILES: CC(C)CNCC(O)COc1c(C2CCC2)ccc(-c2cnc(N)cn2)c1F] | 253 | racemic 1-(3-(5-Aminopyrazin-2-yl)-6-cyclobutyl-2-fluorophenoxy)-3-(isobutylamino)propan-2-ol |
| 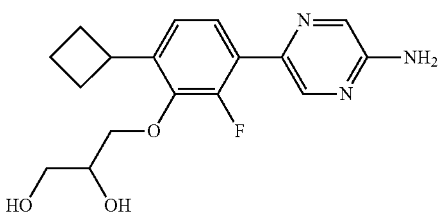 [SMILES: Nc1cnc(-c2ccc(C3CCC3)c(OCC(O)CO)c2F)cn1] | 254 | racemic 3-(3-(5-Aminopyrazin-2-yl)-6-cyclobutyl-2-fluorophenoxy)propane-1,2-diol |
| 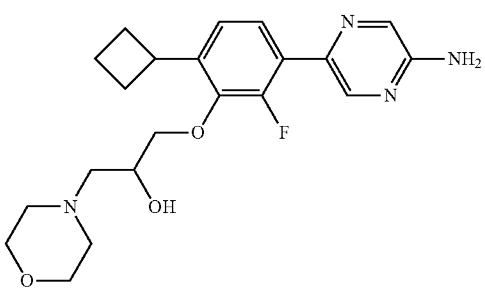 [SMILES: Nc1cnc(-c2ccc(C3CCC3)c(OCC(O)CN3CCOCC3)c2F)cn1] | 255 | racemic 1-(3-(5-aminopyrazin-2-yl)-6-cyclobutyl-2-fluorophenoxy)-3-morpholinopropan-2-ol |
| 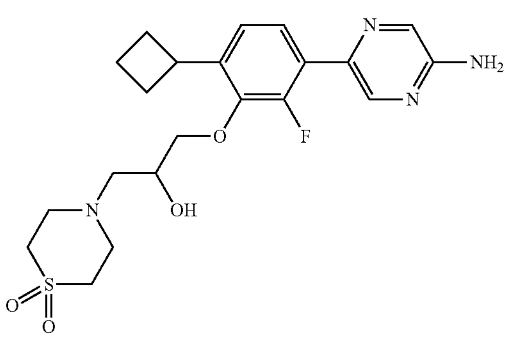 [SMILES: Nc1cnc(-c2ccc(C3CCC3)c(OCC(O)CN3CCS(=O)(=O)CC3)c2F)cn1] | 256 | racemic 4-(3-(3-(5-Aminopyrazin-2-yl)-6-cyclobutyl-2-fluorophenoxy)-2-hydroxypropyl)thiomorpholine 1,1-dioxide |
| 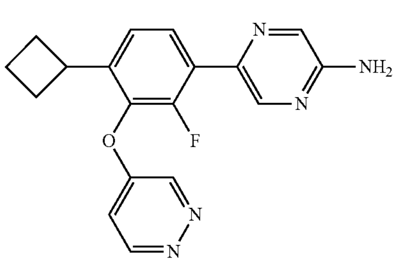 [SMILES: Nc1cnc(-c2ccc(C3CCC3)c(Oc3ccnnc3)c2F)cn1] | 257 | 5-(4-Cyclobutyl-2-fluoro-3-(pyridazin-4-yloxy)phenyl)pyrazin-2-amine |

TABLE 3-continued

| STRUCTURE | COMPOUND # | NAME |
|---|---|---|
| 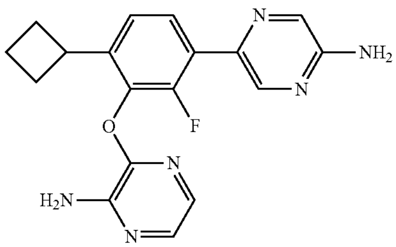 [SMILES: Nc1cnc(-c2ccc(C3CCC3)c(Oc3nccnc3N)c2F)cn1] | 258 | 3-(3-(5-Aminopyrazin-2-yl)-6-cyclobutyl-2-fluorophenoxy)pyrazin-2-amine |
| 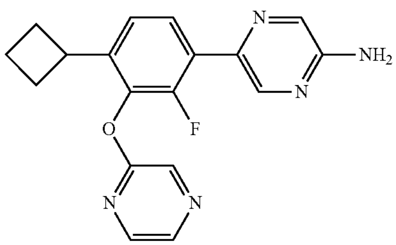 [SMILES: Nc1cnc(-c2ccc(C3CCC3)c(Oc3cnccn3)c2F)cn1] | 259 | 5-(4-Cyclobutyl-2-fluoro-3-(pyrazin-2-yloxy)phenyl)pyrazin-2-amine |
| 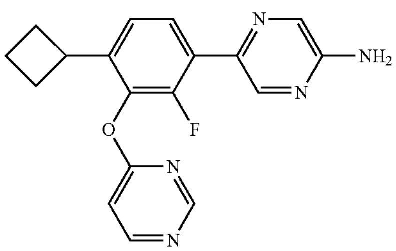 [SMILES: Nc1cnc(-c2ccc(C3CCC3)c(Oc3ccncn3)c2F)cn1] | 260 | 5-(4-Cyclobutyl-2-fluoro-3-(pyrimidin-4-yloxy)phenyl)pyrazin-2-amine |
| 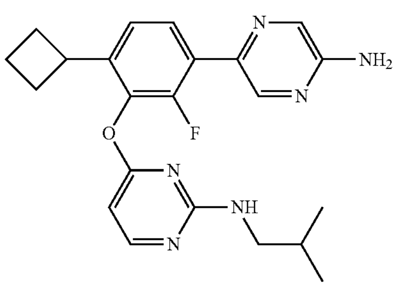 [SMILES: CC(C)CNc1nccc(Oc2c(C3CCC3)ccc(-c3cnc(N)cn3)c2F)n1] | 261 | 4-(3-(5-Aminopyrazin-2-yl)-6-cyclobutyl-2-fluorophenoxy)-N-isobutylpyrimidin-2-amine trifluoroacetic acid salt |
| 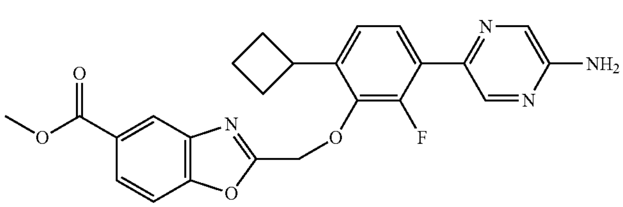 [SMILES: COC(=O)c1ccc2oc(COc3c(C4CCC4)ccc(-c4cnc(N)cn4)c3F)nc2c1] | 262 | Methyl 2-{[3-(5-aminopyrazin-2-yl)-6-cyclobutyl-2-fluorophenoxy]methyl}-1,3-benzoxazole-5-carboxylate |
| 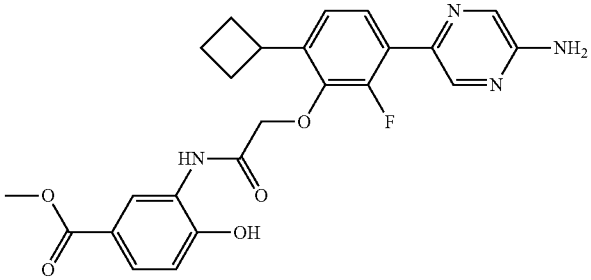 [SMILES: COC(=O)c1ccc(O)c(NC(=O)COc2c(C3CCC3)ccc(-c3cnc(N)cn3)c2F)c1] | 263 | Methyl 3-({[3-(5-aminopyrazin-2-yl)-6-cyclobutyl-2-fluorophenoxy]acetyl}amino)-4-hydroxybenzoate |

TABLE 3-continued

| STRUCTURE | COMPOUND # | NAME |
|---|---|---|
| 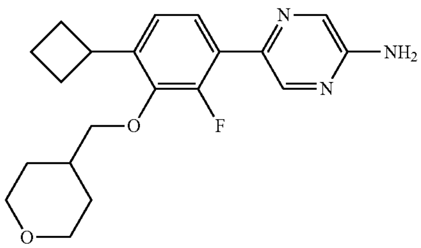 | 264 | 5-[4-Cyclobutyl-2-fluoro-3-(tetrahydro-2H-pyran-4-ylmethoxy)phenyl]pyrazin-2-amine |
| 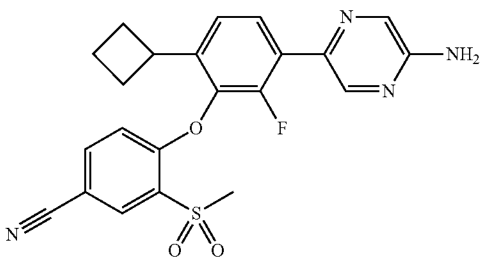 [SMILES: CS(=O)(=O)c1cc(C#N)ccc1Oc1c(C2CCC2)ccc(-c2cnc(N)cn2)c1F] | 265 | 4-[3-(5-Aminopyrazin-2-yl)-6-cyclobutyl-2-fluorophenoxy]-3-(methylsulfonyl)benzonitrile |
| 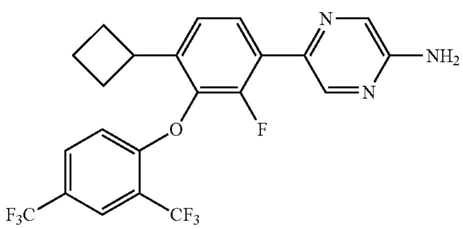 [SMILES: Nc1cnc(-c2ccc(C3CCC3)c(Oc3ccc(C(F)(F)F)cc3C(F)(F)F)c2F)cn1] | 266 | 5-{3-[2,4-Bis(trifluoromethyl)phenoxy]-4-cyclobutyl-2-fluorophenyl}pyrazin-2-amine |
| 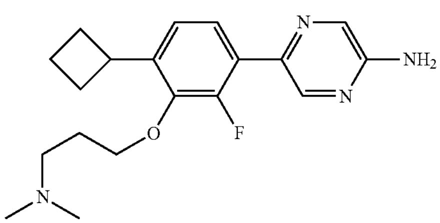 [SMILES: CN(C)CCCOc1c(C2CCC2)ccc(-c2cnc(N)cn2)c1F] | 267 | 5-{4-Cyclobutyl-3-[3-(dimethylamino)propoxy]-2-fluorophenyl}pyrazin-2-amine |
| 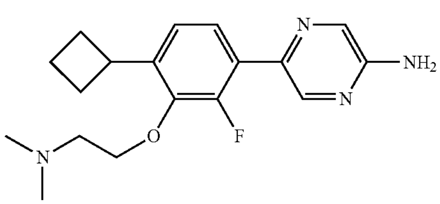 [SMILES: CN(C)CCOc1c(C2CCC2)ccc(-c2cnc(N)cn2)c1F] | 268 | 5-{4-Cyclobutyl-3-[2-(dimethylamino)ethoxy]-2-fluorophenyl}pyrazin-2-amine |
| 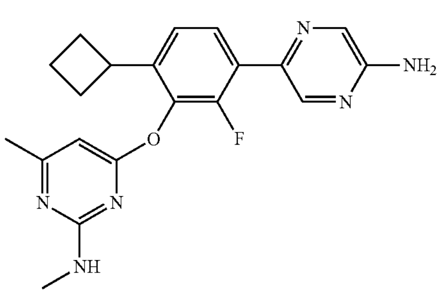 [SMILES: CNc1nc(C)cc(Oc2c(C3CCC3)ccc(-c3cnc(N)cn3)c2F)n1] | 269 | 4-[3-(5-Aminopyrazin-2-yl)-6-cyclobutyl-2-fluorophenoxy]-N,6-dimethylpyrimidin-2-amine |

TABLE 3-continued

| STRUCTURE | COMPOUND # | NAME |
|---|---|---|
| 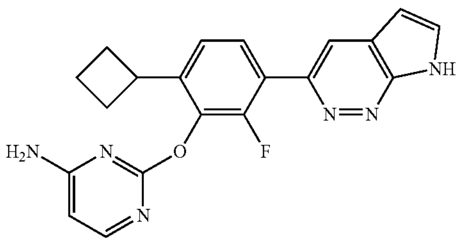 [SMILES: Nc1ccnc(Oc2c(C3CCC3)ccc(-c3cc4cc[nH]c4nn3)c2F)n1] | 270 | 2-[6-Cyclobutyl-2-fluoro-3-(7H-pyrrolo[2,3-c]pyridazin-3-yl)phenoxy]pyrimidin-4-amine |
| 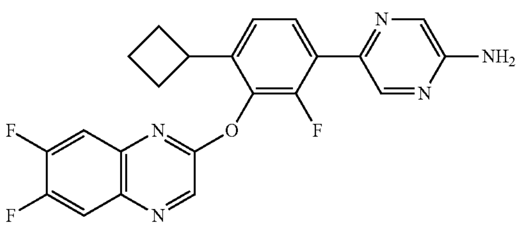 [SMILES: Nc1cnc(-c2ccc(C3CCC3)c(Oc3cnc4cc(F)c(F)cc4n3)c2F)cn1] | 271 | 5-{4-Cyclobutyl-3-[(6,7-difluoroquinoxalin-2-yl)oxy]-2-fluorophenyl}pyrazin-2-amine |
| 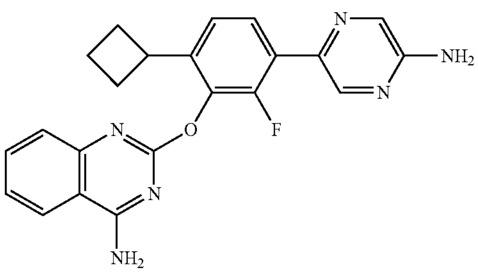 [SMILES: Nc1cnc(-c2ccc(C3CCC3)c(Oc3nc(N)c4ccccc4n3)c2F)cn1] | 272 | 2-[3-(5-Aminopyrazin-2-yl)-6-cyclobutyl-2-fluorophenoxy]quinazolin-4-amine |
| 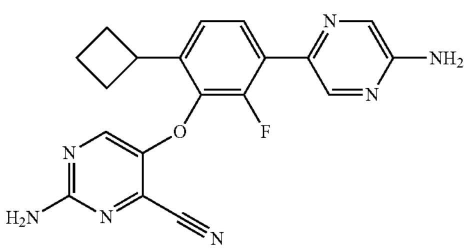 [SMILES: N#Cc1nc(N)ncc1Oc1c(C2CCC2)ccc(-c2cnc(N)cn2)c1F] | 273 | 2-Amino-5-[3-(5-aminopyrazin-2-yl)-6-cyclobutyl-2-fluorophenoxy]pyrimidine-4-carbonitrile |
| 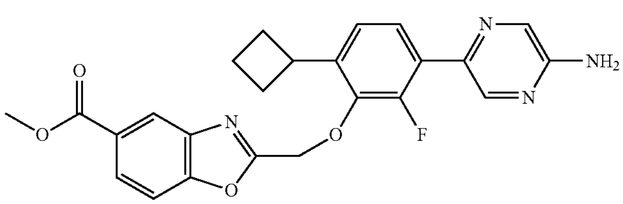 [SMILES: COC(=O)c1ccc2oc(COc3c(C4CCC4)ccc(-c4cnc(N)cn4)c3F)nc2c1] | 274 | Methyl 2-{[3-(5-aminopyrazin-2-yl)-6-cyclobutyl-2-fluorophenoxy]methyl}-1,3-benzoxazole-5-carboxylate |
| 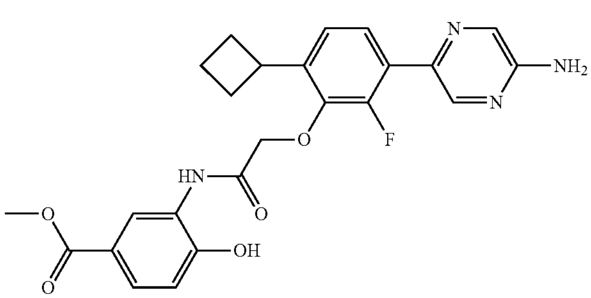 [SMILES: COC(=O)c1ccc(O)c(NC(=O)COc2c(C3CCC3)ccc(-c3cnc(N)cn3)c2F)c1] | 275 | Methyl 3-({[3-(5-aminopyrazin-2-yl)-6-cyclobutyl-2-fluorophenoxy]acetyl}amino)-4-hydroxybenzoate |

TABLE 3-continued

| STRUCTURE | COMPOUND # | NAME |
|---|---|---|
| 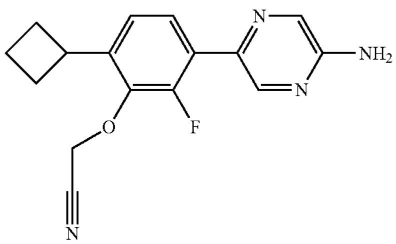 [SMILES: N#CCOc1c(C2CCC2)ccc(-c2cnc(N)cn2)c1F] | 276 | [3-(5-Aminopyrazin-2-yl)-6-cyclobutyl-2-fluorophenoxy]acetonitrile |
| 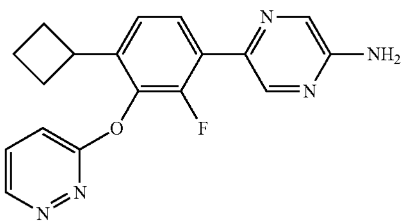 [SMILES: Nc1cnc(-c2ccc(C3CCC3)c(Oc3cccnn3)c2F)cn1] | 277 | 5-[4-Cyclobutyl-2-fluoro-3-(pyridazin-3-yloxy)phenyl]pyrazin-2-amine |
| 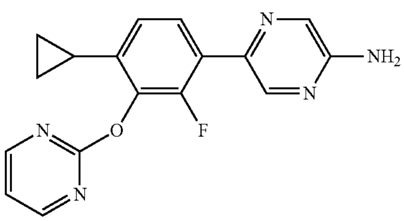 [SMILES: Nc1cnc(-c2ccc(C3CC3)c(Oc3ncccn3)c2F)cn1] | 278 | 5-[4-Cyclopropyl-2-fluoro-3-(pyrimidin-2-yloxy)phenyl]pyran-2-amine |
| 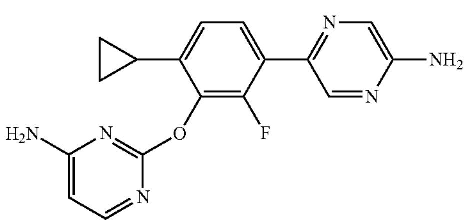 [SMILES: Nc1cnc(-c2ccc(C3CC3)c(Oc3nccc(N)n3)c2F)cn1] | 279 | 2-[3-(5-Aminopyrazin-2-yl)-6-cyclopropyl-2-fluorophenoxy]pyrimidin-4-amine |
| 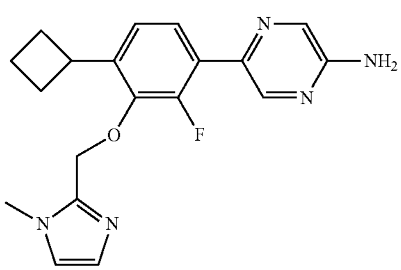 [SMILES: Cn1ccnc1COc1c(C2CCC2)ccc(-c2cnc(N)cn2)c1F] | 280 | 5-{4-Cyclobutyl-2-fluoro-3-[(1-methyl-1H-imidazol-2-yl)methoxy]phenyl}pyrazin-2-amine trifluoroacetic acid salt |
| 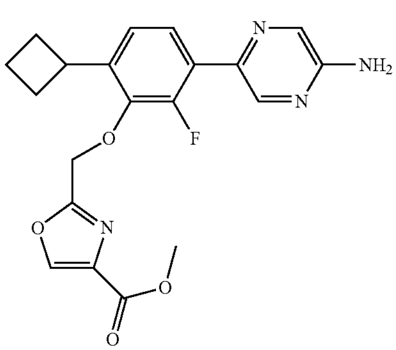 [SMILES: COC(=O)c1coc(COc2c(C3CCC3)ccc(-c3cnc(N)cn3)c2F)n1] | 281 | Methyl 2-{[3-(5-aminopyrazin-2-yl)-6-cyclobutyl-2-fluorophenoxy]methyl}-1,3-oxazole-4-carboxylate trifluoroacetic acid salt |

TABLE 3-continued

| STRUCTURE | COMPOUND # | NAME |
|---|---|---|
| 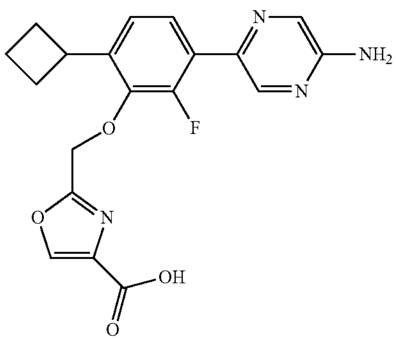 [SMILES: Nc1cnc(-c2ccc(C3CCC3)c(OCc3nc(C(=O)O)co3)c2F)cn1] | 282 | 2-{[3-(5-Aminopyrazin-2-yl)-6-cyclobutyl-2-fluorophenoxy]methyl}-1,3-oxazole-4-carboxylic acid trifluoroacetic acid salt |
| 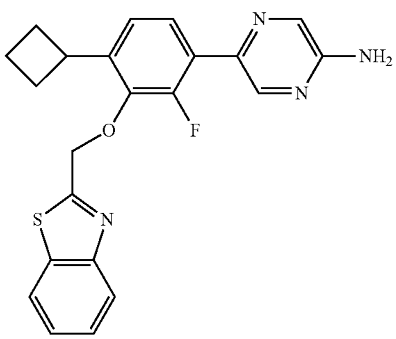 [SMILES: Nc1cnc(-c2ccc(C3CCC3)c(OCc3nc4ccccc4s3)c2F)cn1] | 283 | 5-[3-(1,3-Benzothiazol-2-ylmethoxy)-4-cyclobutyl-2-fluorophenyl]pyrazin-2-amine trifluoroacetic acid salt |
| 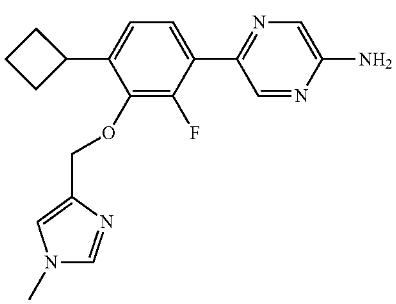 [SMILES: Cn1cnc(COc2c(C3CCC3)ccc(-c3cnc(N)cn3)c2F)c1] | 284 | 5-{4-Cyclobutyl-2-fluoro-3-[(1-methyl-1H-imidazol-4-yl)methoxy]phenyl}pyrazin-2-amine trifluoroacetic acid salt |
| 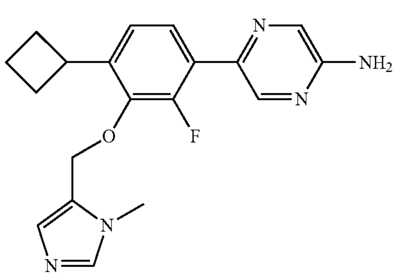 [SMILES: Cn1cncc1COc1c(C2CCC2)ccc(-c2cnc(N)cn2)c1F] | 285 | 5-{4-Cyclobutyl-2-fluoro-3-[(1-methyl-1H-imidazol-5-yl)methoxy]phenyl}pyrazin-2-amine trifluoroacetic acid salt |
| 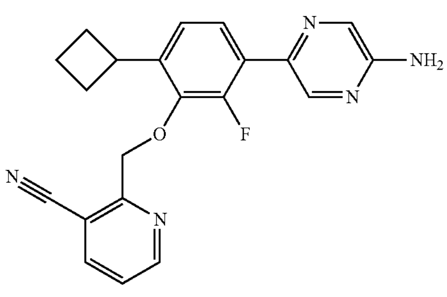 [SMILES: N#Cc1cccnc1COc1c(C2CCC2)ccc(-c2cnc(N)cn2)c1F] | 286 | 2-{[3-(5-Aminopyrazin-2-yl)-6-cyclobutyl-2-fluorophenoxy]methyl}pyridine-3-carbonitrile trifluoroacetic acid salt |

TABLE 3-continued

| STRUCTURE | COMPOUND # | NAME |
|---|---|---|
| 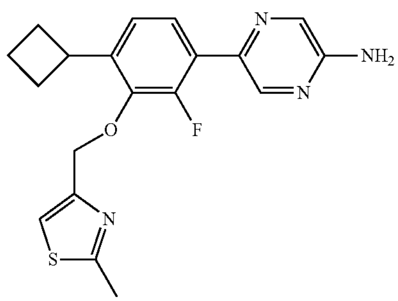 [SMILES: Cc1nc(COc2c(C3CCC3)ccc(-c3cnc(N)cn3)c2F)cs1] | 287 | 5-{4-Cyclobutyl-2-fluoro-3-[(2-methyl-1,3-thiazol-4-yl)methoxy]phenyl}pyrazin-2-amine trifluoroacetic acid salt |
| 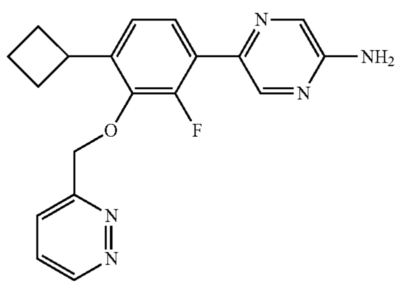 [SMILES: Nc1cnc(-c2ccc(C3CCC3)c(OCc3cccnn3)c2F)cn1] | 288 | 5-[4-Cyclobutyl-2-fluoro-3-(pyridazin-3-ylmethoxy)phenyl]pyrazin-2-amine trifluoroacetic acid salt |
| 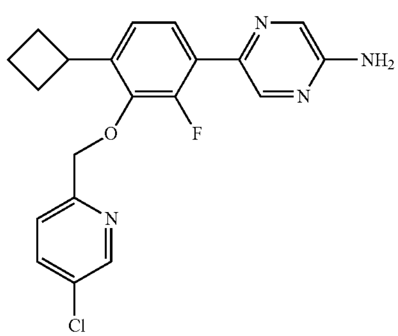 [SMILES: Nc1cnc(-c2ccc(C3CCC3)c(OCc3ccc(Cl)cn3)c2F)cn1] | 289 | 5-{3-[(5-Chloropyridin-2-yl)methoxy]-4-cyclobutyl-2-fluorophenyl}pyrazin-2-amine trifluoroacetic acid salt |
| 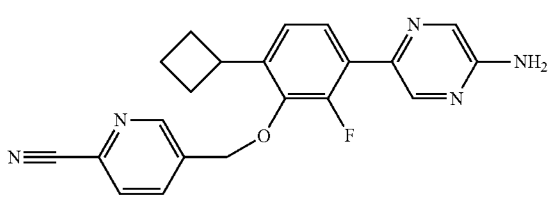 [SMILES: N#Cc1ccc(COc2c(C3CCC3)ccc(-c3cnc(N)cn3)c2F)cn1] | 290 | 5-{[3-(5-Aminopyrazin-2-yl)-6-cyclobutyl-2-fluorophenoxy]methyl}pyridine-2-carbonitrile trifluoroacetic acid salt |
| 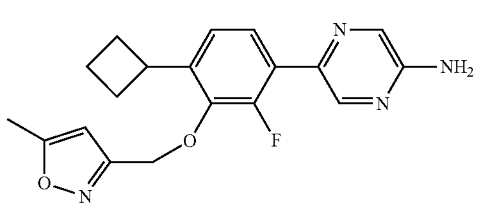 [SMILES: Cc1cc(COc2c(C3CCC3)ccc(-c3cnc(N)cn3)c2F)no1] | 291 | 5-{4-Cyclobutyl-2-fluoro-3-[(5-methylisoxazol-3-yl)methoxy]phenyl}pyrazin-2-amine trifluoroacetic acid salt |

TABLE 3-continued

| STRUCTURE | COMPOUND # | NAME |
|---|---|---|
| 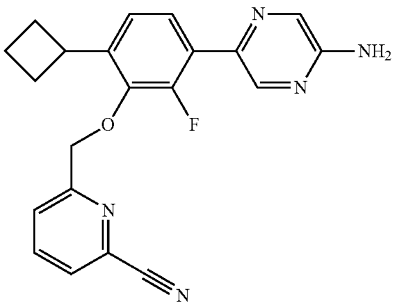 [SMILES: N#Cc1cccc(COc2c(C3CCC3)ccc(-c3cnc(N)cn3)c2F)n1] | 292 | 6-{[3-(5-Aminopyrazin-2-yl)-6-cyclobutyl-2-fluorophenoxy]methyl}pyridine-2-carbonitrile trifluoroacetic acid salt |
| 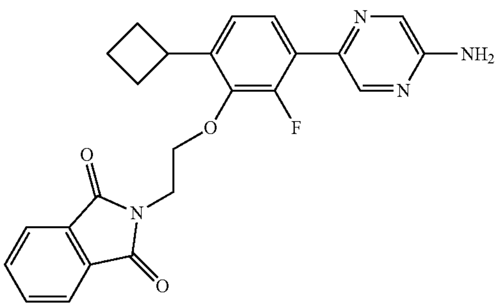 [SMILES: Nc1cnc(-c2ccc(C3CCC3)c(OCCN3C(=O)c4ccccc4C3=O)c2F)cn1] | 293 | 2-{2-[3-(5-Aminopyrazin-2-yl)-6-cyclobutyl-2-fluorophenoxy]ethyl}-1H-isoindole-1,3(2H)-dione |
| 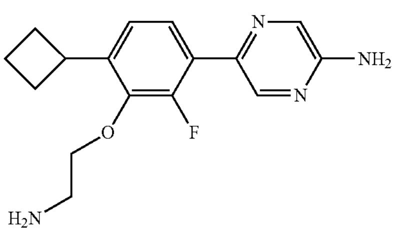 [SMILES: NCCOc1c(C2CCC2)ccc(-c2cnc(N)cn2)c1F] | 294 | 5-[3-(2-Aminoethoxy)-4-cyclobutyl-2-fluorophenyl]pyrazin-2-amine |
| 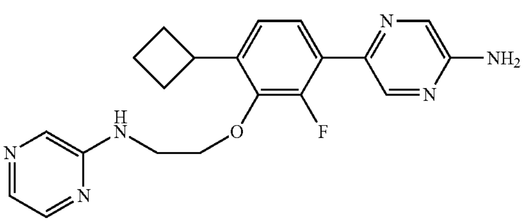 [SMILES: Nc1cnc(-c2ccc(C3CCC3)c(OCCNc3cnccn3)c2F)cn1] | 295 | 5-{4-Cyclobutyl-2-fluoro-3-[2-(pyrazin-2-ylamino)ethoxy]phenyl}pyrazin-2-amine trifluoroacetic acid salt |
| 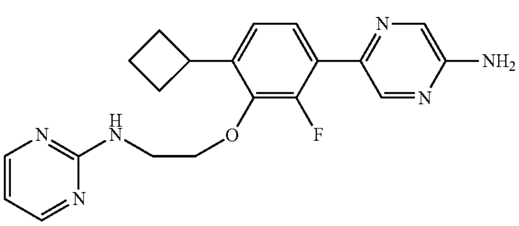 [SMILES: Nc1cnc(-c2ccc(C3CCC3)c(OCCNc3ncccn3)c2F)cn1] | 296 | N-{2-[3-(5-Aminopyrazin-2-yl)-6-cyclobutyl-2-fluorophenoxy]ethyl}pyrimidin-2-amine trifluoroacetic acid salt |
| 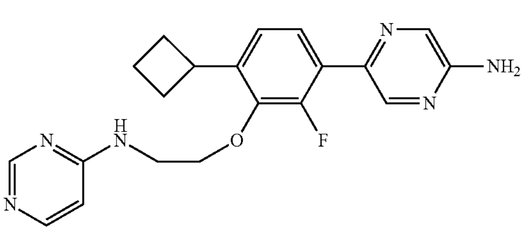 [SMILES: Nc1cnc(-c2ccc(C3CCC3)c(OCCNc3ccncn3)c2F)cn1] | 297 | N-{2-[3-(5-Aminopyrazin-2-yl)-6-cyclobutyl-2-fluorophenoxy]ethyl}pyrimidin-4-amine |

TABLE 3-continued

| STRUCTURE | COMPOUND # | NAME |
|---|---|---|
| 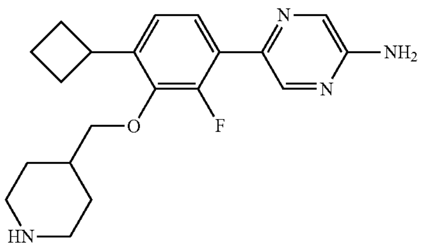 [SMILES: Nc1cnc(-c2ccc(C3CCC3)c(OCC3CCNCC3)c2F)cn1] | 298 | 5-[4-Cyclobutyl-2-fluoro-3-(piperidin-4-ylmethoxy)phenyl]pyrazin-2-amine hydrogen chloride salt |
| 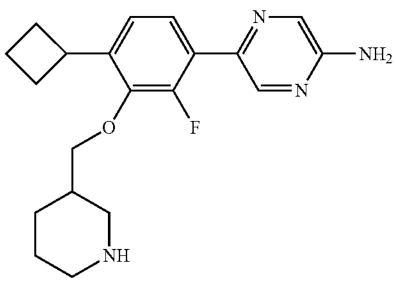 [SMILES: Nc1cnc(-c2ccc(C3CCC3)c(OCC3CCCNC3)c2F)cn1] | 299 | racemic 5-[4-Cyclobutyl-2-fluoro-3-(piperidin-3-ylmethoxy)phenyl]pyrazin-2-amine |
| 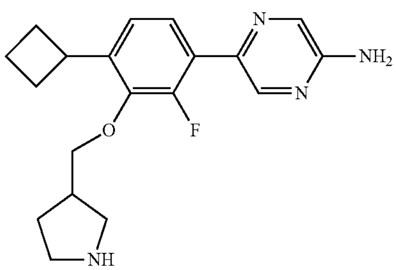 [SMILES: Nc1cnc(-c2ccc(C3CCC3)c(OCC3CCNC3)c2F)cn1] | 300 | racemic 5-[4-Cyclobutyl-2-fluoro-3-(pyrrolidin-3-ylmethoxy)phenyl]pyrazin-2-amine |
| 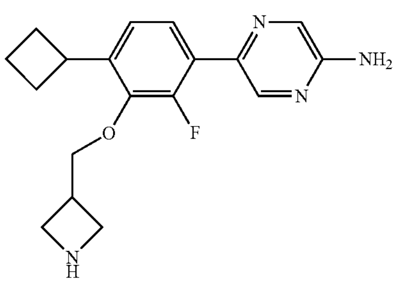 [SMILES: Nc1cnc(-c2ccc(C3CCC3)c(OCC3CNC3)c2F)cn1] | 301 | 5-[3-(Azetidin-3-ylmethoxy)-4-cyclobutyl-2-fluorophenyl]pyrazin-2-amine |
| 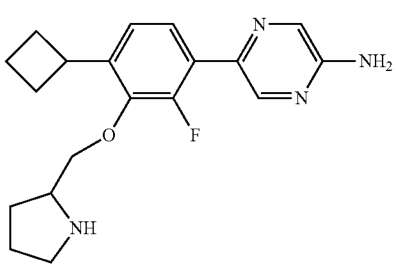 [SMILES: Nc1cnc(-c2ccc(C3CCC3)c(OCC3CCCN3)c2F)cn1] | 302 | racemic 5-[4-Cyclobutyl-2-fluoro-3-(pyrrolidin-2-ylmethoxy)phenyl]pyrazin-2-amine |

TABLE 3-continued

| STRUCTURE | COMPOUND # | NAME |
|---|---|---|
| 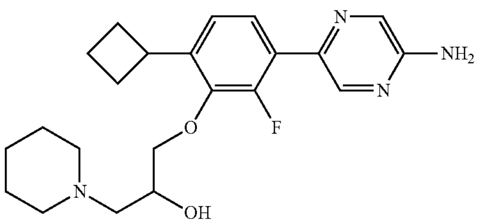 [SMILES: Nc1cnc(-c2ccc(C3CCC3)c(OCC(O)CN3CCCCC3)c2F)cn1] | 303 | racemic 5 1-[3-(5-Aminopyrazin-2-yl)-6-cyclobutyl-2-fluorophenoxy]-3-piperidin-1-ylpropan-2-ol |
| 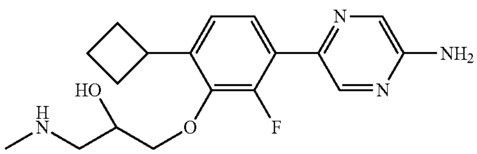 [SMILES: CNCC(O)COc1c(C2CCC2)ccc(-c2cnc(N)cn2)c1F] | 304 | racemic 1-[3-(5-Aminopyrazin-2-yl)-6-cyclobutyl-2-fluorophenoxy]-3-(methylamino)propan-2-ol |
| 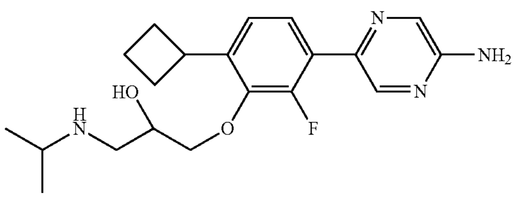 [SMILES: CC(C)NCC(O)COc1c(C2CCC2)ccc(-c2cnc(N)cn2)c1F] | 305 | racemic 1-[3-(5-Aminopyrazin-2-yl)-6-cyclobutyl-2-fluorophenoxy]-3-[(1-methylethyl)amino]propan-2-ol |
| 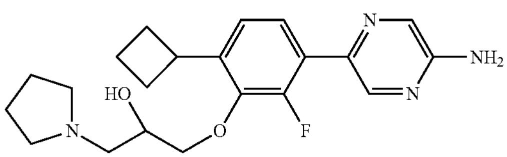 [SMILES: Nc1cnc(-c2ccc(C3CCC3)c(OCC(O)CN3CCCC3)c2F)cn1] | 306 | racemic 1-[3-(5-Aminopyrazin-2-yl)-6-cyclobutyl-2-fluorophenoxy]-3-pyrrolidin-1-ylpropan-2-ol |
| 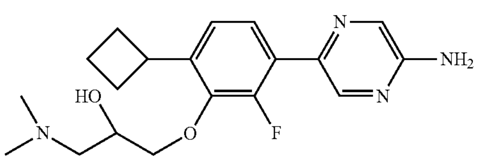 | 307 | racemic 1-[3-(5-Aminopyrazin-2-yl)-6-cyclobutyl-2-fluorophenoxy]-3-(dimethylamino)propan-2-ol |
| 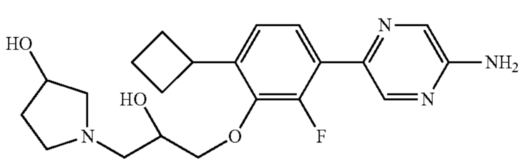 [SMILES: Nc1cnc(-c2ccc(C3CCC3)c(OCC(O)CN3CCC(O)C3)c2F)cn1] | 308 | diastereomeric mixture 1-{3-[3-(5-Aminopyrazin-2-yl)-6-cyclobutyl-2-fluorophenoxy]-2-hydroxypropyl}pyrrolidin-3-ol |
| 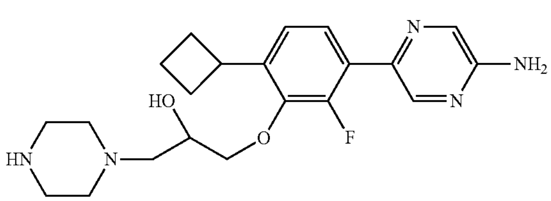 [SMILES: Nc1cnc(-c2ccc(C3CCC3)c(OCC(O)CN3CCNCC3)c2F)cn1] | 309 | racemic 1-[3-(5-Aminopyrazin-2-yl)-6-cyclobutyl-2-fluorophenoxy]-3-piperazin-1-ylpropan-2-ol |
| 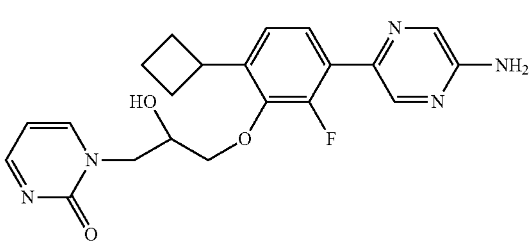 [SMILES: Nc1cnc(-c2ccc(C3CCC3)c(OCC(O)Cn3cccnc3=O)c2F)cn1] | 310 | racemic 1-{3-[3-(5-Aminopyrazin-2-yl)-6-cyclobutyl-2-fluorophenoxy]-2-hydroxypropyl}pyrimidin-2(1H)-one |

TABLE 3-continued

| STRUCTURE | COMPOUND # | NAME |
|---|---|---|
| 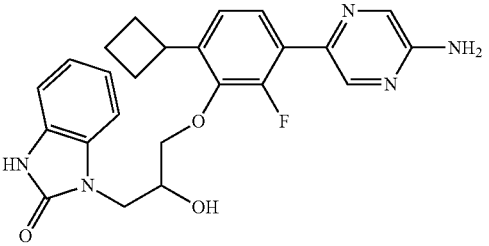 [SMILES: Nc1cnc(-c2ccc(C3CCC3)c(OCC(O)Cn3c(=O)[nH]c4ccccc43)c2F)cn1] | 311 | racemic 1-{3-[3-(5-Aminopyrazin-2-yl)-6-cyclobutyl-2-fluorophenoxy]-2-hydroxypropyl}-1,3-dihydro-2H-benzimidazol-2-one |
| 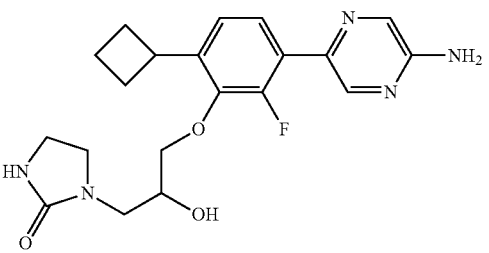 [SMILES: Nc1cnc(-c2ccc(C3CCC3)c(OCC(O)CN3CCNC3=O)c2F)cn1] | 312 | racemic 1-{3-[3-(5-Aminopyrazin-2-yl)-6-cyclobutyl-2-fluorophenoxy]-2-hydroxypropyl}imidazolidin-2-one |
| 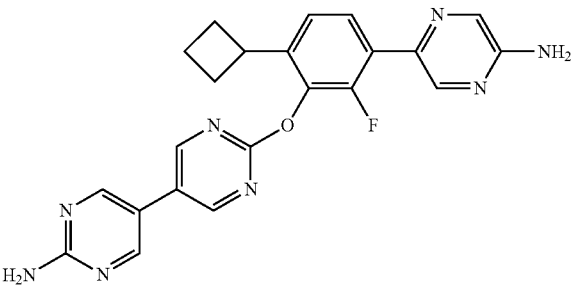 [SMILES: Nc1cnc(-c2ccc(C3CCC3)c(Oc3ncc(-c4cnc(N)nc4)cn3)c2F)cn1] | 313 | 2'-[3-(5-Aminopyrazin-2-yl)-6-cyclobutyl-2-fluorophenoxy]-5,5'-bipyrimidin-2-amine |
| 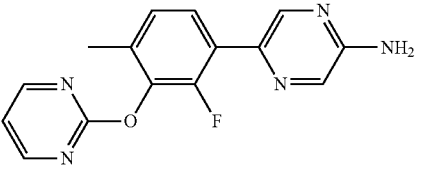 [SMILES: Cc1ccc(-c2cnc(N)cn2)c(F)c1Oc1ncccn1] | 314 | 5-[2-Fluoro-4-methyl-3-(pyrimidin-2-yloxy)phenyl]pyrazin-2-amine |
| 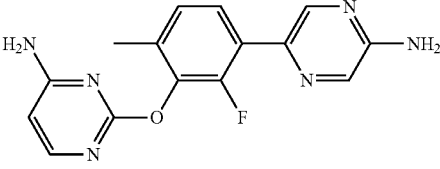 [SMILES: Cc1ccc(-c2cnc(N)cn2)c(F)c1Oc1nccc(N)n1] | 315 | 2-[3-(5-Aminopyrazin-2-yl)-2-fluoro-6-methylphenoxy]pyrimidin-4-amine |
| 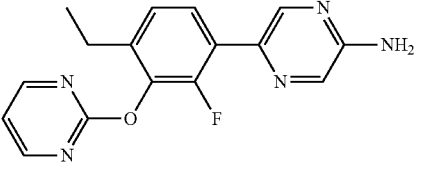 [SMILES: CCc1ccc(-c2cnc(N)cn2)c(F)c1Oc1ncccn1] | 316 | 5-[4-Ethyl-2-fluoro-3-(pyrimidin-2-yloxy)phenyl]pyrazin-2-amine |
| 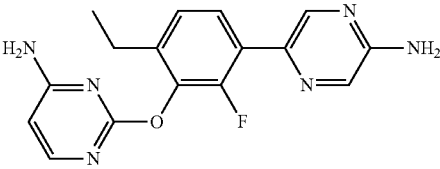 [SMILES: CCc1ccc(-c2cnc(N)cn2)c(F)c1Oc1nccc(N)n1] | 317 | 2-[3-(5-Aminopyrazin-2-yl)-6-ethyl-2-fluorophenoxy]pyrimidin-4-amine |

TABLE 3-continued

| STRUCTURE | COMPOUND # | NAME |
|---|---|---|
| 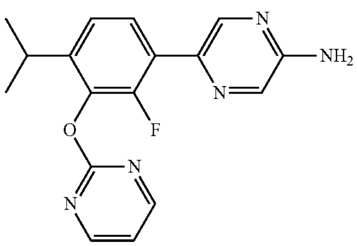 [SMILES: CC(C)c1ccc(-c2cnc(N)cn2)c(F)c1Oc1ncccn1] | 318 | 5-[2-Fluoro-4-(1-methylethyl)-3-(pyrimidin-2-yloxy)phenyl]pyrazin-2-amine |
| 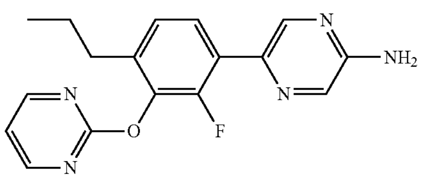 [SMILES: CCCc1ccc(-c2cnc(N)cn2)c(F)c1Oc1ncccn1] | 319 | 5-[2-Fluoro-4-propyl-3-(pyrimidin-2-yloxy)phenyl]pyrazin-2-amine |
| 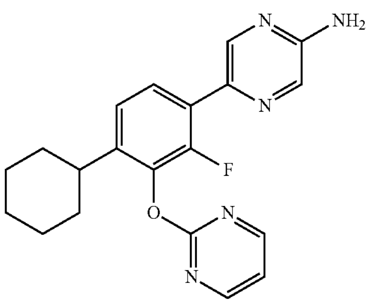 [SMILES: Nc1cnc(-c2ccc(C3CCCCC3)c(Oc3ncccn3)c2F)cn1] | 320 | 5-(4-Cyclohexyl-2-fluoro-3-(pyrimidin-2-yloxy)phenyl)pyrazin-2-amine |
| 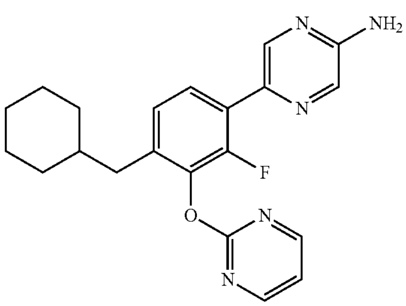 [SMILES: Nc1cnc(-c2ccc(CC3CCCCC3)c(Oc3ncccn3)c2F)cn1] | 321 | 5-(4-(Cyclohexylmethyl)-2-fluoro-3-(pyrimidin-2-yloxy)phenyl)pyrazin-2-amine |
| 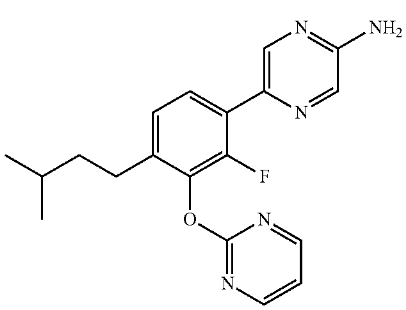 [SMILES: CC(C)CCc1ccc(-c2cnc(N)cn2)c(F)c1Oc1ncccn1] | 322 | 5-(2-Fluoro-4-isopentyl-3-(pyrimidin-2-yloxy)phenyl)pyrazin-2-amine |

TABLE 3-continued

| STRUCTURE | COMPOUND # | NAME |
|---|---|---|
| 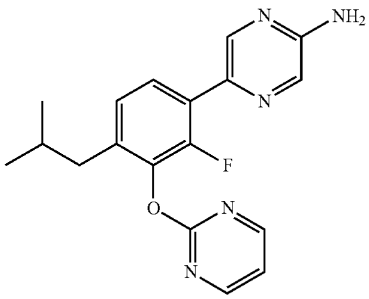 [SMILES: CC(C)Cc1ccc(-c2cnc(N)cn2)c(F)c1Oc1ncccn1] | 323 | 5-(2-Fluoro-4-isobutyl-3-(pyrimidin-2-yloxy)phenyl)pyrazin-2-amine |
| 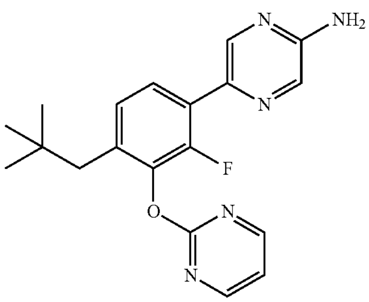 [SMILES: CC(C)(C)Cc1ccc(-c2cnc(N)cn2)c(F)c1Oc1ncccn1] | 324 | 5-(2-Fluoro-4-neopentyl-3-(pyrimidin-2-yloxy)phenyl)pyrazin-2-amine |
| 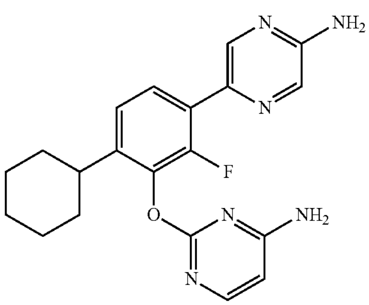 [SMILES: Nc1cnc(-c2ccc(C3CCCCC3)c(Oc3nccc(N)n3)c2F)cn1] | 325 | 2-(3-(5-Aminopyrazin-2-yl)-6-cyclohexyl-2-fluorophenoxy)pyrimidin-4-amine |
| 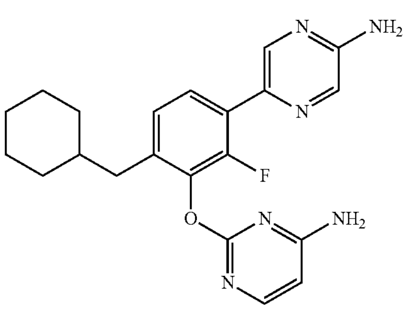 [SMILES: Nc1cnc(-c2ccc(CC3CCCCC3)c(Oc3nccc(N)n3)c2F)cn1] | 326 | 2-(3-(5-Aminopyrazin-2-yl)-6-(cyclohexylmethyl)-2-fluorophenoxy)pyrimidin-4-amine |
| 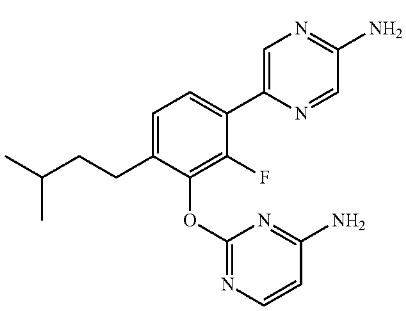 [SMILES: CC(C)CCc1ccc(-c2cnc(N)cn2)c(F)c1Oc1nccc(N)n1] | 327 | 2-(3-(5-Aminopyrazin-2-yl)-2-fluoro-6-isopentylphenoxy)pyrimidin-4-amine |

TABLE 3-continued

| STRUCTURE | COMPOUND # | NAME |
|---|---|---|
| 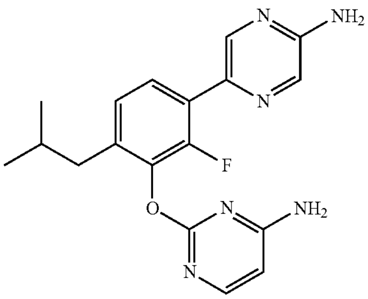 [SMILES: CC(C)Cc1ccc(-c2cnc(N)cn2)c(F)c1Oc1nccc(N)n1] | 328 | 2-(3-(5-Aminopyrazin-2-yl)-2-fluoro-6-isobutylphenoxy)pyrimidin-4-amine |
| 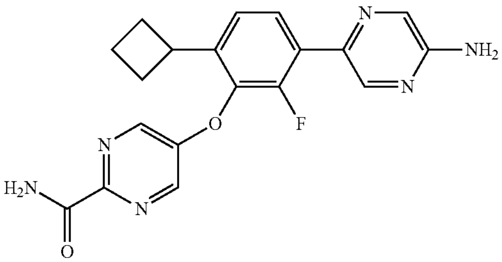 [SMILES: NC(=O)c1ncc(Oc2c(C3CCC3)ccc(-c3cnc(N)cn3)c2F)cn1] | 329 | 5-(3-(5-Aminopyrazin-2-yl)-6-cyclobutyl-2-fluorophenoxy)pyrimidine-2-carboxamide |
| 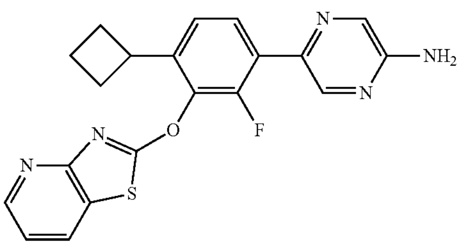 [SMILES: Nc1cnc(-c2ccc(C3CCC3)c(Oc3nc4ncccc4s3)c2F)cn1] | 330 | 5-(4-Cyclobutyl-2-fluoro-3-(thiazolo[4,5-b]pyridin-2-yloxy)phenyl)pyrazin-2-amine |
| 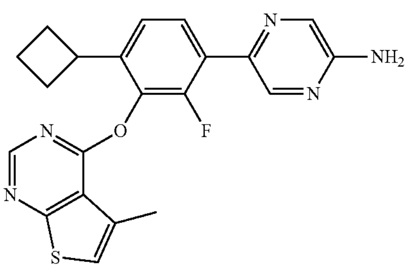 [SMILES: Cc1csc2ncnc(Oc3c(C4CCC4)ccc(-c4cnc(N)cn4)c3F)c12] | 331 | 5-(4-Cyclobutyl-2-fluoro-3-((5-methylthieno[2,3-d]pyrimidin-4-yl)oxy)phenyl)pyrazin-2-amine |
| 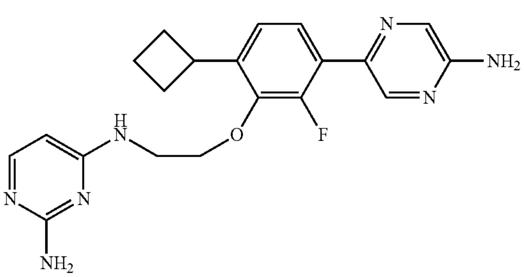 [SMILES: Nc1cnc(-c2ccc(C3CCC3)c(OCCNc3ccnc(N)n3)c2F)cn1] | 332 | N⁴-(2-(3-(5-Aminopyrazin-2-yl)-6-cyclobutyl-2-fluorophenoxy)ethyl)pyrimidine-2,4-diamine |
| 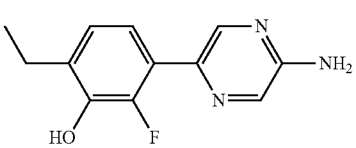 [SMILES: CCc1ccc(-c2cnc(N)cn2)c(F)c1O] | 333 | 3-(5-Aminopyrazin-2-yl)-6-ethyl-2-fluorophenol |

TABLE 3-continued
| STRUCTURE | COMPOUND # | NAME |
|---|---|---|
| 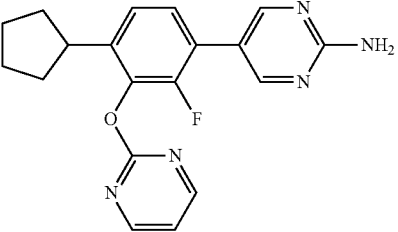 | 334 | 5-[4-Cyclopentyl-2-fluoro-3-(pyrimidin-2-yloxy)phenyl]pyrimidin-2-amine |
| 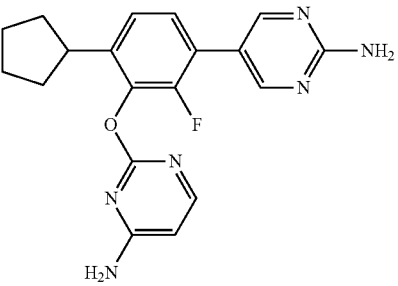 [SMILES: Nc1cnc(-c2ccc(C3CCCC3)c(Oc3nccc(N)n3)c2F)cn1] | 335 | 5-{3-[(4-Aminopyrimidin-2-yl)oxy]-4-cyclopentyl-2-fluorophenyl}pyrimidin-2-amine |
| 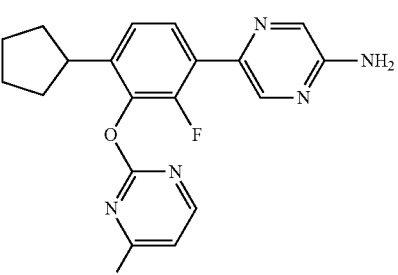 | 336 | 2-[3-(5-Aminopyrazin-2-yl)-6-cyclopentyl-2-fluorophenoxy]pyrimidin-4-amine |
| 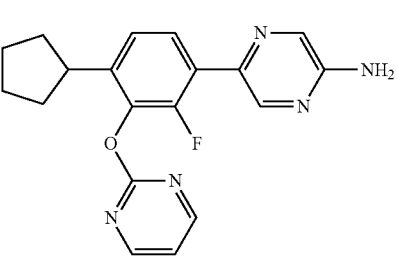 [SMILES: Nc1cnc(-c2ccc(C3CCCC3)c(Oc3ncccn3)c2F)cn1] | 337 | 5-[4-Cyclopentyl-2-fluoro-3-(pyrimidin-2-yloxy)phenyl]pyrazin-2-amine |
| 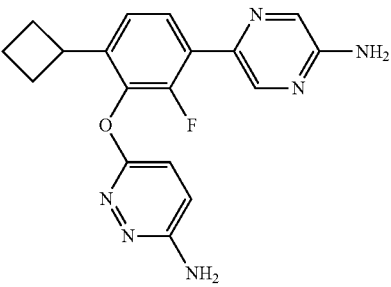 [SMILES: Nc1cnc(-c2ccc(C3CCC3)c(Oc3ccc(N)nn3)c2F)cn1] | 338 | 6-[3-(5-Aminopyrazin-2-yl)-6-cyclobutyl-2-fluorophenoxy]pyridazin-3-amine |

TABLE 3-continued

| STRUCTURE | COMPOUND # | NAME |
|---|---|---|
| 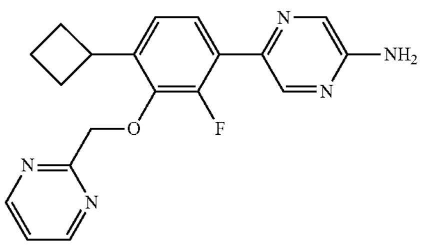 [SMILES: Nc1cnc(-c2ccc(C3CCC3)c(OCc3ncccn3)c2F)cn1] | 339 | 5-[4-Cyclobutyl-2-fluoro-3-(pyrimidin-2-ylmethoxy)phenyl]pyrazin-2-amine |
| 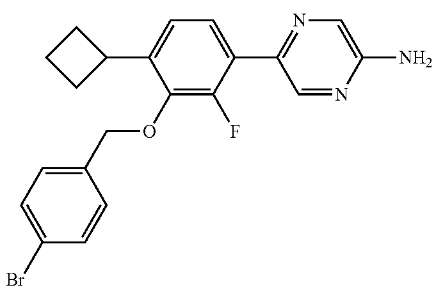 [SMILES: Nc1cnc(-c2ccc(C3CCC3)c(OCc3ccc(Br)cc3)c2F)cn1] | 340 | 5-{3-[(4-Bromobenzyl)oxy]-4-cyclobutyl-2-fluorophenyl}pyrazin-2-amine |
| 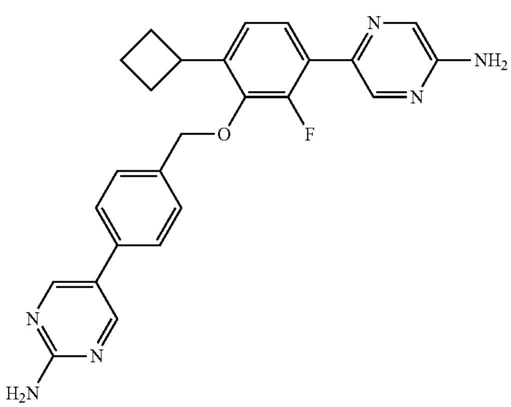 [SMILES: Nc1cnc(-c2ccc(C3CCC3)c(OCc3ccc(-c4cnc(N)nc4)cc3)c2F)cn1] | 341 | 5-(4-{[3-(5-Aminopyrazin-2-yl)-6-cyclobutyl-2-fluorophenoxy]methyl}phenyl)pyrimidin-2-amine |
| 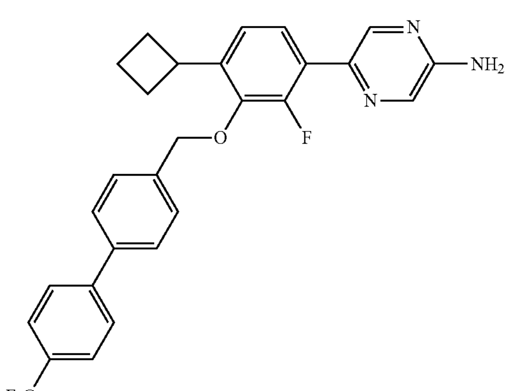 | 342 | 5-(4-Cyclobutyl-2-fluoro-3-{[4'-(trifluoromethyl)biphenyl-4-yl]methoxy}phenyl)pyrazin-2-amine |

TABLE 3-continued

| STRUCTURE | COMPOUND # | NAME |
|---|---|---|
| 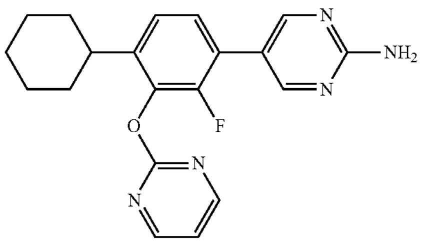 [SMILES: Nc1ncc(-c2ccc(C3CCCCC3)c(Oc3ncccn3)c2F)cn1] | 343 | 5-[4-Cyclohexyl-2-fluoro-3-(pyrimidin-2-yloxy)phenyl]pyrimidin-2-amine |
| 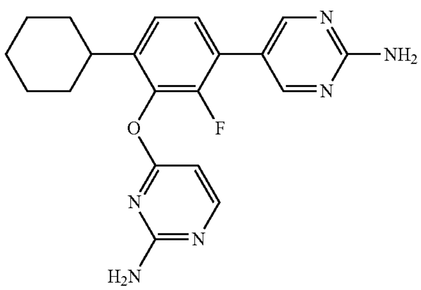 [SMILES: Nc1ncc(-c2ccc(C3CCCCC3)c(Oc3ccnc(N)n3)c2F)cn1] | 344 | 5-{3-[(4-Aminopyrimidin-2-yl)oxy]-4-cyclohexyl-2-fluorophenyl}pyrimidin-2-amine |
| 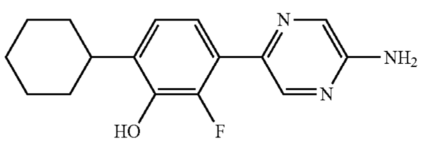 [SMILES: Nc1cnc(-c2ccc(C3CCCCC3)c(O)c2F)cn1] | 345 | 3-(5-Aminopyrazin-2-yl)-6-cyclohexyl-2-fluorophenol |
| 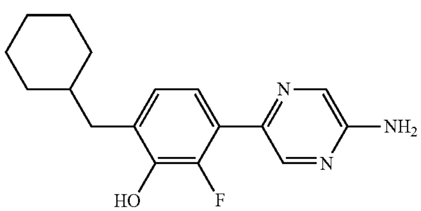 [SMILES: Nc1cnc(-c2ccc(CC3CCCCC3)c(O)c2F)cn1] | 346 | 3-(5-Aminopyrazin-2-yl)-6-(cyclohexylmethyl)-2-fluorophenol |
| 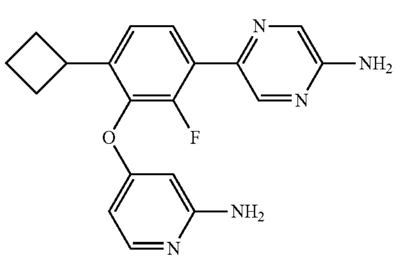 [SMILES: Nc1cnc(-c2ccc(C3CCC3)c(Oc3ccnc(N)c3)c2F)cn1] | 347 | 5-{3-[(2-Aminopyridin-4-yl)oxy]-4-cyclobutyl-2-fluorophenyl}pyrazin-2-amine |
| 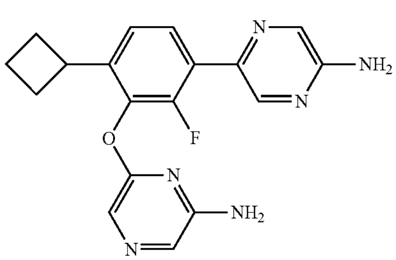 | 348 | 5-{3-[(6-Aminopyrazin-2-yl)oxy]-4-cyclobutyl-2-fluorophenyl}pyrazin-2-amine |

TABLE 3-continued

| STRUCTURE | COMPOUND # | NAME |
|---|---|---|
| 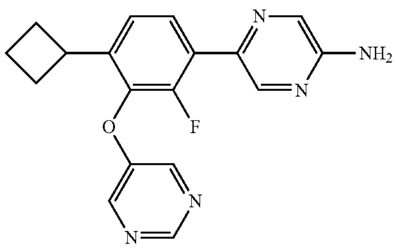 [SMILES: Nc1cnc(-c2ccc(C3CCC3)c(Oc3cncnc3)c2F)cn1] | 349 | 5-[4-Cyclobutyl-2-fluoro-3-(pyrimidin-5-yloxy)phenyl]pyrazin-2-amine |
| 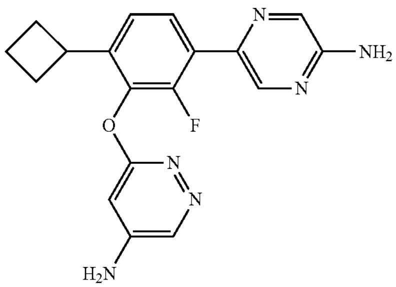 [SMILES: Nc1cnnc(Oc2c(C3CCC3)ccc(-c3cnc(N)cn3)c2F)c1] | 350 | 6-[3-(5-Aminopyrazin-2-yl)-6-cyclobutyl-2-fluorophenoxy]pyridazin-4-amine |
| 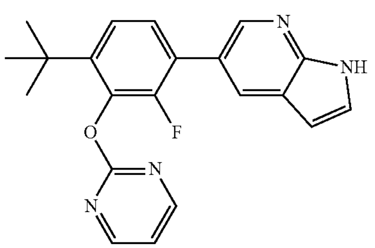 [SMILES: CC(C)(C)c1ccc(-c2cnc3[nH]ccc3c2)c(F)c1Oc1ncccn1] | 351 | 5-[4-tert-Butyl-2-fluoro-3-(pyrimidin-2-yloxy)phenyl]-1H-pyrrolo[2,3-b]pyridine |

C) Synthesis

The invention provides methods of making the disclosed compounds according to traditional organic synthetic methods as well as matrix or combinatorial synthetic methods. Scheme A described suggested synthetic routes. Using the schemes, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Representative compounds of the present invention can be synthesized in accordance with the general synthetic schemes described below and are illustrated more particularly in the specific synthetic examples that follow. The general schemes are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ESI) were recorded in the positive mode on a Hewlett Packard 59987A spectrometer. High resolution mass spectra (HRMS) were obtained on a Micromass Autospec. E spectrometer by fast atom bombardment (FAB) technique.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Scheme A, Intermediates A-N, Examples 1-351 and prophetic Examples 1-36. Compounds analogous to the target compounds of these examples can be made according to similar routes. The disclosed compounds are useful as pharmaceutical agents as described herein.

Abbreviations or acronyms used herein include:

| Abbreviation | Meaning |
| --- | --- |
| BOC/boc | tert-butyloxycarbonyl |
| BOP | benzotriazol-1-yloxy-tris(dimethylamino)phosphonium hexafluorophosphate |
| $CDCl_3$ | deuterated chloroform |
| Cpd | compound |
| DCE | dichloroethane |
| DCM | dichloromethane |
| DMAP | dimethylaminopyridine |
| DIPEA | diisopropyl ethyl amine |
| DMA | N,N-dimethylacetamide |
| DMF | N,N-dimethylformamide |
| DMSO | dimethyl sulfoxide |
| DPBS | Dulbecco's phosphate buffered saline |
| EDC | 1-(3-dimethylaminopropyl)-3-ethylcarbodiimide hydrochloride |
| ESI | Electrospray Ionization |
| $Et_3N$ or TEA | triethylamine |
| $Et_2O$ | diethyl ether |
| EtOAc | ethyl acetate |
| h/hr/hrs | hour(s) |
| HOBT | 1-hydroxybenzotriazole hydrate |
| HBTU | O-benzoiriazol-1-yloxy-N,N,N',N'-tetramethyluronium hexafluorophosphate |
| HATU | 1-[Bis(dimethylamino)methylene]-1H-1,2,3-triazolo[4,5-b]pyridinium 3-oxid hexafluorophosphate |
| LG | Leaving group |
| LiOH | lithium hydroxide |
| MeCN | Acetonitrile |
| MeOH | methanol |
| min | minute(s) |
| MS | mass spectroscopy |
| NMR | nuclear magnetic resonance spectroscopy |
| OTf | Triflate |
| PG | protecting group |
| RT/rt | room temperature |
| TBME | tert-Butyl-methyl ether |
| TFA | trifluoro acetic acid |
| THF | tetrahydrofuran |
| TLC | thin layer chromatography |
| Tos | p-toluenesulfonyl |
| $MgSO_4$ | Magnesium sulfate |
| EtOH | Ethanol |
| $BBr_3$ | Boron tribromide |

General Guidance

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art. The substituents for compounds of Formula (I) or a form thereof, represented in the schemes below, are as previously defined herein.

Unless otherwise specified, reaction solutions were stirred at room temperature under a $N_{2(g)}$ or $Ar_{(g)}$ atmosphere. When solutions were "concentrated to dryness", they were concentrated using a rotary evaporator under reduced pressure, when solutions were dried, they are typically dried over a drying agent such as magnesium sulfate ($MgSO_4$) or sodium sulfate ($Na_2SO_4$).

Normal phase flash column chromatography (FCC) was performed on silica gel with RediSep® silica gel columns using ethyl acetate (EtOAc)/hexanes, $CH_2Cl_2$/MeOH, $CH_2Cl_2$/10% 2 N $NH_3$ in MeOH, $CH_2Cl_2$/i-PrOH, and the like as eluent, unless otherwise indicated.

Reverse phase high performance liquid chromatography (HPLC) was performed under the following conditions: 1) Instrument, Shimadzu; Column, Waters XBridge C18 10 μM (250×50 mm), Phenomenex Gemini column 5 μm C18 (150×21.2 mm) or Waters Xterra RP18 OBD 5 μm (100×30 mm); Gradient, 95:5 to 0:100 water (0.05% trifluoroacetic acid (TFA))/$CH_3CN$ (0.05% TFA); Flow rate, 30-80 mL/min; Detection, UV at λ=220-254 nM; 2) Instrument, Gilson; Column, Phenomenex LUNA column 5 μm C18 (250×50 mm) or Waters XBridge Prep C18 OBD 5 μm (30×150 mm); Gradient, 95:5 to 0:100 water (0.05% TFA)/$CH_3CN$ (0.05% TFA); Flow rate, 30-80 mL/min; Detection, UV at λ=220-254 nM; 3) Instrument, Gilson/Shimadzu: Column, Inertsil ODS-3 column (30×100 mm) or Inertsil ODS-3 (30×50 mm, 5 μm); Gradient, water-acetonitrile with both phases with 0.05% by volume trifluoroacetic acid; 1 min hold at 5% ACN, then 6 min gradient to 99% ACN followed by a hold at that concentration for 3 min. Flow rate, 80 ml/min; heated column at 46° Celsius with detection of UV light at λ=254 nm; and 4) Instrument, Dionex: UVD 170U Diode array detector and ThermoFinnegan Surveyor MSQ plus mass spectrometer for data collection. Waters XBridge C18 5 μM OBD 50×100 mm prep column. All runs utilized water acetonitrile with 20 mM $NH_4OH$ added to the aqueous phase and a flow rate for all gradients was 80 mL/min using four possible gradients: 1) 5-60% MeCN over 12 min, then ramped to 100% MeCN and held for 6.3 min; 2) 30-70% MeCN over 12 min, then ramped to 100% MeCN and held for 6.3 min; 3) 50-80% MeCN over 12 min, then ramped to 100% MeCN and held for 6.3 min; and 4) 60-100% MeCN over 12 min, and then held for 6.3 min. The total run time for all gradient systems was 18.5 min.

Instances where solutions were filtered through a syringe filter, Pall 0.45 μM GHP membrane 13 mm and 25 mm diameter syringe filters were used.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone. Microwave reactions were carried out in either a CEM Discover® or a Biotage Initiator™ or Optimizer™ microwave at specified temperatures. Mass spectra were obtained on an Agilent series 1100 MSD using electrospray ionization (ESI) in positive mode unless otherwise indicated. Calculated mass corresponds to the exact mass. NMR spectra were obtained on either a Bruker model DPX400 (400 MHz), DPX500 (500 MHz), DRX600 (600 MHz) spectrometer. The format of the $^1$H NMR data below is: chemical shift in ppm down field of the tetramethylsilane reference (multiplicity, coupling constant J in Hz, integration).

Hydrochloride salts were obtained by treating the corresponding free bases with HCl (4 N in dioxane, 2 M in $Et_2O$, or 1.25 N in MeOH) at room temperature with mixtures and then either concentrated to obtain the HCl salt, or the resulting solid being isolated by filtration. Trifluoroacetic acid salts were obtained by purification of the crude reaction product by preparative reverse phase HPLC, whereby the final products were isolated as either mono-, di- or tri trifluoroacetic acid salts.

Chemical names were generated using ChemDraw Ultra 12.0 (CambridgeSoft Corp., Cambridge, Mass.) or ACD/Name Version 10.01 (Advanced Chemistry).

The compounds of Formula (I), wherein ring A, L, $R_1$, $R_2$, $R_3$, $R_4$ and $R_5$ are defined as in Formula (I), may be synthesized as outlined by the general synthetic route illustrated in Scheme A.

Referring to Scheme A, compounds of Formulae (XIII) can be prepared from appropriately substituted phenols (X) wherein the phenol (—OP) is protected as either an alkyl or alkyl and aryl silyl ether. Protected phenols, as the methyl ether, can be prepared by known methods or can be obtained commercially. Compounds (X), where W is a hydrogen and X is either bromo or chloro, can be converted to the corresponding boronic acid (XIV) via directed ortho-metallation (DOM) using bases such as LDA, and lithium tetramethyl piperidide (LTMP) (either made in situ or obtained from commercial sources) and triisopropyl borate in solvents such as THF, DME, ether and mixtures thereof at temperatures ranging from −78-0° Celsius. In compounds of formulae (XIV) where X is bromo or chloro and Z is fluoro or hydrogen, compound (XV) can be obtained via sequential Pd cross-coupling reactions to install $Ar^1$ followed by Y. Preferred solvents for cross-coupling reactions were conducted in a solvent, such as DME, DMSO, DMF, DMA, dioxane, THF, EtOH or toluene, or mixtures of the aforementioned solvents, with or without added water in the presence of a base, such as $Na_2CO_3$, $K_2CO_3$, KOAc, $KH_2PO_4$, $K_2HPO_4$, or $K_3PO_4$, using a palladium catalysts, such as $Pd(dppf)Cl_2.CH_2Cl_2$, palladium(II) trifluoroacetate and $Ph_3P$, chloro(2-dicyclohexylphosphino-2',4',6'-triisopropyl-1,1'-biphenyl)[2-(2-aminoethyl)phenyl)]-palladium(II), 1,1'-bis[di-t-butylphosphino)ferrocene]-palladium(II) chloride with temperatures ranging from room temperature to 120° Celsius.

Additionally, compounds of formulae (XI) where W is hydrogen, Z is either H or fluoro, and Y is alkyl or cycloalkyl can be formed from compound (X), where X is bromo, via metal halogen exchange using alkyllithium or alkylmagnesium halide reagents, such as nBuLi or i-PrMgCl, in solvents such as di-ethyl ether or THF at temperatures ranging from −78° Celsius to room temperature followed by treatment with an electrophile. In those instances wherein a ketone is used as the electrophile, such as cyclobutanone or cyclopentanone, reduction of the resulting hydroxyl group can be achieved using known methods such as $Et_3SiH$ in DCM in the presence of TFA. Alternatively, compound of formulae (XI) can be obtained through use of a palladium catalyst, such as palladium(II) acetate, with an added ligand, such as 2-dicyclohexylphosphine-2',6'-dimethoxy-1,1'-biphenyl, to couple (X) to an alkyl or arylzinc reagent, such as cyclobutylzinc bromide, in a solvent, such as THF, at temperatures ranging from rt to 100 Celsius. Compound of formulae (XI) can be further elaborated to those of formulae (XII), using previously described methods such as DOM, borylation, and Pd mediated cross-coupling. Compounds of formulae (X) in which X is alkyl, aryl or heteroaryl can be converted to compounds of formulae (XII) or (XV) through DOM, borylation, and Pd mediated cross-coupling using methods.

Compounds of formulae (XIII) can be obtained from those of formulae (XII) or (XV) by first removing the silyl protecting group using a fluoride source, such as TBAF or CsF in solvents such as THF, followed by subjecting the resultant phenol to $S_N2$ or $S_NAr$ reaction conditions in the presence of a suitable electrophile and solvents such as DMF, DMSO and DMA in the presence of bases such as $K_2CO_3$, $Cs_2CO_3$, $Na_2CO_3$, and $K_2PO_4$ at temperatures ranging from 0-140° Celsius. Alternatively, compounds of formulae (XIII) can prepared via intermediates of formulae (XII) and (XV) wherein P is a methyl group. Removal of the methyl group can be achieved using known methods. Preferred methods for removal of methyl ethers include $BBr_3$ in DCM at temperatures ranging from 78° Celsius to 0° Celsius. Compounds of formulae (XIII) are formed using suitable electrophiles such as various alkyl, aryl, and heteroaryl halides in the presence of bases such as $K_2CO_3$ or $Cs_2CO_3$ with or without the presence of cation chelation agents, such as 18-crown-6, in solvents such as DMSO, DMA, ACN, DMF and mixtures thereof at temperatures ranging from 0-140° Celsius using either conventional or microwave heating.

Scheme A

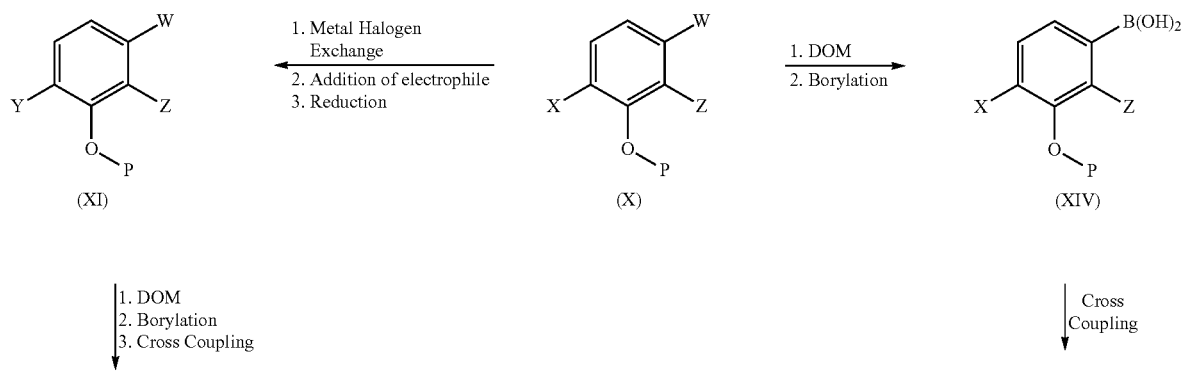

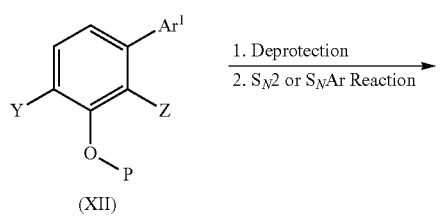

(XII)

1. Deprotection
2. S$_N$2 or S$_N$Ar Reaction

→ -continued

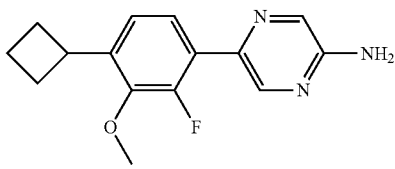 [SMILES: COc1c(C2CCC2)ccc(-c2cnc(N)cn2)c1F]

(XIII)

1. Deprotection
2. S$_N$2 or S$_N$Ar Reaction

→

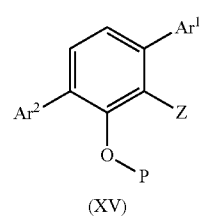

(XV)

EXAMPLES

The following examples are offered by way of illustration; the invention should not be construed as being limited by the chemical reactions and conditions expressed.

Intermediate A

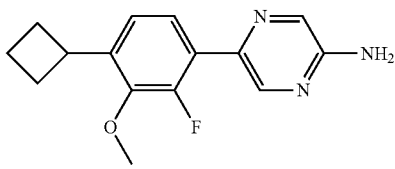 [SMILES: COc1c(C2CCC2)ccc(-c2cnc(N)cn2)c1F]

5-(4-Cyclobutyl-2-fluoro-3-methoxyphenyl)pyrazin-2-amine

Step A: 1-(3-Fluoro-2-methoxyphenyl)cyclobutanol

To a 500 mL round-bottomed flask were added a stir bar, 2-bromo-6-fluoroanisol (11.03 g, 53.8 mmol) and dry THF (215 mL). The flask was purged with nitrogen and cooled to 0° Celsius before adding 2.0 M i-PrMgCl in THF (60 mL, 120 mmol) over the course of 3 min. The resultant mixture was stirred for 2 h before adding cyclobutanone (5.0 mL, 67 mmol). The resultant mixture was stirred for 0.5 hour before diluting with Et$_2$O (500 mL) and washing with saturated NH$_4$Cl followed by brine. The organic layer was isolated, dried over MgSO$_4$, filtered and concentrated to dryness to give a pale-yellow oil. Subjecting the residue to FCC yielded 1-(3-fluoro-2-methoxyphenyl)cyclobutanol as a pale-yellow oil (5.18 g, 49%). $^1$H NMR (600 MHz, CDCl$_3$) δ 7.07-7.03 (m, 1H), 7.03-6.98 (m, 1H), 6.98-6.94 (m, 1H), 3.99 (d, J=2.4, 3H), 3.39 (s, 1H), 2.57-2.45 (m, 2H), 2.41-2.31 (m, 2H), 2.17-2.05 (m, 1H), 1.75-1.65 (m, 1H).

Step B: 1-Cyclobutyl-3-fluoro-2-methoxybenzene

To a 500 mL round-bottomed flask were added a stir bar, 1-(3-fluoro-2-methoxyphenyl)cyclobutanol (5.21 g, 26.6 mmol), dry DCM (250 mL), Et$_3$SiH (39.0 mL, 244 mmol) and TFA (20 mL, 260 mmol). The resultant mixture was stirred at rt for 22 h before concentrating to dryness and subjecting the residue to FCC to give 1-cyclobutyl-3-fluoro-2-methoxybenzene as a pale-yellow oil (3.78 g, 79%). $^1$H NMR (600 MHz, CDCl$_3$) δ 7.03-6.99 (m, 1H), 6.99-6.95 (m, 1H), 6.91 (m, 1H), 3.86 (d, J=1.6, 3H), 3.83-3.72 (m, 1H), 2.39-2.28 (m, 2H), 2.19-2.07 (m, 2H), 2.07-1.98 (m, 1H), 1.89-1.80 (m, 1H).

Step C: (4-Cyclobutyl-2-fluoro-3-methoxyphenyl)boronic acid

To a 500 mL round-bottomed flask were added a stir bar, dry THF (60 mL) and 2,2,6,6-tetramethylpiperidine (8.0 mL, 47 mmol). The flask was cooled to −78° C. (bath temp) and then treated with 2.5 M n-BuLi in hexanes (18.0 mL, 45 mmol) over 2 min. The resultant mixture was stirred for 5 min and then allowed to warm to 0° C. After 35 min, the mixture was re-cooled to −78° Celsius and treated with B(O-iPr)$_3$ (10.20 mL, 44 mmol) over 4 min. After 16 min, a solution consisting of 1-cyclobutyl-3-fluoro-2-methoxybenzene (7.24 g, 40.2 mmol) and dry THF (20.0 mL) was added over the course of 6 min and stirring continued for 3.5 h before adding HOAc (8 mL). The mixture was then poured into water and stirred for 5 min. The aqueous mixture was then extracted with EtOAc (200 mL), the extract dried over MgSO$_4$, filtered and concentrated to dryness to give (4-cyclobutyl-2-fluoro-3-methoxyphenyl)boronic acid as an off-white solid (8.08 g, 90%). The crude product was used directly in the next synthetic step.

Step D: 5-(4-Cyclobutyl-2-fluoro-3-methoxyphenyl) pyrazin-2-amine

To a 1000 mL round-bottom flask were added a stir bar, 2-amino-5-bromopyrazine (19.95 g, 115.3 mmol), (4-cyclobutyl-2-fluoro-3-methoxyphenyl)boronic acid (25.0 g, 112 mmol), Pd(dppf)Cl$_2$.CH$_2$Cl$_2$ (5.92 g, 7.28 mmol) and K$_2$CO$_3$ (47.33 g, 343 mmol). The flask was flushed with nitrogen and then charged with sparged toluene (97 mL), sparged water (97 mL) and sparged DMF (61 mL). The reaction vessel was heated at 80° Celsius for 17 hours before cooling to room temperature. The reaction mixture was filtered and the filtrate was concentrated to dryness. The residue was extracted with EtOAc (200 mL×3), the combined extracts dried over MgSO$_4$, filtered and concentrated to dryness. The residue was subjected to FCC to give the title compound (29.68 g). MS (ESI): mass calcd. for C$_{15}$H$_{16}$FN$_3$O, 273.13; m/z found, 274.1 [M+H]$^+$. $^1$H NMR (500 MHz, DMSO-d$_6$) δ 8.32-8.26 (dd, J=2.5, 1.5, 1H), 8.02-7.96 (d, J=1.5, 1H), 7.54-7.47 (m, 1H), 7.20-7.14 (m, 1H), 6.65 (s, 2H), 3.87-3.79 (d, J=1.0, 3H), 3.79-3.68 (m, 1H), 2.34-2.24 (m, 2H), 2.17-2.06 (m, 2H), 2.06-1.94 (m, 1H), 1.87-1.76 (m, 1H).

Intermediate B

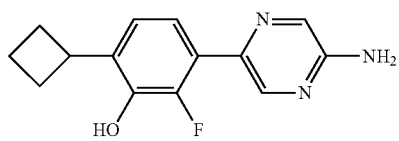 [SMILES: Nc1cnc(-c2ccc(C3CCC3)c(O)c2F)cn1]

3-(5-Aminopyrazin-2-yl)-6-cyclobutyl-2-fluorophenol

Method 1:

Step A: 1-(3-Fluoro-2-methoxyphenyl)cyclobutanol

To a 3-L round-bottom flask were added a stire bar, 2-bromo-6-fluoroanisol (75.00 g, 370 mmol) and dry THF (1460 mL). The flask was purged with nitrogen and cooled to 0° Celsius before adding 2.0 M i-PrMgCl in THF (408 mL, 916 mmol) over the course of 15 min. The resultant mixture was stirred for 2 hours before adding cyclobutanone (34 mL, 455 mmol). The resultant mixture was stirred for 0.5 hour before diluting with $Et_2O$ (2.50 L) and washing with saturated $NH_4Cl$ followed by brine. The organic layer was isolated, dried over $MgSO_4$, filtered and concentrated to dryness to give the crude product. Subjecting the residue to FCC gave the title compound (55.58 g). $^1H$ NMR (400 MHz, $CDCl_3$) δ 6.98-6.88 (m, 3H), 3.90-3.90 (s, 3H), 2.46-2.42 (m, 2H), 2.31-2.28 (m, 2H), 2.04 (m, 1H), 1.67-1.64 (m, 1H).

Step B: 1-Cyclobutyl-3-fluoro-2-methoxybenzene

To a 3-L round-bottom flask were added a stir bar, 1-(3-fluoro-2-methoxyphenyl)-cyclobutanol (80.17 g, 410 mmol), dry DCM (1231 mL), $Et_3SiH$ (200 mL, 1.23 mol) and TFA (93 mL, 1.2 mmol). The resultant mixture was stirred at rt for 22 h before concentrating to dryness and subjecting the residue to FCC to give 1-cyclobutyl-3-fluoro-2-methoxybenzene as a pale-yellow oil (51.90 g, 70.5%). $^1HNMR$ (400 MHz, $CDCl_3$) δ 7.07-6.93 (m, 3H), 3.91 (s, 3H), 3.85-3.81 (m, 1H), 2.40-2.36 (m, 2H), 2.20-2.07 (m, 3H), 1.91-1.88 (m, 1H).

Step C: (4-Cyclobutyl-2-fluoro-3-methoxyphenyl)boronic acid

To a 500 mL round-bottom flask were added a stir bar, dry THF (83 mL) and 2,2,6,6-tetramethylpiperidine (11 mL, 65 mmol). The flask was cooled to −78° C. (bath temp) and then treated with 2.5 M n-BuLi in hexanes (25 mL, 62.5 mmol) over 2 min. The resultant mixture was stirred for 5 min and then allowed to warm to 0° C. After 35 min, the mixture was re-cooled to −78° Celsius and treated with $B(O-iPr)_3$ (14 mL, 60 mmol) over 4 min. After 16 min, a solution consisting of 1-cyclobutyl-3-fluoro-2-methoxybenzene (10.0 g, 55.6 mmol) and dry THF (27 mL) was added over the course of 6 min and stirring continued for 3.5 hours before adding saturated $NH_4Cl$ (200 mL). The mixture was then poured into water and stirred for 5 min. The aqueous mixture was then extracted with EtOAc (200 mL×3), the combined extracts dried over $MgSO_4$, filtered and concentrated to dryness to give the crude product as an off-white solid. The crude product was subjected to FCC to give the title compound (7.21 g). $^1HNMR$ (400 MHz, $CD_3OD$): δ 7.11-7.07 (m, 2H), 3.38 (s, 3H), 3.82-3.80 (m, 1H), 2.37-2.33 (m, 2H), 2.19-2.11 (m, 3H), 2.09-1.90 (m, 1H).

Step D: 5-(4-Cyclobutyl-2-fluoro-3-methoxyphenyl)pyrazin-2-amine

To a 1000 mL round-bottom flask were added a stir bar, 2-amino-5-bromopyrazine (19.95 g, 115.3 mmol), (4-cyclobutyl-2-fluoro-3-methoxyphenyl)boronic acid (25.0 g, 112 mmol), $Pd(dppf)Cl_2 \cdot CH_2Cl_2$ (5.92 g, 7.28 mmol) and $K_2CO_3$ (47.33 g, 343 mmol). The flask was flushed with nitrogen and then charged with sparged toluene (97 mL), sparged water (97 mL) and sparged DMF (61 mL). The reaction vessel was heated at 80° Celsius for 17 hours before cooling to room temperature. The reaction mixture was filtered and the filtrate was concentrated to dryness. The residue was extracted with EtOAc (200 mL×3), the combined extracts dried over $MgSO_4$, filtered and concentrated to dryness. The residue was subjected to FCC to give the title compound (29.68 g). MS (ESI): mass calcd. for $C_{15}H_{16}FN_3O$, 273.13; m/z found, 273.9 $[M+H]^+$.

Step E

To a 3 L round-bottom flask were added a stir bar, 5-(4-cyclobutyl-2-fluoro-3-methoxyphenyl)pyrazin-2-amine (29.68 g, 121.0 mmol) and dry DCM (1190 mL). The flask was purged with nitrogen, stirred until homogeneous and cooled to −78° Celsius. Once cool, the flask was charged with 1.0 M $BBr_3$ in DCM (364 mL, 364 mmol). After 3 hours, the reaction mixture was warmed to room temperature and stirred for an additional 2 hours. The reaction mixture was then poured carefully into a flask containing ice (300 mL) and saturated $NaHCO_3$ resulting in the appearance of a tan ppt. The resultant mixture was subjected to vacuum filtration to give pure title compound as a tan solid (86%). $^1H$ NMR (400 MHz, $CD_3OD$), δ 8.29 (s, 1H), 8.04 (s, 1H), 7.21-7.17 (m, 1H), 7.08-7.05 (d, J=8.4, 1H), 3.87-3.78 (m, 1H), 2.40-2.34 (m, 2H), 2.23-2.12 (m, 2H), 2.10-2.01 (m, 1H), 1.91-1.85 (m, 1H).

Method 2:

Step A: (2-Bromo-6-fluorophenoxy)(tert-butyl)dimethylsilane

A 500-mL three-neck, round bottomed flask, equipped with a stir bar, temperature probe and nitrogen inlet, was charged with 2-bromo-6-fluorophenol (25 g, 130.9 mmol, 1.00 eq), DMF (252 mL, 0.52 M), imidazole (12.3 g, 181 mmol, 1.38 eq) and tertbutyldimethylsilyl chloride (19.7 g, 131 mmol, 1.00 eq). The mixture was heated at 60° Celsius for 3 hours. The reaction was cooled to room temperature and diluted with water. The aqueous phase was extracted with ethyl acetate and the resultant organic solution washed with water and brine and dried over sodium sulfate. The organic phase was concentrated to dryness and purified using FCC to provide (2-bromo-6-fluorophenoxy)(tert-butyl)dimethylsilane as a colorless oil (33 g, 82%).

Step B: (2-Cyclobutyl-6-fluorophenoxy)(tert-butyl)dimethylsilane

A 1-L three-neck, round bottomed flask, equipped with a stir bar, temperature probe and nitrogen inlet was charged with (2-bromo-6-fluorophenoxy)(tert-butyl)dimethylsilane (27.2 g, 89.1 mmol), THF (181.2 mL) and bis(tri-tert-butylphosphine)palladium (3.4 g, 6.68 mmol). Cyclobutylzinc bromide (267.2 mL, 134 mmol) was added and the reaction is heated at 45° Celsius for 22 hours. The reaction was cooled to room temperature and quenched with 1M HCl. The aqueous phase is extracted with MTBE and the combined organic extracts were washed with water, saturated aqueous thiourea, 1 M HCl brine, dried over sodium sulfate and concentrated to dryness to provide (2-cyclobutyl-6-fluorophenoxy)(tert-butyl)dimethylsilane as a light yellow oil (24.5 g, 98%). MS (EI): calcd. for $C_{16}H_{25}FOSi$, 280.5; m/z found 280.1 [M]. $^1H$ NMR (400 MHz, $CDCl_3$), δ 7.08-7.04 (m, 1H), 6.90-6.83 (m, 2H), 3.81 (tt, J=9.4, 7.8 Hz, 1H), 2.32 (dtd, J=10.3, 7.8, 2.4 Hz, 2H), 2.14-1.80 (m, 4H), 1.03 (s, 9H), 0.20 (s, 3H), 0.19 (s, 3H).

Step C: (3-((tert-Butyldimethylsiyl)oxy)-4-cyclobutyl-2-fluorophenyl)boronic acid A 100 mL three neck round-bottomed flask, equipped with a stir bar, temperature probe and nitrogen inlet, was charged with 2,2,6,6-tetramethylpiperidine (1.7 mL, 10 mmol) and THF (10 mL). The mixture was cooled to −78° Celsius and treated with 2.5 M n-BuLi (4.1 mL, 10 mmol). The resultant mixture was stirred for 5 min and then warmed up to 0° Celsius for 40 min. After 40 min the reaction mixture was cooled to −78° Celsius and treated with B(O-iPr)$_3$ (13.0 mL, 10.2 mmol) over the course of 10 min. After stirring for 20 min a solution of (2-cyclobutyl-6-fluorophenoxy)(tert-butyl)dimethylsilane (1.8 g, 6.3 mmol) in THF (4 mL) was added over the course of 2 min. The reaction was stirred at −78° Celsius for 2 hours and then warmed to 0° Celsius. Acetic acid (3.6 mL, 64 mmol) is added and the reaction was warmed to room temperature and diluted with water. The resultant mixture was extracted with ethyl acetate. The organic portion was dried over sodium sulfate and concentrated to dryness to provide (3-((tert-butyldimethylsilyl)-oxy)-4-cyclobutyl-2-fluorophenyl)boronic acid (1.8 g, 86%). $^1$H NMR (500 MHz, CDCl$_3$), δ 7.39-7.32 (m, 1H), 7.18-7.13 (m, 1H), 5.10-4.97 (m, 2H), 3.82 (t, J=8.8 Hz, 1H), 2.41-2.06 (m, 5H), 2.03-1.95 (m, 1H), 1.03 (s, 9H), 0.19 (s, 6H).

Step D: 3-(5-Aminopyrazin-2-yl)-6-cyclobutyl-2-fluorophenol

A 50 mL three-neck flask, equipped with a stir bar, nitrogen inlet and temperature probe, was charged with (3-((tert-butyldimethylsilyl)oxy)-4-cyclobutyl-2-fluorophenyl)boronic acid (1.7 g, 5.3 mmol), toluene (4.7 mL), DMF (2.8 mL) and water (4.7 mL). The solvent mixture was sparged for 30 minutes and then treated with 2-amino-5-bromopyrazine (923 mg, 5.3 mmol), potassium carbonate (2.19 g, 15.8 mmol) and dichloro[1,1′-bis(diphenyl-phosphino)ferrocene]palladium(II).CH$_2$Cl$_2$ (137 mg, 0.17 mmol). The reaction mixture was heated at 80° Celsius for 24 hours. The reaction mixture was then cooled to room temperature, diluted with water (8 mL) and the stirred for two hours. The precipitate was collected by filtration and dried in a vacuum oven at 60° Celsius overnight to give 3-(5-aminopyrazin-2-yl)-6-cyclobutyl-2-fluorophenol (1.2 g, 87%). MS (ESI+) Calcd. for C$_{14}$H$_{14}$FN$_3$O, 260.3; m/z found 260.1 [M+H]$^+$. $^1$H NMR (400 MHz, DMSO), δ 8.24 (m, 1H), 7.98 (d, J=1.5 Hz, 1H), 7.09 (m, 1H), 7.00 (d, J=8.2 Hz, 1H), 6.57 (s, 2H), 3.81-3.72 (m, 1H), 2.34-2.14 (m, 2H), 2.14-1.69 (m, 4H).

Example 1

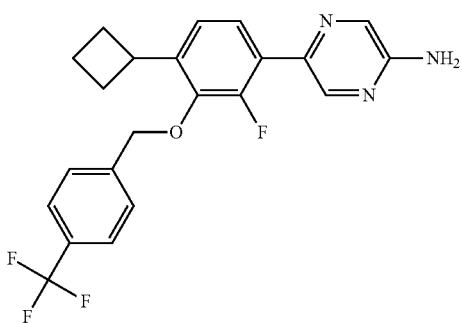 [SMILES: Nc1cnc(-c2ccc(C3CCC3)c(OCc3ccc(C(F)(F)F)cc3)c2F)cn1]

5-(4-Cyclobutyl-2-fluoro-3-{[4-(trifluoromethyl)benzyl]oxy}phenyl)pyrazin-2-amine To a 15 mL round-bottomed flask were added a stir bar, 3-(5-aminopyrazin-2-yl)-6-cyclobutyl-2-fluorophenol (51 mg, 0.20 mmol), 4-trifluoromethylbenzyl bromide (52 mg, 0.22 mmol), powdered KOH (42 mg, 0.75 mmol) and DMSO (2.0 mL). The resultant mixture was stirred at room temperature for 22.5 hours before diluting with 100 mL EtOAc and washing with water (×3). The organic layer was isolated, dried, filtered, and concentrated to dryness. The crude product was subjected to FCC to give the title compound as a pale-yellow solid (54 mg, 66%). MS (ESI): mass calcd. for C$_{22}$H$_{19}$F$_4$N$_3$O, 417.15; m/z found, 418.1 [M+H]$^+$. $^1$H NMR (500 MHz, DMSO-d$_6$) δ 8.36-8.26 (dd, J=2.5, 1.4, 1H), 8.02-7.99 (d, J=1.5, 1H), 7.82-7.76 (dd, J=8.8, 0.9, 2H), 7.74-7.68 (m, 2H), 7.59-7.51 (m, 1H), 7.26-7.19 (d, J=8.3, 1H), 6.68 (s, 2H), 5.12 (s, 2H), 3.79-3.69 (p, J=8.9, 1H), 2.26-2.16 (m, 2H), 2.14-2.04 (m, 2H), 2.00-1.88 (m, 1H), 1.83-1.73 (m, 1H).

Example 2

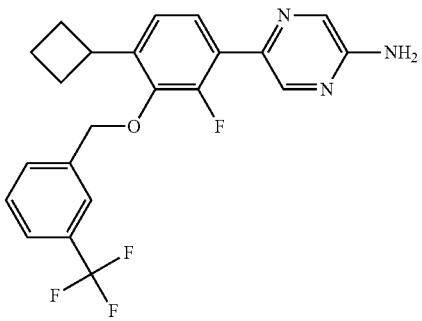 [SMILES: Nc1cnc(-c2ccc(C3CCC3)c(OCc3cccc(C(F)(F)F)c3)c2F)cn1]

5-(4-Cyclobutyl-2-fluoro-3-{[3-(trifluoromethyl)benzyl]oxy}phenyl)pyrazin-2-amine The title compound was prepared using analogous conditions described in Example 1 using 3-trifluoromethylbenzyl bromide. MS (ESI): mass calcd. for C$_{22}$H$_{19}$F$_4$N$_3$O, 417.15; m/z found, 418.1 [M+H]$^+$. $^1$H NMR (600 MHz, CD$_3$OD) δ 8.25 (s, 2H), 7.82-7.78 (d, J=2.0, 1H), 7.76-7.70 (d, J=7.5, 1H), 7.69-7.64 (d, J=7.9, 1H), 7.63-7.56 (m, 2H), 7.26-7.20 (m, 1H), 5.17 (s, 2H), 3.83-3.72 (m, 1H), 2.33-2.22 (m, 2H), 2.21-2.10 (m, 2H), 2.07-1.96 (m, 1H), 1.90-1.80 (m, 1H).

Example 3

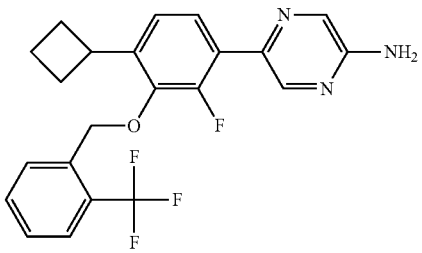 [SMILES: Nc1cnc(-c2ccc(C3CCC3)c(OCc3ccccc3C(F)(F)F)c2F)cn1]

5-(4-Cyclobutyl-2-fluoro-3-{[2-(trifluoromethyl)benzyl]oxy}phenyl)pyrazin-2-amine The title compound was prepared using analogous conditions described in Example 1 using 2-trifluoromethylbenzyl bromide. MS (ESI): mass calcd. for $C_{22}H_{19}F_4N_3O$, 417.15; m/z found, 418.1 [M+H]$^+$. $^1$H NMR (600 MHz, CD$_3$OD) δ 8.29-8.22 (m, 2H), 7.92-7.86 (d, J=7.7, 1H), 7.79-7.74 (m, 1H), 7.73-7.68 (m, 1H), 7.65-7.59 (m, 1H), 7.58-7.53 (m, 1H), 7.29-7.22 (m, 1H), 5.23 (s, 2H), 3.86-3.72 (m, 1H), 2.30-2.20 (m, 2H), 2.20-2.07 (m, 2H), 2.05-1.91 (m, 1H), 1.90-1.78 (m, 1H).

Example 4

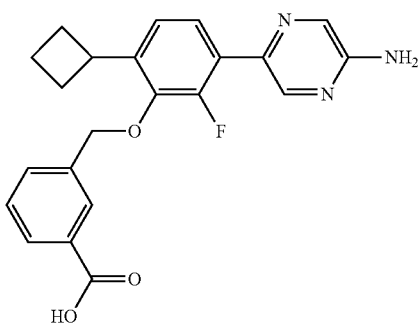 [SMILES: Nc1cnc(-c2ccc(C3CCC3)c(OCc3cccc(C(=O)O)c3)c2F)cn1]

3-{[3-(5-Aminopyrazin-2-yl)-6-cyclobutyl-2-fluorophenoxy]methyl}benzoic acid The title compound was prepared using analogous conditions described in Example 1 using 3-(bromomethyl)benzoic acid. MS (ESI): mass calcd. for $C_{22}H_{20}FN_3O_3$, 393.15; m/z found, 394.1 [M+H]$^+$. $^1$H NMR (600 MHz, CD$_3$OD) δ 8.32-8.24 (m, 1H), 8.21-8.12 (dd, J=12.3, 1.6, 2H), 8.06-7.98 (m, 1H), 7.73-7.66 (m, 1H), 7.59-7.48 (m, 2H), 7.24-7.19 (d, J=8.2, 1H), 5.13 (s, 2H), 3.85-3.75 (m, 1H), 2.28 (m, 2H), 2.20-2.08 (m, 2H), 2.07-1.96 (m, 1H), 1.90-1.80 (m, 1H).

Example 5

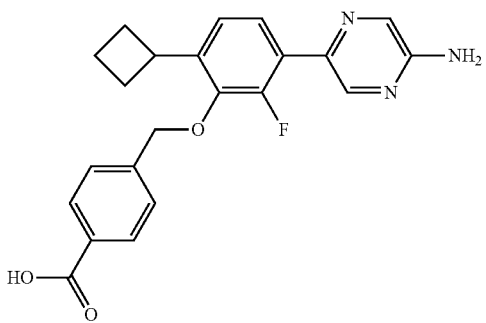 [SMILES: Nc1cnc(-c2ccc(C3CCC3)c(OCc3ccc(C(=O)O)cc3)c2F)cn1]

4-{[3-(5-Aminopyrazin-2-yl)-6-cyclobutyl-2-fluorophenoxy]methyl}benzoic acid The title compound was prepared using analogous conditions described in Example 1 using 4-(bromomethyl)benzoic acid. MS (ESI): mass calcd. for $C_{22}H_{20}FN_3O_3$, 393.42; m/z found, 394.1 [M+H]$^+$. $^1$H NMR (600 MHz, CD$_3$OD) δ 8.37-8.31 (d, J=1.5, 1H), 8.23 (s, 1H), 8.09-8.04 (d, J=8.2, 2H), 7.66-7.60 (m, 1H), 7.60-7.56 (d, J=8.0, 2H), 7.27-7.21 (d, J=8.4, 1H), 5.14 (s, 2H), 3.87-3.74 (p, J=8.7, 1H), 2.35-2.22 (m, 2H), 2.20-2.09 (m, 2H), 2.09-1.97 (m, 1H), 1.89-1.82 (m, 1H).

Example 6

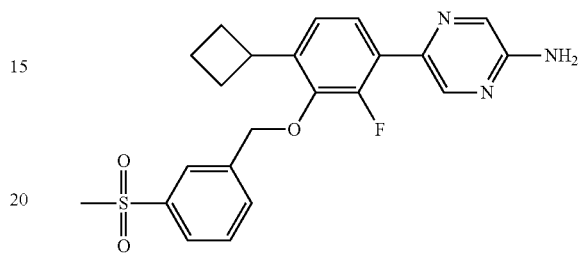

5-(4-Cyclobutyl-2-fluoro-3-{[3-(methylsulfonyl)benzyl]oxy}phenyl)pyrazin-2-amine The title compound was prepared using analogous conditions described in Example 1 using 1-(bromomethyl)-3-(methylsulfonyl)benzene. MS (ESI): mass calcd. for $C_{22}H_{22}FN_3O_3S$, 427.14; m/z found, 428.1 [M+H]$^+$. $^1$H NMR (600 MHz, DMSO-d$_6$) δ 8.34-8.29 (dd, J=2.3, 1.4, 1H), 8.08-8.03 (m, 1H), 8.03-7.99 (d, J=1.5, 1H), 7.96-7.91 (m, 1H), 7.87-7.82 (m, 1H), 7.75-7.69 (m, 1H), 7.58-7.52 (m, 1H), 7.25-7.20 (d, J=8.3, 1H), 6.71 (s, 2H), 5.15 (s, 2H), 3.80-3.69 (m, 1H), 3.24 (s, 3H), 2.28-2.16 (m, 2H), 2.14-2.03 (m, 2H), 2.02-1.89 (m, 1H), 1.86-1.74 (m, 1H).

Example 7

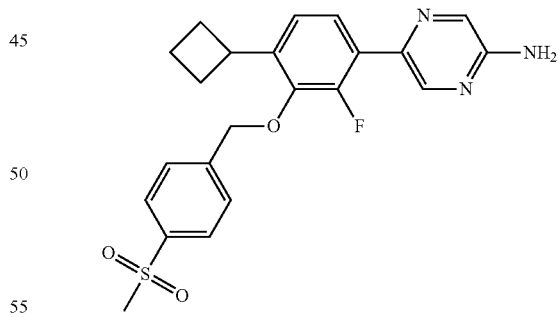

5-(4-Cyclobutyl-2-fluoro-3-{[4-(methylsulfonyl)benzyl]oxy}phenyl)pyrazin-2-amine The title compound was prepared using analogous conditions described in Example 1 using 1-(bromomethyl)-4-(methylsulfonyl)benzene. MS (ESI): mass calcd. for $C_{22}H_{22}FN_3O_3S$, 427.14; m/z found, 428.1 [M+H]$^+$. $^1$H NMR (600 MHz, DMSO-d$_6$) δ 8.36-8.27 (m, 1H), 8.05-7.95 (m, 3H), 7.81-7.72 (m, 2H), 7.61-7.51 (m, 1H), 7.27-7.18 (d, J=8.2, 1H), 5.13 (s, 2H), 3.81-3.71 (m, 1H), 3.24 (s, 3H), 2.27-2.18 (m, 2H), 2.15-2.05 (m, 2H), 2.02-1.92 (m, 1H), 1.85-1.74 (m, 1H).

Example 8

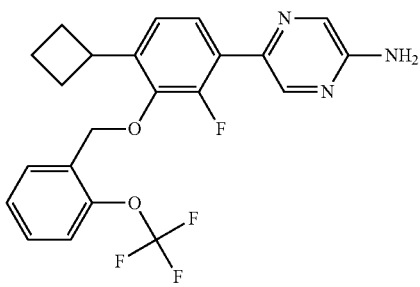 [SMILES: Nc1cnc(-c2ccc(C3CCC3)c(OCc3ccccc3OC(F)(F)F)c2F)cn1]

5-(4-Cyclobutyl-2-fluoro-3-{[2-(trifluoromethoxy)benzyl]oxy}phenyl)pyrazin-2-amine The title compound was prepared using analogous conditions described in Example 1 using 1-(bromomethyl)-2-(trifluoromethoxy)benzene. MS (ESI): mass calcd. for $C_{22}H_{19}F_4N_3O_2$, 433.14; m/z found, 434.1 [M+H]$^+$. $^1$H NMR (600 MHz, DMSO-d$_6$) δ 8.33-8.27 (dd, J=2.3, 1.4, 1H), 8.05-8.01 (m, 1H), 7.73-7.68 (dd, J=7.6, 1.8, 1H), 7.59-7.51 (m, 2H), 7.51-7.41 (m, 2H), 7.25-7.20 (d, J=8.2, 1H), 5.07 (s, 2H), 3.78-3.58 (m, 1H), 2.23-2.12 (m, 2H), 2.12-2.01 (m, 2H), 1.96-1.86 (m, 1H), 1.82-1.73 (m, 1H).

Example 9

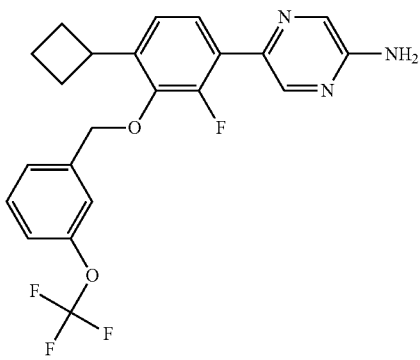

5-(4-Cyclobutyl-2-fluoro-3-{[3-(trifluoromethoxy)benzyl]oxy}phenyl)pyrazin-2-amine The title compound was prepared using analogous conditions described in Example 1 using 1-(bromomethyl)-3-(trifluoromethoxy)benzene. MS (ESI): mass calcd. for $C_{22}H_{19}F_4N_3O_2$, 433.14; m/z found, 434.1 [M+H]$^+$. $^1$H NMR (600 MHz, DMSO-d$_6$) δ 8.33-8.28 (m, 1H), 8.06-8.01 (m, 1H), 7.59-7.52 (m, 2H), 7.52-7.45 (m, 2H), 7.40-7.33 (m, 1H), 7.24-7.18 (d, J=8.2, 1H), 5.09 (s, 2H), 3.77-3.64 (p, J=8.9, 1H), 2.24-2.14 (m, 2H), 2.13-2.01 (m, 2H), 1.98-1.86 (m, 1H), 1.83-1.72 (m, 1H).

Example 10

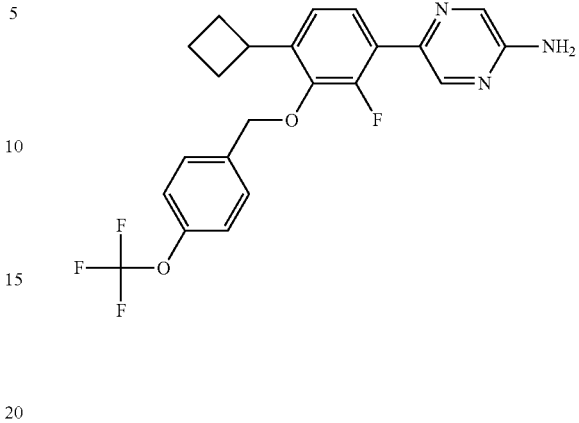

5-(4-Cyclobutyl-2-fluoro-3-{[4-(trifluoromethoxy)benzyl]oxy}phenyl)pyrazin-2-amine The title compound was prepared using analogous conditions described in Example 1 using 1-(bromomethyl)-4-(trifluoromethoxy)benzene. MS (ESI): mass calcd. for $C_{22}H_{19}F_4N_3O_2$, 433.14; m/z found, 434.1 [M+H]$^+$. $^1$H NMR (600 MHz, DMSO-d$_5$) δ 8.33-8.28 (m, 1H), 8.06-8.01 (m, 1H), 7.63-7.58 (m, 2H), 7.57-7.52 (m, 1H), 7.45-7.39 (m, 2H), 7.24-7.20 (d, J=8.2, 1H), 5.04 (s, 2H), 3.76-3.65 (m, 1H), 2.24-2.14 (m, 2H), 2.12-2.02 (m, 2H), 1.99-1.88 (m, 1H), 1.82-1.72 (m, 1H).

Example 11

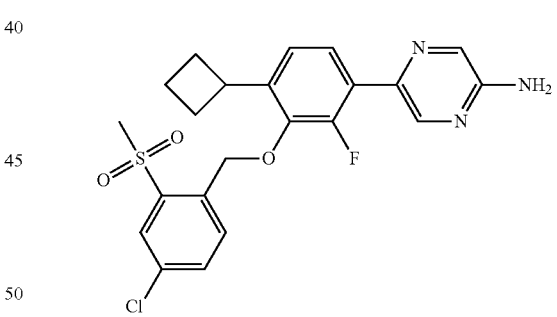

5-(3-{[4-Chloro-2-(methylsulfonyl)benzyl]oxy}-4-cyclobutyl-2-fluorophenyl)pyrazin-2-amine The title compound was prepared using analogous conditions described in Example 1 using 1-(bromomethyl)-4-chloro-2-(methylsulfonyl)benzene. MS (ESI): mass calcd. for $C_{22}H_{21}ClFN_3O_3S$, 461.10; m/z found, 462.1 [M+H]$^+$. $^1$H NMR (600 MHz, DMSO-de) δ 8.30-8.26 (m, 1H), 8.03-8.00 (dd, J=2.9, 1.5, 1H), 8.00-7.97 (d, J=1.7, 1H), 7.95-7.91 (m, 2H), 7.61-7.56 (m, 1H), 7.28-7.23 (d, J=8.3, 1H), 5.45 (s, 2H), 3.83-3.73 (m, 1H), 3.36 (s, 3H), 2.28-2.18 (m, 2H), 2.16-2.04 (m, 2H), 2.01-1.89 (m, 1H), 1.84-1.75 (m, 1H).

Example 12

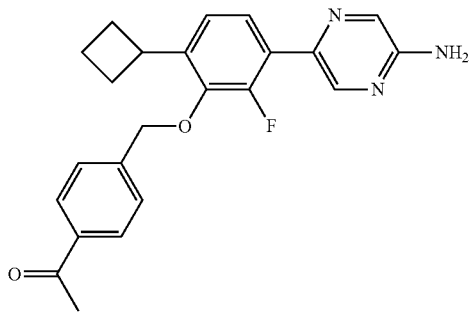

1-(4-{[3-(5-Aminopyrazin-2-yl)-6-cyclobutyl-2-fluorophenoxy]methyl}phenyl)ethanone The title compound was prepared using analogous conditions described in Example 1 using 1-(4-(bromomethyl)phenyl)ethanone. MS (ESI): mass calcd. for $C_{23}H_{22}FN_3O_2$, 391.17; m/z found, 392.1 [M+H]$^+$. $^1$H NMR (600 MHz, DMSO-d$_6$) δ 8.33-8.29 (m, 1H), 8.05-7.98 (m, 3H), 7.66-7.61 (m, 2H), 7.57-7.52 (m, 1H), 7.24-7.20 (d, J=8.2, 1H), 5.45 (s, 2H), 3.81-3.78 (m, 1H), 2.61 (s, 3H), 2.28-2.16 (m, 2H), 2.14-2.03 (m, 2H), 1.99-1.89 (m, 1H), 1.84-1.75 (m, 1H).

Example 13

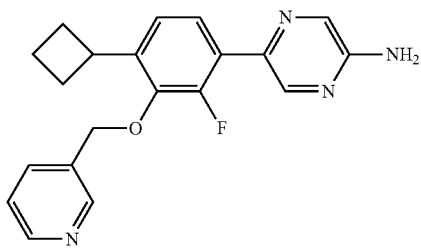 [SMILES: Nc1cnc(-c2ccc(C3CCC3)c(OCc3cccnc3)c2F)cn1]

5-[4-Cyclobutyl-2-fluoro-3-(pyridin-3-ylmethoxy)phenyl]pyrazin-2-amine

The title compound was prepared using analogous conditions described in Example 1 using 3-chloromethylpyridine. MS (ESI): mass calcd. for $C_{20}H_{19}FN_4O$, 350.15; m/z found, 351.1 [M+H]$^+$. $^1$H NMR (600 MHz, CD$_3$OD) δ 9.03-8.97 (d, J=2.1, 1H), 8.88-8.82 (dd, J=5.3, 1.5, 1H), 8.71-8.65 (m, 1H), 8.28-8.23 (m, 1H), 8.22-8.19 (d, J=1.5, 1H), 8.11-8.06 (m, 1H), 7.66-7.60 (m, 1H), 7.29-7.23 (m, 1H), 5.35-5.28 (s, 2H), 3.91-3.80 (m, 1H), 2.39-2.29 (m, 2H), 2.25-2.15 (m, 2H), 2.12-2.00 (m, 1H), 1.92-1.84 (m, 1H).

Example 14

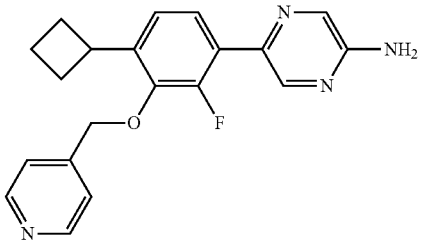

5-[4-Cyclobutyl-2-fluoro-3-(pyridin-4-ylmethoxy)phenyl]pyrazin-2-amine

The title compound was prepared using analogous conditions described in Example 1 using 4-chloromethylpyridine. MS (ESI): mass calcd. for $C_{20}H_{19}FN_4O$, 350.15; m/z found, 351.1 [M+H]$^+$. $^1$H NMR (600 MHz, CD$_3$OD) δ 9.03-8.76 (m, 2H), 8.33-8.16 (m, 4H), 7.67-7.60 (m, 1H), 7.30-7.25 (m, 1H), 5.44 (s, 2H), 3.94-3.85 (m, 1H), 2.42-2.32 (m, 2H), 2.29-2.18 (m, 2H), 2.12-2.02 (m, 1H), 1.95-1.85 (m, 1H).

Example 15

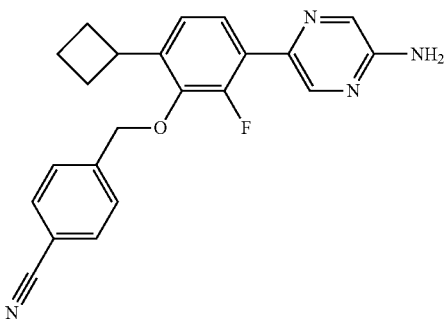 [SMILES: N#Cc1ccc(COc2c(C3CCC3)ccc(-c3cnc(N)cn3)c2F)cc1]

4-{[3-(5-Aminopyrazin-2-yl)-6-cyclobutyl-2-fluorophenoxy]methyl}benzonitrile The title compound was prepared using analogous conditions described in Example 1 using 4-bromomethylbenzonitrile. MS (ESI): mass calcd. for $C_{22}H_{19}FN_4O$, 374.15; m/z found, 375.1 [M+H]$^+$. $^1$H NMR (600 MHz, CD$_3$OD) δ 8.32-8.28 (d, J=1.4, 1H), 8.23 (s, 1H), 7.79-7.75 (m, 2H), 7.69-7.64 (m, 2H), 7.64-7.58 (m, 1H), 7.24-7.20 (m, 1H), 5.12 (s, 2H), 3.84-3.73 (m, 1H), 2.32-2.23 (m, 2H), 2.20-2.09 (m, 2H), 2.08-1.96 (m, 1H), 1.89-1.80 (m, 1H).

Example 16

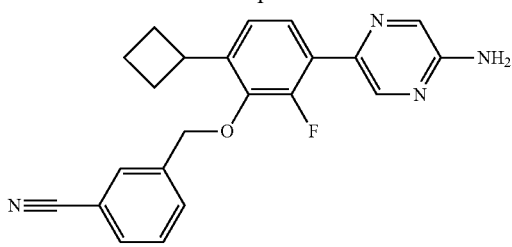

3-{[3-(5-Aminopyrazin-2-yl)-6-cyclobutyl-2-fluorophenoxy]methyl}benzonitrile

The title compound was prepared using analogous conditions described in Example 1 using 3-bromomethylbenzonitrile. MS (ESI): mass calcd. for $C_{22}H_{19}FN_4O$, 374.15; m/z found, 375.1 [M+H]$^+$. $^1$H NMR (500 MHz, CDCl$_3$) δ 8.47-8.42 (dd, J=2.3, 1.5, 1H), 8.10-8.06 (d, J=1.5, 1H), 7.80-7.75 (m, 1H), 7.73-7.67 (m, 1H), 7.65-7.60 (m, 1H), 7.59-7.53 (dd, J=8.2, 7.4, 1H), 7.52-7.47 (m, 1H), 7.18-7.13 (m, 1H), 5.05 (s, 2H), 4.64 (s, 2H), 3.81-3.67 (m, 1H), 2.34-2.22 (m, 2H), 2.19-2.06 (m, 2H), 2.06-1.94 (m, 1H), 1.92-1.78 (m, 1H).

Example 17

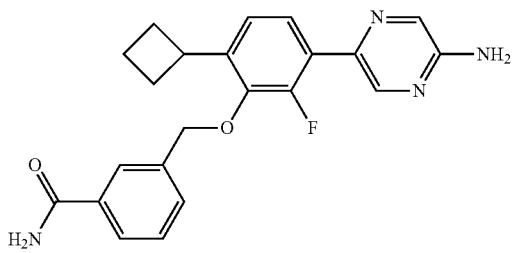 [SMILES: NC(=O)c1cccc(COc2c(C3CCC3)ccc(-c3cnc(N)cn3)c2F)c1]

3-{[3-(5-Aminopyrazin-2-yl)-6-cyclobutyl-2-fluorophenoxy]methyl}benzamide

The title compound was obtained as a side product in the formation of 3-{[3-(5-aminopyrazin-2-yl)-6-cyclobutyl-2-fluorophenoxy]methyl}benzonitrile, Example 16. MS (ESI): mass calcd. for $C_{22}H_{21}FN_4O_2$, 392.16; m/z found, 393.2 [M+H]$^+$. $^1$H NMR (600 MHz, CD$_3$OD) δ 8.28-8.22 (dd, J=5.9, 1.5, 2H), 8.03-7.98 (m, 1H), 7.90-7.83 (m, 1H), 7.69-7.64 (m, 1H), 7.61-7.55 (m, 1H), 7.53-7.47 (m, 1H), 7.24-7.19 (dd, J=7.4, 1.0, 1H), 5.13 (s, 2H), 3.86-3.75 (m, 1H), 2.33-2.21 (m, 2H), 2.19-2.08 (m, 2H), 2.08-1.96 (m, 1H), 1.91-1.79 (m, 1H).

Example 18

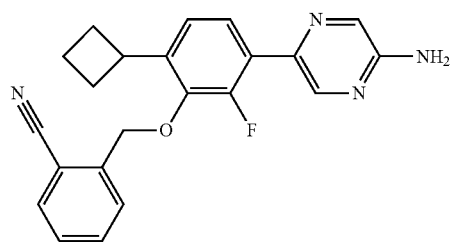 [SMILES: N#Cc1ccccc1COc1c(C2CCC2)ccc(-c2cnc(N)cn2)c1F]

2-{[3-(5-Aminopyrazin-2-yl)-6-cyclobutyl-2-fluorophenoxy]methyl}benzonitrile

The title compound was prepared using analogous conditions described in Example 1 using 2-bromomethylbenzonitrile. MS (ESI): mass calcd. for $C_{22}H_{19}FN_4O$, 374.15; m/z found, 375.1 [M+H]$^+$. $^1$H NMR (500 MHz, DMSO-d$_6$) δ 8.35-8.28 (dd, J=2.5, 1.4, 1H), 8.03-7.97 (d, J=1.5, 1H), 7.95-7.89 (m, 1H), 7.83-7.72 (m, 2H), 7.64-7.52 (m, 2H), 7.25-7.18 (d, J=8.3, 1H), 6.68 (s, 2H), 5.20 (s, 2H), 3.77-3.65 (m, 1H), 2.25-2.12 (m, 2H), 2.12-2.01 (m, 2H), 1.96-1.85 (m, 1H), 1.83-1.70 (m, 1H).

Example 19

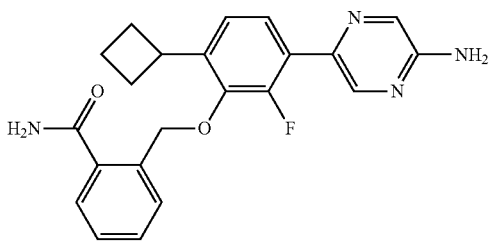 [SMILES: NC(=O)c1ccccc1COc1c(C2CCC2)ccc(-c2cnc(N)cn2)c1F]

2-{[3-(5-Aminopyrazin-2-yl)-6-cyclobutyl-2-fluorophenoxy]methyl}benzamide

The title compound was obtained as a side product in the formation of 2-{[3-(5-aminopyrazin-2-yl)-6-cyclobutyl-2-fluorophenoxy]methyl}benzonitrile, Example 18. MS (ESI): mass calcd. for $C_{22}H_{21}FN_4O_2$, 392.16; m/z found, 393.1 [M+H]$^+$. $^1$H NMR (600 MHz, CD$_3$OD) δ 8.27 (s, 1H), 8.22-8.16 (d, J=1.5, 1H), 7.77-7.72 (dd, J=7.8, 1.2, 1H), 7.63-7.59 (dd, J=7.6, 1.3, 1H), 7.59-7.52 (m, 2H), 7.46-7.41 (m, 1H), 7.26-7.21 (d, J=8.2, 1H), 5.30 (s, 2H), 3.89-3.77 (p, J=8.8, 1H), 2.35-2.23 (m, 2H), 2.20-2.09 (m, 2H), 2.07-1.96 (m, 1H), 1.89-1.78 (m, 1H).

Example 20

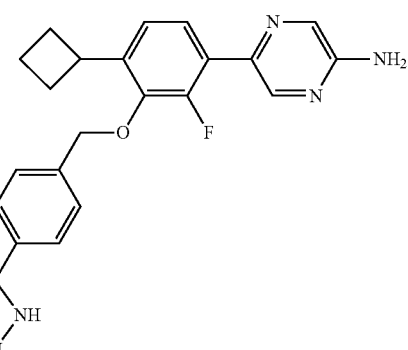

5-(4-Cyclobutyl-2-fluoro-3-{[4-(1H-tetrazol-5-yl)benzyl]oxy}phenyl)pyrazin-2-amine To a 20 mL vial were added a stir bar, 4-{[3-(5-aminopyrazin-2-yl)-6-cyclobutyl-2-fluorophenoxy]methyl}benzonitrile (82 mg, 0.22 mmol), NaN$_3$ (576 mg, 8.85 mmol), NH$_4$Cl (557 mg, 10.4 mmol) and dry DMF (2.0 mL). The resultant mixture was heated at 125° Celsius for 21.5 hours before cooling to rt. The mixture was then passed through a syringe filter and the filtrate subjected to HPLC purification to give the title compound as a yellow solid (47 mg, 40%). MS (ESI): mass calcd. for $C_{22}H_{20}FN_7O$, 417.17; m/z found, 418.1 [M+H]$^+$. $^1$H NMR (500 MHz, DMSO-d$_6$) δ 8.35-8.29 (m, 1H), 8.12-8.06 (m, 2H), 8.04-7.97 (d, J=1.5, 1H), 7.77-7.69 (d, J=7.9, 2H), 7.60-7.51 (m, 1H), 7.24-7.19 (d, J=8.3, 1H), 5.13 (s, 2H), 3.84-3.71 (m, 1H), 2.28-2.18 (m, 2H), 2.17-2.03 (m, 2H), 2.02-1.90 (m, 1H), 1.84-1.74 (m, 1H).

Example 21

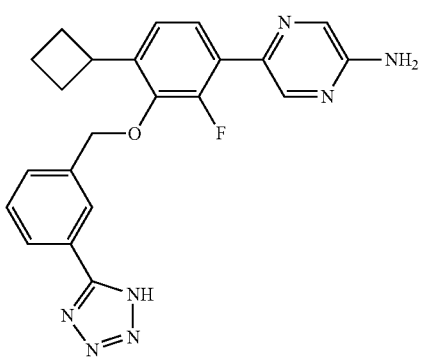 [SMILES: Nc1cnc(-c2ccc(C3CCC3)c(OCc3cccc(-c4nnn[nH]4)c3)c2F)cn1]

5-(4-Cyclobutyl-2-fluoro-3-{[3-(1H-tetrazol-5-yl)benzyl]oxy}phenyl)pyrazin-2-amine The title compound was prepared using analogous conditions described in Example 20 starting from 3-{[3-(5-Aminopyrazin-2-yl)-6-cyclobutyl-2-fluorophenoxy]methyl}benzonitrile. MS (ESI): mass calcd. for $C_{22}H_{20}FN_7O$, 417.17; m/z found, 418.1 [M+H]$^+$. $^1$H NMR (500 MHz, DMSO-d) δ 8.35-8.30 (m, 1H), 8.24-8.19 (m, 1H), 8.08-8.01 (m, 2H), 7.73-7.63 (m, 2H), 7.60-7.52 (m, 1H), 7.26-7.19 (d, J=8.2, 1H), 5.13 (s, 2H), 3.83-3.72 (m, 1H), 2.29-2.18 (m, 2H), 2.15-2.04 (m, 2H), 2.00-1.87 (m, 1H), 1.84-1.73 (m, 1H).

Example 22

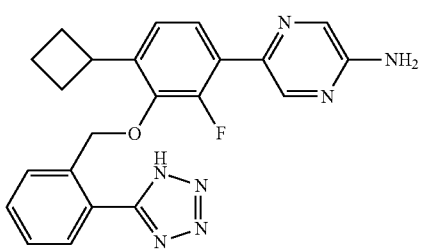

5-(4-Cyclobutyl-2-fluoro-3-{[2-(1H-tetrazol-5-yl)benzyl]oxy}phenyl)pyrazin-2-amine The title compound was prepared using analogous conditions described in Example 20 starting from 2-{[3-(5-Aminopyrazin-2-yl)-6-cyclobutyl-2-fluorophenoxy]methyl}-benzonitrile. MS (ESI): mass calcd. for $C_{22}H_{20}FN_7O$, 417.17; m/z found, 418.1 [M+H]$^+$. $^1$H NMR (500 MHz, DMSO-d$_6$) δ 8.28-8.23 (m, 1H), 8.01-7.97 (d, J=1.5, 1H), 7.90-7.85 (d, J=7.7, 1H), 7.82 (s, 1H), 7.73-7.66 (m, 1H), 7.64-7.57 (d, J=7.7, 1H), 7.55-7.49 (m, 1H), 7.21-7.14 (d, J=8.3, 1H), 6.66 (s, 2H), 5.37 (s, 2H), 3.57-3.46 (m, 1H), 2.15-2.04 (m, 2H), 2.04-1.94 (m, 2H), 1.93-1.82 (m, 1H), 1.79-1.68 (m, 1H).

Example 23

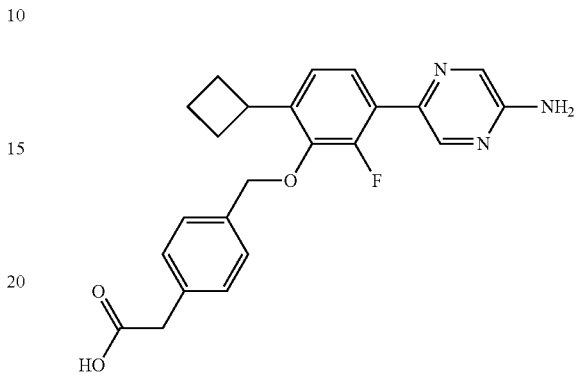

(4-{[3-(5-Aminopyrazin-2-yl)-6-cyclobutyl-2-fluorophenoxy]methyl}phenyl)acetic acid The title compound was prepared using analogous conditions described in Example 1 using 2-(4-(bromomethyl)phenyl)acetic acid. MS (ESI): mass calcd. for $C_{23}H_{22}FN_3O_3$, 407.16; m/z found, 408.1 [M+H]$^+$. $^1$H NMR (600 MHz, CD$_3$OD) δ 8.31-8.15 (m, 2H), 7.60 (s, 1H), 7.54-7.47 (m, 1H), 7.44-7.37 (d, J=7.9, 2H), 7.33-7.29 (d, J=7.8, 2H), 7.19-7.14 (d, J=8.2, 1H), 5.01 (s, 2H), 3.81-3.68 (m, 1H), 3.61 (s, 2H), 2.32-2.20 (m, 2H), 2.18-2.05 (m, 2H), 2.04-1.94 (m, 1H), 1.88-1.77 (m, 1H).

Example 24

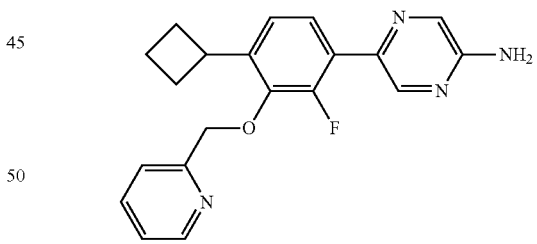

5-[4-Cyclobutyl-2-fluoro-3-(pyridin-2-ylmethoxy)phenyl]pyrazin-2-amine

The title compound was prepared using analogous conditions described in Example 1 using 2-chloromethylpyridine. MS (ESI): mass calcd. for $C_{20}H_{19}FN_4O$, 350.15; m/z found, 351.1 [M+H]$^+$. $^1$H NMR (500 MHz, CD$_3$OD) δ 8.57-8.52 (m, 1H), 8.32-8.28 (dd, J=2.3, 1.5, 1H), 8.06-8.02 (d, J=1.5, 1H), 7.95-7.90 (m, 1H), 7.74-7.69 (m, 1H), 7.55-7.50 (m, 1H), 7.44-7.37 (m, 1H), 7.24-7.18 (m, 1H), 5.16 (s, 2H), 3.86-3.75 (m, 1H), 2.32-2.22 (m, 2H), 2.20-2.08 (m, 2H), 2.07-1.94 (m, 1H), 1.89-1.79 (m, 1H).

Example 25

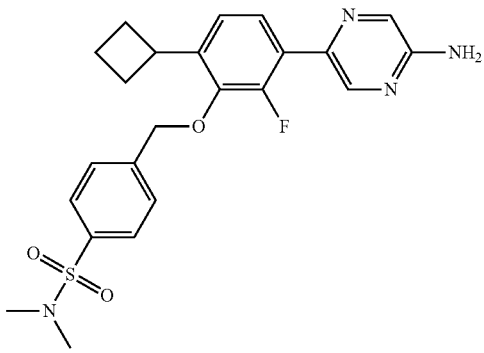 [SMILES: CN(C)S(=O)(=O)c1ccc(COc2c(C3CCC3)ccc(-c3cnc(N)cn3)c2F)cc1]

4-{[3-(5-Aminopyrazin-2-yl)-6-cyclobutyl-2-fluorophenoxy]methyl}-N,N-dimethylbenzenesulfonamide The title compound was prepared using analogous conditions described in Example 1 using 4-(bromomethyl)-N,N-dimethylbenzenesulfonamide. MS (ESI): mass calcd. for $C_{23}H_{25}FN_4O_3S$, 456.16; m/z found, 457.1 [M+H]$^+$. $^1$H NMR (500 MHz, CDCl$_3$) δ 8.50-8.44 (d, J=1.4, 1H), 8.19-8.11 (m, 1H), 7.83-7.74 (m, 2H), 7.69-7.58 (m, 3H), 7.19-7.13 (d, J=8.3, 1H), 5.06 (s, 2H), 3.82-3.67 (m, 1H), 2.74 (s, 6H), 2.35-2.19 (m, 2H), 2.19-2.05 (m, 2H), 2.05-1.92 (m, 2H), 1.89-1.77 (m, 1H).

Example 26

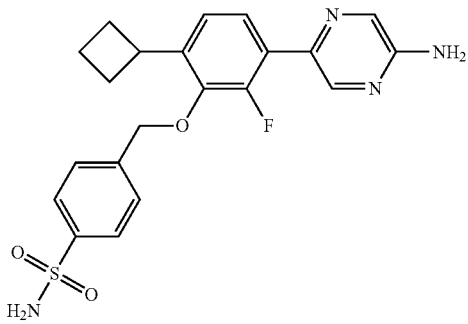 [SMILES: Nc1cnc(-c2ccc(C3CCC3)c(OCc3ccc(S(N)(=O)=O)cc3)c2F)cn1]

4-{[3-(5-Aminopyrazin-2-yl)-6-cyclobutyl-2-fluorophenoxy]methyl}benzenesulfonamide The title compound was prepared using analogous conditions described in Example 1 using 4-(bromomethyl)benzenesulfonamide. MS (ESI): mass calcd. for $C_{21}H_{21}FN_4O_3S$, 428.13; m/z found, 429.1 [M+H]$^+$. $^1$H NMR (500 MHz, DMSO-d$_6$) δ 8.33-8.30 (dd, J=2.4, 1.4, 1H), 8.02-7.99 (d, J=1.5, 1H), 7.90-7.84 (m, 2H), 7.70-7.64 (m, 2H), 7.58-7.52 (m, 1H), 7.39 (s, 2H), 7.25-7.19 (d, J=8.3, 1H), 5.11 (s, 2H), 3.79-3.63 (m, 1H), 2.28-2.16 (m, 2H), 2.16-2.03 (m, 2H), 2.02-1.88 (m, 1H), 1.84-1.74 (m, 1H).

Example 27

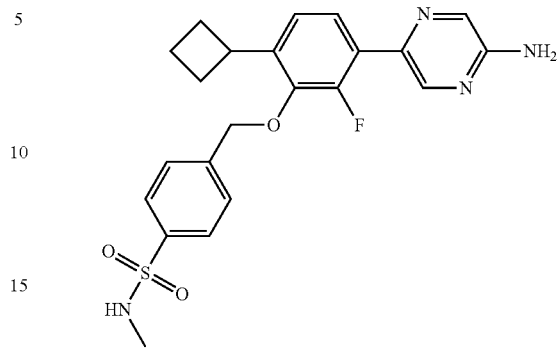

4-{[3-(5-Aminopyrazin-2-yl-6-cyclobutyl-2-fluorophenoxy]methyl}-N-methylbenzenesulfonamide The title compound was prepared using analogous conditions described in Example 1 using 4-(bromomethyl)-N-methylbenzenesulfonamide. MS (ESI): mass calcd. for $C_{22}H_{23}FN_4O_3S$, 442.15; m/z found, 443.2 [M+H]$^+$. $^1$H NMR (500 MHz, DMSO-do) δ 8.34-8.29 (dd, J=2.3, 1.4, 1H), 8.05-7.99 (d, J=1.4, 1H), 7.86-7.79 (m, 2H), 7.73-7.67 (m, 2H), 7.60-7.53 (m, 1H), 7.51-7.44 (m, 1H), 7.25-7.19 (d, J=8.2, 1H), 5.12 (s, 2H), 3.79-3.67 (m, 1H), 2.46-2.37 (d, J=5.0, 3H), 2.27-2.15 (m, 2H), 2.15-2.02 (m, 2H), 2.02-1.88 (m, 1H), 1.84-1.72 (m, 1H).

Example 28

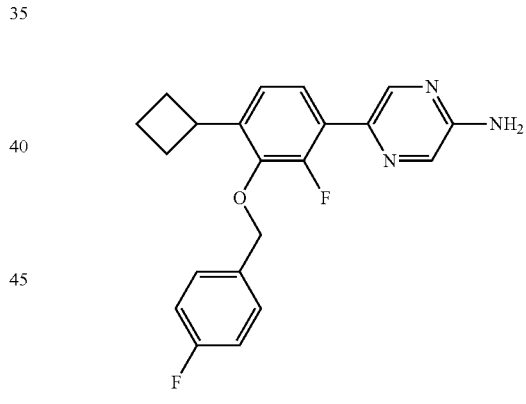

5-{4-Cyclobutyl-2-fluoro-3-[(4-fluorobenzyl)oxy]phenyl}pyrazin-2-amine

To a solution of 3-(5-aminopyrazin-2-yl)-6-cyclobutyl-2-fluorophenol (50 mg, 0.19 mmol) and 1-(bromomethyl)-4-fluorobenzene (36 µL, 0.29 mmol) in DMSO (1 mL) was added 1 pellet (~125 mg) of potassium hydroxide. The reaction was stirred for 16 hours at room temperature before filtering and purifying by HPLC to give 5-{4-cyclobutyl-2-fluoro-3-[(4-fluorobenzyl)oxy]phenyl}pyrazin-2-amine (37 mg, 39%). MS (ESI): mass calcd. for $C_{21}H_{19}F_2N_3O$, 367.15; m/z found, 368.1 [M+H]$^+$. $^1$H NMR (400 MHz, CD$_3$OD) δ 8.30 (d, J=1.3, 1H), 8.22 (s, 1H), 7.58 (m, 1H), 7.50-7.43 (m, 2H), 7.20 (d, J=8.0, 1H), 7.15-7.07 (m, 2H), 5.01 (s, 2H), 3.83-3.68 (m, 1H), 2.31-2.21 (m, 2H), 2.18-1.93 (m, 3H), 1.87-1.78 (m, 1H).

Example 29

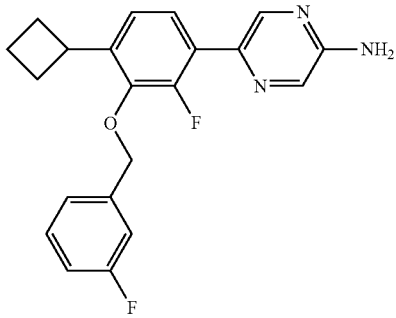

5-{4-Cyclobutyl-2-fluoro-3-[(3-fluorobenzyl)oxy]phenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-3-fluorobenzene. MS (ESI): mass calcd. for $C_{21}H_{19}F_2N_3O$, 367.15; m/z found, 368.1 [M+H]$^+$. $^1$H NMR (400 MHz, CD$_3$OD) δ 8.25 (d, J=4.5, 2H), 7.58 (m, 1H), 7.43-7.37 (m, 1H), 7.29-7.19 (m, 3H), 7.11-7.04 (m, 1H), 5.05 (d, J=9.9, 2H), 3.86-3.73 (m, 1H), 2.34-2.21 (m, 2H), 2.20-1.95 (m, 3H), 1.91-1.80 (m, 1H).

Example 30

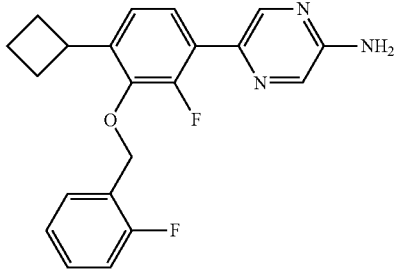 [SMILES: Nc1cnc(-c2ccc(C3CCC3)c(OCc3ccccc3F)c2F)cn1]

5-{4-Cyclobutyl-2-fluoro-3-[(2-fluorobenzyl)oxy]phenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-2-fluorobenzene. MS (ESI): mass calcd. for $C_{21}H_{19}F_2N_3O$, 367.15; m/z found, 368.1 [M+H]$^+$. $^1$H NMR (400 MHz, CD$_3$OD) δ 8.32 (d, J=1.2, 1H), 8.22 (s, 1H), 7.59 (m, 1H), 7.53-7.48 (m, 1H), 7.42-7.35 (m, 1H), 7.24-7.09 (m, 3H), 5.11 (s, 2H), 3.81-3.67 (m, 1H), 2.29-2.17 (m, 2H), 2.15-1.91 (m, 3H), 1.88-1.75 (m, 1H).

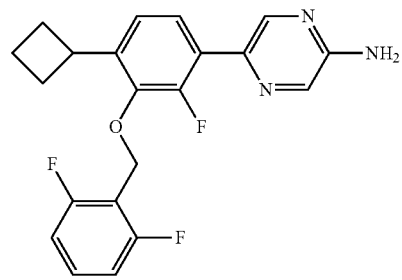

5-{4-Cyclobutyl-3-[(2,6-difluorobenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 2-(bromomethyl)-1,3-difluorobenzene. MS (ESI): mass calcd. for $C_{21}H_{18}F_3N_3O$, 385.14; m/z found, 386.2 [M+H]J. $^1$H NMR (400 MHz, CD$_3$OD) δ 8.24 (s, 1H), 8.18 (d, J=1.4, 1H), 7.59-7.52 (m, 1H), 7.48-7.39 (m, 1H), 7.20 (d, J=7.6, 1H), 7.05-6.97 (m, 2H), 5.19 (s, 2H), 3.80-3.66 (m, 1H), 2.26-2.15 (m, 2H), 2.13-1.91 (m, 3H), 1.86-1.79 (m, 1H).

Example 32

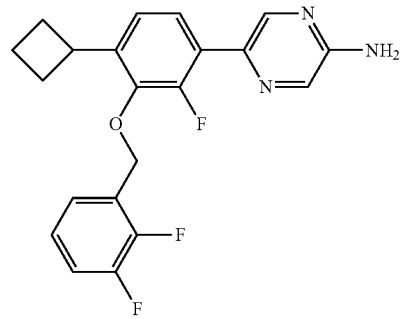

5-{4-Cyclobutyl-3-[(2,3-difluorobenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-2,3-difluorobenzene. MS (ESI): mass calcd. for $C_{21}H_{18}F_3N_3O$, 385.14; m/z found, 386.1 [M+H]$^+$. $^1$H NMR (400 MHz, CD$_3$OD) δ 8.27 (d, J=1.2, 1H), 8.23 (s, 1H), 7.59 (m, 1H), 7.36-7.13 (m, 4H), 5.15 (d, J=1.0, 2H), 3.82-3.69 (m, 1H), 2.29-2.19 (m, 2H), 2.17-1.92 (m, 3H), 1.90-1.78 (m, 1H).

Example 33

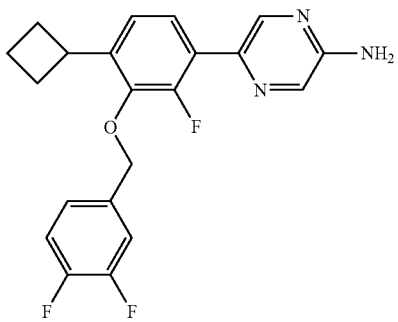

5-{4-Cyclobutyl-3-[(3,4-difluorobenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 4-(bromomethyl)-1,2-difluorobenzene. MS (ESI): mass calcd. for $C_{21}H_{18}F_3N_3O$, 385.14; m/z found, 386.1 [M+H]$^+$. $^1$H NMR (400 MHz, CD$_3$OD) δ 8.29 (d, J=1.3, 1H), 8.23 (s, 1H), 7.59 (m, 1H), 7.45-7.36 (m, 1H), 7.33-7.20 (m, 3H), 5.02 (s, 2H), 3.85-3.72 (m, 1H), 2.34-2.23 (m, 2H), 2.21-1.97 (m, 3H), 1.90-1.81 (m, 1H).

Example 34

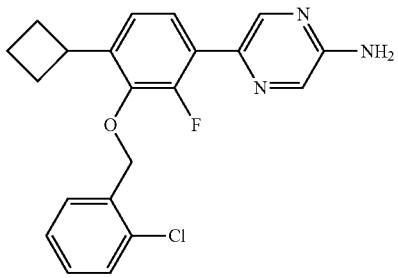 [SMILES: Nc1cnc(-c2ccc(C3CCC3)c(OCc3ccccc3Cl)c2F)cn1]

5-{3-[(2-Chlorobenzyl)oxy]-4-cyclobutyl-2-fluorophenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-2-chlorobenzene. MS (ESI): mass calcd. for $C_{21}H_{19}ClFN_3O$, 383.12; m/z found, 384.1 [M+H]$^+$. $^1$H NMR (400 MHz, CD$_3$OD) δ 8.27-8.23 (m, 2H), 7.63-7.56 (m, 2H), 7.47-7.42 (m, 1H), 7.38-7.32 (m, 2H), 7.22 (d, J=7.8, 1H), 5.16 (d, J=3.7, 2H), 3.85-3.72 (m, 1H), 2.29-2.20 (m, 2H), 2.18-1.91 (m, 3H), 1.88-1.78 (m, 1H).

Example 35

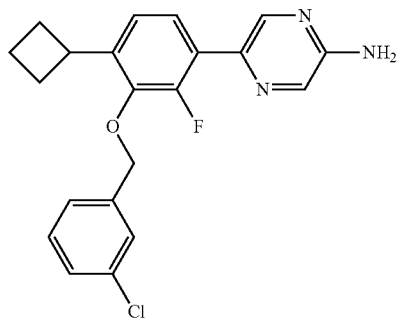

5-{3-[(3-Chlorobenzyl)oxy]-4-cyclobutyl-2-fluorophenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-3-chlorobenzene. MS (ESI): mass calcd. for $C_{21}H_{19}ClFN_3O$, 383.12; m/z found, 384.1 [M+H]$^+$. $^1$H NMR (400 MHz, CD$_3$OD) δ 8.25 (s, 2H), 7.60-7.54 (m, 1H), 7.49 (s, 1H), 7.39-7.33 (m, 3H), 7.21 (d, J=8.3, 1H), 5.04 (s, 2H), 3.84-3.70 (m, 1H), 2.32-2.21 (m, 2H), 2.20-1.94 (m, 3H), 1.91-1.79 (m, 1H).

Example 36

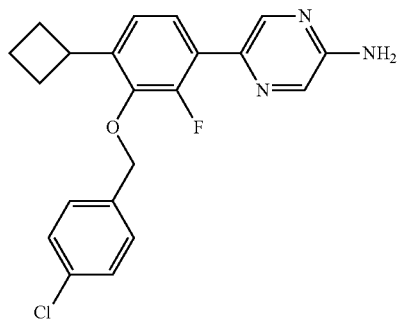

5-{3-[(4-Chlorobenzyl)oxy]-4-cyclobutyl-2-fluorophenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-4-chlorobenzene. MS (ESI): mass calcd. for $C_{21}H_{19}ClFN_3O$, 383.12; m/z found, 384.1 [M+H]$^+$. $^1$H NMR (400 MHz, CD$_3$OD) δ 8.31 (d, J=1.3, 1H), 8.22 (s, 1H), 7.62-7.55 (m, 1H), 7.46-7.36 (m, 4H), 7.20 (d, J=7.9, 1H), 5.00 (d, J=9.7, 2H), 3.82-3.69 (m, 1H), 2.31-2.20 (m, 2H), 2.17-1.93 (m, 3H), 1.90-1.78 (m, 1H).

Example 37

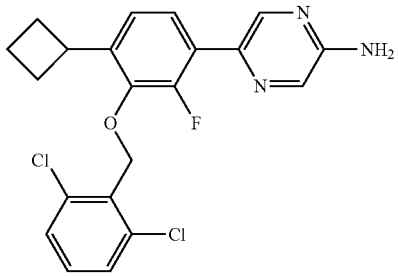

5-{4-Cyclobutyl-3-[(2,6-dichlorobenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 2-(bromomethyl)-1,3-dichlorobenzene. MS (ESI): mass calcd. for $C_{21}H_{18}Cl_2FN_3O$, 417.08; m/z found, 418.0 [M+H]$^+$. $^1$H NMR (400 MHz, CD$_3$OD) δ 8.29 (d, J=1.4, 1H), 8.21 (t, J=1.4, 1H), 7.62-7.56 (m, 1H), 7.47-7.41 (m, 2H), 7.38-7.31 (m, 1H), 7.22 (d, J=7.7, 1H), 5.42 (s, 2H), 3.84-3.70 (m, 1H), 2.19-1.75 (m, 6H).

Example 38

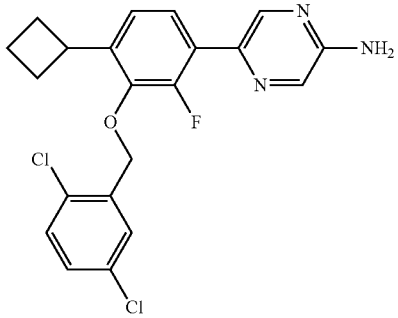

5-{4-Cyclobutyl-3-[(2,5-dichlorobenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 2-(bromomethyl)-1,4-dichlorobenzene. MS (ESI): mass calcd. for $C_{21}H_{18}Cl_2FN_3O$, 417.08; m/z found, 418.0 [M+H]$^+$. $^1$H NMR (400 MHz, CD$_3$OD) δ 8.27-8.21 (m, 2H), 7.66 (d, J=2.5, 1H), 7.59 (m, 1H), 7.47-7.41 (m, 1H), 7.39-7.34 (m, 1H), 7.24 (m, 1H), 5.13 (s, 2H), 3.86-3.73 (m, 1H), 2.33-2.22 (m, 2H), 2.20-2.09 (m, 2H), 2.07-1.96 (m, 1H), 1.92-1.79 (m, 1H).

Example 39

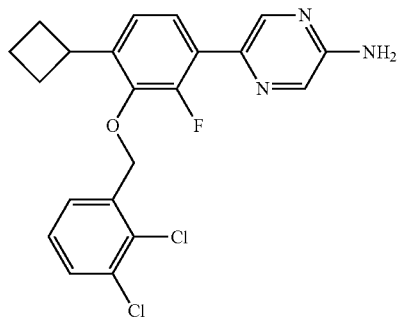

5-{4-Cyclobutyl-3-[(2,3-dichlorobenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-2,3-dichlorobenzene. MS (ESI): mass calcd. for $C_{21}H_{18}Cl_2FN_3O$, 417.08; m/z found, 418.2 [M+H]$^+$. $^1$H NMR (400 MHz, CD$_3$OD) δ 8.25 (s, 2H), 7.62-7.52 (m, 3H), 7.35 (m, 1H), 7.23 (d, J=8.3, 1H), 5.19 (s, 2H), 3.86-3.73 (m, 1H), 2.29-1.78 (m, 7H).

Example 40

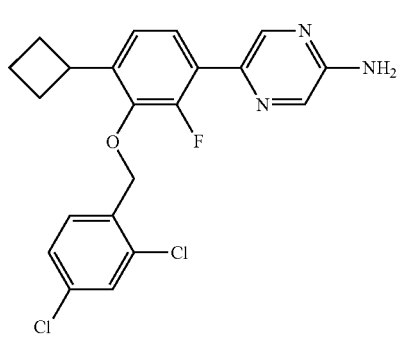 [SMILES: Nc1cnc(-c2ccc(C3CCC3)c(OCc3ccc(Cl)cc3Cl)c2F)cn1]

5-{4-Cyclobutyl-3-[(2,4-dichlorobenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 1-(bromomethyl)-2,4-dichlorobenzene. MS (ESI): mass calcd. for $C_{21}H_{18}Cl_2FN_3O$, 417.08; m/z found, 418.0 [M+H]$^+$. $^1$H NMR (400 MHz, CD$_3$OD) δ 8.27 (d, J=1.3, 1H), 8.24 (s, 1H), 7.63-7.57 (m, 2H), 7.53 (d, J=2.1, 1H), 7.41-7.37 (m, 1H), 7.23 (d, J=7.9, 1H), 5.14 (s, 2H), 3.84-3.72 (m, 1H), 2.30-2.20 (m, 2H), 2.18-1.95 (m, 3H), 1.89-1.79 (m, 1H).

Example 41

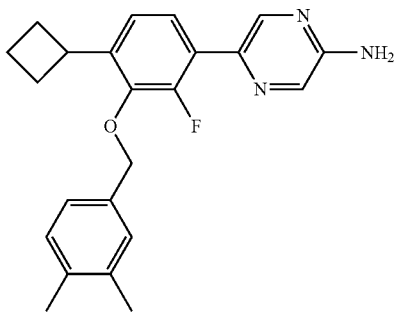 [SMILES: Cc1ccc(COc2c(C3CCC3)ccc(-c3cnc(N)cn3)c2F)cc1C]

5-{4-Cyclobutyl-3-[(3,4-dimethylbenzyl)oxy]-2-fluorophenyl}pyrazin-2-amine

The title compound was prepared in a manner similar to that described in Example 28 using 3-(5-aminopyrazin-2-yl)-6-cyclobutyl-2-fluorophenol and 4-(bromomethyl)-1,2-dimethylbenzene. MS (ESI): mass calcd. for $C_{23}H_{24}FN_3O$, 377.19; m/z found, 378.2 [M+H]$^+$. $^1$H NMR (400 MHz, CD$_3$OD) δ 8.29-8.21 (m, 2H), 7.60-7.53 (m, 1H), 7.23-7.02 (m, 4H), 5.02 (d, J=43.3, 2H), 3.82-3.67 (m, 1H), 2.38 (s, 1H), 2.33 (s, 1H), 2.29-2.16 (m, 6H), 2.15-1.92 (m, 3H), 1.89-1.78 (m, 1H).

Example 42

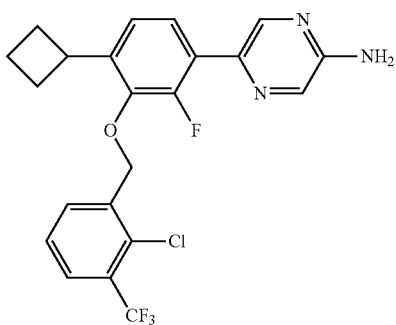 [SMILES: Nc1cnc(-c2ccc(C3CCC3)c(OCc3cccc(C(F)(F)F)c3Cl)c2F)cn1]

5-(3-{[2-Chloro-3-(trifluoromethyl)benzyl]oxy}-4-cyclobutyl-2-fluorophenyl)pyrazin-2-amine The title compound was prepared in a manner similar to that described in Example 28 using 3-(5-aminopyrazin-2-yl)-6-cyclobutyl-2-fluorophenol and 1-(bromomethyl)-2-chloro-3-(trifluoromethyl)benzene. MS (ESI): mass calcd. for $C_{22}H_{18}ClF_4N_3O$, 451.11; m/z found, 452.1 [M+H]$^+$. $^1$H NMR (400 MHz, CD$_3$OD) δ 8.30-8.22 (m, 2H), 7.91 (d, J=7.7, 1H), 7.83-7.77 (m, 1H), 7.64-7.52 (m, 2H), 7.24 (d, J=7.9, 1H), 5.23 (d, J=6.5, 2H), 3.84-3.72 (m, 1H), 2.30-2.18 (m, 2H), 2.17-2.07 (m, 2H), 2.07-1.93 (m, 1H), 1.88-1.79 (m, 1H).

Example 43

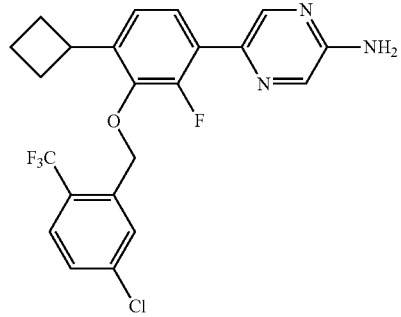

5-(3-{[5-Chloro-2-(trifluoromethyl)benzyl]oxy}-4-cyclobutyl-2-fluorophenyl)pyrazin-2-amine The title compound was prepared in a manner similar to that described in Example 28 using 3-(5-aminopyrazin-2-yl)-6-cyclobutyl-2-fluorophenol and 2-(bromomethyl)-4-chloro-1-(trifluoromethyl)benzene. MS (ESI): mass calcd. for $C_{22}H_{18}ClF_4N_3O$, 451.11; m/z found, 452.1 [M+H]$^+$. $^1$H NMR (400 MHz, CD$_3$OD) δ 8.25 (s, 2H), 7.92 (s, 1H), 7.75 (d, J=8.5, 1H), 7.66-7.60 (m, 1H), 7.57 (d, J=8.4, 1H), 7.27 (d, J=7.9, 1H), 5.21 (s, 2H), 3.85-3.73 (m, 1H), 2.33-2.23 (m, 2H), 2.20-2.11 (m, 2H), 2.07-1.96 (m, 1H), 1.91-1.82 (m, 1H).

Example 44

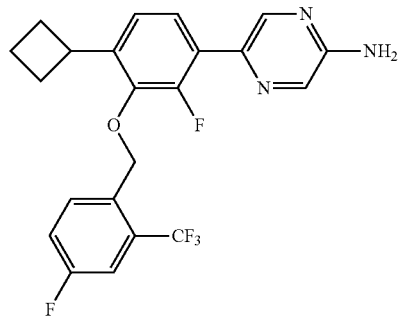 [SMILES: Nc1cnc(-c2ccc(C3CCC3)c(OCc3ccc(F)cc3C(F)(F)F)c2F)cn1]

5-(4-Cyclobutyl-2-fluoro-3-{[4-fluoro-2-(trifluoromethyl)benzyl]oxy}phenyl)pyrazin-2-amine The title compound was prepared in a manner similar to that described in Example 28 using 3-(5-aminopyrazin-2-yl)-6-cyclobutyl-2-fluorophenol and 1-(bromomethyl)-4-fluoro-2-(trifluoromethyl)benzene. MS (ESI): mass calcd. for $C_{22}H_{18}F_5N_3O$, 435.14; m/z found, 436.1 [M+H]$^+$. $^1$H NMR (400 MHz, CD$_3$OD) δ 8.26 (d, J=1.3, 1H), 8.23 (s, 1H), 7.92-7.86 (m, 1H), 7.61 (m, 1H), 7.55-7.51 (m, 1H), 7.49-7.43 (m, 1H), 7.24 (d, J=8.0, 1H), 5.18 (s, 2H), 3.83-3.70 (m, 1H), 2.29-2.19 (m, 2H), 2.18-2.08 (m, 2H), 2.06-1.93 (m, 1H), 1.90-1.79 (m, 1H).

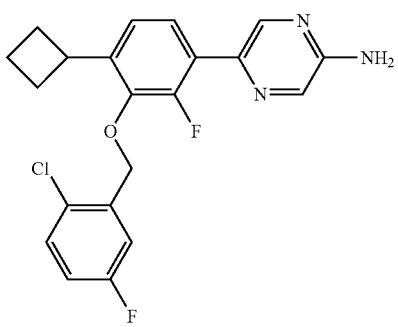 [SMILES: Nc1cnc(-c2ccc(C3CCC3)c(OCc3cc(F)ccc3Cl)c2F)cn1]

5-{3-[(2-Chloro-5-fluorobenzyl)oxy]-4-cyclobutyl-2-fluorophenyl}pyrazin-2-amine

The title compound was prepared in a manner similar to that described in Example 28 using 3-(5-aminopyrazin-2-yl)-6-cyclobutyl-2-fluorophenol and 2-(bromomethyl)-1-chloro-4-fluorobenzene. MS (ESI): mass calcd. for $C_{21}H_{18}ClF_2N_3O$, 401.11; m/z found, 402.1 [M+H]$^+$. $^1$H NMR (400 MHz, CD$_3$OD) δ 8.25 (m, 2H), 7.64-7.57 (m, 1H), 7.48-7.40 (m, 2H), 7.23 (d, J=7.9, 1H), 7.16-7.08 (m, 1H), 5.13 (s, 2H), 3.87-3.75 (m, 1H), 2.33-2.21 (m, 2H), 2.21-1.94 (m, 3H), 1.90-1.80 (m, 1H).

Example 46

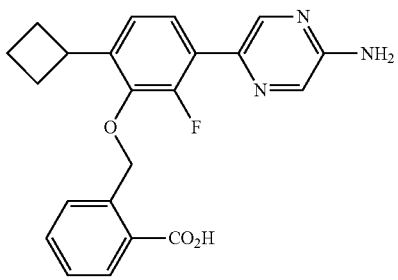

2-{[3-(5-Aminopyrazin-2-yl)-6-cyclobutyl-2-fluoro-phenoxy]methyl}benzoic acid

The title compound was prepared in a manner similar to that described in Example 28 using 3-(5-aminopyrazin-2-yl)-6-cyclobutyl-2-fluorophenol and ethyl 2-(bromomethyl)benzoate. MS (ESI): mass calcd. for $C_{22}H_{20}FN_3O_3$, 393.15; m/z found, 394.2 [M+H]$^+$. $^1$H NMR (400 MHz, CD$_3$OD) δ 8.30 (d, J=1.0, 1H), 8.22 (s, 1H), 8.06-8.02 (m, 1H), 7.87 (d, J=7.7, 1H), 7.66-7.56 (m, 1H), 7.44 (m, 1H), 7.22 (d, J=8.3, 1H), 5.47 (s, 2H), 3.87-3.72 (m, 1H), 2.31-2.20 (m, 2H), 2.17-2.07 (m, 2H), 2.05-1.92 (m, 1H), 1.87-1.77 (m, 1H).

Example 47

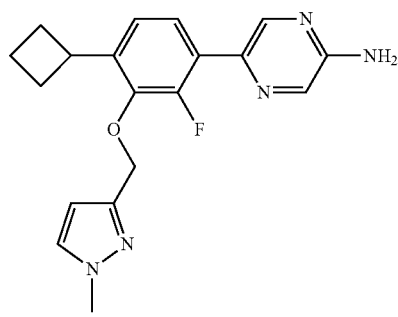 [SMILES: Cn1ccc(COc2c(C3CCC3)ccc(-c3cnc(N)cn3)c2F)n1]

5-{4-Cyclobutyl-2-fluoro-3-[(1-methyl-1H-pyrazol-3-yl)methoxy]phenyl}pyrazin-2-amine The title compound was prepared in a manner similar to that described in Example 96 using 3-(5-aminopyrazin-2-yl)-6-cyclobutyl-2-fluorophenol and 3-(bromomethyl)-1-methyl-1H-pyrazole. MS (ESI): mass calcd. for $C_{19}H_{20}FN_5O$, 353.16; m/z found, 354.1 [M+H]$^+$. $^1$H NMR (400 MHz, CD$_3$OD) δ 8.30-8.25 (m, 1H), 8.18 (m, 1H), 7.58-7.51 (m, 2H), 7.19 (d, J=8.3, 1H), 6.34 (m, 1H), 5.03 (d, J=5.7, 2H), 3.88 (d, J=6.0, 3H), 3.82-3.71 (m, 1H), 2.30-2.20 (m, 2H), 2.15-1.95 (m, 3H), 1.89-1.79 (m, 1H).

Example 48

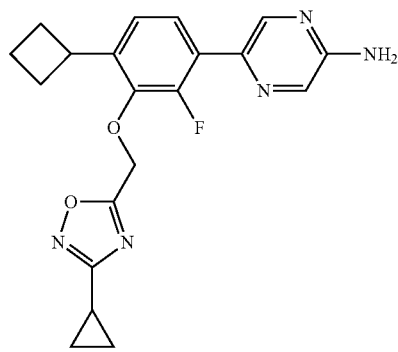 [SMILES: Nc1cnc(-c2ccc(C3CCC3)c(OCc3nc(C4CC4)no3)c2F)cn1]

5-{4-Cyclobutyl-3-[(3-cyclopropyl-1,2,4-oxadiazol-5-yl)methoxy]-2-fluorophenyl}pyrazin-2-amine The title compound was prepared in a manner similar to that described in Example 96 using 3-(5-aminopyrazin-2-yl)-6-cyclobutyl-2-fluorophenol and 5-(bromomethyl)-3-cyclopropyl-1,2,4-oxadiazole. MS (ESI): mass calcd. for $C_2H_{20}FN_5O_2$, 381.16; m/z found, 382.1 [M+H]$^+$. $^1$H NMR (400 MHz, CD$_3$OD) δ 8.25 (d, J=1.6, 1H), 8.16 (d, J=1.4, 1H), 7.59 (m, 1H), 7.22 (d, J=8.3, 1H), 5.26 (d, J=6.7, 2H), 3.85-3.74 (m, 1H), 2.36-2.25 (m, 2H), 2.20-2.01 (m, 4H), 1.92-1.82 (m, 1H), 1.14-1.05 (m, 2H), 1.01-0.95 (m, 2H).

Example 49

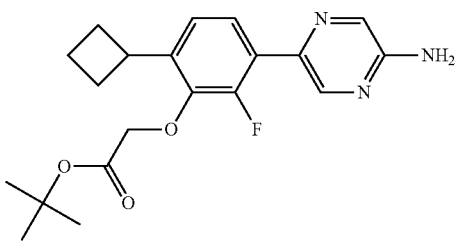 [SMILES: CC(C)(C)OC(=O)COc1c(C2CCC2)ccc(-c2cnc(N)cn2)c1F]

tert-Butyl [3-(5-aminopyrazin-2-yl)-6-cyclobutyl-2-fluorophenoxy]acetate

To a 4 mL vial were added a stir bar, 3-(5-aminopyrazin-2-yl)-6-cyclobutyl-2-fluorophenol (47 mg, 0.18 mmol), tert-butyl bromoacetate (35 μL, 0.24 mmol), powdered KOH (19 mg, 0.34 mmol) and DMSO (1.0 mL). The resultant mixture was stirred at room temperature for 19 hours before passing it through a syringe filter and subjecting the filtrate to HPLC purification to give both the title compound (20 mg, 22%) and recovered 3-(5-aminopyrazin-2-yl)-6-cyclobutyl-2-fluorophenol (20 mg, 26%). MS (ESI): mass calcd. for $C_{20}H_{24}FN_3O_3$, 373.18; m/z found, 374.1 [M+H]+. $^1$H NMR (600 MHz, CDCl$_3$) δ 8.44-8.38 (d, J=1.4, 1H), 8.21-8.16 (d, J=1.4, 1H), 7.64-7.57 (m, 1H), 7.17-7.10 (m, 1H), 4.57-4.49 (d, J=1.3, 2H), 3.99-3.88 (m, 1H), 2.41-2.30 (m, 2H), 2.18-1.99 (m, 3H), 1.91-1.79 (m, 1H), 1.50 (s, 9H).

Example 50

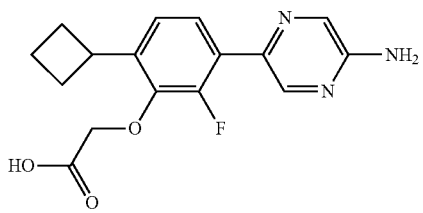 [SMILES: Nc1cnc(-c2ccc(C3CCC3)c(OCC(=O)O)c2F)cn1]

[3-(5-Aminopyrazin-2-yl)-6-cyclobutyl-2-fluorophenoxy]acetic acid

To a 20 mL vial containing tert-butyl [3-(5-aminopyrazin-2-yl)-6-cyclobutyl-2-fluorophenoxy]acetate (17 mg, 0.034 mmol) were added a stir bar and formic acid (1 mL). The reaction mixture was stirred for 20 hours at room temperature and then concentrated to dryness to give the title compound (12 mg, 95%). MS (ESI): mass calcd. for $C_{16}H_{16}FN_3O_3$, 317.12; m/z found, 318.0 [M+H]+. $^1$H NMR (500 MHz, CD$_3$OD) δ 8.25 (s, 1H), 8.14 (s, 1H), 8.07 (s, 1H), 7.55-7.49 (m, 1H), 7.22-7.16 (d, J=8.2, 1H), 4.65 (s, 2H), 4.04-3.86 (p, J=8.7, 1H), 2.42-2.31 (m, 2H), 2.25-2.12 (m, 2H), 2.12-2.00 (m, 1H), 1.94-1.80 (m, 1H).

Example 51

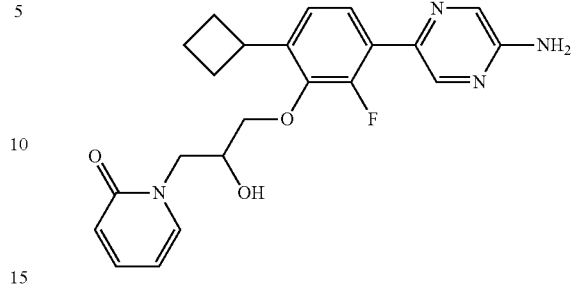

racemic 1-(3-(3-(5-Aminopyrazin-2-yl)-6-cyclobutyl-2-fluorophenoxy)-2-hydroxypropyl)pyridin-2(1H)-one To a 5 mL reaction tube equipped with reflux condenser and under nitrogen, were added 5-(4-cyclobutyl-2-fluoro-3-(oxiran-2-ylmethoxy)phenyl)pyrazin-2-amine (100 mg, 0.317 mmol), Cs$_2$CO$_3$ (103 mg, 0.317 mmol), pyridin-2(1H)-one (151 mg, 1.59 mmol) and DMF (2 mL) to give a yellow suspension. The resulting mixture was heated at 80° Celsius for 3 hours. The mixture was then concentrated to dryness, and the residue purified by HPLC to afford the title compound (110 mg, 85%). MS (ESI): mass calcd. for $C_{22}H_{23}FN_4O_3$, 410.18; m/z found, 411.1 [M+H]+; $^1$H NMR (400 MHz, DMSO-d$_6$): δ 8.29 (dd, J=2.4, 1.5, 1H), 8.00 (m, 1H), 7.66-7.60 (m, 1H), 7.52 (m, 1H), 7.46-7.39 (m, 1H), 7.21 (d, J=8.2, 1H), 6.65 (s, 2H), 6.40 (dd, J=9.1, 0.8, 1H), 6.21 (m, 1H), 5.40 (d, J=5.8, 1H), 4.35 (dd, J=13.0, 3.8, 1H), 4.18-4.08 (m, 1H), 3.93 (d, J=5.1, 2H), 3.85 (dd, J=17.8, 8.9, 1H), 3.74 (dd, J=13.0, 8.4, 1H), 2.30 (m, 2H), 2.13-2.04 (m, 2H), 2.03-1.94 (m, 1H), 1.88-1.78 (m, 1H).

Example 52

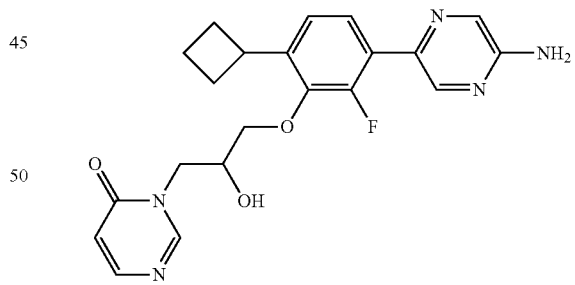

racemic 3-(3-(3-(5-Aminopyrazin-2-yl)-6-cyclobutyl-2-fluorophenoxy)-2-hydroxypropyl)pyrimidin-4(3H)-one The title compound was prepared using analogous conditions described in Example 51 using pyrimidin-4(3H)-one. MS (ESI): mass calcd. for $C_{21}H_{22}FN_5O_3$, 411.17; m/z found, 412.1 [M+H]+. $^1$H NMR (400 MHz, DMSO-d$_6$) δ 8.36 (s, 1H), 8.31-8.27 (m, 1H), 8.00 (d, J=1.5, 1H), 7.92 (d, J=6.6, 1H), 7.52 (m, 1H), 7.22 (d, J=8.2, 1H), 6.65 (s, 2H), 6.43 (dd, J=6.6, 0.7, 1H), 5.53 (s, 1H), 4.37 (dd, J=13.2, 3.3, 1H), 4.11 (dd, J=8.7, 3.5, 1H), 3.96 (d, J=5.3, 2H), 3.90-3.82 (m, 1H), 3.80-3.74 (m, 1H), 2.32 (m, 2H), 2.10 (m, 2H), 2.04-1.92 (m, 1H), 1.86-1.77 (m, 1H).

Example 53

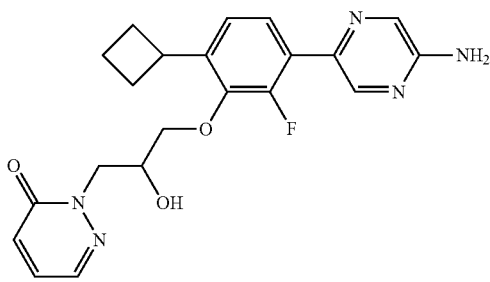

racemic 2-(3-(3-(5-Aminopyrazin-2-yl)-6-cyclobutyl-2-fluorophenoxy)-2-hydroxypropyl)pyridazin-3(2H)-one The title compound was prepared using analogous conditions described in Example 51 using pyridazin-3(2H)-one. MS (ESI): mass calcd. for $C_{21}H_{22}FN_5O_3$, 411.17; m/z found, 412.0 [M+H]$^+$. $^1$H NMR (500 MHz, DMSO-d$_6$) δ 8.30-8.25 (m, 1H), 7.99 (d, J=1.5, 1H), 7.93 (dd, J=3.8, 1.7, 1H), 7.50 (m, 1H), 7.41 (dd, J=9.4, 3.8, 1H), 7.20 (d, J=8.2, 1H), 6.95 (dd, J=9.4, 1.6, 1H), 6.64 (s, 2H), 5.31 (d, J=5.7, 1H), 4.30 (m, 1H), 4.22 (d, J=6.6, 2H), 3.98-3.91 (m, 2H), 3.90-3.79 (m, 1H), 2.28 (dd, J=14.3, 7.8, 2H), 2.08 (dd, J=19.5, 9.4, 2H), 2.03-1.95 (m, 1H), 1.86-1.75 (m, 1H).

Example 54

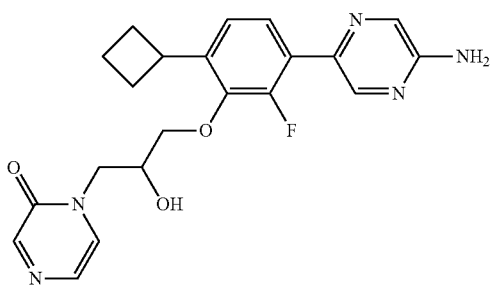

racemic 1-(3-(3-(5-Aminopyrazin-2-yl)-6-cyclobutyl-2-fluorophenoxy)-2-hydroxypropyl)pyrazin-2(1H)-one The title compound was prepared using analogous conditions described in Example 51 using pyrazin-2(1H)-one. MS (ESI): mass calcd. for $C_{21}H_{22}FN_5O_3$, 411.17; m/z found, 412.1 [M+H]$^+$. $^1$H NMR (400 MHz, DMSO-d$_6$) δ 8.35 (d, J=1.5, 1H), 8.07 (dd, J=9.7, 1.3, 2H), 7.66 (dd, J=4.3, 1.1, 1H), 7.58 (m, 1H), 7.39 (d, J=4.3, 1H), 7.28 (d, J=8.2, 1H), 6.70 (s, 2H), 5.54 (s, 1H), 4.41 (dd, J=12.9, 3.4, 1H), 4.22 (s, 1H), 4.02 (d, J=5.2, 2H), 3.91 (dd, J=17.8, 8.8, 1H), 3.82 (dd, J=12.9, 9.0, 1H), 2.41-2.33 (m, 2H), 2.15 (dd, J=19.1, 9.5, 2H), 2.06 (dd, J=18.7, 9.0, 2H), 1.94-1.83 (m, 1H).

Example 55

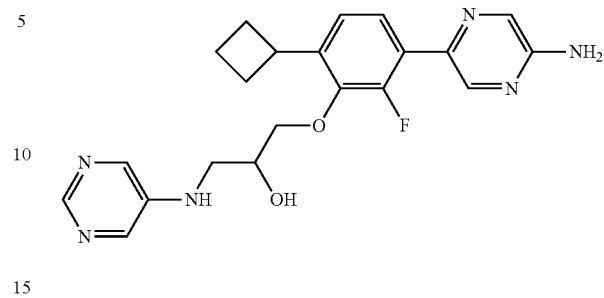

racemic 1-(3-(5-Aminopyrazin-2-yl)-6-cyclobutyl-2-fluorophenoxy)-3-(pyrimidin-5-ylamino)propan-2-ol The title compound was prepared using analogous conditions described in Example 51 using 5-aminopyrimidine. MS (ESI): mass calcd. for $C_{21}H_{23}FN_6O_2$, 410.19; m/z found, 411.1 [M+H]$^+$. $^1$H NMR (400 MHz, DMSO-d$_6$) δ 8.35 (s, 1H), 8.26-8.21 (m, 1H), 8.17 (s, 2H), 7.95 (d, J=1.4, 1H), 7.47 (m, 1H), 7.17 (d, J=8.2, 1H), 6.60 (s, 2H), 6.11 (t, J=6.0, 1H), 5.26 (s, 1H), 4.03-3.91 (m, 3H), 3.85-3.74 (m, 1H), 3.24-3.11 (m, 2H), 2.28-2.16 (m, 2H), 2.10-1.98 (m, 2H), 1.93-1.81 (m, 1H), 1.80-1.69 (m, 1H).

Example 56

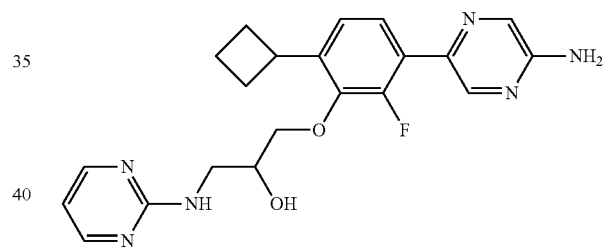

racemic 1-(3-(5-Aminopyrazin-2-yl)-6-cyclobutyl-2-fluorophenoxy)-3-(pyrimidin-2-ylamino)propan-2-ol Step A: 1-Amino-3-(3-(5-aminopyrazin-2-yl)-6-cyclobutyl-2-fluorophenoxy)propan-2-ol A mixture of 5-(4-cyclobutyl-2-fluoro-3-(oxiran-2-ylmethoxy)phenyl)pyrazin-2-amine (500 mg, 1.59 mmol) and 6 N NH$_3$ in MeOH (5 mL) was stirred in a sealed tube at 60 Celsius for approximately 8 hours before cooling to rt and concentrating to dryness to give 1-amino-3-(3-(5-aminopyrazin-2-yl)-6-cyclobutyl-2-fluorophenoxy)propan-2-ol (510 mg, 96%).

Step B

To a 25 mL round-bottomed flask were added a stir bar, 1-amino-3-(3-(5-aminopyrazin-2-yl)-6-cyclobutyl-2-fluorophenoxy)propan-2-ol (150 mg, 0.45 mmol), 2-chloropyrimidine (62 mg, 0.54 mmol), Cs$_2$CO$_3$ (440 mg, 1.35 mmol) and DMF (6 mL). The mixture was stirred at 60° Celsius for approximately 24 hours and then diluted with water (20 mL). The aqueous mixture was extracted with EtOAc (3×30 mL) and the combined extracts dried over Na$_2$SO$_4$, filtered and concentrated to dryness. The residue was purified by HPLC to afford the title compound (25 mg, 55%). MS (ESI): mass calcd. for C$_{21}$H$_{23}$FN$_6$O$_2$, 410.19; m/z found, 411.1 [M+H]$^+$. $^1$HNMR (400 MHz, DMSO-d$_6$) δ 8.33-8.18 (m, 3H), 7.95 (d, J=1.4, 1H), 7.45 (m, 1H), 7.15 (d, J=8.2, 1H), 6.98 (m, 1H), 6.61 (s, 2H), 6.54 (m, 1H), 5.19 (d, J=5.3, 1H), 4.03-3.96 (m, 1H), 3.94-3.85 (m, 2H), 3.83-3.75 (m, 1H), 3.49-3.42 (m, 2H), 2.26-2.17 (m, 2H), 2.09-1.97 (m, 2H), 1.93-1.84 (m, 1H), 1.80-1.71 (m, 1H).

Example 57

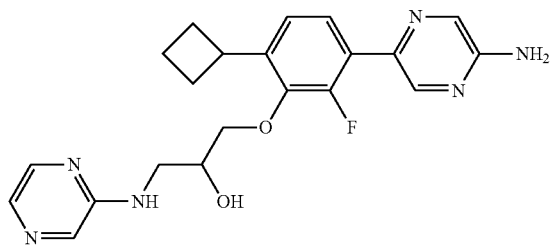 [SMILES: Nc1cnc(-c2ccc(C3CCC3)c(OCC(O)CNc3cnccn3)c2F)cn1]

racemic 1-(3-(5-Aminopyrazin-2-yl)-6-cyclobutyl-2-fluorophenoxy)-3-(pyrazin-2-ylamino)propan-2-ol The title compound was prepared using analogous conditions described in Example 56 using 2-chloropyrazine. MS (ESI): mass calcd. for C$_{21}$H$_{23}$FN$_6$O$_2$, 410.19; m/z found, 411.1 [M+H]$^+$. $^1$H NMR (400 MHz, DMSO-d$_6$) δ 8.23 (s, 1H), 7.95 (s, 1H), 7.88 (s, 1H), 7.60 (s, 1H), 7.45 (s, 1H), 7.22-6.96 (m, 2H), 6.60 (s, 2H), 5.23 (s, 1H), 3.98 (s, 2H), 3.91 (s, 2H), 3.79 (s, 2H), 2.21 (s, 2H), 2.03 (s, 2H), 1.86 (d, J=8.5, 1H), 1.76 (s, 1H).

Example 58

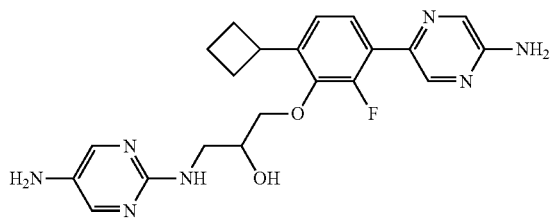 [SMILES: Nc1cnc(NCC(O)COc2c(C3CCC3)ccc(-c3cnc(N)cn3)c2F)nc1]

racemic 1-(3-(5-Aminopyrazin-2-yl)-6-cyclobutyl-2-fluorophenoxy)-3-((5-aminopyrimidin-2-yl)amino)propan-2-ol The title compound was prepared using analogous conditions described in Example 56 using 2-chloro-5-aminopyrimidine. $^1$H NMR (400 MHz, DMSO-d$_6$) δ 9.09 (s, 1H), 8.31-8.25 (m, 1H), 8.00 (d, J=1.5, 1H), 7.94 (s, 2H), 7.49 (m, 1H), 7.19 (d, J=8.3, 1H), 6.64 (s, 2H), 6.38 (m, 1H), 5.18 (d, J=5.2, 1H), 4.04-3.80 (m, 4H), 3.44 (m, 2H), 2.32-2.21 (m, 2H), 2.06 (m, 2H), 1.92 (m, 1H), 1.80 (m, 1H).

Example 59

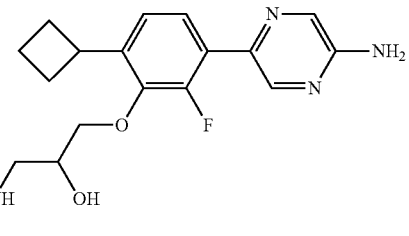

racemic 1-(3-(5-Aminopyrazin-2-yl)-6-cyclobutyl-2-fluorophenoxy)-3-((6-aminopyrimidin-4-yl)amino)propan-2-ol The title compound was prepared using analogous conditions described in Example 56 using 4-amino-6-chloropyrimidine. MS (ESI): mass calcd. for C$_{21}$H$_{24}$FN$_7$O$_2$, 425.20; m/z found, 426.1 [M+H]$^+$. $^1$H NMR (400 MHz, DMSO-d$_6$) δ 8.25 (s, 1H), 7.97 (s, 1H), 7.84 (s, 1H), 7.47 (m, 1H), 7.18 (d, J=8.3, 1H), 6.61 (s, 2H), 6.54 (s, 1H), 6.02 (s, 2H), 5.43 (s, 1H), 5.34 (s, 1H), 3.98-3.78 (m, 6H), 2.24 (s, 2H), 2.10-2.01 (m, 2H), 1.92 (dd, J=18.5, 9.0, 1H), 1.77 (d, J=9.1, 1H).

Example 60

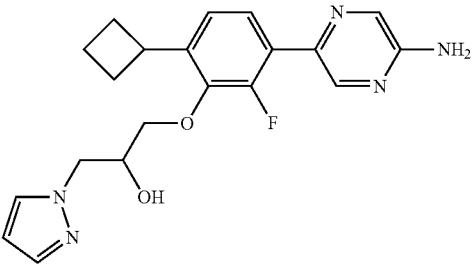 [SMILES: Nc1cnc(-c2ccc(C3CCC3)c(OCC(O)Cn3cccn3)c2F)cn1]

racemic 1-(3-(5-Aminopyrazin-2-yl)-6-cyclobutyl-2-fluorophenoxy)-3-(1H-pyrazol-1-yl)propan-2-ol The title compound was prepared using analogous conditions described in Example 51 using pyrazole. MS (ESI): mass calcd. for C$_{20}$H$_{22}$FN$_5$O$_2$, 383.18; m/z found, 384.0 [M+H]$^+$. $^1$H NMR (400 MHz, CDCl$_3$) δ 8.36 (s, 1H), 8.01 (s, 1H), 7.54-7.42 (m, 3H), 7.08 (d, J=8.2, 1H), 6.23 (d, J=1.9, 1H), 4.64 (s, 2H), 4.43 (dd, J=16.1, 5.7, 1H), 4.32 (m, 2H), 3.89 (dd, J=9.6, 4.8, 1H), 3.83 (dd, J=9.6, 5.5, 1H), 3.73 (dd, J=17.6, 8.5, 1H), 2.31-2.22 (m, 2H), 2.07 (dd, J=18.7, 9.2, 2H), 2.02-1.93 (m, 1H), 1.84-1.77 (m, 1H).

Example 61

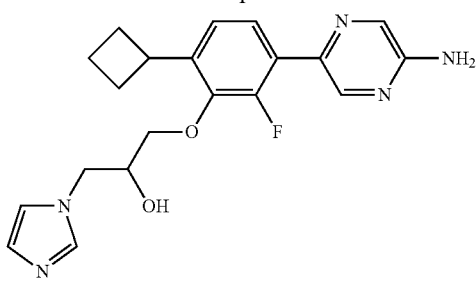

racemic 1-(3-(5-Aminopyrazin-2-yl)-6-cyclobutyl-2-fluorophenoxy)-3-(1H-imidazol-1-yl)propan-2-ol The title compound was prepared using analogous conditions described in Example 51 using imidazole. MS (ESI): mass calcd. for $C_{20}H_{22}FN_5O_2$, 383.18; m/z found, 384.0 [M+H]$^+$. $^1$H NMR (500 MHz, CD$_3$OD) δ 8.32 (s, 1H), 7.99 (s, 1H), 7.48 (m, 1H), 7.09 (d, J=8.3, 1H), 6.11 (s, 2H), 4.83 (s, 1H), 4.32-4.08 (m, 3H), 3.92 (d, J=12.2, 2H), 3.71 (m, 1H), 2.31-2.21 (m, 2H), 2.14-2.03 (m, 2H), 2.02-1.93 (m, 1H), 1.81 (dd, J=19.5, 8.6, 1H).

Example 62

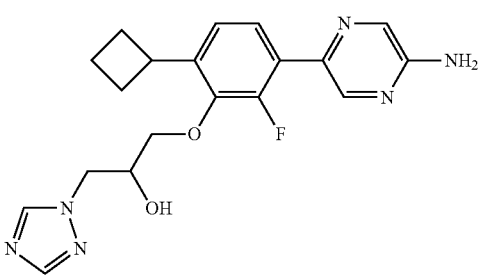 [SMILES: Nc1cnc(-c2ccc(C3CCC3)c(OCC(O)Cn3cncn3)c2F)cn1]

racemic 1-(3-(5-Aminopyrazin-2-yl)-6-cyclobutyl-2-fluorophenoxy)-3-(1H-1,2,4-triazol-1-yl)propan-2-ol The title compound was prepared using analogous conditions described in Example 51 using 1,2,4-triazole. MS (ESI): mass calcd. for $C_{19}H_{21}FN_6O_2$, 384.17; m/z found, 385.0 [M+H]$^+$. $^1$H NMR (500 MHz, CDCl$_3$) δ 8.36 (s, 1H), 8.16 (s, 1H), 8.00 (s, 1H), 7.91 (s, 1H), 7.50 (m, 1H), 7.09 (d, J=8.3, 1H), 4.63 (s, 2H), 4.48 (dd, J=16.7, 6.1, 1H), 4.35 (dd, J=14.0, 4.7, 2H), 3.93 (d, J=4.2, 2H), 3.70 (dd, J=17.6, 8.7, 1H), 2.28 (m, 2H), 2.09 (dd, J=14.4, 5.4, 2H), 2.03-1.95 (m, 1H), 1.82 (dd, J=19.2, 8.7, 1H).

Example 63

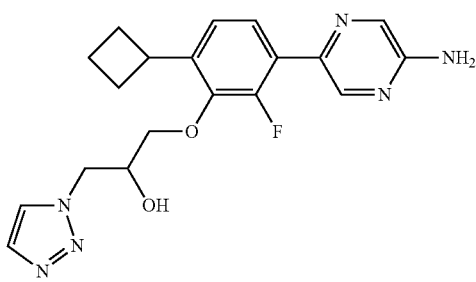

racemic 1-(3-(5-Aminopyrazin-2-yl)-6-cyclobutyl-2-fluorophenoxy)-3-(1H-1,2,3-triazol-1-yl)propan-2-ol The title compound was prepared using analogous conditions described in Example 51 using 1,2,3-triazole. MS (ESI): mass calcd. for $C_{19}H_{21}FN_6O_2$, 384.17; m/z found, 385.0 [M+H]$^+$. $^1$H NMR (400 MHz, CDCl$_3$) δ 8.38-8.32 (m, 1H), 8.01 (d, J=1.5, 1H), 7.71 (d, J=0.8, 1H), 7.68 (d, J=3.8, 1H), 7.51 (m, 1H), 7.09 (d, J=8.2, 1H), 4.75-4.60 (m, 3H), 4.53 (dd, J=14.1, 7.1, 1H), 4.39 (dd, J=13.1, 8.0, 1H), 3.98 (dd, J=9.8, 4.9, 1H), 3.89 (dd, J=9.9, 5.9, 1H), 3.71 (m, 1H), 3.38-3.13 (m, 1H), 2.27 (m, 2H), 2.14-2.05 (m, 2H), 2.03-1.94 (m, 1H), 1.81 (m, 1H).

Example 64

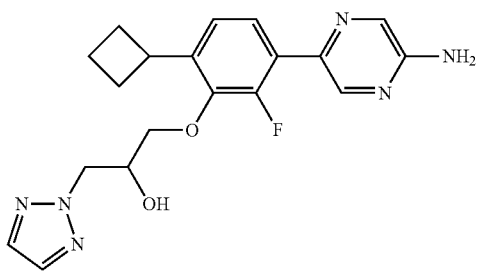 [SMILES: Nc1cnc(-c2ccc(C3CCC3)c(OCC(O)Cn3nccn3)c2F)cn1]

racemic 1-(3-(5-Aminopyrazin-2-yl)-6-cyclobutyl-2-fluorophenoxy)-3-(2H-1,2,3-triazol-2-yl)propan-2-ol The title compound was prepared using analogous conditions described in Example 51 using 1,2,3-triazole. MS (ESI): mass calcd. for $C_{19}H_{21}FN_6O_2$, 384.17; m/z found, 385.0 [M+H]$^+$. $^1$H NMR (400 MHz, CDCl$_3$) 8.39-8.35 (m, 1H), 8.01 (d, J=1.5, 1H), 7.60 (d, J=1.7, 2H), 7.52-7.46 (m, 1H), 7.08 (d, J=8.3, 1H), 4.76 (dd, J=13.9, 4.0, 1H), 4.67 (d, J=7.2, 1H), 4.64 (d, J=7.2, 2H), 4.49-4.42 (m, 1H), 4.03-3.92 (m, 2H), 3.75 (m, 1H), 3.53-3.35 (m, 1H), 2.32-2.22 (m, 2H), 2.12-2.04 (m, 2H), 1.98 (m, 1H), 1.85-1.75 (m, 1H).

Example 65

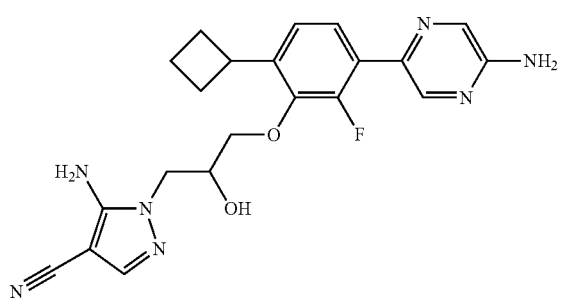 [SMILES: N#Cc1cnn(CC(O)COc2c(C3CCC3)ccc(-c3cnc(N)cn3)c2F)c1N]

racemic 5-Amino-1-(3-(3-(5-aminopyrazin-2-yl)-6-cyclobutyl-2-fluorophenoxy)-2-hydroxypropyl)-1H-pyrazole-4-carbonitrile The title compound was prepared using analogous conditions described in Example 51 using 3-amino-4-cyanopyrazole. MS (ESI): mass calcd. for $C_{21}H_{22}FN_7O_2$, 423.18; m/z found, 424.0 [M+H]$^+$. $^1$H NMR (400 MHz, DMSO-d$_6$) δ 8.24 (s, 1H), 7.95 (s, 1H), 7.59-7.34 (m, 2H), 7.17 (d, J=8.0, 1H), 6.61 (s, 2H), 6.44 (s, 1H), 5.44 (s, 1H), 4.22-4.11 (m, 1H), 4.07-3.96 (m, 2H), 3.92-3.86 (m, 2H), 3.84-3.76 (m, 1H), 2.29-2.20 (m, 2H), 2.08-1.93 (m, 3H), 1.82-1.73 (m, 1H).

Example 66

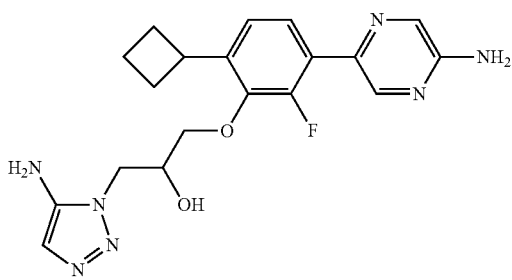 [SMILES: Nc1cnc(-c2ccc(C3CCC3)c(OCC(O)Cn3nncc3N)c2F)cn1]

racemic 1-(5-Amino-1H-1,2,3-triazol-1-yl)-3-(3-(5-aminopyrazin-2-yl)-6-cyclobutyl-2-fluorophenoxy) propan-2-ol Step A: 1H-1,2,3-Triazol-5-amine To a 25 mL round-bottomed flask were added a stir bar, 5-nitro-1H-1,2,3-triazole (300 mg, 2.63 mmol), Raney-Ni (30 mg), and MeOH (5 mL). The flask was subjected to 1 atm of H$_2$ and stirred at room temperature for approximately 3 hours. The mixture was then filtered, and the filtrate was concentrated to dryness to give 1H-1,2,3-triazol-5-amine (181 mg, yield: 82%).

Step B

The title compound was prepared using analogous conditions described in Example 51 using 1H-1,2,3-triazol-5-amine. MS (ESI): mass calcd. for $C_{19}H_{22}FN_7O_2$, 399.18; m/z found, 400.0 [M+H]$^+$. $^1$H NMR (400 MHz, DMSO-de) δ 8.25 (s, 1H), 7.98 (s, 1H), 7.53-7.42 (m, 1H), 7.18 (d, J=8.5, 1H), 6.86 (s, 1H), 6.63 (s, 2H), 5.35 (d, J=4.8, 1H), 4.95 (s, 2H), 4.33-4.16 (m, 3H), 3.89 (s, 2H), 3.85-3.79 (m, 1H), 2.32-2.21 (m, 2H), 2.12-1.92 (m, 3H), 1.82-1.73 (m, 1H).

Example 67

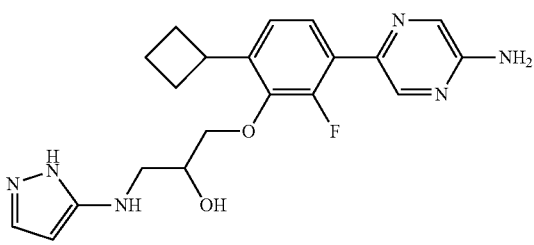 [SMILES: Nc1cnc(-c2ccc(C3CCC3)c(OCC(O)CNc3ccn[nH]3)c2F)cn1]

racemic 1-((1H-Pyrazol-5-yl)amino)-3-(3-(5-aminopyrazin-2-yl-6-cyclobutyl-2-fluorophenoxy)propan-2-ol A mixture of 5-(4-cyclobutyl-2-fluoro-3-(oxiran-2-ylmethoxy)phenyl)pyrazin-2-amine (200 mg, 0.63 mmol), 3-aminopyrazole (79 mg, 0.95 mmol), Yb(OTf)$_3$ (80 mg, 0.13 mmol) and DMF (1 mL) was stirred at 100° Celsius for approximately 24 hours. The mixture was concentrated to dryness and the residue purified by HPLC to give the title compound (15%, 37 mg). MS (ESI): mass calcd. for $C_{20}H_{23}FN_6O_2$, 398.19; m/z found, 399.0 [M+H]$^+$. $^1$H NMR (400 MHz, DMSO-d$_6$) δ 8.25 (s, 1H), 7.97 (d, J=1.4, 1H), 7.50-7.42 (m, 1H), 7.30 (d, J=1.9, 1H), 7.17 (d, J=8.3, 1H), 6.63 (s, 2H), 5.45 (d, J=2.1, 1H), 5.21 (s, 1H), 5.04 (s, 1H), 4.04-3.73 (m, 5H), 3.13-3.05 (m, 1H), 2.28-2.21 (m, 2H), 2.10-1.98 (m, 2H), 1.97-1.87 (m, 1H), 1.82-1.72 (m, 1H).

Example 68

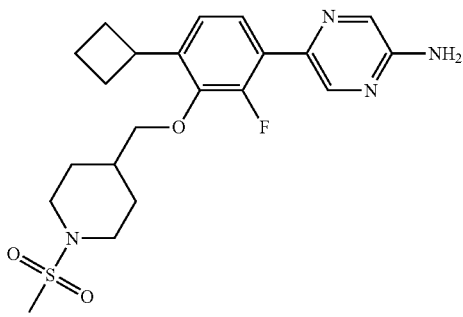 [SMILES: CS(=O)(=O)N1CCC(COc2c(C3CCC3)ccc(-c3cnc(N)cn3)c2F)CC1]

5-(4-Cyclobutyl-2-fluoro-3-{[1-(methylsulfonyl) piperidin-4-yl]methoxy}phenyl)pyrazin-2-amine Step A tert-Butyl 4-{[3-(5-aminopyrazin-2-yl)-6-cyclobutyl-2-fluorophenoxy]methyl}piperidine-1-carboxylate (50 mg, 0.11 mmol) was dissolved in formic acid (1 mL) and treated with 2 eq. of 6 N HCl (aq). The mixture was allowed to stir for 2 hours and then concentrated to give the bis-HCl salt. The crude product was triturated with acetonitrile and then purified by HPLC to give 5-(4-cyclobutyl-2-fluoro-3-(piperidin-4-ylmethoxy)phenyl)pyrazin-2-amine (46 mg, 98%).

Step B 5-(4-Cyclobutyl-2-fluoro-3-(piperidin-4-ylmethoxy)phenyl)pyrazin-2-amine was dissolved in pyridine (0.32 mL) and treated with a solution of methanesulfonyl chloride (10 mg, 0.11 mmol) in DCM (0.25 mL). The reaction was stirred at room temperature for 18 hours before concentrating to dryness. The crude product was purified by FCC to afford the title compound (6 mg, 10%). MS (ESI): mass calcd. for $C_{21}H_{27}FN_4O_3S$, 434.18; m/z found, 435.2 [M+H]$^+$. $^1$H NMR (400 MHz, CDCl$_3$) δ 8.38 (m, 1H), 8.20 (d, J=1.4, 1H), 7.60-7.53 (m, 1H), 7.16 (d, J=8.2, 1H), 3.89 (t, J=7.8, 3H), 3.84-3.72 (m, 1H), 2.81 (s, 3H), 2.75 (m, 2H), 2.40-2.28 (m, 2H), 2.23-1.84 (m, 8H), 1.62-1.48 (m, 2H).

Example 69

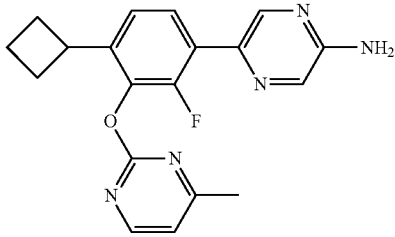 [SMILES: Cc1ccnc(Oc2c(C3CCC3)ccc(-c3cnc(N)cn3)c2F)n1]

5-{4-Cyclobutyl-2-fluoro-3-[(4-methylpyrimidin-2-yl)oxy]phenyl}pyrazin-2-amine

A suspension of 3-(5-aminopyrazin-2-yl)-6-cyclobutyl-2-fluorophenol (25 mg, 0.096 mmol), 2-chloro-4-methylpyrimidine (14 mg, 0.11 mmol), and $K_2CO_3$ (27 mg, 0.19 mmol) in DMSO (2 mL) was heated at 100° Celsius for 16 hours. The reaction was then cooled to room temperature, filtered, and the filtrate directly subjected to HPLC purification to give 5-{4-cyclobutyl-2-fluoro-3-[(4-methylpyrimidin-2-yl)oxy]phenyl}pyrazin-2-amine (15 mg, 45%). MS (ESI): mass calcd. for $C_{19}H_{18}FN_5O$, 351.15; m/z found, 352.1 $[M+H]^+$. $^1H$ NMR (400 MHz, $CDCl_3$) δ 8.37-8.33 (m, 1H), 8.26 (d, J=1.9, 2H), 7.81-7.75 (m, 1H), 7.26 (d, J=8.3, 1H), 7.00-6.97 (m, 1H), 3.75-3.63 (m, 1H), 2.52 (d, J=2.0, 3H), 2.27-2.09 (m, 4H), 2.04-1.92 (m, 1H), 1.87-1.76 (m, 1H).

Example 70

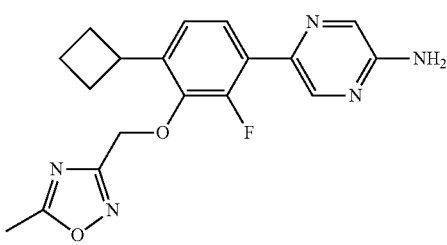 [SMILES: Cc1nc(COc2c(C3CCC3)ccc(-c3cnc(N)cn3)c2F)no1]

5-{4-Cyclobutyl-2-fluoro-3-[(5-methyl-1,2,4-oxadiazol-3-yl)methoxy]phenyl}pyrazin-2-amine The title compound was prepared using conditions similar to those described in Example 101 using acetonitrile with 10% DMF as the solvent and 3-(chloromethyl)-5-methyl-1,2,4-oxadiazole. MS (ESI): mass calcd. for $C_{18}H_{18}FN_5O_2$, 355.14; m/z found, 356.1 $[M+H]^+$. $^1H$ NMR (400 MHz, $CDCl_3$) 8.51-8.46 (m, 1H), 8.09 (d, J=1.4, 1H), 7.61 (m, 1H), 7.16 (d, J=8.2, 1H), 5.15 (s, 2H), 4.72 (s, 2H), 3.91-3.79 (m, 1H), 2.65 (s, 3H), 2.39-2.27 (m, 2H), 2.20-1.96 (m, 3H), 1.92-1.79 (m, 1H).

Example 71

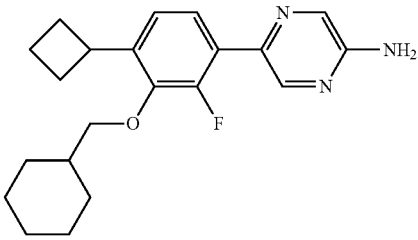 [SMILES: Nc1cnc(-c2ccc(C3CCC3)c(OCC3CCCCC3)c2F)cn1]

5-[4-Cyclobutyl-3-(cyclohexylmethoxy)-2-fluorophenyl]pyrazin-2-amine

The title compound was prepared using conditions similar to those described in Example 101 using acetonitrile with 10% DMF as the solvent and cyclohexylmethyl bromide. MS (ESI): mass calcd. for $C_{21}H_{26}FN_3O$, 355.21; m/z found, 356.1 $[M+H]^+$. $^1H$ NMR (500 MHz, $CDCl_3$) δ 8.46 (s, 1H), 8.08 (d, J=1.4, 1H), 7.54-7.48 (m, 1H), 7.14 (d, J=8.2, 1H), 4.66 (s, 2H), 3.88-3.77 (m, 3H), 2.35 (m, 2H), 2.21-1.99 (m, 3H), 1.96-1.75 (m, 6H), 1.74-1.68 (m, 1H), 1.39-1.05 (m, 5H).

Example 72

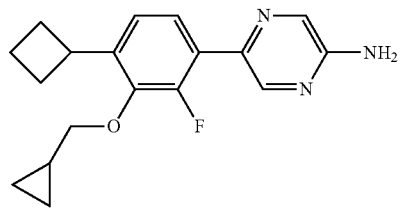

5-[4-Cyclobutyl-3-(cyclopropylmethoxy)-2-fluorophenyl]pyrazin-2-amine

The title compound was prepared using conditions similar to those described in Example 101 using acetonitrile with 10% DMF as the solvent and cyclopropylmethyl bromide. MS (ESI): mass calcd. for $C_{18}H_{20}FN_3O$, 313.16; m/z found, 314.1 $[M+H]^+$. $^1H$ NMR (400 MHz, $CDCl_3$) δ 8.49-8.44 (m, 1H), 8.08 (d, J=1.5, 1H), 7.56-7.49 (m, 1H), 7.15 (d, J=8.3, 1H), 4.65 (s, 2H), 3.95-3.83 (m, 3H), 2.42-2.32 (m, 2H), 2.23-1.98 (m, 3H), 1.93-1.81 (m, 1H), 1.34-1.23 (m, 1H), 0.65-0.58 (m, 2H), 0.36-0.29 (m, 2H).

Example 73

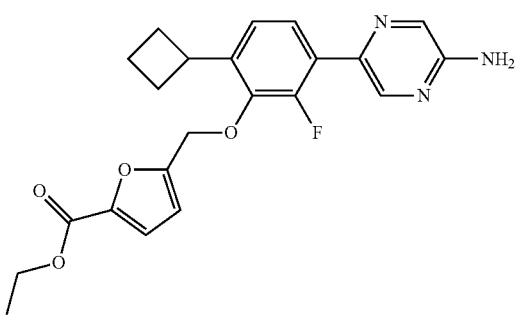 [SMILES: CCOC(=O)c1ccc(COc2c(C3CCC3)ccc(-c3cnc(N)cn3)c2F)o1]

Ethyl 5-{[3-(5-aminopyrazin-2-yl)-6-cyclobutyl-2-fluorophenoxy]methyl}furan-2-carboxylate The title compound was prepared using conditions similar to those described in Example 101 using acetonitrile with 10% DMF as the solvent and ethyl 5-(chloromethyl)-2-furancarboxylate. MS (ESI): mass calcd. for $C_{22}H_{22}FN_3O_4$, 411.16; m/z found, 412.1 [M+H]$^+$. $^1$H NMR (400 MHz, CDCl$_3$) 8.47 (s, 1H), 8.09 (d, J=1.4, 1H), 7.60-7.53 (m, 1H), 7.17-7.11 (m, 2H), 6.50 (d, J=3.4, 1H), 5.09 (s, 2H), 4.71 (s, 2H), 4.38 (q, J=7.1, 2H), 3.83-3.70 (m, 1H), 2.35-2.25 (m, 2H), 2.16-1.95 (m, 3H), 1.90-1.79 (m, 1H), 1.39 (t, J=7.1, 3H).

Example 74

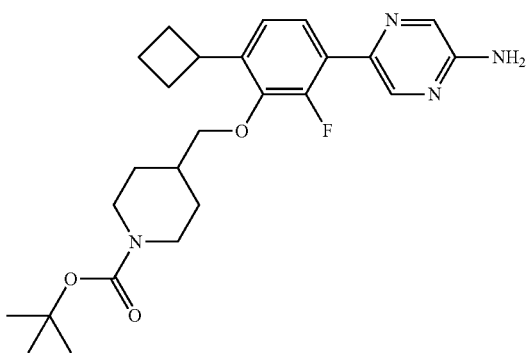 [SMILES: CC(C)(C)OC(=O)N1CCC(COc2c(C3CCC3)ccc(-c3cnc(N)cn3)c2F)CC1]

tert-Butyl 4-{[3-(5-aminopyrazin-2-yl)-6-cyclobutyl-2-fluorophenoxy]methyl}piperidine-1-carboxylate The title compound was prepared using conditions similar to those described in Example 101 using acetonitrile with 10% DMF as the solvent and tert-butyl 4-(bromomethyl)piperidine-1-carboxylate. MS (ESI): mass calcd. for $C_{25}H_{33}FN_4O_3$, 456.25; m/z found, 457.2 [M+H]$^+$. $^1$H NMR (400 MHz, CDCl$_3$) δ 8.45 (s, 1H), 8.09 (d, J=1.4, 1H), 7.59-7.46 (m, 1H), 7.15 (d, J=8.3, 1H), 4.65 (s, 2H), 4.31-4.10 (m, 2H), 3.92-3.73 (m, 3H), 2.92-2.63 (m, 2H), 2.42-2.27 (m, 2H), 2.24-1.93 (m, 4H), 1.94-1.80 (m, 3H), 1.47 (s, 9H), 1.44-1.21 (m, 2H).

Example 75

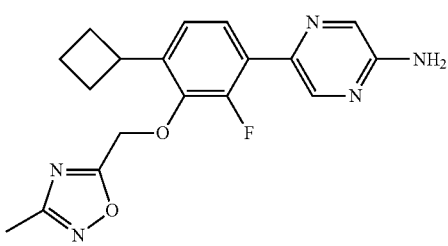 [SMILES: Cc1noc(COc2c(C3CCC3)ccc(-c3cnc(N)cn3)c2F)n1]

5-{4-Cyclobutyl-2-fluoro-3-[(3-methyl-1,2,4-oxadiazol-5-yl)methoxy]phenyl}pyrazin-2-amine The title compound was prepared using conditions similar to those described in Example 101 using acetonitrile with 10% DMF as the solvent and 5-(chloromethyl)-3-methyl-1,2,4-oxadiazole. MS (ESI): mass calcd. for $C_{18}H_{18}FN_5O_2$, 355.14; m/z found, 356.1 [M+H]$^+$. $^1$H NMR (400 MHz, CDCl$_3$) δ 8.47 (dd, J=2.4, 1.6, 1H), 8.09 (d, J=1.5, 1H), 7.66-7.58 (m, 1H), 7.17 (d, J=8.1, 1H), 5.26 (s, 2H), 4.67 (s, 2H), 3.89-3.77 (m, 1H), 2.46 (s, 3H), 2.39-2.29 (m, 2H), 2.21-1.98 (m, 3H), 1.92-1.81 (m, 1H).

Example 76

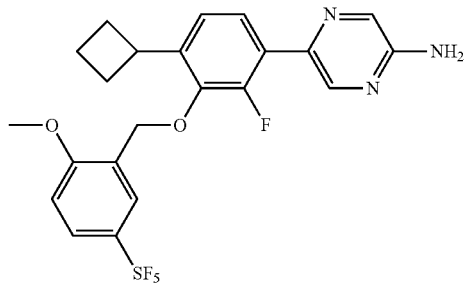

5-(4-Cyclobutyl-2-fluoro-3-{[2-methoxy-5-(pentafluoro-lambda-6-sulfanyl)benzyl]oxy}phenyl)pyrazin-2-amine The title compound was prepared using conditions similar to those described in Example 101 using acetonitrile with 10% DMF as the solvent and 2-methoxy-5-(pentafluorosulfur)benzyl bromide. MS (ESI): mass calcd. for $C_{22}H_{21}F_6N_3O_2S$, 505.13; m/z found, 506.1 [M+H]J. $^1$H NMR (400 MHz, CDCl$_3$) δ 8.50-8.46 (m, 1H), 8.10 (d, J=1.5, 1H), 8.03 (d, J=2.8, 1H), 7.72 (dd, J=9.0, 2.8, 1H), 7.61-7.54 (m, 1H), 7.16 (d, J=8.2, 1H), 6.90 (d, J=9.0, 1H), 5.11 (s, 2H), 4.65 (s, 2H), 3.88 (s, 3H), 3.85-3.73 (m, 1H), 2.33-2.23 (m, 2H), 2.20-2.08 (m, 2H), 2.06-1.91 (m, 2H), 1.91-1.78 (m, 1H).

Example 77

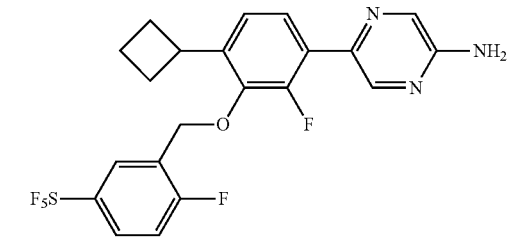

5-(4-Cyclobutyl-2-fluoro-3-{[2-fluoro-5-(pentafluoro-lambda~6~-sulfanyl)benzyl]oxy}phenyl)pyrazin-2-amine The title compound was prepared using conditions similar to those described in Example 101 using acetonitrile with 10% DMF as the solvent and 2-fluoro-5-(pentafluorosulfur)benzyl bromide. MS (ESI): mass calcd. for $C_{21}H_{18}F_7N_3OS$, 493.10 m/z found, 494.1 [M+H]$^+$. $^1$H NMR (400 MHz, CDCl$_3$) δ 8.49-8.46 (m, 1H), 8.13-8.08 (m, 2H), 7.76 (m, 1H), 7.63-7.57 (m, 1H), 7.21-7.14 (m, 2H), 5.17 (s, 2H), 4.69 (s, 2H), 3.82-3.72 (m, 1H), 2.33-2.24 (m, 2H), 2.21-2.09 (m, 2H), 2.08-1.95 (m, 1H), 1.90-1.80 (m, 1H).

Example 78

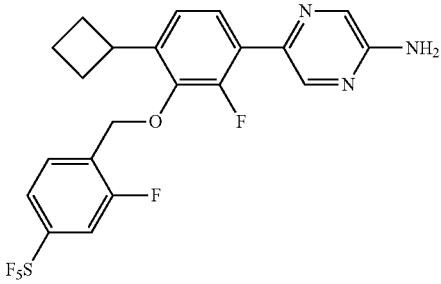

5-(4-Cyclobutyl-2-fluoro-3-{[2-fluoro-4-(pentafluoro-lambda~6~-sulfanyl)benzyl]oxy}phenyl)pyrazin-2-amine The title compound was prepared using conditions similar to those described in Example 101 using acetonitrile with 10% DMF as the solvent and 2-fluoro-4-(pentafluorosulfur)benzyl bromide. MS (ESI): mass calcd. for $C_{21}H_{18}F_7N_3OS$, 493.10; m/z found, 494.1 [M+H]$^+$. $^1$H NMR (400 MHz, CDCl$_3$) δ 8.50-8.45 (m, 1H), 8.10 (d, J=1.5, 1H), 7.79 (m, 1H), 7.66-7.58 (m, 2H), 7.53 (dd, J=9.9, 2.1, 1H), 7.18 (d, J=8.2, 1H), 5.15 (s, 2H), 4.67 (s, 2H), 3.78 (p, J=8.7, 1H), 2.34-2.25 (m, 2H), 2.21-2.10 (m, 2H), 2.09-1.96 (m, 2H), 1.91-1.81 (m, 1H).

Example 79

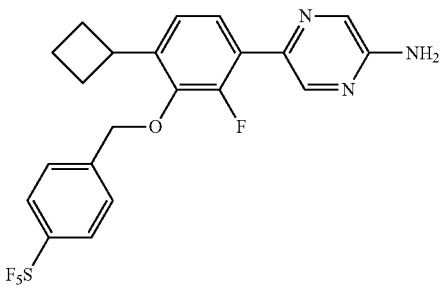

5-(4-Cyclobutyl-2-fluoro-3-{[4-(pentafluoro-lambda~6~-sulfanyl)benzyl]oxy}phenyl)pyrazin-2-amine The title compound was prepared using conditions similar to those described in Example 101 using acetonitrile with 10% DMF as the solvent and 4-(pentafluorosulfur)benzyl bromide. MS (ESI): mass calcd. for $C_{21}H_{19}F_6N_3OS$, 475.11 m/z found, 476.1 [M+H]$^+$. $^1$H NMR (400 MHz, CDCl$_3$) δ 8.49-8.46 (m, 1H), 8.10 (d, J=1.5, 1H), 7.80 (d, J=8.7, 2H), 7.62-7.55 (m, 3H), 7.18 (d, J=8.1, 1H), 5.10 (s, 2H), 4.65 (s, 2H), 3.78 (p, J=8.7, 1H), 2.34-2.25 (m, 2H), 2.22-2.09 (m, 2H), 2.09-1.95 (m, 1H), 1.91-1.81 (m, 1H).

Example 80

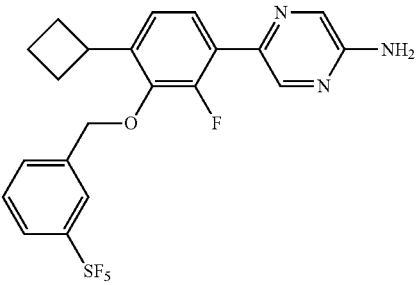

5-(4-Cyclobutyl-2-fluoro-3-{[3-(pentafluoro-lambda~6~-sulfanyl)benzyl]oxy}phenyl)pyrazin-2-amine The title compound was prepared using conditions similar to those described in Example 101 using acetonitrile with 10% DMF as the solvent and 3-(pentafluorosulfur)benzyl bromide. MS (ESI): mass calcd. for $C_{21}H_{19}F_6N_3OS$, 475.11; m/z found, 476.1 [M+H]$^+$. $^1$H NMR (400 MHz, CDCl$_3$) δ 8.48 (dd, J=2.2, 1.6, 1H), 8.10 (d, J=1.5, 1H), 7.91 (s, 1H), 7.74 (d, J=8.2, 1H), 7.59 (dd, J=15.1, 7.3, 2H), 7.50 (m, 1H), 7.17 (d, J=8.1, 1H), 5.12 (s, 2H), 4.67 (s, 2H), 3.82-3.71 (m, 1H), 2.33-2.24 (m, 2H), 2.21-2.08 (m, 2H), 2.08-1.95 (m, 1H), 1.91-1.80 (m, 1H).

Example 81

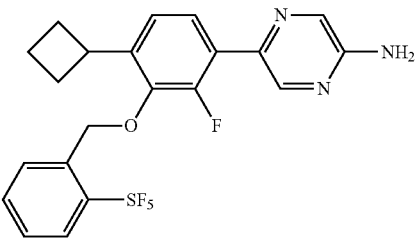

5-(4-Cyclobutyl-2-fluoro-3-{[2-(pentafluoro-lambda~6~-sulfanyl)benzyl]oxy}phenyl)pyrazin-2-amine The title compound was prepared using conditions similar to those described in Example 101 using acetonitrile with 10% DMF as the solvent and 2-(pentafluorosulfur)benzyl bromide. MS (ESI): mass calcd. for $C_{21}H_{19}F_6N_3OS$, 475.11; m/z found, 476.1 [M+H]$^+$. $^1$H NMR (400 MHz, CDCl$_3$) δ 8.49-8.46 (m, 1H), 8.10 (d, J=1.4, 1H), 7.91 (s, 1H), 7.74 (d, J=8.3, 1H), 7.64-7.56 (m, 2H), 7.50 (m, 1H), 7.17 (d, J=8.2, 1H), 5.12 (s, 2H), 4.66 (s, 2H), 3.76 (p, J=8.7, 1H), 2.33-2.24 (m, 2H), 2.20-2.08 (m, 2H), 2.07-1.94 (m, 1H), 1.91-1.79 (m, 1H).

Example 82

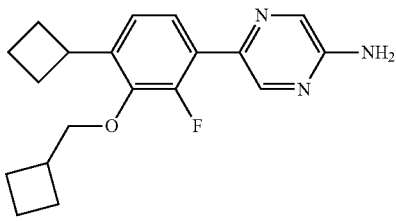 [SMILES: Nc1cnc(-c2ccc(C3CCC3)c(OCC3CCC3)c2F)cn1]

5-[4-Cyclobutyl-3-(cyclobutylmethoxy)-2-fluorophenyl]pyrazin-2-amine

The title compound was prepared using conditions similar to those described in Example 101 using acetonitrile with 10% DMF as the solvent and cyclobutylmethyl bromide. MS (ESI): mass calcd. for $C_{19}H_{22}FN_3O$, 327.17; m/z found, 328.1 [M+H]$^+$. $^1$H NMR (400 MHz, CDCl$_3$) δ 8.47 (dd, J=2.2, 1.6, 1H), 8.08 (d, J=1.5, 1H), 7.51 (dd, J=13.7, 6.1, 1H), 7.14 (d, J=8.0, 1H), 4.70 (s, 2H), 4.00 (dd, J=6.8, 0.9, 2H), 3.88-3.78 (m, 1H), 2.86-2.74 (m, 1H), 2.39-2.30 (m, 2H), 2.22-1.81 (m, 11H).

Example 83

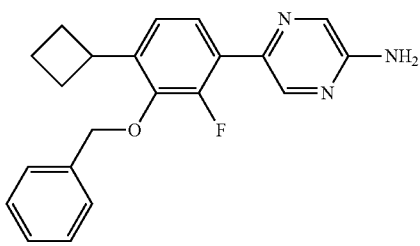 [SMILES: Nc1cnc(-c2ccc(C3CCC3)c(OCc3ccccc3)c2F)cn1]

5-[3-(Benzyloxy)-4-cyclobutyl-2-fluorophenyl]-pyrazin-2-amine

5-[3-(Benzyloxy)-4-chloro-2-fluorophenyl]pyrazin-2-amine (59 mg, 0.18 mmol), 2-dicyclohexylphosphino-2',6'-dimethoxy-1,1'-biphenyl (6 mg, 0.01 mmol) and palladium acetate (2 mg, 0.009 mmol) were added to a vial. The vial was capped, evacuated and back-filled with N$_2$. Cyclobutylzinc bromide (0.5 M solution in THF; 0.54 mL, 0.27 mmol) was added and the mixture heated at 65° Celsius for 18 hours. The reaction mixture was concentrated to dryness and the residue subjected to FCC. Further purification by HPLC and prep TLC gave the title compound (6 mg, 10%). MS (ESI): mass calcd. for $C_{21}H_{20}FN_3O$, 349.16; m/z found, 350.4 [M+H]$^+$. $^1$H NMR (400 MHz, CDCl$_3$) δ 8.52-8.47 (m, 1H), 8.10 (d, J=1.5, 1H), 7.59-7.53 (m, 1H), 7.51-7.46 (m, 2H), 7.44-7.32 (m, 3H), 7.16 (d, J=8.1, 1H), 5.05 (s, 2H), 4.65 (s, 2H), 3.79 (p, J=8.7, 1H), 2.34-2.23 (m, 2H), 2.19-2.07 (m, 2H), 2.06-1.93 (m, 1H), 1.90-1.78 (m, 1H).

Example 84

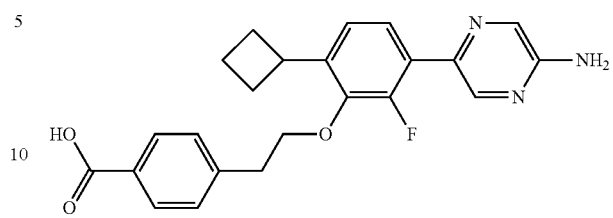

4-{2-[3-(5-Aminopyrazin-2-yl)-6-cyclobutyl-2-fluorophenoxy]ethyl}benzoic acid

To a 5 mL vial containing a stir bar, 3-(5-aminopyrazin-2-yl)-6-cyclobutyl-2-fluorophenol (50 mg, 0.19 mmol) and 4-(2-bromoethyl)benzoic acid (49 mg, 0.21 mmol) were added KOt-Bu (37 mg, 0.42 mmol) and DMSO (0.5 mL). The resultant mixture was stirred at rt for 15 hours. The mixture was passed through a syringe filter and the filtrate subjected to HPLC purification to afford the title compound (10 mg, 13%). MS (ESI): mass calcd. for $C_{23}H_{22}FN_3O_3$, 407.16; m/z found, 408.1 [M+H]$^+$. $^1$H NMR (400 MHz, CDCl$_3$) δ 8.32 (s, 1H), 8.18 (s, 1H), 8.03 (d, J=8.2, 2H), 7.51 (m, 1H), 7.41 (d, J=8.2, 2H), 7.13 (d, J=8.0, 1H), 4.26 (t, J=6.6, 2H), 3.61-3.48 (m, 1H), 3.18 (t, J=6.7, 2H), 2.23-2.00 (m, 4H), 1.98-1.74 (m, 2H).

Example 85

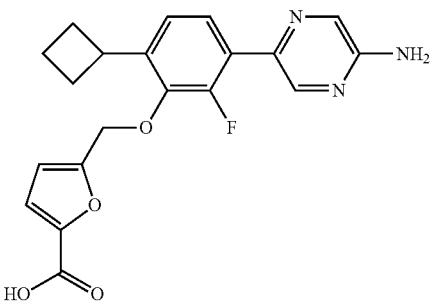 [SMILES: Nc1cnc(-c2ccc(C3CCC3)c(OCc3ccc(C(=O)O)o3)c2F)cn1]

5-{[3-(5-Aminopyrazin-2-yl)-6-cyclobutyl-2-fluorophenoxy]methyl}furan-2-carboxylic acid Ethyl 5-{[3-(5-aminopyrazin-2-yl)-6-cyclobutyl-2-fluorophenoxy]methyl}furan-2-carboxylate (48 mg, 0.12 mmol) was dissolved in THF (2 mL) and treated with aqueous LiOH (1.0 N, 0.5 mL). The mixture was stirred at rt for 15 hours. The reaction mixture was purified using HPLC to afford the title compound. MS (ESI): mass calcd. for $C_{20}H_{18}FN_3O_4$, 383.13; m/z found, 384.1 [M+H]$^+$. $^1$H NMR (400 MHz, CDCl$_3$) δ 8.22-8.15 (m, 2H), 7.50-7.43 (m, 1H), 7.08 (m, 2H), 6.43 (d, J=3.4, 1H), 5.00 (s, 2H), 2.27-2.16 (m, 2H), 2.07-1.89 (m, 3H), 1.80-1.70 (m, 1H).

Example 86

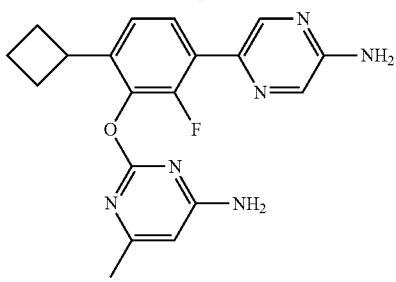 [SMILES: Cc1cc(N)nc(Oc2c(C3CCC3)ccc(-c3cnc(N)cn3)c2F)n1]

2-[3-(5-Aminopyrazin-2-yl)-6-cyclobutyl-2-fluoro-phenoxy]-6-methylpyrimidin-4-amine The title compound was prepared in a manner similar to that described in Example 69 using 3-(5-aminopyrazin-2-yl)-6-cyclobutyl-2-fluorophenol and 2-chloro-6-methylpyrimidin-4-amine. MS (ESI): mass calcd. for $C_{19}H_{19}FN_6O$, 366.16; m/z found, 367.2 [M+H]$^+$. $^1$H NMR (400 MHz, CD$_3$OD) δ 8.29-8.24 (m, 1H), 8.08 (d, J=1.5, 1H), 7.81 (m, 1H), 7.31 (d, J=8.2, 1H), 6.32 (d, J=0.9, 1H), 3.73-3.63 (m, 1H), 2.45 (s, 3H), 2.32-2.18 (m, 4H), 2.12-2.02 (m, 1H), 1.94-1.82 (m, 1H).

Example 87

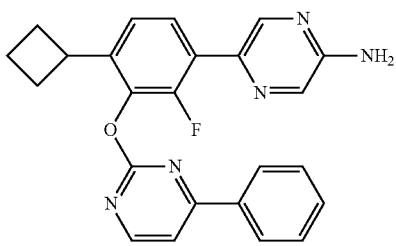

5-{4-Cyclobutyl-2-fluoro-3-[(4-phenylpyrimidin-2-yl)oxy]phenyl}pyrazin-2-amine

The title compound was prepared in a manner similar to that described in Example 69 using 3-(5-aminopyrazin-2-yl)-6-cyclobutyl-2-fluorophenol and 2-chloro-4-phenylpyrimidine. MS (ESI): mass calcd. for $C_{24}H_{20}FN_5O$, 413.17; m/z found, 414.2 [M+H]$^+$. $^1$H NMR (400 MHz, CDCl$_3$) δ 8.57 (d, J=5.0, 1H), 8.45 (s, 1H), 8.16 (s, 1H), 8.06-8.01 (m, 2H), 7.89 (t, J=7.9, 1H), 7.54-7.45 (m, 4H), 7.29 (d, J=8.3, 1H), 3.82-3.70 (m, 1H), 2.28-2.13 (m, 4H), 2.03-1.92 (m, 1H), 1.86-1.75 (m, 1H).

Example 88

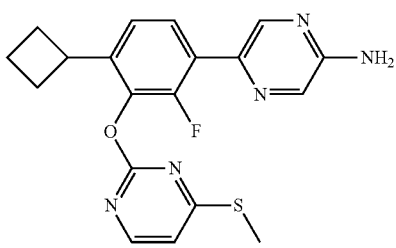

5-(4-Cyclobutyl-2-fluoro-3-{[4-(methylsulfanyl)pyrimidin-2-yl]oxy}phenyl)pyrazin-2-amine The title compound was prepared in a manner similar to that described in Example 69 using 3-(5-aminopyrazin-2-yl)-6-cyclobutyl-2-fluorophenol and 2-chloro-4-(methylthio)pyrimidine. MS (ESI): mass calcd. for $C_{19}H_{18}FN_5OS$, 383.12; m/z found, 384.2 [M+H]$^+$. $^1$H NMR (400 MHz, CD$_3$OD) δ 8.24-8.18 (m, 3H), 7.78 (m, 1H), 7.30 (d, J=8.2, 1H), 7.09 (d, J=5.5, 1H), 3.73-3.58 (m, 1H), 2.32 (s, 3H), 2.24-2.13 (m, 4H), 2.04-1.92 (m, 1H), 1.87-1.77 (m, 1H).

Example 89

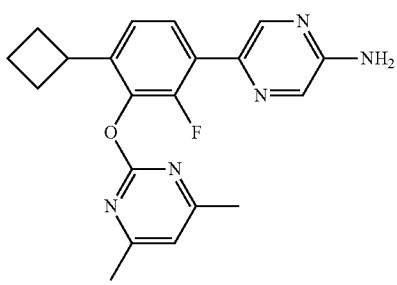 [SMILES: Cc1cc(C)nc(Oc2c(C3CCC3)ccc(-c3cnc(N)cn3)c2F)n1]

5-{4-Cyclobutyl-3-[(4,6-dimethylpyrimidin-2-yl)oxy]-2-fluorophenyl}pyrazin-2-amine The title compound was prepared in a manner similar to that described in Example 69 using 3-(5-aminopyrazin-2-yl)-6-cyclobutyl-2-fluorophenol and 2-chloro-4,6-dimethylpyrimidine. MS (ESI): mass calcd. for $C_{20}H_{20}FN_5O$, 365.16; m/z found, 366.1 [M+H]$^+$. $^1$H NMR (400 MHz, CDCl$_3$) δ 8.35 (d, J=1.2, 1H), 8.21 (s, 1H), 7.86-7.78 (m, 1H), 7.25 (d, J=8.4, 1H), 6.80 (s, 1H), 3.77-3.65 (m, 1H), 2.41 (s, 6H), 2.27-2.08 (m, 4H), 2.02-1.91 (m, 1H), 1.85-1.75 (m, 1H).

Example 90

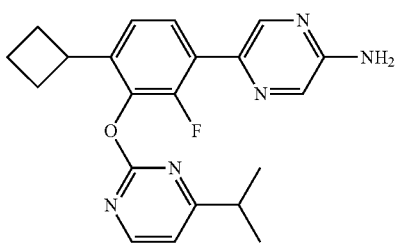

5-(4-Cyclobutyl-2-fluoro-3-{[4-(1-methylethyl)pyrimidin-2-yl]oxy}phenyl)pyrazin-2-amine The title compound was prepared in a manner similar to that described in Example 69 using 3-(5-aminopyrazin-2-yl)-6-cyclobutyl-2-fluorophenol and 2-chloro-4-isopropylpyrimidine. MS (ESI): mass calcd. for $C_{21}H_{22}FN_5O$, 379.18; m/z found, 380.1 [M+H]$^+$. $^1$H NMR (400 MHz, CDCl$_3$) δ 8.56-8.51 (m, 1H), 8.31 (d, J=1.4, 1H), 8.26 (s, 1H), 7.82 (m, 1H), 7.41-7.38 (m, 1H), 7.29 (d, J=8.4, 1H), 3.79-3.66 (m, 1H), 3.41-3.38 (m, 1H), 2.26-2.10 (m, 4H), 2.07-1.94 (m, 1H), 1.89-1.79 (m, 1H), 1.52 (s, 6H).

Example 91

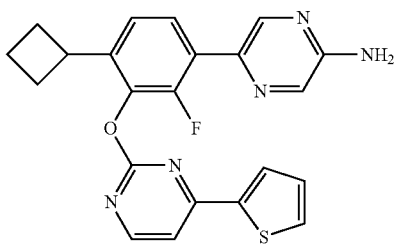 [SMILES: Nc1cnc(-c2ccc(C3CCC3)c(Oc3nccc(-c4cccs4)n3)c2F)cn1]

5-{4-Cyclobutyl-2-fluoro-3-[(4-thiophen-2-ylpyrimidin-2-yl)oxy]phenyl}pyrazin-2-amine The title compound was prepared in a manner similar to that described in Example 69 using 3-(5-aminopyrazin-2-yl)-6-cyclobutyl-2-fluorophenol and 2-chloro-4-(thiophen-2-yl)pyrimidine. MS (ESI): mass calcd. for $C_{22}H_{18}FN_5OS$, 419.12; m/z found, 420.2 [M+H]$^+$. $^1$H NMR (400 MHz, CDCl$_3$) δ 8.47 (d, J=5.3, 1H), 8.42-8.37 (m, 1H), 8.08 (d, J=1.4, 1H), 7.81-7.71 (m, 2H), 7.54-7.51 (m, 1H), 7.34 (d, J=3.2, 1H), 7.26 (d, J=8.3, 1H), 7.16-7.12 (m, 1H), 3.80-3.66 (m, 1H), 2.29-2.10 (m, 4H), 2.03-1.90 (m, 1H), 1.85-1.75 (m, 1H).

Example 92

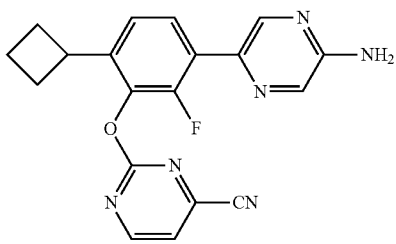 [SMILES: N#Cc1ccnc(Oc2c(C3CCC3)ccc(-c3cnc(N)cn3)c2F)n1]

2-[3-(5-Aminopyrazin-2-yl)-6-cyclobutyl-2-fluorophenoxy]pyrimidine-4-carbonitrile The title compound was prepared in a manner similar to that described in Example 69 using 3-(5-aminopyrazin-2-yl)-6-cyclobutyl-2-fluorophenol and 2-chloropyrimidine-4-carbonitrile. $^1$H NMR (400 MHz, CDCl$_3$) δ 8.76 (d, J=4.9, 5H), 8.71 (d, J=1.5, 5H), 8.47 (d, J=6.0, 4H), 7.97 (s, 4H), 7.93-7.82 (m, 11H), 3.74-3.61 (m, 7H), 2.25-2.10 (m, 23H), 2.03-1.91 (m, 7H), 1.81 (d, J=8.1, 6H).

Example 93

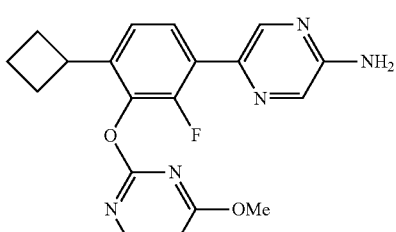

5-{4-Cyclobutyl-2-fluoro-3-[(4-methoxypyrimidin-2-yl)oxy]phenyl}pyrazin-2-amine

The title compound was prepared in a manner similar to that described in Example 69 using 3-(5-aminopyrazin-2-yl)-6-cyclobutyl-2-fluorophenol and 2-chloro-4-methoxypyrimidine. MS (ESI): mass calcd. for $C_{19}H_{18}FN_5O_2$, 367.14; m/z found, 368.1 [M+H]$^+$. $^1$H NMR (400 MHz, CDCl$_3$) δ 8.49-8.45 (m, 1H), 8.18 (d, J=5.7, 1H), 8.08 (d, J=1.5, 1H), 7.82-7.74 (m, 1H), 7.22 (d, J=8.3, 1H), 6.47 (d, J=5.7, 1H), 3.93 (s, 3H), 3.76-3.66 (m, 1H), 2.26-2.12 (m, 4H), 2.03-1.91 (m, 1H), 1.86-1.77 (m, 1H).

Example 94

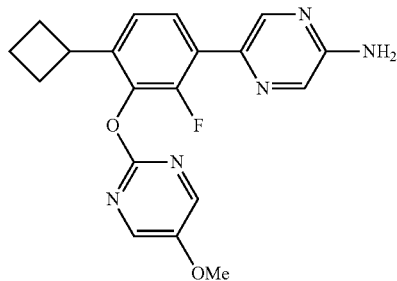 [SMILES: COc1cnc(Oc2c(C3CCC3)ccc(-c3cnc(N)cn3)c2F)nc1]

5-{4-Cyclobutyl-2-fluoro-3-[(5-methoxypyrimidin-2-yl)oxy]phenyl}pyrazin-2-amine

The title compound was prepared in a manner similar to that described in Example 69 using 3-(5-aminopyrazin-2-yl)-6-cyclobutyl-2-fluorophenol and 2-chloro-5-methoxypyrimidine. MS (ESI): mass calcd. for $C_{19}H_{18}FN_5O_2$, 367.14; m/z found, 368.1 [M+H]$^+$. $^1$H NMR (400 MHz, CDCl$_3$) δ 8.29-8.20 (m, 4H), 7.80-7.73 (m, 1H), 7.25 (d, J=8.2, 1H), 3.90 (s, 3H), 3.75-3.63 (m, 1H), 2.27-2.09 (m, 4H), 2.03-1.93 (m, 1H), 1.85-1.76 (m, 1H).

Example 95

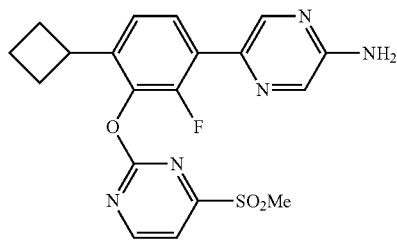

5-(4-Cyclobutyl-2-fluoro-3-{[4-(methylsulfonyl)pyrimidin-2-yl]oxy}phenyl)pyrazin-2-amine The title compound was prepared in a manner similar to that described in Example 69 using 3-(5-aminopyrazin-2-yl)-6-cyclobutyl-2-fluorophenol and 2-chloro-4-(methylsulfonyl)pyrimidine. MS (ESI): mass calcd. for $C_{19}H_{18}FN_5O_3S$, 415.11; m/z found, 416.1 [M+H]$^+$. $^1$H NMR (500 MHz, CDCl$_3$) δ 8.87 (d, J=4.8, 1H), 8.44 (s, 1H), 8.09 (d, J=1.4, 1H), 7.86-7.81 (m, 1H), 7.72 (d, J=4.8, 1H), 7.24 (s, 1H), 4.70 (s, 2H), 3.73-3.63 (m, 1H), 3.20 (s, 3H), 2.27-2.08 (m, 4H), 2.03-1.93 (m, 1H), 1.86-1.78 (m, 1H).

Example 96

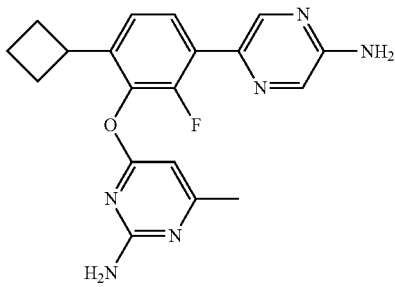 [SMILES: Cc1cc(Oc2c(C3CCC3)ccc(-c3cnc(N)cn3)c2F)nc(N)n1]

4-[3-(5-Aminopyrazin-2-yl)-6-cyclobutyl-2-fluorophenoxy]-6-methylpyrimidin-2-amine A suspension of 3-(5-aminopyrazin-2-yl)-6-cyclobutyl-2-fluorophenol (50 mg, 0.19 mmol), 4-chloro-6-methylpyrimidin-2-amine (30 mg, 0.20 mmol), $K_2CO_3$ (53 mg, 0.39 mmol), and 18-crown-6 (3 mg, 0.01 mmol) in DMSO (2 mL) was heated for 16 hours at 140° Celsius. The reaction was then cooled to room temperature, filtered, and the filtrate directly subjected to HPLC purification to give 4-[3-(5-aminopyrazin-2-yl)-6-cyclobutyl-2-fluorophenoxy]-6-methylpyrimidin-2-amine (12 mg, 16%). MS (ESI): mass calcd. for $C_{19}H_{19}FN_6O$, 366.16; m/z found, 367.3 [M+H]$^+$. $^1$H NMR (400 MHz, CD$_3$OD) δ 8.27-8.22 (m, 1H), 8.11 (d, J=1.5, 1H), 7.78 (m, 1H), 7.29 (d, J=8.3, 1H), 6.67 (d, J=0.8, 1H), 3.68-3.55 (m, 1H), 2.51 (d, J=0.7, 3H), 2.31-2.13 (m, 4H), 2.11-1.98 (m, 1H), 1.91-1.81 (m, 1H).

Example 97

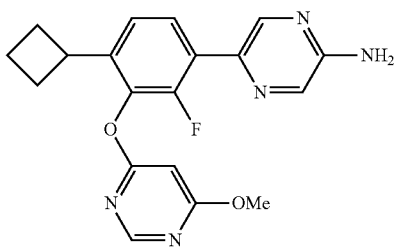 [SMILES: COc1cc(Oc2c(C3CCC3)ccc(-c3cnc(N)cn3)c2F)ncn1]

5-{4-Cyclobutyl-2-fluoro-3-[(6-methoxypyrimidin-4-yl)oxy]phenyl}pyrazin-2-amine

The title compound was prepared in a manner similar to that described in Example 96 using 3-(5-aminopyrazin-2-yl)-6-cyclobutyl-2-fluorophenol and 4-chloro-6-methoxypyrimidine. MS (ESI): mass calcd. for $C_{19}H_{18}FN_5O_2$, 367.14; m/z found, 368.1 [M+H]$^+$. $^1$H NMR (400 MHz, CDCl$_3$) δ 8.47-8.46 (m, 1H), 8.43-8.42 (m, 1H), 8.09-8.08 (m, 1H), 7.82-7.78 (m, 1H), 7.23-7.21 (m, 1H), 6.26-6.25 (m, 1H), 4.67 (s, 2H), 4.00 (s, 3H), 3.64-3.57 (m, 1H), 2.25-2.11 (m, 4H), 2.01-1.92 (m, 1H), 1.84-1.78 (m, 1H).

Example 98

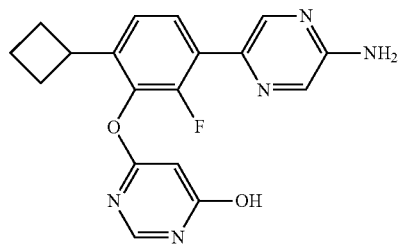 [SMILES: Nc1cnc(-c2ccc(C3CCC3)c(Oc3cc(O)ncn3)c2F)cn1]

6-[3-(5-Aminopyrazin-2-yl-6-cyclobutyl-2-fluorophenoxy]pyrimidin-4-ol

Title compound was obtained as a side product from the reaction described in Example 96 using 3-(5-aminopyrazin-2-yl)-6-cyclobutyl-2-fluorophenol and 4-chloro-6-methoxypyrimidine. MS (ESI): mass calcd. for $C_{18}H_{18}FN_5O_2$, 353.13; m/z found, 354.1 [M+H]$^+$. $^1$H NMR (400 MHz, CDCl$_3$) δ 8.32-8.30 (m, 1H), 8.15-8.13 (m, 1H), 8.00-7.98 (m, 1H), 7.78-7.73 (m, 1H), 7.54-7.52 (m, 1H), 7.28-7.24 (m, 1H), 5.73 (s, 1H), 3.67-3.61 (m, 1H), 2.34-2.25 (m, 2H), 2.24-2.14 (m, 2H), 2.09-1.99 (m, 1H), 1.91-1.82 (s, 1H).

Example 99

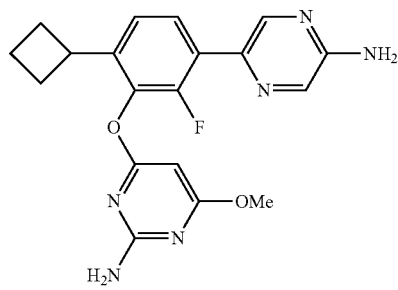 [SMILES: COc1cc(Oc2c(C3CCC3)ccc(-c3cnc(N)cn3)c2F)nc(N)n1]

4-[3-(5-Aminopyrazin-2-yl)-6-cyclobutyl-2-fluorophenoxy]-6-methoxypyrimidin-2-amine The title compound was prepared in a manner similar to that described in Example 96 using 3-(5-aminopyrazin-2-yl)-6-cyclobutyl-2-fluorophenol and 4-chloro-6-methoxypyrimidin-2-amine. MS (ESI): mass calcd. for $C_{19}H_{19}FN_6O_2$, 382.15; m/z found, 383.1 [M+H]$^+$. $^1$H NMR (400 MHz, CD$_3$OD) δ 8.26-8.21 (m, 2H), 7.81-7.74 (m, 1H), 7.31-7.26 (m, 1H), 5.67 (s, 1H), 3.93 (s, 3H), 3.67-3.57 (m, 1H), 2.30-2.13 (m, 4H), 2.08-1.97 (m, 1H), 1.89-1.80 (m, 1H).

Example 100

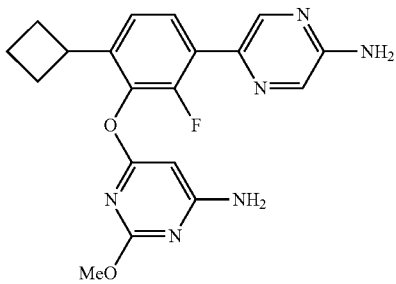 [SMILES: COc1nc(N)cc(Oc2c(C3CCC3)ccc(-c3cnc(N)cn3)c2F)n1]

6-[3-(5-Aminopyrazin-2-yl)-6-cyclobutyl-2-fluorophenoxy]-2-methoxypyrimidin-4-amine The title compound was prepared in a manner similar to that described in Example 96 using 3-(5-aminopyrazin-2-yl)-6-cyclobutyl-2-fluorophenol and 6-chloro-2-methoxypyrimidin-4-amine. MS (ESI): mass calcd. for $C_{19}H_{19}FN_6O_2$, 382.15; m/z found, 383.1 [M+H]$^+$. $^1$H NMR (400 MHz, CD$_3$OD) δ 8.27-8.18 (m, 2H), 7.82 (CDCl$_3$, 1H), 7.33 (d, J=8.3, 1H), 5.69 (d, J=8.6, 1H), 3.86 (d, J=8.8, 3H), 3.71-3.59 (m, 1H), 2.32-2.15 (m, 4H), 2.10-2.00 (m, 1H), 1.87 (t, J=9.0, 1H).

Example 101

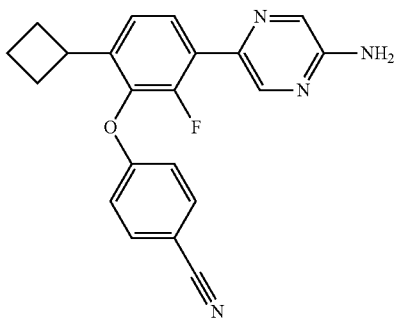 [SMILES: N#Cc1ccc(Oc2c(C3CCC3)ccc(-c3cnc(N)cn3)c2F)cc1]

4-[3-(5-Aminopyrazin-2-yl)-6-cyclobutyl-2-fluorophenoxy]benzonitrile

To a 5 mL vial containing a stir bar, 3-(5-aminopyrazin-2-yl)-6-cyclobutyl-2-fluorophenol (50 mg, 0.19 mmol) and 4-fluorobenzonitrile (26 mg, 0.21 mmol) were added Cs$_2$CO$_3$ (96 mg, 0.29 mmol) and 0.55 mL DMSO. The resultant mixture was stirred at 80° Celsius for approximately 15 hours. The mixture was cooled to room temperature and then passed through a syringe filter. The filtrate was subjected to FCC to give the title compound (36 mg, 52%). MS (ESI): mass calcd. for $C_{21}H_{17}FN_4O$, 360.14; m/z found, 361.1 [M+H]$^+$. $^1$H NMR (400 MHz, CDCl$_3$) δ 8.46-8.42 (m, 1H), 8.11-8.08 (d, J=1.5, 1H), 7.85-7.78 (m, 1H), 7.63-7.56 (m, 2H), 7.29-7.23 (m, 1H), 6.97-6.90 (m, 2H), 4.77-4.66 (s, 2H), 3.63-3.51 (m, 1H), 2.26-2.07 (m, 4H), 2.03-1.89 (m, 1H), 1.87-1.76 (m, 1H).

Example 102

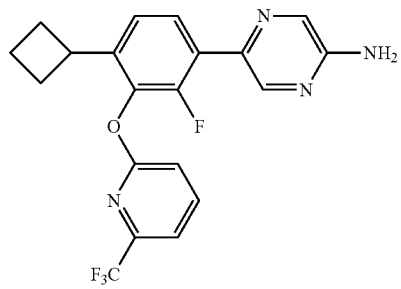

5-(4-Cyclobutyl-2-fluor-3-{[6-(trifluoromethyl)pyridin-2-yl]oxy}phenyl)pyrazin-2-amine The title compound was prepared using conditions similar to those described in Example 101 using 2-fluoro-6-(trifluoromethyl)pyridine. MS (ESI): mass calcd. for $C_{20}H_{16}F_4N_4O$, 404.13; m/z found, 405.1 [M+H]$^+$. $^1$H NMR (400 MHz, CDCl$_3$) 8.45 (dd, J=2.4, 1.6, 1H), 8.09 (d, J=1.5, 1H), 7.84 (dd, J=11.7, 4.0, 1H), 7.81-7.75 (m, 1H), 7.37 (d, J=7.3, 1H), 7.23 (d, J=8.1, 1H), 7.12 (d, J=8.4, 1H), 4.65 (s, 2H), 3.64 (p, J=8.8, 1H), 2.23-2.07 (m, 4H), 2.00-1.87 (m, 1H), 1.85-1.74 (m, 1H).

Example 103

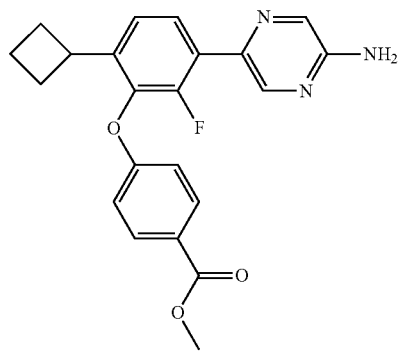 [SMILES: COC(=O)c1ccc(Oc2c(C3CCC3)ccc(-c3cnc(N)cn3)c2F)cc1]

Methyl 4-[3-(5-aminopyrazin-2-yl)-6-cyclobutyl-2-fluorophenoxy]benzoate

The title compound was prepared using conditions similar to those described in Example 101 using methyl 4-fluorobenzoate. MS (ESI): mass calcd. for $C_{22}H_{20}FN_3O_3$, 393.15; m/z found, 394.1 [M+H]$^+$. $^1$H NMR (400 MHz, CDCl$_3$) δ 8.46 (d, J=1.2, 1H), 8.19 (d, J=1.0, 1H), 8.03-7.96 (m, 2H), 7.87 (m, 1H), 7.30 (d, J=8.4, 1H), 6.88 (d, J=8.8, 2H), 3.90 (s, 3H), 3.68-3.57 (m, 1H), 2.26-2.06 (m, 4H), 2.02-1.88 (m, 1H), 1.86-1.75 (m, 1H)

Example 104

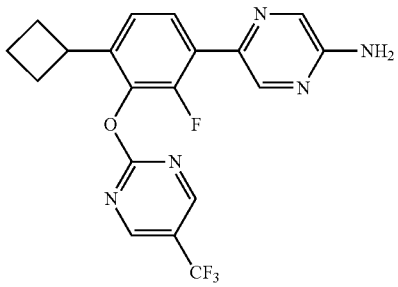

5-(4-Cyclobutyl-2-fluoro-3-{[5-(trifluoromethyl)pyrimidin-2-yl]oxy}phenyl)pyrazin-2-amine The title compound was prepared using conditions similar to those described in Example 101 using 2-chloro-5-(trifluoromethyl)-pyrimidine. MS (ESI): mass calcd. for $C_{19}H_{15}F_4N_5O$, 405.12; m/z found, 406.1 [M+H]$^+$. $^1$H NMR (400 MHz, CDCl$_3$) δ 8.81 (d, J=0.6, 2H), 8.48-8.43 (m, 1H), 8.09 (d, J=1.5, 1H), 7.88-7.79 (m, 1H), 7.25 (d, J=8.3, 1H), 4.76 (s, 2H), 3.67 (p, J=8.9, 1H), 2.27-2.08 (m, 4H), 2.05-1.90 (m, 1H), 1.88-1.76 (m, 1H).

Example 105

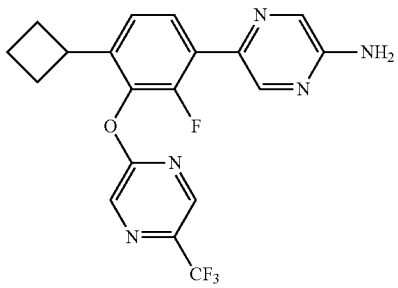 [SMILES: Nc1cnc(-c2ccc(C3CCC3)c(Oc3cnc(C(F)(F)F)cn3)c2F)cn1]

5-(4-Cyclobutyl-2-fluoro-3-{[5-(trifluoromethyl)pyrazin-2-yl]oxy}phenyl)pyrazin-2-amine The title compound was prepared using conditions similar to those described in Example 101 using 2-chloro-5-(trifluoromethyl)pyrazine. MS (ESI): mass calcd. for $C_{19}H_{15}F_4N_5O$, 405.12; m/z found, 406.1 [M+H]$^+$. $^1$H NMR (400 MHz, CDCl$_3$) δ 8.60 (d, J=0.9, 1H), 8.47-8.43 (m, 1H), 8.41 (d, J=0.4, 1H), 8.09 (d, J=1.5, 1H), 7.84 (m, 1H), 7.25 (d, J=8.7, 1H), 4.71 (s, 2H), 3.60 (p, J=8.8, 1H), 2.26-2.08 (m, 4H), 2.05-1.91 (m, 1H), 1.89-1.75 (m, 1H).

Example 106

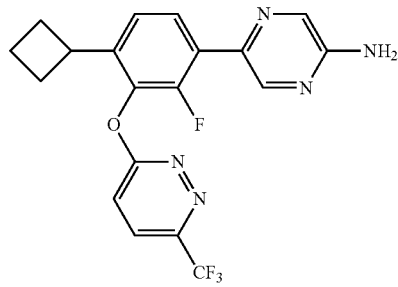

5-(4-Cyclobutyl-2-fluoro-3-{[6-(trifluoromethyl)pyridazin-3-yl]oxy}phenyl)pyrazin-2-amine The title compound was prepared using conditions similar to those described in Example 101 using 3-chloro-6-trifluoromethyl-pyridazine. MS (ESI): mass calcd. for $C_{19}H_{15}F_4N_5O$, 405.12; m/z found, 406.1 [M+H]$^+$. $^1$H NMR (400 MHz, CDCl$_3$) δ 8.46-8.43 (m, 1H), 8.08 (d, J=1.4, 1H), 7.88-7.79 (m, 2H), 7.43 (d, J=9.1, 1H), 7.23 (d, J=8.3, 1H), 4.67 (s, 2H), 3.68-3.56 (m, 1H), 2.24-2.14 (m, 4H), 2.03-1.89 (m, 1H), 1.87-1.77 (m, 1H).

Example 107

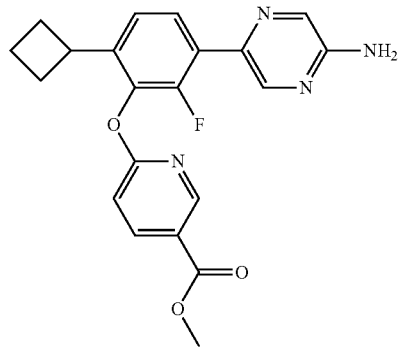 [SMILES: COC(=O)c1ccc(Oc2c(C3CCC3)ccc(-c3cnc(N)cn3)c2F)nc1]

Methyl 6-[3-(5-aminopyrazin-2-yl)-6-cyclobutyl-2-fluorophenoxy]pyridine-3-carboxylate The title compound was prepared using conditions similar to those described in Example 101 using acetonitrile with 10% DMF as the solvent and 6-fluoronicotinic acid methyl ester. MS (ESI): mass calcd. for $C_{21}H_{19}FN_4O_3$, 394.14; m/z found, 395.1 [M+H]. $^1$H NMR (400 MHz, CDCl$_3$) δ 8.77 (dd, J=2.3, 0.5, 1H), 8.46 (s, 1H), 8.31 (dd, J=8.6, 2.3, 1H), 8.08 (d, J=1.3, 1H), 7.83-7.76 (m, 1H), 7.23 (d, J=8.3, 1H), 7.04 (dd, J=8.6, 0.6, 1H), 4.68 (s, 2H), 3.91 (s, 3H), 3.67-3.55 (m, 1H), 2.23-2.07 (m, 4H), 2.00-1.87 (m, 1H), 1.85-1.75 (m, 1H).

Example 108

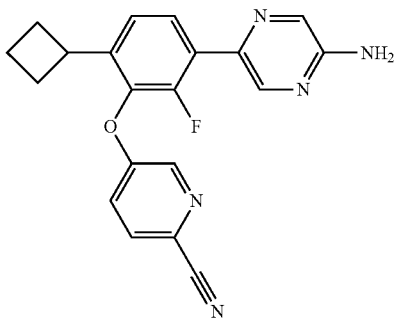

5-[3-(5-Aminopyrazin-2-yl)-6-cyclobutyl-2-fluoro-phenoxy]pyridine-2-carbonitrile The title compound was prepared using conditions similar to those described in Example 101 using acetonitrile with 10% DMF as the solvent and 2-cyano-5-fluoropyridine. MS (ESI): mass calcd. for $C_{20}H_{16}FN_5O$, 361.13; m/z found, 362.0 [M+H]$^+$. $^1$H NMR (400 MHz, CDCl$_3$) δ 8.47 (d, J=2.8, 1H), 8.45-8.41 (m, 1H), 8.10 (d, J=1.5, 1H), 7.88-7.81 (m, 1H), 7.63 (d, J=8.6, 1H), 7.28 (d, J=7.7, 1H), 7.19-7.12 (m, 1H), 4.79 (s, 2H), 3.58 (p, J=8.8, 1H), 2.26-2.07 (m, 4H), 2.05-1.91 (m, 1H), 1.89-1.78 (m, 1H).

Example 109

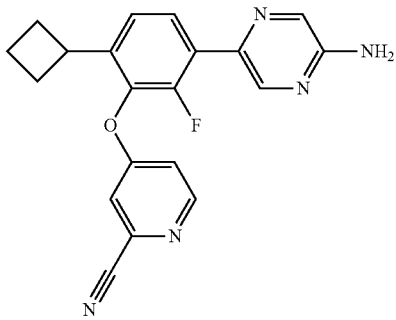 [SMILES: N#Cc1cc(Oc2c(C3CCC3)ccc(-c3cnc(N)cn3)c2F)ccn1]

4-[3-(5-Aminopyrazin-2-yl)-6-cyclobutyl-2-fluoro-phenoxy]pyridine-2-carbonitrile The title compound was prepared using conditions similar to those described in Example 101 using 4-chloro-pyridine-2-carbonitrile. MS (ESI): mass calcd. for $C_{20}H_{16}FN_5O$, 361.13; m/z found, 362.1 [M+H]$^+$. $^1$H NMR (400 MHz, CDCl$_3$) δ 8.54 (d, J=5.7, 1H), 8.47-8.43 (m, 1H), 8.10 (d, J=1.2, 1H), 7.88 (m, 1H), 7.32-7.25 (m, 1H), 7.22 (d, J=2.3, 1H), 6.99 (dd, J=5.7, 2.4, 1H), 4.74 (s, 2H), 3.54 (p, J=8.9, 1H), 2.25-2.08 (m, 4H), 2.05-1.92 (m, 1H), 1.89-1.79 (m, 1H).

Example 110

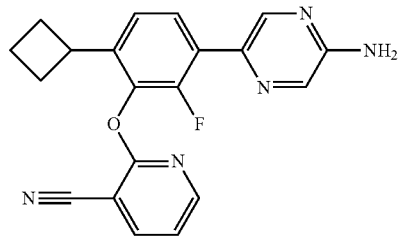 [SMILES: N#Cc1cccnc1Oc1c(C2CCC2)ccc(-c2cnc(N)cn2)c1F]

2-[3-(5-Aminopyrazin-2-yl)-6-cyclobutyl-2-fluoro-phenoxy]pyridine-3-carbonitrile The title compound was prepared using conditions similar to those described in Example 101 using 3-cyano-2-fluoro-pyridine. MS (ESI): mass calcd. for $C_{20}H_{16}FN_5O$, 361.13; m/z found, 362.1 [M+H]$^+$. $^1$H NMR (400 MHz, CDCl$_3$) δ 8.48-8.44 (m, 1H), 8.29 (dd, J=5.0, 1.9, 1H), 8.09 (d, J=1.5, 1H), 8.03 (dd, J=7.6, 1.9, 1H), 7.86-7.78 (m, 1H), 7.23 (d, J=8.3, 1H), 7.11 (dd, J=7.6, 5.0, 1H), 4.66 (s, 2H), 3.65 (p, J=8.9, 1H), 2.29-2.11 (m, 4H), 2.06-1.92 (m, 1H), 1.87-1.76 (m, 1H).

Example 111

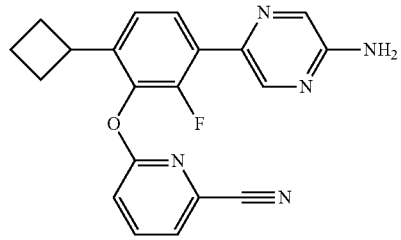

6-[3-(5-Aminopyrazin-2-yl)-6-cyclobutyl-2-fluoro-phenoxy]pyridine-2-carbonitrile The title compound was prepared using conditions similar to those described in Example 101 using 2-cyano-6-fluoro-pyridine. MS (ESI): mass calcd. for $C_{20}H_{16}FN_5O$, 361.13; m/z found, 362.1 [M+H]$^+$. $^1$H NMR (400 MHz, CDCl$_3$) δ 8.46 (dd, J=2.2, 1.6, 1H), 8.10 (d, J=1.5, 1H), 7.86-7.76 (m, 2H), 7.42 (dd, J=7.3, 0.7, 1H), 7.25-7.19 (m, 2H), 4.69 (s, 2H), 3.59 (p, J=8.9, 1H), 2.22-2.09 (m, 4H), 1.99-1.87 (m, 1H), 1.86-1.76 (m, 1H).

Example 112

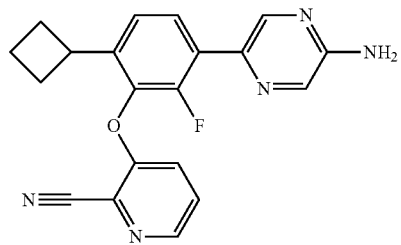 [SMILES: N#Cc1ncccc1Oc1c(C2CCC2)ccc(-c2cnc(N)cn2)c1F]

3-[3-(5-Aminopyrazin-2-yl)-6-cyclobutyl-2-fluorophenoxy]pyridine-2-carbonitrile

The title compound was prepared using conditions similar to those described in Example 101 using 2-cyano-3-fluoropyridine. MS (ESI): mass calcd. for $C_{20}H_{16}FN_5O$, 361.13; m/z found, 362.1 [M+H]$^+$. $^1$H NMR (400 MHz, CDCl$_3$) δ 8.44 (dd, J=2.2, 1.6, 1H), 8.39 (dd, J=4.5, 1.2, 1H), 8.10 (d, J=1.5, 1H), 7.89-7.80 (m, 1H), 7.39 (dd, J=8.7, 4.5, 1H), 7.28 (d, J=7.2, 1H), 7.02 (m, 1H), 4.78 (s, 2H), 3.69-3.58 (m, 1H), 2.31-2.09 (m, 4H), 2.07-1.94 (m, 1H), 1.89-1.78 (m, 1H).

Example 113

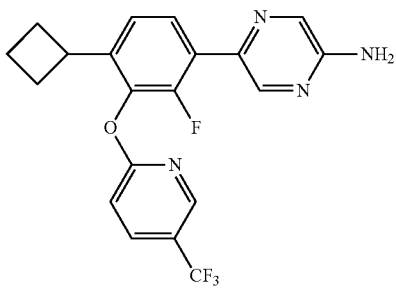

5-(4-Cyclobutyl-2-fluoro-3-{[5-(trifluoromethyl)pyridin-2-yl]oxy}phenyl)pyrazin-2-amine The title compound was prepared using conditions similar to those described in Example 101 using acetonitrile with 10% DMF as the solvent and 2-fluoro-5-(trifluoromethyl)pyridine. MS (ESI): mass calcd. for $C_{20}H_{16}F_4N_4O$, 404.13; m/z found, 405.1 [M+H]$^+$. $^1$H NMR (400 MHz, CDCl$_3$) δ 8.46 (s, 1H), 8.40 (s, 1H), 8.08 (d, J=1.4, 1H), 7.93 (dd, J=8.7, 2.3, 1H), 7.80 (m, 1H), 7.23 (d, J=8.3, 1H), 7.12 (d, J=8.7, 1H), 4.70 (s, 2H), 3.61 (p, J=8.9, 1H), 2.25-2.08 (m, 4H), 2.00-1.89 (m, 1H), 1.86-1.75 (m, 1H).

Example 114

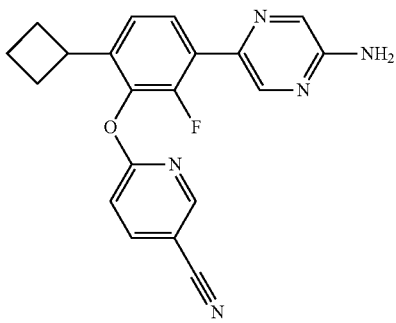 [SMILES: N#Cc1ccc(Oc2c(C3CCC3)ccc(-c3cnc(N)cn3)c2F)nc1]

6-[3-(5-Aminopyrazin-2-yl)-6-cyclobutyl-2-fluorophenoxy]pyridine-3-carbonitrile

The title compound was prepared using conditions similar to those described in Example 101 using acetonitrile with 10% DMF as the solvent and using 5-cyano-2-fluoropyridine. MS (ESI): mass calcd. for $C_{20}H_{16}FN_5O$, 361.13; m/z found, 362.1 [M+H]$^+$. $^1$H NMR (400 MHz, CDCl$_3$) δ 8.47-8.41 (m, 2H), 8.09 (d, J=1.5, 1H), 7.96 (dd, J=8.6, 2.3, 1H), 7.84-7.78 (m, 1H), 7.23 (d, J=8.3, 1H), 7.13 (dd, J=8.6, 0.6, 1H), 4.70 (s, 2H), 3.58 (p, J=8.9, 1H), 2.23-2.08 (m, 4H), 2.02-1.89 (m, 1H), 1.86-1.75 (m, 1H).

Example 115

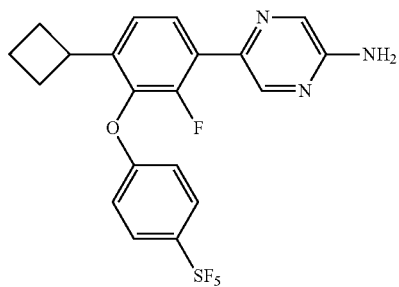

5-{4-Cyclobutyl-2-fluoro-3-[4-(pentafluorolambda~6~-sulfanyl)phenoxy]phenyl}pyrazin-2-amine The title compound was prepared using conditions similar to those described in Example 101 heating at 130° Celsius via microwave irradiation for 1 hour and using 4-fluorophenylsulfur pentafluoride. MS (ESI): mass calcd. for $C_{20}H_{17}F_6N_3OS$, 461.10; m/z found, 462.0 [M+H]$^+$. $^1$H NMR (400 MHz, CDCl$_3$) δ 8.42 (d, J=1.2, 1H), 8.21 (s, 1H), 7.87 (m, 1H), 7.73-7.65 (m, 2H), 7.34-7.27 (m, 1H), 6.89 (d, J=8.9, 2H), 3.90 (s, 2H), 3.68-3.56 (m, 1H), 2.30-2.19 (m, 2H), 2.19-2.09 (m, 2H), 2.06-1.92 (m, 1H), 1.89-1.75 (m, 1H).

Example 116

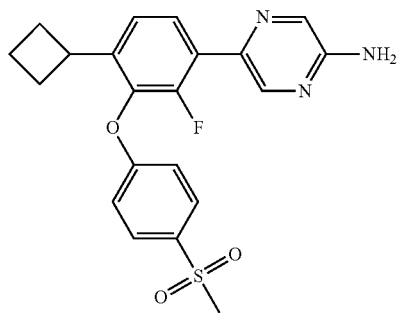 [SMILES: CS(=O)(=O)c1ccc(Oc2c(C3CCC3)ccc(-c3cnc(N)cn3)c2F)cc1]

5-{4-Cyclobutyl-2-fluoro-3-[4-(methylsulfonyl)phenoxy]phenyl}pyrazin-2-amine

The title compound was prepared using conditions similar to those described in Example 101 heating at 130° Celsius via microwave irradiation for 1 hour and using 4-fluorophenyl methyl sulfone. MS (ESI): mass calcd. for $C_{21}H_{20}FN_3O_3S$, 413.12; m/z found, 414.1 [M+H]$^+$. $^1$H NMR (400 MHz, CDCl$_3$) δ 8.47 (d, J=1.2, 1H), 8.18 (s, 1H), 7.94-7.84 (m, 3H), 7.31 (d, J=8.4, 1H), 7.00 (d, J=8.8, 2H), 3.61 (p, J=8.9, 1H), 3.08 (s, 3H), 2.29-2.07 (m, 4H), 2.05-1.91 (m, 1H), 1.88-1.77 (m, 1H).

Example 117

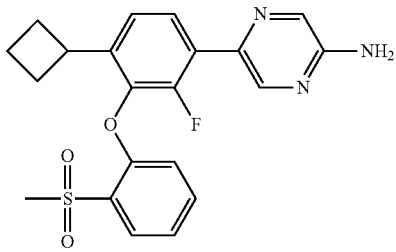

5-{4-Cyclobutyl-2-fluoro-3-[2-(methylsulfonyl)phenoxy]phenyl}pyrazin-2-amine

The title compound was prepared using conditions similar to those described in Example 101 heating at 120° Celsius via microwave irradiation for 1 hour and using 2-fluorophenylmethylsulfone. MS (ESI): mass calcd. for $C_{21}H_{20}FN_3O_3S$, 413.12; m/z found, 414.1 [M+H]$^+$. $^1$H NMR (400 MHz, CDCl$_3$) δ 8.44-8.41 (m, 1H), 8.11-8.06 (m, 2H), 7.87-7.80 (m, 1H), 7.46 (m, 1H), 7.33 (d, J=8.3, 1H), 7.18 (m, 1H), 6.64 (d, J=8.4, 1H), 4.74 (s, 2H), 3.73 (p, J=8.7, 1H), 3.38 (s, 3H), 2.45-2.33 (m, 1H), 2.29-2.16 (m, 1H), 2.12-1.90 (m, 3H), 1.86-1.75 (m, 1H).

Example 118

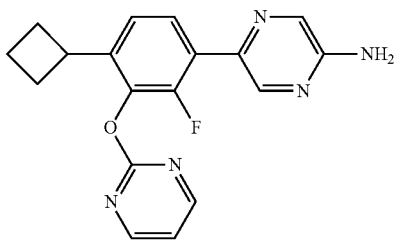

5-[4-Cyclobutyl-2-fluoro-3-(pyrimidin-2-yloxy)phenyl]pyrazin-2-amine

The title compound was prepared using conditions similar to those described in Example 101 heating at 120° Celsius via microwave irradiation for 1 hour and using 2-bromopyrimidine. MS (ESI): mass calcd. for $C_{18}H_{16}FN_5O$, 337.13 m/z found, 338.1 [M+H]$^+$. $^1$H NMR (400 MHz, CDCl$_3$) δ 8.57 (d, J=4.8, 2H), 8.49-8.45 (m, 1H), 8.09 (d, J=1.5, 1H), 7.83-7.77 (m, 1H), 7.24 (d, J=8.2, 1H), 7.83-7.78 (m, 1H), 4.66 (s, 2H), 3.70 (p, J=8.8, 1H), 2.27-2.08 (m, 4H), 2.03-1.89 (m, 1H), 1.85-1.75 (m, 1H).

Example 119

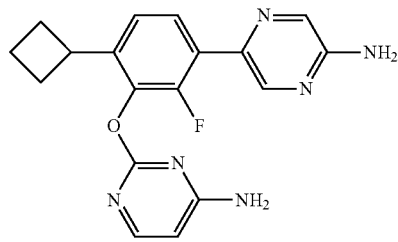

2-[3-(5-Aminopyrazin-2-yl)-6-cyclobutyl-2-fluorophenoxy]pyrimidin-4-amine

Method 1:
The title compound was prepared using conditions similar to those described in Example 101 heating at 120° Celsius via microwave irradiation for 2 hours and using 4-amino-2-chloropyrimidine.

Method 2:
A mixture of 3-(5-aminopyrazin-2-yl)-6-cyclobutyl-2-fluorophenol (17.0 g, 65.6 mmol), K$_2$CO$_3$ (13.6 g, 98.4 mmol), 2-chloropyrimidin-4-amine (8.9 g, 69 mmol), 18-crown-6 (0.87 g, 3.3 mmol), and DMA (131 mL) was stirred at 120° Celsius for 15 hours. Water (306 mL) was added, and the reaction mixture cooled to room temperature. Solid precipitate was collected by vacuum filtration and dried in a vacuum oven at 70° Celsius to give the crude product (23.1 g, 100%). The solid was recrystallized from EtOH and treated successively with activated charcoal and silica-supported thiol to remove residual Pd and afford the title compound (13.0 g, 56%). MS (ESI): mass calcd. for $C_{18}H_{17}FN_6O$, 352.14; m/z found, 353.2 [M+H]$^+$. $^1$H NMR (500 MHz, DMSO-d$_6$) δ 8.25 (s, 1H), 8.01 (d, J=1.5, 1H), 7.83 (d, J=5.8, 1H), 7.66 (m 1H), 7.23 (d, J=8.3, 1H), 7.06 (s, 2H), 6.67 (s, 2H), 6.17 (d, J=5.8, 1H), 3.60-3.47 (m, 1H), 2.19-2.01 (m, 4H), 1.98-1.85 (m, 1H), 1.80-1.68 (m, 1H).

Example 120

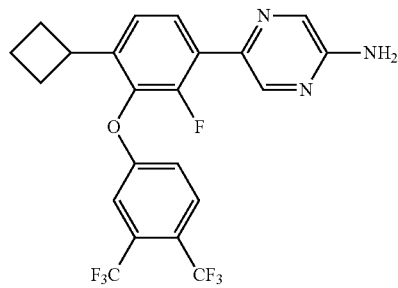

5-{3-[3,4-Bis(trifluoromethyl)phenoxy]-4-cyclobutyl-2-fluorophenyl}pyrazin-2-amine The title compound was prepared using conditions similar to those described in Example 101 heating at 120° Celsius via microwave irradiation 1 hour and using 3,4-bis-(trifluoromethyl)fluorobenzene. MS (ESI): mass calcd. for C$_{22}$H$_{16}$F$_7$N$_3$O, 471.12; m/z found, 472.1 [M+H]$^+$. $^1$H NMR (400 MHz, CDCl$_3$) δ 8.45 (dd, J=2.2, 1.6, 1H), 8.09 (d, J=1.5, 1H), 7.89-7.82 (m, 1H), 7.74 (d, J=8.8, 1H), 7.42 (d, J=2.5, 1H), 7.29 (d, J=8.3, 1H), 7.00 (dd, J=8.8, 2.1, 1H), 4.76 (s, 2H), 3.59 (p, J=8.8, 1H), 2.27-2.07 (m, 4H), 2.05-1.91 (m, 1H), 1.88-1.76 (m, 1H).

Example 121

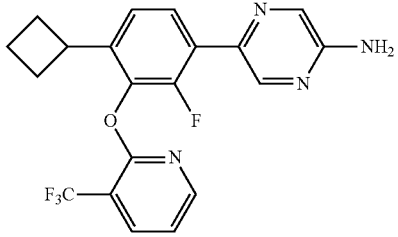

5-(4-Cyclobutyl-2-fluoro-3-{[3-(trifluoromethyl)pyridin-2-yl]oxy}phenyl)pyrazin-2-amine The title compound was prepared using conditions similar to those described in Example 101 heating at 120° Celsius via microwave irradiation for 1 hour and using 2-fluoro-3-(trifluoromethyl)pyridine. MS (ESI): mass calcd. for C$_{20}$H$_{16}$F$_4$N$_4$O, 404.13; m/z found, 405.1 [M+H]$^+$. $^1$H NMR (500 MHz, CDCl$_3$) δ 8.46 (s, 1H), 8.24 (d, J=3.7, 1H), 8.08 (s, 1H), 8.01 (d, J=7.7, 1H), 7.80 (m, 1H), 7.23 (d, J=8.4, 1H), 7.13-7.06 (m, 1H), 4.62 (s, 2H), 3.71-3.60 (m, 1H), 2.28-2.05 (m, 4H), 2.01-1.89 (m, 1H), 1.84-1.74 (m, 1H).

Example 122

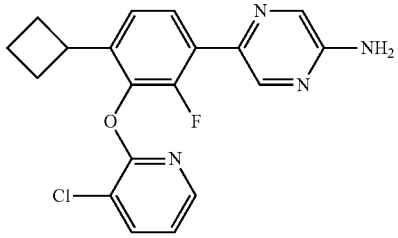 [SMILES: Nc1cnc(-c2ccc(C3CCC3)c(Oc3ncccc3Cl)c2F)cn1]

5-({3-[(3-Chloropyridin-2-yl)oxy]-4-cyclobutyl-2-fluorophenyl}pyrazin-2-amine

The title compound was prepared using conditions similar to those described in Example 101 heating at 120° Celsius via microwave irradiation for 1 hour and using 3-chloro-2-fluoropyridine. MS (ESI): mass calcd. for C$_{19}$H$_{16}$ClFN$_4$O, 370.10; m/z found, 371.1 [M+H]$^+$. $^1$H NMR (600 MHz, DMSO-d$_6$) δ 8.23 (s, 1H), 8.00 (d, J=1.5, 1H), 7.82 (d, J=5.8, 1H), 7.63 (m, 1H), 7.22 (d, J=8.3, 1H), 7.04 (s, 2H), 6.65 (s, 2H), 6.17 (d, J=5.8, 1H), 2.14-2.01 (m, 4H), 1.94-1.84 (m, 1H), 1.76-1.69 (m, 1H).

Example 123

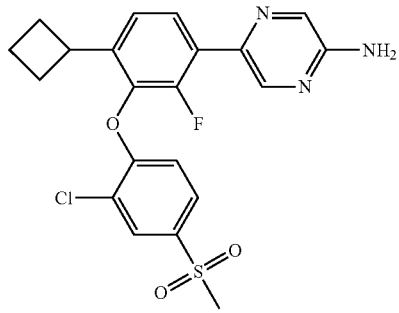

5-{3-[2-Chloro-4-(methylsulfonyl)phenoxy]-4-cyclobutyl-2-fluorophenyl}pyrazin-2-amine The title compound was prepared using conditions similar to those described in Example 101 heating at 80° Celsius via microwave irradiation for 2 hours and using 2-chloro-1-fluoro-4-methylsulfonylbenzene. MS (ESI): mass calcd. for C$_{21}$H$_{19}$ClFN$_3$O$_3$S, 447.08; m/z found, 448.1 [M+H]$^+$. $^1$H NMR (400 MHz, DMSO-d$_6$) δ 8.30-8.26 (m, 1H), 8.13 (d, J=2.3, 1H), 8.01 (d, J=1.5, 1H), 7.85-7.74 (m, 2H), 7.38 (d, J=8.3, 1H), 6.87 (dd, J=8.7, 1.1, 1H), 6.72 (s, 2H), 3.24 (s, 3H), 2.17-2.07 (m, 4H), 1.96-1.84 (m, 1H), 1.81-1.69 (m, 1H).

Example 124

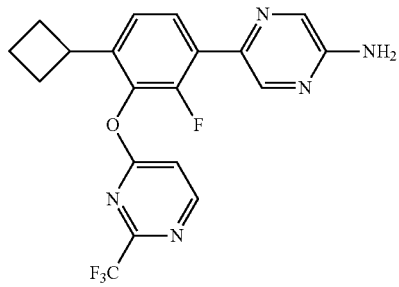

5-(4-Cyclobutyl-2-fluoro-3-{[2-(trifluoromethyl)pyrimidin-4-yl]oxy}phenyl)pyrazin-2-amine The title compound was prepared using conditions similar to those described in Example 101 heating at 80° Celsius via microwave irradiation for 1 hour and using 4-chloro-2-(trifluoromethyl)pyrimidine. MS (ESI): mass calcd. for C$_{19}$H$_{15}$F$_4$N$_5$O, 405.12; m/z found, 406.1 [M+H]$^+$. $^1$H NMR (400 MHz, CDCl$_3$) δ 8.75 (d, J=5.7, 1H), 8.46-8.42 (m, 1H), 8.09 (d, J=1.4, 1H), 7.84 (m, 1H), 7.24 (d, J=8.3, 1H), 7.12 (d, J=5.7, 1H), 4.74 (s, 2H), 3.64-3.52 (m, 1H), 2.24-2.08 (m, 4H), 2.05-1.90 (m, 1H), 1.87-1.77 (m, 1H).

Example 125

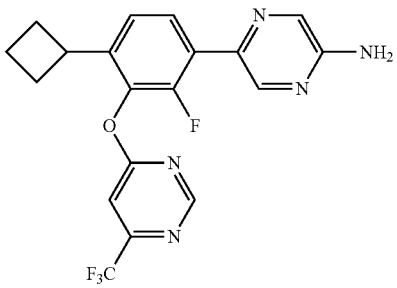

5-(4-Cyclobutyl-2-fluoro-3-{[6-(trifluoromethyl)pyrimidin-4-yl]oxy}phenyl)pyrazin-2-amine The title compound was prepared using conditions similar to those described in Example 101 heating at 80° Celsius via microwave irradiation for 1 hour and using 4-chloro-6-trifluoromethylpyrimidine. MS (ESI): mass calcd. for $C_{19}H_{15}F_4N_5O$, 405.12; m/z found, 406.1 [M+H]$^+$. $^1$H NMR (400 MHz, CDCl$_3$) δ 8.86 (s, 1H), 8.48-8.42 (m, 1H), 8.09 (d, J=1.5, 1H), 7.91-7.82 (m, 1H), 7.38 (d, J=1.0, 1H), 7.28-7.22 (m, 1H), 4.73 (s, 2H), 3.58 (p, J=8.8, 1H), 2.27-2.09 (m, 4H), 2.05-1.91 (m, 1H), 1.88-1.76 (m, 1H).

Example 126

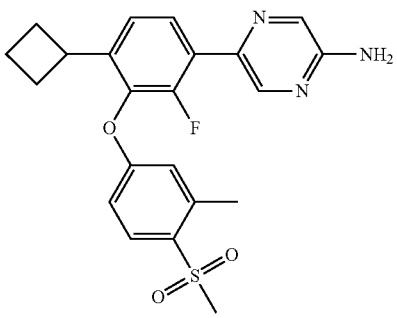 [SMILES: Cc1cc(Oc2c(C3CCC3)ccc(-c3cnc(N)cn3)c2F)ccc1S(C)(=O)=O]

5-{4-Cyclobutyl-2-fluoro-3-[3-methyl-4-(methylsulfonyl)phenoxy]phenyl}pyrazin-2-amine The title compound was prepared using conditions similar to those described in Example 101 heating at 120° Celsius via microwave irradiation for 2 hours and using 4-fluoro-2-methyl-1-(methylsulfonyl)benzene. MS (ESI): mass calcd. for $C_{22}H_{22}FN_3O_3S$, 427.14; m/z found, 428.1 [M+H]$^+$. $^1$H NMR (400 MHz, CDCl$_3$) δ 8.46-8.43 (m, 1H), 8.10 (d, J=1.5, 1H), 7.95 (d, J=8.8, 1H), 7.27 (d, J=9.3, 1H), 6.84 (d, J=2.5, 1H), 6.78 (dd, J=8.8, 2.6, 1H), 4.85 (s, 2H), 3.58 (p, J=8.9, 1H), 3.07 (s, 3H), 2.26-2.07 (m, 4H), 2.00-1.90 (m, 1H), 1.87-1.75 (m, 1H).

Example 127

5-(4-Cyclobutyl-2-fluoro-3-(4-(methylsulfonyl)-2-(trifluoromethyl)phenoxy)phenyl)pyrazin-2-amine The title compound was prepared using conditions similar to those described in Example 101 heating at 120° Celsius via microwave irradiation for 1 hour and using 2-chloro-5-methansulfonylbenzotrifluoride. MS (ESI): mass calcd. for $C_{22}H_{19}F_4N_3O_3S$, 481.11; m/z found, 482.1 [M+H]$^+$. $^1$H NMR (400 MHz, CDCl$_3$) δ 8.46-8.41 (m, 1H), 8.28 (d, J=2.2, 1H), 8.09 (d, J=1.5, 1H), 7.96 (dd, J=8.8, 2.3, 1H), 7.89-7.83 (m, 1H), 7.30 (d, J=8.3, 1H), 6.82 (d, J=8.8, 1H), 4.79 (s, 2H), 3.62 (p, J=8.8, 1H), 3.09 (s, 3H), 2.43-1.91 (m, 4H), 1.88-1.69 (m, 2H).

Example 128

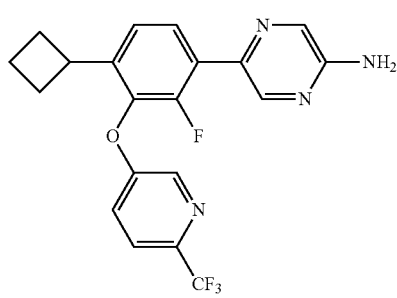 [SMILES: Nc1cnc(-c2ccc(C3CCC3)c(Oc3ccc(C(F)(F)F)nc3)c2F)cn1]

5-(4-Cyclobutyl-2-fluoro-3-{[6-(trifluoromethyl)pyridin-3-yl]oxy}phenyl)pyrazin-2-amine The title compound was prepared using conditions similar to those described in Example 101 heating at 80° Celsius via microwave irradiation for 2 hours and using 5-fluoro-2-(trifluoromethyl)pyridine. MS (ESI): mass calcd. for $C_{20}H_{16}F_4N_4O$, 404.13; m/z found, 405.1 [M+H]$^+$. $^1$H NMR (400 MHz, CDCl$_3$) 8.47 (d, J=2.8, 1H), 8.44 (dd, J=2.2, 1.7, 1H), 8.09 (d, J=1.5, 1H), 7.86-7.80 (m, 1H), 7.60 (d, J=8.7, 1H), 7.28 (d, J 10=7.8, 1H), 7.19 (dd, J=8.7, 2.8, 1H), 4.78 (s, 2H), 3.61 (p, J=8.8, 1H), 2.28-2.08 (m, 4H), 2.04-1.91 (m, 1H), 1.88-1.78 (m, 1H).

Example 129

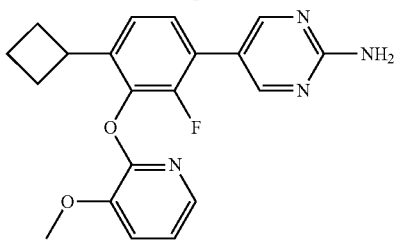

5-{4-Cyclobutyl-2-fluoro-3-[(3-methoxypyridin-2-yl)oxy]phenyl}pyrazin-2-amine

The title compound was prepared using conditions similar to those described in Example 101 heating at 1200 Celsius via microwave irradiation for 1 hour and using 2-fluoro-3-methoxypyridine. MS (ESI): mass calcd. for $C_{20}H_{19}FN_4O_2$, 366.15; m/z found, 367.1 [M+H]$^+$. $^1$H NMR (400 MHz, CDCl$_3$) δ 8.27 (s, 1H), 8.20 (s, 1H), 7.84-7.77 (m, 1H), 7.63 (dd, J=5.0, 1.4, 1H), 7.27-7.21 (m, 2H), 6.99 (dd, J=7.9, 4.9, 1H), 4.01 (s, 3H), 3.74-3.61 (m, 1H), 2.25-2.11 (m, 4H), 2.01-1.88 (m, 1H), 1.87-1.74 (m, 1H).

Example 130

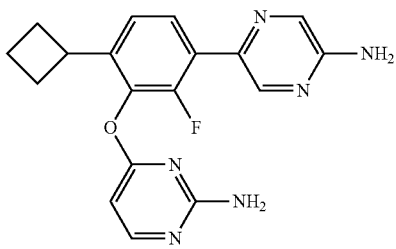

4-[3-(5-Aminopyrazin-2-yl)-6-cyclobutyl-2-fluorophenoxy]pyrimidin-2-amine

The title compound was prepared using conditions similar to those described in Example 101 heating at 120° Celsius via microwave irradiation for 1 hour and using 2-amino-4-chloropyrimidine. MS (ESI): mass calcd. for $C_{18}H_{17}FN_6O$, 352.14; m/z found, 353.1 [M+H]$^+$. $^1$H NMR (400 MHz, CDCl$_3$) δ 8.48-8.45 (m, 1H), 8.15 (d, J=5.7, 1H), 8.06 (d, J=1.5, 1H), 7.81-7.75 (m, 1H), 7.20 (d, J=8.3, 1H), 6.25 (d, J=5.7, 1H), 5.01 (s, 2H), 4.70 (s, 2H), 3.59 (p, J=8.9, 1H), 2.30-2.07 (m, 4H), 2.04-1.90 (m, 1H), 1.87-1.75 (m, 1H).

Example 131

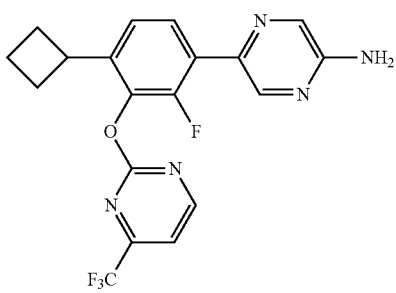 [SMILES: Nc1cnc(-c2ccc(C3CCC3)c(Oc3nccc(C(F)(F)F)n3)c2F)cn1]

5-(4-Cyclobutyl-2-fluoro-3-{[4-(trifluoromethyl)pyrimidin-2-yl]oxy}phenyl)pyrazin-2-amine The title compound was prepared using conditions similar to those described in Example 101 heating at 80° Celsius via microwave irradiation for 1 hour and using 2-chloro-4-(trifluoromethyl)pyrimidine. MS (ESI): mass calcd. for $C_{19}H_{15}F_4N_5O$, 405.12; m/z found, 406.1 [M+H]$^+$. $^1$H NMR (400 MHz, CDCl$_3$) δ 8.77 (d, J=4.8, 1H), 8.45 (dd, J=2.1, 1.7, 1H), 8.09 (d, J=1.5, 1H), 7.87-7.78 (m, 1H), 7.39 (d, J=4.9, 1H), 7.24 (d, J=8.3, 1H), 4.68 (s, 2H), 3.70 (p, J=8.9, 1H), 2.26-2.08 (m, 4H), 2.03-1.90 (m, 1H), 1.86-1.76 (m, 1H).

Example 132

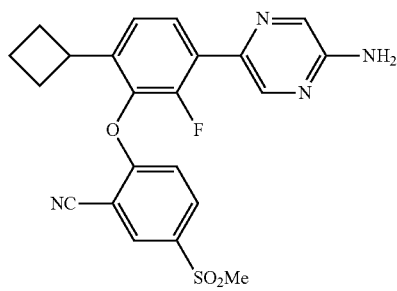 [SMILES: CS(=O)(=O)c1ccc(Oc2c(C3CCC3)ccc(-c3cnc(N)cn3)c2F)c(C#N)c1]

2-[3-(5-Aminopyrazin-2-yl)-6-cyclobutyl-2-fluorophenoxy]-5-(methylsulfonyl)benzonitrile The title compound was prepared using conditions similar to those described in Example 101 heating at 80° Celsius via microwave irradiation for 1 hour and using 2-fluoro-5-(methylsulfonyl)benzonitrile. MS (ESI): mass calcd. for $C_{22}H_{19}FN_4O_3S$, 438.12; m/z found, 439.1 [M+H]$^+$. $^1$H NMR (400 MHz, THF-d$_8$) δ 8.44 (d, J=2.3, 1H), 8.39 (dd, J=2.6, 1.5, 1H), 8.08-7.96 (m, 3H), 7.37 (d, J=8.3, 1H), 6.98 (dd, J=8.9, 1.5, 1H), 6.08 (s, 2H), 3.76-3.65 (m, 1H), 3.12 (s, 3H), 2.35-2.18 (m, 4H), 2.12-1.99 (m, 1H), 1.94-1.82 (m, 1H).

Example 133

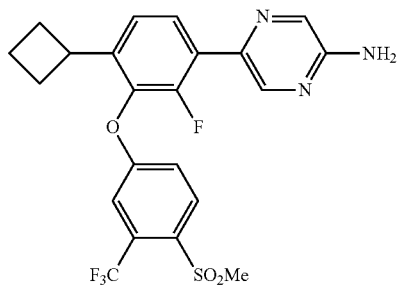 [SMILES: CS(=O)(=O)c1ccc(Oc2c(C3CCC3)ccc(-c3cnc(N)cn3)c2F)cc1C(F)(F)F]

5-{4-Cyclobutyl-2-fluoro-3-[4-(methylsulfonyl)-3-(trifluoromethyl)phenoxy]phenyl}pyrazin-2-amine The title compound was prepared using conditions similar to those described in Example 101 heating at 80° Celsius via microwave irradiation for 1 hour and using 5-bromo-2-(methylsulfonyl)benzotrifluoride. MS (ESI): mass calcd. for $C_{22}H_{19}F_4N_5O_3S$, 481.11; m/z found, 482.1 [M+H]⁺. ¹H NMR (400 MHz, CDCl₃) δ 8.47-8.42 (m, 1H), 8.21 (d, J=8.9, 1H), 8.10 (d, J=1.5, 1H), 7.90-7.82 (m, 1H), 7.49 (d, J=2.6, 1H), 7.29 (d, J=8.3, 1H), 7.04 (dd, J=8.9, 2.5, 1H), 4.75 (s, 2H), 3.57 (p, J=8.8, 1H), 3.18 (s, 3H), 2.27-2.09 (m, 4H), 2.05-1.92 (m, 1H), 1.89-1.78 (m, 1H).

Example 134

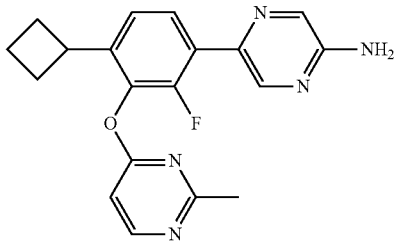 [SMILES: Cc1nccc(Oc2c(C3CCC3)ccc(-c3cnc(N)cn3)c2F)n1]

5-{4-Cyclobutyl-2-fluoro-3-[(2-methylpyrimidin-4-yl)oxy]phenyl}pyrazin-2-amine

The title compound was prepared using conditions similar to those described in Example 101 heating at 80° Celsius via microwave irradiation for 1 hour and using 4-chloro-2-methylpyrimidine. MS (ESI): mass calcd. for $C_{19}H_{18}FN_5O$, 351.15; m/z found, 352.1 [M+H]⁺. ¹H NMR (400 MHz, CDCl₃) δ 8.51-8.43 (m, 2H), 8.09 (d, J=1.3, 1H), 7.80 (m, 1H), 7.23 (d, J=8.3, 1H), 6.70 (d, J=5.8, 1H), 4.71 (s, 2H), 3.59 (p, J=8.9, 1H), 2.55 (s, 3H), 2.25-2.07 (m, 4H), 2.03-1.89 (m, 1H), 1.87-1.72 (m, 1H).

Example 135

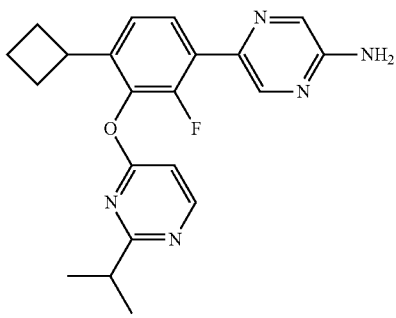 [SMILES: CC(C)c1nccc(Oc2c(C3CCC3)ccc(-c3cnc(N)cn3)c2F)n1]

5-(4-Cyclobutyl-2-fluoro-3-{[2-(1-methylethyl)pyrimidin-4-yl]oxy}phenyl)pyrazin-2-amine The title compound was prepared using conditions similar to those described in Example 101 heating at 80° Celsius via microwave irradiation for 2 hours and using 4-chloro-2-isopropyl-pyrimidine. MS (ESI): mass calcd. for $C_{21}H_{23}FN_6O$, 394.2; m/z found, 395.1 [M+H]⁺. ¹H NMR (400 MHz, CDCl₃) δ 8.52 (d, J=5.7, 1H), 8.47-8.44 (m, 1H), 8.10 (d, J=1.4, 1H), 7.80 (m, 1H), 7.22 (d, J=8.3, 1H), 6.73 (d, J=5.7, 1H), 4.69 (s, 2H), 3.61 (p, J=8.8, 1H), 3.02 (hept, J=6.9, 1H), 2.24-2.06 (m, 4H), 2.03-1.88 (m, 1H), 1.86-1.75 (m, 1H), 1.19 (d, J=6.9, 6H).

Example 136

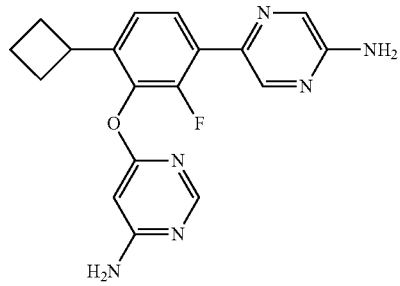 [SMILES: Nc1cnc(-c2ccc(C3CCC3)c(Oc3cc(N)ncn3)c2F)cn1]

6-[3-(5-Aminopyrazin-2-yl)-6-cyclobutyl-2-fluorophenoxy]pyrimidin-4-amine

The title compound was prepared using conditions similar to those described in Example 101 heating at 120° Celsius via microwave irradiation for 3 hours and using 4-amino-6-chloropyrimidine. MS (ESI): mass calcd. for $C_{18}H_{17}FN_6O$, 352.14; m/z found, 353.3 [M+H]⁺. ¹H NMR (400 MHz, CDCl₃) δ 8.49-8.44 (m, 1H), 8.25 (d, J=0.6, 1H), 8.08 (d, J=1.5, 1H), 7.81-7.74 (m, 1H), 7.21 (d, J=8.2, 1H), 5.94 (d, J=0.9, 1H), 4.97 (s, 2H), 4.73 (s, 2H), 3.61 (p, J=8.8, 1H), 2.29-2.09 (m, 4H), 2.04-1.90 (m, 1H), 1.87-1.77 (m, 1H).

Example 137

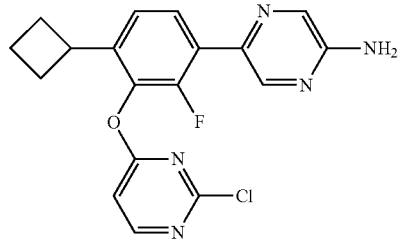 [SMILES: Nc1cnc(-c2ccc(C3CCC3)c(Oc3ccnc(Cl)n3)c2F)cn1]

5-{3-[(2-Chloropyrimidin-4-yl)oxy]-4-cyclobutyl-2-fluorophenyl}pyrazin-2-amine

The title compound was prepared using conditions similar to those described in Example 101 heating at 80° Celsius via microwave irradiation for 2 hours and using 2,4-dichloropyrimidine. MS (ESI): mass calcd. for $C_{18}H_{15}ClFN_5O$, 371.09; m/z found, 372.1 [M+H]⁺. ¹H NMR (400 MHz, DMSO-d₆) δ 8.67 (d, J=5.7, 1H), 8.25 (s, 1H), 8.02 (d, J=1.4, 1H), 7.77 (m, 1H), 7.37-7.29 (m, 2H), 6.70 (s, 2H), 3.55-3.43 (m, 1H), 2.17-2.00 (m, 4H), 1.98-1.83 (m, 1H), 1.81-1.68 (m, 1H).

Example 138

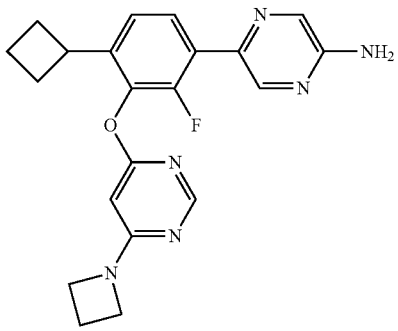 [SMILES: Nc1cnc(-c2ccc(C3CCC3)c(Oc3cc(N4CCC4)ncn3)c2F)cn1]

5-{3-[(6-Azetidin-1-ylpyrimidin-4-yl)oxy]-4-cyclobutyl-2-fluorophenyl}pyrazin-2-amine trifluoroacetate salt The title compound was prepared using conditions similar to those described in Example 101 heating at 120° Celsius via microwave irradiation for 1 hour and using 4-azetidin-1-yl-6-chloro-pyrimidine. MS (ESI): mass calcd. for $C_{21}H_{21}FN_6O$, 392.18; m/z found, 393.1 [M+H]$^+$. $^1$H NMR (400 MHz, CDCl$_3$) δ 8.46 (d, J=1.1, 1H), 8.35 (s, 1H), 8.06 (d, J=0.9, 1H), 7.87 (m, 1H), 7.24 (d, J=8.4, 1H), 5.77 (s, 1H), 4.33 (t, J=7.1, 4H), 3.57 (p, J=8.8, 1H), 2.63-2.52 (m, 2H), 2.29-2.07 (m, 4H), 2.08-1.93 (m, 1H), 1.90-1.77 (m, 1H).

Example 139

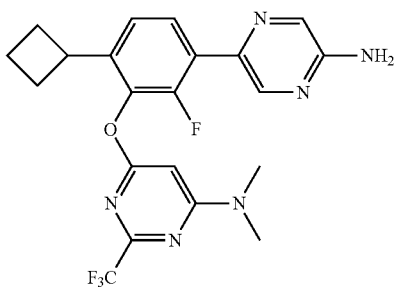 [SMILES: CN(C)c1cc(Oc2c(C3CCC3)ccc(-c3cnc(N)cn3)c2F)nc(C(F)(F)F)n1]

6-[3-(5-Aminopyrazin-2-yl)-6-cyclobutyl-2-fluorophenoxy]-N,N-dimethyl-2-(trifluoromethyl)pyrimidin-4-amine The title compound was prepared using conditions similar to those described in Example 101 heating at 80° Celsius via microwave irradiation for 1 hour and using (6-chloro-2-trifluoromethylpyrimidin-4-yl)dimethyl-amine. MS (ESI): mass calcd. for $C_{21}H_{20}F_4N_6O$, 448.16; m/z found, 449.1 [M+H]$^+$. $^1$H NMR (400 MHz, CDCl$_3$) 8.45 (s, 1H), 8.07 (d, J=1.4, 1H), 7.82-7.74 (m, 1H), 7.22 (d, J=8.3, 1H), 5.84 (s, 1H), 4.79 (s, 2H), 3.62 (p, J=8.9, 1H), 3.11 (s, 6H), 2.27-2.07 (m, 4H), 2.03-1.75 (m, 2H).

Example 140

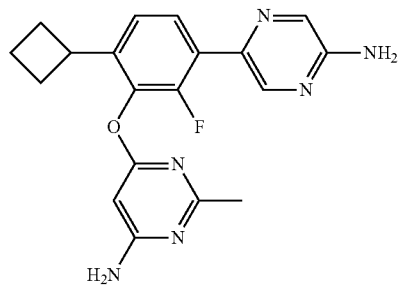 [SMILES: Cc1nc(N)cc(Oc2c(C3CCC3)ccc(-c3cnc(N)cn3)c2F)n1]

6-[3-(5-Aminopyrazin-2-yl)-6-cyclobutyl-2-fluorophenoxy]-2-methylpyrimidin-4-amine trifluoroacetate salt The title compound was prepared using conditions similar to those described in Example 101 heating at 120° Celsius via microwave irradiation for 1 hour and using 4-amino-6-chloro-2-methylpyrimidine. MS (ESI): mass calcd. for $C_{19}H_{19}FN_6O$, 366.16; m/z found, 367.1 [M+H]$^+$. $^1$H NMR (400 MHz, CD$_3$OD) δ 8.25 (d, J=1.7, 1H), 8.11 (d, J=1.5, 1H), 7.82 (m, 1H), 7.34 (d, J=8.2, 1H), 6.03 (s, 1H), 3.69-3.57 (m, 1H), 2.48 (s, 3H), 2.33-2.13 (m, 4H), 2.12-1.97 (m, 1H), 1.92-1.81 (m, 1H).

Example 141

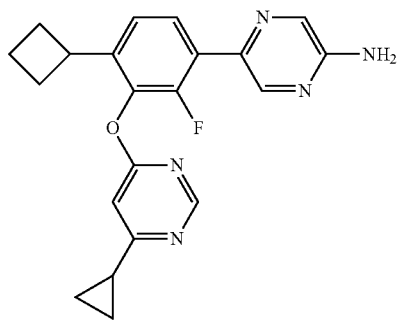 [SMILES: Nc1cnc(-c2ccc(C3CCC3)c(Oc3cc(C4CC4)ncn3)c2F)cn1]

5-{4-Cyclobutyl-3-[(6-cyclopropylpyrimidin-4-yl)oxy]-2-fluorophenyl}pyrazin-2-amine The title compound was prepared using conditions similar to those described in Example 101 heating at 80° Celsius via microwave irradiation for 1 hour and using 4-chloro-6-cyclopropyl-pyrimidine. MS (ESI): mass calcd. for $C_{21}H_{20}FN_5O$, 377.16; m/z found, 378.1 [M+H]$^+$. $^1$H NMR (400 MHz, CDCl$_3$) δ 8.56 (d, J=0.7, 1H), 8.47 (d, J=1.8, 1H), 8.08 (d, J=1.5, 1H), 7.84-7.77 (m, 1H), 7.22 (d, J=8.3, 1H), 6.83 (d, J=1.0, 1H), 4.65 (s, 2H), 3.59 (p, J=9.0, 1H), 2.28-2.09 (m, 4H), 2.04-1.89 (m, 2H), 1.87-1.75 (m, 1H), 1.21-1.15 (m, 2H), 1.13-1.05 (m, 2H).

Example 142

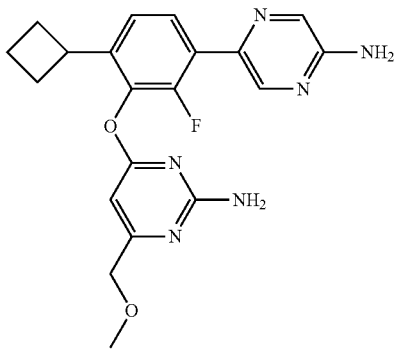

4-[3-(5-Aminopyrazin-2-yl)-6-cyclobutyl-2-fluoro-phenoxy]-6-(methoxymethyl)pyrimidin-2-amine The title compound was prepared using conditions similar to those described in Example 101 heating at 120 Celsius via microwave irradiation for 1 hour and using 4-chloro-6-(methoxymethyl)pyrimidin-2-amine. MS (ESI): mass calcd. for $C_{20}H_{21}FN_6O_2$, 396.17; m/z found, 397.1 [M+H]$^+$. $^1$H NMR (400 MHz, CDCl$_3$) δ 8.51-8.45 (m, 1H), 8.06 (d, J=1.5, 1H), 7.81-7.74 (m, 1H), 7.20 (d, J=8.3, 1H), 6.37 (s, 1H), 5.00 (s, 2H), 4.70 (s, 2H), 4.34 (s, 2H), 3.66-3.53 (m, 1H), 3.47 (s, 3H), 2.30-2.07 (m, 4H), 2.04-1.90 (m, 1H), 1.87-1.74 (m, 1H).

Example 143

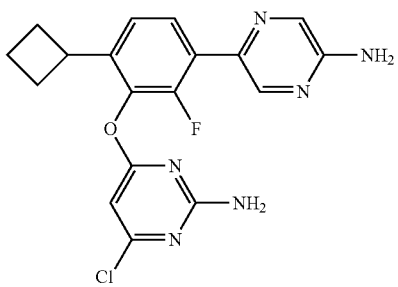 [SMILES: Nc1cnc(-c2ccc(C3CCC3)c(Oc3cc(Cl)nc(N)n3)c2F)cn1]

4-[3-(5-Aminopyrazin-2-yl)-6-cyclobutyl-2-fluoro-phenoxy]-6-chloropyrimidin-2-amine The title compound was prepared using conditions similar to those described in Example 101 heating at 120° Celsius via microwave irradiation for 1 hour and using 2-amino-4,6-dichloropyrimidine. MS (ESI): mass calcd. for $C_{18}H_{16}ClFN_6O$, 386.10; m/z found, 387.0 [M+H]$^+$. $^1$H NMR (500 MHz, CDCl$_3$) δ 8.30-8.23 (m, 2H), 7.77 (m, 1H), 7.23 (d, J=8.2, 1H), 6.29 (d, J=2.6, 1H), 3.64-3.52 (m, 1H), 2.31-2.21 (m, 2H), 2.21-2.09 (m, 2H), 2.08-1.95 (m, 1H), 1.90-1.78 (m, 1H).

Example 144

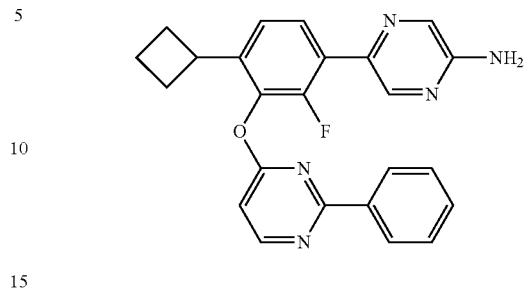

5-{4-Cyclobutyl-2-fluoro-3-[(2-phenylpyrimidin-4-yl)oxy]phenyl}pyrazin-2-amine

The title compound was prepared using conditions similar to those described in Example 101 heating at 80° C. via microwave irradiation for one hour and using 4-chloro-2-phenylpyrimidine. MS (ESI): mass calcd. for $C_{24}H_{20}FN_5O$, 413.16; m/z found, 414.1 [M+H]$^+$. $^1$H NMR (500 MHz, CDCl$_3$) δ 8.68 (d, J=5.7, 1H), 8.50-8.46 (m, 1H), 8.24-8.18 (m, 2H), 8.09 (d, J=1.5, 1H), 7.88-7.81 (m, 1H), 7.44-7.33 (m, 3H), 7.26 (m, 1H), 6.86 (d, J=5.6, 1H), 4.71 (s, 2H), 3.63 (p, J=8.9, 1H), 2.25-2.10 (m, 4H), 1.99-1.88 (m, 1H), 1.83-1.75 (m, 1H).

Example 145

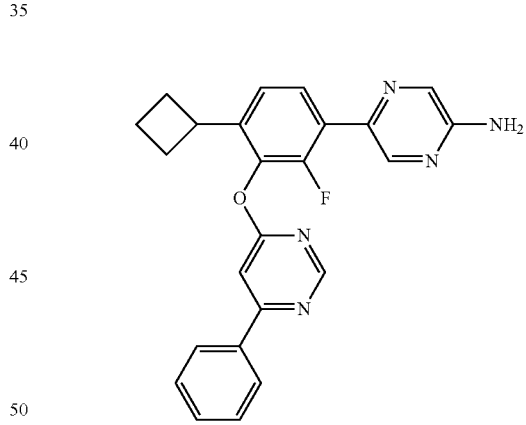

5-{4-Cyclobutyl-2-fluoro-3-[(6-phenylpyrimidin-4-yl)oxy]phenyl}pyrazin-2-amine

The title compound was prepared using conditions similar to those described in Example 101 heating at 80° Celsius via microwave irradiation for 1 hour and using 4-chloro-6-phenylpyrimidine. MS (ESI): mass calcd. for $C_{24}H_{20}FN_5O$, 413.16; m/z found, 414.1 [M+H]$^+$. $^1$H NMR (400 MHz, CDCl$_3$) δ 8.82 (d, J=1.0, 1H), 8.52-8.46 (m, 1H), 8.14-8.06 (m, 3H), 7.88-7.80 (m, 1H), 7.58-7.48 (m, 3H), 7.39 (d, J=1.0, 1H), 7.25 (d, J=8.8, 1H), 4.69 (s, 2H), 3.63 (p, J=8.9, 1H), 2.29-2.10 (m, 4H), 2.05-1.89 (m, 1H), 1.87-1.75 (m, 1H).

Example 146

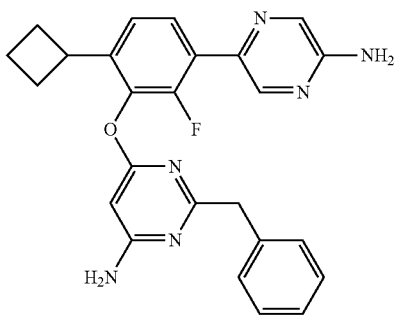 [SMILES: Nc1cnc(-c2ccc(C3CCC3)c(Oc3cc(N)nc(Cc4ccccc4)n3)c2F)cn1]

6-[3-(5-Aminopyrazin-2-yl)-6-cyclobutyl-2-fluorophenoxy]-2-benzylpyrimidin-4-amine The title compound was prepared using conditions similar to those described in Example 101 heating at 120° Celsius via microwave irradiation for 1 hour and using 6-amino-2-benzyl-4-chloropyrimidine. MS (ESI): mass calcd. for $C_{25}H_{23}FN_5O$, 442.19; m/z found, 443.2 [M+H]$^+$. $^1$H NMR (400 MHz, CDCl$_3$) 8.32 (m, 1H), 8.08 (m, 1H), 7.69 (t, J=7.8, 1H), 7.37 (s, 1H), 7.30-7.13 (m, 5H), 5.62 (s, 1H), 3.90 (s, 2H), 3.63-3.52 (m, 1H), 2.26-2.04 (m, 4H), 2.02-1.88 (m, 1H), 1.85-1.74 (m, 1H).

Example 147

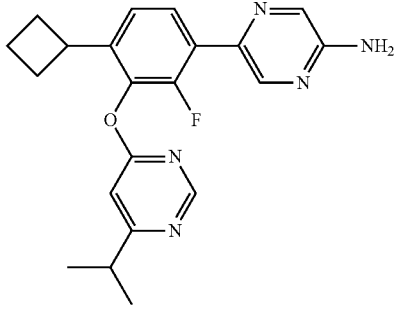 [SMILES: CC(C)c1cc(Oc2c(C3CCC3)ccc(-c3cnc(N)cn3)c2F)ncn1]

5-(4-Cyclobutyl-2-fluoro-3-{[6-(1-methylethyl)pyrimidin-4-yl]oxy}phenyl)pyrazin-2-amine The title compound was prepared using conditions similar to those described in Example 101 heating at 120° Celsius via microwave irradiation for 1 hour and using 4-chloro-6-isopropyl-pyrimidine. MS (ESI): mass calcd. for $C_{21}H_{22}FN_5O$, 379.18; m/z found, 380.1 [M+H]$^+$. $^1$H NMR (400 MHz, CDCl$_3$) δ 8.68 (d, J=0.9, 1H), 8.49-8.43 (m, 1H), 8.08 (d, J=1.5, 1H), 7.84-7.78 (m, 1H), 7.23 (d, J=8.3, 1H), 6.86 (d, J=0.5, 1H), 4.70 (s, 2H), 3.60 (p, J=8.9, 1H), 3.02 (hept, J=6.9, 1H), 2.26-2.08 (m, 4H), 2.04-1.89 (m, 1H), 1.87-1.77 (m, 1H), 1.34 (d, J=6.9, 6H).

Example 148

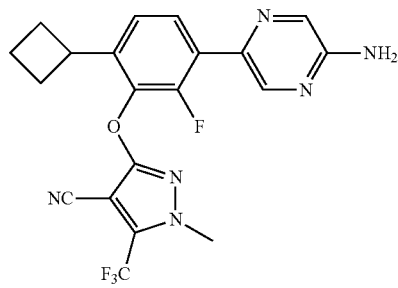 [SMILES: Cn1nc(Oc2c(C3CCC3)ccc(-c3cnc(N)cn3)c2F)c(C#N)c1C(F)(F)F]

3-[3-(5-Aminopyrazin-2-yl)-6-cyclobutyl-2-fluorophenoxy]-1-methyl-5-(trifluoromethyl)-1H-pyrazole-4-carbonitrile The title compound was prepared using conditions similar to those described in Example 101 heating at 80° Celsius via microwave irradiation for 1 hour and using 5-chloro-1-methyl-3-(trifluoromethyl)-1H-pyrazole-4-carbonitrile. MS (ESI): mass calcd. for $C_{20}H_{16}F_4N_6O$, 432.13; m/z found, 433.1 [M+H]$^+$. $^1$H NMR (400 MHz, CDCl$_3$) 8.46 (dd, J=2.2, 1.6, 1H), 8.06 (d, J=1.5, 1H), 7.91 (m, 1H), 7.30-7.20 (m, 1H), 4.76 (s, 2H), 3.95 (s, 3H), 3.74 (p, J=8.8, 1H), 2.38-2.19 (m, 4H), 2.14-1.99 (m, 1H), 1.98-1.85 (m, 1H).

Intermediate C

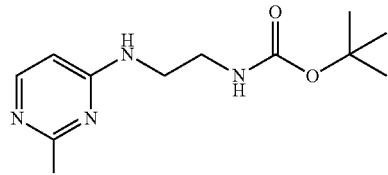

tert-Butyl-(2-((2-chloropyrimidin-4-yl)amino)ethyl)carbamate

Intermediate D

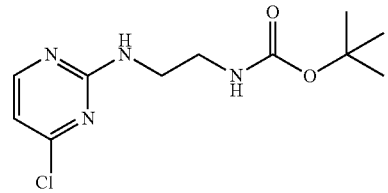 [SMILES: CC(C)(C)OC(=O)NCCNc1nccc(Cl)n1]

tert-Butyl-(2-((4-chloropyrimidin-2-yl)amino)ethyl)carbamate 2,4-Dichloropyrimidine (1.0 g, 6.7 mmol), tert-butyl N-(2-aminoethyl)carbamate (1.06 mL, 6.71 mmol) and triethylamine (1.12 mL, 8.05 mmol) were partially dissolved in acetonitrile (22.5 mL). The mixture was stirred at room temperature for 14 hours before diluting with water and extracting with DCM. The DCM extract was dried over Na$_2$SO$_4$, filtered and concentrated to dryness. The crude mixture was purified by FCC to give tert-butyl-(2-((2-chloropyrimidin-4-yl)amino)ethyl)carbamate (1.07 g, 58%) and tert-butyl-(2-((4-chloropyrimidin-2-yl)amino)ethyl)carbamate (280 mg, 15%).

Example 149

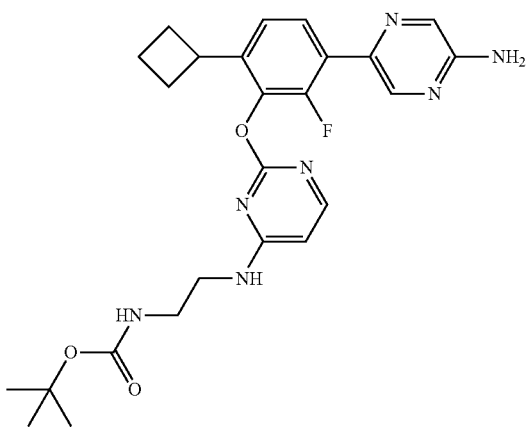

tert-Butyl [2-({2-[3-(5-aminopyrazin-2-yl)-6-cyclobutyl-2-fluorophenoxy]pyrimidin-4-yl}amino)ethyl]carbamate The title compound was prepared using conditions similar to those described in Example 101 heating at 80° Celsius via microwave irradiation for 1 hour and Intermediate C. MS (ESI): mass calcd. for C$_{25}$H$_{30}$FN$_7$O$_3$, 495.24; m/z found, 496.2 [M+H]$^+$. $^1$H NMR (400 MHz, CDCl$_3$) δ 8.43 (s, 1H), 8.14 (d, J=5.6, 1H), 8.07 (s, 1H), 7.73 (m, 1H), 7.19 (d, J=8.3, 1H), 6.20 (d, J=5.6, 1H), 5.51 (s, 1H), 5.03 (s, 1H), 4.81 (s, 2H), 3.66-3.53 (m, 1H), 3.25 (d, J=52.0, 4H), 2.31-2.05 (m, 4H), 2.05-1.89 (m, 1H), 1.87-1.72 (m, 1H), 1.39 (s, 9H).

Example 150

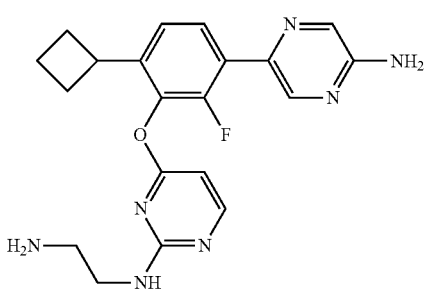 [SMILES: NCCNc1nccc(Oc2c(C3CCC3)ccc(-c3cnc(N)cn3)c2F)n1]

N-{4-[3-(5-Aminopyrazin-2-yl)-6-cyclobutyl-2-fluorophenoxy]pyrimidin-2-yl}ethane-1,2-diamine The title compound was prepared using conditions similar to those described in Example 101 heating at 80° Celsius via microwave irradiation for 1 hour and Intermediate D. MS (ESI): mass calcd. for C$_{20}$H$_{22}$FN$_7$O, 395.19; m/z found, 396.1 [M+H]$^+$. $^1$H NMR (400 MHz, CD$_3$OD) δ 8.30-8.25 (m, 1H), 8.05 (d, J=1.5, 1H), 7.84 (s, 1H), 7.67 (m, 1H), 7.25 (d, J=8.2, 1H), 6.25 (d, J=5.8, 1H), 3.66 (p, J=8.9, 1H), 3.26 (t, J=6.2, 2H), 2.70 (s, 2H), 2.29-2.09 (m, 4H), 2.06-1.93 (m, 1H), 1.88-1.77 (m, 1H).

Example 151

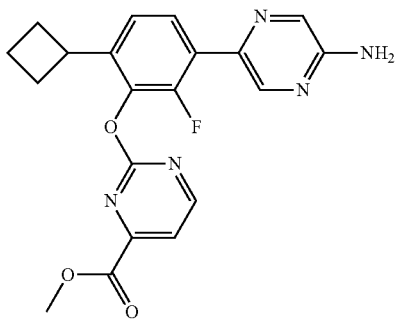 [SMILES: COC(=O)c1ccnc(Oc2c(C3CCC3)ccc(-c3cnc(N)cn3)c2F)n1]

Methyl 2-[3-(5-aminopyrazin-2-yl)-6-cyclobutyl-2-fluorophenoxy]pyrimidine-4-carboxylate trifluoroacetate salt The title compound was prepared using conditions similar to those described in Example 101 heating at 80° Celsius via microwave irradiation for 2 hours and methyl 2-chloropyrimidine-4-carboxylate (280 mg, 15%). MS (ESI): mass calcd. for C$_{20}$H$_{18}$FN$_5$O$_3$, 395.14; m/z found, 396.1 [M+H]$^+$. $^1$H NMR (400 MHz, CDCl$_3$) δ 8.79 (d, J=4.9, 1H), 8.37 (d, J=1.3, 1H), 8.11 (d, J=1.2, 1H), 7.86 (m, 1H), 7.80 (d, J=4.9, 1H), 7.30-7.24 (m, 1H), 4.67 (s, 2H), 4.04 (s, 3H), 3.76-3.63 (m, 1H), 2.27-2.07 (m, 4H), 2.04-1.88 (m, 1H), 1.87-1.74 (m, 1H).

Example 152

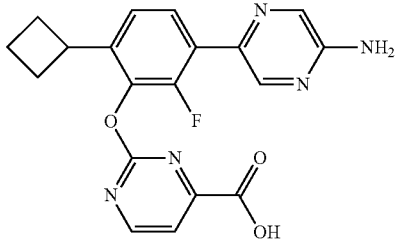 [SMILES: Nc1cnc(-c2ccc(C3CCC3)c(Oc3nccc(C(=O)O)n3)c2F)cn1]

2-[3-(5-Aminopyrazin-2-yl)-6-cyclobutyl-2-fluorophenoxy]pyrimidine-4-carboxylic acid Title compound was found as an additional product in the formation of methyl 2-[3-(5-aminopyrazin-2-yl)-6-cyclobutyl-2-fluorophenoxy]pyrimidine-4-carboxylate, Example 151. MS (ESI): mass calcd. for C$_{19}$H$_{16}$FN$_5$O$_3$, 381.12; m/z found, 382.1 [M+H]$^+$. $^1$H NMR (400 MHz, CD$_3$OD) δ 8.78 (d, J=4.9, 1H), 8.25 (d, J=1.5, 1H), 8.21 (m, 1H), 7.85-7.79

(m, 2H), 7.30 (d, J=8.3, 1H), 3.73-3.61 (m, 1H), 2.24-2.08 (m, 4H), 2.06-1.91 (m, 1H), 1.86-1.75 (m, 1H).

Example 153

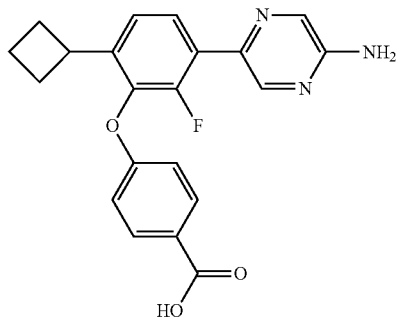

4-[3-(5-Aminopyrazin-2-yl)-6-cyclobutyl-2-fluorophenoxy]benzoic acid

The title compound was prepared using analogous conditions described in Example 85 using Example 103 as a starting material. MS (ESI): mass calcd. for $C_{21}H_{18}FN_3O_3$, 379.13; m/z found, 380.1 [M+H]$^+$. $^1$H NMR (400 MHz, CD$_3$OD) δ 8.24 (s, 1H), 8.16 (s, 1H), 8.03-7.97 (m, 2H), 7.78 (m, 1H), 7.35 (d, J=8.3, 1H), 6.92 (d, J=8.8, 2H), 3.69-3.57 (m, 1H), 2.24-2.11 (m, 4H), 2.04-1.90 (m, 1H), 1.88-1.76 (m, 1H).

Example 154

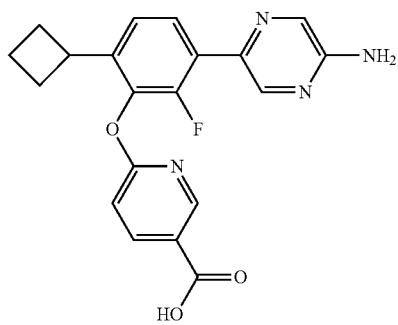 [SMILES: Nc1cnc(-c2ccc(C3CCC3)c(Oc3ccc(C(=O)O)cn3)c2F)cn1]

6-[3-(5-Aminopyrazin-2-yl)-6-cyclobutyl-2-fluorophenoxy]pyridine-3-carboxylic acid The title compound was prepared using analogous conditions described in Example 85 using Example 107 as a starting material. MS (ESI): mass calcd. for $C_{20}H_{17}FN_4O_3$, 380.13; m/z found, 381.1 [M+H]$^+$. $^1$H NMR (400 MHz, DMSO-d$_6$) δ 8.59-8.53 (m, 1H), 8.27 (dd, J=8.6, 2.4, 1H), 8.21-8.16 (m, 1H), 7.98 (d, J=1.5, 1H), 7.67 (m, 1H), 7.26-7.17 (m, 2H), 2.08-1.95 (m, 4H), 1.90-1.76 (m, 1H), 1.73-1.61 (m, 1H).

Example 155

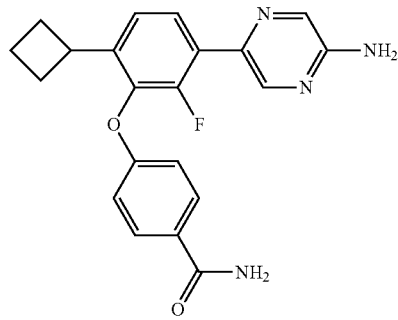 [SMILES: NC(=O)c1ccc(Oc2c(C3CCC3)ccc(-c3cnc(N)cn3)c2F)cc1]

4-[3-(5-Aminopyrazin-2-yl)-6-cyclobutyl-2-fluorophenoxy]benzamide

4-[3-(5-Aminopyrazin-2-yl)-6-cyclobutyl-2-fluorophenoxy]benzonitrile (30 mg, 0.083 mmol) was dissolved in TFA (0.75 mL) and treated with conc. H$_2$SO$_4$ (0.25 mL). The mixture was stirred at room temperature for 20 hours. The mixture was then poured over ice water (100 mL) and the aqueous layer extracted with 10% MeOH/DCM. The water layer was adjusted to pH 7 with aqueous NaOH and extracted again 10% MeOH/DCM. The combined organic extracts were dried and concentrated to dryness. The crude product was purified by FCC to afford the title compound (28 mg, 89%). MS (ESI): mass calcd. for $C_{21}H_{19}FN_4O_2$, 378.15; m/z found, 379.2 [M+H]$^+$. $^1$H NMR (400 MHz, CD$_3$OD) δ 8.26 (s, 1H), 8.05 (s, 1H), 7.89-7.83 (m, 2H), 7.77-7.70 (m, 1H), 7.33 (d, J=8.3, 1H), 6.94-6.87 (m, 2H), 3.69-3.57 (m, 1H), 2.24-2.10 (m, 4H), 2.04-1.89 (m, 1H), 1.87-1.76 (m, 1H).

Example 156

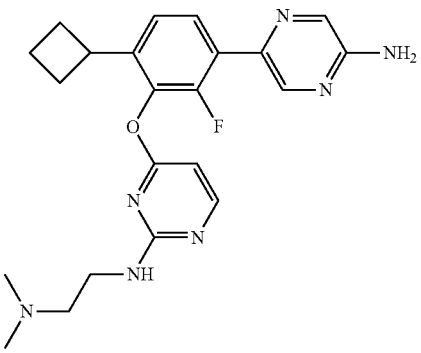 [SMILES: CN(C)CCNc1nccc(Oc2c(C3CCC3)ccc(-c3cnc(N)cn3)c2F)n1]

N'-{4-[3-(5-Aminopyrazin-2-yl)-6-cyclobutyl-2-fluorophenoxy]pyrimidin-2-yl}-N, N-dimethylethane-1,2-diamine hydrochloride 5-{3-[(2-Chloropyrimidin-4-yl)oxy]-4-cyclobutyl-2-fluorophenyl}pyrazin-2-amine (77 mg, 0.21 mmol) was partially dissolved in N,N-dimethylethylenediamine (0.23 mL) and heated via microwave irradiation at 120° Celsius for 2 hours. The reaction mixture was subjected to direct HPLC purification. The post-HPLC material was then subjected to FCC to afford the title compound. The final product was converted to the HCl salt by dissolving it in MeOH and treating the solution with HCl (1.0 M, 0.42 mL) in water. The reaction mixture was then concentrated to dryness to give the title compound (13 mg, 13%). MS (ESI): mass calcd. for $C_{22}H_{26}FN_7O$, 423.22; m/z found, 424.2 [M+H]$^+$. $^1$H NMR (400 MHz, CDCl$_3$) δ 8.50-8.45 (m, 1H), 8.06 (d, J=1.5, 1H), 7.93 (s, 1H), 7.79-7.71 (m, 1H), 7.20 (d, J=8.3, 1H), 6.08 (d, J=5.9, 1H), 5.74 (s, 1H), 4.69 (s, 2H), 3.78-3.65 (m, 1H), 3.37 (s, 2H), 2.51 (t, J=5.9, 2H), 2.30-2.07 (m, 11H), 2.04-1.88 (m, 1H), 1.86-1.73 (m, 1H).

Example 157

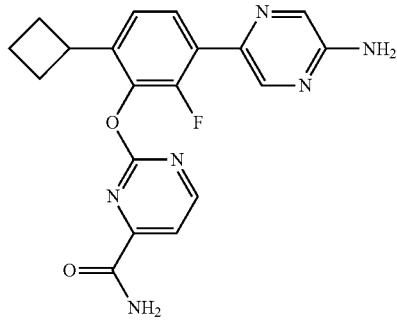

2-[3-(5-Aminopyrazin-2-yl)-6-cyclobutyl-2-fluorophenoxy]pyrimidine-4-carboxamide The title compound was prepared using conditions similar to those described in Example 160 heating for 2 hours at 80° Celsius and using Intermediate B and 2-chloropyrimidine-4-carboxamide. MS (ESI): mass calcd. for $C_{19}H_{17}FN_6O_2$, 380.14; m/z found, 381.1 [M+H]$^+$. $^1$H NMR (400 MHz, DMSO-d$_6$) δ 8.84-8.78 (d, J=4.9, 1H), 8.30-8.21 (m, 2H), 8.06-7.97 (d, J=1.5, 2H), 7.80-7.71 (m, 2H), 7.35-7.28 (d, J=8.3, 1H), 6.78-6.66 (s, 2H), 3.64-3.51 (m, 1H), 2.16-2.01 (m, 4H), 1.98-1.84 (m, 1H), 1.81-1.66 (m, 1H).

Example 158

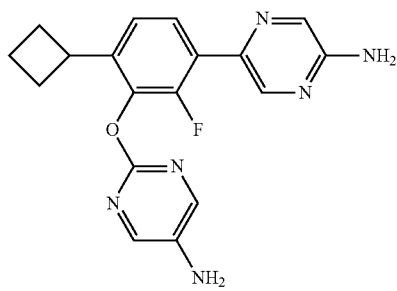 [SMILES: Nc1cnc(Oc2c(C3CCC3)ccc(-c3cnc(N)cn3)c2F)nc1]

2-[3-(5-Aminopyrazin-2-yl)-6-cyclobutyl-2-fluorophenoxy]pyrimidin-5-amine

The title compound was prepared using conditions similar to those described in Example 164 heating for 18 hours at 140° Celsius using Intermediate B and 5-amino-2-chloropyrimidine. MS (ESI): mass calcd. for $C_{18}H_{17}FN_6O$, 352.14; m/z found, 353.1 [M+H]$^+$. $^1$H NMR (400 MHz, CD$_3$OD) δ 8.17-8.13 (m, 1H), 7.95 (d, J=1.5, 1H), 7.92 (s, 2H), 7.62-7.54 (m, 1H), 7.15 (d, J=8.3, 1H), 3.61-3.49 (m, 1H), 2.16-1.98 (m, 4H), 1.96-1.80 (m, 1H), 1.77-1.63 (m, 1H).

Example 159

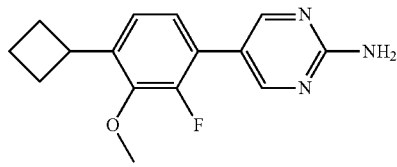

5-(4-Cyclobutyl-2-fluoro-3-methoxyphenyl)pyrimidin-2-amine

The title compound was prepared using analogous conditions described in Step D of Intermediate A using (4-cyclobutyl-2-fluoro-3-methoxyphenyl)boronic acid and 2-amino-5-bromopyrimidine. MS (ESI): mass calcd. for $C_{15}H_{16}FN_3O$, 273.13; m/z found, 274.1 [M+H]$^+$. $^1$H NMR (400 MHz, CDCl$_3$); 8.48 (d, J=1.4, 2H), 7.10 (d, J=8.2, 1H), 7.08-6.99 (m, 1H), 5.24 (s, 2H), 3.90 (d, J=1.4, 3H), 3.88-3.74 (m, 1H), 2.41-2.31 (m, 2H), 2.22-1.99 (m, 3H), 1.93-1.82 (m, 1H).

Intermediate E

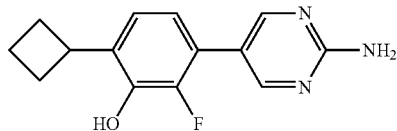

3-(2-Aminopyrimidin-5-yl)-6-cyclobutyl-2-fluorophenol

To a 200 mL flask were added a stir bar, 5-(4-cyclobutyl-2-fluoro-3-methoxyphenyl)pyrimidin-2-amine (729 mg, 2.7 mmol) and dry DCM (27 mL). The flask was purged with nitrogen, stirred until homogeneous and cooled to −78° Celsius. The resulting solution was charged with boron tribromide (1.0 M in DCM, 8.09 mL). The mixture was kept at −78° Celsius for 30 min before warming to room temperature. After 5 hours, the reaction mixture was poured into a 500 mL mixture of ice and saturated NaHCO$_3$. This mixture was partitioned between EtOAc and the aqueous layer. The EtOAc layer was isolated, dried and concentrated to dryness. The resulting solid was purified by FCC to yield the title compound (602 mg, 87%). MS (ESI): mass calcd. for $C_{14}H_{14}FN_3O$, 259.11; m/z found, 260.1 [M+H]$^+$. $^1$H NMR (400 MHz, DMSO-d$_6$) δ 9.41 (d, J=2.0, 1H), 8.39 (d, J=1.4, 2H), 7.04 (d, J=8.0, 1H), 6.89 (m, 1H), 6.83 (s, 2H), 3.80-3.65 (m, 1H), 2.34-2.20 (m, 2H), 2.15-1.89 (m, 3H), 1.89-1.74 (m, 1H).

Example 160

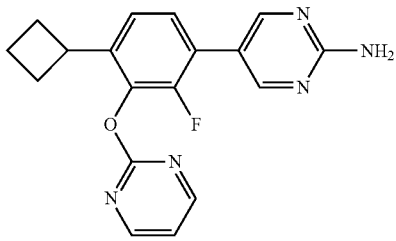 [SMILES: Nc1ncc(-c2ccc(C3CCC3)c(Oc3ncccn3)c2F)cn1]

5-[4-Cyclobutyl-2-fluoro-3-(pyrimidin-2-yloxy)phenyl]pyrimidin-2-amine

To a 5 mL vial containing a stir bar, 3-(2-aminopyrimidin-5-yl)-6-cyclobutyl-2-fluorophenol (80 mg, 0.31 mmol) and 2-chloropyrimidine (41 mg, 0.34 mmol) were added $Cs_2CO_3$ (203 mg, 0.62 mmol) and DMSO (0.8 mL). The resultant mixture was stirred at 120° Celsius for approximately 1 hour via microwave irradiation. The reaction mixture was cooled to room temperature before passing the mixture through a syringe filter and subjecting the filtrate to FCC to afford the title compound (81 mg, 78%). MS (ESI): mass calcd. for $C_{18}H_{16}FN_5O$, 337.13; m/z found, 338.1 [M+H]+. 1H NMR (400 MHz, $CDCl_3$) δ 8.57 (d, J=4.8, 2H), 8.50 (d, J=1.0, 2H), 7.31-7.19 (m, 2H), 7.09-7.05 (m, 1H), 5.40 (s, 2H), 3.71 (p, J=8.9, 1H), 2.28-2.07 (m, 4H), 2.03-1.89 (m, 1H), 1.86-1.74 (m, 1H).

Example 161

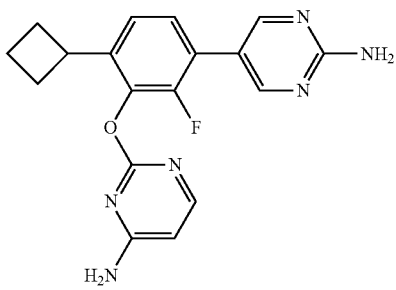

5-{3-[(4-Aminopyrimidin-2-yl)oxy]-4-cyclobutyl-2-fluorophenyl}pyrimidin-2-amine

The title compound was prepared using conditions similar to those described in Example 160 with DMF as the solvent heating via microwave irradiation for 2 hours and using 4-amino-2-chloropyrimidine. MS (ESI): mass calcd. for $C_{18}H_{17}FN_6O$, 352.14; m/z found, 353.1 [M+H]+. 1H NMR (400 MHz, $CDCl_3$) δ 8.50 (d, J=1.3, 2H), 8.01 (d, J=5.7, 1H), 7.25-7.16 (m, 2H), 6.17 (d, J=5.7, 1H), 5.17 (s, 2H), 5.05 (s, 2H), 3.77-3.64 (m, 1H), 2.33-2.07 (m, 4H), 2.04-1.90 (m, 1H), 1.87-1.74 (m, 1H).

Example 162

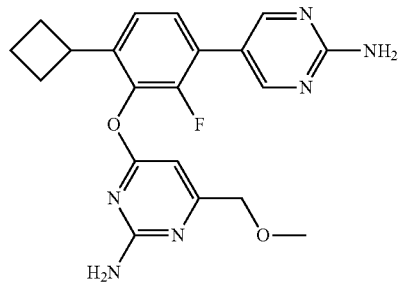 [SMILES: COCc1cc(Oc2c(C3CCC3)ccc(-c3cnc(N)nc3)c2F)nc(N)n1]

4-[3-(2-Aminopyrimidin-5-yl)-6-cyclobutyl-2-fluorophenoxy]-6-(methoxymethyl)pyrimidin-2-amine The title compound was prepared using conditions similar to those described in Example 160 heating via microwave irradiation for 2 hours and using 4-chloro-6-(methoxymethyl)pyrimidin-2-amine. MS (ESI): mass calcd. for $C_{20}H_{21}FN_6O_2$, 396.17; m/z found, 397.1 [M+H]+. 1H NMR (400 MHz, $CDCl_3$) δ 8.48 (d, J=1.0, 2H), 7.25-7.15 (m, 2H), 6.38 (s, 1H), 5.30 (s, 2H), 5.08 (s, 2H), 4.35 (s, 2H), 3.66-3.53 (m, 1H), 3.48 (s, 3H), 2.29-2.06 (m, 4H), 2.05-1.89 (m, 1H).

Example 163

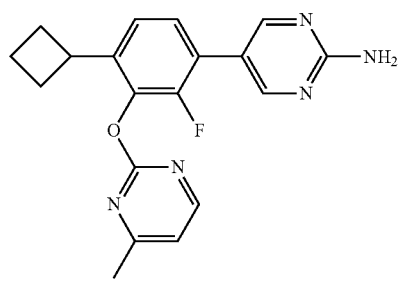 [SMILES: Cc1ccnc(Oc2c(C3CCC3)ccc(-c3cnc(N)nc3)c2F)n1]

5-{4-Cyclobutyl-2-fluoro-3-[(4-methylpyrimidin-2-yl)oxy]phenyl}pyrimidin-2-amine The title compound was prepared using conditions similar to those described in Example 160 heating to 80° Celsius on a hotplate for 3 hours and using 2-chloro-4-methylpyrimidine. MS (ESI): mass calcd. for $C_{19}H_{18}FN_5O$, 351.15; m/z found, 352.1 [M+H]+. 1H NMR (400 MHz, $CDCl_3$) δ 8.50 (d, J=1.3, 2H), 8.33 (d, J=5.0, 1H), 7.26-7.18 (m, 2H), 6.92 (d, J=5.0, 1H), 5.29 (s, 2H), 3.71 (p, J=8.9, 1H), 2.52 (s, 3H), 2.27-2.07 (m, 4H), 2.02-1.90 (m, 1H), 1.85-1.73 (m, 1H).

Example 164

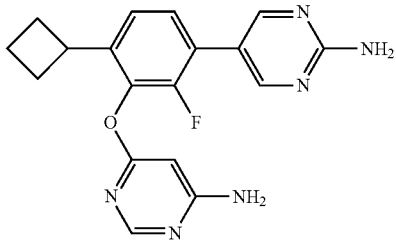 [SMILES: Nc1cc(Oc2c(C3CCC3)ccc(-c3cnc(N)nc3)c2F)ncn1]

5-{3-[(6-Aminopyrimidin-4-yl)oxy]-4-cyclobutyl-2-fluorophenyl}pyrimidin-2-amine

To a 5 mL vial containing a stir bar, 3-(2-aminopyrimidin-5-yl)-6-cyclobutyl-2-fluorophenol (88 mg, 0.34 mmol) and 4-amino-6-chloropyrimidine (46 mg, 0.36 mmol) were added K$_2$CO$_3$ (70 mg, mg, 0.51 mmol), 18-crown-6 (9 mg, 0.03 mmol) and DMA (0.68 mL). The resultant mixture was stirred at 120 Celsius for approximately 3 hours before cooling to room temperature and passing it through a syringe filter and subjecting the filtrate to FCC to afford the title compound (42 mg, 35%). MS (ESI): mass calcd. for C$_{18}$H$_{17}$FN$_6$O, 352.14; m/z found, 353.1 [M+H]$^+$. $^1$H NMR (400 MHz, CDCl$_3$) δ 8.49 (d, J=1.1, 2H), 8.23 (s, 1H), 7.26-7.16 (m, 2H), 5.99 (s, 1H), 5.25 (s, 2H), 5.01 (s, 2H), 3.61 (p, J=8.9, 1H), 2.31-2.08 (m, 4H), 2.00-1.90 (m, 1H), 1.89-1.78 (m, 1H).

Example 165

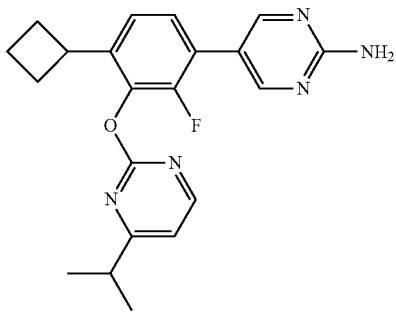 [SMILES: CC(C)c1ccnc(Oc2c(C3CCC3)ccc(-c3cnc(N)nc3)c2F)n1]

5-(4-Cyclobutyl-2-fluoro-3-{[4-(1-methylethyl)pyrimidin-2-yl]oxy}phenyl)pyrimidin-2-amine The title compound was prepared using conditions similar to those described in Example 160 heating to 80° Celsius for 3 hours and using 2-chloro-4-isopropyl-pyrimidine. MS (ESI): mass calcd. for C$_{21}$H$_{22}$FN$_5$O, 379.180; m/z found, 380.1 [M+H]$^+$. $^1$H NMR (400 MHz, CDCl$_3$) δ 8.49 (d, J=1.3, 2H), 8.38 (d, J=5.1, 1H), 7.26-7.18 (m, 2H), 6.92 (d, J=5.1, 1H), 5.19 (s, 2H), 3.79-3.66 (m, 1H), 3.03-2.92 (m, 1H), 2.27-2.06 (m, 4H), 2.03-1.89 (m, 1H), 1.85-1.74 (m, 1H), 1.28 (d, J=6.9, 6H).

Example 166

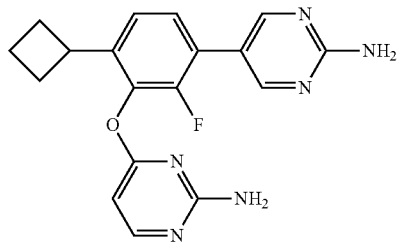

4-[3-(2-Aminopyrimidin-5-yl)-6-cyclobutyl-2-fluorophenoxy]pyrimidin-2-amine

The title compound was prepared using conditions similar to those described in Example 164 heating the reaction for 18 hours and using 2-amino-4-chloropyrimidine. MS (ESI): mass calcd. for C$_{18}$H$_{17}$FN$_6$O, 352.14; m/z found, 353.1 [M+H]$^+$. $^1$H NMR (400 MHz, CDCl$_3$) 8.50 (d, J=1.2, 2H), 8.16 (d, J=5.6, 1H), 7.24 (d, J=7.1, 1H), 7.19 (d, J=8.2, 1H), 6.27 (d, J=5.7, 1H), 5.19 (s, 2H), 4.98 (s, 2H), 3.65-3.54 (m, 1H), 2.29-2.07 (m, 4H), 2.04-1.91 (m, 1H), 1.88-1.76 (m, 1H).

Example 167

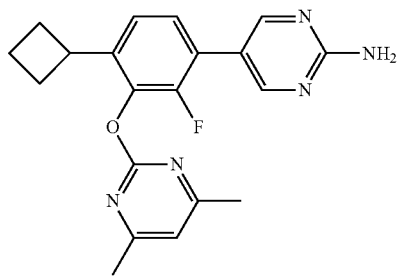 [SMILES: Cc1cc(C)nc(Oc2c(C3CCC3)ccc(-c3cnc(N)nc3)c2F)n1]

5-{4-Cyclobutyl-3-[(4,6-dimethylpyrimidin-2-yl)oxy]-2-fluorophenyl}pyrimidin-2-amine The title compound was prepared using conditions similar to those described in Example 160 heating to 80° Celsius for 3 hours and using 2-chloro-4,6-dimethylpyrimidine. MS (ESI): mass calcd. for C$_{20}$H$_{20}$FN$_5$O, 365.17; m/z found, 366.1 [M+H]$^+$. $^1$H NMR (400 MHz, CDCl$_3$) δ 8.50 (d, J=1.1, 2H), 7.25-7.16 (m, 2H), 6.76 (s, 1H), 5.19 (s, 2H), 3.77-3.65 (m, 1H), 2.39 (s, 6H), 2.27-2.06 (m, 4H), 2.01-1.88 (m, 1H), 1.85-1.75 (m, 1H).

Example 168

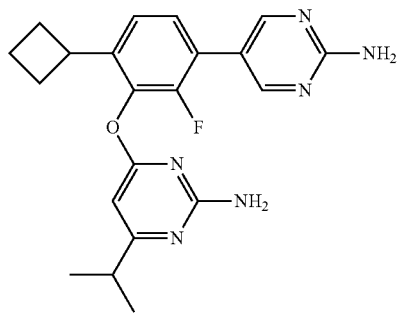 [SMILES: CC(C)c1cc(Oc2c(C3CCC3)ccc(-c3cnc(N)nc3)c2F)nc(N)n1]

4-(3-(2-aminopyrimidin-5-yl)-6-cyclobutyl-2-fluoro-phenoxy)-6-isopropylpyrimidin-2-amine The title compound was prepared using conditions similar to those described in Example 164 heating the reaction for 18 hours and using 2-amino-4-chloro-6-isopropylpyrimidine. MS (ESI): mass calcd. for $C_{21}H_{23}FN_6O$, 394.19; m/z found, 395.1 [M+H]$^+$. $^1$H NMR (400 MHz, CDCl$_3$) δ 8.45 (s, 1H), 8.04 (s, 1H), 7.76 (m, 1H), 7.20 (d, J=8.2 Hz, 1H), 6.12 (s, 1H), 5.03 (s, 2H), 4.75 (s, 2H), 3.60 (p, J=8.8, 1H), 2.85-2.71 (m, 1H), 2.30-2.06 (m, 4H), 2.05-1.90 (m, 1H), 1.89-1.74 (m, 1H), 1.24 (d, J=6.9, 6H).

Example 169

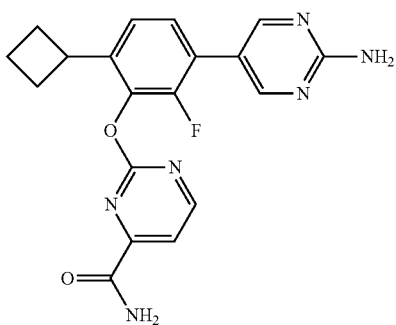 [SMILES: NC(=O)c1ccnc(Oc2c(C3CCC3)ccc(-c3cnc(N)nc3)c2F)n1]

2-[3-(2-Aminopyrimidin-5-yl)-6-cyclobutyl-2-fluorophenoxy]pyrimidine-4-carboxamide The title compound was prepared using conditions similar to those described in Example 160 heating at 80 Celsius via microwave radiation for 2 hours and using 2-chloropyrimidine-4-carboxamide. MS (ESI): mass calcd. for $C_{19}H_{17}FN_6O_2$, 380.14; m/z found, 381.0 [M+H]$^+$. $^1$H NMR (400 MHz, DMSO-d$_6$) δ 8.81 (d, J=4.9, 1H), 8.44 (s, 2H), 8.21 (s, 1H), 7.98 (s, 1H), 7.77 (d, J=4.9, 1H), 7.52-7.42 (m, 1H), 7.30 (d, J=8.2, 1H), 6.89 (s, 2H), 3.63-3.51 (m, 1H), 2.15-2.00 (m, 4H), 1.99-1.84 (m, 1H), 1.81-1.68 (m, 1H).

Example 170

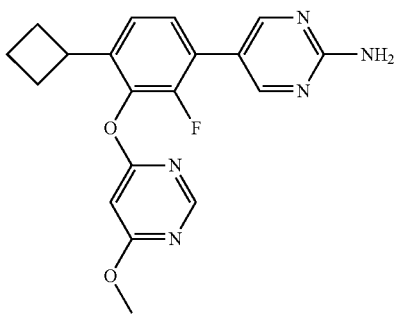 [SMILES: COc1cc(Oc2c(C3CCC3)ccc(-c3cnc(N)nc3)c2F)ncn1]

5-(4-cyclobutyl-2-fluoro-3-((6-methoxypyrimidin-4-yl)oxy)phenyl)pyrimidin-2-amine trifluoroacetate salt The title compound was prepared using conditions similar to those described in Example 164 heating the reaction at 140° Celsius for 18 hours and using 6-chloro-4-pyrimidinyl methyl ether. Both, (4-cyclobutyl-2-fluoro-3-((6-methoxypyrimidin-4-yl)oxy)phenyl)pyrimidin-2-amine trifluoroacetate salt and 6-[3-(2-Aminopyrimidin-5-yl)-6-cyclobutyl-2-fluorophenoxy]pyrimidin-4-ol trifluoroacetate (Example 171), were isolated from this reaction. MS (ESI): mass calcd. for $C_{19}H_{18}FN_5O_2$, 367.14; m/z found, 368.1 [M+H]$^+$. $^1$H NMR (400 MHz, DMSO-d$_6$) δ 8.41-8.36 (d, J=1.2, 2H), 8.33-8.26 (s, 1H), 7.44-7.34 (m, 1H), 7.26-7.17 (d, J=8.1, 1H), 7.03-6.88 (s, 1H), 5.73-5.67 (s, 1H), 3.54-3.39 (m, 1H), 2.18-1.96 (m, 4H), 1.95-1.82 (m, 1H), 1.76-1.64 (m, 1H), 3.32-3.26 (m, 3H).

Example 171

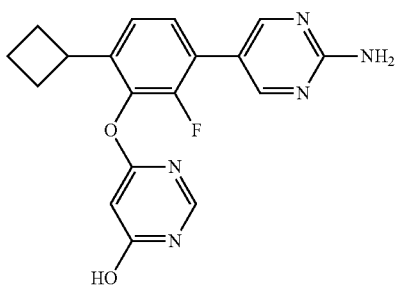 [SMILES: Nc1ncc(-c2ccc(C3CCC3)c(Oc3cc(O)ncn3)c2F)cn1]

6-[3-(2-Aminopyrimidin-5-yl)-6-cyclobutyl-2-fluorophenoxy]pyrimidin-4-ol trifluoroacetate salt Formed as an additional product in the formation of 5-(4-cyclobutyl-2-fluoro-3-((6-methoxypyrimidin-4-yl)oxy)phenyl)pyrimidin-2-amine (Example 170). MS (ESI): mass calcd. for $C_{18}H_{16}FN_5O_2$, 353.13; m/z found, 354.1 [M+H]$^+$. $^1$H NMR (400 MHz, DMSO-d$_6$) δ 12.60 (s, 1H), 8.42 (d, J=1.2, 2H), 8.07-8.01 (m, 1H), 7.42-7.34 (m, 1H), 7.20 (d, J=8.2, 1H), 7.18-6.94 (m, 2H), 5.62 (s, 1H), 3.54-3.39 (m, 1H), 2.19-1.96 (m, 4H), 1.96-1.81 (m, 1H), 1.77-1.64 (m, 1H).

Example 172

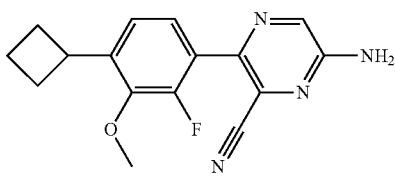 [SMILES: COc1c(C2CCC2)ccc(-c2ncc(N)nc2C#N)c1F]

6-Amino-3-(4-cyclobutyl-2-fluoro-3-methoxyphenyl)pyrazine-2-carbonitrile

The title compound was prepared using analogous conditions described in Intermediate A's Step D using (4-cyclobutyl-2-fluoro-3-methoxyphenyl)boronic acid and 2-amino-5-bromo-6-cyanopyrazine. MS (ESI): mass calcd. for $C_{16}H_{15}FN_4O$, 298.12; m/z found, 299.1 [M+H]$^+$. $^1$H NMR (600 MHz, CDCl$_3$) δ 8.21 (s, 1H), 7.21-7.16 (m, 1H), 7.16-7.10 (m, 1H), 3.86-3.76 (m, 1H), 2.39-2.30 (m, 2H), 2.21-2.09 (m, 2H), 2.09-1.98 (m, 1H), 1.91-1.81 (m, 1H).

Example 173

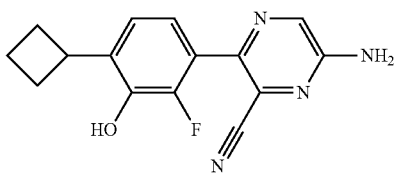

6-Amino-3-(4-cyclobutyl-2-fluoro-3-hydroxyphenyl)pyrazine-2-carbonitrile

The title compound was prepared using analogous conditions described in Intermediate B utilizing 6-amino-3-(4-cyclobutyl-2-fluoro-3-methoxyphenyl)pyrazine-2-carbonitrile. MS (ESI): mass calcd. for $C_{15}H_{13}FN_4O$, 284.11; m/z found, 285.1 [M+H]+. $^1$H NMR (600 MHz, $CD_3OD$) δ 8.17 (s, 1H), 7.13-7.07 (m, 1H), 6.95-6.90 (dd, J=8.0, 6.8, 1H), 3.89-3.79 (m, 1H), 2.43-2.33 (m, 2H), 2.25-2.14 (m, 2H), 2.13-2.01 (m, 1H), 1.92-1.83 (m, 1H).

Example 174

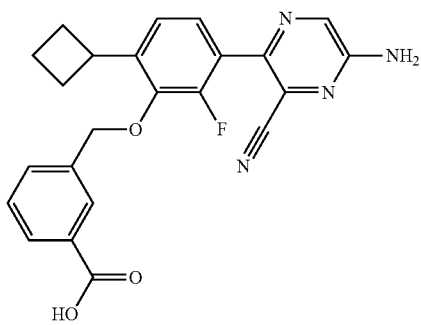 [SMILES: N#Cc1nc(N)cnc1-c1ccc(C2CCC2)c(OCc2cccc(C(=O)O)c2)c1F]

3-{[3-(5-Amino-3-cyanopyrazin-2-yl)-6-cyclobutyl-2-fluorophenoxy]methyl}benzoic acid The title compound was prepared using analogous conditions described in Example 1 using 6-amino-3-(4-cyclobutyl-2-fluoro-3-hydroxyphenyl)pyrazine-2-carbonitrile and methyl 3-(bromomethyl)benzoate. MS (ESI): mass calcd. for $C_{23}H_{19}FN_4O_3$, 418.14; m/z found, 419.1 [M+H]+. $^1$H NMR (600 MHz, DMSO-$d_6$) δ 8.22 (s, 1H), 8.09-8.05 (m, 1H), 7.96-7.91 (m, 1H), 7.73-7.68 (m, 1H), 7.57-7.52 (m, 1H), 7.36 (s, 2H), 7.33-7.26 (m, 2H), 5.09 (s, 2H), 3.80-3.70 (p, J=9.0, 1H), 2.26-2.15 (m, 2H), 2.15-2.04 (m, 2H), 1.99-1.88 (m, 1H), 1.84-1.73 (m, 1H).

Example 175

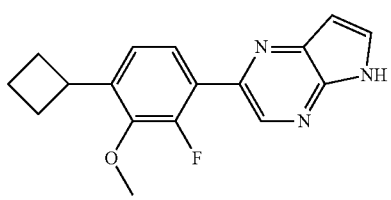 [SMILES: COc1c(C2CCC2)ccc(-c2cnc3[nH]ccc3n2)c1F]

2-(4-Cyclobutyl-2-fluoro-3-methoxyphenyl)-5H-pyrrolo[2,3-b]pyrazine

The title compound was prepared using analogous conditions described in Intermediate A Step D using (4-cyclobutyl-2-fluoro-3-methoxyphenyl)boronic acid and 5-bromo-4,7-diazaindole. MS (ESI): mass calcd. for $C_{17}H_{16}FN_3O$, 297.13; m/z found, 298.1 [M+H]+. $^1$H NMR (600 MHz, $CDCl_3$) δ 9.43-9.28 (s, 1H), 8.72-8.67 (d, J=2.6, 1H), 7.67-7.58 (m, 2H), 7.19-7.13 (m, 1H), 6.82-6.78 (dd, J=3.7, 1.9, 1H), 3.96-3.89 (d, J=1.3, 3H), 3.89-3.77 (m, 1H), 2.42-2.32 (m, 2H), 2.21-2.11 (m, 2H), 2.10-1.99 (m, 1H), 1.92-1.83 (m, 1H).

Example 176

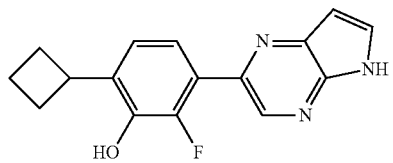

6-Cyclobutyl-2-fluoro-3-(5H-pyrrolo[2,3-b]pyrazin-2-yl)phenol

The title compound was prepared using analogous conditions described in Intermediate B starting with 2-(4-cyclobutyl-2-fluoro-3-methoxyphenyl)-5H-pyrrolo[2,3-b]pyrazine. MS (ESI): mass calcd. for $C_{16}H_{14}FN_3O$, 283.11; m/z found, 284.0 [M+H]+. $^1$H NMR (400 MHz, $CDCl_3$) δ 9.16 (s, 1H), 8.67 (d, J=2.6, 1H), 7.69-7.61 (m, 1H), 7.49-7.39 (m, 1H), 7.14 (d, J=8.1, 1H), 6.84-6.77 (m, 1H), 5.48 (s, 1H), 3.89-3.76 (m, 1H), 2.48-2.34 (m, 2H), 2.30-2.15 (m, 2H), 2.16-1.99 (m, 1H), 1.96-1.82 (m, 1H).

Example 177

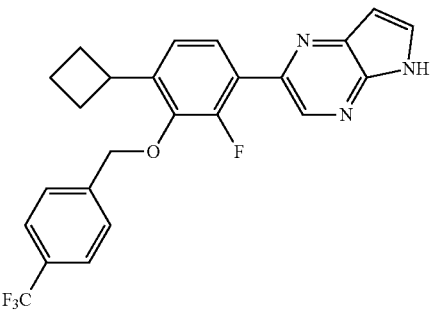 [SMILES: Fc1c(-c2cnc3[nH]ccc3n2)ccc(C2CCC2)c1OCc1ccc(C(F)(F)F)cc1]

2-(4-Cyclobutyl-2-fluoro-3-{[4-(trifluoromethyl)benzyl]oxy}phenyl)-5H-pyrrolo[2,3-b]pyrazine trifluoroacetate salt To a 5 mL vial containing a stir bar, 6-cyclobutyl-2-fluoro-3-(5H-pyrrolo[2,3-b]pyrazin-2-yl)phenol (40 mg, 0.14 mmol) and 4-(trifluoromethyl)benzyl bromide (41 mg, 0.17 mmol) were added KOH (24 mg, 0.42 mmol) and 0.78 mL of DMSO. The resultant mixture was stirred at rt for approximately 20 hours. The mixture was passed through a syringe filter and the filtrate subjected to HPLC purification affording the title compound (12 mg, 15%). MS (ESI): mass calcd. for $C_{24}H_{19}F_4N_3O$, 441.15; m/z found, 442.1 [M+H]$^+$. $^1$H NMR (400 MHz, CDCl$_3$) δ 8.95 (s, 1H), 8.64 (d, J=2.0, 1H), 7.76 (dd, J=3.5, 2.7, 1H), 7.74-7.64 (m, 3H), 7.61 (d, J=8.1, 2H), 7.28-7.23 (m, 1H), 6.92 (dd, J=3.7, 1.9, 1H), 5.14 (s, 2H), 3.82 (p, J=8.7, 1H), 2.37-2.26 (m, 2H), 2.25-2.11 (m, 2H), 2.11-1.97 (m, 1H), 1.94-1.79 (m, 1H).

Example 178

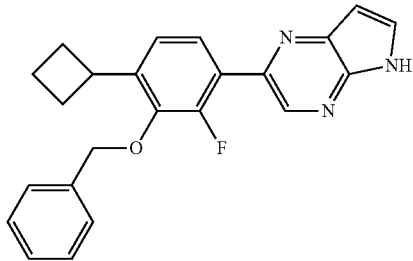 [SMILES: Fc1c(-c2cnc3[nH]ccc3n2)ccc(C2CCC2)c1OCc1ccccc1]

2-[3-(Benzyloxy)-4-cyclobutyl-2-fluorophenyl]-5H-pyrrolo[2,3-b]pyrazine

Step A 2-(3-(Benzyloxy)-4-chloro-2-fluorophenyl)-5H-pyrrolo [2,3-b] was prepared using procedures similar to those described in Example 216 utilizing 5-bromo-4,7-diazaindole. MS (ESI): mass calcd. for $C_{19}H_{13}ClFN_3O$, 353.07; m/z found, 354.1 [M+H]$^+$. $^1$H NMR (400 MHz, CDCl$_3$) δ 9.35 (s, 1H), 8.70 (d, J=2.9, 1H), 7.72-7.65 (m, 2H), 7.58-7.51 (m, 2H), 7.44-7.30 (m, 4H), 6.82 (dd, J=3.7, 1.9, 1H), 5.20 (s, 2H).

Step B

The title compound was prepared using analogous conditions described in Example 83 using 2-(3-(benzyloxy)-4-chloro-2-fluorophenyl)-5H-pyrrolo[2,3-b]pyrazine. MS (ESI): mass calcd. for $C_{23}H_{20}FN_3O$, 373.16; m/z found, 374.1 [M+H]$^+$. $^1$H NMR (400 MHz, CDCl$_3$) δ 10.09 (s, 1H), 8.66 (s, 1H), 7.76-7.65 (m, 2H), 7.51-7.46 (m, 2H), 7.45-7.33 (m, 3H), 7.24 (d, J=8.3, 1H), 6.88 (m, 1H), 5.09 (s, 2H), 3.88-3.76 (m, 1H), 2.36-2.26 (m, 2H), 2.22-2.09 (m, 2H), 2.09-1.95 (m, 1H), 1.91-1.81 (m, 1H).

Example 179

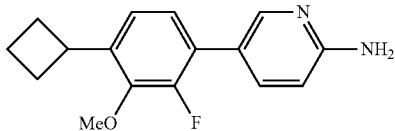

5-(4-Cyclobutyl-2-fluoro-3-methoxyphenyl)pyridin-2-amine hydrochloride salt

Solid (4-cyclobutyl-2-fluoro-3-methoxyphenyl)boronic acid (350 mg, 1.56 mmol), 2-amino-5-bromopyridine (270 mg, 1.56 mmol), and Pd(dppf)Cl$_2$.CH$_2$Cl$_2$ (102 mg, 0.16 mmol) were placed in a round-bottomed flask under nitrogen. The flask was then charged with sparged THF (7 mL), KOH (760 mg, 14 mmol), and water (2 mL). The reaction mixture was stirred at room temperature overnight, then treated with EtOAc (20 mL). The mixture was dried, filtered, and concentrated to dryness. The residue was subjected to FCC to give pure title compound. The material was converted to a hydrochloride salt by dissolving in ether (10 mL) followed by adding a solution of 4 M HCl in 1,4-dioxane (0.3 mL). The precipitate was collected by filtration, washed with ether, and dried to yield the title compound (330 mg, 78%). MS (CI): mass calcd. for $C_{16}H_{17}FN_2O$, 272.13; m/z found, 273.1 [M+H]$^+$. $^1$H NMR (500 MHz, DMSO-d$_6$) δ 14.12 (s, 1H), 8.31-8.05 (m, J=22.9, 5.6, 4H), 7.28-7.19 (m, 2H), 7.08 (d, J=9.3, 1H), 3.83 (d, J=0.8, 3H), 3.80-3.71 (m, 1H), 2.35-2.25 (m, 2H), 2.16-1.96 (m, 3H), 1.87-1.77 (m, J=18.5, 8.7, 1H).

Intermediate F

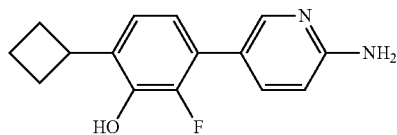 [SMILES: Nc1ccc(-c2ccc(C3CCC3)c(O)c2F)cn1]

5-(4-Cyclobutyl-2-fluoro-3-hydroxyphenyl)pyridin-2-amine

A solution consisting of 5-(4-cyclobutyl-2-fluoro-3-methoxyphenyl)pyridin-2-amine (333 mg, 1.08 mmol) and DCM (10 mL) was cooled to −78° Celsius, and then treated with 1 M BBr$_3$ in DCM (3.3 mL, 3.3 mmol) dropwise. The solution was maintained at −78° Celsius for 30 min, then warmed to room temperature and stirred overnight. The reaction mixture was poured into a beaker containing ice and saturated NaHCO$_3$, then extracted with EtOAc. The organic phase was isolated, dried and concentrated to dryness to afford the title compound. MS (CI): mass calcd. for $C_{15}H_{15}FN_2O$, 258.12; m/z found, 259.2 [M+H]$^+$. $^1$H NMR (500 MHz, DMSO-d$_6$) δ 9.29 (d, J=2.0, 1H), 8.05 (s, 1H), 7.59-7.46 (m, 1H), 7.01 (d, J=8.0, 1H), 6.82 (m, 1H), 6.52 (dd, J=8.6, 0.6, 1H), 6.10 (s, 2H), 3.77-3.66 (m, J=8.6, 1H), 2.32-2.21 (m, 2H), 2.14-2.02 (m, 2H), 2.02-1.90 (m, 1H), 1.85-1.72 (m, 1H).

Example 180

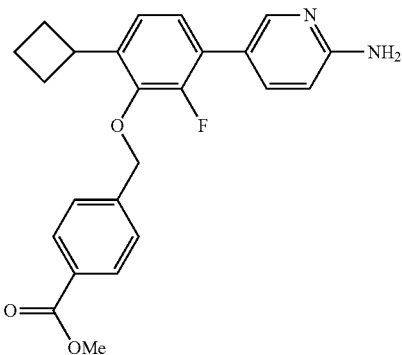

5-Methyl-4-((3-(6-aminopyridin-3-yl)-6-cyclobutyl-2-fluorophenoxy)methyl)benzoate A mixture of 5-(4-cyclobutyl-2-fluoro-3-hydroxyphenyl)pyridin-2-amine (50 mg, 0.19 mmol), Cs$_2$CO$_3$ (190 mg, 0.58 mmol), methyl 4-(bromomethyl)benzoate (56 mg, 0.25 mmol), and DMF (1 mL) was stirred at room temperature for 16 hours. The mixture was poured into water and extracted with EtOAc. The organic phase was isolated, dried, concentrated to dryness and the residue subjected to FCC to give the title compound (74 mg, 94%). MS (CI): mass calcd. for C$_{24}$H$_{23}$FN$_2$O$_3$, 406.17; m/z found, 407.3 [M+H]$^+$. $^1$H NMR (600 MHz, DMSO-d$_6$) δ 8.09 (s, 1H), 8.05-7.97 (m, 2H), 7.62 (d, J=8.4, 2H), 7.57 (d, J=8.6, 1H), 7.23-7.12 (m, 2H), 6.52 (dd, J=8.6, 0.6, 1H), 6.15 (s, 2H), 5.10 (s, 2H), 3.87 (s, 3H), 3.79-3.67 (m, J=8.8, 1H), 2.25-2.15 (m, 2H), 2.14-2.02 (m, 2H), 2.00-1.89 (m, 1H), 1.83-1.72 (m, J=8.9, 8.4, 1H).

Example 181

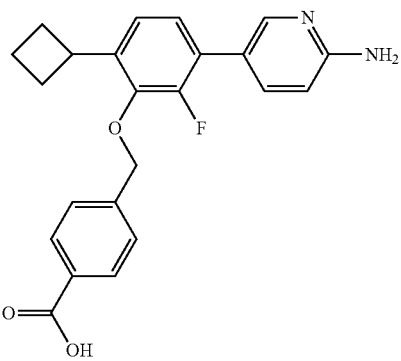 [SMILES: Nc1ccc(-c2ccc(C3CCC3)c(OCc3ccc(C(=O)O)cc3)c2F)cn1]

4-((3-(6-Aminopyridin-3-yl)-6-cyclobutyl-2-fluorophenoxy)methyl)benzoic acid A mixture of 5-methyl-4-((3-(6-aminopyridin-3-yl)-6-cyclobutyl-2-fluorophenoxy)-methyl)-benzoate (54 mg, 0.13 mmol), KOH (2 M, 0.3 mL), THF (2 mL), and MeOH (1 mL) was stirred 16 hours at room temperature. The mixture was concentrated to dryness, treated with water (2 mL) and HCl (1M, 0.75 mL). The resulting precipitate was collected, washed with water, and dried to yield the title compound (0.48 mg, 92%). MS (CI): mass calcd. for C$_{23}$H$_{21}$FN$_2$O$_3$, 392.15; m/z found, 393.3 [M+H]$^+$.

Intermediate F'

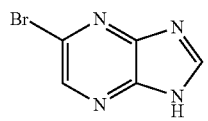

5-Bromo-1H-imidazo-[4,5-b]pyrazine

To a 50 mL round bottom flask fitted with a reflux condenser, under nitrogen were added 5-bromopyrazine-2,3-diamine (400 mg, 2.1 mmol) and triethyl orthoformate (3.1 g, 21.2 mmol). The mixture was heated to reflux and stirred for 24 h. The reaction was cooled to rt, concentrated to dryness and the residue purified by HPLC to give 320 mg (76% yield) of the title compound. MS (ESI): mass calcd. for C$_5$H$_3$BrN$_4$, 197.95; m/z found, 199.1 [M+H]$^+$.

Example 182

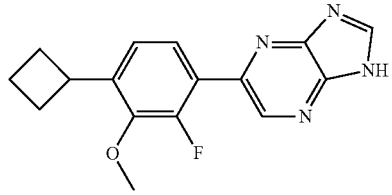 [SMILES: COc1c(C2CCC2)ccc(-c2cnc3[nH]cnc3n2)c1F]

5-(4-Cyclobutyl-2-fluoro-3-methoxyphenyl)-1H-imidazo[4,5-b]pyrazine

To a mixture of 5-bromo-1H-imidazo-[4,5-b]pyrazine (50 mg, 0.25 mmol), (4-cyclobutyl-2-fluoro-3-methoxyphenyl)boronic acid (67 mg, 0.30 mmol) and [1,1'bis(diphenylphosphino)-ferrocene]dichloropalladium(II)CH$_2$Cl$_2$ (10 mg, 0.01 mmol) in a microwave vial were added acetonitrile (2.0 mL) and sodium bicarbonate solution (saturated 2.0 mL). The reaction was de-gassed with nitrogen, vial capped and irradiated via microwave radiation for 90 min at 110° Celsius before cooling to rt. The reaction mixture was diluted with ethyl acetate (50 mL) and washed with water (25 mL) and brine (25 mL). dried (Na$_2$SO$_4$) and concentrated to dryness. The crude residue was purified by HPLC yielding the title compound (30 mg, 40%). MS (ESI): mass calcd. for C$_{16}$H$_{15}$FN$_4$O, 298.12; m/z found, 299.1 [M+H]$^+$. $^1$H NMR (400 MHz, CDCl$_3$) Complex due to the presence of multiple conformations on the NMR time-scale, peaks listed for identification purposes only: δ 11.38 (s), 10.85 (s), 9.02 (d, J=2.03), 8.91 (d, J=2.10), 8.53 (s), 7.87-7.77 (m), 7.58-7.49 (m), 7.26-7.17 (m), 3.96 (s), 3.94 (s), 3.92-3.80 (m), 2.51-2.32 (m), 2.30-1.98 (m), 1.97-1.78 (m).

Example 183

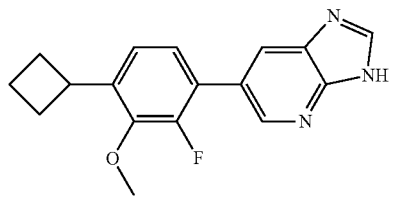

6-(4-Cyclobutyl-2-fluoro-3-methoxyphenyl)-3H-imidazo[4,5-b]pyridine

The title compound was prepared using methods analogous to those described in Example 182 using (4-cyclobutyl-2-fluoro-3-methoxyphenyl)boronic acid and 6-bromo-3H-imidazo[4,5-b]pyridine. MS (ESI): mass calcd. for C$_{17}$H$_{16}$FN$_3$O, 297.13; m/z found, 298.2 [M+H]$^+$. $^1$H NMR (400 MHz, CDCl$_3$) δ 11.41 (s, 1H), 8.62 (s, 1H), 8.30 (s, 2H), 7.22-7.12 (m, 2H), 3.94 (s, 3H), 3.92-3.78 (m, 1H), 2.48-2.33 (m, 2H), 2.29-2.00 (m, 3H), 1.97-1.79 (m, 1H).

Example 184

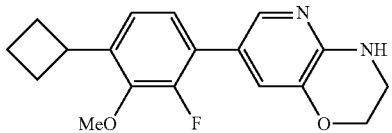

7-(4-Cyclobutyl-2-fluoro-3-methoxyphenyl)-3,4-dihydro-2H-pyrido[3,2-b][1,4]oxazine The title compound was prepared in a manner similar to that described in Example 1 using (4-cyclobutyl-2-fluoro-3-methoxyphenyl)boronic acid and 7-bromo-3,4-dihydro-2H-pyrido[3,2-b][1,4]oxazine. MS (ESI): mass calcd. for $C_{18}H_{19}FN_2O_2$, 314.14; m/z found, 315.2 [M+H]$^+$. $^1$H NMR (500 MHz, CDCl$_3$) δ 7.86 (s, 1H), 7.19 (s, 1H), 7.09-7.02 (m, 2H), 5.44 (s, 1H), 4.28-4.19 (m, 2H), 3.89 (s, 3H), 3.84-3.75 (m, 1H), 3.59 (s, 2H), 2.39-2.31 (m, 2H), 2.20-2.10 (m, 2H), 2.09-2.00 (m, 1H), 1.90-1.82 (m, 1H).

Example 185

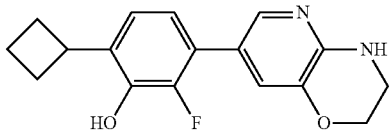

6-Cyclobutyl-3-(3,4-dihydro-2H-pyrido[3,2-b][1,4]oxazin-7-yl)-2-fluorophenol

A solution of 7-(4-cyclobutyl-2-fluoro-3-methoxyphenyl)-3,4-dihydro-2H-pyrido[3,2-b][1,4]oxazine (0.103 g, 0.328 mmol) in CH$_2$Cl$_2$ (10 mL) was cooled to −78° Celsius and treated drop wise with BBr$_3$ (1 M in CH$_2$Cl$_2$, 1.6 mL). The reaction mixture was stirred for 16 hours with gradual warming to room temperature. The mixture was concentrated to dryness, and the residue purified by HPLC to give title compound (81 mg, 82%). MS (ESI): mass calcd. for $C_{17}H_{17}FN_2O_2$, 300.13; m/z found, 301.1 [M+H]$^+$. $^1$H NMR (400 MHz, CDCl$_3$) δ 7.84 (m, 1H), 7.20 (m, 1H), 7.02 (d, J=8.1, 1H), 6.83 (m, 1H), 4.27-4.23 (m, 2H), 3.88-3.74 (m, 1H), 3.63-3.52 (m, 2H), 2.42-2.32 (m, 2H), 2.23-2.10 (m, 2H), 2.08-2.00 (m, 1H), 1.92-1.80 (m, 1H).

Example 186

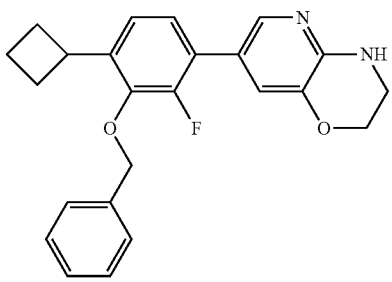 [SMILES: Fc1c(-c2cnc3c(c2)OCCN3)ccc(C2CCC2)c1OCc1ccccc1]

7-[3-(Benzyloxy)-4-cyclobutyl-2-fluorophenyl]-3,4-dihydro-2H-pyrido[3,2-b][1,4]oxazine The title compound was prepared in manner similar to that described in Example 28 using 6-cyclobutyl-3-(3,4-dihydro-2H-pyrido[3,2-b][1,4]oxazin-7-yl)-2-fluorophenol and (bromomethyl)benzene. MS (ESI): mass calcd. for $C_{24}H_{23}FN_2O_2$, 390.17; m/z found, 391.2 [M+H]$^+$. $^1$H NMR (400 MHz, CD$_3$OD) δ 7.72 (s, 1H), 7.64-7.61 (m, 1H), 7.47-7.42 (m, 2H), 7.41-7.31 (m, 3H), 7.23-7.16 (m, 2H), 5.05 (s, 2H), 4.36 (t, J=4.6, 2H), 3.81-3.73 (m, 1H), 3.73-3.65 (m, 2H), 2.31-2.20 (m, 2H), 2.17-1.95 (m, 3H), 1.87-1.79 (m, 1H).

Example 187

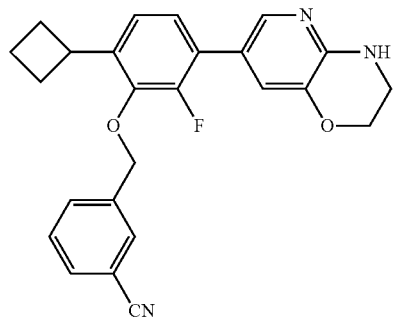 [SMILES: N#Cc1cccc(COc2c(C3CCC3)ccc(-c3cnc4c(c3)OCCN4)c2F)c1]

3-{[6-Cyclobutyl-3-(3,4-dihydro-2H-pyrido[3,2-b][1,4]oxazin-7-yl)-2-fluorophenoxy]methyl}benzonitrile The title compound was prepared in manner similar to that described in Example 28 using 6-cyclobutyl-3-(3,4-dihydro-2H-pyrido[3,2-b][1,4]oxazin-7-yl)-2-fluorophenol and 3-(bromomethyl)benzonitrile. MS (ESI): mass calcd. for $C_{25}H_{22}FN_3O_2$, 415.17; m/z found, 416.2 [M+H]$^+$. $^1$H NMR (400 MHz, CD$_3$OD) δ 7.82 (s, 1H), 7.78 (d, J=7.8, 1H), 7.74-7.70 (m, 2H), 7.68-7.64 (m, 1H), 7.59 (m, 1H), 7.27-7.20 (m, 2H), 5.12 (s, 2H), 4.40-4.33 (m, 2H), 3.84-3.68 (m, 3H), 2.34-2.24 (m, 2H), 2.20-1.97 (m, 3H), 1.90-1.81 (m, 1H).

Example 188

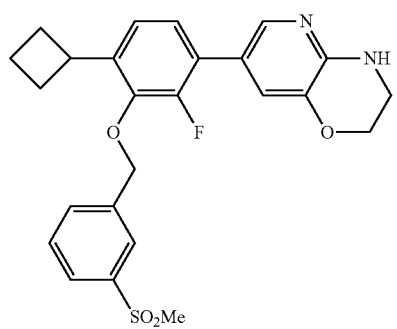

7-(4-Cyclobutyl-2-fluoro-3-{[3-(methylsulfonyl)benzyl]oxy}phenyl)-3,4-dihydro-2H-pyrido[3,2-b][1,4]oxazine The title compound was prepared in manner similar to that described in Example 28 using 6-cyclobutyl-3-(3,4-dihydro-2H-pyrido[3,2-b][1,4]oxazin-7-yl)-2-fluorophenol and 1-(bromomethyl)-3-(methylsulfonyl)benzene. MS (ESI): mass calcd. for $C_{25}H_{25}FN_2O_4S$, 468.15; m/z found, 469.1 $[M+H]^+$. $^1H$ NMR (400 MHz, $CD_3OD$) δ 8.06 (s, 1H), 7.94 (d, J=7.9, 1H), 7.81 (d, J=7.7, 1H), 7.72 (s, 1H), 7.70-7.61 (m, 2H), 7.25-7.19 (m, 2H), 5.18 (s, 2H), 4.38-4.33 (m, 2H), 3.84-3.73 (m, 1H), 3.72-3.67 (m, 2H), 3.12 (s, 3H), 2.34-2.23 (m, 2H), 2.18-1.98 (m, 3H), 1.89-1.79 (m, 1H).

Example 189

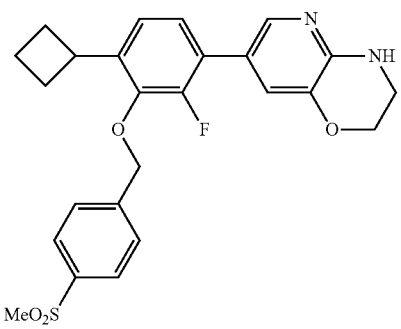 [SMILES: CS(=O)(=O)c1ccc(COc2c(C3CCC3)ccc(-c3cnc4c(c3)OCCN4)c2F)cc1]

7-(4-Cyclobutyl-2-fluoro-3-{[4-(methylsulfonyl)benzyl]oxy}phenyl)-3,4-dihydro-2H-pyrido[3,2-b][1,4]oxazine The title compound was prepared in manner similar to that described in Example 28 using 6-cyclobutyl-3-(3,4-dihydro-2H-pyrido[3,2-b][1,4]oxazin-7-yl)-2-fluorophenol and 1-(bromomethyl)-4-(methylsulfonyl)benzene. MS (ESI): mass calcd. for $C_{25}H_{25}FN_2O_4S$, 468.15; m/z found, 469.1 $[M+H]^+$. $^1H$ NMR (400 MHz, $CD_3OD$) δ 8.02-7.96 (m, 2H), 7.74 (d, J=8.4, 3H), 7.65-7.62 (m, 1H), 7.27-7.20 (m, 2H), 5.17 (s, 2H), 4.38-4.34 (m, 2H), 3.87-3.74 (m, 1H), 3.73-3.66 (m, 2H), 3.13 (d, J=3.7, 3H), 2.34-2.24 (m, 2H), 2.21-1.98 (m, 3H), 1.90-1.80 (m, 1H).

Example 190

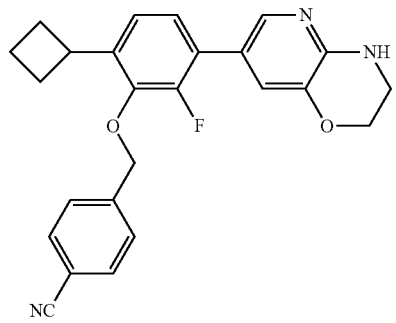 [SMILES: N#Cc1ccc(COc2c(C3CCC3)ccc(-c3cnc4c(c3)OCCN4)c2F)cc1]

4-{[6-Cyclobutyl-3-(3,4-dihydro-2H-pyrido[3,2-b][1,4]oxazin-7-yl)-2-fluorophenoxy]methyl}benzonitrile The title compound was prepared in manner similar to that described in Example 28 using 6-cyclobutyl-3-(3,4-dihydro-2H-pyrido[3,2-b][1,4]oxazin-7-yl)-2-fluorophenol and 4-(bromomethyl)benzonitrile. MS (ESI): mass calcd. for $C_{25}H_{22}FN_3O_2$, 415.17; m/z found, 416.1 $[M+H]^+$. $^1H$ NMR (400 MHz, $CD_3OD$) δ 7.80-7.75 (m, 2H), 7.72 (d, J=0.8, 1H), 7.69-7.61 (m, 3H), 7.26-7.19 (m, 2H), 5.13 (s, 2H), 4.39-4.31 (m, 2H), 3.86-3.74 (m, 1H), 3.72-3.68 (m, 2H), 2.34-2.23 (m, 2H), 2.21-1.95 (m, 3H), 1.90-1.80 (m, 1H).

Example 191

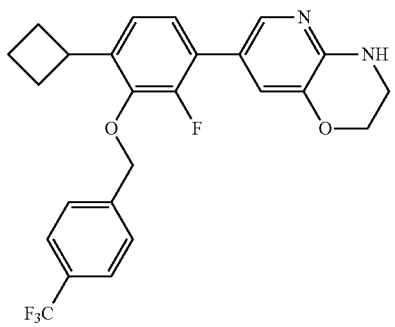

7-(4-Cyclobutyl-2-fluoro-3-{[4-(trifluoromethyl)benzyl]oxy}phenyl)-3,4-dihydro-2H-pyrido[3,2-b][1,4]oxazine The title compound was prepared in manner similar to that described in Example 28 using 6-cyclobutyl-3-(3,4-dihydro-2H-pyrido[3,2-b][1,4]oxazin-7-yl)-2-fluorophenol and 1-(bromomethyl)-4-(trifluoromethyl)benzene. MS (ESI): mass calcd. for $C_{25}H_{22}F_4N_2O_2$, 458.16; m/z found, 459.3 $[M+H]^+$. $^1H$ NMR (400 MHz, $CD_3OD$) δ 7.74-7.61 (m, 6H), 7.26-7.19 (m, 2H), 5.14 (s, 2H), 4.39-4.31 (m, 2H), 3.87-3.74 (m, 1H), 3.72-3.68 (m, 2H), 2.33-2.22 (m, 2H), 2.19-1.97 (m, 3H), 1.89-1.80 (m, 1H).

Example 192

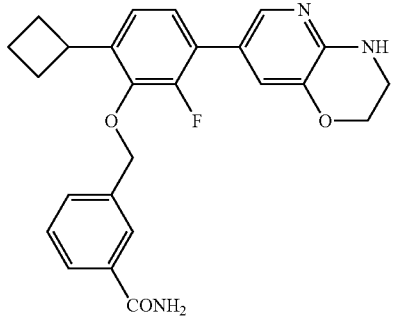 [SMILES: NC(=O)c1cccc(COc2c(C3CCC3)ccc(-c3cnc4c(c3)OCCN4)c2F)c1]

3-{[6-Cyclobutyl-3-(3,4-dihydro-2H-pyrido[3,2-b][1,4]oxazin-7-yl)-2-fluorophenoxy]methyl}benzamide The title compound was prepared in manner similar to that described in Example 28 using 6-cyclobutyl-3-(3,4-dihydro-2H-pyrido[3,2-b][1,4]oxazin-7-yl)-2-fluorophenol and 3-(bromomethyl)benzamide. MS (ESI): mass calcd. for C$_{25}$H$_{24}$FN$_3$O$_3$, 433.18; m/z found, 434.2 [M+H]$^+$. $^1$H NMR (500 MHz, MeOD) 8.01-7.97 (m, 1H), 7.88-7.83 (m, 1H), 7.74-7.71 (m, 1H), 7.67-7.60 (m, 2H), 7.53-7.47 (m, 1H), 7.23-7.19 (m, 2H), 5.14-5.10 (m, 2H), 4.38-4.33 (m, 2H), 3.83-3.75 (m, 1H), 3.72-3.67 (m, 2H), 2.32-2.22 (m, 2H), 2.17-2.07 (m, 2H), 2.06-1.96 (m, 1H), 1.88-1.80 (m, 1H).

Example 193

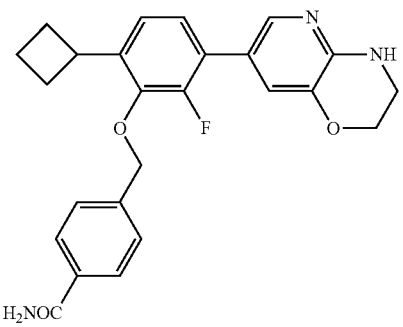

4-{[6-Cyclobutyl-3-(3,4-dihydro-2H-pyrido[3,2-b][1,4]oxazin-7-yl)-2-fluorophenoxy]methyl}benzamide The title compound was prepared in manner similar to that described in Example 28 using 6-cyclobutyl-3-(3,4-dihydro-2H-pyrido[3,2-b][1,4]oxazin-7-yl)-2-fluorophenol and 4-(bromomethyl)benzamide. MS (ESI): mass calcd. for C$_{25}$H$_{24}$FN$_3$O$_3$, 433.18; m/z found, 434.3 [M+H]$^+$. $^1$H NMR (600 MHz, CD$_3$OD) δ 7.90 (d, J=8.3, 2H), 7.72 (s, 1H), 7.62 (d, J=5.3, 1H), 7.56 (d, J=8.3, 2H), 7.23-7.20 (m, 2H), 5.12 (s, 2H), 4.37-4.34 (m, 2H), 3.82-3.76 (m, 1H), 3.72-3.69 (m, 2H), 2.31-2.24 (m, 2H), 2.17-2.11 (m, 2H), 2.06-1.99 (m, 1H), 1.88-1.81 (m, 1H).

Example 194

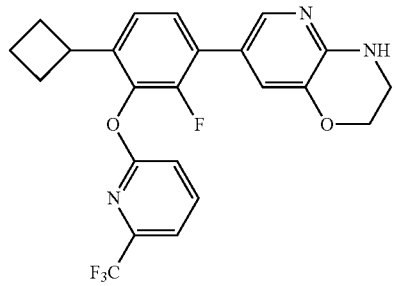

7-(4-Cyclobutyl-2-fluoro-3-{[6-(trifluoromethyl)pyridin-2-yl]oxy}phenyl)-3,4-dihydro-2H-pyrido[3,2-b][1,4]oxazine The title compound was prepared in manner similar to that described in Example 28 using 6-cyclobutyl-3-(3,4-dihydro-2H-pyrido[3,2-b][1,4]oxazin-7-yl)-2-fluorophenol and 2-bromo-6-(trifluoromethyl)pyridine. MS (ESI): mass calcd. for C$_{23}$H$_{19}$F$_4$N$_3$O$_2$, 445.14; m/z found, 446.1 [M+H]$^+$. $^1$H NMR (600 MHz, CD$_3$OD) δ 8.05 (m, 1H), 7.71 (d, J=1.4, 1H), 7.62-7.59 (m, 1H), 7.51 (d, J=7.4, 1H), 7.42 (m, 1H), 7.36-7.30 (m, 2H), 4.37-4.33 (m, 2H), 3.72-3.68 (m, 2H), 3.67-3.61 (m, 1H), 2.22-2.09 (m, 4H), 2.03-1.92 (m, 1H), 1.85-1.76 (m, 1H).

Example 195

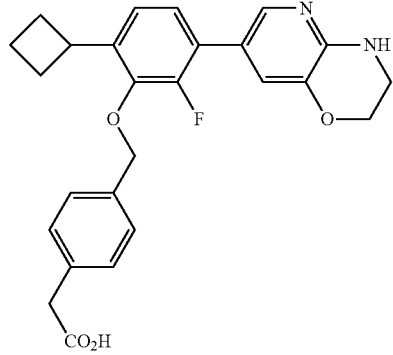 [SMILES: O=C(O)Cc1ccc(COc2c(C3CCC3)ccc(-c3cnc4c(c3)OCCN4)c2F)cc1]

(4-{[6-Cyclobutyl-3-(3,4-dihydro-2H-pyrido[3,2-b][1,4]oxazin-7-yl)-2-fluorophenoxy]methyl}phenyl)acetic acid A solution of 6-cyclobutyl-3-(3,4-dihydro-2H-pyrido[3,2-b][1,4]oxazin-7-yl)-2-fluorophenol (50 mg, 0.17 mmol) and 2-(4-(bromomethyl)phenyl)acetic acid (38 mg, 0.17 mmol) in DMSO (1 mL) was treated with potassium tert-butoxide (38 mg, 0.33 mmol) and stirred for 16 hours at 80° Celsius. The reaction was then cooled to rt, filtered, and the filtrate subjected directly to HPLC purification to give (4-{[6-cyclobutyl-3-(3,4-dihydro-2H-pyrido[3,2-b][1,4]oxazin-7-yl)-2-fluorophenoxy]methyl}phenyl)acetic acid (8 mg, 9%). MS (ESI): mass calcd. for C$_{25}$H$_{25}$FN$_2$O$_4$, 448.18; m/z found, 449.2 [M+H]$^+$. $^1$H NMR (600 MHz, CD$_3$OD) δ 7.72 (s, 1H), 7.60 (s, 1H), 7.40 (d, J=8.1, 2H), 7.31 (d, J=8.1, 2H), 7.19 (d, J=6.0, 2H), 5.04 (s, 2H), 4.38-4.32 (m, 2H), 3.78-3.72 (m, 1H), 3.71-3.67 (m, 2H), 3.63 (s, 2H), 2.29-2.22 (m, 2H), 2.16-2.07 (m, 2H), 2.04-1.97 (m, 1H), 1.84 (t, J=9.6, 1H).

Example 196

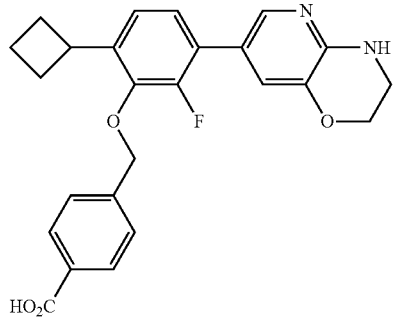 [SMILES: O=C(O)c1ccc(COc2c(C3CCC3)ccc(-c3cnc4c(c3)OCCN4)c2F)cc1]

4-{[6-Cyclobutyl-3-(3,4-dihydro-2H-pyrido[3,2-b][1,4]oxazin-7-yl)-2-fluorophenoxy]methyl}benzoic acid Prepared in a manner similar to that described in Example 195 by reaction of 6-cyclobutyl-3-(3,4-dihydro-2H-pyrido[3,2-b][1,4]oxazin-7-yl)-2-fluorophenol 4-(bromomethyl)benzoic acid. MS (ESI): mass calcd. for $C_{25}H_{23}FN_2O_4$, 434.16; m/z found, 435.1 [M+H]$^+$. $^1$H NMR (600 MHz, CD$_3$OD) δ 8.07-8.03 (m, 2H), 7.73 (d, J=1.3, 1H), 7.66-7.64 (m, 1H), 7.57 (d, J=8.4, 2H), 7.22 (d, J=4.4, 2H), 5.13 (s, 2H), 4.368-4.35 (m, 2H), 3.83-3.76 (m, 1H), 3.74-3.69 (m, 2H), 2.31-2.25 (m, 2H), 2.17-2.09 (m, 2H), 2.06-1.98 (m, 1H), 1.88-1.81 (m, 1H).

Example 197

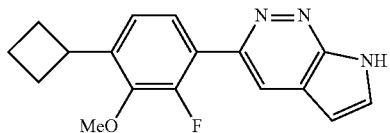

3-(4-Cyclobutyl-2-fluoro-3-methoxyphenyl)-7H-pyrrolo[2,3-c]pyridazine

The title compound was prepared in a manner similar to that described in Example 1 using (4-cyclobutyl-2-fluoro-3-methoxyphenyl)boronic acid and 3-chloro-7H-pyrrolo[2,3-c]pyridazine. MS (ESI): mass calcd. for $C_{17}H_{16}FN_3O$, 297.13; m/z found, 298.1 [M+H]$^+$. $^1$H NMR (500 MHz, CDCl$_3$) δ 12.05 (s, 1H), 8.15 (d, J=2.2, 1H), 7.80 (d, J=3.4, 1H), 7.71 (m, 1H), 7.21 (d, J=8.1, 1H), 6.61 (d, J=3.4, 1H), 3.94 (d, J=1.2, 3H), 2.44-2.35 (m, 2H), 2.25-2.14 (m, 2H), 2.13-2.05 (m, 1H), 1.81 (d, J=7.1, 2H).

Example 198

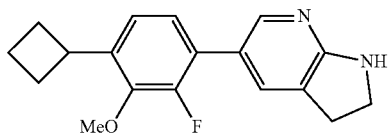

5-(4-Cyclobutyl-2-fluoro-3-methoxyphenyl)-2,3-dihydro-1H-pyrrolo[2,3-b]pyridine

A reaction flask containing 5-bromo-2,3-dihydro-1H-pyrrolo[2,3-b]pyridine (0.5 g, 2.5 mmol), (4-cyclobutyl-2-fluoro-3-methoxyphenyl)boronic acid (0.563 g, 2.51 mmol), potassium carbonate (1.041 g, 7.54 mmol), and [1,1'-bis(diphenylphosphino)ferrocene]-dichloropalladium(II) ♦ CH$_2$Cl$_2$ (0.093 g, 0.13 mmol) was sealed and the atmosphere exchanged with N$_2$ (3×). The flask was charged with freshly sparged DMF (2 mL), toluene (5 mL), and deionized H$_2$O (5 mL). The mixture was heated for 16 hours at 80° Celsius. The reaction mixture was cooled to room temperature, diluted with EtOAc (50 mL) and washed with brine (3×50 mL). The organic layer was isolated, dried over MgSO$_4$, filtered, and concentrated to dryness. The residue was purified by FCC to give the title compound (0.605 g, 81%). MS (ESI): mass calcd. for $C_{18}H_{19}FN_2O$, 298.15; m/z found, 299.2 [M+H]$^+$. $^1$H NMR (400 MHz, CDCl$_3$) δ 7.98 (d, J=0.9 Hz, 1H), 7.44 (s, 1H), 7.09-7.01 (m, 2H), 4.62 (s, 1H), 3.89 (d, J=1.3 Hz, 3H), 3.85-3.74 (m, 1H), 3.72-3.63 (m, 2H), 3.12 (t, J=8.4 Hz, 2H), 2.41-2.30 (m, 2H), 2.22-1.99 (m, 3H), 1.95-1.81 (m, 1H).

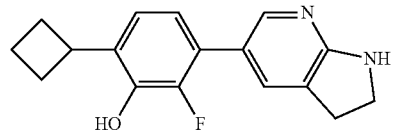 [SMILES: Oc1c(C2CCC2)ccc(-c2cnc3c(c2)CCN3)c1F]

Example 199

6-Cyclobutyl-3-(2,3-dihydro-1H-pyrrolo[2,3-b]pyridin-5-yl)-2-fluorophenol

Prepared in a manner similar to that described in Example 185 by reaction of 5-(4-cyclobutyl-2-fluoro-3-methoxyphenyl)-2,3-dihydro-1H-pyrrolo[2,3-b]pyridine. MS (ESI): mass calcd. for $C_{17}H_{17}FN_2O$, 284.13; m/z found, 285.2 [M+H]$^+$. $^1$H NMR (400 MHz, CD$_3$OD) δ 7.82-7.76 (m, 1H), 7.64 (s, 1H), 7.06 (d, J=8.0, 1H), 6.86 (m, 1H), 3.95 (t, J=8.3, 2H), 3.85-3.72 (m, 1H), 3.30-3.22 (m, 2H), 2.41-2.29 (m, 2H), 2.21-1.99 (m, 3H), 1.90-1.81 (m, 1H).

Intermediate G

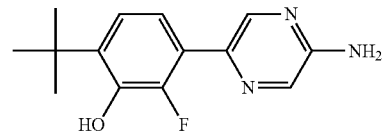 [SMILES: CC(C)(C)c1ccc(-c2cnc(N)cn2)c(F)c1O]

3-(5-Aminopyrazin-2-yl)-6-tert-butyl-2-fluorophenol

Step A

To a 100 mL round-bottomed flask were added a stir bar, 2-(1,1-dimethylethyl)-6-fluorophenol (2.62 g, 15.6 mmol), tert-butyldimethylchlorosilane (4.84 g, 31.1 mmol), imidazole (1.46 g, 21.5 mmol) and dry DMF (48 mL). The flask was purged with nitrogen and heated at 60° Celsius for 24 hours. The mixture was cooled to room temperature and then partitioned between EtOAc and water. The EtOAc layer was washed with water followed by brine. The organic layer was dried over Na$_2$SO$_4$ and concentrated. Purification by FCC yielded tert-butyl(2-(tert-butyl)-6-fluorophenoxy)dimethylsilane (4.2 g, 96%). $^1$H NMR (600 MHz, CDCl$_3$) δ 7.04 (m, 1H), 6.92 (m, 1H), 6.77 (m, 1H), 1.56 (s, 6H), 1.39 (s, 9H), 1.01 (d, J=0.7, 9H).

Step B

To a 100 mL round-bottomed flask were added a stir bar, dry THF (15.0 mL) and 2,2,6,6-tetramethylpiperidine (2.3 mL, 13.6 mmol). The flask was cooled to −78° C. (bath temp) and then treated with 2.5 M n-BuLi in hexanes (5.46 mL, 13.6 mmol) over 2 min. The resultant mixture was stirred for 5 min and then warmed to 0° Celsius. After 65 min, the mixture was re-cooled to −78° Celsius and treated with B(O-iPr)$_3$ (17.5 mL, 13.6 mmol) over 4 min. After 20 min, a solution consisting of tert-butyl(2-(tert-butyl)-6-fluorophenoxy)dimethylsilane (2.57 g, 9.1 mmol) and dry THF (5.0 mL) was added over the course of 2 min and stirring continued for 3 hours. The reaction was gradually warmed to room temperature while stirring for 18 hours, after which time, HOAc (5.2 mL, 91 mmol) was added. The mixture was then poured into water and stirred for 5 min. The aqueous mixture was then extracted with EtOAc (200 mL), the extract dried over Na$_2$SO$_4$, filtered and concentrated to dryness. Purification by FCC yielded (4-(tert-butyl)-3-((tert-butyldimethylsilyl)oxy)-2-fluorophenyl)boronic acid (2.13 g, 72%).

Step C (4-(ter-Butyl)-3-((tert-butyldimethylsilyl)oxy)-2-fluorophenyl)boronic acid was coupled to 2-amino-5-bromopyrazine in an analogous manner to Step D in Intermediate A to give the title compound (658 mg, 78%). MS (ESI): mass calcd. for C$_{14}$H$_{16}$FN$_3$O, 261.13; m/z found, 262.1 [M+H]$^+$. $^1$H NMR (400 MHz, DMSO-d$_6$) δ 9.38 (d, J=3.2, 1H), 8.21 (dd, J=2.3, 1.5, 1H), 7.93 (d, J=1.5, 1H), 7.11 (m, 1H), 6.98 (d, J=8.4, 1H), 6.56 (s, 2H), 1.32 (s, 9H).

Example 200

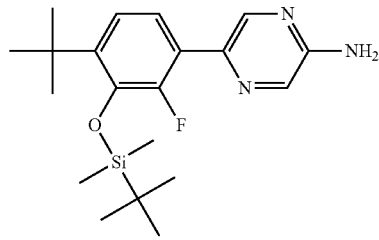 [SMILES: CC(C)(C)c1ccc(-c2cnc(N)cn2)c(F)c1O[Si](C)(C)C(C)(C)C]

5-(4-tert-Butyl-3-{[tert-butyl(dimethyl)silyl]oxy}-2-fluorophenyl)pyrazin-2-amine The title compound was formed as an additional product in the synthesis of Intermediate E in Step C (56 mg 5%) yield. MS (ESI): mass calcd. for C$_{20}$H$_{30}$FN$_3$OSi, 375.21; m/z found, 376.2 [M+H]$^+$. $^1$H NMR (400 MHz, CDCl$_3$) δ 8.47-8.40 (m, 1H), 8.09 (d, J=1.4, 1H), 7.35-7.28 (m, 1H), 7.13 (dd, J=8.5, 1.5, 1H), 4.62 (s, 2H), 1.41 (s, 9H), 1.02 (d, J=0.7, 9H), 0.34 (d, J=4.3, 6H).

Example 201

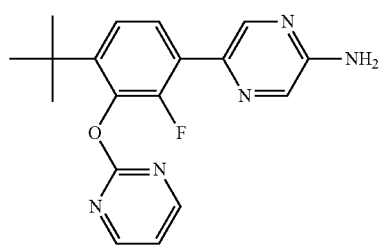

5-[4-tert-Butyl-2-fluoro-3-(pyrimidin-2-yloxy)phenyl]pyrazin-2-amine

The title compound was prepared using conditions similar to those described in Example 160 heating for 4 hours at 120° Celsius and using Intermediate G. MS (ESI): mass calcd. for C$_{18}$H$_{18}$FN$_5$O, 339.15; m/z found, 340.0 [M+H]$^+$. $^1$H NMR (400 MHz, DMSO-d$_6$) δ 8.69 (d, J=4.8, 2H), 8.22 (s, 1H), 8.00 (d, J=1.4, 1H), 7.71-7.62 (m, 1H), 7.35-7.26 (m, 2H), 6.68 (s, 2H), 1.30 (s, 9H).

Example 202

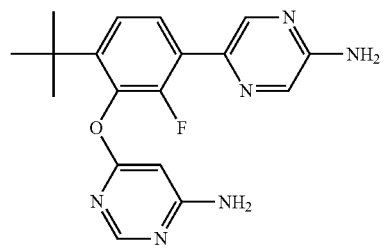

6-[3-(5-Aminopyrazin-2-yl)-6-tert-butyl-2-fluorophenoxy]pyrimidin-4-amine

The title compound was prepared using conditions similar to those described in Example 164 heating for 5 hours at 120° Celsius using Intermediate G and 4-amino-6-chloropyrimidine. MS (ESI): mass calcd. for C$_{18}$H$_{19}$FN$_6$O, 354.16; m/z found, 355.1 [M+H]$^+$. $^1$H NMR (400 MHz, DMSO-d$_6$) δ 8.23 (s, 1H), 8.08-7.99 (m, 2H), 7.65 (m, 1H), 7.29 (d, J=8.6, 1H), 6.92 (s, 2H), 6.71 (s, 2H), 5.94 (s, 1H), 1.30 (s, 9H).

Example 203

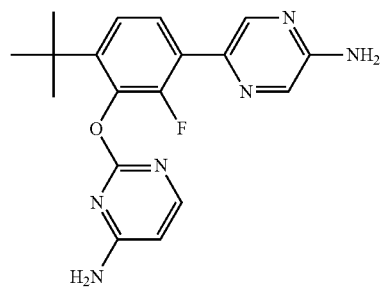

2-[3-(5-Aminopyrazin-2-yl)-6-tert-butyl-2-fluorophenoxy]pyrimidin-4-amine

The title compound was prepared using conditions similar to those described in Example 164 heating for 15 hours at 140° Celsius using Intermediate G and 4-amino-2-chloropyrimidine. MS (ESI): mass calcd. for C$_{18}$H$_{19}$FN$_6$O, 354.16; m/z found, 355.0 [M+H]$^+$. $^1$H NMR (600 MHz, CD$_3$OD) δ 8.25 (s, 1H), 8.04 (d, J=1.4, 1H), 7.88 (d, J=5.9, 1H), 7.66-7.59 (m, 1H), 7.30 (dd, J=8.6, 1.2, 1H), 6.24 (d, J=5.9, 1H), 1.37 (s, 9H).

Example 204

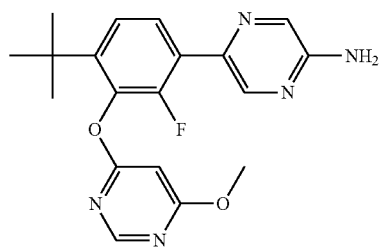 [SMILES: COc1cc(Oc2c(C(C)(C)C)ccc(-c3cnc(N)cn3)c2F)ncn1]

5-{4-tert-Butyl-2-fluor-3-[(6-methoxypyrimidin-4-yl)oxy]phenyl}pyrazin-2-amine

The title compound was prepared using conditions similar to those described in Example 164 heating for 3 hours at 120° Celsius using Intermediate G and 6-chloro-4-pyrimidinyl methyl ether giving title compound and Example 205. MS (ESI): mass calcd. for $C_{19}H_{20}FN_5O_2$, 369.16; m/z found, 370.1 [M+H]$^+$. $^1$H NMR (400 MHz, CDCl$_3$) δ 8.46-8.42 (m, 1H), 8.08 (d, J=1.5, 1H), 7.98 (s, 1H), 7.78-7.69 (m, 1H), 7.32-7.27 (m, 1H), 5.90 (s, 1H), 4.67 (s, 2H), 3.51 (s, 3H), 1.37 (s, 9H).

Example 205

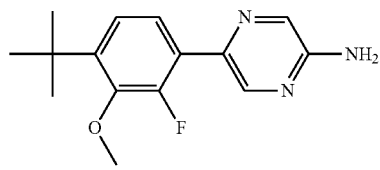

5-(4-tert-Butyl-2-fluoro-3-methoxyphenyl)pyrazin-2-amine

Title compound was formed as an additional product from the preparation of Example 204. MS (ESI): mass calcd. for $C_{15}H_{18}FN_3O$, 275.14; m/z found, 276.1 [M+H]$^+$. $^1$H NMR (400 MHz, CDCl$_3$) δ 8.50-8.45 (m, 1H), 8.09 (d, J=1.5, 1H), 7.48-7.40 (m, 1H), 7.17-7.09 (m, 1H), 4.64 (s, 2H), 3.99 (d, J=2.2, 3H), 1.40 (s, 9H).

Intermediate H

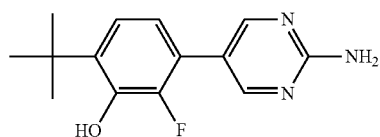 [SMILES: CC(C)(C)c1ccc(-c2cnc(N)nc2)c(F)c1O]

3-(2-Aminopyrimidin-5-yl)-6-tert-butyl-2-fluorophenol

The title compound was prepared using conditions similar to those described Intermediate E using 2-amino-5-bromopyrimidine in Step C. MS (ESI): mass calcd. for $C_{14}H_{16}FN_3O$, 261.13; m/z found, 262.0 [M+H]$^+$. $^1$H NMR (400 MHz, DMSO-d$_6$) δ 9.48 (s, 1H), 8.39 (d, J=1.5, 2H), 7.02 (dd, J=8.3, 1.3, 1H), 6.89-6.76 (m, 3H), 1.37 (s, 9H).

Example 206

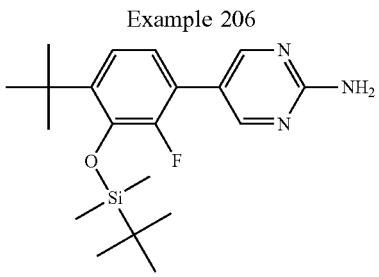

5-(4-tert-Butyl-3-{[tert-butyl(dimethyl)silyl]oxy}-2-fluorophenyl)pyrimidin-2-amine Formed as an additional product during formation of Intermediate F in Step C. MS (ESI): mass calcd. for $C_{20}H_{30}FN_3OSi$, 375.21; m/z found, 376.0 [M+H]$^+$. $^1$H NMR (400 MHz, CDCl$_3$) δ 8.53-8.40 (m, 2H), 7.15-7.08 (m, 1H), 6.87-6.77 (m, 1H), 5.22 (s, 2H), 1.41 (s, 9H), 1.01 (s, 9H), 0.33 (d, J=4.2, 6H).

Example 207

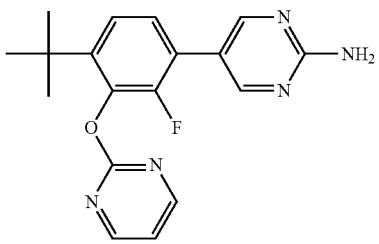

5-[4-tert-Butyl-2-fluoro-3-(pyrimidin-2-yloxy)phenyl]pyrimidin-2-amine

The title compound was prepared using conditions similar to those described in Example 160 heating at 120° Celsius for 2 hours and using Intermediate H. MS (ESI): mass calcd. for $C_{18}H_{18}FN_5O$, 339.15; m/z found, 340.0 [M+H]J. $^1$H NMR (400 MHz, DMSO-d$_6$) δ 8.68 (d, J=4.8, 2H), 8.41 (d, J=1.4, 2H), 7.43-7.35 (m, 1H), 7.35-7.25 (m, 2H), 6.88 (s, 2H), 1.30 (s, 9H).

Example 208

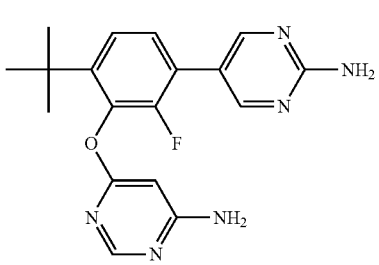

5-{3-[(6-Aminopyrimidin-4-yl)oxy]-4-tert-butyl-2-fluorophenyl}pyrimidin-2-amine

The title compound was prepared using conditions similar to those described in Example 164 heating for 15 hours at 140° Celsius using Intermediate H and 4-amino-6-chloropyrimidine. MS (ESI): mass calcd. for $C_{18}H_{19}FN_6O$, 354.16; m/z found, 355.0 [M+H]$^+$. $^1$H NMR (400 MHz, DMSO-d$_6$) δ 8.41 (d, J=1.0, 2H), 8.04 (s, 1H), 7.41-7.32 (m, 1H), 7.27 (d, J=8.4, 1H), 6.89 (d, J=4.5, 4H), 5.97-5.89 (m, 1H), 1.30 (s, 9H).

Example 209

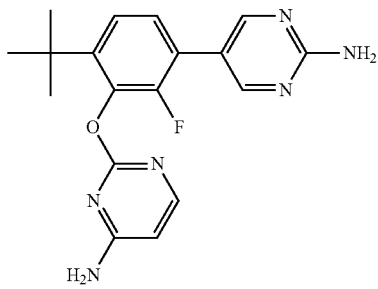

5-{3-[(4-Aminopyrimidin-2-yl)oxy]-4-tert-butyl-2-fluorophenyl}pyrimidin-2-amine

The title compound was prepared using conditions similar to those described in Example 164 heating for 13 hours at 140° Celsius using Intermediate H and 4-amino-2-chloropyrimidine. MS (ESI): mass calcd. for $C_{18}H_{19}FN_6O$, 354.16; m/z found, 355.0 [M+H]$^+$. $^1$H NMR (400 MHz, CDCl$_3$) δ 8.46 (d, J=1.2, 2H), 8.02 (d, J=5.7, 1H), 7.29-7.24 (m, 1H), 7.18-7.09 (m, 1H), 6.12 (d, J=5.7, 1H), 4.98 (s, 2H), 4.80 (s, 2H), 1.40 (s, 9H).

Example 210

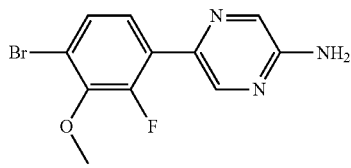

5-(4-Bromo-2-fluoro-3-methoxyphenyl)pyrazin-2-amine

Step A:
(4-Bromo-2-fluoro-3-methoxyphenyl)boronic acid

A solution of 2,2,6,6-tetramethylpiperidine TMP (0.98 ml, 5.76 mmol) in THF (9.8 ml) was cooled to −78° Celsius under N$_2$. To the solution was then added n-BuLi (2.21 N in hexanes, 2.45 mL, 5.41 mmol) slowly over the course of a couple of min. The mixture was then warmed to 0° Celsius for 20-30 min and treated with triisopropyl borate (1.25 ml, 5.41 mmol) was added. After 5 min, 1-bromo-3-fluoro-2-methoxybenzene (1.0 g, 4.9 mmol) was slowly added and the reaction was stirred at −78° Celsius. After 1.5 hours, the resulting mixture was warmed to room temperature with AcOH (2.8 ml, 49 mmol), poured into water, and extracted with EtOAc. The organic extract was isolated, dried over MgSO$_4$, filtered and concentrated to dryness to yield (5-(4-bromo-2-fluoro-3-methoxyphenyl)pyrazin-2-yl)boronic acid as a solid (940 mg, 77%) that was used without further purification.

Step B

A mixture of the crude (4-bromo-2-fluoro-3-methoxyphenyl)boronic acid (940 mg, 1.69 mmol) and 5-bromopyrazin-2-amine (1.31 g, 7.56 mmol) was treated with EtOH (12.4 ml) and toluene (12.8 ml) The resulting suspension was then treated with aqueous Na$_2$CO$_3$ (2.0 N, 9.44 ml, 18.9 mmol). The resulting mixture was then sparged with nitrogen for 10 min, before adding Pd(PPh$_3$)$_4$ (218 mg, 0.189 mmol) and heating at 80° Celsius for 17 hours. The reaction was cooled to room temperature and partitioned between saturated NH$_4$Cl and EtOAc. The organic layer was dried over MgSO$_4$ and concentrated to dryness. The residue was suspended in DCM was and the resultant solid isolated by filtration to afford the title compound (300 mg, 27%), which was used without further purification. Additional product was obtained by concentrating the DCM layer and subjecting the residue to FCC to afford the title compound (560 mg, 50%). MS (ESI): mass calcd. for $C_{11}H_9BrFN_3O$, 296.99; m/z found, 298.0 [M+H]$^+$. $^1$H NMR (500 MHz, DMSO-d$_6$) δ 8.34 (dd, J=2.6, 1.5, 1H), 8.00 (d, J=1.5, 1H), 7.54-7.49 (m, 2H), 6.78 (s, 2H), 3.90 (d, J=0.6, 3H).

Example 211

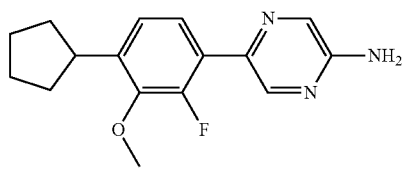 [SMILES: COc1c(C2CCCC2)ccc(-c2cnc(N)cn2)c1F]

5-(4-Cyclopentyl-2-fluoro-3-methoxyphenyl)pyrazin-2-amine

A microwave vial was charged with 5-(4-bromo-2-fluoro-3-methoxyphenyl)-pyrazin-2-amine (50 mg, 0.17 mmol), palladium acetate (2.9 mg, 0.013 mmol) and 2-dicyclohexylphosphine-2',6'-dimethoxy-1,1'-biphenyl (7.7 mg, 0.018 mmol). The vial was evacuated and back filled with nitrogen. Cyclopentylzinc bromide (0.5 M in THF, 0.67 ml, 0.34 mmol) was then added and the mixture heated at 70° Celsius for 19 hours. The reaction was cooled to rt and the mixture subjected to HPLC purification to afford the title compound (7 mg, 15%). MS (ESI): mass calcd. for $C_{16}H_{18}FN_3O$, 287.14; m/z found, 288.1 [M+H]$^+$. $^1$H NMR (500 MHz, CDCl$_3$) δ 8.50-8.46 (m, 1H), 8.09 (d, J=1.5, 1H), 7.54-7.48 (m, 1H), 7.09 (dd, J=8.3, 1.1, 1H), 4.65 (s, 2H), 3.94 (d, J=1.2, 3H), 3.42-3.33 (m, 1H), 2.11-1.99 (m, 2H), 1.88-1.78 (m, 2H), 1.77-1.66 (m, 2H), 1.59-1.53 (m, 2H).

Example 212

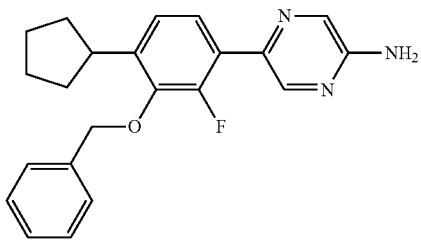

5-[3-(Benzyloxy)-4-cyclopentyl-2-fluorophenyl]
pyrazin-2-amine

The title compound was prepared using analogous conditions described in Example 83 using cyclopentylzinc bromide (0.5 M solution in THF). MS (ESI): mass calcd. for $C_{22}H_{22}FN_3O$, 363.17; m/z found, 364.2 [M+H]$^+$. $^1$H NMR (400 MHz, CDCl$_3$) δ 8.50 (s, 1H), 8.10 (s, 1H), 7.58-7.51 (m, 1H), 7.51-7.45 (m, 2H), 7.43-7.32 (m, 3H), 7.10 (dd, J=8.3, 1.1, 1H), 5.09 (s, 2H), 4.66 (s, 2H), 3.43-3.31 (m, 1H), 2.00-1.89 (m, 2H), 1.84-1.72 (m, 2H), 1.71-1.47 (m, 4H).

Example 213

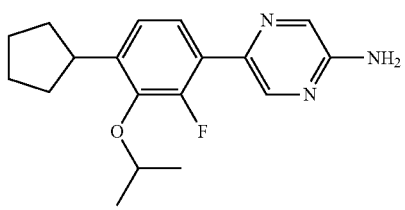 [SMILES: CC(C)Oc1c(C2CCCC2)ccc(-c2cnc(N)cn2)c1F]

5-[4-Cyclopentyl-2-fluoro-3-(1-methylethoxyl)phenyl]pyrazin-2-amine

Step A 5-(4-Chloro-2-fluoro-3-isopropoxyphenyl)pyrazin-2-amine was prepared using procedures similar to those described in Example 216 utilizing 4-chloro-2-fluoro-3-isopropoxyphenylboronic acid. MS (ESI): mass calcd. for $C_{13}H_{13}ClFN_3O$, 281.07; m/z found, 282.0 [M+H]$^+$. $^1$H NMR (400 MHz, CDCl$_3$) δ 8.32 (d, J=3.6, 2H), 7.60 (m, 1H), 7.31-7.22 (m, 1H), 4.52 (m, 1H), 1.41-1.38 (m, 6H).

Step B

The title compound was prepared using analogous conditions described in Example 83 using 5-(4-chloro-3-isopropoxyphenyl)pyrazin-2-amine and cyclopentylzinc bromide (0.5 M solution in THF). MS (ESI): mass calcd. for $C_{18}H_{22}FN_3O$, 315.17; m/z found, 316.1 [M+H]$^+$. $^1$H NMR (500 MHz, CDCl$_3$) δ 8.48-8.45 (m, 1H), 8.08 (d, J=1.5, 1H), 7.52-7.46 (m, 1H), 7.10 (dd, J=8.3, 1.2, 1H), 4.64 (s, 2H), 4.48-4.38 (m, 1H), 3.49-3.40 (m, 1H), 2.10-2.01 (m, 2H), 1.88-1.79 (m, 2H), 1.75-1.67 (m, 2H), 1.58-1.48 (m, 3H), 1.35 (dd, J=6.1, 0.6, 6H).

Example 214

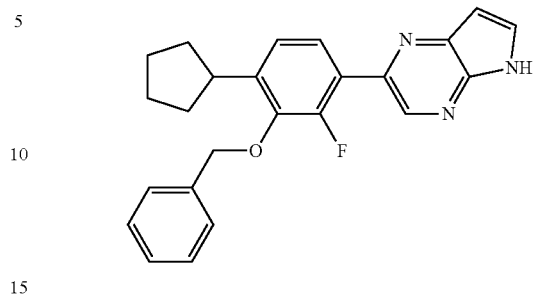

2-[3-(Benzyloxy)-4-cyclopentyl-2-fluorophenyl]-
5H-pyrrolo[2,3-b]pyrazine

Step A

2-[3-(Benzyloxy)-4-chloro-2-fluorophenyl)-5H-pyrrolo[2,3-b]pyrazine] was prepared using procedures similar to those described in Example 216 utilizing 5-bromo-4,7-diazaindole. MS (ESI): mass calcd. for $C_1H_{13}ClFN_3O$, 353.07; m/z found, 354.1 [M+H]$^+$. $^1$H NMR (400 MHz, CDCl$_3$) δ 9.35 (s, 1H), 8.70 (d, J=2.9, 1H), 7.72-7.65 (m, 2H), 7.58-7.51 (m, 2H), 7.44-7.30 (m, 4H), 6.82 (dd, J=3.7, 1.9, 1H), 5.20 (s, 2H).

Step B

The title compound was prepared using analogous conditions described in Example 83 using 2-(3-(benzyloxy)-4-chloro-2-fluorophenyl)-5H-pyrrolo[2,3-b]pyrazine and cyclopentylzinc bromide (0.5 M solution in THF). MS (ESI): mass calcd. for $C_{24}H_{22}FN_3O$, 387.1747; m/z found, 388.2 [M+H]$^+$. $^1$H NMR (400 MHz, CDCl$_3$) δ 9.26 (s, 1H), 8.73 (d, J=2.8, 1H), 7.69-7.61 (m, 2H), 7.50 (dd, J=8.1, 6.5, 2H), 7.43-7.32 (m, 3H), 7.16 (dd, J=8.3, 1.1, 1H), 6.82 (dd, J=3.7, 1.9, 1H), 5.12 (s, 2H), 3.46-3.33 (m, 1H), 2.04-1.91 (m, 2H), 1.87-1.75 (m, 2H), 1.73-1.49 (m, 4H).

Example 215

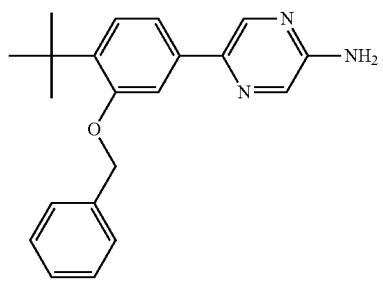 [SMILES: CC(C)(C)c1ccc(-c2cnc(N)cn2)cc1OCc1ccccc1]

5-[3-(Benzyloxy)-4-tert-butylphenyl]pyrazin-2-amine

Step A:
2-(Benzyloxy)-4-bromo-1-(tert-butyl)benzene

5-Bromo-2-tert-butylphenol (1.08 g, 4.71 mmol), benzyl bromide (0.69 mL, 5.7 mmol) and Cs$_2$CO$_3$ (2.3 g, 7.1 mmol)

were added to 23.6 mL of acetonitrile and stirred at room temperature for 64 hours. The reaction mixture was filtered and concentrated to dryness. Purification by FCC resulted in title compound (1.39 g, 92%).

Step B: 2-(3-(Benzyloxy)-4-(tert-butyl)phenyl)-4,4,5,5-tetramethyl-1,3,2-dioxaborolane 2-(Benzyloxy)-4-bromo-1-(tert-butyl)benzene (495 mg, 1.55 mmol) and 4,4,4',4',5,5,5',5'-octamethyl-2,2'-bi(1,3,2-dioxaborolane) (482 mg, 1.86 mmol) were dissolved in 1,4-dioxane (10.3 mL) and treated with KOAc (461 mg, 4.65 mmol). The solution was sparged with $N_2$ and tris((E,E)-dibenzylideneacetone)dipalladium (42 mg, 0.047 mmol) and tricyclohexylphosphine (30 mg, 0.11 mmol) were added. The mixture was heated at 100° Celsius for 4 hours. The reaction mixture was filtered through anhydrous $NaSO_4$ and a plug of diatomacious earth, then subjected to FCC to give title compound (138 mg, 24%).

Step C

2-Amino-5-bromopyrazine (65 mg, 0.38 mmol) and 2-(3-(benzyloxy)-4-(tert-butyl)phenyl)-4,4,5,5-tetramethyl-1,3,2-dioxaborolane, (138 mg, 0.38 mmol) were partially dissolved in DME (2.5 mL) and treated with of 2.0 M aqueous $K_2CO$ (0.83 mL). The solution was sparged and treated with $Pd(dppf)Cl_2 \cdot CH_2Cl_2$ (30 mg, 0.038 mmol). The mixture was stirred at room temperature for 64 hours. The mixture was dried, filtered through a pad of diatomacious earth and then subjected to FCC followed by HPLC to give the title compound (4 mg, 2%). MS (ESI): mass calcd. for $C_{21}H_{23}N_3O$, 333.18; m/z found, 334.2 $[M+H]^+$. $^1H$ NMR (400 MHz, $CDCl_3$) δ 8.30 (d, J=1.4, 1H), 8.18 (d, J=1.4, 1H), 7.56-7.48 (m, 3H), 7.45-7.32 (m, 6H), 5.21 (s, 2H), 1.42 (s, 10H).

Example 216

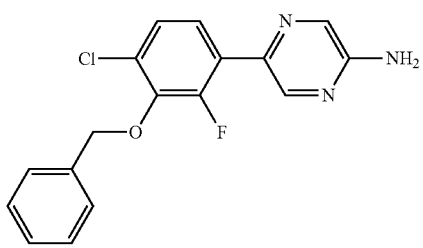 [SMILES: Nc1cnc(-c2ccc(Cl)c(OCc3ccccc3)c2F)cn1]

5-[3-(Benzyloxy)-4-chloro-2-fluorophenyl]pyrazin-2-amine

2-Amino-5-bromopyrazine (100 mg, 0.57 mmol) and 3-benzyloxy-4-chloro-2-fluorophenylboronic acid, (193 mg, 0.57 mmol) were partially dissolved in DME (2.5 mL) and treated with 2.0 M aqueous $K_2CO_3$ (0.83 mL). The solution was sparged and treated with $Pd(dppf)Cl_2 \cdot CH_2Cl_2$ (47 mg, 0.057 mmol). The mixture was stirred at room temperature for 18 hours. The mixture was dried, filtered through a pad of diatomacious earth and then subjected to FCC to give the title compound (146 mg, 77%). MS (ESI): mass calcd. for $C_{17}H_{13}ClFN_3O$, 329.07; m/z found, 330.1 $[M+H]^+$. $^1H$ NMR (400 MHz, $CDCl_3$) δ 8.47 (dd, J=2.4, 1.6, 1H), 8.06 (d, J=1.5, 1H), 7.61-7.50 (m, 3H), 7.43-7.31 (m, 3H), 7.24 (dd, J=8.9, 1.9, 1H), 5.16 (s, 2H), 4.78 (s, 2H).

Example 217

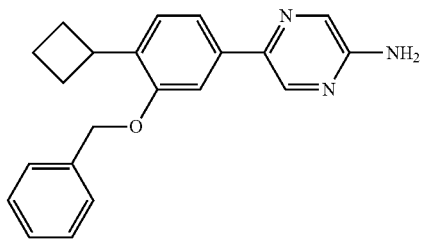 [SMILES: Nc1cnc(-c2ccc(C3CCC3)c(OCc3ccccc3)c2)cn1]

5-[3-(Benzyloxy)-4-cyclobutylphenyl]pyrazin-2-amine

Step A 5-(3-Benzyloxy)-4-chlorophenyl)pyrazin-2-amine was prepared using procedures similar to those described in Example 216 utilizing (3-(benzyloxy)-4-chlorophenyl)-boronic acid. MS (ESI): mass calcd. for $C_{17}H_{14}ClN_3O$, 311.08; m/z found, 312.1 $[M+H]^+$. $^1H$ NMR (500 MHz, $CDCl_3$) δ 8.38 (d, J=1.4, 1H), 8.03 (d, J=1.5, 1H), 7.59 (d, J=1.9, 1H), 7.55-7.48 (m, 2H), 7.47-7.36 (m, 4H), 7.33 (t, J=7.4, 1H), 5.24 (s, 2H), 4.69 (s, 2H).

Step B

The title compound was prepared using analogous conditions described in Example 83 using 5-(3-(benzyloxy)-4-chlorophenyl)pyrazin-2-amine. MS (ESI): mass calcd. for $C_{21}H_{21}N_3O$, 331.17; m/z found, 332.4 $[M+H]^+$. $^1H$ NMR (400 MHz, $CDCl_3$) δ 8.42 (d, J=1.5, 1H), 8.06 (d, J=1.5, 1H), 7.50-7.45 (m, 3H), 7.45-7.37 (m, 3H), 7.36-7.28 (m, 2H), 5.15 (s, 2H), 4.60 (s, 2H), 3.88-3.78 (m, 1H), 2.41-2.30 (m, 2H), 2.23-2.10 (m, 2H), 2.09-1.95 (m, 1H), 1.88-1.78 (m, 1H).

Example 218

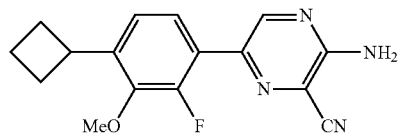

3-amino-6-(4-Cyclobutyl-2-fluoro-3-methoxyphenyl)pyrazine-2-carbonitrile

The title compound was prepared in a manner similar to that described in Example 198 using (4-cyclobutyl-2-fluoro-3-methoxyphenyl)boronic acid and 3-amino-6-bromopyrazine-2-carbonitrile. MS (ESI): mass calcd. for $C_{16}H_{15}FN_4O_2$, 298.12; m/z found, 299.1 $[M+H]^+$. $^1H$ NMR (500 MHz, $CD_3OD$) δ 8.62-8.61 (m, 1H), 7.54-7.46 (m, 1H), 7.21-7.15 (m, 1H), 3.89-3.88 (m, 3H), 3.86-3.79 (m, 1H), 2.41-2.32 (m, 2H), 2.24-2.04 (m, 3H), 1.94-1.85 (m, 1H).

Example 219

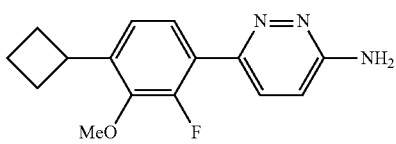

6-(4-Cyclobutyl-2-fluoro-3-methoxyphenyl)pyridazin-3-amine

The title compound was prepared in a manner similar to that described in Example 198 using (4-cyclobutyl-2-fluoro-3-methoxyphenyl)boronic acid and 6-chloropyridazin-3-amine. MS (ESI): mass calcd. for $C_{15}H_{16}FN_3O$, 273.13; m/z found, 274.1 [M+H]+. 1H NMR (400 MHz, CDCl3) δ 7.73-7.62 (m, 2H), 7.17-7.14 (m, 1H), 6.84-6.78 (m, 1H), 3.92-3.87 (m, 3H), 3.86-3.77 (m, 1H), 2.42-2.32 (m, 2H), 2.23-1.98 (m, 3H), 1.93-1.83 (m, 1H).

Example 220

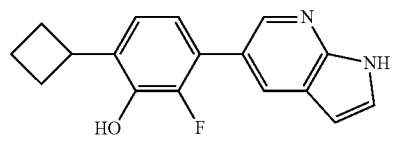

6-Cyclobutyl-2-fluoro-3-(1H-pyrrolo[2,3-b]pyridin-5-yl)phenol

The title compound was prepared in a manner similar to that described in Example 185 by reaction of Intermediate I. MS (ESI): mass calcd. for $C_{17}H_{15}FN_2O$, 282.12; m/z found, 283.1 [M+H]+. 1H NMR (500 MHz, CD3OD) δ 8.90-8.83 (m, 1H), 8.63-8.56 (m, 1H), 7.82-7.75 (m, 1H), 7.18-7.12 (m, 1H), 7.08-7.01 (m, 1H), 6.98-6.93 (m, 1H), 3.91-3.76 (m, 1H), 2.45-2.34 (m, 2H), 2.25-2.14 (m, 2H), 2.11-2.02 (m, 1H), 1.95-1.85 (m, 1H).

Example 221

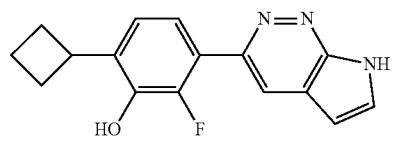

6-Cyclobutyl-2-fluoro-3-(7H-pyrrolo[2,3-c]pyridazin-3-yl)phenol

The title compound was prepared in a manner similar to that described in Example 185 by reaction of 3-(4-cyclobutyl-2-fluoro-3-methoxyphenyl)-7H-pyrrolo[2,3-c]pyridazine. MS (ESI): mass calcd. for $C_{16}H_{14}FN_3O$, 283.11; m/z found, 284.1 [M+H]+. 1H NMR (400 MHz, CD3OD) δ 8.69-8.65 (m, 1H), 8.57-8.51 (m, 1H), 7.31-7.27 (m, 1H), 7.21-7.16 (m, 1H), 7.10-7.05 (m, 1H), 3.95-3.82 (m, 1H), 2.46-2.38 (m, 2H), 2.26-2.07 (m, 3H), 1.95-1.86 (m, 1H).

Example 222

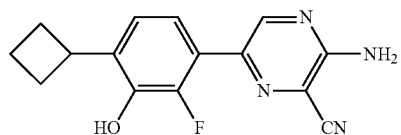

3-Amino-6-(4-cyclobutyl-2-fluoro-3-hydroxyphenyl)pyrazine-2-carbonitrile

The title compound was prepared in a manner similar to that described in Example 185 by reaction of 3-amino-6-(4-cyclobutyl-2-fluoro-3-methoxyphenyl)-pyrazine-2-carbonitrile. MS (ESI): mass calcd. for $C_{15}H_{13}FN_4O$, 284.11; m/z found, 285.1 [M+H]+. 1H NMR (400 MHz, CD3OD) δ 8.63-8.58 (m, 1H), 7.27-7.20 (m, 1H), 7.11-7.05 (m, 1H), 3.89-3.74 (m, 1H), 2.42-2.31 (m, 2H), 2.24-1.99 (m, 3H), 1.92-1.81 (m, 1H).

Example 223

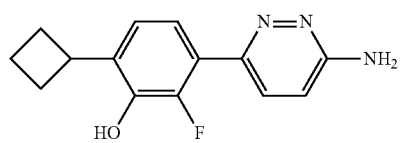

3-(6-Aminopyridazin-3-yl)-6-cyclobutyl-2-fluorophenol

The title compound was prepared in a manner similar to that described in Example 185 by reaction of 6-(4-cyclobutyl-2-fluoro-3-methoxyphenyl)pyridazin-3-amine. MS (ESI): mass calcd. for $C_{14}H_{14}FN_3O$, 259.11; m/z found, 260.1 [M+H]+. 1H NMR (400 MHz, CD3OD) δ 8.15-8.08 (m, 1H), 7.57-7.50 (m, 1H), 7.22-7.16 (m, 1H), 7.15-7.10 (m, 1H), 3.89-3.76 (m, 1H), 2.42-2.33 (m, 2H), 2.22-2.00 (m, 3H), 1.92-1.82 (m, 1H).

Example 224

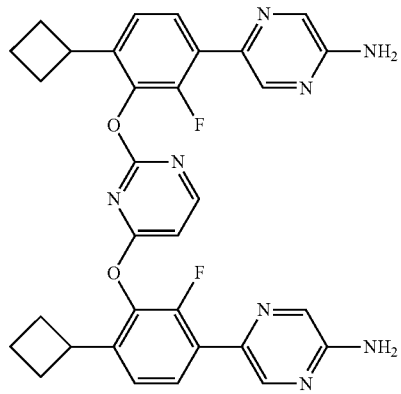 [SMILES: Nc1cnc(-c2ccc(C3CCC3)c(Oc3ccnc(Oc4c(C5CCC5)ccc(-c5cnc(N)cn5)c4F)n3)c2F)cn1]

5,5'-((Pyrimidine-2,4-diylbis(oxy))bis(4-cyclobutyl-2-fluoro-3,1-phenylene))bis(pyrazin-2-amine)

The title compound was prepared in a manner similar to that described in Example 69 using 3-(5-aminopyrazin-2-yl)-6-cyclobutyl-2-fluorophenol and 2-chloro-4-(methylsulfonyl)pyrimidine. MS (ESI): mass calcd. for $C_{32}H_{28}F_2N_8O_2$, 594.23; m/z found, 595.3 [M+H]$^+$. $^1$H NMR (400 MHz, CDCl$_3$) δ 8.50 (d, J=5.7, 1H), 8.36 (d, J=4.4, 2H), 7.95 (d, J=8.4, 2H), 7.61-7.52 (m, 2H), 7.06-6.99 (m, 2H), 6.81 (d, J=5.6, 1H), 3.61-3.41 (m, 2H), 2.20-1.89 (m, 1 OH), 1.78 (d, J=12.3, 2H).

Example 225

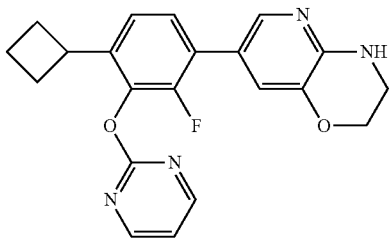 [SMILES: Fc1c(-c2cnc3c(c2)OCCN3)ccc(C2CCC2)c1Oc1ncccn1]

7-(4-Cyclobutyl-2-fluoro-3-(pyrimidin-2-yloxy)phenyl)-3,4-dihydro-2H-pyrido[3,2-b][1,4]oxazine The title compound was prepared in a manner similar to that described in Example 69 using 6-cyclobutyl-3-(3,4-dihydro-2H-pyrido[3,2-b][1,4]oxazin-7-yl)-2-fluorophenol and 2-chloropyrimidine. MS (ESI): mass calcd. for $C_{21}H_{19}FN_4O_2$, 378.15; m/z found, 379.1 [M+H]$^+$. $^1$H NMR (400 MHz, CD$_3$OD) δ 8.63-8.58 (m, 2H), 7.75-7.71 (m, 1H), 7.66-7.62 (m, 1H), 7.46-7.39 (m, 1H), 7.34-7.28 (m, 1H), 7.28-7.23 (m, 1H), 4.39-4.33 (m, 2H), 3.73-3.59 (m, 3H), 2.24-2.08 (m, 4H), 2.04-1.93 (m, 1H), 1.87-1.76 (m, 1H).

Example 226

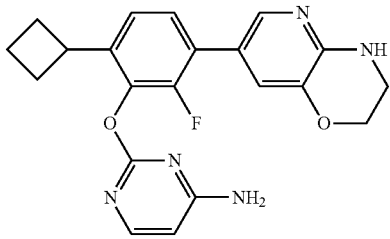 [SMILES: Nc1ccnc(Oc2c(C3CCC3)ccc(-c3cnc4c(c3)OCCN4)c2F)n1]

2-(6-Cyclobutyl-3-(3,4-dihydro-2H-pyrido[3,2-b][1,4]oxazin-7-yl)-2-fluorophenoxy)pyrimidin-4-amine The title compound was prepared in a manner similar to that described in Example 69 using 6-cyclobutyl-3-(3,4-dihydro-2H-pyrido[3,2-b][1,4]oxazin-7-yl)-2-fluorophenol and 2-chloro-4-aminopyrimidine. MS (ESI): mass calcd. for $C_{21}H_{20}FN_5O_2$, 393.16; m/z found, 394.3 [M+H]$^+$. $^1$H NMR (400 MHz, CD$_3$OD) δ 8.05-8.00 (m, 1H), 7.76-7.72 (m, 1H), 7.64-7.61 (m, 1H), 7.51-7.45 (m, 1H), 7.36-7.31 (m, 1H), 6.50-6.45 (m, 1H), 4.39-4.33 (m, 2H), 3.74-3.64 (m, 3H), 2.33-2.23 (m, 2H), 2.23-2.14 (m, 2H), 2.11-2.01 (m, 1H), 1.91-1.83 (m, 1H).

Example 227

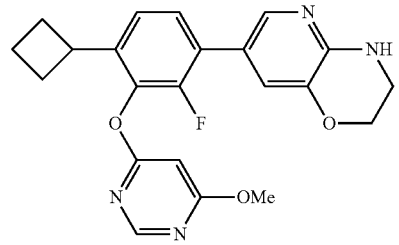 [SMILES: COc1cc(Oc2c(C3CCC3)ccc(-c3cnc4c(c3)OCCN4)c2F)ncn1]

7-(4-Cyclobutyl-2-fluoro-3-((6-methoxypyrimidin-4-yl)oxy)phenyl)-3,4-dihydro-2H-pyrido[3,2-b][1,4]oxazine The title compound was prepared in a manner similar to that described in Example 69 using 6-cyclobutyl-3-(3,4-dihydro-2H-pyrido[3,2-b][1,4]oxazin-7-yl)-2-fluorophenol and 4-chloro-6-methoxypyrimidine. MS (ESI): mass calcd. for $C_{22}H_{21}FN_4O_3$, 408.16; m/z found, 409.1 [M+H]t. $^1$H NMR (400 MHz, CD$_3$OD) δ 8.35-8.30 (m, 1H), 7.75-7.71 (m, 1H), 7.66-7.61 (m, 1H), 7.46-7.39 (m, 1H), 7.34-7.27 (m, 1H), 6.44-6.39 (m, 1H), 4.40-4.31 (m, 2H), 4.05-3.97 (m, 3H), 3.74-3.67 (m, 2H), 3.67-3.54 (m, 1H), 2.28-2.09 (m, 4H), 2.06-1.93 (m, 1H), 1.87-1.78 (m, 1H).

Example 228

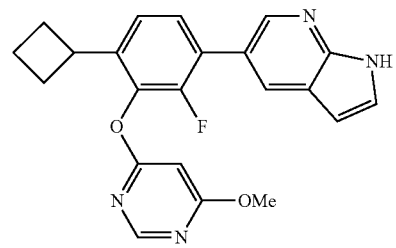 [SMILES: COc1cc(Oc2c(C3CCC3)ccc(-c3cnc4[nH]ccc4c3)c2F)ncn1]

5-(4-Cyclobutyl-2-fluoro-3-((6-methoxypyrimidin-4-yl)oxy)phenyl)-1H-pyrrolo[2,3-l]pyridine The title compound was prepared in a manner similar to that described in Example 69 using 6-cyclobutyl-2-fluoro-3-(1H-pyrrolo[2,3-b]pyridin-5-yl)phenol and 4-chloro-6-methoxypyrimidine. MS (ESI): mass calcd. for $C_{22}H_{19}FN_4O_2$, 390.15; m/z found, 391.1 [M+H]$^+$. $^1$H NMR (400 MHz, CD$_3$OD) δ 8.51-8.44 (m, 2H), 8.38-8.33 (m, 1H), 7.61-7.56 (m, 1H), 7.54-7.47 (m, 1H), 7.38-7.31 (m, 1H), 6.77-6.71 (m, 1H), 6.45-6.39 (m, 1H), 4.03-3.98 (m, 3H), 3.70-3.59 (m, 1H), 2.28-2.13 (m, 4H), 2.08-1.96 (m, 1H), 1.89-1.79 (m, 1H).

Example 229

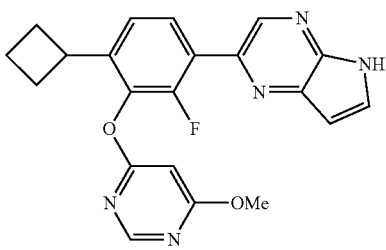 [SMILES: COc1cc(Oc2c(C3CCC3)ccc(-c3cnc4[nH]ccc4n3)c2F)ncn1]

2-(4-Cyclobutyl-2-fluoro-3-((6-methoxypyrimidin-4-yl)oxy)phenyl)-5H-pyrrolo[2,3-b]pyrazine The title compound was prepared in a manner similar to that described in Example 69 using 6-cyclobutyl-2-fluoro-3-(5H-pyrrolo[2,3-b]pyrazin-2-yl)phenol and 4-chloro-6-methoxypyrimidine. MS (ESI): mass calcd. for $C_{21}H_8FN_5O_2$, 391.14; m/z found, 392.1 [M+H]$^+$. $^1$H NMR (400 MHz, CD$_3$OD) δ 8.61-8.57 (m, 1H), 8.38-8.34 (m, 1H), 7.87-7.84 (m, 1H), 7.83-7.77 (m, 1H), 7.40-7.35 (m, 1H), 6.74-6.69 (m, 1H), 6.43-6.40 (m, 1H), 4.03-3.98 (m, 3H), 3.71-3.60 (m, 1H), 2.26-2.15 (m, 4H), 2.08-1.97 (m, 1H), 1.89-1.81 (m, 1H).

Example 230

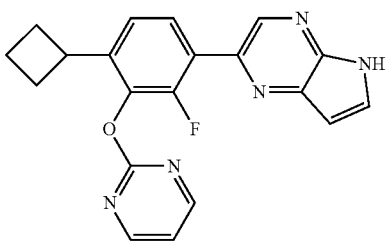 [SMILES: Fc1c(-c2cnc3[nH]ccc3n2)ccc(C2CCC2)c1Oc1ncccn1]

2-(4-Cyclobutyl-2-fluoro-3-(pyrimidin-2-yloxy)phenyl)-5H-pyrrolo[2,3-b]pyrazine

The title compound was prepared in a manner similar to that described in Example 69 using 6-cyclobutyl-2-fluoro-3-(5H-pyrrolo[2,3-b]pyrazin-2-yl)phenol and 2-chloropyrimidine. MS (ESI): mass calcd. for $C_{20}H_{16}FN_5O$, 361.13; m/z found, 362.1 [M+H]$^+$. $^1$H NMR (400 MHz, CD$_3$OD) δ 8.65-8.61 (m, 2H), 8.60-8.56 (m, 1H), 7.86-7.83 (m, 1H), 7.82-7.76 (m, 1H), 7.39-7.35 (m, 1H), 7.28-7.23 (m, 1H), 6.74-6.69 (m, 1H), 3.75-3.64 (m, 1H), 2.26-2.15 (m, 4H), 2.06-1.95 (m, 1H), 1.88-1.78 (m, 1H).

Example 231

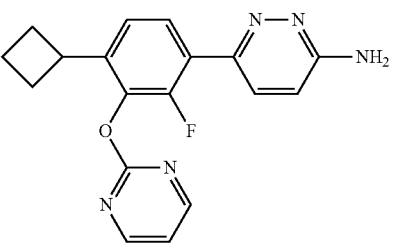 [SMILES: Nc1ccc(-c2ccc(C3CCC3)c(Oc3ncccn3)c2F)nn1]

6-(4-Cyclobutyl-2-fluoro-3-(pyrimidin-2-yloxy)phenyl)pyridazin-3-amine

The title compound was prepared in a manner similar to that described in Example 69 using 3-(6-aminopyridazin-3-yl)-6-cyclobutyl-2-fluorophenol and 2-chloropyrimidine. MS (ESI): mass calcd. for $C_{18}H_{16}FN_5O$, 337.13; m/z found, 338.1 [M+H]$^+$. $^1$H NMR (400 MHz, CD$_3$OD) δ 8.64-8.59 (m, 2H), 8.16-8.10 (m, 1H), 7.76-7.70 (m, 1H), 7.58-7.53 (m, 1H), 7.39-7.34 (m, 1H), 7.29-7.24 (m, 1H), 3.74-3.62 (m, 1H), 2.26-2.09 (m, 4H), 2.06-1.94 (m, 1H), 1.87-1.77 (m, 1H).

Example 232

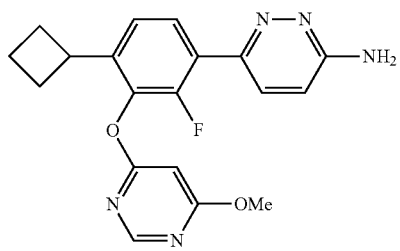 [SMILES: COc1cc(Oc2c(C3CCC3)ccc(-c3ccc(N)nn3)c2F)ncn1]

6-(4-Cyclobutyl-2-fluoro-3-((6-methoxypyrimidin-4-yl)oxy)phenyl)pyridazin-3-amine The title compound was prepared in a manner similar to that described in Example 69 using 3-(6-aminopyridazin-3-yl)-6-cyclobutyl-2-fluorophenol and 4-chloro-6-methoxypyrimidine. MS (ESI): mass calcd. for $C_{19}H_{18}FN_5O_2$, 367.14; m/z found, 368.1 [M+H]$^+$. $^1$H NMR (400 MHz, CD$_3$OD) δ 8.29-8.26 (m, 1H), 8.15-8.10 (m, 1H), 7.76-7.70 (m, 1H), 7.57-7.53 (m, 1H), 7.39-7.35 (m, 1H), 5.84-5.81 (m, 1H), 3.74-3.61 (m, 1H), 3.53-3.47 (m, 3H), 2.35-2.24 (m, 2H), 2.23-2.14 (m, 2H), 2.10-1.99 (m, 1H), 1.90-1.81 (m, 1H).

Example 233

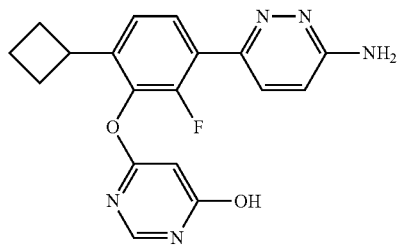 [SMILES: Nc1ccc(-c2ccc(C3CCC3)c(Oc3cc(O)ncn3)c2F)nn1]

6-(3-(6-Aminopyridazin-3-yl)-6-cyclobutyl-2-fluorophenoxy)pyrimidin-4-ol

The title compound was prepared in a manner similar to that described in Example 69 using 3-(6-aminopyridazin-3-yl)-6-cyclobutyl-2-fluorophenol and 4-chloro-6-methoxypyrimidine. MS (ESI): mass calcd. for $C_{18}H_{16}FN_5O_2$, 353.13; m/z found, 354.1 [M+H]$^+$. $^1$H NMR (400 MHz, CD$_3$OD) δ 8.15-8.11 (m, 1H), 8.08-8.05 (m, 1H), 7.76-7.71 (m, 1H), 7.57-7.52 (m, 1H), 7.41-7.35 (m, 1H), 5.81-5.76 (m, 1H), 3.74-3.63 (m, 1H), 2.34-2.24 (m, 2H), 2.24-2.14 (m, 2H), 2.10-2.01 (m, 1H), 1.91-1.82 (m, 1H).

Example 234

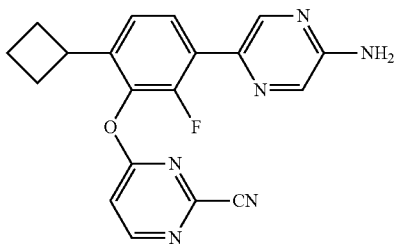 [SMILES: N#Cc1nccc(Oc2c(C3CCC3)ccc(-c3cnc(N)cn3)c2F)n1]

4-(3-(5-Aminopyrazin-2-yl)-6-cyclobutyl-2-fluoro-phenoxy)pyrimidine-2-carbonitrile The title compound was prepared in a manner similar to that described in Example 96 using 3-(5-aminopyrazin-2-yl)-6-cyclobutyl-2-fluorophenol and 4-chloropyrimidine-2-carbonitrile. $^1$H NMR (400 MHz, CD$_3$OD) δ 8.99 (s, 1H), 8.76-8.72 (m, 1H), 8.53 (d, J=6.1, 1H), 8.00 (d, J=6.1, 1H), 7.38-7.30 (m, 1H), 7.12 (d, J=8.1, 1H), 3.89-3.77 (m, 1H), 2.42-2.32 (m, 2H), 2.24-2.14 (m, 2H), 2.11-2.00 (m, 1H), 1.92-1.83 (m, 1H).

Example 235

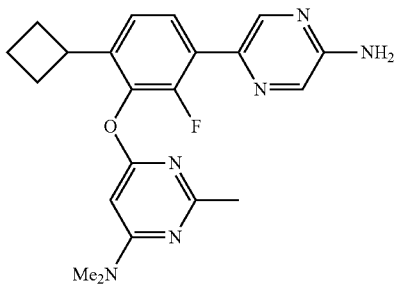 [SMILES: Cc1nc(Oc2c(C3CCC3)ccc(-c3cnc(N)cn3)c2F)cc(N(C)C)n1]

6-(3-(5-Aminopyrazin-2-yl)-6-cyclobutyl-2-fluoro-phenoxy)-N,N,2-trimethylpyrimidin-4-amine The title compound was prepared in a manner similar to that described in Example 96 using 3-(5-aminopyrazin-2-yl)-6-cyclobutyl-2-fluorophenol and 6-chloro-N,N,2-trimethylpyrimidin-4-amine. MS (ESI): mass calcd. for C$_{21}$H$_{23}$FN$_6$O, 394.19; m/z found, 395.1 [M+H]$^+$. $^1$H NMR (400 MHz, CD$_3$OD) δ 8.30-8.25 (m, 1H), 8.11 (d, J=1.5, 1H), 7.89-7.82 (m, 1H), 7.38 (d, J=8.0, 1 H), 5.74 (s, 1H), 3.71-3.61 (m, 1H), 3.17 (s, 6H), 2.53 (s, 3H), 2.34-2.18 (m, 4H), 2.13-2.00 (m, 1H), 1.94-1.83 (m, 1H).

Example 236

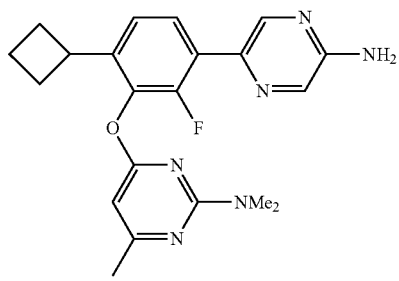 [SMILES: Cc1cc(Oc2c(C3CCC3)ccc(-c3cnc(N)cn3)c2F)nc(N(C)C)n1]

4-(3-(5-Aminopyrazin-2-yl)-6-cyclobutyl-2-fluoro-phenoxy)-N,N,6-trimethylpyrimidin-2-amine The title compound was prepared in a manner similar to that described in Example 96 using 3-(5-aminopyrazin-2-yl)-6-cyclobutyl-2-fluorophenol and 4-chloro-N,N,6-trimethylpyrimidin-2-amine. MS (ESI): mass calcd. for C$_{21}$H$_{23}$FN$_6$O, 394.19; m/z found, 395.1 [M+H]$^+$. $^1$H NMR (400 MHz, CD$_3$OD) δ 8.25-8.22 (m, 1H), 8.12 (d, J=1.5, 1H), 7.82 (t, J=7.9, 1H), 7.33 (d, J=8.3, 1H), 6.65 (d, J=0.7, 1H), 3.67-3.57 (m, 1H), 3.19-2.95 (m, 5H), 2.56 (d, J=0.6, 3H), 2.30-2.15 (m, 4H), 2.08-1.99 (m, 1H), 1.91-1.81 (m, 1H).

Example 237

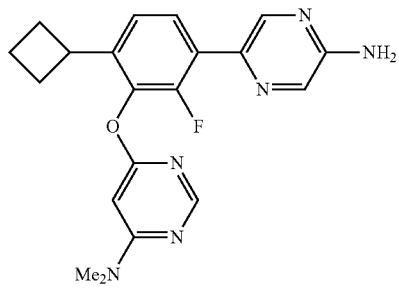 [SMILES: CN(C)c1cc(Oc2c(C3CCC3)ccc(-c3cnc(N)cn3)c2F)ncn1]

6-(3-(5-Aminopyrazin-2-yl)-6-cyclobutyl-2-fluoro-phenoxy-N,N-dimethylpyrimidin-4-amine The title compound was prepared in a manner similar to that described in Example 96 using 3-(5-aminopyrazin-2-yl)-6-cyclobutyl-2-fluorophenol and 6-chloro-N,N-dimethylpyrimidin-4-amine. MS (ESI): mass calcd. for C$_{20}$H$_{21}$FN$_6$O, 380.18; m/z found, 381.1 [M+H]$^+$. $^1$H NMR (400 MHz, CD$_3$OD) δ 8.26 (d, J=1.4, 1H), 8.23-8.18 (m, 2H), 7.86-7.79 (m, 1H), 7.32 (d, J=8.1, 1 H), 6.11 (d, J=0.6, 1 H), 3.70-3.59 (m, 1H), 3.14 (d, J=10.6, 6H), 2.29-2.14 (m, 4H), 2.08-1.95 (m, 1H), 1.90-1.80 (m, 1H).

Example 238

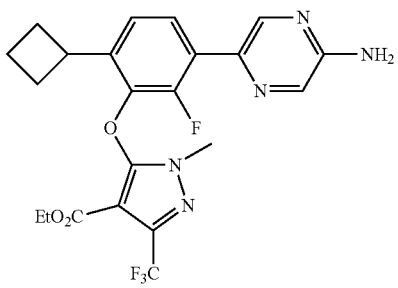 [SMILES: CCOC(=O)c1c(C(F)(F)F)nn(C)c1Oc1c(C2CCC2)ccc(-c2cnc(N)cn2)c1F]

Ethyl 5-(3-(5-aminopyrazin-2-yl)-6-cyclobutyl-2-fluorophenoxy)-1-methyl-3-(trifluoromethyl)-1H-pyrazole-4-carboxylate The title compound was prepared in a manner similar to that described in Example 96 using 3-(5-aminopyrazin-2-yl)-6-cyclobutyl-2-fluorophenol and ethyl 5-chloro-1-methyl-3-(trifluoromethyl)-1H-pyrazole-4-carboxylate. MS (ESI): mass calcd. for $C_{22}H_{21}F_4N_5O_3$, 479.16; m/z found, 480.1 [M+H]$^+$. $^1$H NMR (400 MHz, CD$_3$OD) δ 8.19 (d, J=1.4, 1H), 8.11 (d, J=1.6, 1H), 7.71-7.64 (m, 1H), 7.32 (d, J=8.3, 1H), 3.99-3.86 (m, 6H), 2.42-2.23 (m, 4H), 2.16-2.05 (m, 1H), 1.96-1.87 (m, 1H), 0.98 (t, J=7.1, 3H).

Example 239

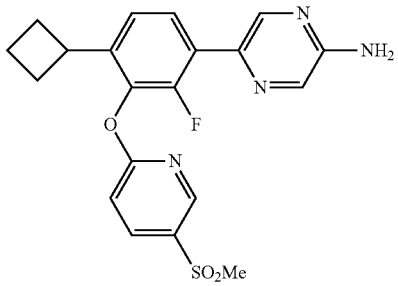 [SMILES: CS(=O)(=O)c1ccc(Oc2c(C3CCC3)ccc(-c3cnc(N)cn3)c2F)nc1]

5-(4-Cyclobutyl-2-fluoro-3-((5-(methylsulfonyl)pyridin-2-yl)oxy)phenyl)pyrazin-2-amine The title compound was prepared in a manner similar to that described in Example 96 using 3-(5-aminopyrazin-2-yl)-6-cyclobutyl-2-fluorophenol and 2-chloro-5-(methylsulfonyl)pyridine. MS (ESI): mass calcd. for $C_{20}H_{19}FN_4O_3S$, 414.12; m/z found, 415.1 [M+H]$^+$. $^1$H NMR (400 MHz, CD$_3$OD) δ 8.61-8.59 (m, 1H), 8.37-8.33 (m, 1H), 8.25 (d, J=1.4, 1H), 8.19 (s, 1H), 7.85-7.78 (m, 1H), 7.33-7.29 (m, 2H), 3.68-3.56 (m, 1H), 3.18 (s, 3H), 2.23-2.12 (m, 4H), 2.04-1.93 (m, 1H), 1.86-1.77 (m, 1H).

Example 240

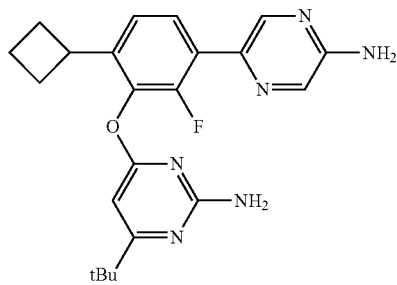 [SMILES: CC(C)(C)c1cc(Oc2c(C3CCC3)ccc(-c3cnc(N)cn3)c2F)nc(N)n1]

4-(3-(5-Aminopyrazin-2-yl)-6-cyclobutyl-2-fluorophenoxy)-6-(tert-butyl)pyrimidin-2-amine The title compound was prepared in a manner similar to that described in Example 96 using 3-(5-aminopyrazin-2-yl)-6-cyclobutyl-2-fluorophenol and 4-(tert-butyl)-6-chloropyrimidin-2-amine. MS (ESI): mass calcd. for $C_{22}H_{25}FN_6O$, 408.21; m/z found, 409.1 [M+H]$^+$. $^1$H NMR (400 MHz, CD$_3$OD) δ 8.27-8.23 (m, 1H), 8.10 (d, J=1.5, 1H), 7.79 (t, J=7.9, 1H), 7.31 (d, J=8.2, 1H), 6.76 (s, 1H), 3.69-3.59 (m, 1H), 2.30-2.15 (m, 4H), 2.09-1.98 (m, 1H), 1.91-1.82 (m, 1H), 1.44 (s, 9H).

Example 241

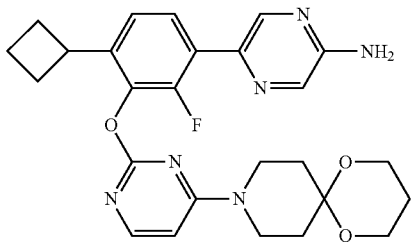 [SMILES: Nc1cnc(-c2ccc(C3CCC3)c(Oc3nccc(N4CCC5(CC4)OCCCO5)n3)c2F)cn1]

5-(3-((4-(1,5-Dioxa-9-azaspiro[5.5]undecan-9-yl)pyrimidin-2-yl)oxy)-4-cyclobutyl-2-fluorophenyl)pyrazin-2-amine The title compound was prepared in a manner similar to that described in Example 96 using 3-(5-aminopyrazin-2-yl)-6-cyclobutyl-2-fluorophenol and 9-(2-chloropyrimidin-4-yl)-1,5-dioxa-9-azaspiro[5.5]undecane. MS (ESI): mass calcd. for $C_{26}H_{29}FN_6O_3$, 492.23; m/z found, 493.2 [M+H]$^+$. $^1$H NMR (400 MHz, CD$_3$OD) δ 8.25 (s, 1H), 8.16 (s, 1H), 8.11 (d, J=7.4, 1H), 7.86 (t, J=7.9, 1H), 7.36 (d, J=8.3, 1H), 6.89-6.86 (m, 1H), 3.87 (t, J=5.5, 4H), 3.74-3.57 (m, 5H), 2.35-2.16 (m, 4H), 2.12-2.02 (m, 1H), 1.96-1.63 (m, 7H).

Example 242

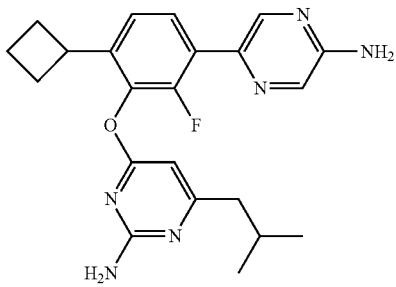 [SMILES: CC(C)Cc1cc(Oc2c(C3CCC3)ccc(-c3cnc(N)cn3)c2F)nc(N)n1]

4-(3-(5-Aminopyrazin-2-yl)-6-cyclobutyl-2-fluorophenoxy)-6-isobutylpyrimidin-2-amine The title compound was prepared in a manner similar to that described in Example 96 using 3-(5-aminopyrazin-2-yl)-6-cyclobutyl-2-fluorophenol and 4-chloro-6-isobutylpyrimidin-2-amine. MS (ESI): mass calcd. for $C_{22}H_{25}FN_6O$, 408.21; m/z found, 409.1 [M+H]$^+$. $^1$H NMR (500 MHz, CD$_3$OD) δ 8.26 (s, 1H), 8.07 (d, J=1.4, 1H), 7.77 (t, J=7.9, 1H), 7.28 (d, J=8.3, 1H), 6.66 (s, 1H), 3.68-3.57 (m, 1H), 2.65 (d, J=7.4, 2H), 2.30-2.23 (m, 2H), 2.21-2.15 (m, 2H), 2.13-2.08 (m, 1H), 2.07-2.01 (m, 1H), 1.91-1.83 (m, 1H), 1.05 (d, J=6.6, 6H).

Intermediate I

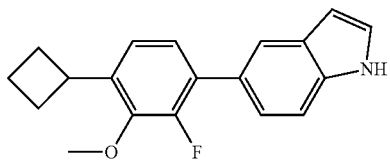 [SMILES: COc1c(C2CCC2)ccc(-c2ccc3[nH]ccc3c2)c1F]

5-(4-Cyclobutyl-2-fluoro-3-methoxyphenyl)-1H-pyrrolo[2,3-b]pyridine

To a 5 mL microwave vial were added a stir bar, 5-bromo-7-azaindole (59 mg, 0.30 mmol), (4-cyclobutyl-2-fluoro-3-methoxyphenyl)boronic acid (74 mg, 0.33 mmol), 14.7 mg Pd(dppf)Cl$_2$·CH$_2$Cl$_2$ (15 mg, 0.18 mmol) and K$_2$CO$_3$ (129 mg, 0.93 mmol). The vial was flushed with nitrogen and then charged with sparged toluene (0.50 mL), sparged water (0.50 mL) and sparged DMF (0.30 mL). The vial was heated at 80° Celsius for 24 hours before cooling to room temperature, diluting the reaction mixture with DCM, drying the mixture over MgSO$_4$ filtering through a plug of diatomacious earth and concentrating to dryness. The dark residue was subjected to FCC to give the title compound as a white solid (67 mg, 76%). MS (ESI): mass calcd. for $C_{18}H_{17}N_2FO$ 296.13, m/z found 297.1 [M+H]$^+$. $^1$H NMR (600 MHz, CDCl$_3$) δ 9.88 (s, 1H), 8.52-8.46 (m, 1H), 8.13-8.09 (m, 1H), 7.42-7.37 (m, 1H), 7.21-7.16 (m, 1H), 7.16-7.11 (m, 1H), 6.59-6.54 (dd, J=3.5, 1.9, 1H), 3.93 (s, 3H), 3.89-3.79 (m, 1H), 2.43-2.34 (m, 2H), 2.24-2.14 (m, 2H), 2.13-2.02 (m, 1H), 1.93-1.85 (m, 1H).

Example 243

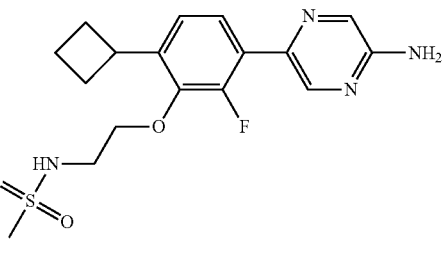

N-(2-(3-(5-Aminopyrazin-2-yl)-6-cyclobutyl-2-fluorophenoxy)-ethyl)-methane-sulfonamide A mixture of N-(2-chloroethyl)methanesulfonamide (146 mg, 0.93 mmol), 3-(5-aminopyrazin-2-yl)-6-cyclobutyl-2-fluorophenol (200 mg, 0.77 mmol), Cs$_2$CO$_3$ (376 mg, 1.16 mmol) and DMF (6 mL) was stirred at room temperature for 16 hours, and then treated with water (10 mL). The mixture was extracted with EtOAc (3×20 ml). The combined organic phases were dried, concentrated to dryness, and the residue purified using FCC to give the title compound (165 mg, 56%). MS (Cl): mass calcd. for $C_{21}H_{21}FN_4O_3S$, 380.13; m/z found, 381.1 [M+H]$^+$. $^1$H NMR (400 MHz, CDCl$_3$) δ 8.43 (s, 1H), 8.08 (s, 1H), 7.55 (m, 1H), 7.15 (d, J=8.2 Hz, 1H), 5.44-5.26 (m, 1H), 4.78 (s, 2H), 4.10 (t, J=4.9 Hz, 2H), 3.84-3.69 (m, 1H), 3.60-3.49 (m, 2H), 3.05 (s, 3H), 2.42-2.27 (m, 2H), 2.22-2.01 (m, 3H), 1.94-1.80 (m, 1H).

Example 244

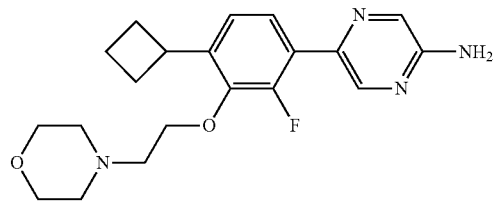 [SMILES: Nc1cnc(-c2ccc(C3CCC3)c(OCCN3CCOCC3)c2F)cn1]

5-(4-Cyclobutyl-2-fluoro-3-(2-morpholinoethoxyl)phenyl)pyrazin-2-amine

The title compound was prepared using analogous conditions described in Example 243 using 4-(2-bromoethyl)morpholine. MS (Cl): mass calcd. for $C_{20}H_{25}FN_4O_2$, 372.20; m/z found, 373.1 [M+H]$^+$. $^1$H NMR (400 MHz, CDCl$_3$) δ 8.51-8.42 (m, 1H), 8.09 (d, J=1.4, 1H), 7.54 (m, 1H), 7.15 (d, J=8.2, 1H), 4.74 (s, 2H), 4.18 (t, J=5.3, 2H), 3.84 (dd, J=18.0, 6.6, 5H), 2.89 (s, 2H), 2.70 (s, 4H), 2.39-2.32 (m, 2H), 2.20-2.12 (m, 2H), 2.08-2.01 (m, 1H), 1.88 (d, J=10.4, 1H).

Example 245

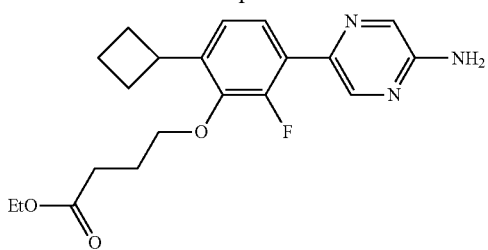

Ethyl 4-(3-(5-aminopyrazin-2-yl)-6-cyclobutyl-2-fluorophenoxy)butanoate

The title compound was prepared using analogous conditions described in Example 243 using ethyl 4-bromobutanoate. MS (CI): mass calcd. for $C_{20}H_{24}FN_3O_3$, 373.18; m/z found, 374.1 [M+H]$^+$. $^1$H NMR (400 MHz, CDCl$_3$) δ 8.52-8.38 (m, 1H), 8.08 (d, J=1.6, 1H), 7.53 (m, 1H), 7.14 (d, J=8.2, 1H), 4.65 (s, 2H), 4.17 (q, J=7.2, 2H), 4.04 (t, J=6.2, 2H), 3.86-3.75 (m, 1H), 2.59 (t, J=7.4, 2H), 2.39-2.30 (m, 2H), 2.20-2.03 (m, 5H), 1.87 (ddd, J=11.3, 10.3, 8.7, 1H), 1.28 (t, J=7.1, 3H).

Example 246

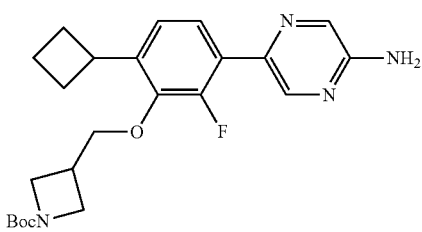 [SMILES: CC(C)(C)OC(=O)N1CC(COc2c(C3CCC3)ccc(-c3cnc(N)cn3)c2F)C1]

tert-Butyl 3-((3-(5-aminopyrazin-2-yl)-6-cyclobutyl-2-fluorophenoxy)methyl)azetidine-1-carboxylate The title compound was prepared using analogous conditions described in Example 243 using tert-butyl 3-(((methylsulfonyl)oxy)methyl)azetidine-1-carboxylate. MS (CI): mass calcd. for $C_{23}H_{29}FN_4O_3$, 428.22; m/z found, 429.2 [M+H]$^+$. $^1$H NMR (400 MHz, CDCl$_3$) δ 8.45 (s, 1H), 8.09 (d, J=1.2, 1H), 7.54 (m, 1H), 7.15 (d, J=8.2, 1H), 4.70 (s, 2H), 4.16 (d, J=6.5, 2H), 4.09 (t, J=8.5, 2H), 3.90-3.83 (m, 2H), 3.82-3.73 (m, 1H), 3.04-2.92 (m, 1H), 2.40-2.28 (m, 2H), 2.21-2.01 (m, 3H), 1.92-1.83 (m, 1H), 1.45 (s, 9H).

Example 247

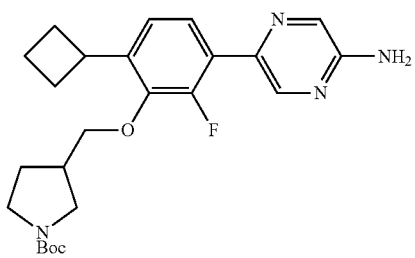 [SMILES: CC(C)(C)OC(=O)N1CCC(COc2c(C3CCC3)ccc(-c3cnc(N)cn3)c2F)C1]

tert-Butyl 3-((3-(5-aminopyrazin-2-yl)-6-cyclobutyl-2-fluorophenoxy)methyl)pyrrolidine-1-carboxylate The title compound was prepared using analogous conditions described in Example 243 using tert-butyl 3-(((methylsulfonyl)oxy)methyl)pyrrolidine-1-carboxylate. MS (CI): mass calcd. for $C_{24}H_{31}FN_4O_3$, 442.24; m/z found, 465.2 [M+Na]$^+$. $^1$H NMR (400 MHz, CDCl$_3$) δ 8.48-8.43 (m, 1H), 8.09 (d, J=1.5, 1H), 7.53 (m, 1H), 7.14 (d, J=8.3, 1H), 4.65 (s, 2H), 4.04-3.91 (m, 2H), 3.86-3.75 (m, 1H), 3.69-3.34 (m, 3H), 3.29-3.25 (m, 1H), 2.71-2.63 (m, 1H), 2.38-2.31 (m, 2H), 2.19-2.03 (m, 4H), 1.92-1.76 (m, 2H), 1.48 (s, 9H).

Example 248

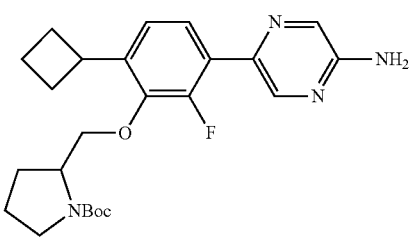 [SMILES: CC(C)(C)OC(=O)N1CCCC1COc1c(C2CCC2)ccc(-c2cnc(N)cn2)c1F]

tert-Butyl 2-((3-(5-aminopyrazin-2-yl)-6-cyclobutyl-2-fluorophenoxy)methyl)pyrrolidine-1-carboxylate The title compound was prepared using analogous conditions described in Example 243 using tert-butyl 2-(((methylsulfonyl)oxy)methyl)pyrrolidine-1-carboxylate. MS (CI): mass calcd. for $C_{24}H_{31}FN_4O_3$, 442.24; m/z found, 443.2 [M+H]$^+$. $^1$H NMR (400 MHz, CDCl$_3$) δ 8.46 (s, 1H), 8.08 (s, 1H), 7.55 (s, 1H), 7.13 (s, 1H), 4.64 (s, 2H), 4.09 (s, 2H), 3.85-3.77 (m, 2H), 3.42 (s, 2H), 2.39-2.25 (m, 3H), 2.18-1.98 (m, 5H), 1.92-1.81 (m, 2H), 1.44 (s, 9H).

Example 249

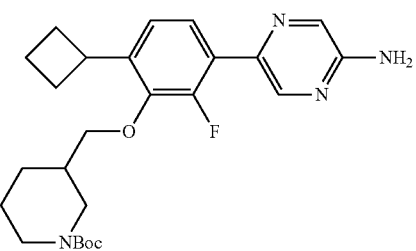 [SMILES: CC(C)(C)OC(=O)N1CCCC(COc2c(C3CCC3)ccc(-c3cnc(N)cn3)c2F)C1]

tert-Butyl 3-((3-(5-aminopyrazin-2-yl)-6-cyclobutyl-2-fluorophenoxy)methyl)piperidine-1-carboxylate The title compound was prepared using analogous conditions described in Example 243 using tert-butyl 2-(bromomethyl)piperidine-1-carboxylate. MS (CI): mass calcd. for $C_{25}H_{33}FN_4O_3$, 456.25; m/z found, 457.2 [M+H]J. $^1$H NMR (400 MHz, CDCl$_3$) δ 8.45 (m, 1H), 8.09 (m, 1H), 7.52 (m, 1H), 7.14 (d, J=8.2, 1H), 4.63 (s, 2H), 4.30-4.18 (m, 1H), 4.04-3.93 (m, 1H), 3.91-3.85 (m, 2H), 3.83-3.75 (m, 1H), 2.88-2.72 (m, 2H), 2.41-2.30 (m, 2H), 2.24-1.96 (m, 5H), 1.95-1.80 (m, 2H), 1.76-1.67 (m, 1H), 1.57-1.50 (m, 1H), 1.48 (s, 9H).

Example 250

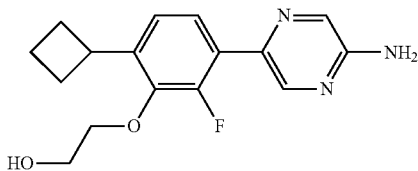

2-(3-(5-Aminopyrazin-2-yl)-6-cyclobutyl-2-fluorophenoxy)ethanol

The title compound was prepared using analogous conditions described in Example 243 using 2-(2-bromoethoxy)tetrahydro-2H-pyran. The initial alkylation product was treated with a 0.2 M methanolic HCl, and the resulting mixture was stirred at room temperature for 30 min. The reaction mixture was concentrated and the residue was subjected to FCC to obtain the titled compound. MS (Cl): mass calcd. for $C_{16}H_{18}FN_3O_2$, 303.14; m/z found, 304.1 [M+H]$^+$. $^1$H NMR (400 MHz, DMSO-d$_6$) δ 8.28 (d, J=1.6, 1H), 7.99 (d, J=1.4, 1H), 7.50 (t, J=7.9, 1H), 7.20 (d, J=8.2, 1H), 6.64 (s, 2H), 4.86 (t, J=5.5, 1H), 3.98 (t, J=5.0, 2H), 3.85 (dd, J=17.8, 8.8, 1H), 3.70 (dd, J=10.4, 5.2, 2H), 2.30 (ddd, J=13.8, 8.3, 5.8, 2H), 2.14-2.05 (m, 2H), 2.02-1.95 (m, 1H), 1.82 (dd, J=18.6, 9.3, 1H).

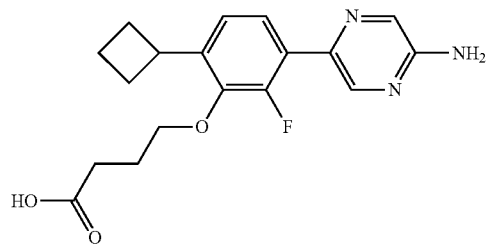

4-(3-(5-Aminopyrazin-2-yl)-6-cyclobutyl-2-fluorophenoxy)butanoic acid

Ethyl 4-(3-(5-aminopyrazin-2-yl)-6-cyclobutyl-2-fluorophenoxy)butanoate (300 mg, 0.8 mmol) was dissolved in THF (6 ml), then a solution of LiOH.H2O (101 mg, 2.41 mmol) and water (2 ml) was added. The reaction was stirred overnight, then the mixture was acidified to pH=7 by adding 1M HCl. The mixture was concentrated to dryness and subjected to FCC to give the title compound (135 mg, 45%). MS (Cl): mass calcd. for $C_{18}H_{20}FN_3O_3$, 345.15; m/z found, 346.1 [M+H]$^+$. $^1$H NMR (400 MHz, DMSO-d$_6$) δ 12.22 (s, 1H), 8.38-8.29 (m, 1H), 8.05 (d, J=1.6, 1H), 7.56 (m, 1H), 7.26 (d, J=8.2, 1H), 6.70 (s, 2H), 4.02 (t, J=6.4, 2H), 3.87-3.77 (m, 1H), 2.50 (t, J=7.3, 2H), 2.40-2.30 (m, 2H), 2.20-1.99 (m, 5H), 1.92-1.83 (m, 1H).

Example 252

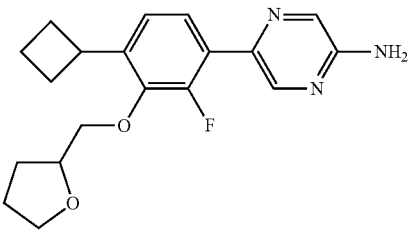 [SMILES: Nc1cnc(-c2ccc(C3CCC3)c(OCC3CCCO3)c2F)cn1]

5-(4-Cyclobutyl-2-fluoro-3-((tetrahydrofuran-2-yl)methoxy)phenyl)pyrazin-2-amine The title compound was prepared using analogous conditions described in Example 243 using 2-(bromomethyl)tetrahydro-[2H]-pyran at 60° Celsius. MS (Cl): mass calcd. for $C_{19}H_{22}FN_3O_2$, 343.17; m/z found, 344.1 [M+H]$^+$. $^1$H NMR (400 MHz, CDCl$_3$) δ 8.56-8.37 (m, 1H), 8.08 (d, J=1.5, 1H), 7.53 (dd, J=10.2, 5.4, 1H), 7.15 (d, J=8.3, 1H), 4.62 (s, 2H), 4.34-4.21 (m, 1H), 4.08-4.03 (m, 1H), 4.00-3.81 (m, 4H), 2.41-2.32 (m, 2H), 2.17-1.82 (m, 8H).

Example 253

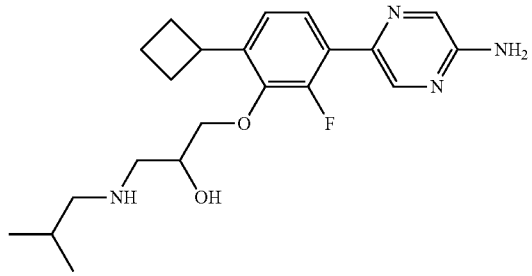 [SMILES: CC(C)CNCC(O)COc1c(C2CCC2)ccc(-c2cnc(N)cn2)c1F]

racemic 1-(3-(5-Aminopyrazin-2-yl)-6-cyclobutyl-2-fluorophenoxy)-3-(isobutylamino)propan-2-ol Step A: 5-(4-cyclobutyl-2-fluoro-3-(oxiran-2-ylmethoxy)phenyl)pyrazin-2-amine The title compound was prepared using analogous conditions described in Example 243 heating at 60° Celsius using (rac)-epichlorohydrin. $^1$H NMR (400 MHz, CDCl$_3$) δ 8.57-8.40 (m, 1H), 8.08 (d, J=1.5, 1H), 7.54 (dd, J=14.2, 6.6, 1H), 7.15 (d, J=8.2, 1H), 4.64 (s, 2H), 4.28 (dd, J=11.2, 3.2, 1H), 3.98 (dd, J=11.2, 6.1, 1H), 3.92-3.81 (m, 1H), 3.38 (td, J=6.4, 3.2, 1H), 2.92-2.86 (m, 1H), 2.72 (dd, J=5.0, 2.6, 1H), 2.43-2.34 (m, 2H), 2.20-2.01 (m, 3H), 1.93-1.83 (m, 1H).

Step B: 1-(3-(5-aminopyrazin-2-yl)-6-cyclobutyl-2-fluorophenoxy)-3-(isobutylamino)-propan-2-ol A mixture of 5-(4-cyclobutyl-2-fluoro-3-(oxiran-2-ylmethoxy)phenyl)pyrazin-2-amine (150 mg, 0.48 mmol), isobutylamine (105 mg, 1.43 mmol) and MeOH (5 mL) was heated in sealed tube to 60° Celsius for 5 hours, then the solvent was removed. The residue was subjected to FCC to give the titled compound (125 mg, 67%). MS (Cl): mass calcd. for $C_{21}H_{29}FN_4O_2$, 388.23; m/z found, 389.2 [M+H]$^+$. $^1$H NMR (400 MHz, CDCl$_3$) δ 8.48-8.39 (m, 1H), 8.08 (d, J=1.4, 1H), 7.54 (m, 1H), 7.14 (d, J=8.2, 1H), 4.72 (s, 2H), 4.45-4.37 (m, 1H), 4.09-3.99 (m, 2H), 3.86-3.73 (m, 1H), 3.29-3.21 (m, 1H), 3.16-3.07 (m, 1H), 2.86-2.69 (m, 2H), 2.41-2.30 (m, 2H), 2.19-2.01 (m, 4H), 1.90-1.81 (m, 1H), 1.05 (d, J=6.7, 6H).

Example 254

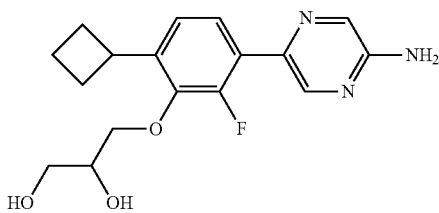 [SMILES: Nc1cnc(-c2ccc(C3CCC3)c(OCC(O)CO)c2F)cn1]

racemic 3-(3-(5-Aminopyrazin-2-yl)-6-cyclobutyl-2-fluorophenoxy)propane-1,2-diol The title compound is a side product found when water opens the epoxide, 5-(4-cyclobutyl-2-fluoro-3-(oxiran-2-ylmethoxy)phenyl)pyrazin-2-amine, using the conditions in Example 253 Step B. MS (Cl): mass calcd. for $C_{17}H_{20}FN_3O_3$, 333.15; m/z found, 334.1 [M+H]$^+$. $^1$H NMR (400 MHz, DMSO-d$_6$) δ8.28 (s, 1H), 7.99 (d, J=1.4, 1H), 7.50 (m, 1H), 7.20 (d, J=8.2, 1H), 6.64 (s, 2H), 4.93 (d, J=5.1, 1H), 4.64 (t, J=5.6, 1H), 4.02-3.97 (m, 1H), 3.92-3.83 (m, 2H), 3.82-3.77 (m, 1H), 3.46 (t, J=5.6, 2H), 2.35-2.27 (m, 2H), 2.14-1.95 (m, 3H), 1.86-1.78 (m, 1H).

Example 255

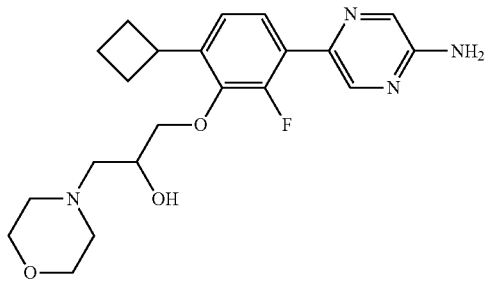 [SMILES: Nc1cnc(-c2ccc(C3CCC3)c(OCC(O)CN3CCOCC3)c2F)cn1]

racemic 1-(3-(5-aminopyrazin-2-yl)-6-cyclobutyl-2-fluorophenoxy)-3-morpholinopropan-2-ol The title compound was prepared using analogous conditions described in Example 253 using morpholine in Step B. MS (Cl): mass calcd. for $C_{21}H_{27}FN_4O_3$, 402.21; m/z found, 403.2 [M+H]$^+$. $^1$H NMR (400 MHz, CDCl$_3$) δ 8.48-8.44 (m, 1H), 8.09 (d, J=1.5, 1H), 7.58-7.53 (m, 1H), 7.16 (d, J=8.2, 1H), 4.67 (s, 2H), 4.18 (s, 1H), 4.03 (d, J=4.9, 2H), 3.88-3.83 (m, 1H), 3.79 (s, 4H), 2.76 (s, 2H), 2.68 (s, 2H), 2.60 (s, 2H), 2.40-2.33 (m, 2H), 2.17 (dt, J=9.3, 5.4, 2H), 2.09-2.00 (m, 1H), 1.93-1.84 (m, 1H)

Example 256

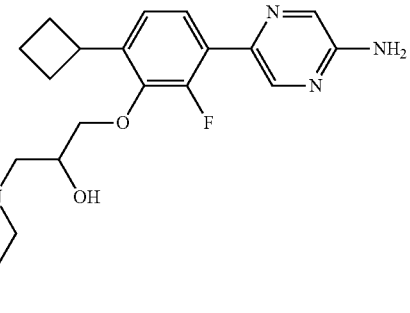

racemic 4-(3-(3-(5-Aminopyrazin-2-yl)-6-cyclobutyl-2-fluorophenoxy)-2-hydroxypropyl)thiomorpholine 1,1-dioxide The title compound was prepared using analogous conditions described in Example 253 using thiomorpholine 1,1-dioxide in Step B. MS (Cl): mass calcd. for $C_{21}H_{27}FN_4O_4S$, 450.17; m/z found, 451.1 [M+H]$^+$. $^1$H NMR (400 MHz, DMSO-d$_6$) δ 8.26 (s, 1H), 7.98 (m, 1H), 7.48 (m, 1H), 7.18 (d, J=8.2, 1H), 6.62 (s, 2H), 4.94 (d, J=4.4, 1H), 3.96-3.79 (m, 4H), 3.12-3.03 (m, 4H), 3.02-2.95 (m, 4H), 2.68 (dd, J=13.2, 4.3, 1H), 2.61-2.52 (m, 1H), 2.31-2.23 (m, 2H), 2.13-1.92 (m, 3H), 1.83-1.73 (m, 1H).

Example 257

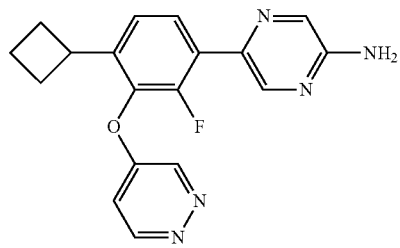 [SMILES: Nc1cnc(-c2ccc(C3CCC3)c(Oc3ccnnc3)c2F)cn1]

5-(4-Cyclobutyl-2-fluoro-3-(pyridazin-4-yloxy)phenyl)pyrazin-2-amine

The title compound was prepared using conditions similar to those described in Example 160 with DMSO as the solvent, heating for 2 hours at 80° Celsius via microwave radiation and substituting Intermediate B and 4-bromopyridazine hydrobromide. MS (ESI): mass calcd. for $C_{18}H_{16}FN_5O$, 337.13; m/z found, 338.1 [M+H]$^+$. $^1$H NMR (400 MHz, CDCl$_3$) δ 9.12-9.05 (m, 1H), 9.01-8.95 (m, 1H), 8.47-8.41 (m, 1H), 8.11 (d, J=1.5 Hz, 1H), 7.91-7.82 (m, 1H), 7.35-7.28 (m, 1H), 6.83-6.75 (m, 1H), 4.84 (s, 2H), 3.63-3.49 (m, 1H), 2.28-2.06 (m, 4H), 2.08-1.90 (m, 1H), 1.90-1.79 (m, 1H).

Example 258

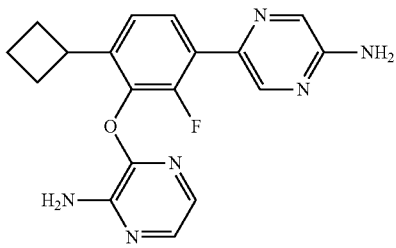

3-(3-(5-Aminopyrazin-2-yl)-6-cyclobutyl-2-fluorophenoxy)pyrazin-2-amine

The title compound was prepared using conditions similar to those described in Example 160 with DMSO as the solvent, heating for 2 hours at 1400 Celsius via microwave radiation and substituting Intermediate B and 2-amino-3-chloropyrazine. MS (ESI): mass calcd. for $C_{18}H_{17}FN_6O$, 352.14; m/z found, 353.1 [M+H]+. 1H NMR (400 MHz, DMSO-de) δ 8.29-8.23 (m, 3H), 8.01 (d, J=1.5 Hz, 3H), 7.76-7.68 (m, 3H), 7.61 (d, J=3.0 Hz, 3H), 7.28 (d, J=8.3 Hz, 3H), 7.14 (d, J=3.0 Hz, 3H), 6.70 (s, 11H), 3.62-3.49 (m, 3H), 2.17-2.00 (m, 12H), 1.98-1.83 (m, 3H), 1.81-1.67 (m, 3H).

Example 259

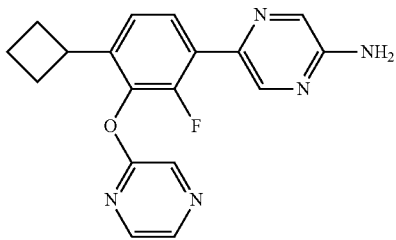 [SMILES: Nc1cnc(-c2ccc(C3CCC3)c(Oc3cnccn3)c2F)cn1]

5-(4-Cyclobutyl-2-fluoro-3-(pyrazin-2-yloxy)phenyl)pyrazin-2-amine

The title compound was prepared using conditions similar to those described in Example 160 with DMSO as the solvent, heating for 2 hours at 80° Celsius via microwave radiation and substituting Intermediate B and 2-fluoropyrazine. MS (ESI): mass calcd. for $C_{18}H_{16}FN_5O$, 337.13; m/z found, 337.9 [M+H]+. 1H NMR (400 MHz, CDCl3) δ 8.53 (d, J=1.3 Hz, 1H), 8.49-8.42 (m, 1H), 8.27 (d, J=2.7 Hz, 1H), 8.12-8.03 (m, 2H), 7.85-7.76 (m, 1H), 7.23 (s, 1H), 4.70 (s, 2H), 3.68-3.56 (m, 1H), 2.26-2.08 (m, 4H), 2.03-1.89 (m, 1H), 1.87-1.76 (m, 1H).

Example 260

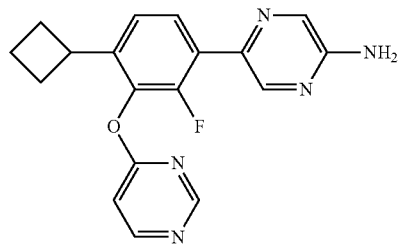

5-(4-Cyclobutyl-2-fluoro-3-(pyrimidin-4-yloxy)phenyl)pyrazin-2-amine

The title compound was prepared using conditions similar to those described in Example 101 with pyridine as a solvent, heating at 80° Celsius for 18 hours and substituting 4-chloropyrimidine hydrochloride. MS (ESI): mass calcd. for $C_{18}H_{16}FN_5O$, 337.13. m/z found, 338.1 [M+H]+. 1H NMR (400 MHz, CDCl3) δ 8.76 (s, 1H), 8.62 (d, J=5.8 Hz, 1H), 8.47-8.45 (m, 1H), 8.09 (d, J=1.4 Hz, 1H), 7.82 (m, 1H), 7.24 (d, J=8.3 Hz, 1H), 7.02 (dd, J=5.8, 1.0 Hz, 1H), 4.67 (s, 2H), 3.59 (m, 1H), 2.25-2.08 (m, 4H), 2.03-1.89 (m, 1H), 1.86-1.76 (m, 1H).

Example 261

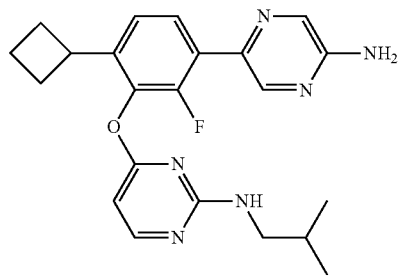 [SMILES: CC(C)CNc1nccc(Oc2c(C3CCC3)ccc(-c3cnc(N)cn3)c2F)n1]

4-(3-(5-Aminopyrazin-2-yl)-6-cyclobutyl-2-fluorophenoxy)-N-isobutylpyrimidin-2-amine trifluoroacetic acid salt Step A: 5-{3-[(2-Chloropyrimidin-4-yl)oxy]-4-cyclobutyl-2-fluorophenyl}pyrazin-2-amine Example 137 was prepared using conditions similar to those described in Example 101 with DMSO as a solvent, heating via microwave irradiation at 120° Celsius for 1 hour and using 2,4-dichloropyrimidine.

Step B

The crude material from Step A was treated with 10 equivalents of isobutylamine and heated via microwave irradiation at 140° Celsius for 1 hour. The resulting mixture was subjected to FCC followed by reverse phase HPLC to give 6 mg (6%) of the title compound. MS (ESI): mass calcd. for $C_{22}H_{25}FN_6O$, 408.21 m/z found, 409.2 [M+H]+. 1H NMR (400 MHz, CDCl3) δ 10.38-10.29 (m, 1H), 8.38 (d, J=1.1 Hz, 1H), 8.22 (s, 1H), 7.99 (d, J=6.8 Hz, 1H), 7.96-7.88 (m, 1H), 7.31-7.23 (m, 1H), 6.46 (d, J=6.8 Hz, 1H), 3.63-3.49 (m, 1H), 2.94-2.84 (m, 2H), 2.31-1.96 (m, 4H), 1.93-1.81 (m, 1H), 1.68-1.54 (m, 1H), 0.66 (d, J=6.7 Hz, 6H).

Example 262

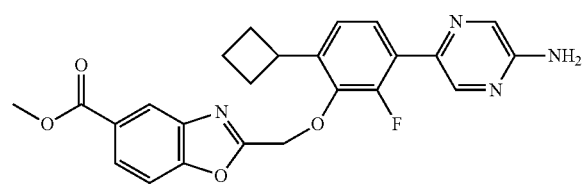

Methyl-2-{[3-(5-aminopyrazin-2-yl)-6-cyclobutyl-2-fluorophenoxy]methyl}-1,3-benzoxazole-5-carboxylate The title compound was prepared using analogous conditions described in Example 69 using methyl 2-(chloromethyl)benzo[d]oxazole-5-carboxylate. MS (ESI): mass calcd. for $C_{24}H_{21}FN_4O_4$, 448.15; m/z found, 449.1 [M+H]$^+$.

Example 263

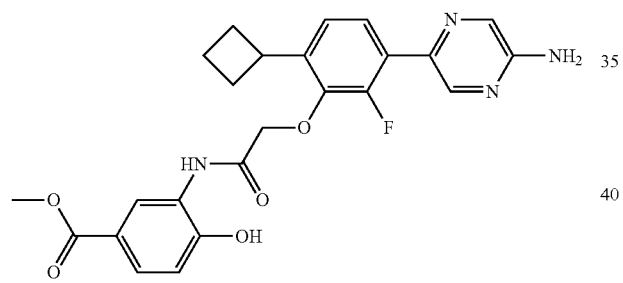

Methyl 3-({[3-(5-aminopyrazin-2-yl)-6-cyclobutyl-2-fluorophenoxy]acetyl}amino)-4-hydroxybenzoate Title compound was a side product from the preparation of Example 262. MS (ESI): mass calcd. for $C_{24}H_{23}FN_4O_5$, 466.17; m/z found, 467.1 [M+H]$^+$.

Example 264

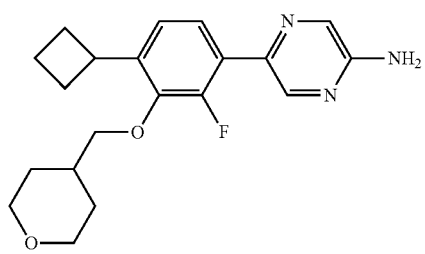

5-[4-Cyclobutyl-2-fluoro-3-(tetrahydro-2H-pyran-4-ylmethoxy)phenyl]pyrazin-2-amine The title compound was prepared using analogous conditions described in Example 69 using 4-bromomethyltetrahydropyran. MS (ESI): mass calcd. for $C_{20}H_{24}FN_3O_2$, 357.19; m/z found, 358.1 [M+H]$^+$.

Example 265

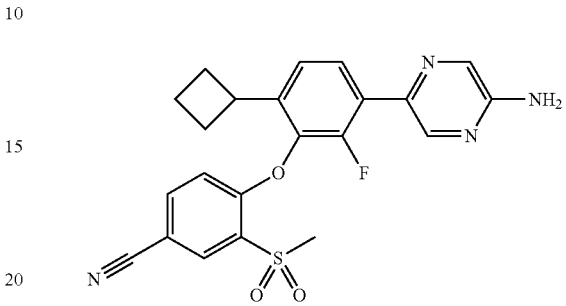

4-[3-(5-Aminopyrazin-2-yl)-6-cyclobutyl-2-fluorophenoxy]-3-(methylsulfonyl)benzonitrile The title compound was prepared using analogous conditions described in Example 69 using 4-fluoro-3-(methylsulphonyl)benzonitrile. MS (ESI): mass calcd. for $C_{22}H_{19}FN_4O_3$, 438.12; m/z found, 439.1 [M+H]$^+$.

Example 266

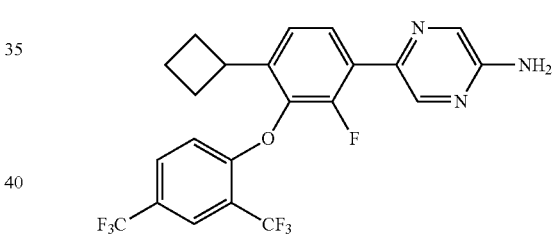

5-{3-[2,4-Bis(trifluoromethyl)phenoxy]-4-cyclobutyl-2-fluorophenyl}pyrazin-2-amine The title compound was prepared using analogous conditions described in Example 69 using 2,4-bis-(trifluoromethyl)fluorobenzene. MS (ESI): mass calcd. for $C_{22}H_{16}F_7N_3O$, 471.12; m/z found, 472.1 [M+H]$^+$.

Example 267

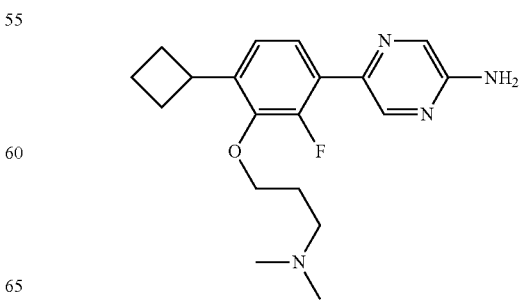

5-{4-Cyclobutyl-3-[3-(dimethylamino)propoxy]-2-fluorophenyl}pyrazin-2-amine

The title compound was prepared using analogous conditions described in Example 243 utilizing 3-chloro-N,N-dimethylpropan-1-amine hydrochloride. MS (ESI): mass calcd. for $C_{19}H_{25}FN_4O$, 344.20; m/z found, 345.2 [M+H]$^+$. $^1$H NMR (400 MHz, CDCl$_3$) δ 8.45 (s, 1H), 8.09 (d, J=1.3, 1H), 7.53 (m, 1H), 7.14 (d, J=8.2, 1H), 4.73 (s, 2H), 4.06 (t, J=6.0, 2H), 3.88-3.71 (m, 1H), 2.90-2.75 (m, 2H), 2.47 (s, 6H), 2.36-2.32 (m, 2H), 2.20-2.02 (m, 5H), 1.89-1.84 (m, 1H).

Example 268

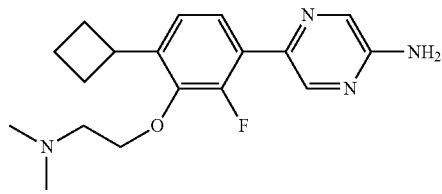 [SMILES: CN(C)CCOc1c(C2CCC2)ccc(-c2cnc(N)cn2)c1F]

5-{4-Cyclobutyl-3-[2-(dimethylamino)ethoxy]-2-fluorophenyl}pyrazin-2-amine

The title compound was prepared using analogous conditions described in Example 243 utilizing 2-chloro-N,N-dimethylethanamine hydrochloride. MS (ESI): mass calcd. for $C_{18}H_{23}FN_4O$, 330.19; m/z found, 331.1 [M+H]$^+$. $^1$H NMR (400 MHz, CDCl$_3$) δ 8.52-8.39 (m, 1H), 8.09 (d, J=1.5, 1H), 7.56 (m, 1H), 7.16 (d, J=8.4, 1H), 4.64 (s, 2H), 4.25 (s, 2H), 3.84-3.79 (m, 1H), 3.06 (s, 2H), 2.64 (s, 6H), 2.41-2.31 (m, 2H), 2.23-2.02 (m, 3H), 1.93-1.83 (m, 1H).

Example 269

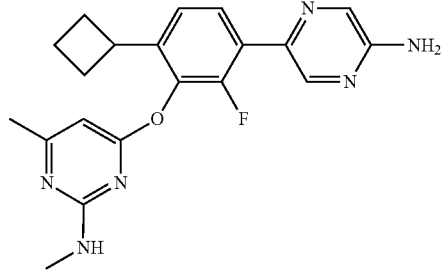 [SMILES: CNc1nc(C)cc(Oc2c(C3CCC3)ccc(-c3cnc(N)cn3)c2F)n1]

4-[3-(5-Aminopyrazin-2-yl)-6-cyclobutyl-2-fluorophenoxy]-N,6-dimethylpyrimidin-2-amine The title compound was prepared using analogous conditions described in Example 69 using 4-chloro-N,6-dimethylpyrimidin-2-amine. MS (ESI): mass calcd. for $C_{20}H_{21}FN_6O$, 380.18; m/z found, 381.2 [M+H]$^+$.

Example 270

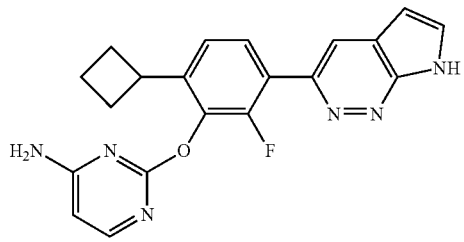 [SMILES: Nc1ccnc(Oc2c(C3CCC3)ccc(-c3cc4cc[nH]c4nn3)c2F)n1]

2-[6-Cyclobutyl-2-fluoro-3-(7H-pyrrolo[2,3-c]pyridazin-3-yl)phenoxy]pyrimidin-4-amine The title compound was prepared using analogous conditions described in Example 69 using 4-amino-2-chloropyrimidine and 6-cyclobutyl-2-fluoro-3-{7-[(4-methylphenyl)-sulfonyl]-7H-pyrrolo[2,3-c]pyridazin-3-yl}phenol. MS (ESI): mass calcd. for $C_{20}H_{17}FN_5O$, 376.14; m/z found, 376.9 [M+H]$^+$.

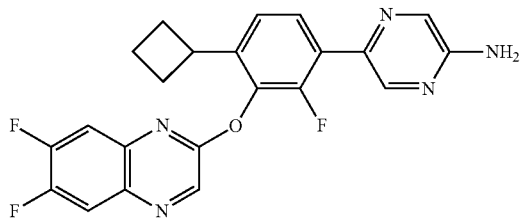 [SMILES: Nc1cnc(-c2ccc(C3CCC3)c(Oc3cnc4cc(F)c(F)cc4n3)c2F)cn1]

5-{4-Cyclobutyl-3-[(6,7-difluoroquinoxalin-2-yl)oxy]-2-fluorophenyl}pyrazin-2-amine The title compound was prepared using conditions similar to those described in Example 101 heating at 120° Celsius via microwave irradiation for 1 hour and using 2-chloro-6,7-difluoroquinoxaline. MS (ESI): mass calcd. for $C_{22}H_{16}F_3N_5O$, 423.13; m/z found, 424.0 [M+H]$^+$. $^1$H NMR (500 MHz, CD$_3$OD) δ 8.86 (s, 1H), 8.31-8.21 (m, 1H), 8.06 (dd, J=1.5, 0.7, 1H), 7.94 (dd, J=10.7, 8.3, 1H), 7.82-7.75 (m, 1H), 7.59 (dd, J=11.1, 8.1, 1H), 7.33 (d, J=8.3, 1H), 3.78-3.54 (m, 1H), 2.19 (t, J=8.9, 4H), 2.01-1.93 (m, 1H), 1.85-1.77 (m, 1H).

Example 272

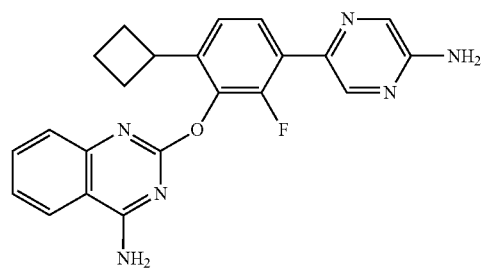 [SMILES: Nc1cnc(-c2ccc(C3CCC3)c(Oc3nc(N)c4ccccc4n3)c2F)cn1]

2-[3-(5-Aminopyrazin-2-yl)-6-cyclobutyl-2-fluorophenoxy]quinazolin-4-amine

The title compound was prepared using conditions similar to those described in Example 101 heating at 120° Celsius via microwave irradiation for 1 hour and using 2-chloroquinazolin-4-amine. MS (ESI): mass calcd. for $C_{22}H_{19}FN_6O$, 402.16; m/z found, 403.2 [M+H]$^+$. $^1$H NMR (500 MHz, CD$_3$OD) δ 8.29 (d, J=2.1, 1H), 8.10-7.97 (m, 2H), 7.69 (dd, J=13.1, 6.9, 2H), 7.55 (d, J=8.5, 1H), 7.41-7.33 (m, 1H), 7.26 (d, J=8.3, 1H), 3.71 (t, J=9.0, 1H), 2.28-2.08 (m, 4H), 2.02-1.92 (m, 1H), 1.81 (d, J=9.6, 1H).

Example 273

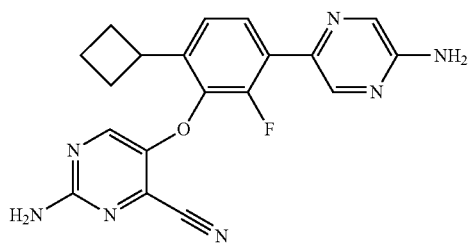 [SMILES: N#Cc1nc(N)ncc1Oc1c(C2CCC2)ccc(-c2cnc(N)cn2)c1F]

2-Amino-5-[3-(5-aminopyrazin-2-yl)-6-cyclobutyl-2-fluorophenoxy]pyrimidine-4-carbonitrile The title compound was prepared using analogous conditions described in Example 69 using 2-amino-5-bromopyrimidine-4-carbonitrile. MS (ESI): mass calcd. for $C_{19}H_{16}FN_7O$, 377.14; m/z found, 377.9 [M+H]$^+$.

Example 274

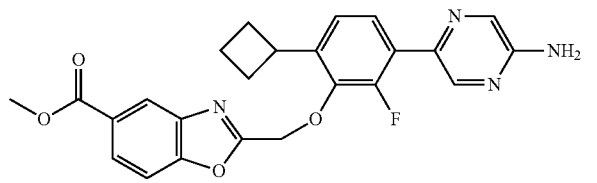 [SMILES: COC(=O)c1ccc2oc(COc3c(C4CCC4)ccc(-c4cnc(N)cn4)c3F)nc2c1]

Methyl 2-{[3-(5-aminopyrazin-2-yl)-6-cyclobutyl-2-fluorophenoxy]methyl}-1,3-benzoxazole-5-carboxylate The title compound was prepared using analogous conditions described in Example 69 using methyl 2-(chloromethyl)benzo[d]oxazole-5-carboxylate. MS (ESI): mass calcd. for $C_{24}H_{21}FN_4O_4$, 448.15; m/z found, 449.1 [M+H]$^+$.

Example 275

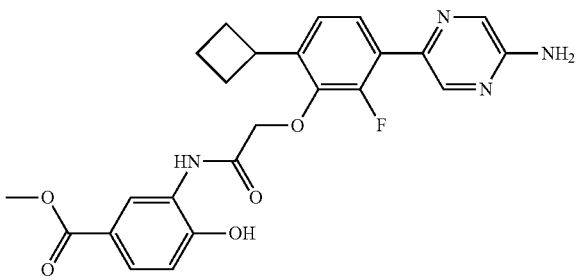 [SMILES: COC(=O)c1ccc(O)c(NC(=O)COc2c(C3CCC3)ccc(-c3cnc(N)cn3)c2F)c1]

Methyl 3-({[3-(5-aminopyrazin-2-yl)-6-cyclobutyl-2-fluorophenoxy]acetyl}amino)-4-hydroxybenzoate Title compound was a side product from the preparation of Example 274. MS (ESI): mass calcd. for $C_{24}H_{23}FN_4O_5$, 466.17; m/z found, 467.1 [M+H]$^+$.

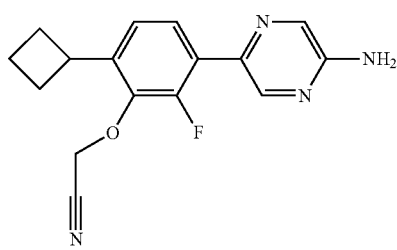

[3-(5-Aminopyrazin-2-yl)-6-cyclobutyl-2-fluorophenoxy]acetonitrile

The title compound was prepared using analogous conditions described in Example 69 using chloroacetonitrile. MS (ESI): mass calcd. for $C_{16}H_{15}FN_4O$, 298.12; m/z found, 299.1 [M+H]$^+$.

Example 277

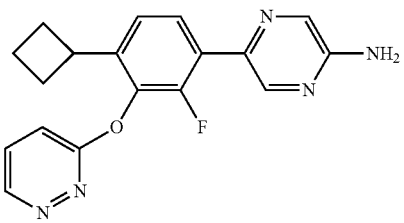 [SMILES: Nc1cnc(-c2ccc(C3CCC3)c(Oc3cccnn3)c2F)cn1]

5-[4-Cyclobutyl-2-fluoro-3-(pyridazin-3-yloxy)phenyl]pyrazin-2-amine

The title compound was prepared using analogous conditions described in Example 69 using 3-chloropyridazine. MS (ESI): mass calcd. for $C_{18}H_{16}FN_5O$, 337.13; m/z found, 338.1 [M+H]$^+$.

Example 278

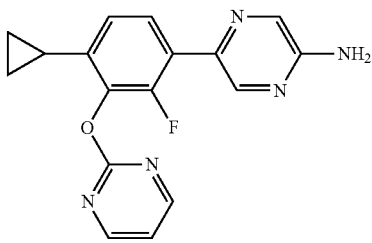 [SMILES: Nc1cnc(-c2ccc(C3CC3)c(Oc3ncccn3)c2F)cn1]

5-[4-Cyclopropyl-2-fluoro-3-(pyrimidin-2-yloxy)phenyl]pyrazin-2-amine

The title compound was prepared using conditions similar to those described in Example 101 heating at 120° Celsius via microwave irradiation for 1 hour and using 2-bromopyrimidine and 3-(5-aminopyrazin-2-yl)-6-cyclopropyl-2-fluorophenol. MS (ESI): mass calcd. for $C_{17}H_{14}FN_5O$, 323.12; m/z found, 324.1 [M+H]$^+$. $^1$H NMR (400 MHz, CD$_3$OD) δ 8.62 (d, J=4.8, 2H), 8.25 (dd, J=2.3, 1.5, 1H), 8.04 (d, J=1.5, 1H), 7.69-7.61 (m, 1H), 7.29-7.21 (m, 1H), 6.95-6.86 (m, 1H), 2.07-1.87 (m, 1H), 0.95-0.82 (m, 2H), 0.74-0.65 (m, 2H).

Example 279

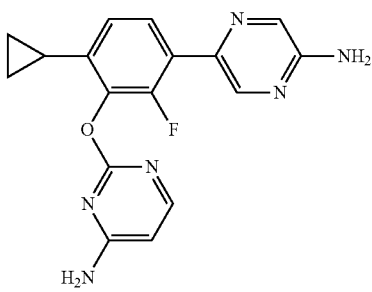 [SMILES: Nc1cnc(-c2ccc(C3CC3)c(Oc3nccc(N)n3)c2F)cn1]

2-[3-(5-Aminopyrazin-2-yl)-6-cyclopropyl-2-fluorophenoxy]pyrimidin-4-amine

The title compound was prepared using conditions similar to those described in Example 101 heating at 120° Celsius via microwave irradiation for 1 hour and using 2-chloropyrimidin-4-amine and 3-(5-aminopyrazin-2-yl)-6-cyclopropyl-2-fluorophenol. MS (ESI): mass calcd. for $C_{17}H_{15}FN_6O$, 338.13; m/z found, 339.1 [M+H]$^+$. $^1$H NMR (400 MHz, CD$_3$OD) δ 8.31-8.22 (m, 1H), 8.03 (d, J=1.5, 1H), 7.88 (d, J=5.9, 1H), 7.65-7.57 (m, 1H), 6.85 (d, J=8.5, 1H), 6.25 (d, J=5.9, 1H), 2.02-1.91 (m, 1H), 0.91 (m, 2H), 0.75-0.68 (m, 2H).

Example 280

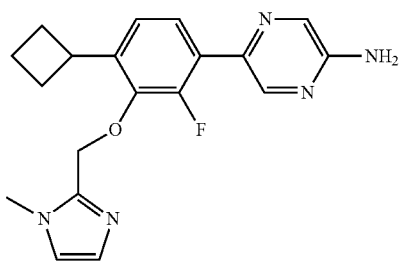 [SMILES: Cn1ccnc1COc1c(C2CCC2)ccc(-c2cnc(N)cn2)c1F]

5-{4-Cyclobutyl-2-fluoro-3-[(1-methyl-1H-imidazol-2-yl)methoxy]phenyl}pyrazin-2-amine trifluoroacetic acid salt The title compound was prepared using analogous conditions described in Example 69 using 2-(chloromethyl)-1-methyl-1H-imidazole hydrochloride. MS (ESI): mass calcd. for $C_{19}H_{20}FN_5O$, 353.17; m/z found, 354.2 [M+H].

Example 281

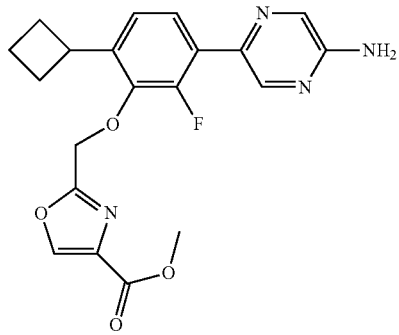

Methyl 2-{[3-(5-aminopyrazin-2-yl)-6-cyclobutyl-2-fluorophenoxy]methyl}-1,3-oxazole-4-carboxylate trifluoroacetic acid salt The title compound was prepared using analogous conditions described in Example 69 using methyl 2-(chloromethyl)oxazole-4-carboxylate. MS (ESI): mass calcd. for $C_{20}H_{19}FN_4O_4$, 398.14; m/z found, 399.1 [M+H]$^+$.

Example 282

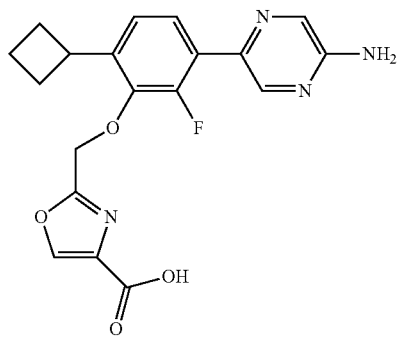 [SMILES: Nc1cnc(-c2ccc(C3CCC3)c(OCc3nc(C(=O)O)co3)c2F)cn1]

2-{[3-(5-Aminopyrazin-2-yl)-6-cyclobutyl-2-fluorophenoxy]methyl}-1,3-oxazole-4-carboxylic acid trifluoroacetic acid salt Title compound was a side product obtained in the preparation of Example 284. MS (ESI): mass calcd. for $C_{19}H_{17}FN_4O_4$, 384.12; m/z found, 385.1 [M+H]$^+$.

Example 283

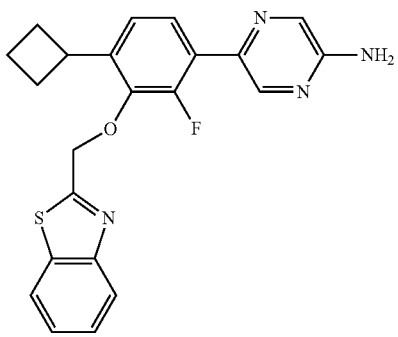 [SMILES: Nc1cnc(-c2ccc(C3CCC3)c(OCc3nc4ccccc4s3)c2F)cn1]

5-[3-(1,3-Benzothiazol-2-ylmethoxy)-4-cyclobutyl-2-fluorophenyl]pyrazin-2-amine trifluoroacetic acid salt The title compound was prepared using analogous conditions described in Example 69 using 2-(chloromethyl)benzo[d]thiazole. MS (ESI): mass calcd. for $C_{22}H_{19}FN_4OS$, 406.13; m/z found, 407.1 [M+H]$^+$.

Example 284

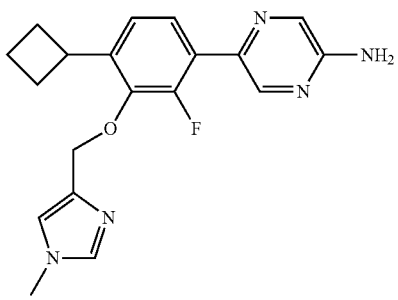 [SMILES: Cn1cnc(COc2c(C3CCC3)ccc(-c3cnc(N)cn3)c2F)c1]

5-{4-Cyclobutyl-2-fluoro-3-[(1-methyl-1H-imidazol-4-yl)methoxy]phenyl}pyrazin-2-amine trifluoroacetic acid salt The title compound was prepared using analogous conditions described in Example 69 using 4-(chloromethyl)-1-methyl-1H-imidazole hydrochloride. MS (ESI): mass calcd. for $C_{19}H_{20}FN_5O$, 353.17; m/z found, 354.1 [M+H]$^+$.

Example 285

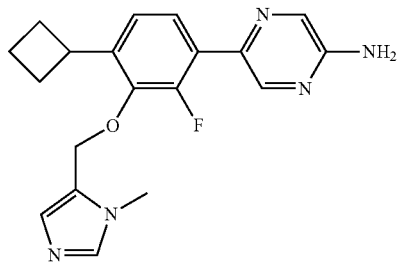 [SMILES: Cn1cncc1COc1c(C2CCC2)ccc(-c2cnc(N)cn2)c1F]

5-{4-Cyclobutyl-2-fluoro-3-[(1-methyl-1H-imidazol-5-yl)methoxy]phenyl}pyrazin-2-amine trifluoroacetic acid salt The title compound was prepared using analogous conditions described in Example 69 using 5-(chloromethyl)-1-methyl-1H-imidazolehydrochloride. MS (ESI): mass calcd. for $C_{19}H_{20}FN_5O$, 353.17; m/z found, 354.1 [M+H]$^+$.

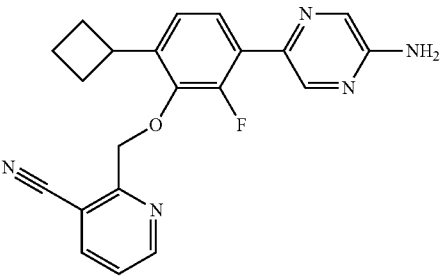 [SMILES: N#Cc1cccnc1COc1c(C2CCC2)ccc(-c2cnc(N)cn2)c1F]

2-{[3-(5-Aminopyrazin-2-yl)-6-cyclobutyl-2-fluorophenoxy]methyl)}pyridine-3-carbonitrile trifluoroacetic acid salt The title compound was prepared using analogous conditions described in Example 69 using 2-(chloromethyl)nicotinonitrile. MS (ESI): mass calcd. for $C_{19}H_{20}FN_5O$, 375.15; m/z found, 354.1 [M+H]$^+$.

Example 287

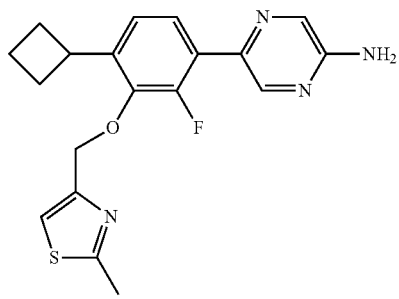 [SMILES: Cc1nc(COc2c(C3CCC3)ccc(-c3cnc(N)cn3)c2F)cs1]

5-{4-Cyclobutyl-2-fluoro-3-[(2-methyl-1,3-thiazol-4-yl)methoxy]phenyl}pyrazin-2-amine trifluoroacetic acid salt The title compound was prepared using analogous conditions described in Example 69 using 4-(chloromethyl)-2-methylthiazole. MS (ESI): mass calcd. for $C_{19}H_{19}FN_4OS$, 370.13; m/z found, 371.0 [M+H]$^+$.

Example 288

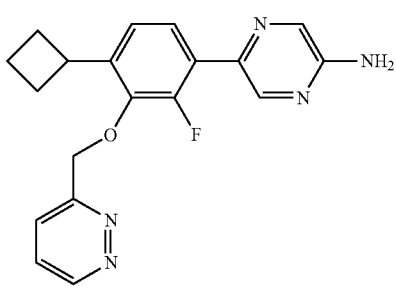 [SMILES: Nc1cnc(-c2ccc(C3CCC3)c(OCc3cccnn3)c2F)cn1]

5-[4-Cyclobutyl-2-fluoro-3-(pyridazin-3-ylmethoxy)phenyl]pyrazin-2-amine trifluoroacetic acid salt The title compound was prepared using analogous conditions described in Example 69 using 3-(chloromethyl)pyridazine. MS (ESI): mass calcd. for $C_{19}H_{18}FN_5O$, 351.15; m/z found, 352.1 [M+H]$^+$.

Example 289

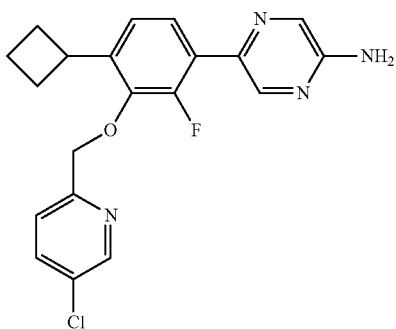 [SMILES: Nc1cnc(-c2ccc(C3CCC3)c(OCc3ccc(Cl)cn3)c2F)cn1]

5-{3-[(5-Chloropyridin-2-yl)methoxy]-4-cyclobutyl-2-fluorophenyl}pyrazin-2-amine trifluoroacetic acid salt The title compound was prepared using analogous conditions described in Example 69 using 5-chloro-2-(chloromethyl)pyridine. MS (ESI): mass calcd. for $C_{20}H_{18}FClN_4O$, 384.12; m/z found, 385.0 [M+H]$^+$.

Example 290

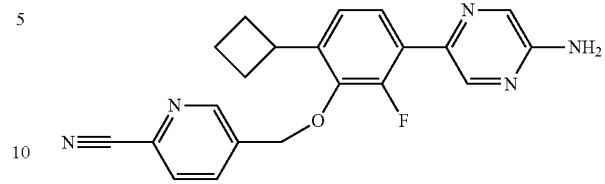

5-{[3-(5-Aminopyrazin-2-yl)-6-cyclobutyl-2-fluorophenoxy]methyl}pyridine-2-carbonitrile trifluoroacetic acid salt The title compound was prepared using analogous conditions described in Example 69 using 5-(chloromethyl)picolinonitrile. MS (ESI): mass calcd. for $C_{21}H_{18}FN_5O$, 375.15; m/z found, 376.1 [M+H]$^+$.

Example 291

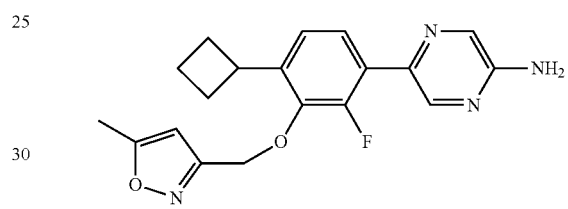

5-{4-Cyclobutyl-2-fluoro-3-[(5-methylisoxazol-3-yl)methoxy]phenyl}pyrazin-2-amine trifluoroacetic acid salt The title compound was prepared using analogous conditions described in Example 69 using 3-(chloromethyl)-5-methylisoxazole. MS (ESI): mass calcd. for $C_{19}H_{19}FN_4O_2$, 354.15; m/z found, 355.1 [M+H]$^+$.

Example 292

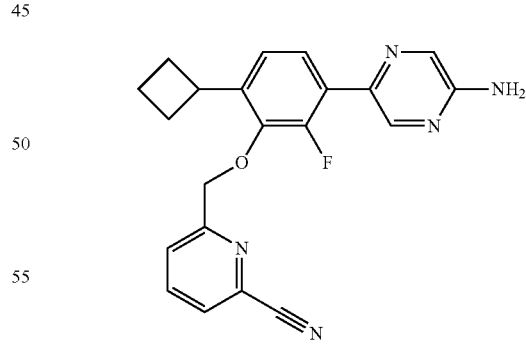

6-{[3-(5-Aminopyrazin-2-yl)-6-cyclobutyl-2-fluorophenoxy]methyl}pyridine-2-carbonitrile trifluoroacetic acid salt The title compound was prepared using analogous conditions described in Example 69 using 6-(chloromethyl)picolinonitrile. MS (ESI): mass calcd. for $C_{21}H_{18}FN_5O$, 375.15; m/z found, 376.0 [M+H]$^+$.

Example 293

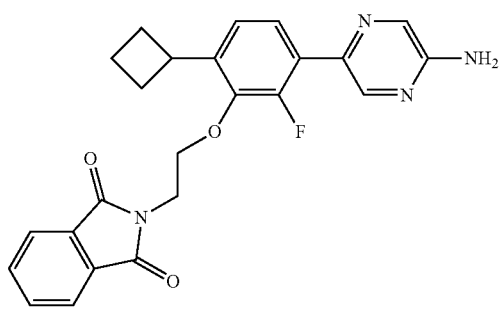 [SMILES: Nc1cnc(-c2ccc(C3CCC3)c(OCCN3C(=O)c4ccccc4C3=O)c2F)cn1]

2-{2-[3-(5-Aminopyrazin-2-yl)-6-cyclobutyl-2-fluorophenoxy]ethyl}-1H-isoindole-1,3(2H)-dione The title compound was prepared using analogous conditions described in Example 69 using 2-(2-bromoethyl)isoindoline-1,3-dione. MS (ESI): mass calcd. for $C_{24}H_{21}FN_4O_3$, 432.16; m/z found, 433.0 [M+H]+.

Example 294

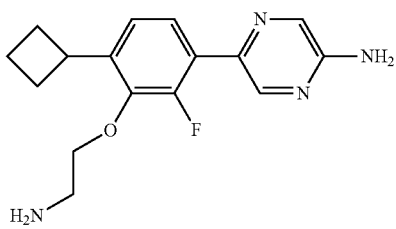

5-[3-(2-Aminoethoxy)-4-cyclobutyl-2-fluorophenyl]pyrazin-2-amine

To a 200 mL round-bottomed flask containing 2-{2-[3-(5-aminopyrazin-2-yl)-6-cyclobutyl-2-fluorophenoxy]ethyl}-1H-isoindole-1,3(2H)-dione (550 mg, 1.27 mmol) were added a stir bar and EtOH (26 mL). The mixture was then thoroughly sparged (bubbling $N_2$) before charging the flask with hydrazine monohydrate (1.00 mL, 21 mmol). The flask was then heated at 77° Celsius for 22 hours. The reaction mixture was cooled to rt, diluted with EtOAc, washed with NaOH (1 N, ×3), dried over MgSO4, filtered and concentrated to dryness to give the desired product (365 mg, 95%). MS (ESI): mass calcd. for $C_{16}H_{19}FN_4O$, 302.15; m/z found, 303.1 [M+H]+.

Example 295

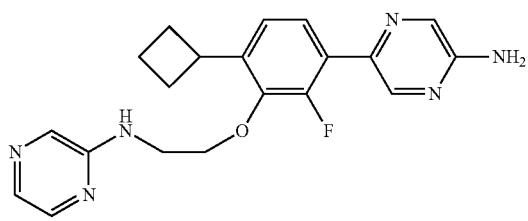 [SMILES: Nc1cnc(-c2ccc(C3CCC3)c(OCCNc3cnccn3)c2F)cn1]

5-{4-Cyclobutyl-2-fluoro-3-[2-(pyrazin-2-ylamino)ethoxy]phenyl}pyrazin-2-amine trifluoroacetic acid salt To a 5 mL microwave vial were added a spin-vane, 5-[3-(2-aminoethoxy)-4-cyclobutyl-2-fluorophenyl]pyrazin-2-amine (47 mg, 0.16 mmol), 2-fluoropyrazine (35 mg, 0.35 mmol), and $Cs_2CO_3$ (115 mg, 0.35 mmol). The flask was thoroughly purged with nitrogen, charged with DMSO (1.0 mL), and heated at 100° Celsius for 14.5 hours before cooling to room temperature, filtering off the solids and subjecting the filtrate to HPLC purification to give the title compound (26 mg, 34%). MS (ESI): mass calcd. for $C_{20}H_{21}FN_6O$, 380.18; m/z found, 381.1 [M+H]+.

Example 296

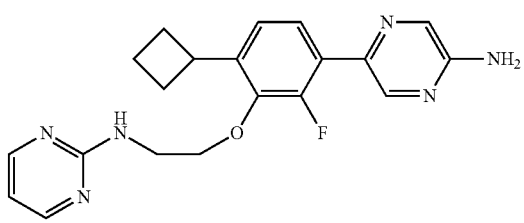 [SMILES: Nc1cnc(-c2ccc(C3CCC3)c(OCCNc3ncccn3)c2F)cn1]

N-{2-[3-(5-Aminopyrazin-2-yl)-6-cyclobutyl-2-fluorophenoxy]ethyl}pyrimidin-2-amine trifluoroacetic acid salt The title compound was prepared using analogous conditions described in Example 295 using 2-chloropyrimidine. MS (ESI): mass calcd. for $C_{20}H_{21}FN_6O$, 380.18; m/z found, 381.1 [M+H]J.

Example 297

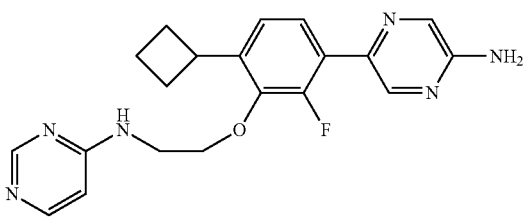 [SMILES: Nc1cnc(-c2ccc(C3CCC3)c(OCCNc3ccncn3)c2F)cn1]

N-{2-[3-(5-Aminopyrazin-2-yl)-6-cyclobutyl-2-fluorophenoxy]ethyl}pyrimidin-4-amine The title compound was prepared using analogous conditions described in Example 295 using 4-chloropyrimidine. MS (ESI): mass calcd. for $C_{20}H_{21}FN_6O$, 380.18; m/z found, 381.1 [M+H]+.

Example 298

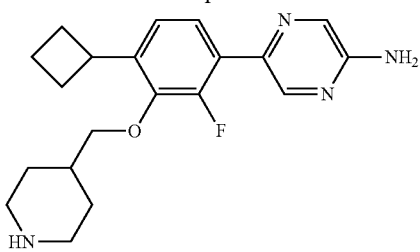

5-[4-Cyclobutyl-2-fluoro-3-(piperidin-4-ylmethoxy)phenyl]pyrazin-2-amine hydrogen chloride salt The title compound was prepared using analogous conditions described in Step A of Example 68 using tert-butyl 4-((3-(5-aminopyrazin-2-yl)-6-cyclobutyl-2-fluorophenoxy)-methyl)piperidine-1-carboxylate. MS (ESI): mass calcd. for $C_{20}H_{25}FN_4O$, 356.20; m/z found, 357.1 [M+H]$^+$.

Example 299

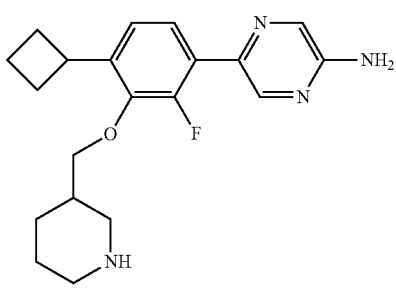 [SMILES: Nc1cnc(-c2ccc(C3CCC3)c(OCC3CCCNC3)c2F)cn1]

racemic 5-[4-Cyclobutyl-2-fluoro-3-(piperidin-3-ylmethoxy)phenyl]pyrazin-2-amine The title compound was prepared using analogous conditions described in Step A of Example 68 utilizing racemic tert-butyl 3-((3-(5-aminopyrazin-2-yl)-6-cyclobutyl-2-fluorophenoxy)methyl)piperidine-1-carboxylate. MS (ESI): mass calcd. for $C_{20}H_{25}FN_4O$, 356.20; m/z found, 357.2 [M+H]$^+$, $^1$H NMR (400 MHz, CDCl$_3$) δ 8.60 (s, 1H), 8.43 (s, 1H), 8.08 (s, 1H), 7.53 (m, 1H), 7.13 (d, J=8.2, 1H), 4.69 (s, 2H), 3.96-3.83 (m, 2H), 3.80-3.68 (m, 1H), 3.65-3.57 (m, 1H), 3.52-3.35 (m, 1H), 2.93-2.76 (m, 2H), 2.55-2.38 (m, 1H), 2.38-2.27 (m, 2H), 2.19-1.83 (m, 7H), 1.63-1.44 (m, 1H).

Example 300

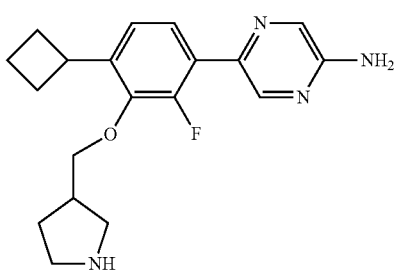 [SMILES: Nc1cnc(-c2ccc(C3CCC3)c(OCC3CCNC3)c2F)cn1]

racemic 5-[4-Cyclobutyl-2-fluoro-3-(pyrrolidin-3-ylmethoxy)phenyl]pyrazin-2-amine The title compound was prepared using analogous conditions described in Step A of Example 68 utilizing racemic tert-butyl 3-((3-(5-aminopyrazin-2-yl)-6-cyclobutyl-2-fluoro-phenoxy)methyl)pyrrolidine-1-carboxylate. MS (ESI): mass calcd. for $C_{19}H_{23}FN_4O$, 342.19; m/z found, 343.2 [M+H]$^+$. $^1$H NMR (400 MHz, CDCl$_3$) δ 9.90 (s, 1H), 8.43 (d, J=1.7, 1H), 8.08 (d, J=1.1, 1H), 7.53 (m, 1H), 7.14 (d, J=8.2, 1H), 4.73 (s, 2H), 4.12-3.97 (m, 2H), 3.78-3.64 (m, 2H), 3.55-3.39 (m, 2H), 3.38-3.28 (m, 1H), 2.99-2.81 (m, 1H), 2.39-2.26 (m, 3H), 2.19-2.01 (m, 4H), 1.92-1.83 (m, 1H).

Example 301

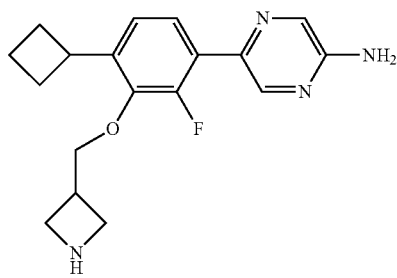 [SMILES: Nc1cnc(-c2ccc(C3CCC3)c(OCC3CNC3)c2F)cn1]

5-[3-(Azetidin-3-ylmethoxy)-4-cyclobutyl-2-fluorophenyl]pyrazin-2-amine

The title compound was prepared using analogous conditions described in Step A of Example 68 utilizing tert-butyl-3-((3-(5-aminopyrazin-2-yl)-6-cyclobutyl-2-fluorophenoxy)-methyl)azetidine-1-carboxylate. MS (ESI): mass calcd. for $C_{18}H_{21}FN_4O$, 328.17; m/z found, 329.5 [M+H]$^+$. $^1$H NMR (400 MHz, DMSO-d$_6$) δ 8.35 (s, 1H), 8.27 (s, 1H), 7.98 (s, 1H), 7.52 (m, 1H), 7.20 (d, J=8.2, 1H), 6.65 (s, 2H), 4.10 (d, J=5.7, 2H), 4.06-3.96 (m, 2H), 3.87-3.77 (m, 2H), 3.77-3.69 (m, 1H), 3.17-3.09 (m, 1H), 2.33-2.19 (m, 2H), 2.15-1.92 (m, 3H), 1.87-1.74 (m, 1H).

Example 302

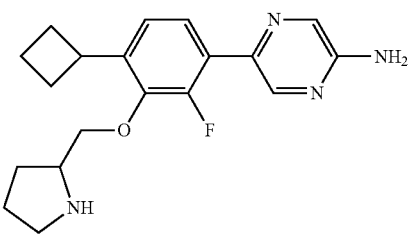 [SMILES: Nc1cnc(-c2ccc(C3CCC3)c(OCC3CCCN3)c2F)cn1]

racemic 5-[4-Cyclobutyl-2-fluoro-3-(pyrrolidin-2-ylmethoxy)phenyl]pyrazin-2-amine The title compound was prepared using analogous conditions described in Step A of Example 68 utilizing racemic tert-butyl 2-((3-(5-aminopyrazin-2-yl)-6-cyclobutyl-2-fluorophenoxy)methyl)pyrrolidine-1-carboxylate. MS (ESI):

mass calcd. for $C_{19}H_{23}FN_4O$, 342.19; m/z found, 343.1 [M+H]$^+$. $^1$H NMR (400 MHz, DMSO-d$_6$) δ 8.26 (d, J=1.5, 1H), 7.97 (d, J=1.4, 1H), 7.49 (m, 1H), 7.19 (d, J=8.2, 1H), 6.63 (s, 2H), 3.98-3.88 (m, 2H), 3.85-3.76 (m, 1H), 3.59-3.52 (m, 1H), 3.01-2.91 (m, 2H), 2.32-2.24 (m, 2H), 2.17-1.89 (m, 5H), 1.84-1.70 (m, 3H), 1.61-1.51 (m, 1H).

Example 303

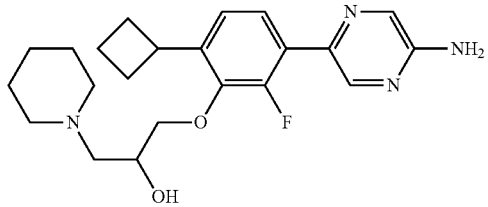 [SMILES: Nc1cnc(-c2ccc(C3CCC3)c(OCC(O)CN3CCCCC3)c2F)cn1]

racemic 5 1-[3-(5-Aminopyrazin-2-yl)-6-cyclobutyl-2-fluorophenoxy]-3-piperidin-1-ylpropan-2-ol The title compound was prepared using analogous conditions described in Example 51 utilizing piperidine. MS (ESI): mass calcd. for $C_{22}H_{29}FN_4O_2$, 400.23; m/z found, 401.2 [M+H]$^+$. $^1$H NMR (400 MHz, CD$_3$OD) δ 8.28-8.23 (m, 1H), 8.03 (d, J=1.5, 1H), 7.50 (m, 1H), 7.22 (d, J=8.2, 1H), 4.58 (s, 2H), 4.43-4.34 (m, 1H), 4.04-3.94 (m, 2H), 3.95-3.85 (m, 1H), 3.34 (dd, J=8.4, 4.9, 2H), 3.23 (d, J=13.2, 2H), 2.37 (m, 2H), 2.25-2.12 (m, 2H), 2.08 (m, 1H), 1.93-1.79 (m, 5H), 1.68 (s, 2H).

Example 304

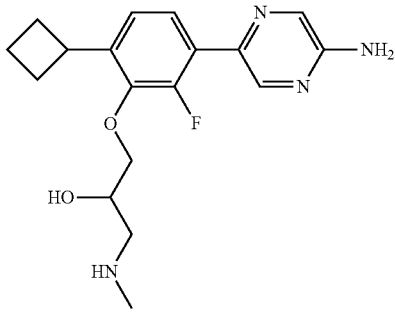 [SMILES: CNCC(O)COc1c(C2CCC2)ccc(-c2cnc(N)cn2)c1F]

racemic 1-[3-(5-Aminopyrazin-2-yl)-6-cyclobutyl-2-fluorophenoxy]-3-(methylamino)propan-2-ol The title compound was prepared using analogous conditions described in Example 51 utilizing methylamine. MS (ESI): mass calcd. for $C_{18}H_{23}FN_4O_2$, 346.18; m/z found, 347.4 [M+H]$^+$. $^1$H NMR (400 MHz, CD$_3$OD) 8.32-8.23 (m, 1H), 8.11-8.00 (m, 1H), 7.51 (m, 1H), 7.23 (d, J=8.2, 1H), 4.29-4.21 (m, 1H), 4.08-3.98 (m, 2H), 3.95-3.86 (m, 1H), 3.39-3.35 (m, 1H), 3.25-3.20 (m, 1H), 2.79 (s, 3H), 2.44-2.34 (m, 2H), 2.23-2.06 (m, 3H), 1.96-1.86 (m, 1H).

Example 305

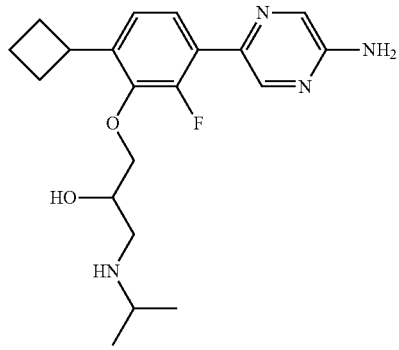 [SMILES: CC(C)NCC(O)COc1c(C2CCC2)ccc(-c2cnc(N)cn2)c1F]

racemic 1-[3-(5-Aminopyrazin-2-yl)-6-cyclobutyl-2-fluorophenoxy]-3-[(1-methylethyl)amino]propan-2-ol The title compound was prepared using analogous conditions described in Example 51 utilizing isopropylamine. MS (ESI): mass calcd. for $C_{20}H_{27}FN_4O_2$, 374.21; m/z found, 375.5 [M+H]$^+$. $^1$H NMR (400 MHz, DMSO-d$_6$) δ 8.31-8.21 (m, 1H), 7.97 (d, J=1.4, 1H), 7.50 (m, 1H), 7.19 (d, J=8.2, 1H), 6.64 (s, 2H), 5.73 (s, 1H), 4.19-4.07 (m, 1H), 3.99-3.89 (m, 2H), 3.88-3.76 (m, 1H), 3.27-3.22 (m, 1H), 3.15-3.07 (m, 1H), 2.98-2.88 (m, 1H), 2.34-2.23 (m, 2H), 2.14-1.90 (m, 3H), 1.86-1.73 (m, 1H), 1.24-1.14 (m, 6H).

Example 306

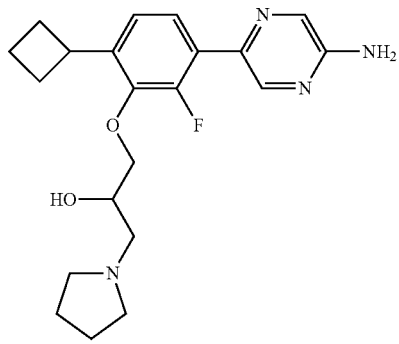 [SMILES: Nc1cnc(-c2ccc(C3CCC3)c(OCC(O)CN3CCCC3)c2F)cn1]

racemic 1-[3-(5-Aminopyrazin-2-yl)-6-cyclobutyl-2-fluorophenoxy]-3-pyrrolidin-1-ylpropan-2-ol The title compound was prepared using analogous conditions described in Example 51 utilizing pyrrolidine. MS (ESI): mass calcd. for $C_{21}H_{27}FN_4O_2$, 386.21; m/z found, 387.2 [M+H]$^+$. $^1$H NMR (400 MHz, CDCl$_3$) δ 8.54-8.36 (m, 1H), 8.09 (d, J=1.4, 1H), 7.55 (m, 1H), 7.15 (d, J=8.2, 1H), 4.71 (s, 2H), 4.23-4.12 (m, 1H), 4.02 (d, J=5.1, 2H), 3.94-3.78 (m, 1H), 3.20 (s, 1H), 2.99-2.92 (m, 1H), 2.91-2.83 (m, 2H), 2.78-2.68 (m, 3H), 2.42-2.31 (m, 2H), 2.21-2.01 (m, 3H), 1.93-1.81 (m, 5H).

Example 307

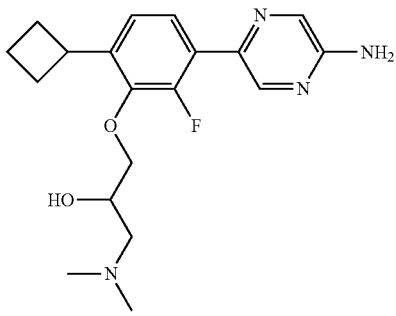

racemic 1-[3-(5-Aminopyrazin-2-yl)-6-cyclobutyl-2-fluorophenoxy]-3-(dimethylamino)propan-2-ol The title compound was prepared using analogous conditions described in Example 51 utilizing dimethylamine. MS (ESI): mass calcd. for $C_{19}H_{25}FN_4O_2$, 360.20; m/z found, 361.2 [M+H]$^+$. $^1$H NMR (400 MHz, DMSO-d$_6$) δ 8.26 (s, 1H), 7.97 (d, J=1.4, 1H), 7.49 (m, 1H), 7.19 (d, J=8.2, 1H), 6.64 (s, 2H), 5.41 (s, 1H), 4.08 (s, 1H), 3.91-3.79 (m, 3H), 2.88-2.82 (m, 1H), 2.81-2.72 (m, 1H), 2.51 (s, 6H), 2.32-2.23 (m, 2H), 2.12-1.92 (m, 3H), 1.84-1.73 (m, 1H).

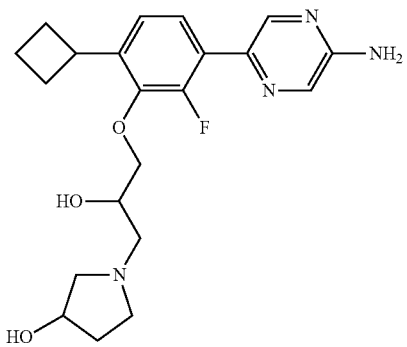 [SMILES: Nc1cnc(-c2ccc(C3CCC3)c(OCC(O)CN3CCC(O)C3)c2F)cn1]

diastereomeric mixture of 1-{3-[3-(5-Aminopyrazin-2-yl)-6-cyclobutyl-2-fluorophenoxy]-2-hydroxypropyl}pyrrolidin-3-ol The title compound was prepared using analogous conditions described in Example 51 utilizing racemic 3-hydroxypyrrolidine. MS (ESI): mass calcd. for $C_{21}H_{27}FN_4O_3$, 402.21; m/z found, 403.2 [M+H]$^+$. $^1$H NMR (400 MHz, DMSO-d$_6$) δ 8.28-8.23 (m, 1H), 7.97 (d, J=1.4, 1H), 7.48 (m, 1H), 7.19 (d, J=8.4, 1H), 6.63 (s, 2H), 5.46-5.14 (m, 1H), 4.96 (d, J=14.5, 1H), 4.28-4.21 (m, 1H), 4.06-3.98 (m, 1H), 3.93-3.79 (m, 3H), 3.07-2.64 (m, 6H), 2.33-2.24 (m, 2H), 2.13-1.94 (m, 4H), 1.86-1.75 (m, 1H), 1.70-1.57 (m, 1H).

Example 309

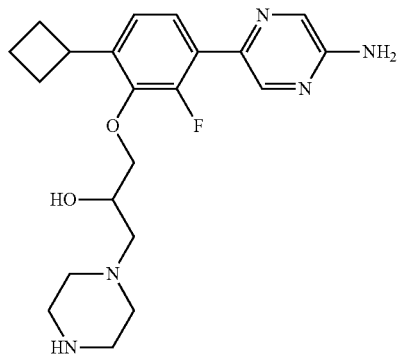 [SMILES: Nc1cnc(-c2ccc(C3CCC3)c(OCC(O)CN3CCNCC3)c2F)cn1]

racemic 1-[3-(5-Aminopyrazin-2-yl)-6-cyclobutyl-2-fluorophenoxy]-3-piperazin-1-ylpropan-2-ol The title compound was prepared using analogous conditions described in Example 51 utilizing piperazine. MS (ESI): mass calcd. for $C_{21}H_{28}FN_5O_2$, 401.22; m/z found, 402.2 [M+H]$^+$. $^1$H NMR (400 MHz, DMSO-d$_6$) δ 8.28 (s, 1H), 8.00 (d, J=1.4, 1H), 7.50 (m, 1H), 7.21 (d, J=8.3, 1H), 6.66 (s, 2H), 4.95 (s, 1H), 4.01-3.82 (m, 4H), 2.97 (t, J=4.9, 4H), 2.63 (s, 3H), 2.58-2.53 (m, 1H), 2.52-2.49 (m, 2H), 2.47-2.41 (m, 1H), 2.35-2.26 (m, 2H), 2.16-1.94 (m, 3H), 1.88-1.78 (m, 1H).

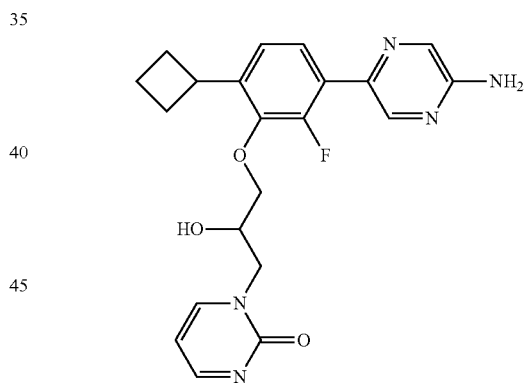

racemic 1-{3-[3-(5-Aminopyrazin-2-yl)-6-cyclobutyl-2-fluorophenoxy]-2-hydroxypropyl}pyrimidin-2(1H)-one The title compound was prepared using analogous conditions described in Example 51 utilizing 2-pyrimidinone. MS (ESI): mass calcd. for $C_{21}H_{22}FN_5O_3$, 411.17; m/z found, 412.1 [M+H]$^+$. $^1$H NMR (400 MHz, DMSO-d$_5$) δ 8.55 (dd, J=4.2, 2.8, 1H), 8.32-8.26 (m, 1H), 8.10 (dd, J=6.5, 2.8, 1H), 8.00 (d, J=1.5, 1H), 7.52 (m, 1H), 7.22 (d, J=8.3, 1H), 6.64 (s, 2H), 6.43 (dd, J=6.4, 4.2, 1H), 5.48 (d, J=5.8, 1H), 4.33 (dd, J=13.0, 3.3, 1H), 4.19 (t, J=7.1, 1H), 3.96 (d, J=5.2, 2H), 3.85 (dd, J=17.7, 8.7, 1H), 3.71 (dd, J=13.0, 9.0, 1H), 2.32 (m, 2H), 2.10 (m, 2H), 2.00 (dd, J=17.9, 7.9, 1H), 1.87-1.78 (m, 1H).

Example 311

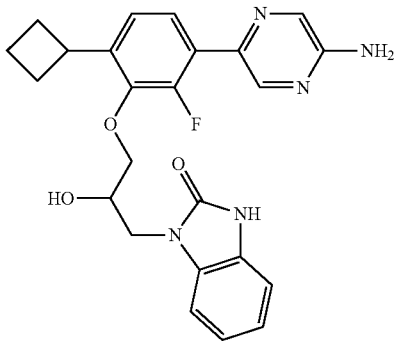 [SMILES: Nc1cnc(-c2ccc(C3CCC3)c(OCC(O)Cn3c(=O)[nH]c4ccccc43)c2F)cn1]

racemic 1-{3-[3-(5-Aminopyrazin-2-yl)-6-cyclobutyl-2-fluorophenoxy]-2-hydroxypropyl}-1,3-dihydro-2H-benzimidazol-2-one The title compound was prepared using analogous conditions described in Example 51 utilizing 1H-benzo[d]imidazol-2(3H)-one. MS (ESI): mass calcd. for $C_{24}H_{24}FN_5O_3$, 449.19; m/z found, 450.0 [M+H]$^+$. $^1$H NMR (400 MHz, DMSO-d$_6$) δ 10.83 (s, 1H), 8.29-8.24 (m, 1H), 7.99 (d, J=1.5, 1H), 7.50 (m, 1H), 7.23-7.13 (m, 2H), 7.06-6.93 (m, 3H), 6.63 (s, 2H), 5.36 (d, J=4.9, 1H), 4.18 (s, 1H), 4.00-3.91 (m, 3H), 3.89-3.78 (m, 2H), 2.32-2.20 (m, 2H), 2.14-2.01 (m, 2H), 1.99-1.89 (m, 1H), 1.79 (dd, J=18.7, 9.1, 1H).

Example 312

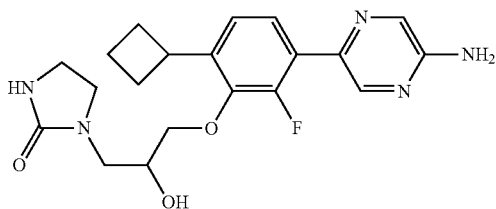 [SMILES: Nc1cnc(-c2ccc(C3CCC3)c(OCC(O)CN3CCNC3=O)c2F)cn1]

racemic 1-{3-[3-(5-Aminopyrazin-2-yl)-6-cyclobutyl-2-fluorophenoxy]-2-hydroxypropyl}imidazolidin-2-one The title compound was prepared using analogous conditions described in Example 51 utilizing imidazolidin-2-one. MS (ESI): mass calcd. for $C_{20}H_{24}FN_5O_3$, 401.19; m/z found, 402.1 [M+H]$^+$. $^1$H NMR (400 MHz, DMSO-d$_6$) δ 8.28 (s, 1H), 7.99 (s, 1H), 7.50 (m, 1H), 7.21 (d, J=8.2, 1H), 6.64 (s, 2H), 6.31 (s, 1H), 5.20 (d, J=4.7, 1H), 3.94 (s, 1H), 3.87 (s, 3H), 3.25 (dd, J=19.6, 11.7, 5H), 3.09 (dd, J=13.8, 7.0, 1H), 2.30 (d, J=7.9, 2H), 2.15-2.05 (m, 2H), 2.00 (d, J=9.9, 1H), 1.82 (d, J=9.1, 1H).

Example 313

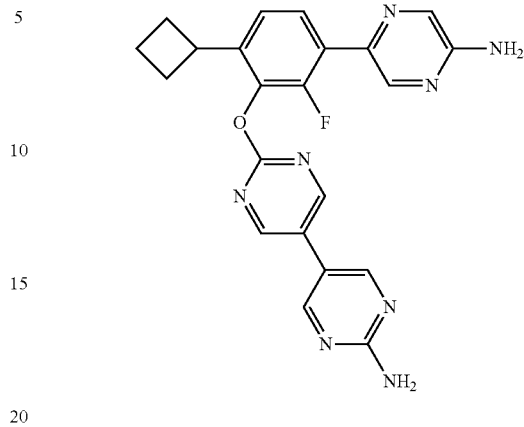

2'-[3-(5-Aminopyrazin-2-yl-6-cyclobutyl-2-fluorophenoxy]-5,5'-bipyrimidin-2-amine

Step A: 5-(3-((5-Bromopyrimidin-2-yl)oxy)-4-cyclobutyl-2-fluorophenyl)pyrazin-2-amine To a microwave vial containing a stir-bar was added 3-(5-aminopyrazin-2-yl)-6-cyclobutyl-2-fluorophenol (100 mg, 0.386 mmol), 5-bromo-2-chloropyrimidine (74 mg, 0.39 mmol), cesium carbonate (188 mg, 0.580), and DMSO (2 mL). The vial was sealed and heated in the microwave for 30 minutes at 120° Celsius. The mixture was cooled to rt then passed through a syringe filter and the filtrate subjected to HPLC purification to give the title compound. $^1$H NMR (500 MHz, 2 mL) δ 8.69 (d, J=1.5, 2H), 8.24 (s, 1H), 8.10 (s, 1H), 7.79-7.69 (m, 1H), 7.27 (d, J=8.3, 1H), 3.72-3.58 (m, 1H), 2.23-2.10 (m, 3H), 2.02-1.94 (m, 1H), 1.89-1.75 (m, 1H).

Step B: 2'-[3-(5-Aminopyrazin-2-yl)-6-cyclobutyl-2-fluorophenoxy]-5,5'-bipyrimidin-2-amine 5-(3-((5-Bromopyrimidin-2-yl)oxy)-4-cyclobutyl-2-fluorophenyl)pyrazin-2-amine (60 mg, 0.14 mmol) and 5-(4,4,5,5-tetramethyl-1,3,2-dioxaborolan-2-yl)pyrimidin-2-amine (32 mg, 0.14 mmol) were added to a sealable microwave vial equipped with a stir-bar. 1,4-Dioxane (0.58 mL) and Na$_2$CO$_3$ (2 M, 0.14 mL) were added And the mixture sparged with Ar for 10 min before adding Pd(dppf)Cl$_2$.CH$_2$Cl$_2$ (5 mg, 0.007 mmol) and heating the reaction mixture at 80° Celsius for 15 hours. The reaction was then cooled to rt, diluted with water (5 mL), and extracted with ethyl acetate (3×10 mL). The combined organic extracts were dried over Na$_2$SO$_4$, filtered, and concentrated to dryness. The crude product was purified by HPLC to give the title compound. MS (ESI): mass calcd. for $C_{22}H_{19}FN_8O$, 430.17; m/z found, 431.1 [M+H]$^+$. $^1$H NMR (500 MHz, CD$_3$OD) δ 8.83 (s, 2H), 8.67 (s, 2H), 8.23 (s, 1H), 8.16 (s, 1H), 7.82-7.74 (m, 1H), 7.30 (d, J=8.3, 1H), 3.68 (p, J=8.9, 1H), 2.31-2.08 (m, 4H), 2.07-1.92 (m, 1H), 1.92-1.76 (m, 1H).

Intermediate J

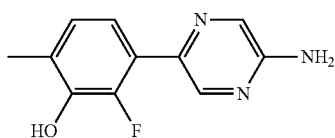 [SMILES: Cc1ccc(-c2cnc(N)cn2)c(F)c1O]

3-(5-Aminopyrazin-2-yl)-2-fluoro-6-methylphenol

Step A:
tert-Butyl(2-fluoro-6-methylphenoxy)dimethylsilane

To a stirred solution of 2-fluoro-6-methylphenol (176 mg, 1.40 mmol) in DCM (6.3 mL), cooled to 0° Celsius, were added imidazole (142 mg, 2.09 mmol) followed by tert-butyldimethylsilyl chloride (231 mg, 1.54 mmol). The flask was warmed to rt and stirred for 2 hours. The reaction mixture was then poured in to water (50 mL) and extracted with DCM (3×50 mL). The combined organic extracts were dried over sodium sulfate, filtered, and concentrated to dryness to provide the title compound that was used without further purification. $^1$H NMR (500 MHz, CDCl$_3$) δ 6.91-6.85 (m, 2H), 6.80-6.73 (m, 1H), 2.24 (t, J=0.7, 3H), 1.02 (s, 9H), 0.20 (d, J=2.5, 6H).

Step B: (3-((tert-Butyldimethylsilyl)oxy)-2-fluoro-4-methylphenyl)boronic acid

To a 25 mL flask vial were added a stir-bar, 2.1 mL dry THF, and 2,2,6,6-tetramethylpiperidine (0.22 mL, 1.0 mmol). The flask was cooled to −78° Celsius and then treated with n-BuLi (0.48 mL, 1.9 mmol, 2.5 M in hexanes) over 2 minutes. The resultant mixture was stirred for 5 min and then warmed to 0° Celsius. After 30 min, the mixture was re-cooled to −78° Celsius and treated with B(O-iPr)$_3$ (0.26 mL, 1.1 mmol) over 4 min. After 15 min, a solution consisting of tert-butyl(2-fluoro-6-methylphenoxy)dimethylsilane (247 mg, 1.03 mmol) in dry THF (2.1 mL) was added over the course of 6 min and stirring continued for 1 hour at −78° Celsius. The mixture was then warmed to rt, treated with HOAc (0.5 mL), and then poured into water (100 mL) and stirred for 5 min. The aqueous mixture was then extracted with EtOAc (3×100 mL), the combined extracts dried over Na$_2$SO$_4$, filtered, and concentrated to dryness to give the title compound, which was used directly in the next synthetic step.

Step C: 5-(3-((tert-Butyldimethylsilyl)oxy)-2-fluoro-4-methylphenyl)pyrazin-2-amine (3-((tert-Butyldimethylsilyl)oxy)-2-fluoro-4-methylphenyl)boronic acid (292 mg, 1.03 mmol), 2-amino-5-bromopyrazine (179 mg, 1.03 mmol), 1,4-dioxane (6.1 mL), and Na$_2$CO$_3$ (2.1 mL, 2 M) were added to a microwave vial and the resultant mixture sparged with argon for 10 minutes. Pd(dppf)Cl$_2$.DCM was then added the mixture, the vial sealed, and then heated at 80° Celsius for 16 hours. The reaction mixture was then cooled to rt, diluted with water (5 mL), and extracted with EtOAc (4×5 mL). The combined organic extracts were then dried over Na$_2$SO$_4$, filtered, and concentrated to dryness to provide the title compound. This compound was used directly in the next synthetic step without purification.

Step D:
3-(5-Aminopyrazin-2-yl)-2-fluoro-6-methylphenol 5-(3-((tert-Butyldimethylsilyl)oxy)-2-fluoro-4-methylphenyl)pyrazin-2-amine (342 mg, 1.03 mmol) was dissolved in THF (1.2 mL) at rt and then treated with tetrabutylammonium fluoride (1.2 mL, 1 M in THF). The reaction was stirred for 1 hour at rt, before diluting with water (10 mL) and extracting with EtOAc (10 mL×4). The combined organic extracts were washed with brine, dried over Na$_2$SO$_4$, filtered, and concentrated to dryness. The crude product was purified by FCC to provide the title compound. $^1$H NMR (500 MHz, CD$_3$OD) δ 8.26 (dd, J=2.3, 1.5, 1H), 8.01 (d, J=1.5, 1H), 7.09 (m, 1H), 6.94 (m, 1H), 2.25 (s, 3H).

Intermediate K

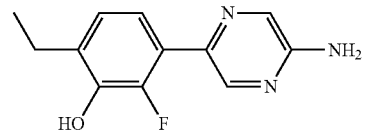 [SMILES: CCc1ccc(-c2cnc(N)cn2)c(F)c1O]

3-(5-Aminopyrazin-2-yl)-6-ethyl-2-fluorophenol

Step A: 2-Fluoro-6-vinylphenol

To a round-bottomed flask containing a stir-bar were added, methyltriphenylphosphonium bromide (5.6 g, 16 mmol) and anhydrous THF (50 mL). The mixture was stirred until homogeneous and then cooled to 0° Celsius. The flask was then charged drop-wise with n-BuLi (6.85 mL, 2.5 M in hexanes). The resultant solution was stirred for 30 minutes and then transferred via cannula to a stirred mixture of 3-fluoro-2-hydroxybenzaldehyde (1 g, 7 mmol) and THF (28 mL) at rt under an argon atmosphere. The resultant mixture was stirred for 3 h before quenching with saturated NH$_4$Cl (50 mL), diluting with water, and extracting with ether (3×100 mL). The combined ethereal extracts were dried over magnesium sulfate, filtered through a plug of silica gel, and then concentrated to dryness to provide the title compound that was used without further purification. $^1$H NMR (500 MHz, CDCl$_3$) δ 7.20 (m, 1H), 7.04-6.92 (m, 2H), 6.80 (m, 1H), 5.81 (dd, J=17.8, 1.3, 1H), 5.69 (s, 1H), 5.35 (dd, J=11.2, 1.3, 1H).

Step B:
tert-Butyl(2-fluoro-6-vinylphenoxy)dimethylsilane

The title compound was prepared in an analogous way to tert-butyl(2-fluoro-6-methylphenoxy)dimethylsilane in Step A of Intermediate J using 2-fluoro-6-vinylphenol. $^1$H NMR (500 MHz, CDCl$_3$) δ 7.26 (m, 1H), 7.03 (dd, J=17.8, 11.1, 1H), 6.96 (m, 1H), 6.89-6.81 (m, 1H), 5.68 (dd, J=17.8, 1.3, 1H), 5.34-5.24 (m, 1H), 1.02 (s, 9H), 0.19 (d, J=2.4, 6H).

Step C:
tert-Butyl(2-ethyl-6-fluorophenoxy)dimethylsilane

To a stirred solution of tert-butyl(2-fluoro-6-vinylphenoxy)dimethylsilane (1.18 g, 4.67 mmol) in ethyl acetate (61 mL) under nitrogen, was added 497 mg of 10% palladium on carbon. The flask was then equipped with a hydrogen containing balloon and the reaction mixture stirred rapidly for 4 hours. The hydrogen balloon was removed, the reaction mixture sparged with nitrogen, and then filtered through a plug of Celite®, eluting with EtOAc. The filtrate was concentrated to dryness to afford the title compound that was used without further purification. $^1$H NMR (500 MHz, CDCl$_3$) δ 6.94-6.85 (m, 2H), 6.85-6.77 (m, 1H), 2.65 (q, J=7.6, 2H), 1.19 (t, J=7.5, 3H), 1.02 (s, 9H), 0.21 (d, J=2.7, 6H).

Step D: 3-(5-Aminopyrazin-2-yl)-6-ethyl-2-fluorophenol

The title compound was prepared in an analogous way to 3-(5-aminopyrazin-2-yl)-2-fluoro-6-methylphenol in Steps B-D of Intermediate J using tert-butyl(2-ethyl-6-fluorophenoxy)dimethylsilane. $^1$H NMR (500 MHz, CD$_3$OD) δ 8.26 (dd, J=2.3, 1.5, 1H), 8.02 (d, J=1.5, 1H), 7.12 (dd, J=8.0, 7.3, 1H), 6.99-6.93 (m, 1H), 2.68 (q, J=7.5, 2H), 1.21 (t, J=7.5, 3H).

Intermediate L

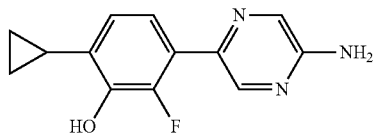 [SMILES: Nc1cnc(-c2ccc(C3CC3)c(O)c2F)cn1]

3-(5-Aminopyrazin-2-yl)-6-cyclopropyl-2-fluorophenol

The title compound was prepared using conditions similar to those described in Method 2 for 3-(5-aminopyrazin-2-yl)-6-cyclobutyl-2-fluorophenol using cyclopropylzinc bromide in Step B. $^1$H NMR (500 MHz, CD$_3$OD) δ 8.29-8.24 (m, 1H), 8.02 (d, J=1.5, 1H), 7.16-7.05 (m, 1H), 6.65 (dd, J=8.2, 1.3, 1H), 2.28-2.11 (m, 1H), 1.02-0.90 (m, 2H), 0.72-0.63 (m, 2H).

Intermediate M

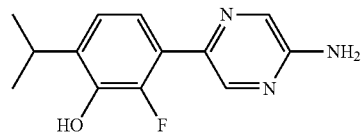 [SMILES: CC(C)c1ccc(-c2cnc(N)cn2)c(F)c1O]

3-(5-Aminopyrazin-2-yl)-2-fluoro-6-isopropylphenol

The title compound was prepared using conditions similar to those described in Method 2 for 3-(5-aminopyrazin-2-yl)-6-cyclobutyl-2-fluorophenol using isopropylzinc bromide in Step B. MS (ESI): mass calcd. for C$_{13}$H$_{14}$FN$_3$O, 247.11; m/z found, 248.1 [M+H]$^+$.

Intermediate N

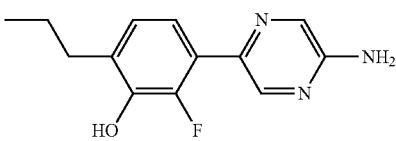 [SMILES: CCCc1ccc(-c2cnc(N)cn2)c(F)c1O]

3-(5-Aminopyrazin-2-yl)-2-fluoro-6-propylphenol

The title compound was prepared using conditions similar to those described in Method 2 for 3-(5-aminopyrazin-2-yl)-6-cyclobutyl-2-fluorophenol using propylzinc bromide in Step B. MS (ESI): mass calcd. for C$_{13}$H$_{14}$FN$_3$O, 247.11; m/z found, 248.1 [M+H]$^+$.

Example 314

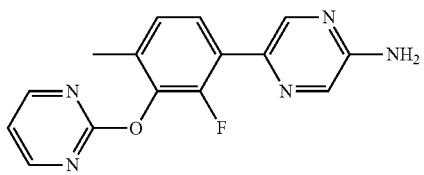

5-[2-Fluoro-4-methyl-3-(pyrimidin-2-yloxy)phenyl]pyrazin-2-amine

The title compound was prepared using conditions similar to those described in Example 101 heating at 120° Celsius via microwave irradiation for 1 hour and using 2-chloropyrimidine and 3-(5-aminopyrazin-2-yl)-2-fluoro-6-methylphenol. MS (ESI): mass calcd. for C$_{15}$H$_{12}$FN$_5$O, 297.10; m/z found, 298.0 [M+H]$^+$. $^1$H NMR (500 MHz, CD$_3$OD) δ 8.61 (d, J=4.8, 2H), 8.22-8.20 (m, 1H), 8.20-8.19 (m, 1H), 7.73-7.68 (m, 1H), 7.27-7.24 (m, 1H), 7.22 (m, 1H), 2.23 (d, J=0.7, 3H).

Example 315

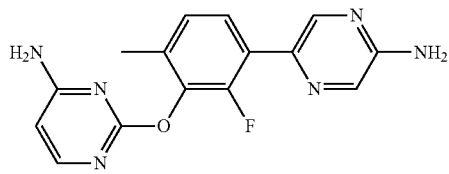 [SMILES: Cc1ccc(-c2cnc(N)cn2)c(F)c1Oc1nccc(N)n1]

2-[3-(5-Aminopyrazin-2-yl)-2-fluoro-6-methylphenoxy]pyrmidin-4-amine

The title compound was prepared using conditions similar to those described in Example 101 heating at 120° Celsius via microwave irradiation for 1 hour and using 2-chloropyrimidin-4-amine and 3-(5-aminopyrazin-2-yl)-2-fluoro-6-methylphenol. MS (ESI): mass calcd. for C$_{15}$H$_{13}$FN$_6$O, 312.11; m/z found, 313.0 [M+H]$^+$. $^1$H NMR (500 MHz, CD$_3$OD) δ 8.29-8.25 (m, 1H), 8.04 (d, J=1.5, 1H), 7.87 (d, J=5.9, 1H), 7.63-7.53 (m, 1H), 7.15 (d, J=8.1, 1H), 6.25 (d, J=5.9, 1H), 2.22 (s, 3H).

Example 316

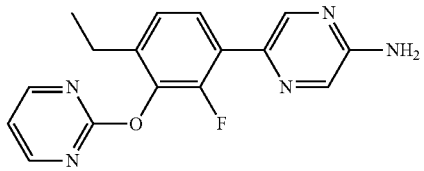 [SMILES: CCc1ccc(-c2cnc(N)cn2)c(F)c1Oc1ncccn1]

5-[4-Ethyl-2-fluoro-3-(pyrimidin-2-yloxy)phenyl]
pyrazin-2-amine

The title compound was prepared using conditions similar to those described in Example 101 heating at 1200 Celsius via microwave irradiation for 1 hour and using 2-chloropyrimidine and 3-(5-aminopyrazin-2-yl)-6-ethyl-2-fluorophenol. MS (ESI): mass calcd. for $C_{16}H_{14}FN_5O$, 311.12; m/z found, 312.3 [M+H]$^+$. $^1$H NMR (CD$_3$OD) δ 8.61 (d, J=4.8, 2H), 8.20 (dd, J=6.7, 1.6, 2H), 7.74 (dd, J=8.3, 7.5, 1H), 7.29-7.21 (m, 2H), 2.63 (q, J=7.6, 2H), 1.17 (t, J=7.6, 3H)

Example 317

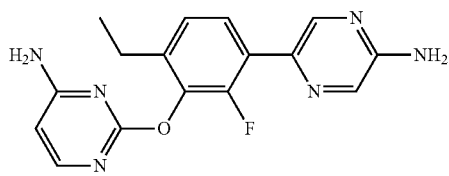

2-[3-(5-Aminopyrazin-2-yl)-6-ethyl-2-fluorophenoxy]pyrimidin-4-amine

The title compound was prepared using conditions similar to those described in Example 101 heating at 1200 Celsius via microwave irradiation for 1 hour and using 2-chloropyrimidine-4-amine and 3-(5-aminopyrazin-2-yl)-6-ethyl-2-fluorophenol. MS (ESI): mass calcd. for $C_{16}H_{15}FN_6O$, 326.13; m/z found, 327.3 [M+H]$^+$. $^1$H NMR (CD$_3$OD) 8.27 (m, 1H), 8.04 (d, J=1.5, 1H), 7.87 (d, J=5.9, 1H), 7.63 (m, 1H), 7.17 (dd, J=8.1, 1.3, 1H), 6.24 (d, J=5.9, 1H), 2.62 (q, J=7.6, 2H), 1.19 (t, J=7.6, 3H)

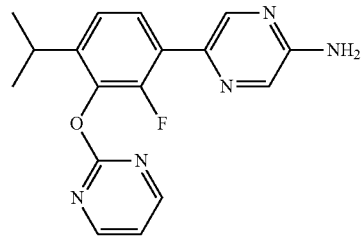 [SMILES: CC(C)c1ccc(-c2cnc(N)cn2)c(F)c1Oc1ncccn1]

5-[2-Fluoro-4-(1-methylethyl)-3-(pyrimidin-2-yloxy)
phenyl]pyrazin-2-amine

The title compound was prepared using conditions similar to those described in Example 101 heating at 120° Celsius via microwave irradiation for 1 hour and using 2-chloropyrimidine and 3-(5-aminopyrazin-2-yl)-2-fluoro-6-isopropylphenol. MS (ESI): mass calcd. for $C_{17}H_{16}FN_5O$, 325.13; m/z found, 326.3 [M+H]$^+$. $^1$H NMR (500 MHz, CD$_3$OD) δ 8.62 (d, J=4.8, 2H), 8.25 (s, 1H), 8.04 (d, J=1.5, 1H), 7.72 (t, J=7.9, 1H), 7.28 (dd, J=8.4, 1.4, 1H), 7.25 (m, 1H), 3.18-3.10 (m, 1H), 1.22 (d, J=6.9, 6H).

Example 319

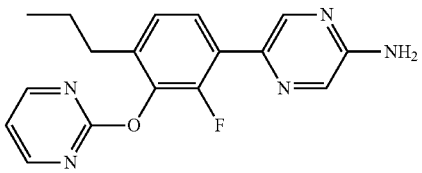

5-[2-Fluoro-4-propyl-3-(pyrimidin-2-yloxy)phenyl]
pyrazin-2-amine

The title compound was prepared using conditions similar to those described in Example 101 heating at 120° Celsius via microwave irradiation for 1 hour and using 2-chloropyrimidine and 3-(5-aminopyrazin-2-yl)-2-fluoro-6-propylphenol. MS (ESI): mass calcd. for $C_{17}H_{16}FN_5O$, 325.13; m/z found, 326.3 [M+H]$^+$. $^1$H NMR (500 MHz, CD$_3$OD) δ 8.61 (d, J=4.8, 2H), 8.25 (s, 1H), 8.04 (d, J=1.5, 1H), 7.71-7.62 (m, 1H), 7.27-7.23 (m, 1H), 7.20 (dd, J=8.2, 1.4, 1H), 2.58 (t, J=7.6, 2H), 1.66-1.51 (m, 2H), 0.90 (t, J=7.3, 3H).

Example 320

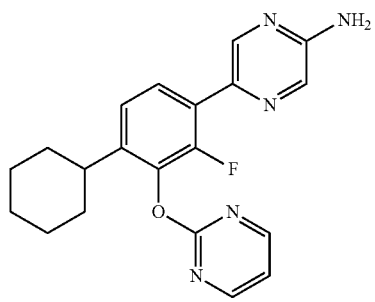

5-(4-Cyclohexyl-2-fluoro-3-(pyrimidin-2-yloxy)
phenyl)pyrazin-2-amine

Step A: tert-Butyl(2-cyclohexyl-6-fluorophenoxy)
dimethylsilane

A solution consisting of (2-bromo-6-fluorophenoxy)(tert-butyl)dimethylsilane (0.832 g, 2.73 mmol) and bis(tri-tert-butylphosphine)palladium(0) (0.070 g, 0.14 mmol) and dry THF (5 mL) was treated with cyclohexylzinc(II) bromide (7.0 mL, 3.5 mmol, 0.5 M in THF). The resultant mixture was heated for 45 minutes at 50° C., cooled to rt, and concentrated to dryness. The resultant residue was subjected to FCC purification to the title compound (0.841 g, 89%) which was used without purification.

Step B: (3-((tert-Butyldimethylsilyl)oxy)-4-cyclohexyl-2-fluorophenyl)boronic acid A solution consisting of 2,2,6,6-tetramethylpiperidine (0.50 mL, 3.0 mmol) and dry THF (2 mL) was cooled to −78° C. and treated with n-butyllithium (1.1 mL, 2.75 mmol, 2.5 M in hexanes). After stirring for 5 minutes, the reaction was warmed to rt for 5 minutes before cooling back down to −78° C. The reaction was then treated with tert-butyl(2-cyclohexyl-6-fluorophenoxy)dimethylsilane (0.719 g, 2.33 mmol) and triisopropyl borate (0.60 mL, 2.6 mmol) and stirred for 5 minutes. The reaction mixture was warmed to rt, quenched with saturated NH$_4$Cl (2 mL), and extracted with EtOAc (2×5 mL). The combined organic extracts were washed with brine (3×5 mL), dried over MgSO$_4$, filtered, and concentrated to dryness to yield the title compound (0.833 g, 101%), which was used without purification.

Step C: 5-(3-((tert-Butyldimethylsilyl)oxy)-4-cyclohexyl-2-fluorophenyl)pyrazin-2-amine A mixture of (3-((tert-butyldimethylsilyl)oxy)-4-cyclohexyl-2-fluorophenyl)boronic acid (0.821 g, 2.33 mmol), 5-bromopyrazin-2-amine (0.40 g, 2.3 mmol), K$_2$CO$_3$ (0.659 g, 4.77 mmol), Pd(dppf)Cl$_2$·CH$_2$Cl$_2$ (0.086 g, 0.12 mmol), deoxygenated toluene (10 mL), and deoxygenated deionized water (10 mL) was heated for 16 hours at 80° Celsius. The reaction mixture was then cooled to rt, diluted with dichloromethane (25 mL), and washed with brine (2×25 mL). The organic layer was dried over MgSO$_4$, filtered, and concentrated to dryness to yield the title compound (0.936 g, 100%) which was used without purification.

Step D: 3-(5-Aminopyrazin-2-yl)-6-cyclohexyl-2-fluorophenol

A solution consisting of 5-(3-((tert-butyldimethylsilyl)oxy)-4-cyclohexyl-2-fluorophenyl)pyrazin-2-amine (936 mg, 2.33 mmol) and THF (15 mL) was treated with tetrabutylammonium fluoride (5 mL, 5 mmol, 1 M in THF). The reaction mixture was stirred for 16 hours at which point it was concentrated to dryness and purified by FCC to yield the title compound (0.403 g, 60%) which was used without further purification. MS (ESI): mass calcd. for C$_{16}$H$_{18}$FN$_3$O, 287.14; m/z found, 288.1 [M+H]$^+$. $^1$H NMR (500 MHz, CDCl$_3$) δ 8.47-8.45 (m, 1H), 8.09 (d, J=1.5, 1H), 7.32 (m, 1H), 7.06-7.03 (m, 1H), 5.60 (d, J=6.3, 1H), 4.65 (s, 2H), 3.00-2.92 (m, 1H), 1.94-1.81 (m, 4H), 1.80-1.74 (m, 1H), 1.52-1.38 (m, 4H), 1.33-1.25 (m, 1H).

Step E: 5-(4-Cyclohexyl-2-fluoro-3-(pyrimidin-2-yloxy)phenyl)pyrazin-2-amine

A mixture consisting of 3-(5-aminopyrazin-2-yl)-6-cyclohexyl-2-fluorophenol (0.05 g, 0.2 mmol), 2-chloropyrimidine (0.025 g, 0.22 mmol), K$_2$CO$_3$ (0.05 g, 0.4 mmol), and 18-crown-6 (0.01 g, 0.04 mmol), and DMSO (2 mL) was heated via microwave irradiation for 1 hour at 120° Celsius. After cooling to room temperature, the reaction mixture was filtered and purified directly via HPLC to yield the title compound (42 mg, 65%). MS (ESI): mass calcd. for C$_{20}$H$_{20}$FN$_5$O, 365.17; m/z found, 366.1 [M+H]$^+$. $^1$H NMR (500 MHz, CD$_3$OD) δ 8.63-8.60 (m, 2H), 8.28-8.24 (m, 1H), 8.20-8.18 (m, 1H), 7.80-7.76 (m, 1H), 7.31-7.23 (m, 2H), 2.81-2.74 (m, 1H), 1.83-1.68 (m, 5H), 1.53-1.43 (m, 2H), 1.35-1.24 (m, 3H).

Example 321

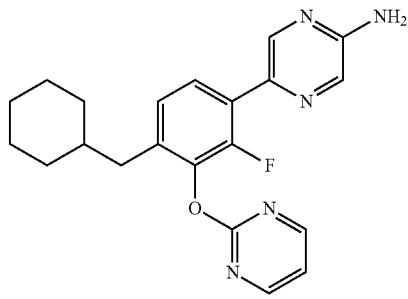 [SMILES: Nc1cnc(-c2ccc(CC3CCCCC3)c(Oc3ncccn3)c2F)cn1]

5-(4-(Cyclohexylmethyl)-2-fluoro-3-(pyrimidin-2-yloxy)phenyl)pyrazin-2-amine

The title compound was prepared in a manner analogous to that described in Example 320 using (cyclohexylmethyl)zinc(II) bromide in Step A. MS (ESI): mass calcd. for C$_{21}$H$_{22}$FN$_5$O, 379.18; m/z found, 380.1 [M+H]$^+$. $^1$H NMR (500 MHz, CD$_3$OD) δ 8.61 (d, J=4.8, 2H), 8.26 (d, J=1.5, 1H), 8.21-8.19 (m, 1H), 7.75-7.71 (m, 1H), 7.27-7.24 (m, 1H), 7.20-7.15 (m, 1H), 2.49 (d, J=7.1, 2H), 1.68-1.60 (m, 5H), 1.55-1.47 (m, 1H), 1.17-1.09 (m, 3H), 0.98-0.88 (m, 2H).

Example 322

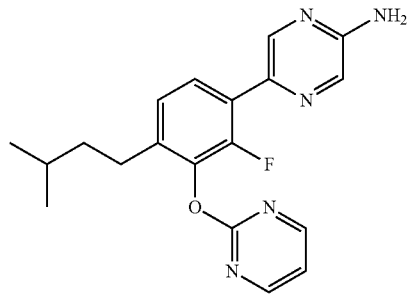

5-(2-Fluoro-4-isopentyl-3-(pyrimidin-2-yloxy)phenyl)pyrazin-2-amine

The title compound was prepared in a manner analogous to that described in Example 320 using isopentylzinc(II) bromide in Step A. MS (ESI): mass calcd. for C$_{19}$H$_{20}$FN$_5$O, 353.17; m/z found, 354.1 [M+H]$^+$. $^1$H NMR (500 MHz, CD$_3$OD) δ 8.65-8.59 (m, 2H), 8.28-8.26 (m, 1H), 8.21-8.19 (m, 1H), 7.77-7.73 (m, 1H), 7.29-7.20 (m, 2H), 2.65-2.57 (m, 2H), 1.56-1.48 (m, 1H), 1.46-1.39 (m, 2H), 0.85 (s, 3H), 0.83 (s, 3H).

Example 323

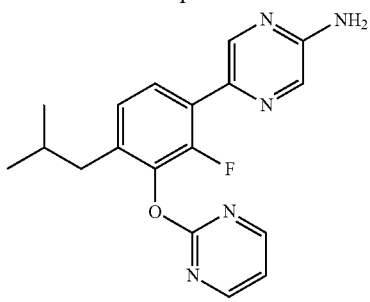

5-(2-Fluoro-4-isobutyl-3-(pyrimidin-2-yloxy)phenyl)pyrazin-2-amine

The title compound was prepared in a manner analogous to that described in Example 320 using isobutylzinc(II) bromide in Step A. MS (ESI): mass calcd. for $C_{18}H_{18}FN_5O$, 339.15; m/z found, 340.1 [M+H]$^+$. $^1$H NMR (500 MHz, CD$_3$OD) δ 8.61 (d, J=4.8, 2H), 8.27 (d, J=1.4, 1H), 8.20 (m, 1H), 7.75 (t, J=7.8, 1H), 7.25 (m, 1H), 7.22-7.19 (m, 1H), 2.49 (d, J=7.3, 2H), 1.91-1.84 (m, 1H), 0.88 (d, J=6.6, 6H).

Example 324

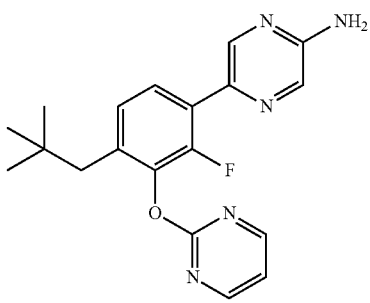 [SMILES: CC(C)(C)Cc1ccc(-c2cnc(N)cn2)c(F)c1Oc1ncccn1]

5-(2-Fluoro-4-neopentyl-3-(pyrimidin-2-yloxy)phenyl)pyrazin-2-amine

The title compound was prepared in a manner analogous to that described in Example 320 using neopentylzinc(II) bromide in Step A. MS (ESI): mass calcd. for $C_{19}H_{20}FN_5O$, 353.17; m/z found, 354.1 [M+H]$^+$. $^1$H NMR (500 MHz, CD$_3$OD) δ 8.61 (d, J=4.8, 2H), 8.26-8.25 (m, 1H), 8.21 (s, 1H), 7.74 (t, J=7.9, 1H), 7.24 (m, 1H), 7.22-7.19 (m, 1H), 2.53 (s, 2H), 0.94 (s, 9H).

Example 325

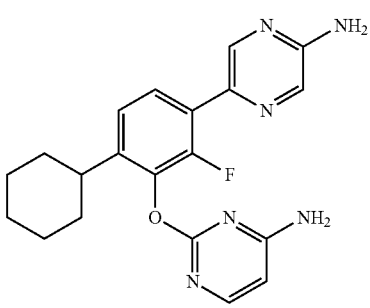 [SMILES: Nc1cnc(-c2ccc(C3CCCCC3)c(Oc3nccc(N)n3)c2F)cn1]

2-(3-(5-Aminopyrazin-2-yl)-6-cyclohexyl-2-fluorophenoxy)pyrimidin-4-amine

The title compound was prepared in a manner analogous to that described in Example 320 using 2-chloropyrimidin-4-amine in Step E. MS (ESI): mass calcd. for $C_{20}H_{21}FN_6O$, 380.18; m/z found, 381.1 [M+H]$^+$. $^1$H NMR (500 MHz, CD$_3$OD) δ 8.26-8.25 (m, 1H), 8.13 (d, J=1.5, 1H), 8.06 (d, J=7.0, 1H), 7.80 (m, 1H), 7.32-7.29 (m, 1H), 6.51 (d, J=7.0, 1H), 2.79-2.71 (m, 1H), 1.89-1.80 (m, 4H), 1.78-1.73 (m, 1H), 1.56-1.47 (m, 2H), 1.44-1.26 (m, 3H).

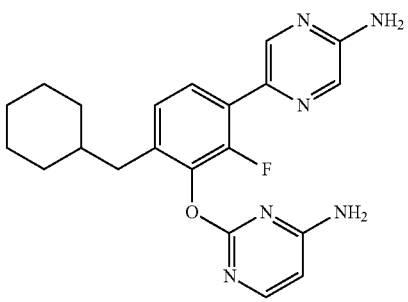

2-(3-(5-Aminopyrazin-2-yl)-6-(cyclohexylmethyl)-2-fluorophenoxy)pyrimidin-4-amine The title compound was prepared in a manner analogous to that described in Example 320 using (cyclohexylmethyl)zinc(III) bromide in Step A and 2-chloropyrimidin-4-amine in Step E. MS (ESI): mass calcd. for $C_{21}H_{23}FN_6O$, 394.19; m/z found, 395.1 [M+H]$^+$. $^1$H NMR (500 MHz, CD$_3$OD) δ 8.28-8.26 (m, 1H), 8.11 (d, J=1.5, 1H), 8.05 (d, J=7.0, 1H), 7.76 (t, J=7.9, 1H), 7.22-7.19 (m, 1H), 6.51 (d, J=7.1, 1H), 2.53 (d, J=7.2, 2H), 1.73-1.65 (m, 5H), 1.60-1.52 (m, 1H), 1.23-1.14 (m, 3H), 1.04-0.94 (m, 2H).

Example 327

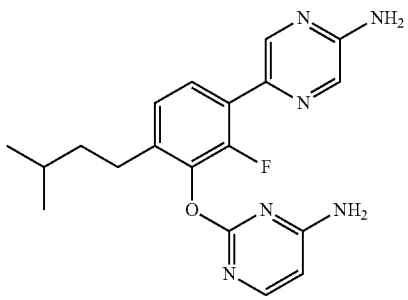

2-(3-(5-Aminopyrazin-2-yl)-2-fluoro-6-isopentylphenoxy)pyrimidin-4-amine

The title compound was prepared in a manner analogous to that described in Example 320 using isopentylzinc(II) bromide in Step A and 2-chloropyrimidin-4-amine in Step E. MS (ESI): mass calcd. for $C_{19}H_{21}FN_6O$, 368.18; m/z found, 369.1 [M+H]$^+$. $^1$H NMR (500 MHz, CD$_3$OD) δ 8.27-8.26 (m, 1H), 8.11 (d, J=1.5, 1H), 8.05 (d, J=7.0, 1H), 7.77 (t, J=7.9, 1H), 7.26-7.23 (m, 1H), 6.51 (d, J=7.0, 1H), 2.68-2.62 (m, 2H), 1.62-1.54 (m, 1H), 1.52-1.46 (m, 2H), 0.91 (d, J=6.5, 6H).

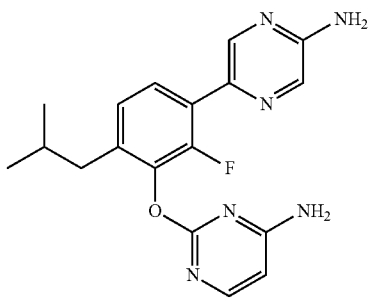 [SMILES: CC(C)Cc1ccc(-c2cnc(N)cn2)c(F)c1Oc1nccc(N)n1]

2-(3-(5-Aminopyrazin-2-yl)-2-fluoro-6-isobutylphenoxy)pyrimidin-4-amine

The title compound was prepared in a manner analogous to that described in Example 320 using isobutylzinc(II) bromide in Step A and 2-chloropyrimidin-4-amine in Step E. MS (ESI): mass calcd. for $C_{16}H_{19}FN_6O$, 354.16; m/z found, 355.1 [M+H]$^+$. $^1$H NMR (500 MHz, CD$_3$OD) δ 8.28-8.26 (m, 1H), 8.12 (d, J=1.5, 1H), 8.05 (d, J=7.0, 1H), 7.77 (t, J=7.9, 1H), 7.24-7.21 (m, 1H), 6.50 (d, J=7.0, 1H), 2.53 (d, J=7.3, 2H), 1.97-1.87 (m, 1H), 0.94 (d, J=6.6, 6H).

Example 329

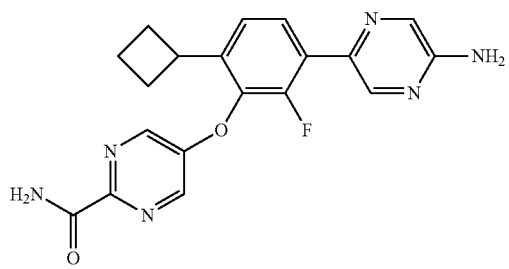

5-(3-(5-Aminopyrazin-2-yl)-6-cyclobutyl-2-fluorophenoxy)pyrimidine-2-carboxamide The title compound was prepared using analogous conditions to those described in Example 69 utilizing 5-bromo-2-cyanopyrimidine. MS (ESI): mass calcd. for $C_{19}H_{17}FN_6O$, 380.14; m/z found, 381.1 [M+H]$^+$. $^1$H NMR (500 MHz, CD$_3$OD) δ 8.56 (s, 2H), 8.27 (s, 1H), 8.10 (d, J=1.5, 1H), 7.88-7.81 (m, 1H), 7.40 (d, J=8.2, 1H), 3.76-3.64 (m, 1H), 2.33-2.14 (m, 5H), 2.10-1.97 (m, 1H), 1.93-1.80 (m, 1H).

Example 330

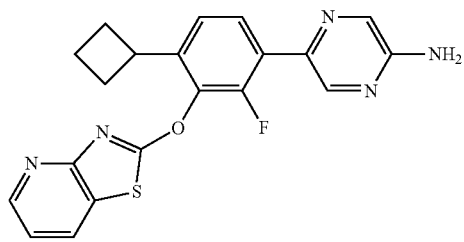 [SMILES: Nc1cnc(-c2ccc(C3CCC3)c(Oc3nc4ncccc4s3)c2F)cn1]

5-(4-Cyclobutyl-2-fluoro-3-(thiazolo[4,5-b]pyridin-2-yloxy)phenyl)pyrazin-2-amine The title compound was prepared using analogous conditions to those described in Example 69 utilizing 2-chlorothiazolo[4,5-b]pyridine. MS (ESI): mass calcd. for $C_{20}H_{16}FN_5O$, 393.11; m/z found, 394.0 [M+H]$^+$. $^1$H NMR (400 MHz, DMSO-d$_6$) δ 8.52 (dd, J=4.8, 1.7, 1H), 8.45 (dd, J=8.0, 1.7, 1H), 8.33-8.28 (m, 1H), 8.03 (d, J=1.5, 1H), 7.91-7.83 (m, 1H), 7.42-7.34 (m, 2H), 6.72 (br s, 2H), 3.67 (p, J=8.9, 1H), 2.27-2.09 (m, 4H), 2.03-1.89 (m, 1H), 1.84-1.73 (m, 1H).

Example 331

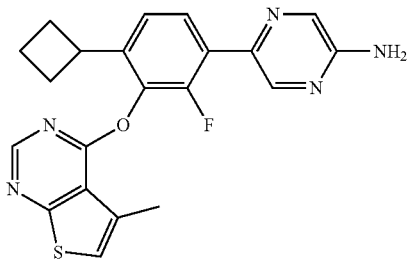 [SMILES: Cc1csc2ncnc(Oc3c(C4CCC4)ccc(-c4cnc(N)cn4)c3F)c12]

5-(4-Cyclobutyl-2-fluoro-3-((5-methylthieno[2,3-d]pyrimidin-4-yl)oxy)phenyl)pyrazin-2-amine The title compound was prepared using analogous conditions to those described in Example 69 utilizing 4-chloro-5-methylthieno[2,3-d]pyrimidine. MS (ESI): mass calcd. for $C_{21}H_{18}FN_5OS$, 407.12; m/z found, 408.1 [M+H]$^+$. $^1$H NMR (500 MHz, DMSO-d$_6$) δ 8.56 (s, 1H), 8.29-8.25 (m, 1H), 8.01 (d, J=1.5, 1H), 7.82-7.76 (m, 1H), 7.61 (d, J=1.4, 1H), 7.32 (d, J=8.3, 1H), 6.70 (s, 2H), 3.63-3.53 (m, 1H), 2.66 (d, J=1.3, 3H), 2.31-2.22 (m, 1H), 2.22-2.12 (m, 1H), 2.10-2.01 (m, 1H), 2.01-1.95 (m, 1H), 1.94-1.84 (m, 1H), 1.78-1.69 (m, 1H).

Example 332

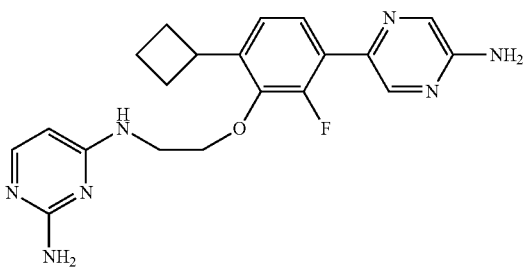 [SMILES: Nc1cnc(-c2ccc(C3CCC3)c(OCCNc3ccnc(N)n3)c2F)cn1]

N'-(2-(3-(5-Aminopyrazin-2-yl)-6-cyclobutyl-2-fluorophenoxy)ethyl)pyrimidine-2,4-diamine The title compound was prepared using analogous conditions described in Example 295 utilizing 2-amino-4-chloropyrimidine. MS (ESI): mass calcd. for $C_{20}H_{22}FN_7O$, 395.19; m/z found, 396.2 [M+H]$^+$. $^1$H NMR (600 MHz, CD$_3$OD) δ 8.30-8.24 (m, 1H), 8.03 (d, J=1.5, 1H), 7.64 (br s, 1H), 7.50-7.43 (m, 1H), 7.19 (d, J=8.2, 1H), 5.93 (d, J=6.1, 1H), 4.14 (t, J=5.4, 2H), 3.83 (m, 1H), 3.78-3.67 (m, 2H), 2.31-2.21 (m, 2H), 2.17-2.06 (m, 2H), 2.05-1.93 (m, 1H), 1.87-1.78 (m, 1H).

Example 333

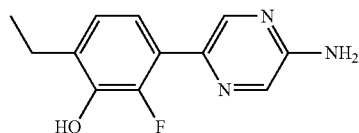 [SMILES: CCc1ccc(-c2cnc(N)cn2)c(F)c1O]

3-(5-Aminopyrazin-2-yl)-6-ethyl-2-fluorophenol

The title compound was prepared in a manner analogous to that described for Intermediate K. MS (ESI): mass calcd. for $C_{12}H_{12}FN_3O$, 233.10; m/z found, 234.1 [M+H]$^+$. $^1$H NMR (CD$_3$OD) δ 8.26 (dd, J=2.3, 1.5 Hz, 1H), 8.02 (d, J=1.5 Hz, 1H), 7.12 (dd, J=8.0, 7.3 Hz, 1H), 6.99-6.93 (m, 1H), 2.68 (q, J=7.5 Hz, 2H), 1.21 (t, J=7.5 Hz, 3H)

Example 334

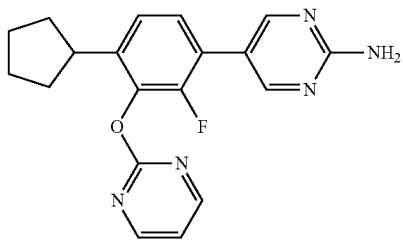 [SMILES: Nc1ncc(-c2ccc(C3CCCC3)c(Oc3ncccn3)c2F)cn1]

5-[4-Cyclopentyl-2-fluoro-3-(pyrimidin-2-yloxy)phenyl]pyrimidin-2-amine

The title compound was prepared in a manner analogous to that described in Example 320 using cyclopentylzinc(II) bromide in Step A and 5-bromopyrimidin-2-amine in Step C. MS (ESI): mass calcd. for $C_{19}H_{18}FN_5O$, 351.15; m/z found, 352.0 [M+H]$^+$. $^1$H NMR (500 MHz, CD$_3$OD) δ 8.61 (d, J=4.8 Hz, 2H), 8.55 (d, J=1.2 Hz, 2H), 7.41-7.35 (m, 1H), 7.34-7.28 (m, 1H), 7.25 (t, J=4.8 Hz, 1H), 3.25-3.15 (m, 1H), 2.00-1.88 (m, 2H), 1.87-1.73 (m, 2H), 1.71-1.53 (m, 4H).

Example 335

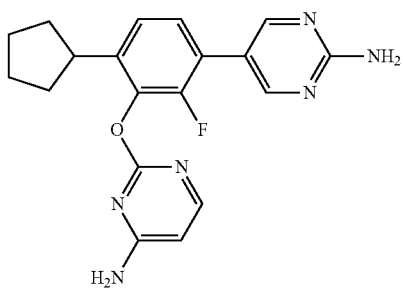

5-{3-[(4-Aminopyrimidin-2-yl)oxy]-4-cyclopentyl-2-fluorophenyl}pyrimidin-2-amine. #55672500#

The title compound was prepared in a manner analogous to that described in Example 320 using cyclopentylzinc(III) bromide in Step A, 5-bromopyrimidin-2-amine in Step C and 2-chloropyrimidin-4-amine in Step E. MS (ESI): mass calcd. for $C_{19}H_{19}FN_6O$, 366.16; m/z found, 367.2 [M+H]$^+$. $^1$H NMR (500 MHz, CD$_3$OD) δ 8.45 (d, J=1.2 Hz, 2H), 7.87 (d, J=5.9 Hz, 1H), 7.31-7.27 (m, 1H), 7.26-7.21 (m, 1H), 6.25 (d, J=5.9 Hz, 1H), 3.26-3.10 (m, 1H), 2.04-1.91 (m, 2H), 1.85-1.74 (m, 2H), 1.70-1.55 (m, 4H).

Example 336

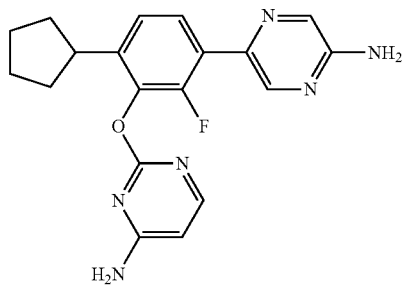 [SMILES: Nc1cnc(-c2ccc(C3CCCC3)c(Oc3nccc(N)n3)c2F)cn1]

2-[3-(5-Aminopyrazin-2-yl)-6-cyclopentyl-2-fluorophenoxy]pyrimidin-4-amine

The title compound was prepared in a manner analogous to that described in Example 320 using cyclopentylzinc(II) bromide in Step A and 2-chloropyrimidin-4-amine in Step E. MS (ESI): mass calcd. for $C_{19}H_{19}FN_6O$, 366.16; m/z found, 367.2 [M+H]$^+$. $^1$H NMR (500 MHz, MeOD) δ 8.35-8.21 (m, 1H), 8.04 (d, J=1.5 Hz, 1H), 7.87 (d, J=5.9 Hz, 1H), 7.71-7.57 (m, 1H), 7.30-7.17 (m, 1H), 6.24 (d, J=5.9 Hz, 1H), 3.23-3.12 (m, 1H), 2.03-1.89 (m, 2H), 1.88-1.74 (m, 2H), 1.72-1.52 (m, 4H).

Example 337

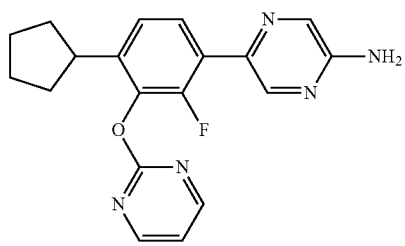 [SMILES: Nc1cnc(-c2ccc(C3CCCC3)c(Oc3ncccn3)c2F)cn1]

5-[4-Cyclopentyl-2-fluoro-3-(pyrimidin-2-yloxy)phenyl]pyrazin-2-amine

The title compound was prepared in a manner analogous to that described in Example 320 using cyclopentylzinc(III) bromide in Step A. MS (ESI): mass calcd. for $C_{19}H_{18}FN_5O$, 351.15; m/z found, 352.2 [M+H]$^+$. $^1$H NMR (500 MHz, CD$_3$OD) δ 8.61 (d, J=4.8 Hz, 2H), 8.24-8.21 (m, 1H), 8.11 (d, J=1.5 Hz, 1H), 7.75-7.70 (m, 1H), 7.29 (dd, J=8.5, 1.4

Hz, 1H), 7.26-7.22 (m, 1H), 3.25-3.10 (m, 1H), 2.01-1.88 (m, 2H), 1.87-1.70 (m, 2H), 1.70-1.56 (m, 4H).

Example 338

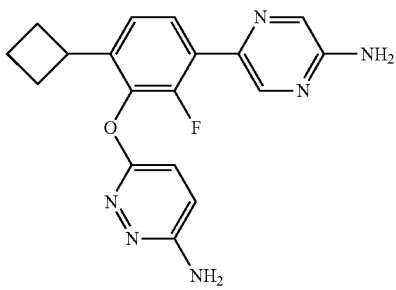

6-[3-(5-Aminopyrazin-2-yl)-6-cyclobutyl-2-fluorophenoxy]pyridazin-3-amine

The title compound was prepared in a manner analogous to that described in Example 160 using 6-fluoropyridazin-3-amine. MS (ESI): mass calcd. for $C_{18}H_{17}FN_6O$, 352.14; m/z found, 353.1 [M+H]$^+$. $^1$H NMR (500 MHz, MeOD) δ 8.26 (dd, J=2.3, 1.4 Hz, 1H), 8.04 (d, J=1.5 Hz, 1H), 7.72-7.61 (m, 1H), 7.25 (d, J=8.3 Hz, 1H), 7.22 (d, J=9.4 Hz, 1H), 7.08 (d, J=9.4 Hz, 1H), 3.66 (p, J=9.0 Hz, 1H), 2.27-2.09 (m, 4H), 2.05-1.93 (m, 1H), 1.87-1.77 (m, 1H).

Example 339

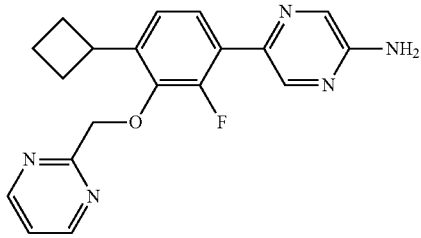 [SMILES: Nc1cnc(-c2ccc(C3CCC3)c(OCc3ncccn3)c2F)cn1]

5-[4-Cyclobutyl-2-fluoro-3-(pyrimidin-2-ylmethoxy)phenyl]pyrazin-2-amine

The title compound was prepared using analogous conditions described in Example 243 using 2-(chloromethyl)pyrimidine. MS (ESI): mass calcd. for $C_{19}H_{18}FN_5O$, 351.15; m/z found, 352.2 [M+H]$^+$. $^1$H NMR (500 MHz, CD$_3$OD) δ 8.84 (d, J=5.0 Hz, 2H), 8.27 (dd, J=2.4, 1.5 Hz, 1H), 8.03 (d, J=1.5 Hz, 1H), 7.52 (dd, J=8.2, 7.4 Hz, 1H), 7.48 (t, J=5.0 Hz, 1H), 7.24-7.17 (m, 1H), 5.24 (s, 2H), 4.00-3.85 (m, 1H), 2.33-2.21 (m, 2H), 2.21-2.08 (m, 2H), 2.08-1.94 (m, 1H), 1.92-1.77 (m, 1H).

Example 340

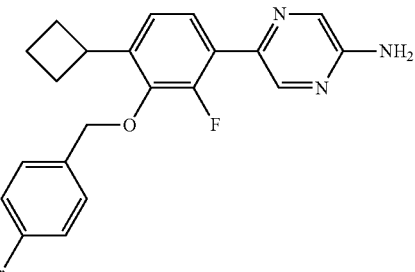

5-{3-[(4-Bromobenzyl)oxy]4-cyclobutyl-2-fluorophenyl}pyrazin-2-amine

The title compound was prepared using analogous conditions described in Example 243 using 1-bromo-4-(bromomethyl)benzene. MS (ESI): mass calcd. for $C_{21}H_{19}BrFN_3O$, 427.07; m/z found, 428.1 [M+H]$^+$. $^1$H NMR (400 MHz, CD$_3$OD) δ 8.29 (dd, J=2.3, 1.5 Hz, 1H), 8.04 (d, J=1.5 Hz, 1H), 7.57-7.52 (m, 2H), 7.52-7.46 (m, 1H), 7.43-7.35 (m, 2H), 7.23-7.13 (m, 1H), 5.02 (s, 2H), 3.76 (p, J=8.8 Hz, 1H), 2.32-2.20 (m, 2H), 2.20-2.07 (m, 2H), 2.07-1.96 (m, 1H), 1.91-1.77 (m, 1H).

Example 341

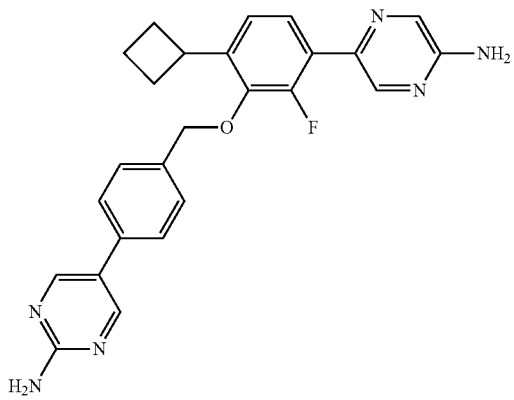

5-(4-{[3-(5-Aminopyrazin-2-yl)-6-cyclobutyl-2-fluorophenoxy]methyl}phenyl)pyrimidin-2-amine To a sealable vial were added 5-{3-[(4-bromobenzyl)oxy]-4-cyclobutyl-2-fluorophenyl}pyrazin-2-amine (42 mg, 0.098 mmol) and (2-aminopyrimidin-5-yl)boronic acid (13 mg, 0.098 mmol), followed by 1,4-dioxane (0.5 mL) and Na$_2$CO$_3$ (0.2 mL, 2 M). The mixture was sparged with argon for 10 minutes then Pd(dppf)Cl$_2$.CH$_2$Cl$_2$ (4 mg, 0.005 mmol) was added and the vial was sealed. The vial was heated at 80° C. for 3 hours before cooling it to RT and partitioning its contents between EtOAc (50 mL) and water (50 mL). The aqueous layer was washed with EtOAc (50 mL) and the combined organic extracts were dried with Na$_2$SO$_4$, filtered and concentrated to dryness. The resultant residue was purified by prep-HPLC to provide the title compound. MS (ESI): mass calcd. for $C_{25}H_{23}FN_6O$, 442.19; m/z found, 443.1 [M+H]$^+$. $^1$H NMR (400 MHz, CD$_3$OD) δ 8.72 (s, 2H), 8.30-8.27 (m, 1H), 8.10 (d, J=1.5 Hz, 1H), 7.67-7.62 (m, 2H), 7.62-7.57 (m, 2H), 7.56-7.49 (m, 1H), 7.20 (d, J=8.3 Hz, 1H), 5.11 (s, 2H), 3.81 (t, J=8.9 Hz, 1H), 2.34-2.22 (m, 2H), 2.21-2.08 (m, 2H), 2.01 (q, J=10.0 Hz, 1H), 1.92-1.80 (m, 1H).

Example 342

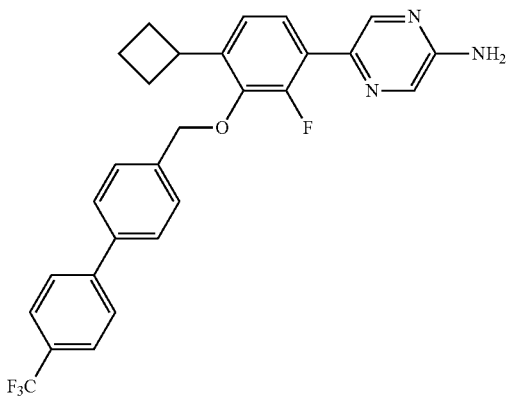 [SMILES: Nc1cnc(-c2ccc(C3CCC3)c(OCc3ccc(-c4ccc(C(F)(F)F)cc4)cc3)c2F)cn1]

5-(4-Cyclobutyl-2-fluor-3-{[4-(trifluoromethyl)biphenyl-4-yl]methoxy}phenyl)pyrazin-2-amine The title compound was prepared in an analogous manner to Example 341 using (4-(trifluoromethyl)phenyl)boronic acid. MS (ESI): mass calcd. for $C_{28}H_{23}F_4N_3O$, 493.18; m/z found, 494.1 [M+H]$^+$. $^1$H NMR (400 MHz, MeOD) δ 8.32-8.28 (m, 1H), 8.07 (d, J=1.5 Hz, 1H), 7.88-7.81 (m, 2H), 7.78-7.70 (m, 4H), 7.62-7.57 (m, 2H), 7.51 (dd, J=8.2, 7.4 Hz, 1H), 7.20 (d, J=8.3 Hz, 1H), 5.12 (s, 2H), 3.93-3.74 (m, 1H), 2.35-2.22 (m, 2H), 2.22-2.09 (m, 2H), 2.08-1.94 (m, 1H), 1.90-1.79 (m, 1H).

Example 343

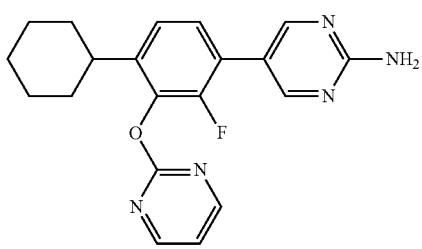

5-[4-Cyclohexyl-2-fluoro-3-(pyrimidin-2-yloxy)phenyl]pyrimidin-2-amine

Step A:
1-bromo-3-fluoro-2-(methoxymethoxy)benzene

To a solution consisting of 2-bromo-6-fluorophenol (5.0 g, 26 mmol), DIPEA (9.0 mL, 52.4 mmol) and CH$_2$Cl$_2$ (131 mL) was added chloro(methoxy)methane (2.2 mL, 29 mmol). The reaction mixture was stirred at RT for 1 h, then washed with sat. aq. NaHCO$_3$ (30 mL). The organic layer was isolated, concentrated to dryness and the resultant residue was purified by FCC to afford the title compound (5.5 g, 89%). $^1$H NMR (500 MHz, CDCl$_3$) δ 7.36-7.31 (m, 1H), 7.10-7.03 (m, 1H), 6.97-6.92 (m, 1H), 5.20 (s, 2H), 3.65 (s, 3H).

Step B:
1-Cyclohexyl-3-fluoro-2-(methoxymethoxy)benzene

To a round-bottomed flask, were added a stir bar, 1-bromo-3-fluoro-2-(methoxymethoxy)benzene (12.9 g, 12.3 mmol) and THF (41 mL). The flask was sealed with a rubber septa and flushed with N$_2$ for 5 minutes. Bis(tri-tert-butylphosphine)palladium(0) (473 mg, 0.92 mmol) was then added to the flask, followed by cyclohexylzinc(II) bromide (0.5 M in THF, 37 mL, 19 mmol). The reaction mixture was heated at 60° C. for 1 h, cooled to RT, concentrated onto silica gel and purified by FCC to afford the title compound (2.4 g, 80%). $^1$H NMR (400 MHz, CDCl$_3$) δ 7.02-6.96 (m, 2H), 6.96-6.86 (m, 1H), 5.11 (s, 2H), 3.61 (s, 3H), 3.07-2.97 (m, 1H), 1.89-1.77 (m, 4H), 1.46-1.21 (m, 6H).

Step C: (4-Cyclohexyl-2-fluoro-3-(methoxymethoxy)phenyl)boronic acid

To a solution of 2,2,6,6-tetramethylpiperidine (3.2 mL, 19 mmol) and THF (40 mL), at −78° C., was added n-butyllithium (2.3 M in hexanes, 8.2 mL, 19 mmol) drop-wise. The reaction mixture was allowed to warm to 0° C., stirred 5 min, and cooled to −78° C. Triisopropyl borate (4.3 mL, 19 mmol) was added, followed by a solution consisting of 1-cyclohexyl-3-fluoro-2-(methoxymethoxy)benzene (3.0 g, 13 mmol) and THF (20 mL). The mixture was stirred for 5 min at −78° C., warmed to RT, and quenched with sat. NH$_4$Cl (20 mL). The mixture was partitioned between water (20 mL) and EtOAc (40 mL). The organic phases were separated and the aqueous solution was further extracted with EtOAc (2×40 mL). The organic extracts were combined, concentrated to dryness and the crude product was used directly.

Step D: 5-(4-Cyclohexyl-2-fluoro-3-(methoxymethoxy)phenyl)pyrimidin-2-amine

A solution consisting of (4-cyclohexyl-2-fluoro-3-(methoxymethoxy)phenyl)boronic acid (1.4 g, 5.0 mmol), 2-amino-5-bromopyrimidine (0.95 g, 5.5 mmol) and THF (25 mL) was sparged with N$_2$ for 10 min. A solution of Na$_2$CO$_3$ (25 mL, 50 mmol, 2 M) was then added and the mixture was further sparged with N$_2$ for 20 min. 1,1″bis(di-t-butylphosphino)ferrocene palladium dichloride (162 mg, 0.25 mmol) was added, the reaction mixture was heated at 50° C. for 2 h, cooled to RT and diluted with EtOAc (50 mL). The organic phase was isolated, concentrated onto silica, and purified by FCC to provide the title compound (0.84 g, 51%). MS (ESI): mass calcd. for $C_{18}H_{22}FN_3O_2$, 331.17; m/z found, 332.3 [M+H]$^+$.

Step E: 3-(2-Aminopyrimidin-5-yl)-6-cyclohexyl-2-fluorophenol

To a solution consisting of 5-(4-cyclohexyl-2-fluoro-3-(methoxymethoxy)phenyl)pyrimidin-2-amine (840 mg, 2.5 mmol) and CH$_2$Cl$_2$ (25 mL), was added TFA (0.6 mL, 7.6 mmol), and the reaction mixture was stirred at RT for 12 h.

The reaction mixture was then diluted with CH$_2$Cl$_2$ (95 mL) and washed with sat. aq. NaHCO$_3$ (50 mL). The organic layer was isolated, concentrated to dryness, and the resulting residue was purified by FCC to afford the title compound.

Step F: 5-[4-Cyclohexyl-2-fluoro-3-(pyrimidin-2-yloxy)phenyl]pyrimidin-2-amine

To a microwave vial equipped with a stir-bar, were added 3-(2-aminopyrimidin-5-yl)-6-cyclohexyl-2-fluorophenol (100 mg, 0.35 mmol), 2-chloropyrimidine (42 mg, 0.35 mmol), K$_2$CO$_3$ (96 mg, 0.70 mmol), 18-crown-6 (5 mg, 0.02 mmol) and DMA (0.5 mL). The vial was capped and irradiated in a microwave reactor for 10 min at 110° C., before cooling to RT and diluting with EtOAc (10 mL) and water (5 mL). The organic layer was isolated, concentrated to dryness and the resultant residue was purified by prep-HPLC to provide the title compound (65 mg, 39%). MS (ESI): mass calcd. for C$_{20}$H$_{20}$FN$_5$O 365.17; m/z found, 366.1 [M+H]$^+$. $^1$H NMR (400 MHz, CD$_3$OD) δ 8.62 (d, J=4.8 Hz, 2H), 8.56 (d, J=1.2 Hz, 2H), 7.44-7.36 (m, 1H), 7.30 (dd, J=8.3, 1.4 Hz, 1H), 7.26 (t, J=4.8 Hz, 1H), 2.85-2.70 (m, 1H), 1.86-1.64 (m, 5H), 1.59-1.39 (m, 2H), 1.35-1.21 (m, 3H).

Example 344

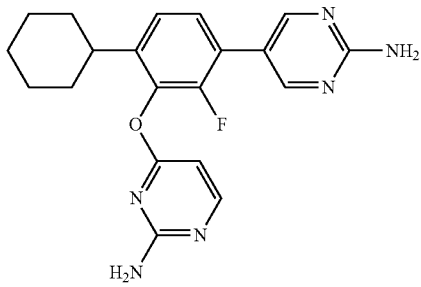 [SMILES: Nc1ncc(-c2ccc(C3CCCCC3)c(Oc3ccnc(N)n3)c2F)cn1]

5-{3-[(4-Aminopyrimidin-2-yl)oxy]-4-cyclohexyl-2-fluorophenyl}pyrimidin-2-amine

The title compound was prepared using analogous conditions to those described in Example 343 using 4-amino-2-chloropyrimidine in step F. MS (ESI): mass calcd. for C$_{20}$H$_{21}$FN$_6$O, 380.18; m/z found, 381.1 [M+H]$^+$. $^1$H NMR (400 MHz, CD$_3$OD) δ 8.44 (d, J=1.4 Hz, 2H), 7.87 (d, J=6.0 Hz, 1H), 7.34-7.26 (m, 1H), 7.22 (d, J=8.3 Hz, 1H), 6.25 (d, J=6.0 Hz, 1H), 2.84-2.68 (m, 1H), 1.87-1.65 (m, 5H), 1.52-1.20 (m, 5H).

Example 345

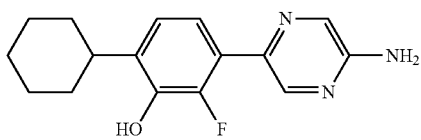

3-(5-Aminopyrazin-2-yl)-6-cyclohexyl-2-fluorophenol

The title compound was prepared in a manner analogous to that described in Steps A-D for Example 320 using cyclohexylzinc(II) bromide in Step A. MS (ESI): mass calcd. for C$_{16}$H$_{18}$FN$_3$O, 287.14; m/z found, 288.1 [M+H]$^+$. $^1$H NMR (500 MHz, CDCl$_3$) δ 8.47-8.45 (m, 1H), 8.09 (d, J=1.5 Hz, 1H), 7.36-7.29 (m, 1H), 7.06-7.03 (m, 1H), 5.60 (d, J=6.3 Hz, 1H), 4.65 (s, 2H), 3.00-2.92 (m, 1H), 1.94-1.81 (m, 4H), 1.80-1.74 (m, 1H), 1.52-1.38 (m, 4H), 1.33-1.25 (m, 1H).

Example 346

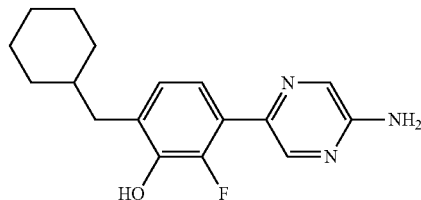 [SMILES: Nc1cnc(-c2ccc(CC3CCCCC3)c(O)c2F)cn1]

3-(5-Aminopyrazin-2-yl)-6-(cyclohexylmethyl)-2-fluorophenol

The title compound was prepared in a manner analogous to that described in Steps A-D for Example 320 using (cyclohexylmethyl)zinc(II) bromide in Step A. $^1$H NMR (500 MHz, CDCl$_3$) δ 8.47-8.45 (m, 1H), 8.09 (d, J=1.5 Hz, 1H), 7.30-7.26 (m, 1H), 6.95-6.93 (m, 1H), 5.62 (s, 1H), 4.66 (s, 2H), 2.56 (d, J=7.1 Hz, 2H), 1.74-1.58 (m, 7H), 1.23-1.13 (m, 3H), 1.05-0.94 (m, 2H).

Example 347

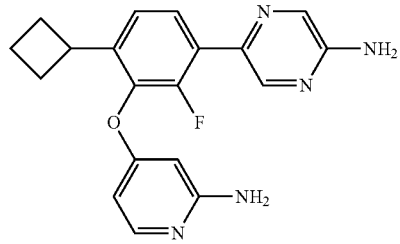 [SMILES: Nc1cnc(-c2ccc(C3CCC3)c(Oc3ccnc(N)c3)c2F)cn1]

5-{3-[(2-Aminopyridin-4-yl)oxy]-4-cyclobutyl-2-fluorophenyl}pyrazin-2-amine

The title compound was prepared using conditions similar to those described in Example 164 using 2-amino-4-bromopyridine with DMSO as the solvent, heating via microwave irradiation at 140° C. for 10 hours. MS (ESI): mass calcd. for C$_{19}$H$_{18}$FN$_5$O, 351.15; m/z found, 352.1 [M+H]$^+$. $^1$H NMR (400 MHz, CDCl$_3$) δ 8.49-8.46 (m, 1H), 8.09 (d, J=1.5 Hz, 1H), 7.93 (d, J=5.9 Hz, 1H), 7.83-7.76 (m, 1H), 7.24 (d, J=8.3 Hz, 1H), 6.30-6.24 (m, 1H), 5.89 (d, J=2.2 Hz, 1H), 4.71 (s, 2H), 4.40 (s, 2H), 3.64-3.53 (m, 1H), 2.29-2.07 (m, 4H), 2.03-1.90 (m, 1H), 1.87-1.76 (m, 1H).

Example 348

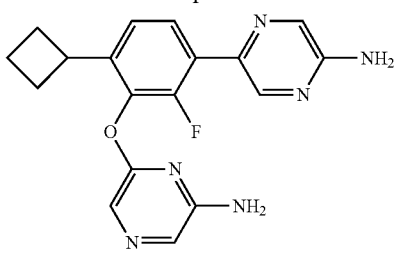

5-{3-[(6-Aminopyrazin-2-yl)oxy]-4-cyclobutyl-2-fluorophenyl}pyrazin-2-amine

The title compound was prepared using conditions similar to those described in Example 164 using 2-amino-6-chloropyrazine with DMSO as the solvent, heating via microwave irradiation at 140° C. for 6 hours. MS (ESI): mass calcd. for $C_{18}H_{17}FN_6O$, 352.14; m/z found, 353.1 [M+H]$^+$. $^1$H NMR (400 MHz, DMSO-d$_6$) δ 8.28-8.24 (m, 1H), 8.00 (d, J=1.5 Hz, 1H), 7.72-7.65 (m, 1H), 7.55 (d, J=3.8 Hz, 2H), 7.26 (d, J=8.3 Hz, 1H), 6.70 (s, 2H), 6.51 (s, 2H), 3.60-3.47 (m, 1H), 2.22-2.03 (m, 4H), 1.99-1.85 (m, 1H), 1.83-1.70 (m, 1H).

Example 349

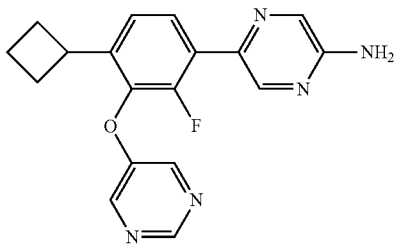

5-[4-Cyclobutyl-2-fluoro-3-(pyrimidin-5-yloxy)phenyl]pyrazin-2-amine

The title compound was prepared using conditions similar to those described in Example 164 using 5-bromopyrimidine with DMSO as the solvent, heating via microwave irradiation at 140=C for 2 hours. MS (ESI): mass calcd. for $C_{18}H_{16}FN_5O$, 337.13; m/z found, 338.1 [M+H]$^+$. $^1$H NMR (400 MHz, CDCl$_3$) δ 8.94 (s, 1H), 8.46-8.42 (m, 1H), 8.40 (s, 2H), 8.09 (d, J=1.5 Hz, 1H), 7.87-7.80 (m, 1H), 7.31-7.27 (m, 1H), 4.78 (s, 2H), 3.69-3.58 (m, 1H), 2.30-2.10 (m, 4H), 2.07-1.92 (m, 1H), 1.90-1.76 (m, 1H).

Example 350

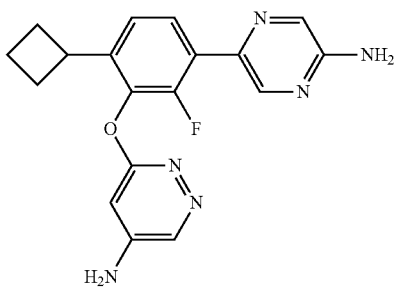 [SMILES: Nc1cnnc(Oc2c(C3CCC3)ccc(-c3cnc(N)cn3)c2F)c1]

6-[3-(5-Aminopyrazin-2-yl)-6-cyclobutyl-2-fluorophenoxy]pyridazin-4-amine

The title compound was prepared using conditions similar to those described in Example 164 using 6-chloro-4-pyridazinamine with DMSO as the solvent, heating via microwave irradiation at 180° C. for 2 hours. MS (ESI): mass calcd. for $C_{18}H_{17}FN_6O$, 352.14; m/z found, 353.1 [M+H]$^+$. $^1$H NMR (500 MHz, DMSO-d$_6$) δ 8.32 (d, J=2.0 Hz, 1H), 8.25 (s, 1H), 8.04-7.97 (m, 1H), 7.74-7.67 (m, 1H), 7.26 (d, J=8.3 Hz, 1H), 6.68 (s, 2H), 6.60 (s, 2H), 6.23 (d, J=2.0 Hz, 1H), 3.58-3.46 (m, 1H), 2.17-2.02 (m, 4H), 1.98-1.84 (m, 1H), 1.80-1.69 (m, 1H).

Example 351

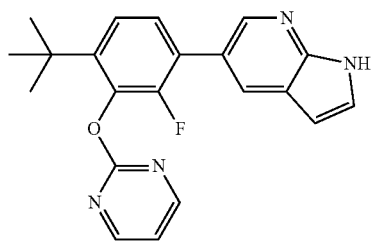 [SMILES: CC(C)(C)c1ccc(-c2cnc3[nH]ccc3c2)c(F)c1Oc1ncccn1]

5-[4-tert-Butyl-2-fluoro-3-(pyrimidin-2-yloxy)phenyl]-1H-pyrrolo[2,3-b]pyridine

Step A: (3-bromo-6-(tert-butyl)-2-fluorophenoxy)(tert-butyl)dimethylsilane

To a 100 mL round-bottomed flask were added a stir-bar, THF (38.0 mL), tert-butyl(2-(tert-butyl)-6-fluorophenoxy)dimethylsilane (5.0 g, 18 mmol), and N,N,N',N'-tetramethylethylenediamine (1.6 mL, 19 mmol). The flask was cooled to −78° C. and then treated with sec-BuLi (14 mL, 20 mmol, 1.4 M in hexanes) over 6 min. The resulting mixture was stirred for 2 hr, before treating it with a solution consisting of carbon tetrabromide (8.7 mL, 26 mmol) and THF (8.0 mL) over the course of 2 min. The resulting mixture was stirred for an additional 2 h at −78° C. The reaction mixture was then warmed to RT and stirred another 18 h. The reaction mixture was then poured into sat. aq NH$_4$Cl and extracted with EtOAc (200 mL). The organic phase was isolated, dried over Na$_2$SO$_4$, filtered and concentrated to dryness. Purification by FCC yielded the title compound.

Step B: 3-Bromo-6-(tert-butyl)-2-fluorophenol

To a 100 mL round-bottomed flask were added a stir-bar, (3-bromo-6-(tert-butyl)-2-fluorophenoxy)(tert-butyl)dimethylsilane (6.4 g, 18 mmol), THF (44.0 mL) and TBAF (25.0 g, 24.0 mmol, 1M in THF). The mixture was stirred for 2 hr and then poured into NH$_4$Cl (100 mL, sat. aq.). The aqueous mixture was then extracted with EtOAc (200 mL), the organic extract was dried over Na$_2$SO$_4$, filtered and concentrated to dryness. Purification by FCC yielded the title compound.

Step C: 2-(3-Bromo-6-(tert-butyl)-2-fluorophenoxy)pyrimidine

To a 20 mL microwave vial were added a stir-bar, 3-bromo-6-(tert-butyl)-2-fluorophenol (1.4 g, 5.7 mmol), 2-chloropyrimidine (0.76 g, 6.3 mmol), cesium carbonate (3.6 g, 11 mmol), and acetonitrile (11.0 mL). The mixture was heated at 80° C. for 18 hr. The reaction mixture was filtered and the filtrate was directly subjected to FCC to provide the title compound (0.95 g, 51%) $^1$H NMR (400 MHz, CDCl$_3$) δ 8.58 (d, J=4.8 Hz, 2H), 7.37 (dd, J=8.8, 6.7 Hz, 1H), 7.12 (dd, J=8.8, 1.9 Hz, 1H), 7.09-7.05 (m, 1H), 1.35 (s, 9H).

Step D: 5-[4-tert-Butyl-2-fluoro-3-(pyrimidin-2-yloxy)phenyl]-1H-pyrrolo[2,3-b]pyridine 5-(4,4,5,5-Tetramethyl-1,3,2-dioxaborolan-2-yl)-1H-pyrrolo[2,3-b]pyridine was coupled to 2-(3-bromo-6-(tert-butyl)-2-fluorophenoxy)pyrimidine in an analogous manner to Step D in Intermediate A to give the title compound (10 mg, 8%). MS (ESI): mass calcd. for C$_{21}$H$_{19}$FN$_4$O, 362.15; m/z found, 363.1 [M+H]$^+$. $^1$H NMR (400 MHz, CDCl$_3$) δ 10.11 (s, 1H), 8.60 (d, J=4.8 Hz, 2H), 8.53-8.46 (m, 1H), 8.15-8.08 (m, 1H), 7.40-7.30 (m, 3H), 7.11-7.01 (m, 1H), 6.53 (dd, J=3.5, 1.8 Hz, 1H), 1.45-1.41 (m, 9H).

The following Examples 1-36 summarized in Table 4 are prophetic and unless otherwise specified, can be readily synthesized by a person skilled in the art utilizing the above described reaction schemes or by synthesis routes generally known to a person skilled in the art. One skilled in the art based on presently disclosed compounds would conclude the following prophetic compounds to be active against FLAP.

TABLE 4

Prophetic Examples

| STRUCTURE | No. | NAME |
|---|---|---|
| 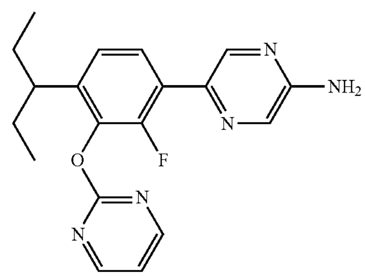 [SMILES: CCC(CC)c1ccc(-c2cnc(N)cn2)c(F)c1Oc1ncccn1] | 1 | 5-(2-fluoro-4-(pentan-3-yl)-3-(pyrimidin-2-yloxy)phenyl)pyrazin-2-amine |
| 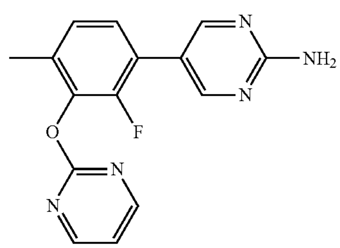 [SMILES: Cc1ccc(-c2cnc(N)nc2)c(F)c1Oc1ncccn1] | 2 | 5-(2-fluoro-4-methyl-3-(pyrimidin-2-yloxy)phenyl)pyrimidin-2-amine |
| 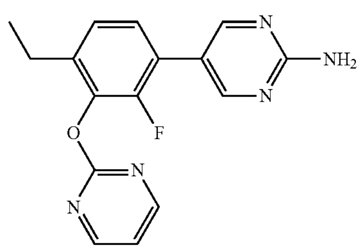 [SMILES: CCc1ccc(-c2cnc(N)nc2)c(F)c1Oc1ncccn1] | 3 | 5-(4-ethyl-2-fluoro-3-(pyrimidin-2-yloxy)phenyl)pyrimidin-2-amine |
| 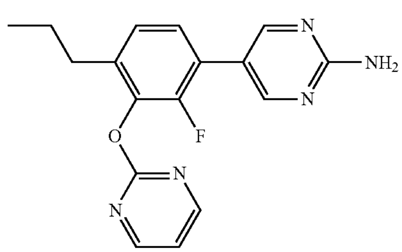 [SMILES: CCCc1ccc(-c2cnc(N)nc2)c(F)c1Oc1ncccn1] | 4 | 5-(2-fluoro-4-propyl-3-(pyrimidin-2-yloxy)phenyl)pyrimidin-2-amine |

TABLE 4-continued

Prophetic Examples

| STRUCTURE | No. | NAME |
|---|---|---|
| 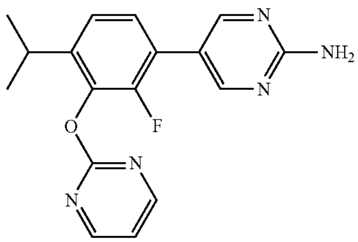 [SMILES: CC(C)c1ccc(-c2cnc(N)nc2)c(F)c1Oc1ncccn1] | 5 | 5-(2-fluoro-4-isopropyl-3-(pyrimidin-2-yloxy)phenyl)pyrimidin-2-amine |
| 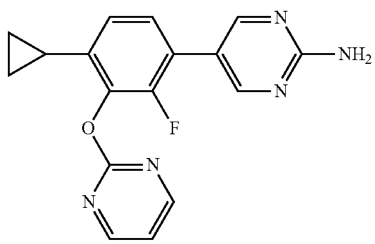 [SMILES: Nc1ncc(-c2ccc(C3CC3)c(Oc3ncccn3)c2F)cn1] | 6 | 5-(4-cyclopropyl-2-fluoro-3-(pyrimidin-2-yloxy)phenyl)pyrimidn-2-amine |
| 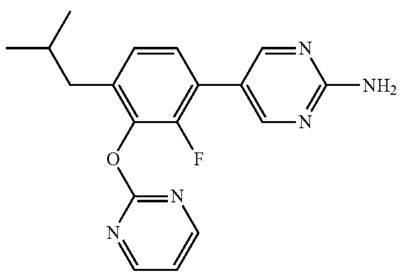 [SMILES: CC(C)Cc1ccc(-c2cnc(N)nc2)c(F)c1Oc1ncccn1] | 7 | 5-(2-fluoro-4-isobutyl-3-(pyrimidin-2-yloxy)phenyl)pyrimidin-2-amine |
| 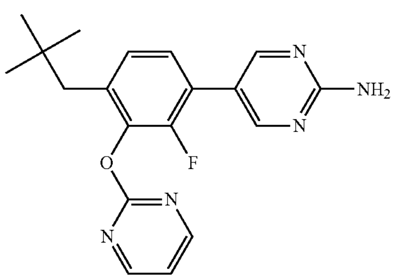 [SMILES: CC(C)(C)Cc1ccc(-c2cnc(N)nc2)c(F)c1Oc1ncccn1] | 8 | 5-(2-fluoro-4-neopentyl-3-(pyrimidin-2-yloxy)phenyl)pyrimidin-2-amine |
| 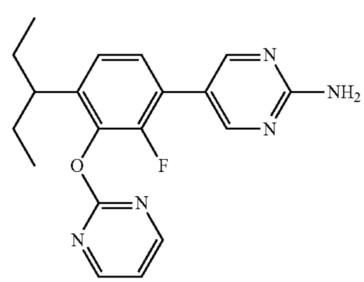 [SMILES: CCC(CC)c1ccc(-c2cnc(N)nc2)c(F)c1Oc1ncccn1] | 9 | 5-(2-fluoro-4-(pentan-3-yl)-3-(pyrimidin-2-yloxy)phenyl)pyrimidin-2-amine |
| 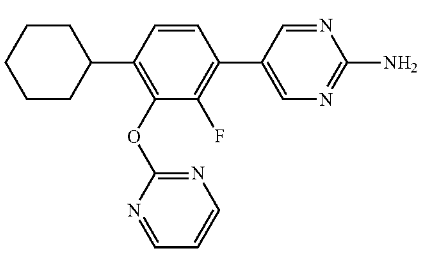 [SMILES: Nc1ncc(-c2ccc(C3CCCCC3)c(Oc3ncccn3)c2F)cn1] | 10 | 5-(4-cyclohexyl-2-fluoro-3-(pyrimidin-2-yloxy)phenyl)pyrimidin-2-amine |

TABLE 4-continued

Prophetic Examples

| STRUCTURE | No. | NAME |
|---|---|---|
| 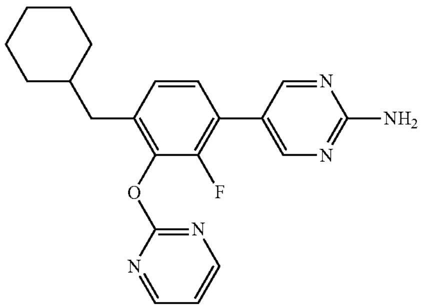 [SMILES: Nc1ncc(-c2ccc(CC3CCCCC3)c(Oc3ncccn3)c2F)cn1] | 11 | 5-(4-(cyclohexylmethyl)-2-fluoro-3-(pyrimidin-2-yloxy)phenyl)pyrimidin-2-amine |
| 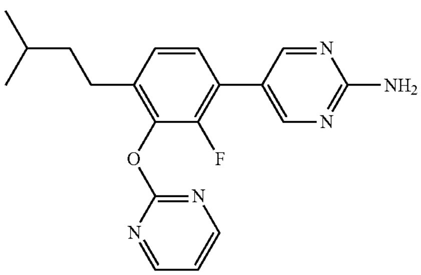 [SMILES: CC(C)CCc1ccc(-c2cnc(N)nc2)c(F)c1Oc1ncccn1] | 12 | 5-(2-fluoro-4-isopentyl-3-(pyrimidin-2-yloxy)phenyl)pyrimidin-2-amine |
| 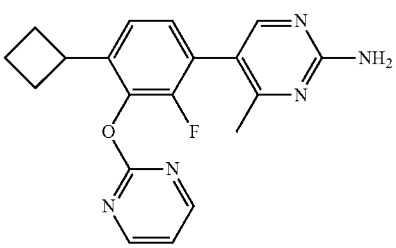 [SMILES: Cc1nc(N)ncc1-c1ccc(C2CCC2)c(Oc2ncccn2)c1F] | 13 | 5-(4-cyclobutyl-2-fluoro-3-(pyrimidin-2-yloxy)phenyl)-4-methylpyrimidin-2-amine |
| 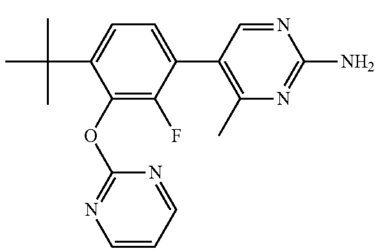 [SMILES: Cc1nc(N)ncc1-c1ccc(C(C)(C)C)c(Oc2ncccn2)c1F] | 14 | 5-(4-(tert-butyl)-2-fluoro-3-(pyrimidin-2-yloxy)phenyl)-methylpyrimidin-2-amine |
| 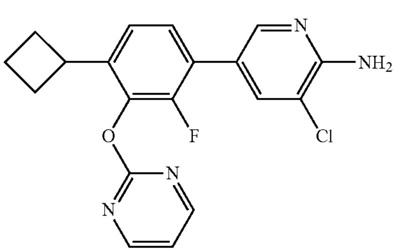 [SMILES: Nc1ncc(-c2ccc(C3CCC3)c(Oc3ncccn3)c2F)cc1Cl] | 15 | 3-chloro-5-(4-cyclobutyl-2-fluoro-3-(pyrimidin-2-yloxy)phenyl)pyridin-2-amine |

TABLE 4-continued

Prophetic Examples

| STRUCTURE | No. | NAME |
|---|---|---|
| 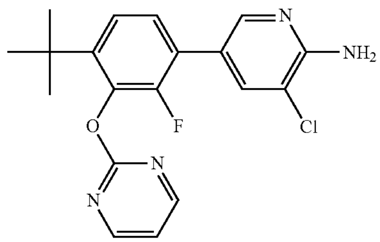 [SMILES: CC(C)(C)c1ccc(-c2cnc(N)c(Cl)c2)c(F)c1Oc1ncccn1] | 16 | 5-(4-(tert-butyl)-2-fluoro-3-(pyrimidin-2-yloxy)phenyl)-3-chloropyridin-2-amine |
| 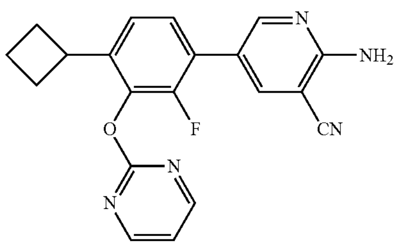 [SMILES: N#Cc1cc(-c2ccc(C3CCC3)c(Oc3ncccn3)c2F)cnc1N] | 17 | 2-amino-5-(4-cyclobutyl-2-fluoro-3-(pyrimidin-2-yloxy)phenyl)nicotinonitrile |
| 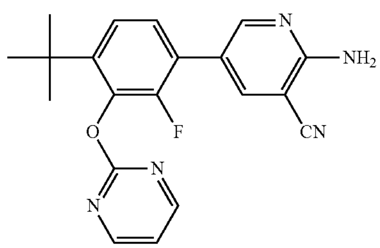 [SMILES: CC(C)(C)c1ccc(-c2cnc(N)c(C#N)c2)c(F)c1Oc1ncccn1] | 18 | 2-amino-5-(4-(tert-butyl)-2-fluoro-3-(pyrimidin-2-yloxy)phenyl)nicotinonitrile |
| 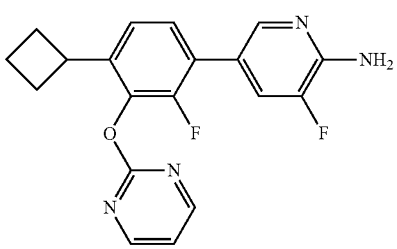 [SMILES: Nc1ncc(-c2ccc(C3CCC3)c(Oc3ncccn3)c2F)cc1F] | 19 | 5-(4-cyclobutyl-2-fluoro-3-(pyrimidin-2-yloxy)phenyl)-3-fluoropyridin-2-amine |
| 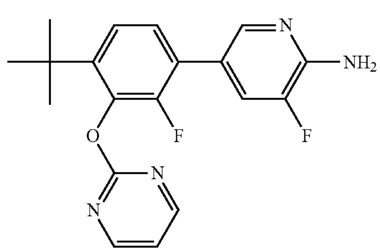 [SMILES: CC(C)(C)c1ccc(-c2cnc(N)c(F)c2)c(F)c1Oc1ncccn1] | 20 | 5-(4-(tert-butyl)-2-fluoro-3-(pyrimidin-2-yloxy)phenyl)-3-fluoropyridin-2-amine |
| 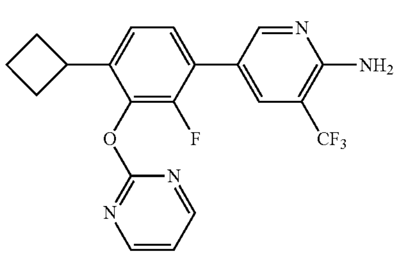 | 21 | 5-(4-cyclobutyl-2-fluoro-3-(pyrimidin-2-yloxy)phenyl)-3-(trifluoromethyl)pyridin-2-amine |

TABLE 4-continued

| Prophetic Examples | | |
|---|---|---|
| STRUCTURE | No. | NAME |
| | 22 | 5-(4-(tert-butyl)-2-fluoro-3-(pyrimidin-2-yloxy)phenyl)-3-(trifluoromethyl)pyridin-2-amine |
| | 23 | 5-(4-cyclobutyl-2-fluoro-3-(pyrimidin-2-yloxy)phenyl)pyridine-2,3-diamine |
| | 24 | 5-(4-(tert-butyl)-2-fluoro-3-(pyrimidin-2-yloxy)phenyl)pyridine-2,3-diamine |
| | 25 | 5-(4-cyclobutyl-2-fluoro-3-(pyrimidin-2-yloxy)phenyl)-3-methylpyrazin-2-amine |
| | 26 | 5-(4-(tert-butyl)-2-fluoro-3-(pyrimidin-2-yloxy)phenyl)-3-methylpyrazin-2-amine |
| | 27 | 3-chloro-5-(4-cyclobutyl-2-fluoro-3-(pyrimidin-2-yloxy)phenyl)pyrazin-2-amine |

TABLE 4-continued

Prophetic Examples

| STRUCTURE | No. | NAME |
|---|---|---|
| 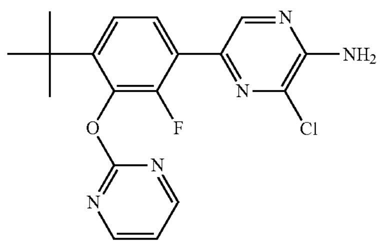 [SMILES: CC(C)(C)c1ccc(-c2cnc(N)c(Cl)n2)c(F)c1Oc1ncccn1] | 28 | 5-(4-(tert-butyl)-2-fluoro-3-(pyrimidin-2-yloxy)phenyl)-3-chloropyrazin-2-amine |
| 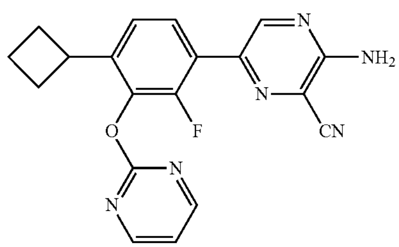 [SMILES: N#Cc1nc(-c2ccc(C3CCC3)c(Oc3ncccn3)c2F)cnc1N] | 29 | 3-amino-6-(4-cyclobutyl-2-fluoro-3-(pyrimidin-2-yloxy)phenyl)pyrazine-2-carbonitrile |
| 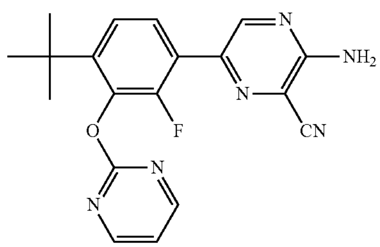 [SMILES: CC(C)(C)c1ccc(-c2cnc(N)c(C#N)n2)c(F)c1Oc1ncccn1] | 30 | 3-amino-6-(4-(tert-butyl)-2-fluoro-3-(pyrimidin-2-yloxy)phenyl)pyrazine-2-carbonitrile |
| 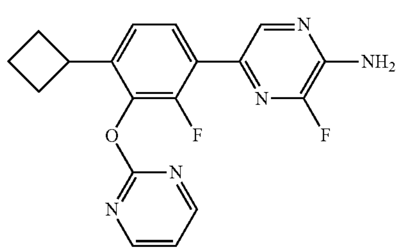 [SMILES: Nc1ncc(-c2ccc(C3CCC3)c(Oc3ncccn3)c2F)nc1F] | 31 | 5-(4-cyclobutyl-2-fluoro-3-(pyrimidin-2-yloxy)phenyl)-3-fluoropyrazin-2-amine |
| 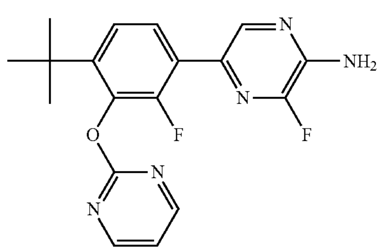 [SMILES: CC(C)(C)c1ccc(-c2cnc(N)c(F)n2)c(F)c1Oc1ncccn1] | 32 | 5-(4-(tert-butyl)-2-fluoro-3-(pyrimidin-2-yloxy)phenyl)-3-fluoropyrazin-2-amine |
| 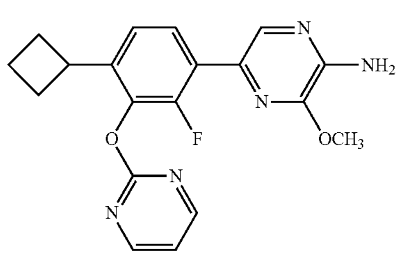 [SMILES: COc1nc(-c2ccc(C3CCC3)c(Oc3ncccn3)c2F)cnc1N] | 33 | 5-(4-cyclobutyl-2-fluoro-3-(pyrimidin-2-yloxy)phenyl)-3-methoxypyrazin-2-amine |

TABLE 4-continued

Prophetic Examples

| STRUCTURE | No. | NAME |
|---|---|---|
| 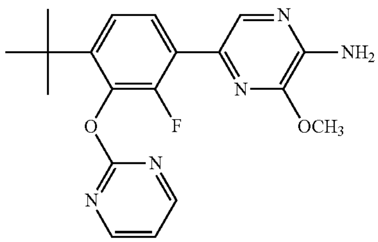 [SMILES: COc1nc(-c2ccc(C(C)(C)C)c(Oc3ncccn3)c2F)cnc1N] | 34 | 5-(4-(tert-butyl)-2-fluoro-3-(pyrimidin-2-yloxy)phenyl)-3-methoxypyrazin-2-amine |
| 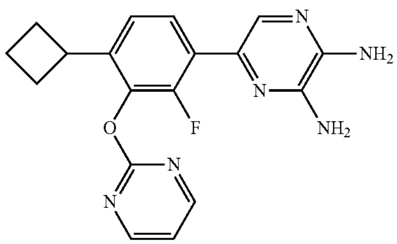 [SMILES: Nc1ncc(-c2ccc(C3CCC3)c(Oc3ncccn3)c2F)nc1N] | 35 | 5-(4-cyclobutyl-2-fluoro-3-(pyrimidin-2-yloxy)phenyl)pyrazine-2,3-diamine |
| 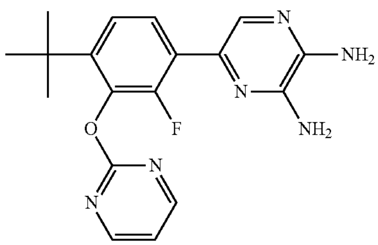 [SMILES: CC(C)(C)c1ccc(-c2cnc(N)c(N)n2)c(F)c1Oc1ncccn1] | 36 | 5-(4-(tert-butyl)-2-fluoro-3-(pyrimidin-2-yloxy)phenyl)pyrazine-2,3-diamine |

D) General Administration, Formulation, and Dosages

The present invention provides substituted heteroaryl ketone compounds which are useful as FLAP modulators.

The invention features a method for treating a subject in need thereof with an FLAP-mediated disease and/or disorder, said method comprising administering to the subject a therapeutically effective amount of a compound of the invention. In particular, the invention also provides a method for treating or inhibiting the progression of an FLAP-mediated disease and/or disorder, or associated symptoms or complications thereof in a subject afflicted with such a disease and/or disorder, wherein the method comprises administering to the subject a therapeutically effective amount of a compound of the invention.

Embodiments of the present invention include a method wherein the compound of Formula (I) is a FLAP modulator.

Embodiments of the present invention include a use of the compound of Formula (I) in the manufacture of a medicament for treating an FLAP-mediated disease and/or disorder.

Embodiments of the present invention include a use of the compound of Formula (I) as a medicine.

The compounds of Formula (I) have an FLAP-modulating effect and are useful as therapeutic agents for various FLAP-mediated disorders and/or disorders, or associated symptoms or complications, for example, respiratory disorders, cardiac and cardiovascular diseases, autoimmune disorders, carcinogenesis, and associated symptoms or complications thereof.

The compounds of Formula (I) may be administered orally or parenterally, and after formulation into preparations suitable for the intended administration route, they can be used as therapeutic agents for treating an FLAP-mediated disease and/or disorder. FLAP-mediated diseases and/or disorders include, but are not limited, diseases and/or disorders that are related to leukotriene synthesis pathway, and therefore may be treated, controlled or in some cases prevented, by treatment with the compounds of this invention.

One aspect of the present invention provides a method for the treatment of diseases and/or disorders, or associated symptoms or complications thereof, responsive to the modulation of FLAP in a subject in need thereof which comprises administering to the subject a therapeutically or prophylactically effective amount of a compound of Formula (I) or a form thereof.

Another aspect of the present invention provides a method for the treatment of a disease and/or disorder selected from the group consisting of respiratory diseases and/or disorders, cardiac and cardiovascular diseases and/or disorders, autoimmune diseases and/or disorders, carcinogenesis, and associated symptoms or complications thereof, in a subject in need thereof which comprises administering to the subject a therapeutically or prophylactically effective amount of a compound of Formula (I) or a form thereof.

More specifically, this invention is directed to a method of treating exacerbations, non-allergic asthma, aspirin exacerbated respiratory disease, pulmonary arterial hypertension, fibrotic lung diseases, acute respiratory distress syndrome, obstructive sleep apnea and chronic obstructive pulmonary disease, or associated symptoms or complications thereof, in a subject afflicted with such a disease and/or disorder, wherein the method comprises administering to the subject a therapeutically or prophylactically effective amount of a compound of Formula (I) or a form thereof.

Furthermore, this invention is directed to a method of treating myocardial infarction, atherosclerosis and coronary artery disease, stroke, aortic aneurisms, atherosclerosis, or associated symptoms or complications thereof, in a subject afflicted with such a disease and/or disorder, wherein the method comprises administering to the subject a therapeutically or prophylactically effective amount of a compound of Formula (I) or a form thereof.

Yet, this invention is also directed to a method of treating rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, chronic sinusitis, allergic dermatitis and asthma, wherein the method comprises administering to the subject a therapeutically or prophylactically effective amount of a compound of Formula (I) or a form thereof.

Finally, this invention is also directed to a method of treating tumor cell proliferation, differentiation, and apoptosis, tumor-associated angiogenesis, as well as the migration and invasion of carcinoma cells, wherein the method comprises administering to the subject a therapeutically or prophylactically effective amount of a compound of Formula (I) or a form thereof.

Another aspect of the present invention provides a pharmaceutical composition comprising at least one compound of Formula (I) or a form thereof, and a pharmaceutically acceptable carrier.

The invention also features a method for treating a subject in need thereof with an FLAP-mediated disease and/or disorder, said method comprising administering to the subject a therapeutically effective amount of a pharmaceutical composition comprising at least one compound of the invention.

Yet another aspect of the present invention relates to the use of a compound of Formula (I) or a form thereof, for the manufacture of a medicament useful for the treatment of an FLAP-mediated disease and/or disorder in a subject in need thereof.

In a clinical use of the compounds of the invention, pharmaceutically-acceptable additives may be added thereto to formulate various preparations in accordance with the intended administration route thereof, and the preparations may be administered.

Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals, including humans and other mammals. Any ordinary physician, veterinarian or clinician may readily determine the necessity, if any, of treatment with an instant compound.

Those of skill in the treatment of diseases and/or disorders, or associated symptoms or complications thereof, mediated by FLAP can determine the effective daily amount from the test results presented hereinafter and other information. The exact dosage and frequency of administration depends on the particular compound of invention used, the particular disease and/or disorder, or associated symptoms or complications thereof, being treated, the severity of the disease and/or disorder, or associated symptoms or complications thereof, being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the FLAP diseases and/or disorders described in the present invention using any of the compounds as defined herein, the dosage form will contain a pharmaceutically acceptable carrier containing between from about 1 mg to about 1000 mg; particularly from about 0.5 mg to about 500 mg of the compound, and may be constituted into any form suitable for the mode of administration selected. The dosages, however, may be varied depending upon the requirement of the subjects, the severity of the disease and/or disorder, or associated symptoms or complications thereof, being treated and the compound being employed. The use of either daily administration or post-periodic dosing may be employed.

When the compound of the invention is, for example, put into clinical use, then its dose and its administration frequency may vary depending on the sex, the age, the body weight and the condition of the patient and on the type and the range of the necessary treatment with the compound. For oral administration, in general, the dose of the compound may be in a range of from about 0.01 mg/kg/day to about 100 mg/kg of body weight/day or in a range of from about 0.03 mg/kg/day to about 1 mg/kg/day. The oral administration frequency is preferably from one to a few times per day. For parenteral administration, the dose may be in a range of from about 0.001 mg/kg/day to about 10 mg/kg/day, in a range of from about 0.001 mg/kg/day to about 0.1 mg/kg/day or, in a range of from about 0.01 mg/kg/day to about 0.1 mg/kg/day. The parenteral administration frequency is preferably from one to a few times per day. For oral administration, the compositions are preferably provided in the form of tablets containing from about 1.0 mg to about 1000 mg of the active ingredient, particularly 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds may be administered on a regimen of 1 to 4 times per day, preferably once or twice per day.

Ordinary physicians, veterinarians and clinicians may readily determine the effective dose of the pharmaceutical compound necessary to treat, prevent, inhibit, retard or stop the intended disease, and may readily treat the diseased patient with the compound.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for 1 to 4 times per day, preferably once or twice per day administration; for example, an insoluble salt of the active compound, such as the decanoate salt, may be adapted to provide a depot preparation for intramuscular injection.

The preparation may contain the compound of the invention in an amount in a range of from about 1.0 to about 100% by weight or, in a range of from about 1.0 to about 60% by weight of the preparation. The preparation may contain any other therapeutically-effective compound.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

E) Use

Dosages

For preparing pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as cross-linked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, camauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agents include pharmaceutical grade lecithins. Suitable flocculating agents include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms; however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as FLAP modulators is required for a subject in need thereof.

In their use, the compounds of the invention may be combined with any other therapeutic agents that are useful for the treatment of an FLAP-mediated disorder.

The combination includes not only the composition of compounds of the invention and one other active substance but also the composition of compounds of the invention and two or more other active substances or non-drug therapy. The scope of possible combinations of a compound of the invention and one, two or more active substances are within the knowledge of one skilled in the art for the treatment of an FLAP-mediated disorder.

Specifically, the combination of a FLAP modulator with prostaglandin modulators, cyclooxygenase-1 modulators, or cyclooxygenase-2 modulators might be used to treat inflammatory and autoimmune diseases and/or disorders as well as cardiovascular diseases and/or disorders, or vascular injury (Z. Yu et al., "Disruption of the 5-lipoxygenase pathway attenuates atherogenesis consequent to COX-2 deletion in mice," *Proc. Natl. Acad. Sci. USA*, 2012, 109(17), 6727-32; Z. Yu et al., "Myeloid Cell 5-Lipoxygenase Activating Protein Modulates the Response to Vascular Injury," *Circ. Res.*, 2012, Epub December 18). Due to the synergy of histamine and leukotrienes, the combination of a FLAP modulator and a histamine receptor 1 or 4 antagonist might have utility in treating respiratory, allergic, dermatological and autoimmune disorders (A. Reicin et al., "Montelukast, a leukotriene receptor antagonist, in combination with loratadine, a histamine receptor antagonist, in the treatment of chronic asthma," *Arch. Intern. Med.*, 2000, 160(16), 2418-88; S. Sanada et al., "The effectiveness of montelukast for the treatment of anti-histamine-resistant chronic urticaria," *Arch. Dermatol. Res.*, 2005, 297(3), 134-38).

Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

F) Biological Examples

The ability of the compounds of the present invention to treat a FLAP-mediated disease and/or disorder, or associated symptoms or complications thereof, was determined using the following procedures. Binding assay data represent the average value obtained from two different assay plates, with samples run in duplicate on each plate. Human whole blood assay data represent a single replicate on an assay plate using whole blood from at least one healthy donor.

FLAP Binding Assay

The assay below is used to test the modulatory activity of compounds against FLAP. Human and mouse FLAP-encoding DNA was amplified by polymerase chain reaction and cloned into pFastBac1 (Invitrogen) with a NH2-terminal 6-His tag for expression in *Spodoptera frugiperda* (Sf-9) cells. FLAP-containing membranes were prepared as was a FITC-labeled FLAP modulator (3-(3-(tert-butylthio)-1-(4-chlorobenzyl)-5-(quinolin-2-ylmethoxy)-1H-indol-2-yl)-2,2-dimethylpropanoic acid). The FLAP binding assay is performed in HTRF format (homogeneous time resolved fluorescence). FLAP-containing membranes (1 µg/well final for human) are incubated in the presence of the HTRF ligand, [5-[({[2-(2-{3-[3-(tert-butylsulfanyl)-1-(4-chlorobenzyl)-5-(quinolin-2-ylmethoxy)-1H-indol-2-yl]-2,2-dimethylpropanoyl}hydrazino)-2-oxoethyl]sulfanyl}acetyl)amino]-2-(6-hydroxy-3-oxo-3H-xanthen-9-yl)benzoic acid] (25 nM final), a terbium labeled anti-His tag antibody (0.5 ng/well final, from Cisbio) and compounds. The reaction is allowed to proceed for two hours after which the plate is read on an Envision plate reader in HTRF mode. Data are expressed as a HTRF ratio.

For human FLAP binding assays, data are analyzed with 3DX Explorer software. A ratio is calculated with the relative light units at 520 nm over the relative light units at 495 nm. For analysis, data from multiple runs are averaged and each compound may be tested in 2 to 20 runs. Each run comprises two plates and each plate includes duplicates. Data from each plate is averaged and data are imported into 3DX. The data from multiple runs are aggregated as the average of duplicates of the calculated ratios in order to calculate $K_i$ and $IC_{50}$ values. The letters ND and/or the absence of data in any of the boxes in Table 5 and Table 6 indicates that $K_i$ or $IC_{50}$ values were not determined.

Human Whole Blood Assay

An in vitro cellular assay was performed using human whole blood collected in heparin-containing tubes, which was used to test the ability of compounds to modulate the leukotriene pathway in human whole blood. The blood was diluted 1:1 in RPMI medium, pre-incubated for 15 min at 37° Celsius with test compounds at various concentrations, and then stimulated with calcium ionophore, A23187 (7 µg/mL), for 30 min at 37° Celsius. The samples were then centrifuged and plasma was removed. The plasma was diluted in assay buffer and $LTB_4$ levels were measured using a commercial kit (Enzo Life Sciences). The concentration of each compound that was required for half-maximal inhibition (modulation) of recombinant enzyme activity ($IC_{50}$) was calculated by a 4-parameter equation using the program GraphPad Prism (GraphPad software).

TABLE 5

FLAP binding and Human Whole Blood assay data

| Cmp No. | FLAP Binding wild type HTRF $K_i$ (µM) | Human Whole Blood LTB4 $IC_{50}$ 1:1 (µM) |
|---|---|---|
| A | 0.064 | 0.5311 |
| B | 0.354 | 0.9601 |
| 1 | 0.286 | 0.5882 |
| 2 | 0.158 | 0.5255 |
| 3 | 0.250 | 0.2712 |
| 4 | 0.004 | 0.2983 |
| 5 | 0.011 | 0.2632 |
| 6 | 0.014 | 1.2165 |
| 7 | 0.007 | 1.4025 |

TABLE 5-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 8 | 0.750 | |
| 9 | 0.808 | |
| 10 | 0.866 | |
| 11 | 0.750 | |
| 12 | 0.090 | |
| 13 | 0.250 | 1.2900 |
| 14 | 0.122 | 2.2888 |
| 15 | 0.193 | 1.2379 |
| 16 | 0.098 | 0.4670 |
| 17 | 0.016 | 0.2755 |
| 18 | 0.120 | 1.1684 |
| 19 | 0.100 | 0.8115 |
| 20 | 0.005 | >10 |
| 21 | 0.008 | 4.1267 |
| 22 | 0.006 | >10 |
| 23 | 0.002 | 0.3633 |
| 24 | 0.100 | >10 |
| 25 | 0.012 | 0.5758 |
| 26 | 0.020 | >10 |
| 27 | 0.006 | 0.8048 |
| 28 | 0.304 | |
| 29 | 0.224 | 1.0605 |
| 30 | 0.354 | |
| 31 | 0.170 | 1.9552 |
| 32 | 0.354 | |
| 33 | 0.250 | 1.4135 |
| 34 | 0.304 | 1.5696 |
| 35 | 0.173 | 1.1387 |
| 36 | 0.220 | 2.5433 |
| 37 | 0.250 | 2.4963 |
| 38 | 0.250 | 0.7364 |
| 39 | 0.750 | |
| 40 | 0.612 | |
| 41 | 0.250 | 1.3462 |
| 42 | 2.000 | |
| 43 | 0.430 | |
| 44 | 1.500 | |
| 45 | 0.193 | 0.7196 |
| 46 | 0.008 | 5.6157 |
| 47 | 0.042 | 0.2998 |
| 48 | 0.012 | 0.1751 |
| 49 | 0.132 | 1.1471 |
| 50 | 1.500 | |
| 51 | 0.324 | |
| 52 | 0.366 | 0.6797 |
| 53 | 0.138 | 0.6449 |
| 54 | 0.296 | 0.9087 |
| 55 | 0.152 | 0.5550 |
| 56 | 0.082 | 0.6437 |
| 57 | 0.036 | 0.3454 |
| 58 | 0.030 | 0.3736 |
| 59 | 0.327 | 1.5371 |
| 60 | 0.116 | 0.7318 |
| 61 | 0.262 | 0.6971 |
| 62 | 0.315 | 0.8316 |
| 63 | 0.120 | 0.2125 |
| 64 | 0.086 | 0.2753 |
| 65 | 0.018 | 0.1067 |
| 66 | 0.422 | 0.7534 |
| 67 | 0.176 | 0.7268 |
| 68 | 0.750 | |
| 69 | 0.030 | 0.0739 |
| 70 | 0.034 | 0.4127 |
| 71 | 0.620 | |
| 72 | 0.018 | 0.7372 |
| 73 | 0.275 | 1.0249 |
| 74 | 0.750 | |
| 75 | 0.370 | |
| 76 | 0.250 | 1.7656 |
| 77 | 0.200 | 1.3823 |
| 78 | 0.173 | 1.2888 |
| 79 | 0.250 | 2.2295 |
| 80 | 0.304 | 3.2931 |
| 81 | 0.394 | |
| 82 | 0.304 | |
| 83 | 0.037 | 0.6046 |
| 84 | 0.070 | 0.8865 |
| 85 | 0.028 | 10 |
| 86 | 0.005 | 0.0351 |
| 87 | 0.001 | 0.0067 |
| 88 | 0.004 | 0.0361 |
| 89 | 0.004 | 0.0222 |
| 90 | | 0.0538 |
| 91 | 0.001 | 0.0048 |
| 92 | | 6.6635 |
| 93 | 0.003 | 0.0308 |
| 94 | 0.027 | 0.1010 |
| 95 | 0.005 | >1 |
| 96 | 0.007 | 0.0338 |
| 97 | 0.032 | 0.1534 |
| 98 | 0.008 | 0.1751 |
| 99 | 0.006 | 0.0407 |
| 100 | 0.001 | 0.0126 |
| 101 | 0.023 | 0.9143 |
| 102 | 0.002 | 0.1028 |
| 103 | 0.035 | 0.6750 |
| 104 | 0.100 | 2.8054 |
| 105 | 0.250 | |
| 106 | 0.084 | 0.3759 |
| 107 | 0.0069 | 0.1770 |
| 108 | 0.0246 | 1.3056 |
| 109 | 0.0089 | 0.3075 |
| 110 | 0.0024 | 0.0522 |
| 111 | 0.0019 | 0.0654 |
| 112 | 0.0148 | 0.1812 |
| 113 | 0.0270 | 0.6076 |
| 114 | 0.0172 | 0.3746 |
| 115 | 0.297 | 1.1064 |
| 116 | 0.0146 | 0.5034 |
| 117 | 2.500 | |
| 118 | 0.0105 | 0.0657 |
| 119 | 0.006 | 0.0263 |
| 120 | 0.304 | |
| 121 | 0.250 | |
| 122 | 0.004 | 0.4596 |
| 123 | 0.007 | 4.4771 |
| 124 | 0.003 | 0.1192 |
| 125 | 0.250 | |
| 126 | 0.0107 | 0.4059 |
| 127 | 2.200 | |
| 128 | 0.297 | |
| 129 | 0.119 | 0.2813 |
| 130 | 0.0037 | 0.0841 |
| 131 | 0.0056 | 0.0679 |
| 132 | 0.0170 | 0.1327 |
| 133 | 0.0102 | 0.0796 |
| 134 | 0.0062 | 0.0397 |
| 135 | 0.0013 | 0.0124 |
| 136 | 0.0035 | 0.0459 |
| 137 | 0.0037 | 0.0510 |
| 138 | 0.0055 | 0.0703 |
| 139 | 0.0039 | 0.0485 |
| 140 | 0.0013 | 0.0117 |
| 141 | 0.0050 | 0.0586 |
| 142 | 0.0017 | 0.0185 |
| 143 | 0.0029 | 0.0377 |
| 144 | 0.0011 | 0.0223 |
| 145 | 0.0054 | 0.1774 |
| 146 | 0.0004 | 0.0045 |
| 147 | 0.0064 | 0.1854 |
| 148 | 0.1007 | |
| 149 | 0.0013 | 0.1119 |
| 150 | 0.1764 | 3.5859 |
| 151 | 0.0089 | 0.0754 |
| 152 | 0.0625 | >10 |
| 153 | 0.0023 | 0.4245 |
| 154 | 0.0125 | >10 |
| 155 | 0.0041 | 0.1701 |
| 156 | 2.236 | |
| 157 | 0.0206 | 0.1090 |

TABLE 5-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 158 | 0.0078 | 0.0359 |
| 159 | 0.0557 | 3.3052 |
| E | 0.0995 | 1.0950 |
| 160 | 0.0947 | 0.4935 |
| 161 | 0.0222 | 0.0880 |
| 162 | 0.0072 | 0.1238 |
| 163 | 0.0704 | 0.4941 |
| 164 | 0.0368 | 0.1185 |
| 165 | 0.0056 | 0.3039 |
| 166 | 0.0117 | 0.1286 |
| 167 | 0.0147 | 0.0456 |
| 168 | 0.0028 | 0.0361 |
| 169 | 0.2053 | 0.2680 |
| 170 | 0.0903 | 1.4256 |
| 171 | 0.0398 | 0.2519 |
| 172 | 0.394 | 1.6615 |
| 173 | 0.682 | |
| 174 | 0.0054 | 1.2142 |
| 175 | 0.1 | 1.2835 |
| F | 0.075 | 1.2960 |
| 176 | 0.1 | 0.8917 |
| 177 | 0.093 | 0.7711 |
| 178 | 0.354 | |
| 179 | 0.750 | |
| 180 | 0.370 | |
| 181 | 0.041 | 10.0000 |
| 182 | 1.936 | |
| 183 | 0.328 | >10 |
| 184 | 0.0140 | 0.8310 |
| 185 | 0.0196 | 1.0074 |
| 186 | 0.0205 | 0.5309 |
| 187 | 0.0120 | 0.3551 |
| 188 | 0.0086 | 1.1036 |
| 189 | 0.0098 | 1.1397 |
| 190 | 0.0472 | 1.0575 |
| 191 | 0.2500 | 3.4316 |
| 192 | 0.0053 | 0.4184 |
| 193 | 0.0037 | 0.7688 |
| 194 | 0.0029 | 0.1682 |
| 195 | 0.0022 | 0.4457 |
| 196 | 0.0041 | 0.8712 |
| 197 | 0.750 | |
| 198 | 0.0187 | 2.3681 |
| 199 | 0.0242 | 1.0566 |
| G | 0.0779 | 0.5748 |
| 200 | 0.1551 | 1.3583 |
| 201 | 0.0085 | 0.0518 |
| 202 | 0.0061 | 0.0805 |
| 203 | 0.0069 | 0.0308 |
| 204 | 0.0815 | 0.1713 |
| 205 | 0.0402 | 0.1496 |
| H | 0.0723 | 0.2866 |
| 206 | 0.7690 | |
| 207 | 0.0474 | 0.0726 |
| 208 | 0.0465 | 0.2146 |
| 209 | 0.0233 | 0.0511 |
| 210 | 2.500 | |
| 211 | 0.527 | |
| 212 | 0.0640 | 1.0950 |
| 213 | 0.0921 | 1.0146 |
| 214 | 0.0308 | |
| 215 | 0.620 | |
| 216 | 0.866 | |
| 217 | 1.250 | |
| 218 | 0.0773 | >5.000 |
| 219 | >10 | |
| 220 | 0.0218 | 1.117 |
| 221 | 0.5932 | |
| 222 | 0.1798 | 3.475 |
| 223 | >10 | |
| 224 | 0.0232 | 0.2867 |
| 225 | 0.0025 | 0.0684 |
| 226 | 0.0014 | 0.0901 |
| 227 | 0.0085 | 0.3317 |
| 228 | 0.0244 | 0.4804 |
| 229 | 0.0077 | 0.4075 |
| 230 | 0.0025 | 0.2379 |
| 231 | 2.1389 | |
| 232 | 1.5907 | |
| 233 | 1.6792 | |
| 234 | 1.3002 | >10 |
| 235 | 0.0033 | 0.1132 |
| 236 | 0.0022 | 0.0371 |
| 237 | 0.0033 | 0.0847 |
| 238 | 0.1551 | 0.5710 |
| 239 | 0.0083 | 0.1967 |
| 240 | 0.0236 | 0.1045 |
| 241 | 0.0012 | 0.0207 |
| 242 | 0.0036 | 0.0300 |
| I | 0.090 | 1.6688 |
| 243 | 0.2355 | 0.8588 |
| 244 | 0.4622 | 1.8168 |
| 245 | 0.0622 | 2.8016 |
| 246 | 0.0986 | 1.5929 |
| 247 | 0.2594 | 0.4173 |
| 248 | 0.2610 | 10 |
| 249 | 0.2076 | 1.2636 |
| 250 | 0.0992 | 0.3567 |
| 251 | 1.1951 | |
| 252 | 0.0296 | >1 |
| 253 | 0.8541 | |
| 254 | 0.9922 | |
| 255 | 1.1392 | 1.1387 |
| 256 | 0.4335 | 0.7180 |
| 257 | 0.0311 | 0.3324 |
| 258 | 0.0038 | 0.0101 |
| 259 | 0.0070 | 0.1344 |
| 260 | 0.0199 | 0.1973 |
| 261 | 0.0013 | 0.0401 |
| 262 | 0.0196 | 0.1596 |
| 263 | 0.1375 | 1.9579 |
| 264 | >10 | |
| 265 | >10 | |
| 266 | >10 | |
| 267 | >10 | |
| 268 | >10 | |
| 269 | 0.0009 | 0.0151 |
| 270 | 0.7995 | |
| 271 | 0.0051 | 0.0853 |
| 272 | 0.0005 | 0.0419 |
| 273 | >10 | |
| 274 | 0.0196 | 0.1596 |
| 275 | 0.1375 | 1.9579 |
| 276 | 0.0392 | 0.4063 |
| 277 | 0.0177 | 0.1346 |
| 278 | 0.1000 | 0.2160 |
| 279 | 0.0675 | 0.1466 |
| 280 | >10 | |
| 281 | 0.1006 | 0.3696 |
| 282 | 0.0294 | >10 |
| 283 | 0.0976 | |
| 284 | >10 | |
| 285 | >10 | |
| 286 | | |
| 287 | | |
| 288 | 0.3646 | 0.7825 |
| 289 | 0.2292 | 0.5059 |
| 290 | 0.0399 | 0.5761 |
| 291 | 0.0466 | |
| 292 | 0.0372 | 0.412.5 |
| 293 | 0.0165 | 1 |
| 294 | 0.6914 | |
| 295 | 0.0042 | 0.1488 |
| 296 | 0.0068 | 0.3499 |
| 297 | 0.0144 | 0.2626 |
| 298 | >10 | |
| 299 | >10 | |
| 300 | >10 | |
| 301 | >10 | |
| 302 | >10 | |

TABLE 5-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 303 | >10 | |
| 304 | >10 | |
| 305 | >10 | |
| 306 | >10 | |
| 307 | >10 | |
| 308 | >10 | |
| 309 | >10 | |
| 310 | >10 | |
| 311 | 0.0081 | 0.1099 |
| 312 | 0.9745 | |
| 313 | 0.0024 | 0.0270 |
| 314 | >10 | |
| 315 | 1.3649 | |
| 316 | 0.2893 | |
| 317 | 0.1978 | 0.4639 |
| 318 | 0.0581 | 0.1031 |
| 319 | 0.3367 | 0.2845 |
| 320 | 0.0364 | 0.1674 |
| 321 | 0.1165 | >10 |
| 322 | 0.5730 | |
| 323 | 0.2106 | 0.1406 |
| 324 | 0.0738 | 0.2600 |
| 325 | 0.0095 | 0.0527 |
| 326 | 0.3584 | |
| 327 | 0.5278 | |
| 328 | 0.1127 | 0.3125 |
| 329 | 0.0097 | 0.0390 |
| 330 | 0.0051 | >1 |
| 331 | 0.0037 | 0.0129 |
| 332 | 0.0458 | 0.4500 |

The following compounds were tested in additional runs for the assays described above and the data is provided in Table 6.

TABLE 6

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| A | 0.0526 | 0.5311 |
| B | 0.0839 | 0.9601 |
| 1 | 0.0628 | 0.5882 |
| 2 | 0.0861 | 0.8954 |
| 3 | 0.1184 | 0.2712 |
| 4 | 0.0058 | 0.2983 |
| 5 | 0.0102 | 0.2632 |
| 6 | 0.0136 | 1.2165 |
| 7 | 0.0074 | 1.4025 |
| 8 | ~0.7500 | |
| 9 | ~0.8077 | |
| 10 | ~0.8659 | |
| 11 | ~0.7500 | |
| 12 | ~0.0899 | |
| 13 | 0.0271 | 1.2900 |
| 14 | 0.0226 | 2.2888 |
| 15 | ~0.1933 | 1.2379 |
| 16 | 0.0199 | 0.4670 |
| 17 | 0.0125 | 0.2820 |
| 18 | 0.0590 | 1.1684 |
| 19 | 0.0038 | 0.8115 |
| 20 | 0.0051 | >10 |
| 21 | 0.0081 | 4.1267 |
| 22 | 0.0059 | >10 |
| 23 | 0.0037 | 0.3633 |
| 24 | 0.0162 | >10 |
| 25 | 0.0122 | 0.5758 |
| 26 | ~0.0199 | >10 |
| 27 | 0.0064 | 0.8048 |
| 28 | 0.0662 | |
| 29 | 0.0246 | 1.0605 |
| 30 | 0.0335 | |
| 31 | ~0.1699 | 1.9552 |
| 32 | ~0.3535 | |
| 33 | ~0.2499 | 1.4135 |
| 34 | ~0.3041 | 1.5696 |
| 35 | ~0.1732 | 1.1387 |
| 36 | ~0.2199 | 2.5433 |
| 37 | ~0.2499 | 2.4963 |
| 38 | ~0.2499 | 0.7364 |
| 39 | ~0.7500 | |
| 40 | ~0.6123 | |
| 41 | ~0.2499 | 1.3462 |
| 42 | ~1.9998 | |
| 43 | ~0.4301 | |
| 44 | ~1.5000 | |
| 45 | ~0.1933 | 0.7196 |
| 46 | 0.0069 | 5.6157 |
| 47 | 0.0418 | 0.2998 |
| 48 | 0.0121 | 0.1751 |
| 49 | ~0.1339 | 1.1471 |
| 50 | 0.7872 | |
| 51 | 0.3240 | |
| 52 | 0.3661 | 0.6797 |
| 53 | 0.1381 | 0.6449 |
| 54 | 0.2957 | 0.9087 |
| 55 | 0.1516 | 0.5550 |
| 56 | 0.0819 | 0.6437 |
| 57 | 0.0356 | 0.3454 |
| 58 | 0.0303 | 0.3736 |
| 59 | 0.3269 | 1.5371 |
| 60 | 0.1161 | 0.7318 |
| 61 | 0.2618 | 0.6971 |
| 62 | 0.3145 | 0.8316 |
| 63 | 0.1202 | 0.2125 |
| 64 | 0.0860 | 0.2753 |
| 65 | 0.0182 | 0.1067 |
| 66 | 0.4216 | 0.7534 |
| 67 | 0.1762 | 0.7268 |
| 68 | 0.1355 | |
| 69 | 0.0140 | 0.0739 |
| 70 | 0.0342 | 0.4127 |
| 71 | 0.4208 | |
| 72 | 0.0237 | 0.7372 |
| 73 | 0.2748 | 1.0249 |
| 74 | 0.1747 | |
| 75 | ~0.3699 | |
| 76 | ~0.2499 | 1.7656 |
| 77 | ~0.1999 | 1.3823 |
| 78 | ~0.1732 | 1.2888 |
| 79 | ~0.2499 | 2.2295 |
| 80 | ~0.3041 | 3.2931 |
| 81 | ~0.3937 | |
| 82 | 0.2085 | |
| 83 | 0.0445 | 0.6046 |
| 84 | ~0.0700 | 0.8865 |
| 85 | 0.0281 | ~10 |
| 86 | 0.0062 | 0.0351 |
| 87 | 0.0021 | 0.0067 |
| 88 | 0.0035 | 0.0361 |
| 89 | 0.0053 | 0.0222 |
| 90 | 0.0538 | |
| 91 | 0.0008 | 0.0048 |
| 92 | | 6.6635 |
| 93 | 0.0052 | 0.0308 |
| 94 | 0.0445 | 0.1010 |
| 95 | 0.0047 | >1 |
| 96 | 0.0071 | 0.0338 |
| 97 | 0.0317 | 0.1261 |
| 98 | 0.0084 | 0.1239 |
| 99 | 0.0055 | 0.0407 |
| 100 | 0.0012 | 0.0126 |
| 101 | 0.0233 | 0.9143 |
| 102 | 0.0018 | 0.1028 |
| 103 | ~0.0353 | 0.6750 |
| 104 | 0.0183 | 2.8054 |

TABLE 6-continued

FLAP binding and Human Whole Blood assay data

| Cmp No. | FLAP Binding wild type HTRF $K_i$ (μM) | Human Whole Blood LTB4 $IC_{50}$ 1:1 (μM) |
|---|---|---|
| 105 | 0.0394 | |
| 106 | 0.0123 | 0.3759 |
| 107 | 0.0054 | 0.1770 |
| 108 | 0.0281 | 1.3056 |
| 109 | 0.0112 | 0.3075 |
| 110 | 0.0026 | 0.0522 |
| 111 | 0.0024 | 0.0654 |
| 112 | 0.0136 | 0.1812 |
| 113 | 0.0308 | 0.6076 |
| 114 | 0.0102 | 0.3746 |
| 115 | 0.0537 | 1.1064 |
| 116 | 0.0139 | 0.5034 |
| 117 | ~2.4997 | |
| 118 | 0.0105 | 0.0657 |
| 119 | 0.0066 | 0.0274 |
| 120 | ~0.3041 | |
| 121 | 0.0072 | |
| 122 | 0.0037 | 0.4596 |
| 123 | 0.0070 | 4.4771 |
| 124 | 0.0028 | 0.1192 |
| 125 | ~0.2499 | |
| 126 | 0.0107 | 0.4059 |
| 127 | ~2.2003 | |
| 128 | ~0.2973 | |
| 129 | ~0.1192 | 0.2813 |
| 130 | 0.0037 | 0.0214 |
| 131 | 0.0056 | 0.0679 |
| 132 | 0.0170 | 0.1327 |
| 133 | 0.0102 | 0.0796 |
| 134 | 0.0046 | 0.0397 |
| 135 | 0.0013 | 0.0124 |
| 136 | 0.0039 | 0.0566 |
| 137 | 0.0043 | 0.0510 |
| 138 | 0.0053 | 0.0703 |
| 139 | 0.0038 | 0.0485 |
| 140 | 0.0013 | 0.0117 |
| 141 | 0.0055 | 0.0586 |
| 142 | 0.0017 | 0.0185 |
| 143 | 0.0029 | 0.0377 |
| 144 | 0.0011 | 0.0223 |
| 145 | 0.0054 | 0.1774 |
| 146 | 0.0004 | 0.0045 |
| 147 | 0.0064 | 0.1854 |
| 148 | 0.1007 | |
| 149 | 0.0013 | 0.1119 |
| 150 | 0.1764 | 3.5859 |
| 151 | 0.0089 | 0.0754 |
| 152 | 0.0625 | >10 |
| 153 | 0.0023 | 0.4245 |
| 154 | 0.0176 | >10 |
| 155 | 0.0049 | 0.1279 |
| 156 | ~2.2361 | |
| 157 | 0.0206 | 0.1090 |
| 158 | 0.0078 | 0.0359 |
| 159 | 0.0557 | 3.3052 |
| E | 0.0995 | 1.0950 |
| 160 | 0.0947 | 0.4935 |
| 161 | 0.0222 | 0.0880 |
| 162 | 0.0072 | 0.1238 |
| 163 | 0.0704 | 0.4941 |
| 164 | 0.0368 | 0.1185 |
| 165 | 0.0056 | 0.3039 |
| 166 | 0.0117 | 0.1286 |
| 167 | 0.0147 | 0.0456 |
| 168 | 0.0028 | 0.0361 |
| 169 | 0.2053 | 0.2680 |
| 170 | 0.0903 | 1.4256 |
| 171 | 0.0398 | 0.2519 |
| 172 | ~0.3937 | 1.6615 |
| 173 | ~0.6818 | |
| 174 | 0.0039 | 1.2142 |
| 175 | ~0.1 | 1.2835 |
| 176 | ~0.0750 | 1.2960 |
| 177 | ~0.1 | 0.8917 |
| 178 | ~0.0930 | 0.7711 |
| 179 | ~0.3535 | |
| F | ~0.7500 | |
| 180 | ~0.3699 | |
| 181 | 0.0407 | 10.0000 |
| 182 | ~1.9364 | |
| 183 | ~0.3279 | >10 |
| 184 | 0.0140 | 0.8310 |
| 185 | 0.0196 | 1.0074 |
| 186 | 0.0205 | 0.5309 |
| 187 | 0.0120 | 0.3551 |
| 188 | 0.0086 | 1.1036 |
| 189 | 0.0098 | 1.1397 |
| 190 | 0.0472 | 1.0575 |
| 191 | ~0.2499 | 3.4316 |
| 192 | 0.0053 | 0.4184 |
| 193 | 0.0037 | 0.7688 |
| 194 | 0.0029 | 0.1682 |
| 195 | 0.0022 | 0.4457 |
| 196 | 0.0041 | 0.8712 |
| 197 | ~0.7500 | |
| 198 | 0.0187 | 2.3681 |
| 199 | 0.0242 | 1.0566 |
| G | 0.0779 | 0.5748 |
| 200 | 0.1551 | 1.3583 |
| 201 | 0.0085 | 0.0518 |
| 202 | 0.0061 | 0.0805 |
| 203 | 0.0069 | 0.0308 |
| 204 | 0.0085 | 0.1713 |
| 205 | 0.0402 | 0.1496 |
| H | 0.0723 | 0.2866 |
| 206 | 0.7690 | |
| 207 | 0.0515 | 0.0780 |
| 208 | 0.0465 | 0.1605 |
| 209 | 0.0233 | 0.0511 |
| 210 | ~2.4997 | |
| 211 | ~0.5267 | |
| 212 | 0.0640 | 1.0950 |
| 213 | 0.0921 | 1.0146 |
| 214 | 0.0308 | 1.0872 |
| 215 | 0.7049 | |
| 216 | 0.7135 | |
| 217 | 1.0378 | |
| 218 | 0.0773 | >5.00034 |
| 219 | >10 | |
| 220 | 0.0218 | 1.1169 |
| 221 | 0.5932 | |
| 222 | 0.1798 | 3.4754 |
| 223 | >10 | |
| 224 | 0.0232 | 0.2867 |
| 225 | 0.0232 | 0.2867 |
| 226 | 0.0014 | 0.0901 |
| 227 | 0.0085 | 0.3317 |
| 228 | 0.0244 | 0.4804 |
| 229 | 0.0077 | 0.4075 |
| 230 | 0.0025 | 0.2379 |
| 231 | 2.1389 | |
| 232 | 1.5907 | |
| 233 | 1.6792 | |
| 234 | 1.3002 | >10 |
| 235 | 0.0033 | 0.1132 |
| 236 | 0.0022 | 0.0371 |
| 237 | 0.0033 | 0.0847 |
| 238 | 0.1551 | 0.5710 |
| 239 | 0.0083 | 0.1967 |
| 240 | 0.0236 | 0.1045 |
| 241 | 0.0012 | 0.0207 |
| 242 | 0.0036 | 0.0300 |
| I | ~0.0899 | 1.6688 |
| 243 | 0.2355 | 0.8588 |
| 244 | 0.4622 | 1.8168 |
| 245 | 0.0622 | 2.8016 |
| 246 | 0.0986 | 1.5929 |
| 247 | 0.2594 | 0.4173 |
| 248 | 0.2610 | ~10 |
| 249 | 0.2817 | 1.2636 |

TABLE 6-continued

FLAP binding and Human Whole Blood assay data

| Cmp No. | FLAP Binding wild type HTRF $K_i$ (µM) | Human Whole Blood LTB4 $IC_{50}$ 1:1 (µM) |
|---|---|---|
| 250 | 0.0992 | 0.3567 |
| 251 | 1.1951 | |
| 252 | 0.0296 | >1 |
| 253 | 0.8541 | |
| 254 | 0.9922 | |
| 255 | 1.1392 | 1.1387 |
| 256 | 0.4335 | 0.7180 |
| 257 | 0.0311 | 0.3324 |
| 258 | 0.0038 | 0.0101 |
| 259 | 0.0070 | 0.1344 |
| 260 | 0.0199 | 0.1973 |
| 261 | 0.0022 | 0.0401 |
| 262 | 0.0196 | 0.1568 |
| 263 | 0.1375 | 1.9579 |
| 264 | 0.1013 | |
| 265 | >10 | |
| 266 | >10 | |
| 267 | >10 | |
| 268 | >10 | |
| 269 | 0.0009 | 0.0151 |
| 270 | 0.7995 | |
| 271 | 0.0051 | 0.0853 |
| 272 | 0.0005 | 0.0419 |
| 273 | >10 | |
| 274 | 0.0196 | 0.1568 |
| 275 | 0.1375 | 1.9579 |
| 276 | 0.0392 | 1.8557 |
| 277 | 0.0177 | 0.1909 |
| 278 | 0.1001 | 0.2160 |
| 279 | 0.0676 | 0.1141 |
| 280 | >10 | |
| 281 | 0.1006 | 0.4533 |
| 282 | 0.0294 | >10 |
| 283 | 0.0976 | 0.5378 |
| 284 | >10 | |
| 285 | >10 | |
| 286 | 0.0817 | 1.1882 |
| 287 | 0.0176 | >1 |
| 288 | 0.3646 | |
| 289 | 0.2292 | 0.7825 |
| 290 | 0.0399 | 0.5059 |
| 291 | 0.0466 | 0.5761 |
| 292 | 0.0372 | 0.4125 |
| 293 | 0.0165 | 0.1004 |
| 294 | 0.6914 | |
| 295 | 0.0042 | 0.1881 |
| 296 | 0.0068 | 0.2829 |
| 297 | 0.0144 | 0.2125 |
| 298 | 0.8680 | |
| 299 | 1.9566 | |
| 300 | >10 | |
| 301 | >10 | |
| 302 | >10 | |
| 303 | >10 | |
| 304 | >10 | |
| 305 | >10 | |
| 306 | >10 | |
| 307 | >10 | |
| 308 | >10 | |
| 309 | >10 | |
| 310 | >10 | |
| 311 | 0.0081 | 0.2658 |
| 312 | 0.9745 | |
| 313 | 0.0024 | 0.0270 |
| 314 | | >10 |
| 315 | 1.3649 | |
| 316 | 1.3649 | |
| 317 | 0.1979 | 0.4640 |
| 318 | 0.0582 | 0.1041 |
| 319 | 0.3367 | 0.2846 |
| 320 | 0.0365 | 0.1674 |
| 321 | 0.1165 | >10 |
| 322 | 0.5731 | |
| 323 | 0.2107 | 0.1407 |
| 324 | 0.0738 | 0.2601 |
| 325 | 0.0096 | 0.0528 |
| 326 | 0.3584 | |
| 327 | 0.5278 | |
| 328 | 0.1128 | 0.3125 |
| 329 | 0.0097 | 0.0391 |
| 330 | 0.0051 | >1 |
| 331 | 0.0037 | 0.0129 |
| 332 | 0.0459 | 0.4501 |
| 333 | 0.4211 | |
| 334 | 0.0046 | 0.0527 |
| 335 | 0.0036 | 0.0369 |
| 336 | 0.0039 | 0.0238 |
| 337 | 0.0148 | 0.1615 |
| 338 | 0.0017 | 0.0959 |
| 339 | 0.1077 | 1.6376 |
| 340 | 0.6501 | |
| 341 | 0.0226 | 0.1238 |
| 342 | 0.0081 | 0.0263 |
| 343 | 0.0054 | 0.0144 |
| 344 | 0.0269 | 0.0915 |
| 345 | 0.0142 | 0.0151 |
| 346 | 0.0453 | 0.1762 |
| 347 | 0.0476 | 0.3961 |
| 348 | 0.0131 | 0.1467 |
| 349 | 0.0310 | >1 |
| 350 | 0.0529 | 0.4491 |
| 351 | 0.0544 | 0.1242 |

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

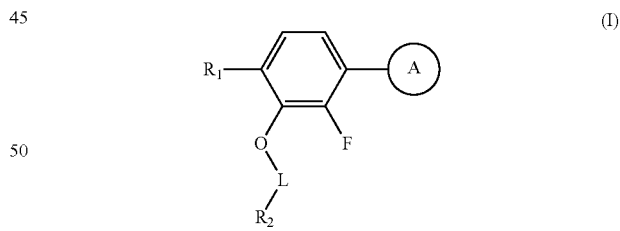

wherein

L is a bond, —$CH_2$—, —$CH_2CH_2$—, —$CH_2CH_2CH_2$—, —$CH_2CH_2NH$—, —$CH_2C(=O)NH$—, —$CH_2C(OH)(H)CH_2$—, or —$CH_2C(OH)(H)CH_2NH$—;

$R_1$ is halo, $C_{1-5}$alkyl, $C_{3-6}$cycloalkyl, or cyclohexylmethyl;

$R_2$ is H, $C_{1-4}$alkyl, hydroxyl, amino, cyano, —$CH_2C(=O)O$-(tert-butyl), —$CH_2C(=O)O$-(ethyl), —$CH_2C(=O)OH$, —$NHS(=O)_2CH_3$, tert-butyl(dimethyl)silyl, —$NHCH_3$, —$N(CH_3)_2$, —NH-(isopropyl), optionally substituted phenyl, optionally substituted 5-membered or 6-membered heteroaryl, $C_{3-6}$cycloalkyl, or optionally substituted heterocyclyl;

wherein the 5-membered or 6-membered heteroaryl, the heterocyclyl, or the phenyl is optionally and independently substituted with 1-4 substituents selected from the group consisting of:

$C_{1-4}$alkyl, —$CH_2$-methoxy, —C(=O)OH, —$CH_2$C(=O)OH, —C(=O)—O—$CH_2CH_3$, —C(=O)—O—$CH_3$, —C(=O)—O-(tert-butyl), —$NH_2$, —N($CH_3$)$_2$, —NH-(isobutyl), —NH($CH_2$)$_2$NHC(=O)—O-tert-butyl, —NH($CH_2$)$_2$NH$_2$, —NH($CH_2$)$_2$N($CH_3$)$_2$, —C(=O)NH$_2$, —C(=O)CH$_3$, oxo, halo, hydroxyl, methoxy, trifluoromethyl, trifluoromethoxy, methoxymethyl, —S(=O)$_2$CH$_3$, —S(=O)$_2$NH$_2$, —S(=O)$_2$NH(CH$_3$), —S(=O)$_2$N(CH$_3$)$_2$, —S—CH$_3$, cyano, 1H-tetrazol-5-yl, thiophen-2-yl, cyclopropyl, azetidin-1-yl, phenyl, 4'-(trifluoromethyl) phenyl, benzyl, 1,5-dioxa-9-azaspiro[5.5]undecan-9-yl, 5-pyrimidinyl-2-amine, and pentafluoro-lambda~6~-sulfanyl;

ring A is selected from the group consisting of:

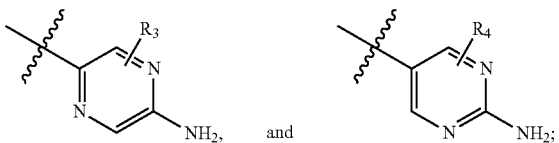

$R_3$ is H, cyano, methyl, methoxy, halo, or —NH$_2$ and $R_4$ is H, or methyl;

or a pharmaceutically acceptable salt thereof.

2. The compound of claim 1, wherein

L is a bond or —CH$_2$—;

$R_1$ is tert-butyl or cyclobutyl;

$R_2$ is optionally substituted phenyl or an optionally substituted 6-membered heteroaryl;

wherein the substitution of the phenyl or the 6-membered heteroaryl is selected from a group consisting of:

hydroxyl, fluoro, methoxy, cyano, amino, —C(=O)—NH$_2$, and pentafluoro-lambda~6~-sulfanyl;

ring A is

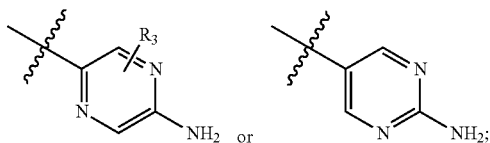

and $R_3$ is H or cyano;

or a pharmaceutically acceptable salt thereof.

3. The compound of claim 2, wherein

L is a bond or —CH$_2$—;

$R_1$ is tert-butyl or cyclobutyl;

$R_2$ is optionally substituted substituted phenyl, optionally substituted pyridine or optionally substituted pyrimidine;

wherein the substitution of the phenyl, the pyridine or the pyrimidine is selected from a group consisting of:

hydroxyl, fluoro, methoxy, cyano, amino, —C(=O)—NH$_2$, and pentafluoro-lambda~6~-sulfanyl; and ring A is

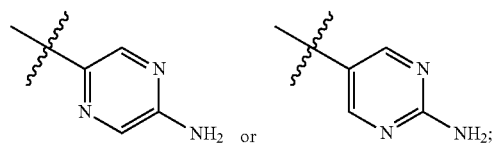 [SMILES: *c1cnc(N)cn1 ; *c1cnc(N)nc1]

or a pharmaceutically acceptable salt thereof.

4. A compound selected from the group consisting of:
5-(4-Cyclobutyl-2-fluoro-3-methoxyphenyl)pyrazin-2-amine,
3-(5-Aminopyrazin-2-yl)-6-cyclobutyl-2-fluorophenol,
5-(4-Cyclobutyl-2-fluoro-3-{[4-(trifluoromethyl)benzyl]oxy}phenyl)pyrazin-2-amine,
5-(4-Cyclobutyl-2-fluoro-3-{[3-(trifluoromethyl)benzyl]oxy}phenyl)pyrazin-2-amine,
5-(4-Cyclobutyl-2-fluoro-3-{[2-(trifluoromethyl)benzyl]oxy}phenyl)pyrazin-2-amine,
3-{[3-(5-Aminopyrazin-2-yl)-6-cyclobutyl-2-fluorophenoxy]methyl}benzoic acid,
4-{[3-(5-Aminopyrazin-2-yl)-6-cyclobutyl-2-fluorophenoxy]methyl}benzoic acid,
5-(4-Cyclobutyl-2-fluoro-3-{[3-(methylsulfonyl)benzyl]oxy}phenyl)pyrazin-2-amine,
5-(4-Cyclobutyl-2-fluoro-3-{[4-(methylsulfonyl)benzyl]oxy}phenyl)pyrazin-2-amine,
5-(4-Cyclobutyl-2-fluoro-3-{[2-(trifluoromethoxy)benzyl]oxy}phenyl)pyrazin-2-amine,
5-(4-Cyclobutyl-2-fluoro-3-{[3-(trifluoromethoxy)benzyl]oxy}phenyl)pyrazin-2-amine,
5-(4-Cyclobutyl-2-fluoro-3-{[4-(trifluoromethoxy)benzyl]oxy}phenyl)pyrazin-2-amine,
5-(3-{[4-Chloro-2-(methylsulfonyl)benzyl]oxy}-4-cyclobutyl-2-fluorophenyl)pyrazin-2-amine,
1-(4-{[3-(5-Aminopyrazin-2-yl)-6-cyclobutyl-2-fluorophenoxy]-methyl}phenyl)-ethanone,
5-[4-Cyclobutyl-2-fluoro-3-(pyridin-3-ylmethoxy)phenyl]pyrazin-2-amine,
5-[4-Cyclobutyl-2-fluoro-3-(pyridin-4-ylmethoxy)phenyl]pyrazin-2-amine,
4-{[3-(5-Aminopyrazin-2-yl)-6-cyclobutyl-2-fluorophenoxy]methyl}benzonitrile,
3-{[3-(5-Aminopyrazin-2-yl)-6-cyclobutyl-2-fluorophenoxy]methyl}benzonitrile,
3-{[3-(5-Aminopyrazin-2-yl)-6-cyclobutyl-2-fluorophenoxy]methyl}benzamide,
2-{[3-(5-Aminopyrazin-2-yl)-6-cyclobutyl-2-fluorophenoxy]methyl}benzonitrile,
2-{[3-(5-Aminopyrazin-2-yl)-6-cyclobutyl-2-fluorophenoxy]methyl}benzamide,
5-(4-Cyclobutyl-2-fluoro-3-{[4-(1H-tetrazol-5-yl)benzyl]oxy}phenyl)pyrazin-2-amine,
5-(4-Cyclobutyl-2-fluoro-3-{[3-(1H-tetrazol-5-yl)benzyl]oxy}phenyl)pyrazin-2-amine,
5-(4-Cyclobutyl-2-fluoro-3-{[2-(1H-tetrazol-5-yl)benzyl]oxy}phenyl)pyrazin-2-amine,
(4-{[3-(5-Aminopyrazin-2-yl)-6-cyclobutyl-2-fluorophenoxy]methyl}phenyl)acetic acid,
5-[4-Cyclobutyl-2-fluoro-3-(pyridin-2-ylmethoxy)phenyl]pyrazin-2-amine,
4-{[3-(5-Aminopyrazin-2-yl)-6-cyclobutyl-2-fluorophenoxy]methyl}-N,N-dimethyl-benzenesulfonamide,
4-{[3-(5-Aminopyrazin-2-yl)-6-cyclobutyl-2-fluorophenoxy]-methyl}-benzenesulfonamide,
4-{[3-(5-Aminopyrazin-2-yl)-6-cyclobutyl-2-fluorophenoxy]methyl}-N-methylbenzenesulfonamide, 5-{4-Cyclobutyl-2-fluoro-3-[(4-fluorobenzyl)oxy]phenyl}pyrazin-2-amine,
5-{4-Cyclobutyl-2-fluoro-3-[(3-fluorobenzyl)oxy]phenyl}pyrazin-2-amine,
5-{4-Cyclobutyl-2-fluoro-3-[(2-fluorobenzyl)oxy]phenyl}pyrazin-2-amine,
5-{4-Cyclobutyl-3-[(2,6-difluorobenzyl)oxy]-2-fluorophenyl}pyrazin-2-amine,
5-{4-Cyclobutyl-3-[(2,3-difluorobenzyl)oxy]-2-fluorophenyl}pyrazin-2-amine,
5-{4-Cyclobutyl-3-[(3,4-difluorobenzyl)oxy]-2-fluorophenyl}pyrazin-2-amine,
5-{3-[(2-Chlorobenzyl)oxy]-4-cyclobutyl-2-fluorophenyl}pyrazin-2-amine,
5-{3-[(3-Chlorobenzyl)oxy]-4-cyclobutyl-2-fluorophenyl}pyrazin-2-amine,
5-{3-[(4-Chlorobenzyl)oxy]-4-cyclobutyl-2-fluorophenyl}pyrazin-2-amine,
5-{4-Cyclobutyl-3-[(2,6-dichlorobenzyl)oxy]-2-fluorophenyl}pyrazin-2-amine,
5-{4-Cyclobutyl-3-[(2,5-dichlorobenzyl)oxy]-2-fluorophenyl}pyrazin-2-amine,
5-{4-Cyclobutyl-3-[(2,3-dichlorobenzyl)oxy]-2-fluorophenyl}pyrazin-2-amine,
5-{4-Cyclobutyl-3-[(2,4-dichlorobenzyl)oxy]-2-fluorophenyl}pyrazin-2-amine,
5-{4-Cyclobutyl-3-[(3,4-dimethylbenzyl)oxy]-2-fluorophenyl}pyrazin-2-amine,
5-(3-{[2-Chloro-3-(trifluoromethyl)benzyl]oxy}-4-cyclobutyl-2-fluorophenyl)pyrazin-2-amine,
5-(3-{[5-Chloro-2-(trifluoromethyl)benzyl]oxy}-4-cyclobutyl-2-fluorophenyl)pyrazin-2-amine,
5-(4-Cyclobutyl-2-fluoro-3-{[4-fluoro-2-(trifluoromethyl)benzyl]oxy}phenyl)pyrazin-2-amine,
5-{3-[(2-Chloro-5-fluorobenzyl)oxy]-4-cyclobutyl-2-fluorophenyl}pyrazin-2-amine,
2-{[3-(5-Aminopyrazin-2-yl)-6-cyclobutyl-2-fluorophenoxy]methyl}benzoic acid,
5-{4-Cyclobutyl-2-fluoro-3-[(1-methyl-1H-pyrazol-3-yl)methoxy]phenyl}pyrazin-2-amine,
5-{4-Cyclobutyl-3-[(3-cyclopropyl-1,2,4-oxadiazol-5-yl)methoxy]-2-fluorophenyl}pyrazin-2-amine,
tert-Butyl [3-(5-aminopyrazin-2-yl)-6-cyclobutyl-2-fluorophenoxy]acetate, [3-(5-Aminopyrazin-2-yl)-6-cyclobutyl-2-fluorophenoxy]acetic acid,
(racemic) 1-(3-(3-(5-Aminopyrazin-2-yl)-6-cyclobutyl-2-fluorophenoxy)-2-hydroxypropyl)pyridin-2(1H)-one,
(racemic) 3-(3-(3-(5-Aminopyrazin-2-yl)-6-cyclobutyl-2-fluorophenoxy)-2-hydroxypropyl)pyrimidin-4(3H)-one,
(racemic) 2-(3-(3-(5-Aminopyrazin-2-yl)-6-cyclobutyl-2-fluorophenoxy)-2-hydroxypropyl)pyridazin-3(2H)-one,
(racemic) 1-(3-(3-(5-Aminopyrazin-2-yl)-6-cyclobutyl-2-fluorophenoxy)-2-hydroxypropyl)pyrazin-2(1H)-one,
(racemic) 1-(3-(5-Aminopyrazin-2-yl)-6-cyclobutyl-2-fluorophenoxy)-3-(pyrimidin-5-ylamino)propan-2-ol,
(racemic) 1-(3-(5-Aminopyrazin-2-yl)-6-cyclobutyl-2-fluorophenoxy)-3-(pyrimidin-2-ylamino)propan-2-ol,
(racemic) 1-(3-(5-Aminopyrazin-2-yl)-6-cyclobutyl-2-fluorophenoxy)-3-(pyrazin-2-ylamino)propan-2-ol,
(racemic) 1-(3-(5-Aminopyrazin-2-yl)-6-cyclobutyl-2-fluorophenoxy)-3-((5-aminopyrimidin-2-yl)amino)propan-2-ol,
(racemic) 1-(3-(5-Aminopyrazin-2-yl)-6-cyclobutyl-2-fluorophenoxy)-3-((6-aminopyrimidin-4-yl)amino)propan-2-ol,
(racemic) 1-(3-(5-Aminopyrazin-2-yl)-6-cyclobutyl-2-fluorophenoxy)-3-(1H-pyrazol-1-yl)propan-2-ol,
(racemic) 1-(3-(5-Aminopyrazin-2-yl)-6-cyclobutyl-2-fluorophenoxy)-3-(1H-imidazol-1-yl)propan-2-ol,
(racemic) 1-(3-(5-Aminopyrazin-2-yl)-6-cyclobutyl-2-fluorophenoxy)-3-(1H-1,2,4-triazol-1-yl)propan-2-ol,
(racemic) 1-(3-(5-Aminopyrazin-2-yl)-6-cyclobutyl-2-fluorophenoxy)-3-(1H-1,2,3-triazol-1-yl)propan-2-ol,
(racemic) 1-(3-(5-Aminopyrazin-2-yl)-6-cyclobutyl-2-fluorophenoxy)-3-(2H-1,2,3-triazol-2-yl)propan-2-ol,
(racemic) 5-Amino-1-(3-(3-(5-Aminopyrazin-2-yl)-6-cyclobutyl-2-fluorophenoxy)-2-hydroxypropyl)-1H-pyrazole-4-carbonitrile,
(racemic) 1-(5-Amino-1H-1,2,3-triazol-1-yl)-3-(3-(5-aminopyrazin-2-yl)-6-cyclobutyl-2-fluorophenoxy)propan-2-ol,
(racemic) 1-((1H-Pyrazol-5-yl)amino)-3-(3-(5-aminopyrazin-2-yl)-6-cyclobutyl-2-fluorophenoxy)propan-2-ol,
5-(4-Cyclobutyl-2-fluoro-3-{[1-(methylsulfonyl)piperidin-4-yl]methoxy}-phenyl)-pyrazin-2-amine,
5-{4-Cyclobutyl-2-fluoro-3-[(4-methylpyrimidin-2-yl)oxy]-phenyl}pyrazin-2-amine,
5-{4-Cyclobutyl-2-fluoro-3-[(5-methyl-1,2,4-oxadiazol-3-yl)methoxy]phenyl}pyrazin-2-amine,
5-[4-Cyclobutyl-3-(cyclohexylmethoxy)-2-fluorophenyl]pyrazin-2-amine,
5-[4-Cyclobutyl-3-(cyclopropylmethoxy)-2-fluorophenyl]pyrazin-2-amine,
Ethyl 5-{[3-(5-aminopyrazin-2-yl)-6-cyclobutyl-2-fluorophenoxy]methyl}furan-2-carboxylate,
tert-Butyl 4-{[3-(5-aminopyrazin-2-yl)-6-cyclobutyl-2-fluorophenoxy]-methyl}-piperidine-1-carboxylate,
5-{4-Cyclobutyl-2-fluoro-3-[(3-methyl-1,2,4-oxadiazol-5-yl)-methoxy]-phenyl}-pyrazin-2-amine,
5-(4-Cyclobutyl-2-fluoro-3-{[2-methoxy-5-(pentafluoro-lambda~6~-sulfanyl)-benzyl]-oxy}phenyl)pyrazin-2-amine,
5-(4-Cyclobutyl-2-fluoro-3-{[2-fluoro-5-(pentafluoro-lambda~6~-sulfanyl)benzyl]-Oxy}phenyl)pyrazin-2-amine,
5-(4-Cyclobutyl-2-fluoro-3-{[2-fluoro-4-(pentafluoro-lambda~6~-sulfanyl)benzyl]-oxy}phenyl)pyrazin-2-amine,
5-(4-Cyclobutyl-2-fluoro-3-{[4-(pentafluoro-lambda~6~-sulfanyl)benzyl]-oxy}-phenyl)pyrazin-2-amine,
5-(4-Cyclobutyl-2-fluoro-3-{[3-(pentafluoro-lambda~6~-sulfanyl)benzyl]-oxy}-phenyl)pyrazin-2-amine,
5-(4-Cyclobutyl-2-fluoro-3-{[2-(pentafluoro-lambda~6~-sulfanyl)benzyl]-oxy}-phenyl)-pyrazin-2-amine,
5-[4-Cyclobutyl-3-(cyclobutylmethoxy)-2-fluorophenyl]pyrazin-2-amine,
5-[3-(Benzyloxy)-4-cyclobutyl-2-fluorophenyl]pyrazin-2-amine,
4-{2-[3-(5-Aminopyrazin-2-yl)-6-cyclobutyl-2-fluorophenoxy]ethyl}benzoic acid,
5-{[3-(5-Aminopyrazin-2-yl)-6-cyclobutyl-2-fluorophenoxy]methyl}furan-2-carboxylic acid,
2-[3-(5-Aminopyrazin-2-yl)-6-cyclobutyl-2-fluorophenoxy]-6-methylpyrimidin-4-amine,
5-{4-Cyclobutyl-2-fluoro-3-[(4-phenylpyrimidin-2-yl)oxy]phenyl}pyrazin-2-amine,
5-(4-Cyclobutyl-2-fluoro-3-{[4-(methylsulfanyl)pyrimidin-2-yl]oxy}phenyl)pyrazin-2-amine, 5-{4-Cyclobutyl-3-[(4,6-dimethylpyrimidin-2-yl)oxy]-2-fluorophenyl}pyrazin-2-amine,
5-(4-Cyclobutyl-2-fluoro-3-{[4-(1-methylethyl)pyrimidin-2-yl]oxy}phenyl)pyrazin-2-amine,
5-{4-Cyclobutyl-2-fluoro-3-[(4-thiophen-2-ylpyrimidin-2-yl)oxy]phenyl}pyrazin-2-amine,
2-[3-(5-Aminopyrazin-2-yl)-6-cyclobutyl-2-fluorophenoxy]pyrimidine-4-carbonitrile,
5-{4-Cyclobutyl-2-fluoro-3-[(4-methoxypyrimidin-2-yl)oxy]phenyl}pyrazin-2-amine,
5-{4-Cyclobutyl-2-fluoro-3-[(5-methoxypyrimidin-2-yl)oxy]phenyl}pyrazin-2-amine,
5-(4-Cyclobutyl-2-fluoro-3-{[4-(methylsulfonyl)pyrimidin-2-yl]oxy}phenyl)pyrazin-2-amine,
4-[3-(5-Aminopyrazin-2-yl)-6-cyclobutyl-2-fluorophenoxy]-6-methylpyrimidin-2-amine,
5-{4-Cyclobutyl-2-fluoro-3-[(6-methoxypyrimidin-4-yl)oxy]phenyl}pyrazin-2-amine,
6-[3-(5-Aminopyrazin-2-yl)-6-cyclobutyl-2-fluorophenoxy]pyrimidin-4-ol,
4-[3-(5-Aminopyrazin-2-yl)-6-cyclobutyl-2-fluorophenoxy]-6-methoxypyrimidin-2-amine,
6-[3-(5-Aminopyrazin-2-yl)-6-cyclobutyl-2-fluorophenoxy]-2-methoxypyrimidin-4-amine,
4-[3-(5-Aminopyrazin-2-yl)-6-cyclobutyl-2-fluorophenoxy]benzonitrile,
5-(4-Cyclobutyl-2-fluoro-3-{[6-(trifluoromethyl)pyridin-2-yl]oxy}phenyl)pyrazin-2-amine,
Methyl 4-[3-(5-aminopyrazin-2-yl)-6-cyclobutyl-2-fluorophenoxy]benzoate,
5-(4-Cyclobutyl-2-fluoro-3-{[5-(trifluoromethyl)pyrimidin-2-yl]oxy}phenyl)pyrazin-2-amine,
5-(4-Cyclobutyl-2-fluoro-3-{[5-(trifluoromethyl)pyrazin-2-yl]oxy}phenyl)pyrazin-2-amine,
5-(4-Cyclobutyl-2-fluoro-3-{[6-(trifluoromethyl)pyridazin-3-yl]oxy}phenyl)pyrazin-2-amine,
Methyl 6-[3-(5-aminopyrazin-2-yl)-6-cyclobutyl-2-fluorophenoxy]pyridine-3-carboxylate,
5-[3-(5-Aminopyrazin-2-yl)-6-cyclobutyl-2-fluorophenoxy]pyridine-2-carbonitrile,
4-[3-(5-Aminopyrazin-2-yl)-6-cyclobutyl-2-fluorophenoxy]pyridine-2-carbonitrile,
2-[3-(5-Aminopyrazin-2-yl)-6-cyclobutyl-2-fluorophenoxy]pyridine-3-carbonitrile,
6-[3-(5-Aminopyrazin-2-yl)-6-cyclobutyl-2-fluorophenoxy]pyridine-2-carbonitrile,
3-[3-(5-Aminopyrazin-2-yl)-6-cyclobutyl-2-fluorophenoxy]pyridine-2-carbonitrile,
5-(4-Cyclobutyl-2-fluoro-3-{[5-(trifluoromethyl)pyridin-2-yl]oxy}phenyl)pyrazin-2-amine,
6-[3-(5-Aminopyrazin-2-yl)-6-cyclobutyl-2-fluorophenoxy]pyridine-3-carbonitrile,
5-{4-Cyclobutyl-2-fluoro-3-[4-(pentafluoro-lambda~6~-sulfanyl)phenoxy]-phenyl}-pyrazin-2-amine,
5-{4-Cyclobutyl-2-fluoro-3-[4-(methylsulfonyl)phenoxy]phenyl}pyrazin-2-amine,
5-{4-Cyclobutyl-2-fluoro-3-[2-(methylsulfonyl)phenoxy]phenyl}pyrazin-2-amine,
5-[4-Cyclobutyl-2-fluoro-3-(pyrimidin-2-yloxy)phenyl]pyrazin-2-amine,
2-[3-(5-Aminopyrazin-2-yl)-6-cyclobutyl-2-fluorophenoxy]pyrimidin-4-amine,
5-{3-[3,4-Bis(trifluoromethyl)phenoxy]-4-cyclobutyl-2-fluorophenyl}pyrazin-2-amine,
5-(4-Cyclobutyl-2-fluoro-3-{[3-(trifluoromethyl)pyridin-2-yl]oxy}phenyl)pyrazin-2-amine,
5-{3-[(3-Chloropyridin-2-yl)oxy]-4-cyclobutyl-2-fluorophenyl}pyrazin-2-amine,
5-{3-[2-Chloro-4-(methylsulfonyl)phenoxy]-4-cyclobutyl-2-fluorophenyl}pyrazin-2-amine,
5-(4-Cyclobutyl-2-fluoro-3-{[2-(trifluoromethyl)pyrimidin-4-yl]oxy}phenyl)pyrazin-2-amine,
5-(4-Cyclobutyl-2-fluoro-3-{[6-(trifluoromethyl)pyrimidin-4-yl]oxy}phenyl)pyrazin-2-amine,
5-{4-Cyclobutyl-2-fluoro-3-[3-methyl-4-(methylsulfonyl)phenoxy]phenyl}pyrazin-2-amine,
5-(4-cyclobutyl-2-fluoro-3-(4-(methylsulfonyl)-2-(trifluoromethyl)phenoxy)-phenyl)-pyrazin-2-amine,
5-(4-Cyclobutyl-2-fluoro-3-{[6-(trifluoromethyl)pyridin-3-yl]oxy}phenyl)pyrazin-2-amine,
5-{4-Cyclobutyl-2-fluoro-3-[(3-methoxypyridin-2-yl)oxy]phenyl}pyrazin-2-amine,
4-[3-(5-Aminopyrazin-2-yl)-6-cyclobutyl-2-fluorophenoxy]pyrimidin-2-amine,
5-(4-Cyclobutyl-2-fluoro-3-{[4-(trifluoromethyl)pyrimidin-2-yl]oxy}phenyl)pyrazin-2-amine,
2-[3-(5-Aminopyrazin-2-yl)-6-cyclobutyl-2-fluorophenoxy]-5-(methylsulfonyl)-benzonitrile,
5-{4-Cyclobutyl-2-fluoro-3-[4-(methylsulfonyl)-3-(trifluoromethyl)-phenoxy]-phenyl}-pyrazin-2-amine,
5-{4-Cyclobutyl-2-fluoro-3-[(2-methylpyrimidin-4-yl)oxy]phenyl}pyrazin-2-amine,
5-(4-Cyclobutyl-2-fluoro-3-{[2-(1-methylethyl)pyrimidin-4-yl]oxy}phenyl)pyrazin-2-amine,
6-[3-(5-Aminopyrazin-2-yl)-6-cyclobutyl-2-fluorophenoxy]pyrimidin-4-amine,
5-{3-[(2-Chloropyrimidin-4-yl)oxy]-4-cyclobutyl-2-fluorophenyl}pyrazin-2-amine,
5-{3-[(6-Azetidin-1-ylpyrimidin-4-yl)oxy]-4-cyclobutyl-2-fluorophenyl}pyrazin-2-amine,
6-[3-(5-Aminopyrazin-2-yl)-6-cyclobutyl-2-fluorophenoxy]-N,N-dimethyl-2-(trifluoromethyl)pyrimidin-4-amine,
6-[3-(5-Aminopyrazin-2-yl)-6-cyclobutyl-2-fluorophenoxy]-2-methylpyrimidin-4-amine,
5-{4-Cyclobutyl-3-[(6-cyclopropylpyrimidin-4-yl)oxy]-2-fluorophenyl}pyrazin-2-amine,
4-[3-(5-Aminopyrazin-2-yl)-6-cyclobutyl-2-fluorophenoxy]-6-(methoxymethyl)pyrimidin-2-amine,
4-[3-(5-Aminopyrazin-2-yl)-6-cyclobutyl-2-fluorophenoxy]-6-chloropyrimidin-2-amine,
5-{4-Cyclobutyl-2-fluoro-3-[(2-phenylpyrimidin-4-yl)oxy]phenyl}pyrazin-2-amine,
5-{4-Cyclobutyl-2-fluoro-3-[(6-phenylpyrimidin-4-yl)oxy]phenyl}pyrazin-2-amine,
6-[3-(5-Aminopyrazin-2-yl)-6-cyclobutyl-2-fluorophenoxy]-2-benzylpyrimidin-4-amine,
5-(4-Cyclobutyl-2-fluoro-3-{[6-(1-methylethyl)pyrimidin-4-yl]oxy}phenyl)pyrazin-2-amine,
3-[3-(5-Aminopyrazin-2-yl)-6-cyclobutyl-2-fluorophenoxy]-1-methyl-5-(trifluoromethyl)-1H-pyrazole-4-carbonitrile,
tert-Butyl [2-({2-[3-(5-aminopyrazin-2-yl)-6-cyclobutyl-2-fluorophenoxy]pyrimidin-4-yl}amino)ethyl]carbamate,
N-{4-[3-(5-Aminopyrazin-2-yl)-6-cyclobutyl-2-fluorophenoxy]pyrimidin-2-yl}ethane-1,2-diamine,
Methyl 2-[3-(5-aminopyrazin-2-yl)-6-cyclobutyl-2-fluorophenoxy]pyrimidine-4-carboxylate,
2-[3-(5-Aminopyrazin-2-yl)-6-cyclobutyl-2-fluorophenoxy]pyrimidine-4-carboxylic acid,
4-[3-(5-Aminopyrazin-2-yl)-6-cyclobutyl-2-fluorophenoxy]benzoic acid, 6-[3-(5-Aminopyrazin-2-yl)-6-cyclobutyl-2-fluorophenoxy]pyridine-3-carboxylic acid,
4-[3-(5-Aminopyrazin-2-yl)-6-cyclobutyl-2-fluorophenoxy]benzamide,
N'-{4-[3-(5-Aminopyrazin-2-yl)-6-cyclobutyl-2-fluorophenoxy]pyrimidin-2-yl}-N,N-dimethylethane-1,2-diamine,
2-[3-(5-Aminopyrazin-2-yl)-6-cyclobutyl-2-fluorophenoxy]pyrimidine-4-carboxamide,
2-[3-(5-Aminopyrazin-2-yl)-6-cyclobutyl-2-fluorophenoxy]pyrimidin-5-amine,
5-(4-Cyclobutyl-2-fluoro-3-methoxyphenyl)pyrimidin-2-amine,
3-(2-Aminopyrimidin-5-yl)-6-cyclobutyl-2-fluorophenol,
5-[4-Cyclobutyl-2-fluoro-3-(pyrimidin-2-yloxy)phenyl]pyrimidin-2-amine,
5-{3-[(4-Aminopyrimidin-2-yl)oxy]-4-cyclobutyl-2-fluorophenyl}pyrimidin-2-amine,
4-[3-(2-Aminopyrimidin-5-yl)-6-cyclobutyl-2-fluorophenoxy]-6-(methoxymethyl)pyrimidin-2-amine,
5-{4-Cyclobutyl-2-fluoro-3-[(4-methylpyrimidin-2-yl)oxy]phenyl}pyrimidin-2-amine,
5-{3-[(6-Aminopyrimidin-4-yl)oxy]-4-cyclobutyl-2-fluorophenyl}pyrimidin-2-amine,
5-(4-Cyclobutyl-2-fluoro-3-{[4-(1-methylethyl)pyrimidin-2-yl]oxy}phenyl)pyrimidin-2-amine,
4-[3-(2-Aminopyrimidin-5-yl)-6-cyclobutyl-2-fluorophenoxy]pyrimidin-2-amine,
5-{4-Cyclobutyl-3-[(4,6-dimethylpyrimidin-2-yl)oxy]-2-fluorophenyl}pyrimidin-2-amine,
4-(3-(2-Aminopyrimidin-5-yl)-6-cyclobutyl-2-fluorophenoxy)-6-isopropylpyrimidin-2-amine,
2-[3-(2-Aminopyrimidin-5-yl)-6-cyclobutyl-2-fluorophenoxy]pyrimidine-4-carboxamide,
5-(4-cyclobutyl-2-fluoro-3-((6-methoxypyrimidin-4-yl)oxy)phenyl)pyrimidin-2-amine,
6-[3-(2-Aminopyrimidin-5-yl)-6-cyclobutyl-2-fluorophenoxy]pyrimidin-4-ol,
6-Amino-3-(4-cyclobutyl-2-fluoro-3-methoxyphenyl)pyrazine-2-carbonitrile,
6-Amino-3-(4-cyclobutyl-2-fluoro-3-hydroxyphenyl)pyrazine-2-carbonitrile,
3-{[3-(5-Amino-3-cyanopyrazin-2-yl)-6-cyclobutyl-2-fluorophenoxy]methyl}benzoic acid,
2-(4-Cyclobutyl-2-fluoro-3-methoxyphenyl)-5H-pyrrolo[2,3-b]pyrazine,
6-Cyclobutyl-2-fluoro-3-(5H-pyrrolo[2,3-b]pyrazin-2-yl)phenol,
2-(4-Cyclobutyl-2-fluoro-3-{[4-(trifluoromethyl)benzyl]oxy}phenyl)-5H-pyrrolo[2,3-b]pyrazine,
2-[3-(Benzyloxy)-4-cyclobutyl-2-fluorophenyl]-5H-pyrrolo[2,3-b]pyrazine,
5-(4-cyclobutyl-2-fluoro-3methoxyphenyl)-1H-imidazo[4,5-b]pyrazine,
3-(5-Aminopyrazin-2-yl)-6-tert-butyl-2-fluorophenol,
5-(4-tert-Butyl-3-{[tert-butyl(dimethyl)silyl]oxy}-2-fluorophenyl)pyrazin-2-amine,
5-[4-tert-Butyl-2-fluoro-3-(pyrimidin-2-yloxy)phenyl]pyrazin-2-amine,
6-[3-(5-Aminopyrazin-2-yl)-6-tert-butyl-2-fluorophenoxy]pyrimidin-4-amine,
2-[3-(5-Aminopyrazin-2-yl)-6-tert-butyl-2-fluorophenoxy]pyrimidin-4-amine,
5-{4-tert-Butyl-2-fluoro-3-[(6-methoxypyrimidin-4-yl)oxy]phenyl}pyrimidin-2-amine,
5-(4-tert-Butyl-2-fluoro-3-methoxyphenyl)pyrazin-2-amine,
3-(2-Aminopyrimidin-5-yl)-6-tert-butyl-2-fluorophenol,
5-(4-tert-Butyl-3-{[tert-butyl(dimethyl)silyl]oxy}-2-fluorophenyl)pyrimidin-2-amine,
5-[4-tert-Butyl-2-fluoro-3-(pyrimidin-2-yloxy)phenyl]pyrimidin-2-amine,
5-{3-[(6-Aminopyrimidin-4-yl)oxy]-4-tert-butyl-2-fluorophenyl}pyrimidin-2-amine,
5-{3-[(4-Aminopyrimidin-2-yl)oxy]-4-tert-butyl-2-fluorophenyl}pyrimidin-2-amine,
5-(4-Bromo-2-fluoro-3-methoxyphenyl)pyrazin-2-amine,
5-(4-Cyclopentyl-2-fluoro-3-methoxyphenyl)pyrazin-2-amine,
5-[3-(Benzyloxy)-4-cyclopentyl-2-fluorophenyl]pyrazin-2-amine,
5-[4-Cyclopentyl-2-fluoro-3-(1-methylethoxy)phenyl]pyrazin-2-amine,
2-[3-(Benzyloxy)-4-cyclopentyl-2-fluorophenyl]-5H-pyrrolo[2,3-b]pyrazine,
3-Amino-6-(4-cyclobutyl-2-fluoro-3-methoxyphenyl)pyrazine-2-carbonitrile,
3-Amino-6-(4-cyclobutyl-2-fluoro-3-hydroxyphenyl)pyrazine-2-carbonitrile,
2-(4-Cyclobutyl-2-fluoro-3-((6-methoxypyrimidin-4-yl)oxy)phenyl)-5H-pyrrolo[2,3-b]pyrazine,
2-(4-Cyclobutyl-2-fluoro-3-(pyrimidin-2-yloxy)phenyl)-5H-pyrrolo[2,3-b]pyrazine,
4-(3-(5-Aminopyrazin-2-yl)-6-cyclobutyl-2-fluorophenoxy)pyrimidine-2-carbonitrile,
6-(3-(5-Aminopyrazin-2-yl)-6-cyclobutyl-2-fluorophenoxy)-N,N,2-trimethylpyrimidin-4-amine,
4-(3-(5-Aminopyrazin-2-yl)-6-cyclobutyl-2-fluorophenoxy)-N,N,6-trimethylpyrimidin-2-amine,
6-(3-(5-Aminopyrazin-2-yl)-6-cyclobutyl-2-fluorophenoxy)-N,N-dimethylpyrimidin-4-amine,
Ethyl 5-(3-(5-aminopyrazin-2-yl)-6-cyclobutyl-2-fluorophenoxy)-1-methyl-3-(trifluoromethyl)-1H-pyrazole-4-carboxylate,
5-(4-Cyclobutyl-2-fluoro-3-((5-(methylsulfonyl)pyridin-2-yl)oxy)phenyl)pyrazin-2-amine,
4-(3-(5-Aminopyrazin-2-yl)-6-cyclobutyl-2-fluorophenoxy)-6-(tert-butyl)pyrimidin-2-amine,
5-(3-((4-(1,5-Dioxa-9-azaspiro[5.5]undecan-9-yl)pyrimidin-2-yl)oxy)-4-cyclobutyl-2-fluorophenyl)pyrazin-2-amine,
4-(3-(5-Aminopyrazin-2-yl)-6-cyclobutyl-2-fluorophenoxy)-6-isobutylpyrimidin-2-amine,
N-(2-(3-(5-Aminopyrazin-2-yl)-6-cyclobutyl-2-fluorophenoxy)-ethyl)-methane-sulfonamide, 5-(4-Cyclobutyl-2-fluoro-3-(2-morpholinoethoxy)phenyl)pyrazin-2-amine,
Ethyl 4-(3-(5-Aminopyrazin-2-yl)-6-cyclobutyl-2-fluorophenoxy)butanoate,
tert-Butyl 3-((3-(5-aminopyrazin-2-yl)-6-cyclobutyl-2-fluorophenoxy)methyl)-azetidine-1-carboxylate,
tert-Butyl 3-((3-(5-aminopyrazin-2-yl)-6-cyclobutyl-2-fluorophenoxy)methyl)-pyrrolidine-1-carboxylate,
tert-Butyl 2-((3-(5-aminopyrazin-2-yl)-6-cyclobutyl-2-fluorophenoxy)methyl)-pyrrolidine-1-carboxylate,
tert-Butyl 3-((3-(5-aminopyrazin-2-yl)-6-cyclobutyl-2-fluorophenoxy)-methyl)-piperidine-1-carboxylate,
2-(3-(5-Aminopyrazin-2-yl)-6-cyclobutyl-2-fluorophenoxy)ethanol,
4-(3-(5-Aminopyrazin-2-yl)-6-cyclobutyl-2-fluorophenoxy)butanoic acid,
5-(4-Cyclobutyl-2-fluoro-3-((tetrahydrofuran-2-yl)methoxy)phenyl)pyrazin-2-amine, (racemic) 1-(3-(5-Aminopyrazin-2-yl)-6-cyclobutyl-2-fluorophenoxy)-3-(isobutylamino)-propan-2-ol,
(racemic) 3-(3-(5-Aminopyrazin-2-yl)-6-cyclobutyl-2-fluorophenoxy)propane-1,2-diol,
(racemic) 1-(3-(5-Aminopyrazin-2-yl)-6-cyclobutyl-2-fluorophenoxy)-3-morpholinopropan-2-ol,
(racemic) 4-(3-(3-(5-Aminopyrazin-2-yl)-6-cyclobutyl-2-fluorophenoxy)-2-hydroxypropyl)-thiomorpholine 1,1-dioxide,
5-(4-Cyclobutyl-2-fluoro-3-(pyridazin-4-yloxy)phenyl)pyrazin-2-amine,
3-(3-(5-Aminopyrazin-2-yl)-6-cyclobutyl-2-fluorophenoxy)pyrazin-2-amine,
5-(4-Cyclobutyl-2-fluoro-3-(pyrazin-2-yloxy)phenyl)pyrazin-2-amine,
5-(4-Cyclobutyl-2-fluoro-3-(pyrimidin-4-yloxy)phenyl)pyrazin-2-amine,
4-(3-(5-Aminopyrazin-2-yl)-6-cyclobutyl-2-fluorophenoxy)-N-isobutylpyrimidin-2-amine,
Methyl 3-({[3-(5-aminopyrazin-2-yl)-6-cyclobutyl-2-fluorophenoxy]acetyl}amino)-4-hydroxybenzoate,
5-[4-Cyclobutyl-2-fluoro-3-(tetrahydro-2H-pyran-4-ylmethoxy)phenyl]pyrazin-2-amine,
4-[3-(5-Aminopyrazin-2-yl)-6-cyclobutyl-2-fluorophenoxy]-3-(methylsulfonyl)benzonitrile,
5-{3-[2,4-Bis(trifluoromethyl)phenoxy]-4-cyclobutyl-2-fluorophenyl}pyrazin-2-amine,
5-{4-Cyclobutyl-3-[3-(dimethylamino)propoxy]-2-fluorophenyl}pyrazin-2-amine,
5-{4-Cyclobutyl-3-[2-(dimethylamino)ethoxy]-2-fluorophenyl}pyrazin-2-amine,
2-Amino-5-[3-(5-aminopyrazin-2-yl)-6-cyclobutyl-2-fluorophenoxy]pyrimidine-4-carbonitrile,
Methyl 3-({[3-(5-aminopyrazin-2-yl)-6-cyclobutyl-2-fluorophenoxy]acetyl}amino)-4-hydroxybenzoate,
[3-(5-Aminopyrazin-2-yl)-6-cyclobutyl-2-fluorophenoxy]acetonitrile,
5-[4-Cyclobutyl-2-fluoro-3-(pyridazin-3-yloxy)phenyl]pyrazin-2-amine,
5-[4-Cyclopropyl-2-fluoro-3-(pyrimidin-2-yloxy)phenyl]pyrazin-2-amine,
2-[3-(5-Aminopyrazin-2-yl)-6-cyclopropyl-2-fluorophenoxy]pyrimidin-4-amine,
5-{4-Cyclobutyl-2-fluoro-3-[(1-methyl-1H-imidazol-2-yl)methoxy]phenyl}pyrazin-2-amine,
Methyl 2-{[3-(5-aminopyrazin-2-yl)-6-cyclobutyl-2-fluorophenoxy]methyl}-1,3-oxazole-4-carboxylate,
2-{[3-(5-Aminopyrazin-2-yl)-6-cyclobutyl-2-fluorophenoxy]methyl}-1,3-oxazole-4-carboxylic acid,
5-{4-Cyclobutyl-2-fluoro-3-[(1-methyl-1H-imidazol-4-yl)methoxy]phenyl}pyrazin-2-amine,
5-{4-Cyclobutyl-2-fluoro-3-[(1-methyl-1H-imidazol-5-yl)methoxy]phenyl}pyrazin-2-amine,
2-{[3-(5-Aminopyrazin-2-yl)-6-cyclobutyl-2-fluorophenoxy]methyl}pyridine-3-carbonitrile,
5-{4-Cyclobutyl-2-fluoro-3-[(2-methyl-1,3-thiazol-4-yl)methoxy]phenyl}pyrazin-2-amine,
5-[4-Cyclobutyl-2-fluoro-3-(pyridazin-3-ylmethoxy)phenyl]pyrazin-2-amine,
5-{3-[(5-Chloropyridin-2-yl)methoxy]-4-cyclobutyl-2-fluorophenyl}pyrazin-2-amine,
5-{[3-(5-Aminopyrazin-2-yl)-6-cyclobutyl-2-fluorophenoxy]methyl}pyridine-2-carbonitrile,
5-{4-Cyclobutyl-2-fluoro-3-[(5-methylisoxazol-3-yl)methoxy]phenyl}pyrazin-2-amine,
6-{[3-(5-Aminopyrazin-2-yl)-6-cyclobutyl-2-fluorophenoxy]methyl}pyridine-2-carbonitrile, 5-[3-(2-Aminoethoxy)-4-cyclobutyl-2-fluorophenyl]pyrazin-2-amine,
5-{4-Cyclobutyl-2-fluoro-3[2-(pyrazin-2-ylamino)ethoxy]phenyl}pyrazin-2-amine,
N-{2-[3-(5-Aminopyrazin-2-yl)-6-cyclobutyl-2-fluorophenoxy]ethyl}pyrimidin-2-amine,
N-{2-[3-(5-Aminopyrazin-2-yl)-6-cyclobutyl-2-fluorophenoxy]ethyl}pyrimidin-4-amine,
5-[4-Cyclobutyl-2-fluoro-3-(piperidin-4-ylmethoxy)phenyl]pyrazin-2-amine,
(racemic) 5-[4-Cyclobutyl-2-fluoro-3-(piperidin-3-ylmethoxy)phenyl]pyrazin-2-amine,
(racemic) 5-[4-Cyclobutyl-2-fluoro-3-(pyrrolidin-3-ylmethoxy)phenyl]pyrazin-2-amine,
5-[3-(Azetidin-3-ylmethoxy)-4-cyclobutyl-2-fluorophenyl]pyrazin-2-amine,
(racemic) 5-[4-Cyclobutyl-2-fluoro-3-(pyrrolidin-2-ylmethoxy)phenyl]pyrazin-2-amine,
(racemic) 5 1-[3-(5-Aminopyrazin-2-yl)-6-cyclobutyl-2-fluorophenoxy]-3-piperidin-1-ylpropan-2-ol,
(racemic) 1-[3-(5-Aminopyrazin-2-yl)-6-cyclobutyl-2-fluorophenoxy]-3-(methylamino)propan-2-ol,
(racemic) 1-[3-(5-Aminopyrazin-2-yl)-6-cyclobutyl-2-fluorophenoxy]-3-[(1-methylethyl)amino]propan-2-ol,
(racemic) 1-[3-(5-Aminopyrazin-2-yl)-6-cyclobutyl-2-fluorophenoxy]-3-pyrrolidin-1-ylpropan-2-ol,
(racemic) 1-[3-(5-Aminopyrazin-2-yl)-6-cyclobutyl-2-fluorophenoxy]-3-(dimethylamino)propan-2-ol,
(diastereomeric mixture) 1-{3-[3-(5-Aminopyrazin-2-yl)-6-cyclobutyl-2-fluorophenoxy]-2-hydroxypropyl}pyrrolidin-3-ol,
(racemic) 1-[3-(5-Aminopyrazin-2-yl)-6-cyclobutyl-2-fluorophenoxy]-3-piperazin-1-ylpropan-2-ol,
(racemic) 1-{3-[3-(5-Aminopyrazin-2-yl)-6-cyclobutyl-2-fluorophenoxy]-2-hydroxypropyl}pyrimidin-2(1H)-one,
(racemic) 1-{3-[3-(5-Aminopyrazin-2-yl)-6-cyclobutyl-2-fluorophenoxy]-2-hydroxypropyl}imidazolidin-2-one,
2'-[3-(5-Aminopyrazin-2-yl)-6-cyclobutyl-2-fluorophenoxy]-5,5'-bipyrimidin-2-amine,
5-[2-Fluoro-4-methyl-3-(pyrimidin-2-yloxy)phenyl]pyrazin-2-amine,
2-[3-(5-Aminopyrazin-2-yl)-2-fluoro-6-methylphenoxy]pyrimidin-4-amine,
5-[4-Ethyl-2-fluoro-3-(pyrimidin-2-yloxy)phenyl]pyrazin-2-amine,
2-[3-(5-Aminopyrazin-2-yl)-6-ethyl-2-fluorophenoxy]pyrimidin-4-amine,
5[2-Fluoro-4-(1-methylethyl)-3-(pyrimidin-2-yloxy)phenyl]pyrazin-2-amine,
5[2-Fluoro-4-propyl-3-(pyrimidin-2-yloxy)phenyl]pyrazin-2-amine,
5-(4-Cyclohexyl-2-fluoro-3-(pyrimidin-2-yloxy)phenyl)pyrazin-2-amine,
5-(4-(Cyclohexylmethyl)-2-fluoro-3-(pyrimidin-2-yloxy)phenyl)pyrazin-2-amine,
5-(2-Fluoro-4-isopentyl-3-(pyrimidin-2-yloxy)phenyl)pyrazin-2-amine,
5-(2-Fluoro-4-isobutyl-3-(pyrimidin-2-yloxy)phenyl)pyrazin-2-amine,
5-(2-Fluoro-4-neopentyl-3-(pyrimidin-2-yloxy)phenyl)pyrazin-2-amine,
2-(3-(5-Aminopyrazin-2-yl)-6-cyclohexyl-2-fluorophenoxy)pyrimidin-4-amine, 2-(3-(5-Aminopyrazin-2-yl)-6-(cyclohexylmethyl)-2-fluorophenoxy)pyrimidin-4-amine,
2-(3-(5-Aminopyrazin-2-yl)-2-fluoro-6-isopentylphenoxy)pyrimidin-4-amine,
2-(3-(5-Aminopyrazin-2-yl)-2-fluoro-6-isobutylphenoxy)pyrimidin-4-amine,
5-(3-(5-Aminopyrazin-2-yl)-6-cyclobutyl-2-fluorophenoxy)pyrimidine-2-carboxamide,
$N^4$-(2-(3-(5-Aminopyrazin-2-yl)-6-cyclobutyl-2-fluorophenoxy)ethyl)pyrimidine-2,4-diamine,
5-(2-Fluoro-4-(pentan-3-yl)-3-(pyrimidin-2-yloxy)phenyl)pyrazin-2-amine,
5-(2-Fluoro-4-methyl-3-(pyrimidin-2-yloxy)phenyl)pyrimidin-2-amine,
5-(4-Ethyl-2-fluoro-3-(pyrimidin-2-yloxy)phenyl)pyrimidin-2-amine,
5-(2-Fluoro-4-propyl-3-(pyrimidin-2-yloxy)phenyl)pyrimidin-2-amine,
5-(2-Fluoro-4-isopropyl-3-(pyrimidin-2-yloxy)phenyl)pyrimidin-2-amine,
5-(4-Cyclopropyl-2-fluoro-3-(pyrimidin-2-yloxy)phenyl)pyrimidin-2-amine,
5-(2-Fluoro-4-isobutyl-3-(pyrimidin-2-yloxy)phenyl)pyrimidin-2-amine,
5-(2-Fluoro-4-neopentyl-3-(pyrimidin-2-yloxy)phenyl)pyrimidin-2-amine,
5-(2-Fluoro-4-(pentan-3-yl)-3-(pyrimidin-2-yloxy)phenyl)pyrimidin-2-amine,
5-(4-Cyclohexyl-2-fluoro-3-(pyrimidin-2-yloxy)phenyl)pyrimidin-2-amine,
5-(4-(Cyclohexylmethyl)-2-fluoro-3-(pyrimidin-2-yloxy)phenyl)pyrimidin-2-amine,
5-(2-Fluoro-4-isopentyl-3-(pyrimidin-2-yloxy)phenyl)pyrimidin-2-amine,
5-(4-Cyclobutyl-2-fluoro-3-(pyrimidin-2-yloxy)phenyl)-4-methylpyrimidin-2-amine,
5-(4-(tert-Butyl)-2-fluoro-3-(pyrimidin-2-yloxy)phenyl)-4-methylpyrimidin-2-amine,
3-Chloro-5-(4-cyclobutyl-2-fluoro-3-(pyrimidin-2-yloxy)phenyl)pyridin-2-amine,
5-(4-(tert-Butyl)-2-fluoro-3-(pyrimidin-2-yloxy)phenyl)-3-chloropyridin-2-amine,
2-Amino-5-(4-cyclobutyl-2-fluoro-3-(pyrimidin-2-yloxy)phenyl)nicotinonitrile,
2-Amino-5-(4-(tert-butyl)-2-fluoro-3-(pyrimidin-2-yloxy)phenyl)nicotinonitrile,
5-(4-Cyclobutyl-2-fluoro-3-(pyrimidin-2-yloxy)phenyl)-3-fluoropyridin-2-amine,
5-(4-(tert-Butyl)-2-fluoro-3-(pyrimidin-2-yloxy)phenyl)-3-fluoropyridin-2-amine,
5-(4-Cyclobutyl-2-fluoro-3-(pyrim id in-2-yloxy)phenyl)-3-(trifluoromethyl)pyridin-2-amine,
5-(4-(tert-Butyl)-2-fluoro-3-(pyrimidin-2-yloxy)phenyl)-3-(trifluoromethyl)pyridin-2-amine,
5-(4-Cyclobutyl-2-fluoro-3-(pyrimidin-2-yloxy)phenyl)pyridine-2,3-diamine,
5-(4-(tert-Butyl)-2-fluoro-3-(pyrimidin-2-yloxy)phenyl)pyridine-2,3-diamine,
5-(4-Cyclobutyl-2-fluoro-3-(pyrimidin-2-yloxy)phenyl)-3-methylpyrazin-2-amine,
5-(4-(tert-Butyl)-2-fluoro-3-(pyrimidin-2-yloxy)phenyl)-3-methylpyrazin-2-amine,
3-Chloro-5-(4-cyclobutyl-2-fluoro-3-(pyrimidin-2-yloxy)phenyl)pyrazin-2-amine,
5-(4-(tert-Butyl)-2-fluoro-3-(pyrimidin-2-yloxy)phenyl)-3-chloropyrazin-2-amine,
3-Amino-6-(4-cyclobutyl-2-fluoro-3-(pyrimidin-2-yloxy)phenyl)pyrazine-2-carbonitrile,
3-Amino-6-(4-(tert-butyl)-2-fluoro-3-(pyrimidin-2-yloxy)phenyl)pyrazine-2-carbonitrile,
5-(4-Cyclobutyl-2-fluoro-3-(pyrimidin-2-yloxy)phenyl)-3-fluoropyrazin-2-amine,
5-(4-(tert-Butyl)-2-fluoro-3-(pyrimidin-2-yloxy)phenyl)-3-fluoropyrazin-2-amine,
5-(4-Cyclobutyl-2-fluoro-3-(pyrimidin-2-yloxy)phenyl)-3-methoxypyrazin-2-amine,
5-(4-(tert-Butyl)-2-fluoro-3-(pyrimidin-2-yloxy)phenyl)-3-methoxypyrazin-2-amine,
5-(4-Cyclobutyl-2-fluoro-3-(pyrimidin-2-yloxy)phenyl)pyrazine-2,3-diamine,
5-(4-(tert-Butyl)-2-fluoro-3-(pyrimidin-2-yloxy)phenyl)pyrazine-2,3-diamine,
3-(5-Aminopyrazin-2-yl)-6-ethyl-2-fluorophenol,
5-{3-[(2-Aminopyridin-4-yl)oxy]-4-cyclobutyl-2-fluorophenyl}pyrazin-2-amine,
5-{3-[(6-Aminopyrazin-2-yl)oxy]-4-cyclobutyl-2-fluorophenyl}pyrazin-2-amine,
5-[4-Cyclobutyl-2-fluoro-3-(pyrimidin-5-yloxy)phenyl]pyrazin-2-amine,
6-[3-(5-Aminopyrazin-2-yl)-6-cyclobutyl-2-fluorophenoxy]pyridazin-4-amine,
3-(5-Aminopyrazin-2-yl)-6-cyclohexyl-2-fluorophenol,
3-(5-Aminopyrazin-2-yl)-6-(cyclohexylmethyl)-2-fluorophenol,
5-[4-Cyclopentyl-2-fluoro-3-(pyrimidin-2-yloxy)phenyl]pyrimidin-2-amine,
5-[4-Cyclopentyl-2-fluoro-3-(pyrimidin-2-yloxy)phenyl]pyrazin-2-amine,
2-[3-(5-Aminopyrazin-2-yl)-6-cyclopentyl-2-fluorophenoxy]pyrimidin-4-amine,
5-{3-[(4-Aminopyrimidin-2-yl)oxy]-4-cyclopentyl-2-fluorophenyl}pyrimidin-2-amine,
6-[3-(5-Aminopyrazin-2-yl)-6-cyclobutyl-2-fluorophenoxy]pyridazin-3-amine,
5-[4-Cyclobutyl-2-fluoro-3-(pyrimidin-2-ylmethoxy)phenyl]pyrazin-2-amine,
5-{3-[(4-Bromobenzyl)oxy]-4-cyclobutyl-2-fluorophenyl}pyrazin-2-amine,
5-(4-{[3-(5-Aminopyrazin-2-yl)-6-cyclobutyl-2-fluorophenoxy]methyl}phenyl)pyrimidin-2-amine,
5-(4-Cyclobutyl-2-fluoro-3-{[4'-(trifluoromethyl)biphenyl-4-yl]methoxy}phenyl)pyrazin-2-amine,
5-[4-Cyclohexyl-2-fluoro-3-(pyrimidin-2-yloxy)phenyl]pyrimidin-2-amine, and
5-{3-[(4-Aminopyrimidin-2-yl)oxy]-4-cyclohexyl-2-fluorophenyl}pyrimidin-2-amine,
and pharmaceutically acceptable salts thereof.

5. A pharmaceutical composition comprising at least one compound of claim 1 and at least one pharmaceutically acceptable carrier.

6. The pharmaceutical composition of claim 5 comprising at least one compound of claim 4.

7. A process for making a pharmaceutical composition comprising admixing any of the compounds according to claim 1 and a pharmaceutically acceptable carrier.

8. A process for the preparation of a compound of claim 1, wherein L is a bond, $R_1$ is cyclobutyl, ring A is

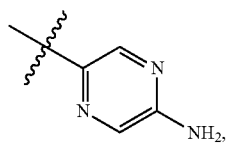

and $R_2$ is optionally substituted phenyl or optionally substituted 5-membered or 6-membered heteroaryl, said process comprising:

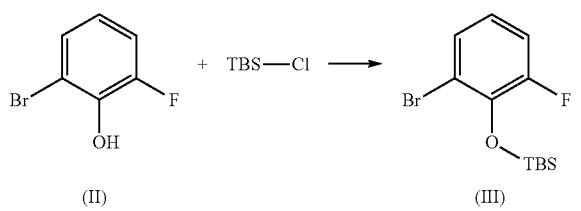

reacting a compound of Formula (II) with tert-butyldimethylsilyl (TBS) chloride in the presence of a solvent to yield the corresponding compound of Formula (III);

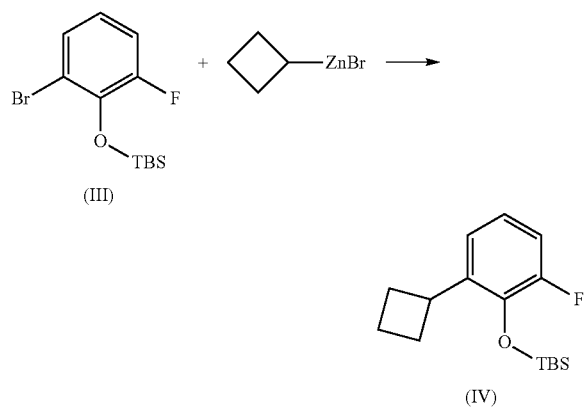

reacting a compound of Formula (III) with cyclobutylzinc bromide in the presence of a palladium catalyst to yield the corresponding compound of Formula (IV);

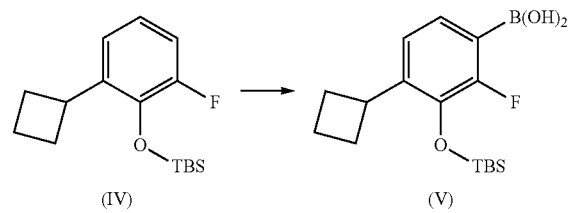

reacting a compound of Formula (IV) with Tri-iso-propyl borate in the presence of an acid and n-Butyllithium to yield the corresponding compound of Formula (V);

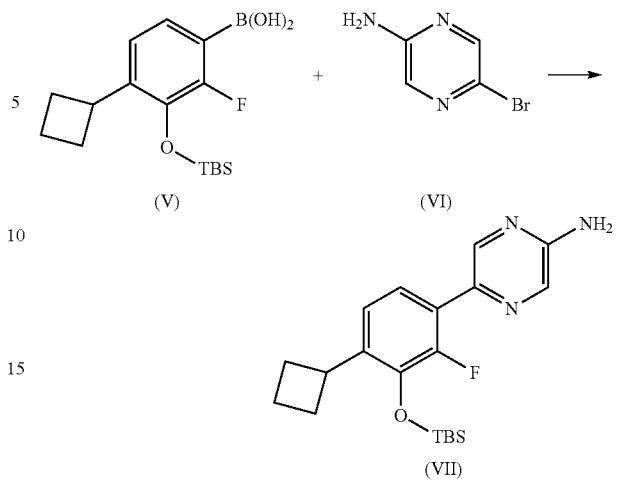

reacting a compound of Formula (V) with a compound of Formula (VI) in the presence of a catalyst and a base to yield the corresponding compound of Formula (VII);

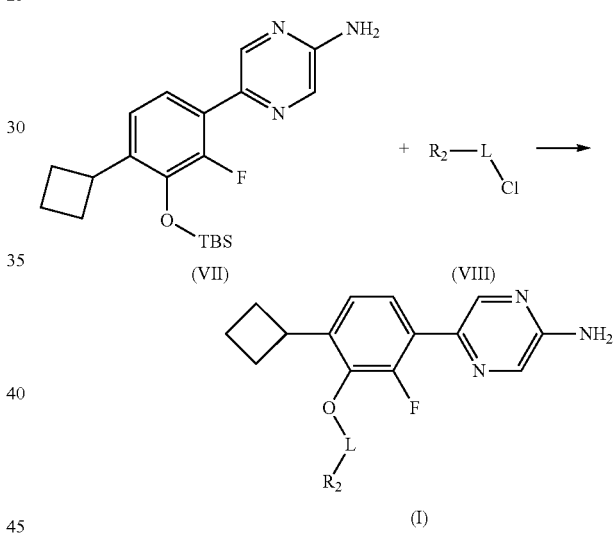

reacting a compound of Formula (VII) with a compound of Formula (VIII) in the presence of 18-crown-6 and a base to yield the corresponding compound of Formula (I).

9. A compound selected from the group consisting of:
5-[4-Cyclobutyl-2-fluoro-3-(pyrimidin-2-yloxy)phenyl] pyrazin-2-amine,
5-{3-[(4-Aminopyrimidin-2-yl)oxy]-4-cyclobutyl-2-fluorophenyl}pyrimidin-2-amine,
5-[4-tert-Butyl-2-fluoro-3-(pyrimidin-2-yloxy)phenyl] pyrazin-2-amine,
2-[3-(5-Aminopyrazin-2-yl)-6-tert-butyl-2-fluorophenoxy]pyrimidin-4-amine,
5-[4-tert-Butyl-2-fluoro-3-(pyrimidin-2-yloxy)phenyl] pyrimidin-2-amine,
5-{3-[(4-Aminopyrimidin-2-yl)oxy]-4-tert-butyl-2-fluorophenyl}pyrimidin-2-amine,
2-[3-(5-Aminopyrazin-2-yl)-6-cyclopentyl-2-fluorophenoxy]pyrimidin-4-amine, and- 2-[3-(5-Aminopyrazin-2-yl)-6-cyclobutyl-2-fluorophenoxy]pyrimidin-4-amine, and
pharmaceutically acceptable salts thereof.

10. A compound of claim 9 which is:
5-[4-Cyclobutyl-2-fluoro-3-(pyrimidin-2-yloxy)phenyl]pyrazin-2-amine,
and pharmaceutically acceptable salts thereof.

11. A compound of claim 9 which is:
5-{3-[(4-Aminopyrimidin-2-yl)oxy]-4-cyclobutyl-2-fluorophenyl}pyrimidin-2-amine,
and pharmaceutically acceptable salts thereof.

12. A compound of claim 9 which is:
5-[4-tert-Butyl-2-fluoro-3-(pyrimidin-2-yloxy)phenyl]pyrazin-2-amine,
and pharmaceutically acceptable salts thereof.

13. A compound of claim 9 which is:
2-[3-(5-Aminopyrazin-2-yl)-6-tert-butyl-2-fluorophenoxy]pyrimidin-4-amine,
and pharmaceutically acceptable salts thereof.

14. A compound of claim 9 which is:
5-[4-tert-Butyl-2-fluoro-3-(pyrimidin-2-yloxy)phenyl]pyrimidin-2-amine,
and pharmaceutically acceptable salts thereof.

15. A compound of claim 9 which is:
5-{3-[(4-Aminopyrimidin-2-yl)oxy]-4-tert-butyl-2-fluorophenyl}pyrimidin-2-amine,
and pharmaceutically acceptable salts thereof.

16. A compound of claim 9 which is:
2-[3-(5-Aminopyrazin-2-yl)-6-cyclopentyl-2-fluorophenoxy]pyrimidin-4-amine, and
and pharmaceutically acceptable salts thereof.

17. A compound of claim 9 which is:
2-[3-(5-Aminopyrazin-2-yl)-6-cyclobutyl-2-fluorophenoxy]pyrimidin-4-amine,
and pharmaceutically acceptable salts thereof.

18. A pharmaceutical composition of claim 5 comprising at least one compound of claim 9.

* * * * *